United States Patent [19]

Higashida et al.

[11] Patent Number: 5,629,406

[45] Date of Patent: May 13, 1997

[54] INHIBITORS OF HIV PROTEASE

[75] Inventors: Susumu Higashida; Mitsuya Sakurai; Yuichiro Yabe; Takashi Nishigaki; Tomoaki Komai; Hiroshi Handa, all of Tokyo, Japan

[73] Assignee: Sankyo Company, Limited, Tokyo, Japan

[21] Appl. No.: 227,588

[22] Filed: Apr. 14, 1994

Related U.S. Application Data

[63] Continuation of Ser. No. 102,467, Aug. 5, 1993, abandoned.

[30] Foreign Application Priority Data

Aug. 7, 1992 [JP] Japan .................................. 4-211746

[51] Int. Cl.[6] .................................................. A61K 38/06
[52] U.S. Cl. .......................... 530/331; 548/535; 562/561
[58] Field of Search ......................... 514/18, 19; 530/331, 530/332, 323

[56] References Cited

FOREIGN PATENT DOCUMENTS 0490667  6/1992  European Pat. Off. .......... C07K 5/02
0498680  8/1992  European Pat. Off. .

OTHER PUBLICATIONS

Chemical Abstracts, vol. 116, No. 5, Feb. 3, 1992, Abstract No. 116: 42 041h of Tsutomu et al, "Rational design and synthesis of a novel class of active site-targeted HIV protease inhibitors containing a hydroxymethylcarbonyl isostere. Use of phenylnorstatine as a transition state mimic."
Chemical Abstracts, vol. 117, No. 1, Jul. 6, 1992, Abstract No. 117: 8 449h of Tsutomu et al, "Design and synthesis of HIV protease inhibitors containing a hydroxymethylcarbonyl isostere as a transition state mimic."

*Primary Examiner*—David Lukton
*Attorney, Agent, or Firm*—Frishauf, Holtz, Goodman, Langer & Chick, P.C.

[57] ABSTRACT

Compounds of formula (I):

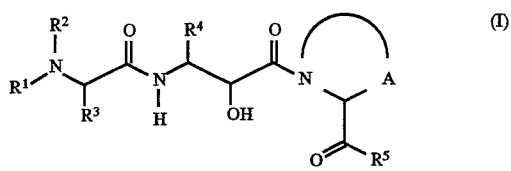

wherein: $R^1$ is hydrogen, alkyl, aralkyl, —$COR^a$, —$COR^b$, —$CSR^a$, —$CSR^b$, —$SO_2R^b$, —$CONHR^b$, —$CSNHR^b$, —$CONR^bR^b$ or —$CSNR^bR^b$; $R^2$ is hydrogen or alkyl; $R^3$ is hydrogen, alkylidene, substituted alkyl, or $R^b$; $R^4$ is optionally substituted alkyl, cycloalkyl, or aryl; $R^5$ is $R^bO$—, $R^bR^bN$—, $R^bHN$—, aralkyloxycarbonyloxy or aralkyloxycarbonylamino, or $R^5$ is —$(CH_2)_p$—D—$(CH_2)_r$—, where D is a single bond, carbonyl, oxygen, sulfur, —NH—, —($CH_2$=$CH_2$)— or —NHCO—; and p and r are each 0 or an integer from 1 to 5; A is —$(CH_2)_m$—B—$(CH_2)_n$— where B is a single bond, carbonyl, oxygen, sulfur, —NH—, —($CH_2$=$CH_2$)— or —NHCO—; and m and n are each 0 or an integer from 1 to 5; $R^a$ is alkoxy, aralkyloxy, aryloxy or alkoxycarbonyl; $R^b$ is optionally substituted alkyl, cycloalkyl, heterocyclic, aryl or arylalkenyl; and pharmaceutically acceptable salts and esters thereof and pro-drugs therefor, have the ability to inhibit the activity of HIV protease and may thus be used for the treatment and prophylaxis of AIDS.

6 Claims, No Drawings

INHIBITORS OF HIV PROTEASE

This application is a continuation of application Ser. No. 08/102,467, filed Aug. 5, 1993, now abandoned.

BACKGROUND OF THE INVENTION

The present invention relates to a series of new peptides which have the ability to inhibit the activity of protease originating in the human immunodeficiency virus ("HIV"), hereinafter referred to as "HIV protease". The compounds thus have the ability to interfere with the maturation and replication of the virus and so may be used to treat individuals infected with HIV. The invention also provides methods and compositions using these compounds as well as processes for preparing them.

The pol genetic region of HIV contains genetic information relating to the activities of protease, reverse transcriptase, RNase H and endonuclease, and it is known that these enzymes are essential for the maturation of HIV particles and that HIV with infectious activity can never mature if the virus is deficient in any one of these enzyme activities (Science, December 1988).

Accordingly, attempts have been made to develop compounds capable of inhibiting these enzymes. For example, several compounds, including pepstatin A, are known to have this class of activity. Examples of such compounds are disclosed in Japanese Patent Kokai Application No. Hei 2-42048 (European Patent Publication No. 346 847); Japanese Patent Kokai Application No. Hei 2-117615 (European Patent Publication No. 357 332); Japanese Patent Kokai Application No. Hei 2-145515 (European Patent Publication No. 369 141); Japanese Patent Kokai Application No. Hei 2-152949 (European Patent Publication No. 356 223); Japanese Patent Kokai Application No. Hei 2-202898 (European Patent Publication No. 372 537); Japanese Patent Kokai Application No. Hei 2-202899 (European Patent Publication No. 373 497); Japanese Patent Kokai Application No. Hei 2-209854 (European Patent Publication No. 337 714); Proceedings of the National Academy of the United States of America 85, 6612 (1988); Biochemical and Biophysical Research Communications 159, 420 (1988); Biochemistry 29, 264 (1990); Proceedings of the National Academy of the United States of America 86, 9752 (1989); Nature 343, 90 (1990); Science 246, 1149 (1989); Science 247, 454 (1990); Science 248, 358 (1990); Science 249, 527 (1990); and Journal of Medicinal Chemistry 33, 1285 (1990)].

The prior art compounds, however, have a different structure from the compounds of the present invention.

BRIEF SUMMARY OF INVENTION

It is an object of the present invention to provide a series of new peptide derivatives.

It is a further object of the invention to provide such peptide derivatives, at least some of which have the ability to inhibit the activity of HIV protease.

Other objects and advantages of the invention will become apparent as the description proceeds.

The compounds of the present invention are those compounds of formula (I):

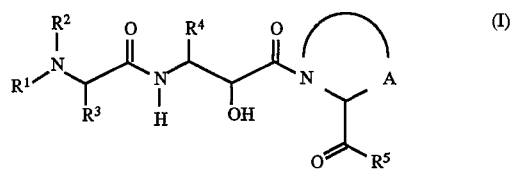

wherein:

$R^1$ represents a hydrogen atom, an alkyl group, an aralkyl group, or a group of formula —$COR^a$, —$COR^b$, —$CSR^a$, —$CSR^b$, —$SO_2R^b$, —$CONHR^b$, —$CSNHR^b$, —$CONR^bR^b$ or $CSNR^bR^b$;

$R^2$ represents a hydrogen atom or an alkyl group;

$R^3$ represents a hydrogen atom, an alkylidene group having from 1 to 4 carbon atoms, a substituted alkyl group which is substituted by at least one substituent preferably selected from the group consisting of substituents A, defined below, or $R^3$ represents any of the groups defined for $R^b$;

$R^4$ represents an unsubstituted alkyl group, a substituted alkyl group which is substituted by at least one substituent preferably selected from the group consisting of substituents B, a cycloalkyl group, or an aryl group;

$R^5$ represents a group of formula $R^bO$—, a group of formula $R^bR^bN$—, a group of formula $R^bHN$—, or an aralkyloxycarbonyloxy or aralkyloxycarbonylamino group, or $R^5$ represents a group of formula

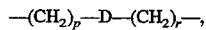

wherein:

D represents a single bond, a carbonyl group, an oxygen atom, a sulfur atom, a group of formula —NH—, a group of formula —($CH_2$=$CH_2$)— or a group of formula —NHCO—; and p and r are each selected from the group consisting of 0 and integers from 1 to 5, provided that, where D represents a single bond, p is an integer from 1 to 5, or a group of formula —($CH_2$)$_p$—D—($CH_2$)$_r$— which is substituted by at least one substituent preferably selected from the group consisting of the groups defined for $R^a$ the groups defined for $R^b$ and substituents B, said group being attached at one end to the carbonyl group in formula (I) and at the other end to the group represented by A;

A represents a group of formula

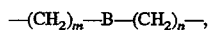

wherein:

B represents a single bond, a carbonyl group, an oxygen atom, a sulfur atom, a group of formula —NH—, a group of formula —($CH_2$=$CH_2$)— or a group of formula —NHCO—; and m and n are each selected from the group consisting of 0 and integers from 1 to 5, provided that (m+n) is an integer from 1 to 5, or a group of formula —($CH_2$)$_m$—B—($CH_2$)$_n$— which is substituted by at least one substituent preferably selected from the group consisting of the groups defined for $R^a$, the groups defined for $R^b$ and substituents B;

$R^a$ represents an alkoxy group, an aralkyloxy group, an aryloxy group or an alkoxycarbonyl group;

$R^b$ represents an unsubstituted alkyl group, a substituted alkyl group which is substituted by at least one substituent preferably selected from the group consisting of substituents C, defined below, a cycloalkyl group, a heterocyclic group, an aryl group or an arylalkenyl group; and, where there is more than one group $R^b$, these may be the same or different;

said substituents A are selected from the group consisting of heterocyclic groups, heterocyclyl-carbonyl groups, cyano groups, amino groups, alkylamino groups, hydroxyamino groups, dialkylamino groups, alkylthio groups, sulfamoyl groups, sulfimoyl groups, hydroxy groups, alkylsulfinyl groups, alkylsulfonyl groups, aminosulfonyl groups, aminosulfinyl groups, alkoxy groups, alkoxycarbonyl groups, carboxy groups, heterocyclyloxy groups, alkylphosphonyl groups, and groups of formula —CONHR$^c$ or —OCONHR$^c$, where $R^c$ represents a hydrogen atom or an alkyl group;

said substituents B are selected from the group consisting of cycloalkyl groups, cycloalkyloxy groups, heterocyclic groups, heterocyclyloxy groups, aryl groups, aryloxy groups, arylthio groups, hydroxy groups, cyano groups, halogen atoms and groups of formula —NR$^d$R$^d$, where each $R^d$ is independently selected from the group consisting of hydrogen atoms, alkyl groups, aryl groups and substituted alkyl groups which are substituted by at least one substituent preferably selected from the group consisting of substituents D, defined below;

said substituents C are selected from the group consisting of said substituents B, cycloalkyl groups, heterocyclic groups, aryl groups and arylalkenyl groups;

said substituents D are selected from the group consisting of heterocyclic groups, alkylamino groups, dialkylamino groups and hydroxy groups;

said alkyl groups, said alkoxy groups and the alkyl and alkoxy parts of said alkoxycarbonyl, alkylamino, dialkylamino, alkylthio, alkylsulfinyl, alkylsulfonyl and alkylphosphonyl groups and of the haloalkyl groups referred to hereafter preferably have from 1 to 6 carbon atoms;

said cycloalkyl and cycloalkyloxy groups preferably have from 3 to 10 carbon atoms in at least one carbocyclic ring and are unsubstituted or are substituted by at least one substituent preferably selected from the group consisting of substituents E, defined below;

said substituents E are selected from the group consisting of amino groups, alkylamino groups, dialkylamino groups, aralkylamino groups, diaralkylamino groups, alkoxycarbonylamino groups, aryloxycarbonylamino groups and aralkyloxycarbonylamino groups;

said aryl groups and the aryl parts of said aralkyl, aryloxy and arylalkenyl groups are aromatic carbocyclic groups which preferably have from 6 to 14 carbon atoms in at least one aromatic ring and which are unsubstituted or are substituted by at least one substituent selected from the group consisting of substituents F, defined below, and such groups in which an aromatic ring is fused with a cycloalkyl ring having from 3 to 10 ring carbon atoms;

said substituents F are selected from the group consisting of aryl groups, alkyl groups, aralkyl groups, alkoxy groups, hydroxy groups, nitro groups, cyano groups, carboxy groups, halogen atoms, haloalkyl groups, aliphatic carboxylic acyl groups preferably having from 1 to 20 carbon atoms, aliphatic carboxylic acyloxy groups preferably having from 1 to 20 carbon atoms, alkylenedioxy groups preferably having from 1 to 4 carbon atoms, heterocyclic groups heterocyclyl-carbonyl groups, and groups of formula —NR$^e$R$^e$ or —CONR$^e$R$^e$, where each $R^e$ is independently selected from the group consisting of hydrogen atoms, alkyl groups, aryl groups, aralkyl groups, alkoxycarbonyl groups, aralkyloxycarbonyl groups, aryloxycarbonyl groups, heterocyclyl-carbonyl groups, heterocyclyl-alkanoyl groups, heterocyclyl-alkyl groups, aliphatic carboxylic acyl groups, and alkylaminocarbonyl groups in which the alkyl part is unsubstituted or is substituted by at least one of substituents E, defined above, in which the alkyl and aralkyl groups and the alkoxy, aralkyl, aryl, heterocyclyl and alkyl parts of groups are as defined herein;

said aralkyl groups and the aralkyl parts of said aralkyloxycarbonyloxy, aralkyloxycarbonylamino, aralkyloxy, aralkylamino and diaralkylamino groups are alkyl groups having from 1 to 6 carbon atoms which are substituted by at least one aryl group, as defined above;

said aralkenyl groups are alkenyl groups having from 2 to 4 carbon atoms which are substituted by at least one aryl group, as defined above;

said heterocyclic groups and the heterocyclic parts of said heterocyclyloxy and heterocyclyl-alkyl groups have from 3 to 10 ring atoms of which from 1 to 4 are hetero-atoms selected from the group consisting of nitrogen, oxygen and sulfur hetero-atoms and of which the remaining ring atoms are carbon atoms, said heterocyclic groups being unsubstituted or being substituted by at least one substituent selected from the group consisting of substituents G, defined below, and such groups in which a heterocyclic ring is fused through one or more atoms to a cycloalkyl or aryl group, as defined above;

said aromatic heterocyclic groups are heterocyclic groups as defined above but which have from 5 to 10 ring atoms and are aromatic;

said substituents G are selected from the group consisting of oxygen atoms (to form an oxo group), and said substituents F;

and pharmaceutically acceptable salts and esters thereof and pro-drugs therefor.

The invention also provides a pharmaceutical composition for treating an HIV infection, which comprises at least one anti-HIV agent in admixture with a pharmaceutically acceptable carrier or diluent, wherein the anti-HIV agent is a compound of formula (I), as defined above, or a pharmaceutically acceptable salt or ester thereof.

The invention still further provides a method for treating HIV infections in a susceptible mammal, by administering to said mammal an effective amount of at least one anti-HIV agent, wherein said anti-HIV agent is a compound of formula (I), as defined above, or a pharmaceutically acceptable salt or ester thereof.

The invention also provides processes for preparing the compounds of the present invention, which are described in greater detail hereafter.

DETAILED DESCRIPTION OF INVENTION

In the compounds of the present invention, where a cyclic group is a substituent on another group, they may be attached to each other by a bond or by a spiro attachment.

In the compounds of the present invention, where $R^1$ represents an alkyl group, this may be a straight or branched chain alkyl group having from 1 to 6 carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which we prefer the straight and branched chain alkyl groups having from 1 to 4 carbon atoms, especially the methyl and ethyl groups.

Where $R^2$, $R^3$, $R^4$, $R^b$, $R^c$, $R^d$, $R^e$ or substituent A, D, E or F includes or represents an alkyl group, this may be any of the alkyl groups exemplified above; similarly, the alkyl parts of the alkylamino, dialkylamino, alkylthio, alkylsulfinyl, alkylsulfonyl and alkylphosphonyl groups may also be any of those exemplified above. Preferred such groups are the straight and branched chain alkyl groups having from 1 to 4 carbon atoms, especially the methyl and ethyl groups.

Where $R^1$ represents an aralkyl group, this is as defined above, and examples include any of the alkyl groups having from 1 to 6, preferably from 1 to 4, carbon atoms exemplified above and substituted by at least one aryl group, such as those exemplified hereafter. There is no particular limitation on the number of aryl substituents on the alkyl group, except such as may be imposed by the number of substitutable positions or possibly by steric constraints, but, in general, from 1 to 3 aryl groups are preferred, 2 or 1 being more preferred and 1 being most preferred. The aryl group forming part of the aralkyl group may itself be unsubstituted or it may be substituted by at least one substituent selected from the group consisting of substituents F, defined above and exemplified below. Again, there is no particular limitation on the number of substituents on the aryl group, except such as may be imposed by the number of substitutable positions or possibly by steric constraints, but, in general, from 1 to 5 substituents are preferred, from 1 to 3 being more preferred and 1 being most preferred. Specific examples of such groups include the benzyl, α-naphthylmethyl, β-naphthylmethyl, 2-methylbenzyl, 3-methylbenzyl, 4-methylbenzyl, 2,4,6-trimethylbenzyl, 3,4,5-trimethylbenzyl, 2-methoxybenzyl, 3-methoxybenzyl, 4-methoxybenzyl, 3,4-dimethoxybenzyl, 2-nitrobenzyl, 4-nitrobenzyl, 2-chlorobenzyl, 3-chlorobenzyl, 4-chlorobenzyl, 4-bromobenzyl, 4-cyanobenzyl, α or β-naphthylmethyl, benzhydryl (i.e. diphenylmethyl), trityl (i.e. triphenylmethyl), phenethyl, 1-phenylethyl, 1-(α or β-naphthyl)ethyl, 2-(α or β-naphthyl)ethyl, 1-phenylpropyl, 2-phenylpropyl, 3-phenylpropyl, 1-(α or β-naphthyl)propyl, 2-(α or β-naphthyl)propyl, 3-(α or β-naphthyl)propyl, 1-phenylbutyl, 2-phenylbutyl, 3-phenylbutyl, 4-phenylbutyl, 1-(α or β-naphthyl)butyl, 2-(α or β-naphthyl)butyl, 3-(α or β-naphthyl)butyl, 4-(α or β-naphthyl)butyl, 1-phenylpentyl, 2-phenylpentyl, 3-phenylpentyl, 4-phenylpentyl, 5-phenylpentyl, 1-(α or β-naphthyl)pentyl, 2-(α or β-naphthyl)pentyl, 3-(α or β-naphthyl)pentyl, 4-(α or β-naphthyl)pentyl, 5-(α or β-naphthyl)pentyl, 1-phenylhexyl, 2-phenylhexyl, 3-phenylhexyl, 4-phenylhexyl, 5-phenylhexyl, 6-phenylhexyl, 1-(α or β-naphthyl)hexyl, 2-(α or β-naphthyl)hexyl, 3-(α or β-naphthyl)hexyl, 4-(α or β-naphthyl)hexyl, 5-(α or β-naphthyl)hexyl and 6-(α or β-naphthyl)hexyl groups. Of these, we prefer the unsubstituted aralkyl groups and more prefer the unsubstituted benzyl and 2-phenethyl groups.

Where $R^3$ represents an alkylidene group, this has from 1 to 4 carbon atoms and may be a straight or branched chain group. Examples of such groups include the methylene, ethylidene, propylidene, isopropylidene, butylidene, isobutylidene and t-butylidene groups, of which the methylene group is preferred.

Where $R^5$ represents an aralkyloxycarbonyloxy group or an aralkyloxycarbonylamino group or $R^a$ represents an aralkyloxy group, the aralkyl part may be any of the aralkyl groups listed above, but is preferably a benzyl group or a p-nitrobenzyl group.

Where $R^4$, $R^b$, substituent B or substituent C represents a cycloalkyl group, this is a saturated cyclic hydrocarbon group, which may be a single ring or may be two or more condensed rings, and includes cyclic terpenyl groups. Examples include the cyclopropyl, cyclobutyl, cyclopentyl, cyclohexyl, cycloheptyl, norbornyl and adamantyl groups. Of these, we prefer those groups having from 5 to 10 ring carbon atoms, more preferably 6 ring carbon atoms.

Where substituent B represents a cycloalkyloxy group, this is a saturated cyclic hydrocarbon group, which may be a single ring or may be two or more condensed rings, and includes cyclic terpenyloxy groups. Examples include the cyclopropyloxy, cyclobutyloxy, cyclopentyloxy, cyclohexyloxy, cycloheptyloxy, norbornyloxy and adamantyloxy groups. Of these, we prefer those groups having from 5 to 10 ring carbon atoms, more preferably 6 ring carbon atoms.

Where $R^4$, $R^b$, $R^d$, substituent B or substituent C represents an aryl group, this is a carbocyclic aromatic group having from 6 to 14 ring, preferably from 6 to 10, more preferably 6 or 10, and most preferably 6, carbon atoms in one or more aromatic rings. Such groups may also be condensed with one or more cycloalkyl groups, as defined and exemplified above, with the complete condensed group preferably having a total of from 6 to 14 ring carbon atoms (counting both the carbon atoms in the aromatic ring or rings and those in the cycloalkyl ring or rings). The group may also be unsubstituted or substituted, and, if substituted, the substituents are selected from the group consisting of substituents F, defined above and exemplified below. In the case of the substituted groups, there is no particular limitation on the number of substituents on the aryl group, except such as may be imposed by the number of substitutable positions or possibly by steric constraints, but, in general, from 1 to 5 substituents are preferred, from 1 to 4 being more preferred and 1, 2 or 3 being most preferred. Also, where the group is substituted, it is preferred that it should not be further substituted by a group which is also substituted by another aryl group. Specific examples of the fully aromatic groups include the phenyl, (α or β-naphthyl), indenyl, phenanthrenyl and anthracenyl groups, of which we prefer those aromatic hydrocarbon groups having from 6 to 10 ring carbon atoms, the phenyl group being most preferred. Specific examples of groups in which an aromatic ring is condensed with a cycloalkyl ring include the indanyl (preferably 2-indanyl) and 1,2,3,4-tetrahydronaphthyl groups.

Specific examples of substituents F include:
aryl groups, such as those exemplified above and below;
alkyl groups, such as those exemplified above;
the hydroxy, nitro and cyano groups;
alkoxy groups, which may be straight or branched chain groups, for example the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups, of which we prefer the straight and branched chain alkoxy groups having from 1 to 4 carbon atoms, especially the methoxy and ethoxy groups;

the carboxy group, which may be esterified, e.g. as exemplified in more detail hereafter, but preferably with an alkyl group (such as those exemplified above in relation to $R^1$ etc.), a haloalkyl group (such as those exemplified below) or an aralkyl group (such as those exemplified above in relation to $R^1$);

halogen atoms, such as the fluorine, chlorine, bromine and iodine atoms, preferably the fluorine, chlorine or bromine atom, and most preferably the fluorine or chlorine atom;

haloalkyl groups having from 1 to 6 carbon atoms (for example in which the alkyl part is as exemplified above in relation to $R^1$) and which are substituted by at least one, and preferably from 1 to 5 (except the halomethyl groups, which are preferably substituted by from 1 to 3) halogen atoms, for example the trifluoromethyl, trichloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl, 2,2-dibromoethyl, 3-chloropropyl, 3,3,3-trichloropropyl, perfluoroethyl, 4-fluorobutyl, 5-bromopentyl, 6-chlorohexyl and 6,6,6-trifluorohexyl groups;

aliphatic carboxylic acyl groups preferably having from 1 to 20 carbon atoms, more preferably from 1 to 10 carbon atoms and most preferably from 2 to 6 carbon atoms, which group may be a straight or branched chain group, such as an alkanoyl group (for example, the formyl, acetyl, propionyl, butyryl, isobutyryl, pivaloyl, valeryl, isovaleryl, octanoyl, lauroyl, myristoyl, tridecanoyl, palmitoyl and stearoyl groups), any of which may be substituted or unsubstituted and, if substituted are substituted by one or more of the following substituents:

halogen atoms, for example to form a halogenated alkanoyl group preferably having from 2 to 20 carbon atoms, more preferably from 2 to 10 carbon atoms and still more preferably from 2 to 6 carbon atoms and most preferably 2 or 3 carbon atoms (for example, the chloroacetyl, bromoacetyl, dichloroacetyl, trichloroacetyl and trifluoroacetyl groups), alkoxy groups, for example to form a lower alkoxyalkanoyl group in which the alkoxy and alkanoyl parts preferably each have from 1 to 6, more preferably from 1 to 4 and most preferably 1 or 2, carbon atoms (for example, the methoxyacetyl, ethoxyacetyl, propoxyacetyl, butoxyacetyl, 3-methoxypropionyl and 3-ethoxypropionyl groups), carboxy groups and esterified carboxy groups, which may be the residues of dicarboxylic acids, groups of formula —$NR^fR^f$, in which each $R^f$, which may be the same as each other or different from each other represents a hydrogen atom, an alkyl group, an alkoxycarbonyl group, an aralkyloxycarbonyl group, a heterocyclyl-alkyl group, an aminoalkyl group, an alkylaminoalkyl group, a dialkylaminoalkyl group or a hydroxyalkyl group, in all of which the alkyl and alkoxy groups have from 1 to 6 carbon atoms, to form an amino-acid residue [for example the glycyl, glutamyl, sarcosyl, N-methylglutamyl, N-t-butylglutamyl, N-t-butoxycarbonylglutamyl, N-t-butoxycarbonyl-N-methylglutamyl, α-(3-morpholinopropylamino)acetyl, α-(3-dimethylaminopropylamino)acetyl and α-(2-hydroxyethylamino)acetyl groups], or an unsaturated aliphatic acyl group preferably having from 3 to 6, and more preferably from 3 to 5 carbon atoms [for example, the acryloyl, methacryloyl, crotonoyl and (E)-2-methyl-2-butenoyl groups];

aliphatic carboxylic acyloxy groups preferably having from 1 to 20 carbon atoms, more preferably from 1 to 10 carbon atoms and most preferably from 2 to 6 carbon atoms, which group may be a straight or branched chain group, such as an alkanoyloxy group (for example, the formyloxy, acetoxy, propionyloxy, butyryloxy, isobutyryloxy, pivaloyloxy, valeryloxy, isovaleryloxy, octanoyloxy, lauroyloxy, myristoyloxy, tridecanoyloxy, palmitoyloxy and stearoyloxy groups), any of which may be substituted or unsubstituted and, if substituted are substituted by one or more of the following substituents:

halogen atoms, for example to form a halogenated alkanoyloxy group preferably having from 2 to 20 carbon atoms, more preferably from 2 to 10 carbon atoms and still more preferably from 2 to 6 carbon atoms and most preferably 2 or 3 carbon atoms (for example, the chloroacetoxy, bromoacetoxy, dichloroacetoxy, trichloroacetoxy and trifluoroacetoxy groups), alkoxy groups, for example to form a lower alkoxyalkanoyloxy group in which the alkoxy and alkanoyloxy parts preferably each have from 1 to 6, more preferably from 1 to 4 and most preferably 1 or 2, carbon atoms (for example, the methoxyacetoxy, ethoxyacetoxy, propoxyacetoxy, butoxyacetoxy, 3-methoxypropionyloxy and 3-ethoxypropionyloxy groups), carboxy groups and esterified carboxy groups, groups of formula —$NR^fR^f$, in which each $R^f$, which may be the same as each other or different from each other is as defined above [for example the glycyloxy, glutamyloxy, N-methylglutamyloxy, N-t-butylglutamyloxy, N-t-butoxycarbonylglutamyloxy, N-t-butoxycarbonyl-N-methylglutamyloxy, α-(3-morpholinopropylamino)acetoxy, α-(3-dimethylaminopropylamino)acetoxy and α-(2-hydroxyethylamino)acetoxy groups], or an unsaturated aliphatic acyloxy group preferably having from 3 to 6, and more preferably from 3 to 5 carbon atoms [for example, the acryloyloxy, methacryloyloxy, crotonoyloxy and (E)-2-methyl-2-butenoyloxy groups];

alkylenedioxy groups which preferably have from 1 to 4 carbon atoms, such as the methylenedioxy, ethylenedioxy and propylenedioxy groups; and groups of formula —$NR^eR^e$ or —$CONR^eR^e$, for example:
the carbamoyl group;
mono- and di- alkyl-substituted carbamoyl groups, i.e. a carbamoyl group substituted with one or two straight or branched chain alkyl groups each having from 1 to 6 carbon atoms, for example the methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, isopentylcarbamoyl, 2-methylbutylcarbamoyl, neopentylcarbamoyl, hexylcarbamoyl, 4-methylpentylcarbamoyl, 3-methylpentylcarbamoyl, 2-methylpentylcarbamoyl, 3,3-dimethylbutylcarbamoyl, 2,2-dimethylbutylcarbamoyl, 1,1-dimethylbutylcarbamoyl, 1,2-dimethylbutylcarbamoyl, 1,3-dimethylbutylcarbamoyl, 2,3-dimethylbutylcarbamoyl, dimethylcarbamoyl, diethylcarbamoyl, dipropylcarbamoyl, diisopropylcarbamoyl, dibutylcarbamoyl, diisobutylcarbamoyl, di-sec-butylcarbamoyl and di-t-butylcarbamoyl groups, of which we prefer the alkyl-substituted carbamoyl groups in which the or each alkyl group has from 1 to 4 carbon atoms, and more prefer the methylcarbamoyl and dimethylcarbamoyl groups; the amino group;

mono- and di- alkyl-substituted amino groups, i.e. a amino group substituted with one or two straight or branched chain alkyl groups each having from 1 to 6 carbon atoms, for example the methylamino, ethylamino, propylamino, isopropylamino, butylamino, isobutylamino, sec-butylamino, t-butylamino, pentylamino, isopentylamino, 2-methylbutylamino, neopentylamino, hexylamino, 4-methylpentylamino, 3-methylpentylamino, 2-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino, dimethylamino, diethylamino, dipropylamino, diisopropylamino, dibutylamino, diisobutylamino, di-sec-butylamino and di-t-butylamino groups, of which we prefer the alkyl-substituted amino groups in which the or each alkyl group has from 1 to 4 carbon atoms, and more prefer the methylamino and dimethylamino groups;

aralkyloxycarbonylamino groups, such as the benzyloxycarbonylamino group;

aryloxycarbonylamino groups, such as the phenyloxycarbonylamino and p-nitrophenyloxycarbonylamino groups;

halogenated aliphatic acylamino groups, preferably having from 2 to 20 carbon atoms, more preferably from 2 to 10 carbon atoms and still more preferably from 2 to 6 carbon atoms and most preferably 2 or 3 carbon atoms (for example, the chloroacetamido, bromoacetamido, dichloroacetamido, trichloroacetamido and trifluoroacetamido groups;

heterocyclyl-carbonylamino groups (in which the heterocyclic part is as defined above and exemplified below), especially a prolylamino, t-butoxycarbonylprolylamino or morpholinocarbonylamino group;

optionally substituted glutamylamino groups, such as the glutamylamino and $N^2$-benzyloxycarbonyl-glutamylamino groups, especially the α-glutamyl groups and esterified groups, such as the β-benzyl esters; and alkylaminocarbonylamino groups in which the alkyl part is unsubstituted or is substituted by at least one of substituents E, defined above, for example the methylaminocarbonylamino, aminomethylaminocarbonylamino, ethylaminocarbonylamino, 2-aminoethylaminocarbonylamino, propylaminocarbonylamino, 3-aminopropylaminocarbonylamino, butylaminocarbonylamino, 2-aminoethylaminocarbonylamino and 3-(dimethylamino)propylaminocarbonylamino groups.

Specific examples of preferred aryl groups include: the unsubstituted groups, such as the phenyl and naphthyl groups; aryl groups substituted with a halogen atom or atoms, such as the 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl, 2,6-dichlorophenyl, 2,4-dichlorophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-tribromophenyl, 2,3,4-tribromophenyl, 3,4,5-tribromophenyl, 2,5,6-trichlorophenyl, 2,4,6-trichlorophenyl, 1-fluoro-2-naphthyl, 2-fluoro-1-naphthyl, 3-fluoro-1-naphthyl, 1-chloro-2-naphthyl, 2-chloro-1-naphthyl, 3-bromo-1-naphthyl, 3,8-difluoro-1-naphthyl, 2,3-difluoro-1-naphthyl, 4,8-difluoro-1-naphthyl, 5,6-difluoro-1-naphthyl, 3,8-dichloro-1-naphthyl, 2,3-dichloro-1-naphthyl, 4,8-dibromo-1-naphthyl, 5,6-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl and 2,4,8-trifluoro-1-naphthyl groups; aryl groups substituted with a haloalkyl group or groups, such as the 2-trifluoromethylphenyl, 3-trifluoromethylphenyl, 4-trifluoromethylphenyl, 2-trichloromethylphenyl, 3-dichloromethylphenyl, 4-trichloromethylphenyl, 2-tribromomethylphenyl, 3-dibromomethylphenyl, 4-dibromomethylphenyl, 3,5-bistrifluoromethylphenyl, 2,5-bistrifluoromethylphenyl, 2,6-bistrifluoromethylphenyl, 2,4-bistrifluoromethylphenyl, 3,5-bistribromomethylphenyl, 2,5-bisdibromomethylphenyl, 2,6-bisdichloromethylphenyl, 2,4-bisdichloromethylphenyl, 2,3,6-tristrifluoromethylphenyl, 2,3,4-tristrifluoromethylphenyl, 3,4,5-tristrifluoromethylphenyl, 2,5,6-tristrifluoromethylphenyl, 2,4,6-tristrifluoromethylphenyl, 2,3,6-tristribromomethylphenyl, 2,3,4-trisdibromomethylphenyl, 3,4,5-tristribromomethylphenyl, 2,5,6-trisdichloromethylphenyl, 2,4,6-trisdichloromethylphenyl, 1-trifluoromethyl-2-naphthyl, 2-trifluoromethyl-1-naphthyl, 3-trifluoromethyl-1-naphthyl, 1-trichloromethyl-2-naphthyl, 2-dichloromethyl-1-naphthyl, 3-tribromomethyl-1-naphthyl, 3,8-bistrifluoromethyl-1-naphthyl, 2,3-bistrifluoromethyl-1-naphthyl, 4,8-bistrifluoromethyl-1-naphthyl, 5,6-bistrifluoromethyl-1-naphthyl, 3,8-bistrichloromethyl-1-naphthyl, 2,3-bisdichloromethyl-1-naphthyl, 4,8-bisdibromomethyl-1-naphthyl, 5,6-bistribromomethyl-1-naphthyl, 2,3,6-tristrifluoromethyl-1-naphthyl, 2,3,4-tristrifluoromethyl-1-naphthyl, 3,4,5-tristrifluoromethyl-1-naphthyl, 4,5,6-tristrifluoromethyl-1-naphthyl and 2,4,8-tristrifluoromethyl-1-naphthyl groups; aryl groups substituted with an alkyl group or groups, such as the 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylphenyl, 2,4-dipropylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-tributylphenyl, 2,3,4-tripentylphenyl, 3,4,5-tributylphenyl, 2,5,6-tripropylphenyl, 2,4,6-tripropylphenyl, 1-methyl-2-naphthyl, 2-methyl-1-naphthyl, 3-methyl-1-naphthyl, 1-ethyl-2-naphthyl, 2-propyl-1-naphthyl, 3-butyl-1-naphthyl, 3,8-dimethyl-1-naphthyl, 2,3-dimethyl-1-naphthyl, 4,8-dimethyl-1-naphthyl, 5,6-dimethyl-1-naphthyl, 3,8-diethyl-1-naphthyl, 2,3-dipropyl-1-naphthyl, 4,8-dipentyl-1-naphthyl, 5,6-dibutyl-1-naphthyl, 2,3,6-trimethyl-1-naphthyl, 2,3,4-trimethyl-1-naphthyl, 3,4,5-trimethyl-1-naphthyl, 4,5,6-trimethyl-1-naphthyl and 2,4,8-trimethyl-1-naphthyl groups; aryl groups substituted with an alkoxy group or groups, such as the 2-methoxyphenyl, 3-methoxyphenyl, 4-methoxyphenyl, 2-ethoxyphenyl, 3-propoxyphenyl, 4-ethoxyphenyl, 2-butoxyphenyl, 3-pentyloxyphenyl, 4-pentyloxyphenyl, 3,5-dimethoxyphenyl, 2,5-dimethoxyphenyl, 2,6-dimethoxyphenyl 2,4-dimethoxyphenyl, 3,5-dibutoxyphenyl, 2,5-dipentyloxyphenyl, 2,6-dipropoxyphenyl, 2,4-dipropoxyphenyl, 2,3,6-trimethoxyphenyl, 2,3,4-trimethoxyphenyl, 3,4,5-trimethoxyphenyl, 2,5,6-trimethoxyphenyl, 2,4,6-trimethoxyphenyl, 2,3,6-tributoxyphenyl, 2,3,4-tripentyloxyphenyl, 3,4,5-tributoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 1-ethoxy-2-naphthyl, 2-propoxy-1-naphthyl, 3-butoxy-1-naphthyl, 3,8-dimethoxy-1-naphthyl, 2,3-dimethoxy-1-naphthyl, 4,8-dimethoxy-1-naphthyl, 5,6-dimethoxy-1-naphthyl, 3,8-diethoxy-1-naphthyl, 2,3-dipropoxy-1-naphthyl, 4,8-dipentyloxy-1-naphthyl, 5,6-dibutoxy-1-naphthyl, 2,3,6-trimethoxy-1-naphthyl, 2,3,4-trimethoxy-1-naphthyl, 3,4,5-trimethoxy-1-naphthyl, 4,5,6-trimethoxy-1-naphthyl and 2,4,8-trimethoxy-1-naphthyl groups; aryl groups substituted with an amino group or groups, such as the 2-aminophenyl, 3-aminophenyl, 4-aminophenyl, 3,5-diaminophenyl, 2,5-diaminophenyl, 2,6-diaminophenyl, 2,4-diaminophenyl, 2,3,6-triaminophenyl, 2,3,4-triaminophenyl, 3,4,5-triaminophenyl, 2,5,6-triaminophenyl, 2,4,6-triaminophenyl, 1-amino-2-naphthyl, 2-amino-1-naphthyl, 3-amino-1-naphthyl, 3,8-diamino-1-naphthyl, 2,3-diamino-1-naphthyl, 4,8-diamino-1-naphthyl, 5,6-diamino-1-naphthyl, 2,3,6-triamino-1-naphthyl, 2,3,4-triamino-1-naphthyl, 3,4,5-triamino-1-naphthyl, 4,5,6-triamino-1-naphthyl and 2,4,8-triamino-1-naphthyl groups; aryl groups substituted with a hydroxy group or groups, such as the 2-hydroxyphenyl, 3-hydroxyphenyl, 4-hydroxyphenyl, 3,5-dihydroxyphenyl, 2,5-dihydroxyphenyl, 2,6-dihydroxyphenyl, 2,4-dihydroxyphenyl, 2,3,6-trihydroxyphenyl, 2,3,4-trihydroxyphenyl, 3,4,5-trihydroxyphenyl, 2,5,6-trihydroxyphenyl, 2,4,6-trihydroxyphenyl, 1-hydroxy-2-naphthyl, 2-hydroxy-1-naphthyl, 3-hydroxy-1-naphthyl, 3,8-dihydroxy-1-naphthyl, 2,3-dihydroxy-1-naphthyl, 4,8-dihydroxy-1-naphthyl, 5,6-dihydroxy-1-naphthyl, 2,3,6-trihydroxy-1-naphthyl, 2,3,4-trihydroxy-1-naphthyl, 3,4,5-trihydroxy-1-naphthyl, 4,5,6-tri-hydroxy-1-naphthyl and 2,4,8-trihydroxy-1-naphthyl groups; aryl groups substituted with a cyano group or groups, such as the 2-cyanophenyl, 3-cyanophenyl, 4-cyanophenyl, 3,5-dicyanophenyl, 2,5-dicyanophenyl, 2,6-dicyanophenyl, 2,4-dicyanophenyl, 2,3,6-tricyanophenyl, 2,3,4-tricyanophenyl, 3,4,5-tricyanophenyl, 2,5,6-tricyanophenyl, 2,4,6-tricyanophenyl, 1-cyano-2-naphthyl, 2-cyano-1-naphthyl, 3-cyano-1-naphthyl, 3,8-dicyano-1-naphthyl, 2,3-dicyano-1-naphthyl, 4,8-dicyano-1-naphthyl, 5,6-dicyano-1-naphthyl, 2,3,6-tricyano-1-naphthyl, 2,3,4-tricyano-1-naphthyl, 3,4,5-tricyano-1-naphthyl, 4,5,6-tricyano-1-naphthyl and 2,4,8-tricyano-1-naphthyl groups; aryl groups substituted with an aliphatic acyl group or groups, such as the 2-acetylphenyl, 3-acetylphenyl, 4-acetylphenyl, 3,5-diacetylphenyl, 2,5-diacetylphenyl, 2,6-diacetylphenyl, 2,4-diacetylphenyl, 2,3,6-tripropionylphenyl, 2,3,4-tripropionylphenyl, 3,4,5-tripropionylphenyl, 2,5,6-tributyrylphenyl, 2,4,6-tributyrylphenyl, 1-acetyl-2-naphthyl, 2-acetyl-1-naphthyl, 3-acetyl-1-naphthyl, 3,8-diacetyl-1-naphthyl, 2,3-dipropionyl-1-naphthyl, 4,8-dibutyryl-1-naphthyl, 5,6-dibutyryl-1-naphthyl, 2,3,6-triacetyl-1-naphthyl, 2,3,4-triacetyl-1-naphthyl, 3,4,5-tripropionyl-1-naphthyl, 4,5,6-tributyryl-1-naphthyl, and 2,4,8-tripropionyl-1-naphthyl groups; aryl groups substituted with a carboxyl group or groups, such as the 2-carboxyphenyl, 3-carboxyphenyl, 4-carboxyphenyl, 3,5-dicarboxyphenyl, 2,5-dicarboxyphenyl, 2,6-dicarboxyphenyl and 2,4-dicarboxyphenyl groups; aryl groups substituted with a carbamoyl group or groups, such as the 2-carbamoylphenyl, 3-carbamoylphenyl, 4-carbamoylphenyl, 3,5-dicarbamoylphenyl, 2,5-dicarbamoylphenyl, 2,6-dicarbamoylphenyl and 2,4-dicarbamoylphenyl groups; and aryl groups substituted with an alkylenedioxy group or groups, such as the 3,4-methylenedioxyphenyl group. The aryl group may also have any combination of two or more different substituents selected from the above list.

Of these aryl groups, the most preferred are the 4-fluorophenyl, 4-methylphenyl, 4-methoxyphenyl, 4-aminophenyl and 4-hydroxyphenyl groups.

In the case of substituents B, where this is an aryloxy group, it may be the aryloxy equivalent of any of the aryl groups defined and exemplified above.

Preferred examples of such aryloxy groups include: the unsubstituted aryloxy groups, such as the phenyloxy and α- and β- naphthyloxy groups; aryloxy groups substituted with a halogen atom or atoms, such as the 2-fluorophenyloxy, 3-fluorophenyloxy, 4-fluorophenyloxy, 2-chlorophenyloxy, 3-chlorophenyloxy, 4-chlorophenyloxy, 2-bromophenyloxy, 3-bromophenyloxy, 4-bromophenyloxy, 3,5-difluorophenyloxy, 2,5-difluorophenyloxy, 2,6-difluorophenyloxy, 2,4-difluorophenyloxy, 3,5-dibromophenyloxy, 2,5-dibromophenyloxy, 2,6-dichlorophenyloxy, 2,4-dichlorophenyloxy, 2,3,6-trifluorophenyloxy, 2,3,4-trifluorophenyloxy, 3,4,5-trifluorophenyloxy, 2,5,6-trifluorophenyloxy, 2,4,6-trifluorophenyloxy, 2,3,6-tribromophenyloxy, 2,3,4-tribromophenyloxy, 3,4,5-tribromophenyloxy, 2,5,6-trichlorophenyloxy, 2,4,6-trichlorophenyloxy, 1-fluoro-2-naphthyloxy, 2-fluoro-1-naphthyloxy, 3-fluoro-1-naphthyloxy, 1-chloro-2-naphthyloxy, 2-chloro-1-naphthyloxy, 3-bromo-1-naphthyloxy, 3,8-difluoro-1-naphthyloxy, 2,3-difluoro-1-naphthyloxy, 4,8-difluoro-1-naphthyloxy, 5,6-difluoro-1-naphthyloxy, 3,8-dichloro-1-naphthyloxy, 2,3-dichloro-1-naphthyloxy, 4,8-dibromo-1-naphthyloxy, 5,6-dibromo-1-naphthyloxy, 2,3,6-trifluoro-1-naphthyloxy, 2,3,4-trifluoro-1-naphthyloxy, 3,4,5-trifluoro-1-naphthyloxy, 4,5,6-trifluoro-1-naphthyloxy and 2,4,8-trifluoro-1-naphthyloxy groups; aryloxy groups substituted with a haloalkyl group or groups, such as the 2-trifluoromethylphenyloxy, 3-trifluoromethylphenyloxy, 4-trifluoromethylphenyloxy, 2-trichloromethylphenyloxy, 3-dichloromethylphenyloxy, 4-trichloromethylphenyloxy, 2-tribromomethylphenyloxy, 3-dibromomethylphenyloxy, 4-dibromomethylphenyloxy, 3,5- bistrifluoromethylphenyloxy, 2,5-bistrifluoromethylphenyloxy, 2,6-bistrifluoromethylphenyloxy, 2,4-bistrifluoromethylphenyloxy, 3,5-bistribromomethylphenyloxy, 2,5-bisdibromomethylphenyloxy, 2,6-bisdichloromethylphenyloxy, 2,4-bisdichloromethylphenyloxy, 2,3,6-tristrifluoromethylphenyloxy, 2,3,4-tristrifluoromethylphenyloxy, 3,4,5-tristrifluoromethylphenyloxy, 2,5,6-tristrifluoromethylphenyloxy, 2,4,6-tristrifluoromethylphenyloxy, 2,3,6-tristribromomethylphenyloxy, 2,3,4-trisdibromomethylphenyloxy, 3,4,5-tristribromomethylphenyloxy, 2,5,6-trisdichloromethylphenyloxy, 2,4,6-trisdichloromethylphenyloxy, 1-trifluoromethyl-2-naphthyloxy, 2-trifluoromethyl-1-naphthyloxy, 3-trifluoromethyl-1-naphthyloxy, 1-trichloromethyl-2-naphthyloxy, 2-dichloromethyl-1-naphthyloxy, 3-tribromomethyl-1-naphthyloxy, 3,8-bistrifluoromethyl-1-naphthyloxy, 2,3-bistrifluoromethyl-1-naphthyloxy, 4,8-bistrifluoromethyl-1-naphthyloxy, 5,6-bistrifluoromethyl-1-naphthyloxy, 3,8-bistrichloromethyl-1-naphthyloxy, 2,3-bisdichloromethyl-1-naphthyloxy, 4,8-bisdibromomethyl-1-naphthyloxy, 5,6-bistribromomethyl-1-naphthyloxy, 2,3,6-tristrifluoromethyl-1-naphthyloxy, 2,3,4-tristrifluoromethyl-1-naphthyloxy, 3,4,5-tristrifluoromethyl-1-naphthyloxy, 4,5,6-tristrifluoromethyl-1-naphthyloxy and 2,4,8-tristrifluoromethyl-1-naphthyloxy groups; aryloxy groups substituted with a lower alkyl group or groups, such as the 2-methylphenyloxy, 3-methylphenyloxy, 4-methylphenyloxy, 2-ethylphenyloxy, 3-propylphenyloxy, 4-ethylphenyloxy, 2-butylphenyloxy, 3-pentylphenyloxy, 4-pentylphenyloxy, 3,5-dimethylphenyloxy, 2,5-dimethylphenyloxy, 2,6-dimethylphenylox, 2,4-dimethylphenyloxy, 3,5-dibutylphenyloxy, 2,5-dipentylphenyloxy, 2,6-dipropylphenyloxy, 2,4-dipropylphenyloxy, 2,3,6-trimethylphenyloxy, 2,3,4-trimethylphenyloxy, 3,4,5-trimethylphenyloxy, 2,5,6-trimethylphenyloxy, 2,4,6-trimethylphenyloxy, 2,3,6-tributylphenyloxy, 2,3,4-tripentylphenyloxy, 3,4,5-tributylphenyloxy, 2,5,6-tripropylphenyloxy, 2,4,6-tripropylphenyloxy, 1-methyl-2-naphthyloxy, 2-methyl-1-naphthyloxy, 3-methyl-1-naphthyloxy, 1-ethyl-2-naphthyloxy, 2-propyl-1-naphthyloxy, 3-butyl-1-naphthyloxy, 3,8-dimethyl-1-naphthyloxy, 2,3-dimethyl-1-naphthyloxy, 4,8-dimethyl-1-naphthyloxy, 5,6-dimethyl-1-naphthyloxy, 3,8-diethyl-1-naphthyloxy, 2,3-dipropyl-1-naphthyloxy, 4,8-dipentyl-1-naphthyloxy, 5,6-dibutyl-1-naphthyloxy, 2,3,6-trimethyl-1-naphthyloxy, 2,3,4-trimethyl-1-naphthyloxy, 3,4,5-trimethyl-1-naphthyloxy, 4,5,6-trimethyl-1-naphthyloxy and 2,4,8-trimethyl-1-naphthyl oxy groups; aryloxy groups substituted with a lower alkoxy group or groups, such as 2-methoxyphenyloxy, 3-methoxyphenyloxy, 4-methoxyphenyloxy, 2-ethoxyphenyloxy, 3-propoxyphenyloxy, 4-ethoxyphenyloxy, 2-butoxyphenyloxy, 3-pentyloxyphenyloxy, 4-pentyloxyphenyloxy, 3,5-dimethoxyphenyloxy, 2,5-dimethoxyphenyloxy, 2,6-dimethoxyphenyloxy, 2,4-dimethoxyphenyloxy, 3,5-dibutoxyphenyloxy, 2,5-dipentyloxyphenyloxy, 2,6-dipropoxyphenyloxy, 2,4-dipropoxyphenyloxy, 2,3,6-trimethoxyphenyloxy, 2,3,4-trimethoxyphenyloxy, 3,4,5-trimethoxyphenyloxy, 2,5,6-trimethoxyphenyloxy, 2,4,6-trimethoxyphenyloxy, 2,3,6-tributoxyphenyloxy, 2,3,4-tripentyloxyphenyloxy, 3,4,5-tributoxyphenyloxy, 2,5,6-tripropoxyphenyloxy, 2,4,6-tripropoxyphenyloxy, 1-methoxy-2-naphthyloxy, 2-methoxy-1-naphthyloxy, 3-methoxy-1-naphthyloxy, 1-ethoxy-2-naphthyloxy, 2-propoxy-1-naphthyloxy, 3-butoxy-1-naphthyloxy, 3,8-dimethoxy-1-naphthyloxy, 2,3-dimethoxy-1-naphthyloxy, 4,8-dimethoxy-1-naphthyloxy, 5,6-dimethoxy-1-naphthyloxy, 3,8-diethoxy-1-naphthyloxy, 2,3-dipropoxy-1-naphthyloxy, 4,8-dipentyloxy-1-naphthyloxy, 5,6-dibutoxy-1-naphthyloxy, 2,3,6-trimethoxy-1-naphthyloxy, 2,3,4-trimethoxy-1-naphthyloxy, 3,4,5-trimethoxy-1-naphthyloxy, 4,5,6-trimethoxy-1-naphthyloxy and 2,4,8-trimethoxy-1-naphthyloxy groups; aryloxy groups substituted with an amino group or groups, such as the 2-aminophenyloxy, 3-aminophenyloxy, 4-aminophenyloxy, 3,5-diaminophenyloxy, 2,5-diaminophenyloxy, 2,6-diaminophenyloxy, 2,4-diaminophenyloxy, 2,3,6-triaminophenyloxy, 2,3,4-triaminophenyloxy, 3,4,5-triaminophenyloxy, 2,5,6-triaminophenyloxy, 2,4,6-triaminophenyloxy, 1-amino-2-naphthyloxy, 2-amino-1-naphthyloxy, 3-amino-1-naphthyloxy, 3,8-diamino-1-naphthyloxy, 2,3-diamino-1-naphthyloxy, 4,8-diamino-1-naphthyloxy, 5,6-diamino-1-naphthyloxy, 2,3,6-triamino-1-naphthyloxy, 2,3,4-triamino-1-naphthyloxy, 3,4,5-triamino-1-naphthyloxy, 4,5,6-triamino-1-naphthyloxy and 2,4,8-triamino-1-naphthyloxy groups; aryloxy groups substituted with a hydroxyl group or groups, such as the 2-hydroxyphenyloxy, 3-hydroxyphenyloxy, 4-hydroxyphenyloxy, 3,5-dihydroxyphenyloxy, 2,5-dihydroxyphenyloxy, 2,6-dihydroxyphenyloxy, 2,4-dihydroxyphenyloxy, 2,3,6-trihydroxyphenyloxy, 2,3,4-trihydroxyphenyloxy, 3,4,5-trihydroxyphenyloxy, 2,5,6-trihydroxyphenyloxy, 2,4,6-trihydroxyphenyloxy, 1-hydroxy-2-naphthyloxy, 2-hydroxy-1-naphthyloxy, 3-hydroxy-1-naphthyloxy, 3,8-dihydroxy-1-naphthyloxy, 2,3-dihydroxy-1-naphthyloxy, 4,8-dihydroxy-1-naphthyloxy, 5,6-dihydroxy-1-naphthyloxy, 2,3,6-trihydroxy-1-naphthyloxy, 2,3,4-trihydroxy-1-naphthyloxy, 3,4,5-trihydroxy-1-naphthyloxy, 4,5,6-trihydroxy-1-naphthyloxy and 2,4,8-trihydroxy-1-naphthyloxy groups; aryloxy groups substituted with a cyano group or groups such as the 2-cyanophenyloxy, 3-cyanophenyloxy, 4-cyanophenyloxy, 3,5-dicyanophenyloxy, 2,5-dicyanophenyloxy, 2,6-dicyanophenyloxy, 2,4-dicyanophenyloxy, 2,3,6-tricyanophenyloxy, 2,3,4-tricyanophenyloxy, 3,4,5-tricyanophenyloxy, 2,5,6-tricyanophenyloxy, 2,4,6-tricyanophenyloxy, 1-cyano-2-naphthyloxy, 2-cyano-1-naphthyloxy, 3-cyano-1-naphthyloxy, 3,8-dicyano-1-naphthyloxy, 2,3-dicyano-1-naphthyloxy, 4,8-dicyano-1-napthyloxy, 5,6-dicyano-1-naphthyloxy, 2,3,6-tricyano-1-naphthyloxy, 2,3,4-tricyano-1-naphthyloxy, 3,4,5-tricyano-1-naphthyloxy, 4,5,6-tricyano-1-naphthyloxy and 2,4,8-tricyano-1-naphthyloxy groups; aryloxy groups substituted with an aliphatic acyl group or groups, such as the 2-acetylphenyloxy, 3-acetylphenyloxy, 4-acetylphenyloxy, 3,5-diacetylphenyloxy, 2,5-diacetylphenyloxy, 2,6-diacetylphenyloxy, 2,4-diacetylphenyloxy, 2,3,6-tripropionylphenyloxy, 2,3,4-tripropionylphenyloxy, 3,4,5-tripropionylphenyloxy, 2,5,6-tributyrylphenyloxy, 2,4,6-tributyrylphenyloxy, 1-acetyl-2-naphthyloxy, 2-acetyl-1-naphthyloxy, 3-acetyl-1-naphthyloxy, 3,8-diacetyl-1-naphthyloxy, 2,3-dipropionyl-1-naphthyloxy, 4,8-dibutyryl-1-naphthyloxy, 5,6-dibutyryl-1-naphthyloxy, 2,3,6-triacetyl-1-naphthyloxy, 2,3,4-triacetyl-1-naphthyloxy, 3,4,5-tripropionyl-1-naphthyloxy, 4,5,6-tributyryl-1-naphthyloxy and 2,4,8-tributyryl-1-naphthyloxy groups; aryloxy groups substituted with a carboxyl group or groups, such as the 2-carboxyphenyloxy, 3-carboxyphenyloxy, 4-carboxyphenyloxy, 3,5-dicarboxyphenyloxy, 2,5-dicarboxyphenyloxy, 2,6-dicarboxyphenyloxy and 2,4-dicarboxyphenyloxy groups; aryloxy groups substituted with a carbamoyl group or groups, such as the 2-carbamoylphenyloxy, 3-carbamoylphenyloxy, 4-carbamoylphenyloxy, 3,5-dicarbamoylphenyloxy, 2,5-dicarbamoylphenyloxy, 2,6-dicarbamoylphenyloxy and 2,4-dicarbamoylphenyloxy groups; and aryloxy groups substituted with an alkylenedioxy group or groups, such as the 3,4-methylenedioxyphenyloxy group. The aryloxy group may also have any combination of two or more different substituents selected from the above list.

Of these aryloxy groups, the most preferred are the 4-fluorophenyloxy, 4-methylphenyloxy, 4-methoxyphenyloxy, 4-aminophenyloxy and 4-hydroxyphenyloxy groups.

Where $R^a$ or Substituent A represents an alkoxycarbonyl group, the alkoxy part preferably has from 1 to 6 carbon atoms and may be a straight or branched chain group. Examples of such groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, 2-methoxybutoxycarbonyl, neopentyloxycarbonyl, 1-ethoxypropoxycarbonyl, hexyloxycarbonyl, 4-methoxypentyloxycarbonyl, 3-methoxypentyloxycarbonyl, 2-methoxypentyloxycarbonyl, 1-methoxypentyloxycarbonyl, 3,3-dimethoxybutoxycarbonyl, 2,2-dimethoxybutoxycarbonyl, 1,1-dimethoxybutoxycarbonyl, 1,2-dimethoxybutoxycarbonyl, 1,3-dimethoxybutoxycarbonyl, 2,3-dimethoxybutoxycarbonyl and 2-ethoxybutoxycarbonyl groups, of which we prefer the straight and branched chain alkoxycarbonyl groups having from 1 to 4 carbon atoms, especially the methoxycarbonyl and ethoxycarbonyl groups.

Where $R^a$ or substituent A represents an alkoxy group, this may be a straight or branched chain group, for example a methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy groups, of which we prefer the straight and branched chain alkoxy groups having from 1 to 4 carbon atoms, especially the methoxy and ethoxy groups.

Where $R^a$ represents an aralkyloxy group, the aralkyl part may be as defined above in relation to $R^1$. Specific examples of such groups include the benzyloxy, α-naphthylmethyloxy, β-naphthylmethyloxy, 2-methylbenzyloxy, 3-methylbenzyloxy, 4-methylbenzyloxy, 2,4,6-trimethylbenzyloxy, 3,4,5-trimethylbenzyloxy, 2-methoxybenzyloxy, 3-methoxybenzyloxy, 4-methoxybenzyloxy, 3,4-dimethoxybenzyloxy, 2-nitrobenzyloxy, 4-nitrobenzyloxy, 2-chlorobenzyloxy, 3-chlorobenzyloxy, 4-chlorobenzyloxy, 4-bromobenzyloxy, 4-cyanobenzyloxy, α or β-naphthylmethyloxy, benzhydryloxy (i.e. diphenylmethoxy), trityloxy (i.e. triphenylmethoxy), phenethyloxy, 1-phenylethoxy, 1-(α or β-naphthyl)ethoxy, 2-(α or β-naphthyl)ethoxy, 1-phenylpropoxy, 2-phenylpropoxy, 3-phenylpropoxy, 1-(α or β-naphthyl)propoxy, 2-(α or β-naphthyl)propoxy, 3-(α or β-naphthyl) propoxy, 1-phenylbutoxy, 2-phenylbutoxy, 3-phenylbutoxy, 4-phenylbutoxy, 1-(α or β-naphthyl)butoxy, 2-(α or β-naphthyl)butoxy, 3-(α or β-naphthyl)butoxy, 4-(α or β-naphthyl)butoxy, 1-phenylpentyloxy, 2-phenylpentyloxy, 3-phenylpentyloxy, 4-phenylpentyloxy, 5-phenylpentyloxy, 1-(α or β-naphthyl)pentyloxy, 2-(α or β-naphthyl)pentyloxy, 3-(α or β-naphthyl)pentyloxy, 4-(α or β-naphthyl)pentyloxy, 5-(α or β-naphthyl)pentyloxy, 1-phenylhexyloxy, 2-phenylhexyloxy, 3-phenylhexyloxy, 4-phenylhexyloxy, 5-phenylhexyloxy, 6-phenylhexyloxy, 1-(α or β-naphthyl)hexyloxy, 2-(α or β-naphthyl)hexyloxy, 3-(α or β-naphthyl)hexyloxy, 4-(α or β-naphthyl)hexyloxy, 5-(α or β-naphthyl)hexyloxy and 6-(α or β-naphthyl) hexyloxy groups. Of these, we prefer the unsubstituted aralkyloxy groups and more prefer the unsubstituted benzyloxy and 2-phenethyloxy groups.

Where $R^b$ or substituent C represents an arylalkenyl group, the alkenyl part has from 2 to 4, preferably 3 or 4 and more preferably 3, carbon atoms, and the aryl part may be any of the aryl groups exemplified above. Suitable alkenyl groups include the vinyl, allyl, methallyl, isopropenyl, 1-butenyl, 2-butenyl and 3-butenyl groups. The most preferred arylalkenyl group is the cinnamyl (3-phenyl-2-propenyl) group.

Where $R^b$ or substituent A, B, C or D represents a heterocyclic group, this preferably has from 3 to 10 ring atoms, of which from 1 to 4 are hetero-atoms selected from the group consisting of nitrogen, oxygen and sulfur hetero-atoms. The group may be a monocyclic group or it may consist of two or more rings attached to each other by fusion or by a spiro attachment. In the case of those groups having 4 hetero-atoms in a ring, we prefer that 3 or 4 of them should be nitrogen atoms and 1 or 0 should be an oxygen or sulfur atom. In the case of those groups having 3 hetero-atoms in a ring, we prefer that 1, 2 or 3 should be nitrogen atoms and, correspondingly, 2, 1 or 0 should be oxygen and/or sulfur atoms. In the case of those groups having 1 or 2 hetero-atoms in a ring, the hetero-atoms may be freely chosen from nitrogen, oxygen and sulfur atoms. Preferably, however, the group contains at least one nitrogen atom. The group may be substituted or unsubstituted and, if substituted, the substituents are selected from the group consisting of substituents G, as defined and exemplified above.

The groups may also be saturated, unsaturated or partially saturated and, if fully unsaturated, may be aromatic in character. Examples of such non-aromatic groups include the azetidinyl, morpholinyl (especially morpholino), thiomorpholinyl, pyrrolidinyl, hydroxypyrrolidinyl, t-butoxypyrrolidinyl, chloropyrrolidinyl, pyrrolinyl, imidazolidinyl, imidazolinyl, pyrazolidinyl, pyrazolinyl, thiazolidinyl, 5,5-dimethylthiazolidinyl, oxazolidinyl, piperidyl and piperazinyl groups. Of these, we prefer the saturated heterocyclic groups having from 4 to 6 ring atoms and containing at least one nitrogen atom, and optionally an oxygen or sulfur atom or atoms. The most preferred groups are the pyrrolidinyl, hydroxypyrrolidinyl, chloropyrrolidinyl, thiazolidinyl, 5,5-dimethylthiazolidinyl and oxazolidinyl groups.

These heterocyclyl groups may optionally be condensed with one or more other cyclic groups such as, for example, the aryl groups and cycloalkyl groups defined and exemplified above. Examples of such groups include: the 1,2,3,4-tetrahydroisoquinolyl, decahydroisoquinolyl, 1,2,3,4-tetrahydroquinolyl, decahydroquinolyl, isoindolinyl and indolinyl groups.

In the case of those heterocyclic groups which are fully unsaturated and have aromatic character, these necessarily have at least 5 ring atoms and thus have from 5 to 10 ring atoms, more preferably from 5 to 7 ring atoms. The groups also preferably contain from 1 to 3 hetero-atoms selected from the group consisting of nitrogen, oxygen and sulfur atoms. Examples of such groups include: the furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl groups. Of these, we prefer those aromatic heterocyclic groups containing 5 or 6 ring atoms of which from 1 to 3 are sulfur, oxygen or/and nitrogen atoms or containing 4 ring nitrogen atoms. The most preferred aromatic heterocyclic groups are those containing 5 or 6 ring atoms of which at least one is a nitrogen atom, and which may optionally contain an oxygen or sulfur atom or atoms, or containing 4 ring nitrogen atoms. Examples of preferred groups include: the pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl groups. More preferred examples include: the imidazolyl, oxazolyl, isoxazolyl and thiazolyl groups.

These heterocyclic groups may optionally be condensed with one or more other cyclic groups, for example, the aryl groups defined and exemplified above. Examples of such heterocyclic groups include: the benzofuranyl, chromenyl, xanthenyl, phenoxathinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, carbazolyl, carbolinyl and acridinyl groups.

The heterocyclyloxy groups included in substituents A and B and the heterocyclyl-carbonyl groups and heterocyclyl-alkyl groups included in substituents F may have any of the above aromatic or non-aromatic heterocyclic groups as the heterocyclic part of the group.

Where substituent B represents a halogen atom, this may be, for example, the fluorine, chlorine, bromine or iodine atom, preferably the fluorine, chlorine or bromine atom, and most preferably the fluorine or chlorine atom.

It will be seen in the above definitions that a substituent group may be itself substituted by a further substituent, and that further substituent may itself be still further substituted and so on. Since the compounds of the present invention are oligopeptides, although this provision of substituents on substituents may continue along several generations, beyond a certain point, which will vary depending upon the substituents but which will be well recognized by those skilled in the art, this must stop. In general, we prefer that, where a substituent defined in one of substituents A through F may be further substituted, that further substituent may be still further substituted and the still further substituent may be finally substituted, but the final substituent may not be further substituted. However, this may vary from case to case, as will be clear to those skilled in the art.

The compounds of the present invention can form salts. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with triethylamine, diisopropylamine, cyclohexylamine or dicyclohexylamine; and salts with a basic amino acid, such as lysine or arginine. Also, since the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, perchloric acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Those compounds of the present invention containing a carboxy group can form esters. There is no particular restriction on the nature of the ester, provided that, where the compound is to be used for therapeutic purposes, the ester is pharmaceutically acceptable, that is it is not more toxic (or unacceptably more toxic) or less active (or unacceptably less active) than the corresponding free acid. Examples of suitable ester groups include:

alkyl groups having from 1 to 20 carbon atoms, more preferably from 1 to 6 carbon atoms, such as those exemplified above and higher alkyl groups as are well known in the art, such as the heptyl, octyl, nonyl, decyl, dodecyl, tridecyl, pentadecyl, octadecyl, nonadecyl and icosyl groups, but most preferably the methyl, ethyl and t-butyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents F defined and exemplified above, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred;

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents F defined and exemplified above, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenacyl groups, which may be unsubstituted or have at least one of substituents F defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, norcaryl, norpinanyl, norbornyl, menthenyl, camphenyl and norbornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy- 2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy) ethyl, 1-(cyclohexylacetoxy)propyl, 2-methyl-1-(cyclohexylacetoxy)propyl, (cyclopentylacetoxy) methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy) ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents F, defined and exemplified above] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxyalkyl groups, alkoxycarbonyloxyalkyl groups, cycloalkylcarbonyloxyalkyl groups, phthalidyl groups and (5-substituted 2-oxo-1,3-dioxolen-4-yl)methyl groups.

Preferred classes of compounds of the present invention are those compounds of formula (I) and salts and esters thereof, in which:

(1) $R^1$ represents a group of formula —$COR^a$, —$COR^b$, —$SO_2R^b$ or —$CONR^bR^b$, in which $R^a$ and $R^b$ are as defined above;

(2) more preferably, $R^1$ represents a group of formula —$COR^a$, —$COR^{b'}$, —$SO_2R^{b'}$ or —$CONR^bR^{b'}$, in which $R^a$ is as defined above and $R^{b'}$ represents an aryl group, an unsubstituted aromatic heterocyclic group or an aromatic heterocyclic group having at least one substituent selected from the group consisting of alkyl or alkoxy groups each having from 1 to 6 carbon atoms and hydroxy groups;

(3) most preferably; $R^1$ represents a group of formula —$COR^a$ or —$COR^{b'}$, where $R^a$ and $R^{b'}$ are as defined above;

(4) $R^2$ represents a hydrogen atom or an alkyl group having from 1 to 4 carbon atoms;

(5) more preferably, $R^2$ represents a hydrogen atom or a methyl group;

(6) $R^3$ represents a substituted alkyl group having from 1 to 6 carbon atoms and substituted by at least one substituent selected from the group consisting of substituents A', defined below, or $R^3$ represents any of the groups represented by $R^{b''}$;

$R^{b''}$ represents an unsubstituted alkyl group having from 1 to 6 carbon atoms or a substituted alkyl group having from 1 to 6 carbon atoms and substituted by at least one substituent selected from the group consisting of substituents B''', defined below;

said substituents A' are selected from the group consisting of cyano, carbamoyl, carboxy, alkylthio, alkylsulfonyl, aminosulfonyl and aminosulfinyl groups, where said alkylthio and alkylsulfonyl groups have from 1 to 6 carbon atoms;

said substituents B''' are selected from the group consisting of halogen atoms and hydroxy groups;

(7) more preferably, $R^3$ represents a substituted alkyl group having from 1 to 6 carbon atoms and substituted by at least one substituent selected from the group consisting of substituents A', defined above;

(8) $R^4$ represents a substituted alkyl group having from 1 to 6 carbon atoms and substituted by at least one substituent selected from the group consisting of substituents B, defined above;

(9) more preferably, $R^4$ represents a substituted alkyl group having from 1 to 6 carbon atoms and substituted by at least one substituent selected from the group consisting of substituents B', defined below;

said substituents B' are selected from the group consisting of cycloalkyl groups having from 3 to 7 ring carbon atoms, heterocyclic groups as defined above and aryl groups as defined above;

(10) most preferably, $R^4$ represents a substituted alkyl group having from 1 to 6 carbon atoms and substituted by at least one substituent selected from the group consisting of substituents B", defined below;

said substituents B" are selected from the group consisting of aromatic heterocyclic groups as defined above and aryl groups as defined above;

(11) $R^5$ represents a group of formula $R^{b''}$O—, a group of formula $R^{b''}R^{b''}$N— or a group of formula $R^{b''}$HN—, where:

$R^{b''}$ is as defined in (6) above;

(12) more preferably, $R^5$ represents a t-butylamino group, a 1,1-dimethyl-2-hydroxyethylamino group, a 1,1-dimethyl-2-hydroxypropylamino group, a butylamino group, a 3-hydroxypropylamino group, a 2-hydroxyethylamino group or a t-butyloxy group;

(13) A represents a group of formula

—$(CH_2)_m$—B—$(CH_2)_n$—, wherein:

B represents a single bond, a carbonyl group, an oxygen atom, a sulfur atom, a group of formula —NH—, a group of formula —($CH_2$=$CH_2$)— or a group of formula —NHCO—; and $\underline{m}$ and $\underline{n}$ are each selected from the group consisting of 0 and integers from 1 to 3, provided that ($\underline{m}$+$\underline{n}$) is 1 to 3, or a group of formula —$(CH_2)_m$—B—$(CH_2)_n$— which is substituted by at least one substituent selected from the group consisting of the groups defined for $R^a$, the groups defined for $R^b$ and substituents B;

(14) more preferably A represents a group of formula

—$(CH_2)_m$—B—$(CH_2)_n$—, wherein:

B represents a single bond, a carbonyl group or a group of formula —($CH_2$=$CH_2$); and $\underline{m}$ and $\underline{n}$ are each selected from the group consisting of 0 and integers from 1 to 3, provided that ($\underline{m}$+$\underline{n}$) is 1 to 3, or a group of formula —$(CH_2)_m$—B—$(CH_2)_n$— which is substituted by at least one substituent selected from halogen atoms, hydroxy groups and alkoxy groups.

Also preferred are salts and esters of the above compounds and pro-drugs for these compounds.

Specific examples of the compounds of the present invention are those compounds of formula (I-1) and (I-2), in which the substituents are as defined in the respective one of Tables 1 and 2, below, i.e. Table 1 relates to formula (I-1) and Table 2 relates to formula (I-2). In the Tables, the following abbreviations are used:

| | |
|---|---|
| Ac | acetyl |
| Azep | azepinyl |
| Azet | azetidinyl |
| Azir | aziridinyl |
| tBoc | t-butoxycarbonyl |
| Boz | benzoyl |
| Bu | butyl |
| iBu | isobutyl |
| tBu | t-butyl |
| Byr | butyryl |
| Bfur | benzofuranyl |
| Bz | benzyl |
| Bzc | benzyloxycarbonyl |
| Bza | benzyloxycarbonylamino |
| Bzhy | benzhydryl |
| Bzim | benzimidazolyl |
| Bzisox | benzisoxazolyl |
| Bzoxaz | benzoxazolyl |
| Bzthiaz | benzthiazolyl |
| Car | carbamoyl |
| Deh | dehydro |
| Dhiq | decahydroisoquinolyl |
| Diaz | diaza |
| Et | ethyl |
| Glu | glutamyl |
| Gly | glycyl |
| cHx | cyclohexyl |
| Hia | hydroxyamino |
| Imin | imino |
| Imid | imidazolyl |
| Ind | indolyl |
| Inda | indazolyl |
| Indi | indolinyl |
| Me | methyl |
| Mes | methanesulfonyl |
| Mec | methoxycarbonyl |
| Mor | morpholino |
| MPh | p-methoxyphenyl |
| MPhO | p-methoxyphenoxy |
| Np | naphthyl |
| Npo | naphthoxy |
| Oxaz | oxyaza |
| Ph | phenyl |
| Pho | phenoxy |
| Pip | piperidyl |
| Pipr | piperadinyl |
| Pro | prolyl |
| Pr | propyl |
| iPr | isopropyl |
| iPn | isopentyl |
| Prc | propoxycarbonyl |
| Pyr | pyridyl |
| Pyrd | pyrrolidinyl |
| Pyz | pyrazinyl |
| Quix | quinoxalinyl |
| Quin | quinolinyl |
| Sam | sulfamoyl |
| Sar | sarcosyl |
| Sfo | sulfo |
| Sim | sulfimoyl |
| Thi | thienyl |
| Thiz | thiazolyl |
| Thz | thiazolidinyl |
| Thf | tetrahydrofuryl | and ThiaPro represents a group of formula:

$$\begin{array}{c} -N \diagdown CH_2 \\ \phantom{-N} \diagdown S \\ H_2C \diagdown \phantom{S} \diagup \\ \phantom{H_2C} \diagdown CH_2 \\ CO- \end{array}$$

$$R^1N(H)-CH(R^3)-CO-N(H)-CH(R^4)-CH(OH)-CO-Z-R^5 \quad (I-1)$$

$$R^1N(CH_3)-CH(R^3)-CO-N(H)-CH(R^4)-CH(OH)-CO-Z-R^5 \quad (I-2)$$

$$Z = \text{(N-containing ring with A and C=O)} \quad (A)$$

TABLE 1

| Cpd. No. | R¹ | R³ | R⁴ | Z | R⁵ |
|---|---|---|---|---|---|
| 1 | Bzc | CarCH₂ | Bz | 2-Azir-CO- | tBuNH- |
| 2 | Bzc | CarCH₂ | Bz | 2-Azet-CO- | tBuNH- |
| 3 | Bzc | CarCH₂ | Bz | 4-Oxo-2-Azet-CO- | tBuNH- |
| 4 | Bzc | CarCH₂ | Bz | 3-Oxo-2-Azet-CO- | tBuNH- |
| 5 | Bzc | CarCH₂ | Bz | 3-HO-2-Azet-CO- | tBuNH- |
| 6 | Bzc | CarCH₂ | Bz | 3-Cl-2-Azet-CO- | tBuNH- |
| 7 | Bzc | CarCH₂ | Bz | 3-I-2-Azet-CO- | tBuNH- |
| 8 | Bzc | CarCH₂ | Bz | 3-F-2-Azet-CO- | tBuNH- |
| 9 | Bzc | CarCH₂ | Bz | 3,3-diF-2-Azet-CO- | tBuNH- |
| 10 | Bzc | CarCH₂ | Bz | 3-MeOImin-2-Azet-CO- | tBuNH- |
| 11 | Bzc | CarCH₂ | Bz | 3-Mec-2-Azet-CO- | tBuNH- |
| 12 | Bzc | CarCH₂ | Bz | 3-CN-2-Azet-CO- | tBuNH- |
| 13 | Bzc | CarCH₂ | Bz | 3-Me₂N-2-Azet-CO- | tBuNH- |
| 14 | 2-Quix-CO- | CarCH₂ | Bz | 2-Azir-CO- | tBuNH- |
| 15 | 2-Quix-CO- | CarCH₂ | Bz | 2-Azet-CO- | tBuNH- |
| 16 | 2-Quix-CO- | CarCH₂ | Bz | 4-Oxo-2-Azet-CO- | tBuNH- |
| 17 | 2-Quix-CO- | CarCH₂ | Bz | 3-Oxo-2-Azet-CO- | tBuNH- |
| 18 | 2-Quix-CO- | CarCH₂ | Bz | 3-HO-2-Azet-CO- | tBuNH- |
| 19 | 2-Quix-CO- | CarCH₂ | Bz | 3-Cl-2-Azet-CO- | tBuNH- |
| 20 | 2-Quix-CO- | CarCH₂ | Bz | 3-I-2-Azet-CO- | tBuNH- |
| 21 | 2-Quix-CO- | CarCH₂ | Bz | 3-Br-2-Azet-CO- | tBuNH- |
| 22 | 2-Quix-CO- | CarCH₂ | Bz | 3-F-2-Azet-CO- | tBuNH- |

TABLE 1-continued

| Cpd. No. | R¹ | R³ | R⁴ | Z | R⁵ |
|---|---|---|---|---|---|
| 23 | 2-Quix-CO- | CarCH₂ | Bz | 3,3-diF-2-Azet-CO- | tBuNH- |
| 24 | 2-Quix-CO- | CarCH₂ | Bz | 3-MeOImin-2-Azet-CO- | tBuNH- |
| 25 | 2-Quix-CO- | CarCH₂ | Bz | 3-Mec-2-Azet-CO- | tBuNH- |
| 26 | 2-Quix-CO- | CarCH₂ | Bz | 3-CN-2-Azet-CO- | tBuNH- |
| 27 | 2-Quix-CO- | CarCH₂ | Bz | 2-Me₂N-2-Azet-CO- | tBuNH- |
| 28 | 2-Quin-CO- | CarCH₂ | Bz | 2-Azir-CO- | tBuNH- |
| 29 | 2-Quin-CO- | CarCH₂ | Bz | 2-Azet-CO- | tBuNH- |
| 30 | 2-Quin-CO- | CarCH₂ | Bz | 4-Oxo-2-Azet-CO- | tBuNH- |
| 31 | 2-Quin-CO- | CarCH₂ | Bz | 3-Oxo-2-Azet-CO- | tBuNH- |
| 32 | 2-Quin-CO- | CarCH₂ | Bz | 3-HO-2-Azet-CO- | tBuNH- |
| 33 | 2-Quin-CO- | CarCH₂ | Bz | 3-Cl-2-Azet-CO- | tBuNH- |
| 34 | 2-Quin-CO- | CarCH₂ | Bz | 3-I-2-Azet-CO- | tBuNH- |
| 35 | 2-Quin-CO- | CarCH₂ | Bz | 3-F-2-Azet-CO- | tBuNH- |
| 36 | 2-Quin-CO- | CarCH₂ | Bz | 3,3-diF-2-Azet-CO- | tBuNH- |
| 37 | 2-Quin-CO- | CarCH₂ | Bz | 3-MeOImin-2-Azet-CO- | tBuNH- |
| 38 | 2-Quin-CO- | CarCH₂ | Bz | 3-Mec-2-Azet-CO- | tBuNH- |
| 39 | 2-Quin-CO- | CarCH₂ | Bz | 3-CN-2-Azet-CO- | tBuNH- |
| 40 | 2-Quin-CO- | CarCH₂ | Bz | 2-Me₂N-2-Azet-CO- | tBuNH- |
| 41 | 3-Quin-CO- | CarCH₂ | Bz | 2-Azir-CO- | tBuNH- |
| 42 | 3-Quin-CO- | CarCH₂ | Bz | 2-Azet-CO- | tBuNH- |
| 43 | 3-Quin-CO- | CarCH₂ | Bz | 4-Oxo-2-Azet-CO- | tBuNH- |
| 44 | 3-Quin-CO- | CarCH₂ | Bz | 3-Oxo-2-Azet-CO- | tBuNH- |
| 45 | 3-Quin-CO- | CarCH₂ | Bz | 3-HO-2-Azet-CO- | tBuNH- |
| 46 | 3-Quin-CO- | CarCH₂ | Bz | 3-Cl-2-Azet-CO- | tBuNH- |
| 47 | 3-Quin-CO- | CarCH₂ | Bz | 3-Br-2-Azet-CO- | tBuNH- |
| 48 | 3-Quin-CO- | CarCH₂ | Bz | 3-I-2-Azet-CO- | tBuNH- |
| 49 | 3-Quin-CO- | CarCH₂ | Bz | 3-F-2-Azet-CO- | tBuNH- |
| 50 | 3-Quin-CO- | CarCH₂ | Bz | 3,3-diF-2-Azet-CO- | tBuNH- |
| 51 | 3-Quin-CO- | CarCH₂ | Bz | 3-MeOImin-2-Azet-CO- | tBuNH- |
| 52 | 3-Quin-CO- | CarCH₂ | Bz | 3-Mec-2-Azet-CO- | tBuNH- |
| 53 | 3-Quin-CO- | CarCH₂ | Bz | 3-CN-2-Azet-CO- | tBuNH- |
| 54 | 3-Quin-CO- | CarCH₂ | Bz | 2-Me₂N-2-Azet-CO- | tBuNH- |
| 55 | 2-Bfur-CO- | CarCH₂ | Bz | 2-Azir-CO- | tBuNH- |
| 56 | 2-Bfur-CO- | CarCH₂ | Bz | 2-Azet-CO- | tBuNH- |
| 57 | 2-Bfur-CO- | CarCH₂ | Bz | 4-Oxo-2-Azet-CO- | tBuNH- |
| 58 | 2-Bfur-CO- | CarCH₂ | Bz | 3-Oxo-2-Azet-CO- | tBuNH- |
| 59 | 2-Bfur-CO- | CarCH₂ | Bz | 3-HO-2-Azet-CO- | tBuNH- |
| 60 | 2-Bfur-CO- | CarCH₂ | Bz | 3-Cl-2-Azet-CO- | rBuNH- |
| 61 | 2-Bfur-CO- | CarCH₂ | Bz | 3-Br-2-Azet-CO- | tBuNH- |
| 62 | 2-Bfur-CO- | CarCH₂ | Bz | 3-I-2-Azet-CO- | tBuNH- |
| 63 | 2-Bfur-CO- | CarCH₂ | Bz | 3-F-2-Azet-CO- | tBuNH- |
| 64 | 2-Bfur-CO- | CarCH₂ | Bz | 3,3-diF-2-Azet-CO- | tBuNH- |
| 65 | 2-Bfur-CO- | CarCH₂ | Bz | 3-MeOImin-2-Azet-CO- | tBuNH- |
| 66 | 2-Bfur-CO- | CarCH₂ | Bz | 3-Mec-2-Azet-CO- | tBuNH- |
| 67 | 2-Bfur-CO- | CarCH₂ | Bz | 3-CN-2-Azet-CO- | tBuNH- |
| 68 | 2-Bfur-CO- | CarCH₂ | Bz | 2-Me₂N-2-Azet-CO- | tBuNH- |
| 69 | 3-Bfur-CO- | CarCH₂ | Bz | 2-Azir-CO- | tBuNH- |
| 70 | 3-Bfur-CO- | CarCH₂ | Bz | 2-Azet-CO- | tBuNH- |
| 71 | 3-Bfur-CO- | CarCH₂ | Bz | 4-Oxo-2-Azet-CO- | tBuNH- |
| 72 | 3-Bfur-CO- | CarCH₂ | Bz | 3-Oxo-2-Azet-CO- | tBuNH- |
| 73 | 3-Bfur-CO- | CarCH₂ | Bz | 3-HO-2-Azet-CO- | tBuNH- |
| 74 | 3-Bfur-CO- | CarCH₂ | Bz | 3-Cl-2-Azet-CO- | tBuNH- |
| 75 | 3-Bfur-CO- | CarCH₂ | Bz | 3-Br-2-Azet-CO- | tBuNH- |
| 76 | 3-Bfur-CO- | CarCH₂ | Bz | 3-I-2-Azet-CO- | tBuNH- |
| 77 | 3-Bfur-CO- | CarCH₂ | Bz | 3-F-2-Azet-CO- | tBuNH- |
| 78 | 3-Bfur-CO- | CarCH₂ | Bz | 3,3-diF-2-Azet-CO- | tBuNH- |
| 79 | 3-Bfur-CO- | CarCH₂ | Bz | 3-MeOImin-2-Azet-CO- | tBuNH- |
| 80 | 3-Bfur-CO- | CarCH₂ | Bz | 3-Mec-2-Azet-CO- | tBuNH- |
| 81 | 3-Bfur-CO- | CarCH₂ | Bz | 3-CN-2-Azet-CO- | tBuNH- |
| 82 | 3-Bfur-CO- | CarCH₂ | Bz | 3-Me₂N-2-Azet-CO- | tBuNH- |
| 83 | 2-Ind-CO- | CarCH₂ | Bz | 2-Azir-CO- | tBuNH- |
| 84 | 2-Ind-CO- | CarCH₂ | Bz | 2-Azet-CO- | tBuNH- |
| 85 | 2-Ind-CO- | CarCH₂ | Bz | 4-Oxo-2-Azet-CO- | tBuNH- |
| 86 | 2-Ind-CO- | CarCH₂ | Bz | 3-Oxo-2-Azet-CO- | tBuNH- |
| 87 | 2-Ind-CO- | CarCH₂ | Bz | 3-HO-2-Azet-CO- | tBuNH- |
| 88 | 2-Ind-CO- | CarCH₂ | Bz | 3-Cl-2-Azet-CO- | tBuNH- |
| 89 | 2-Ind-CO- | CarCH₂ | Bz | 3-Br-2-Azet-CO- | tBuNH- |
| 90 | 2-Ind-CO- | CarCH₂ | Bz | 3-I-2-Azet-CO- | tBuNH- |
| 91 | 2-Ind-CO- | CarCH₂ | Bz | 3-F-2-Azet-CO- | tBuNH- |
| 92 | 2-Ind-CO- | CarCH₂ | Bz | 3,3-diF-2-Azet-CO- | tBuNH- |
| 93 | 2-Ind-CO- | CarCH₂ | Bz | 3-MeOImin-2-Azet-CO- | tBuNH- |
| 94 | 2-Ind-CO- | CarCH₂ | Bz | 3-Mec-2-Azet-CO- | tBuNH- |
| 95 | 2-Ind-CO- | CarCH₂ | Bz | 3-CN-2-Azet-CO- | tBuNH- |
| 96 | 2-Ind-CO- | CarCH₂ | Bz | 3-Me₂N-2-Azet-CO- | tBuNH- |
| 97 | 3-Ind-CO- | CarCH₂ | Bz | 2-Azir-CO- | tBuNH- |
| 98 | 3-Ind-CO- | CarCH₂ | Bz | 2-Azet-CO- | tBuNH- |

TABLE 1-continued

| Cpd. No. | R¹ | R³ | R⁴ | Z | R⁵ |
|---|---|---|---|---|---|
| 99 | 3-Ind-CO- | CarCH₂ | Bz | 4-Oxo-2-Azet-CO- | tBuNH- |
| 100 | 3-Ind-CO- | CarCH₂ | Bz | 3-Oxo-2-Azet-CO- | tBuNH- |
| 101 | 3-Ind-CO- | CarCH₂ | Bz | 3-HO-2-Azet-CO- | tBuNH- |
| 102 | 3-Ind-CO- | CarCH₂ | Bz | 3-Cl-2-Azet-CO- | tBuNH- |
| 103 | 3-Ind-CO- | CarCH₂ | Bz | 3-Br-2-Azet-CO- | tBuNH- |
| 104 | 3-Ind-CO- | CarCH₂ | Bz | 3-I-2-Azet-CO- | tBuNH- |
| 105 | 3-Ind-CO- | CarCH₂ | Bz | 3-F-2-Azet-CO- | tBuNH- |
| 106 | 3-Ind-CO- | CarCH₂ | Bz | 3,3-diF-2-Azet-CO- | tBuNH- |
| 107 | 3-Ind-CO- | CarCH₂ | Bz | 3-MeOImin-2-Azet-CO- | tBuNH- |
| 108 | 3-Ind-CO- | CarCH₂ | Bz | 3-Mec-2-Azet-CO- | tBuNH- |
| 109 | 3-Ind-CO- | CarCH₂ | Bz | 3-CN-2-Azet-CO- | tBuNH- |
| 110 | 3-Ind-CO- | CarCH₂ | Bz | 3-Me₂N-2-Azet-CO- | tBuNH- |
| 111 | tBoc | CarCH₂ | Bz | 2-Azir-CO- | tBuNH- |
| 112 | tBoc | CarCH₂ | Bz | 2-Azet-CO- | tBuNH- |
| 113 | tBoc | CarCH₂ | Bz | 4-Oxo-2-Azet-CO- | tBuNH- |
| 114 | tBoc | CarCH₂ | Bz | 3-Oxo-2-Azet-CO- | tBuNH- |
| 115 | tBoc | CarCH₂ | Bz | 3-HO-2-Azet-CO- | tBuNH- |
| 116 | tBoc | CarCH₂ | Bz | 3-Cl-2-Azet-CO- | tBuNH- |
| 117 | tBoc | CarCH₂ | Bz | 3-Br-2-Azet-CO- | tBuNH- |
| 118 | tBoc | CarCH₂ | Bz | 3-I-2-Azet-CO- | tBuNH- |
| 119 | tBoc | CarCH₂ | Bz | 3-F-2-Azet-CO- | tBuNH- |
| 120 | tBoc | CarCH₂ | Bz | 3,3-diF-2-Azet-CO- | tBuNH- |
| 121 | tBoc | CarCH₂ | Bz | 3-MeOImin-2-Azet-CO- | tBuNH- |
| 122 | tBoc | CarCH₂ | Bz | 3-Mec-2-Azet-CO- | tBuNH- |
| 123 | tBoc | CarCH₂ | Bz | 3-CN-2-Azet-CO- | tBuNH- |
| 124 | tBoc | CarCH₂ | Bz | 3-Me₂N-2-Azet-CO- | tBuNH- |
| 125 | PhoAc- | CarCH₂ | Bz | 2-Azir-CO- | tBuNH- |
| 126 | PhoAc- | CarCH₂ | Bz | 2-Azet-CO- | tBuNH- |
| 127 | PhoAc- | CarCH₂ | Bz | 4-Oxo-2-Azet-CO- | tBuNH- |
| 128 | PhoAc- | CarCH₂ | Bz | 3-Oxo-2-Azet-CO- | tBuNH- |
| 129 | PhoAc- | CarCH₂ | Bz | 3-HO-2-Azet-CO- | tBuNH- |
| 130 | PhoAc- | CarCH₂ | Bz | 3-Cl-2-Azet-CO- | tBuNH- |
| 131 | PhoAc- | CarCH₂ | Bz | 3-Br-2-Azet-CO- | tBuNH- |
| 132 | PhoAc- | CarCH₂ | Bz | 3-I-2-Azet-CO- | tBuNH- |
| 133 | PhoAc- | CarCH₂ | Bz | 3-F-2-Azet-CO- | tBuNH- |
| 134 | PhoAc- | CarCH₂ | Bz | 3,3-diF-2-Azet-CO- | tBuNH- |
| 135 | PhoAc- | CarCH₂ | Bz | 3-MeOImin-2-Azet-CO- | tBuNH- |
| 136 | PhoAc- | CarCH₂ | Bz | 3-Mec-2-Azet-CO- | tBuNH- |
| 137 | PhoAc- | CarCH₂ | Bz | 3-CN-2-Azet-CO- | tBuNH- |
| 138 | PhoAc- | CarCH₂ | Bz | 3-Me₂N-2-Azet-CO- | tBuNH- |
| 139 | MPhoAc- | CarCH₂ | Bz | 2-Azir-CO- | tBuNH- |
| 140 | MPhoAc- | CarCH₂ | Bz | 2-Azet-CO- | tBuNH- |
| 141 | MPhoAc- | CarCH₂ | Bz | 4-Oxo-2-Azet-CO- | tBuNH- |
| 142 | MPhoAc- | CarCH₂ | Bz | 3-Oxo-2-Azet-CO- | tBuNH- |
| 143 | MPhoAc- | CarCH₂ | Bz | 3-HO-2-Azet-CO- | tBuNH- |
| 144 | MPhoAc- | CarCH₂ | Bz | 3-Cl-2-Azet-CO- | tBuNH- |
| 145 | MPhoAc- | CarCH₂ | Bz | 3-Br-2-Azet-CO- | tBuNH- |
| 146 | MPhoAc- | CarCH₂ | Bz | 3-I-2-Azet-CO- | tBuNH- |
| 147 | MPhoAc- | CarCH₂ | Bz | 3-F-2-Azet-CO- | tBuNH- |
| 148 | 3-Bzisox-CO- | CarCH₂ | Bz | 2-Azir-CO- | tBuNH- |
| 149 | 3-Bzisox-CO- | CarCH₂ | Bz | 2-Azet-CO- | tBuNH- |
| 150 | 3-Bzisox-CO- | CarCH₂ | Bz | 4-Oxo-2-Azet-CO- | tBuNH- |
| 151 | 3-Bzisox-CO- | CarCH₂ | Bz | 3-Oxo-2-Azet-CO- | tBuNH- |
| 152 | 3-Bzisox-CO- | CarCH₂ | Bz | 3-HO-2-Azet-CO- | tBuNH- |
| 153 | 3-Bzisox-CO- | CarCH₂ | Bz | 3-Cl-2-Azet-CO- | tBuNH- |
| 154 | 3-Bzisox-CO- | CarCH₂ | Bz | 3-Br-2-Azet-CO- | tBuNH- |
| 155 | 3-Bzisox-CO- | CarCH₂ | Bz | 3-I-2-Azet-CO- | tBuNH- |
| 156 | 3-Bzisox-CO- | CarCH₂ | Bz | 3-F-2-Azet-CO- | tBuNH- |
| 157 | 3-Bzisox-CO- | CarCH₂ | Bz | 3,3-diF-2-Azet-CO- | tBuNH- |
| 158 | 3-Bzisox-CO- | CarCH₂ | Bz | 3-MeOImin-2-Azet-CO- | tBuNH- |
| 159 | 3-Bzisox-CO- | CarCH₂ | Bz | 3-Mec-2-Azet-CO- | tBuNH- |
| 160 | 3-Bzisox-CO- | CarCH₂ | Bz | 3-CN-2-Azet-CO- | tBuNH- |
| 161 | 3-Bzisox-CO- | CarCH₂ | Bz | 3-Me₂N-2-Azet-CO- | tBuNH- |
| 162 | 5-Gly-O-2-Ind-CO- | CarCH₂ | Bz | 2-Azir-CO- | tBuNH- |
| 163 | 5-Gly-O-2-Ind-CO- | CarCH₂ | Bz | 2-Azet-CO- | tBuNH- |
| 164 | 5-Gly-O-2-Ind-CO- | CarCH₂ | Bz | 4-Oxo-2-Azet-CO- | tBuNH- |
| 165 | 5-Gly-O-2-Ind-CO- | CarCH₂ | Bz | 3-Oxo-2-Azet-CO- | tBuNH- |
| 166 | 5-Gly-O-2-Ind-CO- | CarCH₂ | Bz | 3-HO-2-Azet-CO- | tBuNH- |
| 167 | 5-Gly-O-2-Ind-CO- | CarCH₂ | Bz | 3-Cl-2-Azet-CO- | tBuNH- |
| 168 | 5-Gly-O-2-Ind-CO- | CarCH₂ | Bz | 3-Br-2-Azet-CO- | tBuNH- |
| 169 | 5-Gly-O-2-Ind-CO- | CarCH₂ | Bz | 3-I-2-Azet-CO- | tBuNH- |
| 170 | 5-Gly-O-2-Ind-CO- | CarCH₂ | Bz | 3-F-2-Azet-CO- | tBuNH- |
| 171 | 5-Gly-O-2-Ind-CO- | CarCH₂ | Bz | 3,3-diF-2-Azet-CO- | tBuNH- |
| 172 | 5-Gly-O-2-Ind-CO- | CarCH₂ | Bz | 3-MeOImin-2-Azet-CO- | tBuNH- |
| 173 | 5-Gly-O-2-Ind-CO- | CarCH₂ | Bz | 3-Mec-2-Azet-CO- | tBuNH- |
| 174 | 5-Gly-O-2-Ind-CO- | CarCH₂ | Bz | 3-CN-2-Azet-CO- | tBuNH- |

TABLE 1-continued

| Cpd. No. | R¹ | R³ | R⁴ | Z | R⁵ |
|---|---|---|---|---|---|
| 175 | 5-Gly-O-2-Ind-CO- | CarCH₂ | Bz | 3-Me₂N-2-Azet-CO- | tBuNH- |
| 176 | 4-NH₂-PhoAc- | CarCH₂ | Bz | 2-Azir-CO- | tBuNH- |
| 177 | 4-NH₂-PhoAc- | CarCH₂ | Bz | 2-Azet-CO- | tBuNH- |
| 178 | 4-NH₂-PhoAc- | CarCH₂ | Bz | 4-Oxo-2-Azet-CO- | tBuNH- |
| 179 | 4-NH₂-PhoAc- | CarCH₂ | Bz | 3-Oxo-2-Azet-CO- | tBuNH- |
| 180 | 4-NH₂-PhoAc- | CarCH₂ | Bz | 3-HO-2-Azet-CO- | tBuNH- |
| 181 | 4-NH₂-PhoAc- | CarCH₂ | Bz | 3-Cl-2-Azet-CO- | tBuNH- |
| 182 | 4-NH₂-PhoAc- | CarCH₂ | Bz | 3-Br-2-Azet-CO- | tBuNH- |
| 183 | 4-NH₂-PhoAc- | CarCH₂ | Bz | 3-I-2-Azet-CO- | tBuNH- |
| 184 | 4-NH₂-PhoAc- | CarCH₂ | Bz | 3-F-2-Azet-CO- | tBuNH- |
| 185 | 4-NH₂-PhoAc- | CarCH₂ | Bz | 3,3-diF-2-Azet-CO- | tBuNH- |
| 186 | 4-NH₂-PhoAc- | CarCH₂ | Bz | 3-MeOImin-2-Azet-CO- | tBuNH- |
| 187 | 4-NH₂-PhoAc- | CarCH₂ | Bz | 3-Mec-2-Azet-CO- | tBuNH- |
| 188 | 4-NH₂-PhoAc- | CarCH₂ | Bz | 3-CN-2-Azet-CO- | tBuNH- |
| 189 | 4-NH₂-PhoAc- | CarCH₂ | Bz | 3-Me₂N-2-Azet-CO- | tBuNH- |
| 190 | 4-NH₂-Bzc | CarCH₂ | Bz | 2-Azir-CO- | tBuNH- |
| 191 | 4-NH₂-Bzc | CarCH₂ | Bz | 2-Azet-CO- | tBuNH- |
| 192 | 4-NH₂-Bzc | CarCH₂ | Bz | 4-Oxo-2-Azet-CO- | tBuNH- |
| 193 | 4-NH₂-Bzc | CarCH₂ | Bz | 3-Oxo-2-Azet-CO- | tBuNH- |
| 194 | 4-NH₂-Bzc | CarCH₂ | Bz | 3-HO-2-Azet-CO- | tBuNH- |
| 195 | 4-NH₂-Bzc | CarCH₂ | Bz | 3-Cl-2-Azet-CO- | tBuNH- |
| 196 | 4-NH₂-Bzc | CarCH₂ | Bz | 3-Br-2-Azet-CO- | tBuNH- |
| 197 | 4-NH₂-Bzc | CarCH₂ | Bz | 3-I-2-Azet-CO- | tBuNH- |
| 198 | 4-NH₂-Bzc | CarCH₂ | Bz | 3-F-2-Azet-CO- | tBuNH- |
| 199 | 4-NH₂-Bzc | CarCH₂ | Bz | 3-diF-2-Azet-CO- | tBuNH- |
| 200 | 4-NH₂-Bzc | CarCH₂ | Bz | 3-MeOImin-2-Azet-CO- | tBuNH- |
| 201 | 4-NH₂-Bzc | CarCH₂ | Bz | 3-Mec-2-Azet-CO- | tBuNH- |
| 202 | 4-NH₂-Bzc | CarCH₂ | Bz | 3-CN-2-Azet-CO- | tBuNH- |
| 203 | 4-NH₂-Bzc | CarCH₂ | Bz | 3-Me₂N-2-Azet-CO- | tBuNH- |
| 204 | 4-Me₂N-PhoAc- | CarCH₂ | Bz | 2-Azir-CO- | tBuNH- |
| 205 | 4-Me₂N-PhoAc- | CarCH₂ | Bz | 2-Azet-CO- | tBuNH- |
| 206 | 4-Me₂N-PhoAc- | CarCH₂ | Bz | 4-Oxo-2-Azet-CO- | tBuNH- |
| 207 | 4-Me₂N-PhoAc- | CarCH₂ | Bz | 3-Oxo-2-Azet-CO- | tBuNH- |
| 208 | 4-Me₂N-PhoAc- | CarCH₂ | Bz | 3-HO-2-Azet-CO- | tBuNH- |
| 209 | 4-Me₂N-PhoAc- | CarCH₂ | Bz | 3-Cl-2-Azet-CO- | tBuNH- |
| 210 | 4-Me₂N-PhoAc- | CarCH₂ | Bz | 3-Br-2-Azet-CO- | tBuNH- |
| 211 | 4-Me₂N-PhoAc- | CarCH₂ | Bz | 3-I-2-Azet-CO- | tBuNH- |
| 212 | 4-Me₂N-PhoAc- | CarCH₂ | Bz | 3-F-2-Azet-CO- | tBuNH- |
| 213 | 4-Me₂N-PhoAc- | CarCH₂ | Bz | 3-diF-2-Azet-CO- | tBuNH- |
| 214 | 4-Me₂N-PhoAc- | CarCH₂ | Bz | 3-MeOImin-2-Azet-CO- | tBuNH- |
| 215 | 4-Me₂N-PhoAc- | CarCH₂ | Bz | 3-Mec-2-Azet-CO- | tBuNH- |
| 216 | 4-Me₂N-PhoAc- | CarCH₂ | Bz | 3-CN-2-Azet-CO- | tBuNH- |
| 217 | 4-Me₂N-PhoAc- | CarCH₂ | Bz | 3-Me₂N-2-Azet-CO- | tBuNH- |
| 218 | 4-MeNH-PhoAc- | CarCH₂ | Bz | 2-Azir-CO- | tBuNH- |
| 219 | 4-MeNH-PhoAc- | CarCH₂ | Bz | 2-Azet-CO- | tBuNH- |
| 220 | 4-MeNH-PhoAc- | CarCH₂ | Bz | 4-Oxo-2-Azet-CO- | tBuNH- |
| 221 | 4-MeNH-PhoAc- | CarCH₂ | Bz | 3-Oxo-2-Azet-CO- | tBuNH- |
| 222 | 4-MeNH-PhoAc- | CarCH₂ | Bz | 3-HO-2-Azet-CO- | tBuNH- |
| 223 | 4-MeNH-PhoAc- | CarCH₂ | Bz | 3-Cl-2-Azet-CO- | tBuNH- |
| 224 | 4-MeNH-PhoAc- | CarCH₂ | Bz | 3-Br-2-Azet-CO- | tBuNH- |
| 225 | 4-MeNH-PhoAc- | CarCH₂ | Bz | 3-I-2-Azet-CO- | tBuNH- |
| 226 | 4-MeNH-PhoAc- | CarCH₂ | Bz | 3-F-2-Azet-CO- | tBuNH- |
| 227 | 4-MeNH-PhoAc- | CarCH₂ | Bz | 3,3-diF-2-Azet-CO- | tBuNH- |
| 228 | 4-MeNH-PhoAc- | CarCH₂ | Bz | 3-MeOImin-2-Azet-CO- | tBuNH- |
| 229 | 4-MeNH-PhoAc- | CarCH₂ | Bz | 3-Mec-2-Azet-CO- | tBuNH- |
| 230 | 4-MeNH-PhoAc- | CarCH₂ | Bz | 3-CN-2-Azet-CO- | tBuNH- |
| 231 | 4-MeNH-PhoAc- | CarCH₂ | Bz | 3-Me₂N-2-Azet-CO- | tBuNH- |
| 232 | 4-Bza-PhoAc- | CarCH₂ | Bz | 2-Az 4r-CO- | tBuNH- |
| 233 | 4-Bza-PhoAc- | CarCH₂ | Bz | 2-Azet-CO- | tBuNH- |
| 234 | 4-Bza-PhoAc- | CarCH₂ | Bz | 4-Oxo-2-Azet-CO- | tBuNH- |
| 235 | 4-Bza-PhoAc- | CarCH₂ | Bz | 3-Oxo-2-Azet-CO- | tBuNH- |
| 236 | 4-Bza-PhoAc- | CarCH₂ | Bz | 3-HO-2-Azet-CO- | tBuNH- |
| 237 | 4-Bza-PhoAc- | CarCH₂ | Bz | 3-Cl-2-Azet-CO- | tBuNH- |
| 238 | 4-Bza-PhoAc- | CarCH₂ | Bz | 3-Br-2-Azet-CO- | tBuNH- |
| 239 | 4-Bza-PhoAc- | CarCH₂ | Bz | 3-I-2-Azet-CO- | tBuNH- |
| 240 | 4-Bza-PhoAc- | CarCH₂ | Bz | 3-F-2-Azet-CO- | tBuNH- |
| 241 | 4-Bza-PhoAc- | CarCH₂ | Bz | 3,3-diF-2-Azet-CO- | tBuNH- |
| 242 | 4-Bza-PhoAc- | CarCH₂ | Bz | 3-MeOImin-2-Azet-CO- | tBuNH- |
| 243 | 4-Bza-PhoAc- | CarCH₂ | Bz | 3-Mec-2-Azet-CO- | tBuNH- |
| 244 | 4-Bza-PhoAc- | CarCH₂ | Bz | 3-CN-2-Azet-CO- | tBuNH- |
| 245 | 4-Bza-PhoAc- | CarCH₂ | Bz | 3-Me₂N-2-Azet-CO- | tBuNH- |
| 246 | 4-Gly-NH-PhoAc- | CarCH₂ | Bz | 2-Azir-CO- | tBuNH- |
| 247 | 4-Gly-NH-PhoAc- | CarCH₂ | Bz | 2-Azet-CO- | tBuNH- |
| 248 | 4-Gly-NH-PhoAc- | CarCH₂ | Bz | 4-Oxo-2-Azet-CO- | tBuNH- |
| 249 | 4-Gly-NH-PhoAc- | CarCH₂ | Bz | 3-Oxo-2-Azet-CO- | tBuNH- |
| 250 | 4-Gly-NH-PhoAc- | CarCH₂ | Bz | 3-HO-2-Azet-CO- | tBuNH- |

TABLE 1-continued

| Cpd. No. | R¹ | R³ | R⁴ | Z | R⁵ |
| --- | --- | --- | --- | --- | --- |
| 251 | 4-Gly-NH-PhoAc- | CarCH₂ | Bz | 3-Cl-2-Azet-CO- | tBuNH- |
| 252 | 4-Gly-NH-PhoAc- | CarCH₂ | Bz | 3-Br-2-Azet-CO- | tBuNH- |
| 253 | 4-Gly-NH-PhoAc- | CarCH₂ | Bz | 3-I-2-Azet-CO- | tBuNH- |
| 254 | 4-Gly-NH-PhoAc- | CarCH₂ | Bz | 3-F-2-Azet-CO- | tBuNH- |
| 255 | 4-Gly-NH-PhoAc- | CarCH₂ | Bz | 3-diF-2-Azet-CO- | tBuNH- |
| 256 | 4-Gly-NH-PhoAc- | CarCH₂ | Bz | 3-MeOImin-2-Azet-CO- | tBuNH- |
| 257 | 4-Gly-NH-PhoAc- | CarCH₂ | Bz | 3-Mec-2-Azet-CO- | tBuNH- |
| 258 | 4-Gly-NH-PhoAc- | CarCH₂ | Bz | 3-CN-2-Azet-CO- | tBuNH- |
| 259 | 4-Gly-NH-PhoAc- | CarCH₂ | Bz | 3-Me₂N-2-Azet-CO- | tBuNH- |
| 260 | 4-[(N-Me-Gly)-NMe]-PhoAc- | CarCH₂ | Bz | 2-Azir-CO- | tBuNH- |
| 261 | 4-[(N-Me-Gly)-NMe]-PhoAc- | CarCH₂ | Bz | 2-Azet-CO- | tBuNH- |
| 262 | 4-[(N-Me-Gly)-NMe]-PhoAc- | CarCH₂ | Bz | 4-Oxo-2-Azet-CO- | tBuNH- |
| 263 | 4-[(N-Me-Gly)-NMe]-PhoAc- | CarCH₂ | Bz | 3-Oxo-2-Azet-CO- | tBuNH- |
| 264 | 4-[(N-Me-Gly)-NMe]-PhoAc- | CarCH₂ | Bz | 3-HO-2-Azet-CO- | tBuNH- |
| 265 | 4-[(N-Me-Gly)-NMe]-PhoAc- | CarCH₂ | Bz | 3-Cl-2-Azet-CO- | tBuNH- |
| 266 | 4-[(N-Me-Gly)-NMe]-PhoAc- | CarCH₂ | Bz | 3-Br-2-Azet-CO- | tBuNH- |
| 267 | 4-[(N-Me-Gly)-NMe]-PhoAc- | CarCH₂ | Bz | 3-I-2-Azet-CO- | tBuNH- |
| 268 | 4-[(N-Me-Gly)-NMe]-PhoAc- | CarCH₂ | Bz | 3-F-2-Azet-CO- | tBuNH- |
| 269 | 4-[(N-Me-Gly)-NMe]-PhoAc- | CarCH₂ | Bz | 3,3-diF-2-Azet-CO- | tBuNH- |
| 270 | 4-[(N-Me-Gly)-NMe]-PhoAc- | CarCH₂ | Bz | 3-MeOImin-2-Azet-CO- | tBuNH- |
| 271 | 4-[(N-Me-Gly)-NMe]-PhoAc- | CarCH₂ | Bz | 3-Mec-2-Azet-CO- | tBuNH- |
| 272 | 4-[(N-Me-Gly)-NMe]-PhoAc- | CarCH₂ | Bz | 3-CN-2-Azet-CO- | tBuNH- |
| 273 | 4-[(N-Me-Gly)-NMe]-PhoAc- | CarCH₂ | Bz | 3-Me₂N-2-Azet-CO- | tBuNH- |
| 274 | 4-[MorAc-NMe]-PhoAc- | CarCH₂ | Bz | 2-Azir-CO- | tBuNH- |
| 275 | 4-[MorAc-NMe]-PhoAc- | CarCH₂ | Bz | 2-Azet-CO- | tBuNH- |
| 276 | 4-[MorAc-NMe]-PhoAc- | CarCH₂ | Bz | 4-Oxo-2-Azet-CO- | tBuNH- |
| 277 | 4-[MorAc-NMe]-PhoAc- | CarCH₂ | Bz | 3-Oxo-2-Azet-CO- | tBuNH- |
| 278 | 4-[MorAc-NMe]-PhoAc- | CarCH₂ | Bz | 3-HO-2-Azet-CO- | tBuNH- |
| 279 | 4-[MorAc-NMe]-PhoAc- | CarCH₂ | Bz | 3-Cl-2-Azet-CO- | tBuNH- |
| 280 | 4-[MorAc-NMe]-PhoAc- | CarCH₂ | Bz | 3-Br-2-Azet-CO- | tBuNH- |
| 281 | 4-[MorAc-NMe]-PhoAc- | CarCH₂ | Bz | 3-I-2-Azet-CO- | tBuNH- |
| 282 | 4-[MorAc-NMe]-PhoAc- | CarCH₂ | Bz | 3-F-2-Azet-CO- | tBuNH- |
| 283 | 4-[MorAc-NMe]-PhoAc- | CarCH₂ | Bz | 3,3-diF-2-Azet-CO- | tBuNH- |
| 284 | 4-[MorAc-NMe]-PhoAc- | CarCH₂ | Bz | 3-MeOImin-2-Azet-CO- | tBuNH- |
| 285 | 4-[MorAc-NMe]-PhoAc- | CarCH₂ | Bz | 3-Mec-2-Azet-CO- | tBuNH- |
| 286 | 4-[MorAc-NMe]-PhoAc- | CarCH₂ | Bz | 3-CN-2-Azet-CO- | tBuNH- |
| 287 | 4-[MorAc-NMe]-PhoAc- | CarCH₂ | Bz | 3-Me₂N-2-Azet-CO- | tBuNH- |
| 288 | 2-Quix-CO- | CarCH₂ | Bz | 5-HO-Pro- | tBuNH- |
| 289 | 2-Quix-CO- | CarCH₂ | Bz | 4-HO-Pro- | tBuNH- |
| 290 | 2-Quix-CO- | CarCH₂ | Bz | 3-HO-Pro- | tBuNH- |
| 291 | 2-Quix-CO- | CarCH₂ | Bz | 4,5-diHO-Pro- | tBuNH- |
| 292 | 2-Quix-CO- | CarCH₂ | Bz | 3,4-diHO-Pro- | tBuNH- |
| 293 | 2-Quix-CO- | CarCH₂ | Bz | 3,4,5-triHO-Pro- | tBuNH- |
| 294 | 2-Quix-CO- | CarCH₂ | Bz | 5-Oxo-Pro- | tBuNH- |
| 295 | 2-Quix-CO- | CarCH₂ | Bz | 4-Oxo-Pro- | tBuNH- |
| 296 | 2-Quix-CO- | CarCH₂ | Bz | 3-Oxo-Pro- | tBuNH- |
| 297 | 2-Quix-CO- | CarCH₂ | Bz | 4-Mor-Pro- | tBuNH- |
| 298 | 2-Quix-CO- | CarCH₂ | Bz | 4-Me₂N-Pro- | tBuNH- |
| 299 | 2-Quix-CO- | CarCH₂ | Bz | 4-Cl-Pro- | tBuNH- |
| 300 | 2-Quix-CO- | CarCH₂ | Bz | 3-Cl-Pro- | tBuNH- |
| 301 | 2-Quix-CO- | CarCH₂ | Bz | 3,4-diCl-Pro- | tBuNH- |
| 302 | 2-Quix-CO- | CarCH₂ | Bz | 4-Br-Pro- | tBuNH- |
| 303 | 2-Quix-CO- | CarCH₂ | Bz | 3-Br-Pro- | tBuNH- |
| 304 | 2-Quix-CO- | CarCH₂ | Bz | 3,4-diBr-Pro- | tBuNH- |
| 305 | 2-Quix-CO- | CarCH₂ | Bz | 4-F-Pro- | tBuNH- |
| 306 | 2-Quix-CO- | CarCH₂ | Bz | 3-F-Pro- | tBuNH- |
| 307 | 2-Quix-CO- | CarCH₂ | Bz | 4,4-diF-Pro- | tBuNH- |
| 308 | 2-Quix-CO- | CarCH₂ | Bz | 3,4-diF-Pro- | tBuNH- |
| 309 | 2-Quix-CO- | CarCH₂ | Bz | 4-I-Pro- | tBuNH- |
| 310 | 2-Quix-CO- | CarCH₂ | Bz | 3-I-Pro- | tBuNH- |
| 311 | 2-Quix-CO- | CarCH₂ | Bz | 4,4-diMeO-Pro- | tBuNH- |
| 312 | 2-Quix-CO- | CarCH₂ | Bz | 4-MeOImin-Pro- | tBuNH- |
| 313 | 2-Quix-CO- | CarCH₂ | Bz | 4-Ph-S-Pro- | tBuNH- |
| 314 | 2-Quix-CO- | CarCH₂ | Bz | 4-tBuO-Pro- | tBuNH- |
| 315 | 2-Quix-CO- | CarCH₂ | Bz | 4-CN-4-OH-Pro- | tBuNH- |
| 316 | 2-Quix-CO- | CarCH₂ | Bz | Spiro(2,5-dioxo-imidazolidine-4,4'-prolyl)- | tBuNH- |
| 317 | 2-Quix-CO- | CarCH₂ | Bz | 4-CN-Pro- | tBuNH- |
| 318 | 2-Quix-CO- | CarCH₂ | Bz | 4-Mec-Pro- | tBuNH- |
| 319 | 2-Quix-CO- | CarCH₂ | Bz | 4-COOH-Pro- | tBuNH- |
| 320 | 2-Quix-CO- | CarCH₂ | Bz | 3-Deh-Pro- | tBuNH- |
| 321 | 2-Quix-CO- | CarCH₂ | Bz | ThiaPro- | tBuNH- |
| 322 | 2-Quix-CO- | CarCH₂ | Bz | 3,3,5,5-tetMe-ThiaPro- | tBuNH- |
| 323 | 2-Quix-CO- | CarCH₂ | Bz | 3,3-diMe-ThiaPro- | tBuNH- |
| 324 | 2-Quix-CO- | CarCH₂ | Bz | 2,5-Oxaz-3-Oxo-bicyclo[2,2,1]hept-5-yl | |

TABLE 1-continued

| Cpd. No. | R¹ | R³ | R⁴ | Z | R⁵ |
|---|---|---|---|---|---|
| 325 | 2-Quix-CO- | CarCH₂ | Bz | 2-tBu-2,5-diaza-3-Oxo-bicyclo-[2,2,1]hept-5-yl- | |
| 326 | Bzc | CarCH₂ | Bz | 5-HO-Pro- | tBuNH- |
| 327 | Bzc | CarCH₂ | Bz | 4-HO-Pro- | tBuNH- |
| 328 | Bzc | CarCH₂ | Bz | 3-HO-Pro- | tBuNH- |
| 329 | Bzc | CarCH₂ | Bz | 4,5-diHO-Pro- | tBuNH- |
| 330 | Bzc | CarCH₂ | Bz | 3,4-diHO-Pro- | tBuNH- |
| 331 | Bzc | CarCH₂ | Bz | 3,4,5-triHO-Pro- | tBuNH- |
| 332 | Bzc | CarCH₂ | Bz | 5-Oxo-Pro- | tBuNH- |
| 333 | Bzc | CarCH₂ | Bz | 4-Oxo-Pro- | tBuNH- |
| 334 | Bzc | CarCH₂ | Bz | 3-Oxo-Pro- | tBuNH- |
| 335 | Bzc | CarCH₂ | Bz | 4-Mor-Pro- | tBuNH- |
| 336 | Bzc | CarCH₂ | Bz | 4-Me₂N-Pro- | tBuNH- |
| 337 | Bzc | CarCH₂ | Bz | 4-Cl-Pro- | tBuNH- |
| 338 | Bzc | CarCH₂ | Bz | 3-Cl-Pro- | tBuNH- |
| 339 | Bzc | CarCH₂ | Bz | 3,4-diCl-Pro- | tBuNH- |
| 340 | Bzc | CarCH₂ | Bz | 4-Br-Pro- | tBuNH- |
| 341 | Bzc | CarCH₂ | Bz | 3-Br-Pro- | tBuNH- |
| 342 | Bzc | CarCH₂ | Bz | 3,4-diBr-Pro- | tBuNH- |
| 343 | Bzc | CarCH₂ | Bz | 4-F-Pro- | tBuNH- |
| 344 | Bzc | CarCH₂ | Bz | 3-F-Pro- | tBuNH- |
| 345 | Bzc | CarCH₂ | Bz | 4,4-diF-Pro- | tBuNH- |
| 346 | Bzc | CarCH₂ | Bz | 3,4-diF-Pro- | tBuNH- |
| 347 | Bzc | CarCH₂ | Bz | 4-I-Pro- | tBuNH- |
| 348 | Bzc | CarCH₂ | Bz | 3-I-Pro- | tBuNH- |
| 349 | Bzc | CarCH₂ | Bz | 4,4-diMeO-Pro- | tBuNH- |
| 350 | Bzc | CarCH₂ | Bz | 4-MeOImin-Pro- | tBuNH- |
| 351 | Bzc | CarCH₂ | Bz | 4-Ph-S-Pro- | tBuNH- |
| 352 | Bzc | CarCH₂ | Bz | 4-tBuO-Pro- | tBuNH- |
| 353 | Bzc | CarCH₂ | Bz | 4-CN-4-HO-Pro- | tBuNH- |
| 354 | Bzc | CarCH₂ | Bz | Spiro(2,5-dioxo-imidazolidine-4,4'-prolyl)- | tBuNH- |
| 355 | Bzc | CarCH₂ | Bz | 4-CN-Pro- | tBuNH- |
| 356 | Bzc | CarCH₂ | Bz | 4-Mec-Pro- | tBuNH- |
| 357 | Bzc | CarCH₂ | Bz | 4-COOH-Pro- | tBuNH- |
| 358 | Bzc | CarCH₂ | Bz | 3-Deh-Pro- | tBuNH- |
| 359 | Bzc | CarCH₂ | Bz | ThiaPro- | tBuNH- |
| 360 | Bzc | CarCH₂ | Bz | 3,3,5,5-tetMe-ThiaPro- | tBuNH- |
| 361 | Bzc | CarCH₂ | Bz | 3,3,-diMe-ThiaPro- | tBuNH- |
| 362 | Bzc | CarCH₂ | Bz | 2,5-Oxaz-3-Oxo-bicyclo[2,2,1]-hept-S-yl- | |
| 363 | Bzc | CarCH₂ | Bz | 2-tBu-2,5-diaza-3-Oxo-bicyclo-[2,2,1]hept-5-yl- | |
| 364 | 2-Quin-CO- | CarCH₂ | Bz | 5-HO-Pro- | tBuNH- |
| 365 | 2-Quin-CO- | CarCH₂ | Bz | 4-HO-Pro- | tBuNH- |
| 366 | 2-Quin-CO- | CarCH₂ | Bz | 3-HO-Pro- | tBuNH- |
| 367 | 2-Quin-CO- | CarCH₂ | Bz | 4,5-diHO-Pro- | tBuNH- |
| 368 | 2-Quin-CO- | CarCH₂ | Bz | 3,4-diHO-Pro- | tBuNH- |
| 369 | 2-Quin-CO- | CarCH₂ | Bz | 3,4,5-triHO-Pro- | tBuNH- |
| 370 | 2-Quin-CO- | CarCH₂ | Bz | 5-Oxo-Pro- | tBuNH- |
| 371 | 2-Quin-CO- | CarCH₂ | Bz | 4-Oxo-Pro- | tBuNH- |
| 372 | 2-Quin-CO- | CarCH₂ | Bz | 3-Oxo-Pro- | tBuNH- |
| 373 | 2-Quin-CO- | CarCH₂ | Bz | 4-Mor-Pro- | tBuNH- |
| 374 | 2-Quin-CO- | CarCH₂ | Bz | 4-Me₂N-Pro- | tBuNH- |
| 375 | 2-Quin-CO- | CarCH₂ | Bz | 4-Cl-Pro- | tBuNH- |
| 376 | 2-Quin-CO- | CarCH₂ | Bz | 3-Cl-Pro- | tBuNH- |
| 377 | 2-Quin-CO- | CarCH₂ | Bz | 3,4-diCl-Pro- | tBuNH- |
| 378 | 2-Quin-CO- | CarCH₂ | Bz | 4-Br-Pro- | tBuNH- |
| 379 | 2-Quin-CO- | CarCH₂ | Bz | 3-Br-Pro- | tBuNH- |
| 380 | 2-Quin-CO- | CarCH₂ | Bz | 3,4-diBr-Pro- | tBuNH- |
| 381 | 2-Quin-CO- | CarCH₂ | Bz | 4-F-Pro- | tBuNH- |
| 382 | 2-Quin-CO- | CarCH₂ | Bz | 3-F-Pro- | tBuNH- |
| 383 | 2-Quin-CO- | CarCH₂ | Bz | 4,4-diF-Pro- | tBuNH- |
| 384 | 2-Quin-CO- | CarCH₂ | Bz | 3,4-diF-Pro- | tBuNH- |
| 385 | 2-Quin-CO- | CarCH₂ | Bz | 4-I-Pro- | tBuNH- |
| 386 | 2-Quin-CO- | CarCH₂ | Bz | 3-I-Pro- | tBuNH- |
| 387 | 2-Quin-CO- | CarCH₂ | Bz | 4,4-diMeO-Pro- | tBuNH- |
| 388 | 2-Quin-CO- | CarCH₂ | Bz | 4-MeOImin-Pro- | tBuNH- |
| 389 | 2-Quin-CO- | CarCH₂ | Bz | 4-Ph-S-Pro- | tBuNH- |
| 390 | 2-Quin-CO- | CarCH₂ | Bz | 4-tBuO-Pro- | tBuNH- |
| 391 | 2-Quin-CO- | CarCH₂ | Bz | 4-CN-4-HO-Pro- | tBuNH- |
| 392 | 2-Quin-CO- | CarCH₂ | Bz | Spiro(2,5-dioxo-imidazolidine-4,4'-prolyl)- | tBuNH- |
| 393 | 2-Quin-CO- | CarCH₂ | Bz | 4-CN-Pro- | tBuNH- |
| 394 | 2-Quin-CO- | CarCH₂ | Bz | 4-Mec-Pro- | tBuNH- |
| 395 | 2-Quin-CO- | CarCH₂ | Bz | 4-COOH-Pro- | tBuNH- |

TABLE 1-continued

| Cpd. No. | R¹ | R³ | R⁴ | Z | R⁵ |
|---|---|---|---|---|---|
| 396 | 2-Quin-CO- | CarCH₂ | Bz | 3-Deh-Pro- | tBuNH- |
| 397 | 2-Quin-CO- | CarCH₂ | Bz | ThiaPro- | tBuNH- |
| 398 | 2-Quin-CO- | CarCH₂ | Bz | 3,3,5,5-tetMe-ThiaPro- | tBuNH- |
| 399 | 2-Quin-CO- | CarCH₂ | Bz | 3,3-diMe-ThiaPro- | tBuNH- |
| 400 | 2-Quin-CO- | CarCH₂ | Bz | 2,5-Oxaz-3-Oxo-bicyclo[2,2,1]-hept-5-yl- | |
| 401 | 2-Quin-CO- | CarCH₂ | Bz | 2-tBu-2,5-diaza-3-Oxo-bicyclo-[2,2,1]hept-5-yl- | |
| 402 | 2-Ind-CO- | CarCH₂ | Bz | 5-HO-Pro- | tBuNH- |
| 403 | 2-Ind-CO- | CarCH₂ | Bz | 4-HO-Pro- | tBuNH- |
| 404 | 2-Ind-CO- | CarCH₂ | Bz | 3-HO-Pro- | tBuNH- |
| 405 | 2-Ind-CO- | CarCH₂ | Bz | 4,5-diHO-Pro- | tBuNH- |
| 406 | 2-Ind-CO- | CarCH₂ | Bz | 3,4-diHO-Pro- | tBuNH- |
| 407 | 2-Ind-CO- | CarCH₂ | Bz | 3,4,5-triHO-Pro- | tBuNH- |
| 408 | 2-Ind-CO- | CarCH₂ | Bz | 5-Oxo-Pro- | tBuNH- |
| 409 | 2-Ind-CO- | CarCH₂ | Bz | 4-Oxo-Pro- | tBuNH- |
| 410 | 2-Ind-CO- | CarCH₂ | Bz | 3-Oxo-Pro- | tBuNH- |
| 411 | 2-Ind-CO- | CarCH₂ | Bz | 4-Mor-Pro- | tBuNH- |
| 412 | 2-Ind-CO- | CarCH₂ | Bz | 4-Me₂N-Pro- | tBuNH- |
| 413 | 2-Ind-CO- | CarCH₂ | Bz | 4-Cl-Pro- | tBuNH- |
| 414 | 2-Ind-CO- | CarCH₂ | Bz | 3-Cl-Pro- | tBuNH- |
| 415 | 2-Ind-CO- | CarCH₂ | Bz | 3,4-diCl-Pro- | tBuNH- |
| 416 | 2-Ind-CO- | CarCH₂ | Bz | 4-Br-Pro- | tBuNH- |
| 417 | 2-Ind-CO- | CarCH₂ | Bz | 3-Br-Pro- | tBuNH- |
| 418 | 2-Ind-CO- | CarCH₂ | Bz | 3,4-diBr-Pro- | tBuNH- |
| 419 | 2-Ind-CO- | CarCH₂ | Bz | 4-F-Pro- | tBuNH- |
| 420 | 2-Ind-CO- | CarCH₂ | Bz | 3-F-Pro- | tBuNH- |
| 421 | 2-Ind-CO- | CarCH₂ | Bz | 4,4-diF-Pro- | tBuNH- |
| 422 | 2-Ind-CO- | CarCH₂ | Bz | 3,4-diF-Pro- | tBuNH- |
| 423 | 2-Ind-CO- | CarCH₂ | Bz | 4-I-Pro- | tBuNH- |
| 424 | 2-Ind-CO- | CarCH₂ | Bz | 3-I-Pro- | tBuNH- |
| 425 | 2-Ind-CO- | CarCH₂ | Bz | 4,4-diMeO-Pro- | tBuNH- |
| 426 | 2-Ind-CO- | CarCH₂ | Bz | 4-MeO-Imin-Pro- | tBuNH- |
| 427 | 2-Ind-CO- | CarCH₂ | Bz | 4-Ph-S-Pro- | tBuNH- |
| 428 | 2-Ind-CO- | CarCH₂ | Bz | 4tBu-O-Pro- | tBuNH- |
| 429 | 2-Ind-CO- | CarCH₂ | Bz | 4-CN-4-HO-Pro- | tBuNH- |
| 430 | 2-Ind-CO- | CarCH₂ | Bz | Spiro(2,5-dioxo-imidazolidine-4,4'-prolyl)- | tBuNH- |
| 431 | 2-Ind-CO- | CarCH₂ | Bz | 4-CN-Pro- | tBuNH- |
| 432 | 2-Ind-CO- | CarCH₂ | Bz | 4-Mec-Pro- | tBuNH- |
| 433 | 2-Ind-CO- | CarCH₂ | Bz | 4-COOH-Pro- | tBuNH- |
| 434 | 2-Ind-CO- | CarCH₂ | Bz | 3-Deh-Pro- | tBuNH- |
| 435 | 2-Ind-CO- | CarCH₂ | Bz | ThiaPro- | tBuNH- |
| 436 | 2-Ind-CO- | CarCH₂ | Bz | 3,3,5,5-tetMe-ThiaPro- | tBuNH- |
| 437 | 2-Ind-CO- | CarCH₂ | Bz | 3,3-diMe-ThiaPro- | tBuNH- |
| 438 | 2-Ind-CO- | CarCH₂ | Bz | 2,5-Oxaz-3-Oxo-bicyclo[2,2,1]-hept-5-yl- | |
| 439 | 2-Ind-CO- | CarCH₂ | Bz | 2-tBu-2,5-diaza-3-Oxo-bicyclo-[2,2,1]hept-5-yl- | |
| 440 | tBoc | CarCH₂ | Bz | 5-HO-Pro- | tBuNH- |
| 441 | tBoc | CarCH₂ | Bz | 4-HO-Pro- | tBuNH- |
| 442 | tBoc | CarCH₂ | Bz | 3-HO-Pro- | tBuNH- |
| 443 | tBoc | CarCH₂ | Bz | 4,5-diHO-Pro- | tBuNH- |
| 444 | tBoc | CarCH₂ | Bz | 3,4-diHO-Pro- | tBuNH- |
| 445 | tBoc | CarCH₂ | Bz | 3,4,5-triHO-Pro- | tBuNH- |
| 446 | tBoc | CarCH₂ | Bz | 5-Oxo-Pro- | tBuNH- |
| 447 | tBoc | CarCH₂ | Bz | 4-Oxo-Pro- | tBuNH- |
| 448 | tBoc | CarCH₂ | Bz | 3-Oxo-Pro- | tBuNH- |
| 449 | tBoc | CarCH₂ | Bz | 4-Mor-Pro- | tBuNH- |
| 450 | tBoc | CarCH₂ | Bz | 4-Me₂N-Pro- | tBuNH- |
| 451 | tBoc | CarCH₂ | Bz | 4-Cl-Pro- | tBuNH- |
| 452 | tBoc | CarCH₂ | Bz | 3-Cl-Pro- | tBuNH- |
| 453 | tBoc | CarCH₂ | Bz | 3,4-diCl-Pro- | tBuNH- |
| 454 | tBoc | CarCH₂ | Bz | 4-Br-Pro- | tBuNH- |
| 455 | tBoc | CarCH₂ | Bz | 3-Br-Pro- | tBuNH- |
| 456 | tBoc | CarCH₂ | Bz | 3,4-diBr-Pro- | tBuNH- |
| 457 | tBoc | CarCH₂ | Bz | 4-F-Pro- | tBuNH- |
| 458 | tBoc | CarCH₂ | Bz | 3-F-Pro- | tBuNH- |
| 459 | tBoc | CarCH₂ | Bz | 4,4-diF-Pro- | tBuNH- |
| 460 | tBoc | CarCH₂ | Bz | 3,4-diF-Pro- | tBuNH- |
| 461 | tBoc | CarCH₂ | Bz | 4-I-Pro- | tBuNH- |
| 462 | tBoc | CarCH₂ | Bz | 3-I-Pro- | tBuNH- |
| 463 | tBoc | CarCH₂ | Bz | 4,4-diMeO-Pro- | tBuNH- |
| 464 | tBoc | CarCH₂ | Bz | 4-MeOImin-Pro- | tBuNH- |
| 465 | tBoc | CarCH₂ | Bz | 4-Ph-S-Pro- | tBuNH- |
| 466 | tBoc | CarCH₂ | Bz | 4-tBuO-Pro- | tBuNH- |

TABLE 1-continued

| Cpd. No. | R¹ | R³ | R⁴ | Z | R⁵ |
|---|---|---|---|---|---|
| 467 | tBoc | CarCH₂ | Bz | 4-CN-4-HO-Pro- | tBuNH- |
| 468 | tBoc | CarCH₂ | Bz | Spiro(2,5-dioxo-imidazolidine-4,4'-prolyl)- | tBuNH- |
| 469 | tBoc | CarCH₂ | Bz | 4-CN-Pro- | tBuNH- |
| 470 | tBoc | CarCH₂ | Bz | 4-Mec-Pro- | tBuNH- |
| 471 | tBoc | CarCH₂ | Bz | 4-COOH-Pro- | tBuNH- |
| 472 | tBoc | CarCH₂ | Bz | 3-Deh-Pro- | tBuNH- |
| 473 | tBoc | CarCH₂ | Bz | ThiaPro- | tBuNH- |
| 474 | tBoc | CarCH₂ | Bz | 3,3,5,5-tetMe-ThiaPro- | tBuNH- |
| 475 | tBoc | CarCH₂ | Bz | 3,3-diMe-ThiaPro- | tBuNH- |
| 476 | tBoc | CarCH₂ | Bz | 2,5-Oxaz-3-Oxo-bicyclo[2,2,1]hept-5-yl- | |
| 477 | tBoc | CarCH₂ | Bz | 2-tBu-2,5-diaza-3-Oxo-bicyclo-[2,2,1]hept-5-yl- | |
| 478 | MPhoAc- | CarCH₂ | Bz | 5-HO-Pro- | tBuNH- |
| 479 | MPhoAc- | CarCH₂ | Bz | 4-HO-Pro- | tBuNH- |
| 480 | MPhoAc- | CarCH₂ | Bz | 3-HO-Pro- | tBuNH- |
| 481 | MPhoAc- | CarCH₂ | Bz | 4,5-diHO-Pro- | tBuNH- |
| 482 | MPhoAc- | CarCH₂ | Bz | 3,4-diHO-Pro- | tBuNH- |
| 483 | MPhoAc- | CarCH₂ | Bz | 3,4,5-triHO-Pro- | tBuNH- |
| 484 | MPhoAc- | CarCH₂ | Bz | 5-Oxo-Pro- | tBuNH- |
| 485 | MPhoAc- | CarCH₂ | Bz | 4-Oxo-Pro- | tBuNH- |
| 486 | MPhoAc- | CarCH₂ | Bz | 3-Oxo-Pro- | tBuNH- |
| 487 | MPhoAc- | CarCH₂ | Bz | 4-Mor-Pro- | tBuNH- |
| 488 | MPhoAc- | CarCH₂ | Bz | 4-Me₂N-Pro- | tBuNH- |
| 489 | MPhoAc- | CarCH₂ | Bz | 4-Cl-Pro- | tBuNH- |
| 490 | MPhoAc- | CarCH₂ | Bz | 3-Cl-Pro- | tBuNH- |
| 491 | MPhoAc- | CarCH₂ | Bz | 3,4-diCl-Pro- | tBuNH- |
| 492 | MPhoAc- | CarCH₂ | Bz | 4-Br-Pro- | tBuNH- |
| 493 | MPhoAc- | CarCH₂ | Bz | 3-Br-Pro- | tBuNH- |
| 494 | MPhoAc- | CarCH₂ | Bz | 3,4-diBr-Pro- | tBuNH- |
| 495 | MPhoAc- | CarCH₂ | Bz | 4-F-Pro- | tBuNH- |
| 496 | MPhoAc- | CarCH₂ | Bz | 3-F-Pro- | tBuNH- |
| 497 | MPhoAc- | CarCH₂ | Bz | 4,4-diF-Pro- | tBuNH- |
| 498 | MPhoAc- | CarCH₂ | Bz | 3,4-diF-Pro- | tBuNH- |
| 499 | MPhoAc- | CarCH₂ | Bz | 4-I-Pro- | tBuNH- |
| 500 | MPhoAc- | CarCH₂ | Bz | 3-I-Pro- | tBuNH- |
| 501 | MPhoAc- | CarCH₂ | Bz | 4,4-diMeO-Pro- | tBuNH- |
| 502 | MPhoAc- | CarCH₂ | Bz | 4-MeOImin-Pro- | tBuNH- |
| 503 | MPhoAc- | CarCH₂ | Bz | 4-Ph-S-Pro- | tBuNH- |
| 504 | MPhoAc- | CarCH₂ | Bz | 4-tBuO-Pro- | tBuNH- |
| 505 | MPhoAc- | CarCH₂ | Bz | 4-CN-4-HO-Pro- | tBuNH- |
| 506 | MPhoAc- | CarCH₂ | Bz | Spiro(2,5-dioxo-imidazolidine-4,4'-prolyl)- | tBuNH- |
| 507 | MPhoAc- | CarCH₂ | Bz | 4-CN-Pro- | tBuNH- |
| 508 | MPhoAc- | CarCH₂ | Bz | 4-Mec-Pro- | tBuNH- |
| 509 | MPhoAc- | CarCH₂ | Bz | 4-COOH-Pro- | tBuNH- |
| 510 | MPhoAc- | CarCH₂ | Bz | 3-Deh-Pro- | tBuNH- |
| 511 | MPhoAc- | CarCH₂ | Bz | ThiaPro- | tBuNH- |
| 512 | MPhoAc- | CarCH₂ | Bz | 3,3,5,5-tetMe-ThiaPro- | tBuNH- |
| 513 | MPhoAc- | CarCH₂ | Bz | 3,3-diMe-ThiaPro- | tBuNH- |
| 514 | MPhoAc- | CarCH₂ | Bz | 2,5-Oxaz-3-Oxo-bicyclo[2,2,1]hept-5-yl- | |
| 515 | MPhoAc- | CarCH₂ | Bz | 2-tBu-2,5-diaza-3-Oxo-bicyclo-[2,2,1]hept-5-yl- | |
| 516 | 4-NH₂-PhoAc- | CarCH₂ | Bz | 5-HO-Pro- | tBuNH- |
| 517 | 4-NH₂-PhoAc- | CarCH₂ | Bz | 4-HO-Pro- | tBuNH- |
| 518 | 4-NH₂-PhoAc- | CarCH₂ | Bz | 3-HO-Pro- | tBuNH- |
| 519 | 4-NH₂-PhoAc- | CarCH₂ | Bz | 4,5-diHO-Pro- | tBuNH- |
| 520 | 4-NH₂-PhoAc- | CarCH₂ | Bz | 3,4-diHO-Pro- | tBuNH- |
| 521 | 4-NH₂-PhoAc- | CarCH₂ | Bz | 3,4,5-triHO-Pro- | tBuNH- |
| 522 | 4-NH₂-PhoAc- | CarCH₂ | Bz | 5-Oxo-Pro- | tBuNH- |
| 523 | 4-NH₂-PhoAc- | CarCH₂ | Bz | 4-Oxo-Pro- | tBuNH- |
| 524 | 4-NH₂-PhoAc- | CarCH₂ | Bz | 3-Oxo-Pro- | tBuNH- |
| 525 | 4-NH₂-PhoAc- | CarCH₂ | Bz | 4-Mor-Pro- | tBuNH- |
| 526 | 4-NH₂-PhoAc- | CarCH₂ | Bz | 4-Me₂N-Pro- | tBuNH- |
| 527 | 4-NH₂-PhoAc- | CarCH₂ | Bz | 4-Cl-Pro- | tBuNH- |
| 528 | 4-NH₂-PhoAc- | CarCH₂ | Bz | 5-Cl-Pro- | tBuNH- |
| 529 | 4-NH₂-PhoAc- | CarCH₂ | Bz | 3,4-diCl-Pro- | tBuNH- |
| 530 | 4-NH₂-PhoAc- | CarCH₂ | Bz | 4-Br-Pro- | tBuNH- |
| 531 | 4-NH₂-PhoAc- | CarCH₂ | Bz | 3-Br-Pro- | tBuNH- |
| 532 | 4-NH₂-PhoAc- | CarCH₂ | Bz | 3,4-diBr-Pro- | tBuNH- |
| 533 | 4-NH₂-PhoAc- | CarCH₂ | Bz | 4-F-Pro- | tBuNH- |
| 534 | 4-NH₂-PhoAc- | CarCH₂ | Bz | 3-F-Pro- | tBuNH- |
| 535 | 4-NH₂-PhoAc- | CarCH₂ | Bz | 4,4-diF-Pro- | tBuNH- |
| 536 | 4-NH₂-PhoAc- | CarCH₂ | Bz | 3,4-diF-Pro- | tBuNH- |

TABLE 1-continued

| Cpd. No. | R¹ | R³ | R⁴ | Z | R⁵ |
|---|---|---|---|---|---|
| 537 | 4-NH₂-PhoAc- | CarCH₂ | Bz | 4-I-Pro- | tBuNH- |
| 538 | 4-NH₂-PhoAc- | CarCH₂ | Bz | 3-I-Pro- | tBuNH- |
| 539 | 4-NH₂-PhoAc- | CarCH₂ | Bz | 4,4-diMeO-Pro- | tBuNH- |
| 540 | 4-NH₂-PhoAc- | CarCH₂ | Bz | 4-MeOImin-Pro- | tBuNH- |
| 541 | 4-NH₂-PhoAc- | CarCH₂ | Bz | 4-Ph-S-Pro- | tBuNH- |
| 542 | 4-NH₂-PhoAc- | CarCH₂ | Bz | 4-tBuO-Pro- | tBuNH- |
| 543 | 4-NH₂-PhoAc- | CarCH₂ | Bz | 4-CN-4-HO-Pro- | tBuNH- |
| 544 | 4-NH₂-PhoAc- | CarCH₂ | Bz | Spiro(dioxo-2,5-imidazolidine-4,4'-prolyl)- | tBuNH- |
| 545 | 4-NH₂-PhoAc- | CarCH₂ | Bz | 4-CN-Pro- | tBuNH- |
| 546 | 4-NH₂-PhoAc- | CarCH₂ | Bz | 4-Mec-Pro- | tBuNH- |
| 547 | 4-NH₂-PhoAc- | CarCH₂ | Bz | 4-COOH-Pro- | tBuNH- |
| 548 | 4-NH₂-PhoAc- | CarCH₂ | Bz | 3-Deh-Pro- | tBuNH- |
| 549 | 4-NH₂-PhoAc- | CarCH₂ | Bz | ThiaPro- | tBuNH- |
| 550 | 4-NH₂-PhoAc- | CarCH₂ | Bz | 3,3,5,5-tetMe-ThiaPro- | tBuNH- |
| 551 | 4-NH₂-PhoAc- | CarCH₂ | Bz | 3,3-diMe-ThiaPro- | tBuNH- |
| 552 | 4-NH₂-PhoAc- | CarCH₂ | Bz | 2,5-Oxaz-3-Oxo-bicyclo[2,2,1]-hept-5-yl- | |
| 553 | 4-NH₂-PhoAc- | CarCH₂ | Bz | 2-tBu-2,5-diaza-3-Oxo-bicyclo-[2,2,1]hept-5-yl- | |
| 554 | 4-Bzc-NH-PhoAc- | CarCH₂ | Bz | 5-HO-Pro- | tBuNH- |
| 555 | 4-Bzc-NH-PhoAc- | CarCH₂ | Bz | 4-HO-Pro- | tBuNH- |
| 556 | 4-Bzc-NH-PhoAc- | CarCH₂ | Bz | 3-HO-Pro- | tBuNH- |
| 557 | 4-Bzc-NH-PhoAc- | CarCH₂ | Bz | 4,5-diHO-Pro- | tBuNH- |
| 558 | 4-Bzc-NH-PhoAc- | CarCH₂ | Bz | 3,4-diHO-Pro- | tBuNH- |
| 559 | 4-Bzc-NH-PhoAc- | CarCH₂ | Bz | 3,4,5-triHO-Pro- | tBuNH- |
| 560 | 4-Bzc-NH-PhoAc- | CarCH₂ | Bz | 5-Oxo-Pro- | tBuNH- |
| 561 | 4-Bzc-NH-PhoAc- | CarCH₂ | Bz | 4-Oxo-Pro- | tBuNH- |
| 562 | 4-Bzc-NH-PhoAc- | CarCH₂ | Bz | 3-Oxo-Pro- | tBuNH- |
| 563 | 4-Bzc-NH-PhoAc- | CarCH₂ | Bz | 4-Mor-Pro- | tBuNH- |
| 564 | 4-Bzc-NH-PhoAc- | CarCH₂ | Bz | 4-Me₂N-Pro- | tBuNH- |
| 565 | 4-Bzc-NH-PhoAc- | CarCH₂ | Bz | 4-Cl-Pro- | tBuNH- |
| 566 | 4-Bzc-NH-PhoAc- | CarCH₂ | Bz | 3-Cl-Pro- | tBuNH- |
| 567 | 4-Bzc-NH-PhoAc- | CarCH₂ | Bz | 3,4-diCl-Pro- | tBuNH- |
| 568 | 4-Bzc-NH-PhoAc- | CarCH₂ | Bz | 4-Br-Pro- | tBuNH- |
| 569 | 4-Bzc-NH-PhoAc- | CarCH₂ | Bz | 3-Br-Pro- | tBuNH- |
| 570 | 4-Bzc-NH-PhoAc- | CarCH₂ | Bz | 3,4-diBr-Pro- | tBuNH- |
| 571 | 4-Bzc-NH-PhoAc- | CarCH₂ | Bz | 4-F-Pro- | tBuNH- |
| 572 | 4-Bzc-NH-PhoAc- | CarCH₂ | Bz | 3-F-Pro- | tBuNH- |
| 573 | 4-Bzc-NH-PhoAc- | CarCH₂ | Bz | 4,4-diF-Pro- | tBuNH- |
| 574 | 4-Bzc-NH-PhoAc- | CarCH₂ | Bz | 3,4-diF-Pro- | tBuNH- |
| 575 | 4-Bzc-NH-PhoAc- | CarCH₂ | Bz | 4-I-Pro- | tBuNH- |
| 576 | 4-Bzc-NH-PhoAc- | CarCH₂ | Bz | 3-I-Pro- | tBuNH- |
| 577 | 4-Bzc-NH-PhoAc- | CarCH₂ | Bz | 4,4-diMeO-Pro- | tBuNH- |
| 578 | 4-Bzc-NH-PhoAc- | CarCH₂ | Bz | 4-MeOImin-Pro- | tBuNH- |
| 579 | 4-Bzc-NH-PhoAc- | CarCH₂ | Bz | 4-Ph-S-Pro- | tBuNH- |
| 580 | 4-Bzc-NH-PhoAc- | CarCH₂ | Bz | 4-tBuO-Pro- | tBuNH- |
| 581 | 4-Bzc-NH-PhoAc- | CarCH₂ | Bz | 4-CN-4-HO-Pro- | tBuNH- |
| 582 | 4-Bzc-NH-PhoAc- | CarCH₂ | Bz | Spiro(2,5-dioxo-imidazolidine-4,4'-prolyl)- | tBuNH- |
| 583 | 4-Bzc-NH-PhoAc- | CarCH₂ | Bz | 4-CN-Pro- | tBuNH- |
| 584 | 4-Bzc-NH-PhoAc- | CarCH₂ | Bz | 4-Mec-Pro- | tBuNH- |
| 585 | 4-Bzc-NH-PhoAc- | CarCH₂ | Bz | 4-COOH-Pro- | tBuNH- |
| 586 | 4-Bzc-NH-PhoAc- | CarCH₂ | Bz | 3-Deh-Pro- | tBuNH- |
| 587 | 4-Bzc-NH-PhoAc- | CarCH₂ | Bz | ThiaPro- | tBuNH- |
| 588 | 4-Bzc-NH-PhoAc- | CarCH₂ | Bz | 3,3,5,5-tetMe-ThiaPro- | tBuNH- |
| 589 | 4-Bzc-NH-PhoAc- | CarCH₂ | Bz | 3,3-diMe-ThiaPro- | tBuNH- |
| 590 | 4-Bzc-NH-PhoAc- | CarCH₂ | Bz | 2,5-Oxaz-3-Oxo-bicyclo[2,2,1]-hept-5-yl- | |
| 591 | 4-Bzc-NH-PhoAc- | CarCH₂ | Bz | 2-tBu-2,5-diaza-3-Oxo-bicyclo-[2,2,1]hept-5-yl- | |
| 592 | 4-[MorAc-NMe]-PhoAc- | CarCH₂ | Bz | 5-HO-Pro- | tBuNH- |
| 593 | 4-[MorAc-NMe]-Pho-Ac | CarCH₂ | Bz | 4-HO-Pro- | tBuNH- |
| 594 | 4-[MorAc-NMe]-PhoAc- | CarCH₂ | Bz | 3-HO-Pro- | tBuNH- |
| 595 | 4-[MorAc-NMe]-PhoAc- | CarCH₂ | Bz | 4,5-diHO-Pro- | tBuNH- |
| 596 | 4-[MorAc-NMe]-PhoAc- | CarCH₂ | Bz | 3,4-diHO-Pro- | tBuNH- |
| 597 | 4-[MorAc-NMe]-PhoAc- | CarCH₂ | Bz | 3,4,5-triHO-Pro- | tBuNH- |
| 598 | 4-[MorAc-NMe]-PhoAc- | CarCH₂ | Bz | 5-Oxo-Pro- | tBuNH- |
| 599 | 4-[MorAc-NMe]-PhoAc- | CarCH₂ | Bz | 4-Oxo-Pro- | tBuNH- |
| 600 | 4-[MorAc-NMe]-PhoAc- | CarCH₂ | Bz | 3-Oxo-Pro- | tBuNH- |
| 601 | 4-[MorAc-NMe]-PhoAc- | CarCH₂ | Bz | 4-Mor-Pro- | tBuNH- |
| 602 | 4-[MorAc-NMe]-PhoAc- | CarCH₂ | Bz | 4-Me₂N-Pro- | tBuNH- |
| 603 | 4-[MorAc-NMe]-PhoAc- | CarCH₂ | Bz | 4-Cl-Pro- | tBuNH- |
| 604 | 4-[MorAc-NMe]-PhoAc- | CarCH₂ | Bz | 3-Cl-Pro- | tBuNH- |

TABLE 1-continued

| Cpd. No. | R¹ | R³ | R⁴ | Z | R⁵ |
|---|---|---|---|---|---|
| 605 | 4-[MorAc-NMe]-PhoAc- | CarCH₂ | Bz | 3,4-diCl-Pro- | tBuNH- |
| 606 | 4-[MorAc-NMe]-PhoAc- | CarCH₂ | Bz | 4-Br-Pro- | tBuNH- |
| 607 | 4-[MorAc-NMe]-PhoAc- | CarCH₂ | Bz | 3-Br-Pro- | tBuNH- |
| 608 | 4-[MorAc-NMe]-PhoAc- | CarCH₂ | Bz | 3,4-diBr-Pro- | tBuNH- |
| 609 | 4-[MorAc-NMe]-PhoAc- | CarCH₂ | Bz | 4-F-Pro- | tBuNH- |
| 610 | 4-[MorAc-NMe]-PhoAc- | CarCH₂ | Bz | 3-F-Pro- | tBuNH- |
| 611 | 4-[MorAc-NMe]-PhoAc- | CarCH₂ | Bz | 4,4-diF-Pro- | tBuNH- |
| 612 | 4-[MorAc-NMe]-PhoAc- | CarCH₂ | Bz | 3,4-diF-Pro- | tBuNH- |
| 613 | 4-[MorAc-NMe]-PhoAc- | CarCH₂ | Bz | 4-I-Pro- | tBuNH- |
| 614 | 4-[MorAc-NMe]-PhoAc- | CarCH₂ | Bz | 3-I-Pro- | tBuNH- |
| 615 | 4-[MorAc-NMe]-PhoAc- | CarCH₂ | Bz | 4,4-diMeO-Pro- | tBuNH- |
| 616 | 4-[MorAc-NMe]-PhoAc- | CarCH₂ | Bz | 4-MeOImin-Pro- | tBuNH- |
| 617 | 4-[MorAc-NMe]-PhoAc- | CarCH₂ | Bz | 4-Ph-S-Pro- | tBuNH- |
| 618 | 4-[MorAc-NMe]-PhoAc- | CarCH₂ | Bz | 4-tBuO-Pro- | tBuNH- |
| 619 | 4-[MorAc-NMe]-PhoAc- | CarCH₂ | Bz | 4-CN-4-HO-Pro- | tBuNH- |
| 620 | 4-[MorAc-NMe]-PhoAc- | CarCH₂ | Bz | Spiro(2,5-dioxo-imidazolidine-4,4'-prolyl)- | tBuNH- |
| 621 | 4-[MorAc-NMe]-PhoAc- | CarCH₂ | Bz | 4-CN-Pro- | tBuNH- |
| 622 | 4-[MorAc-NMe]-PhoAc- | CarCH₂ | Bz | 4-Mec-Pro- | tBuNH- |
| 623 | 4-[MorAc-NMe]-PhoAc- | CarCH₂ | Bz | 4-COOH-Pro- | tBuNH- |
| 624 | 4-[MorAc-NMe]-PhoAc- | CarCH₂ | Bz | 3-Deh-Pro- | tBuNH- |
| 625 | 4-[MorAc-NMe]-PhoAc- | CarCH₂ | Bz | ThiaPro- | tBuNH- |
| 626 | 4-[MorAc-NMe]-PhoAc- | CarCH₂ | Bz | 3,3,5,5-tetMe-ThiaPro- | tBuNH- |
| 627 | 4-[MorAc-NMe]-PhoAc- | CarCH₂ | Bz | 3,3-diMe-Thio-Pro- | tBuNH- |
| 628 | 4-[MorAc-NMe]-PhoAc- | CarCH₂ | Bz | 2,5-Oxaz-3-Oxo-bicyclo[2,2,1]hept-5-yl- | tBuNH- |
| 629 | 4-[MorAc-NMe]-PhoAc- | CarCH₂ | Bz | 2-tBu-2,5-diaza-Oxo-bicyclo[2,2,1]hept-5-yl- | tBuNH- |
| 630 | 4-NH₂-PhoAc- | CarCH₂ | Bz | Pro- | tBuNH- |
| 631 | 3-NH₂-PhoAc- | CarCH₂ | Bz | Pro- | tBuNH- |
| 632 | 2-NH₂-PhoAc- | CarCH₂ | Bz | Pro- | tBuNH- |
| 633 | 2,3-diNH₂-PhoAc- | CarCH₂ | Bz | Pro- | tBuNH- |
| 634 | 2,4-diNH₂-PhoAc- | CarCH₂ | Bz | Pro- | tBuNH- |
| 635 | 4-NH₂-Ph-Ac- | CarCH₂ | Bz | Pro- | tBuNH- |
| 636 | 4-NH₂-Bzc- | CarCH₂ | Bz | Pro- | tBuNH- |
| 637 | 4-Me₂N-PhoAc- | CarCH₂ | Bz | Pro- | tBuNH- |
| 638 | 4-[Me(Bz)N]-PhoAc- | CarCH₂ | Bz | Pro- | tBuNH- |
| 639 | 4-Mor-PhoAc- | CarCH₂ | Bz | Pro- | tBuNH- |
| 640 | 4-[N-Bz-Pipr]-PhoAc- | CarCH₂ | Bz | Pro- | tBuNH- |
| 641 | 4-MeNH-PhoAc- | CarCH₂ | Bz | Pro- | tBuNH- |
| 642 | 4-[(4'Me-Bzc)-NH]-Pho-Ac- | CarCH₂ | Bz | Pro- | tBuNH- |
| 643 | 4-[Bzc-NH]-PhoAc- | CarCH₂ | Bz | Pro- | tBuNH- |
| 644 | 4-[tBoc-NH]-PhoAc- | CarCH₂ | Bz | Pro- | tBuNH- |
| 645 | 4-tBoc-NMe-PhoAc- | CarCH₂ | Bz | Pro- | tBuNH- |
| 646 | 4-[Gly-NH]-PhoAc- | CarCH₂ | Bz | Pro- | tBuNH- |
| 647 | 4-[Gly-NMe]-PhoAc- | CarCH₂ | Bz | Pro- | tBuNH- |
| 648 | 4-[(N-Me-Gly)NMe]-PhoAc- | CarCH₂ | Bz | Pro- | tBuNH- |
| 649 | 4-[(N-tBoc-Gly)NMe]-PhoAc- | CarCH₂ | Bz | Pro- | tBuNH- |
| 650 | 4-[(N-t-Boc-N-Me-Gly)-NMe]-PhoAc- | CarCH₂ | Bz | Pro- | tBuNH- |
| 651 | 4-NH₂-PhoAc- | CarCH₂ | Bz | Pro- | tBuNH- |
| 652 | tBoc | CarCH₂ | Bz | Pro- | tBuNH- |
| 653 | 4-[(4'-MeO-Bzc)NH]-PhoAc- | CarCH₂ | Bz | Pro- | tBuNH- |
| 654 | N-Me-4-PipO-Ac- | CarCH₂ | Bz | Pro- | tBuNH- |
| 655 | 4-NH₂-cHxO-Ac- | CarCH₂ | Bz | Pro- | tBuNH- |
| 656 | 4-[MorAc-NMe]-PhoAc- | CarCH₂ | Bz | Pro- | tBuNH- |
| 657 | 2-Quix-CO- | CarCH₂ | Bz | 2-Azep-CO- | tBuNH- |
| 658 | 2-Quix-CO- | CarCH₂ | Bz | 7-HO-2-Azep-CO- | tBuNH- |
| 659 | 2-Quix-CO- | CarCH₂ | Bz | 6-HO-2-Azep-CO- | tBuNH- |
| 660 | 2-Quix-CO- | CarCH₂ | Bz | 5-HO-2-Azep-CO- | tBuNH- |
| 661 | 2-Quix-CO- | CarCH₂ | Bz | 4-HO-2-Azep-CO- | tBuNH- |
| 662 | 2-Quix-CO- | CarCH₂ | Bz | 3-HO-2-Azep-CO- | tBuNH- |
| 663 | 2-Quix-CO- | CarCH₂ | Bz | 6-Cl-2-Azep-CO- | tBuNH- |
| 664 | 2-Quix-CO- | CarCH₂ | Bz | 5-Cl-2-Azep-CO- | tBuNH- |
| 665 | 2-Quix-CO- | CarCH₂ | Bz | 4-Cl-2-Azep-CO- | tBuNH- |
| 666 | 2-Quix-CO- | CarCH₂ | Bz | 3-Cl-2-Azep-CO- | tBuNH- |
| 667 | 2-Quix-CO- | CarCH₂ | Bz | 6-Br-2-Azep-CO- | tBuNH- |
| 668 | 2-Quix-CO- | CarCH₂ | Bz | 5-Br-2-Azep-CO- | tBuNH- |
| 669 | 2-Quix-CO- | CarCH₂ | Bz | 4-Br-2-Azep-CO- | tBuNH- |
| 670 | 2-Quix-CO- | CarCH₂ | Bz | 3-Br-2-Azep-CO- | tBuNH- |
| 671 | 2-Quix-CO- | CarCH₂ | Bz | 6-F-2-Azep-CO- | tBuNH- |
| 672 | 2-Quix-CO- | CarCH₂ | Bz | 5-F-2-Azep-CO- | tBuNH- |

TABLE 1-continued

| Cpd. No. | R¹ | R³ | R⁴ | Z | R⁵ |
|---|---|---|---|---|---|
| 673 | 2-Quix-CO- | CarCH₂ | Bz | 4-F-2-Azep-CO- | tBuNH- |
| 674 | 2-Quix-CO- | CarCH₂ | Bz | 3-F-2-Azep-CO- | tBuNH- |
| 675 | 2-Quix-CO- | CarCH₂ | Bz | 3,3-diF-2-Azep-CO- | tBuNH- |
| 676 | 2-Quix-CO- | CarCH₂ | Bz | 6-Oxo-2-Azep-CO- | tBuNH- |
| 677 | 2-Quix-CO- | CarCH₂ | Bz | 5-Oxo-2-Azep-CO- | tBuNH- |
| 678 | 2-Quix-CO- | CarCH₂ | Bz | 4-Oxo-2-Azep-CO- | tBuNH- |
| 679 | 2-Quix-CO- | CarCH₂ | Bz | 3-Oxo-2-Azep-CO- | tBuNH- |
| 680 | 2-Quix-CO- | CarCH₂ | Bz | 1,4-Diaz-2-Oxo-5-Azep-CO- | tBuNH- |
| 681 | 2-Quix-CO- | CarCH₂ | Bz | 1,4-Diaz-5-Oxo-2-Azep-CO- | tBuNH- |
| 682 | 2-Quix-CO- | CarCH₂ | Bz | 1,4-Oxaz-2-Oxo-5-Azep-CO- | tBuNH- |
| 683 | 2-Quix-CO- | CarCH₂ | Bz | 1,4-Oxaz-7-Oxo-3-Azep-CO- | tBuNH- |
| 684 | 2-Quix-CO- | CarCH₂ | Bz | 1,4-Oxaz-7-Oxo-5-Azep-CO- | tBuNH- |
| 685 | 2-Quix-CO- | CarCH₂ | Bz | 1,4-Diaz-7-Oxo-5-Azep-CO- | tBuNH- |
| 686 | 2-Quix-CO- | CarCH₂ | Bz | 6-HO-2-Pip-CO- | tBuNH- |
| 687 | 2-Quix-CO- | CarCH₂ | Bz | 5-HO-2-Pip-CO- | tBuNH- |
| 688 | 2-Quix-CO- | CarCH₂ | Bz | 4-HO-2-Pip-CO- | tBuNH- |
| 689 | 2-Quix-CO- | CarCH₂ | Bz | 3-HO-2-Pip-CO- | tBuNH- |
| 690 | 2-Quix-CO- | CarCH₂ | Bz | 5-Cl-2-Pip-CO- | tBuNH- |
| 691 | 2-Quix-CO- | CarCH₂ | Bz | 4-Cl-2-Pip-CO- | tBuNH- |
| 692 | 2-Quix-CO- | CarCH₂ | Bz | 3-Cl-2-Pip-CO- | tBuNH- |
| 693 | 2-Quix-CO- | CarCH₂ | Bz | 5-Br-2-Pip-CO- | tBuNH- |
| 694 | 2-Quix-CO- | CarCH₂ | Bz | 4-Br-2-Pip-CO- | tBuNH- |
| 695 | 2-Quix-CO- | CarCH₂ | Bz | 3-Br-2-Pip-CO- | tBuNH- |
| 696 | 2-Quix-CO- | CarCH₂ | Bz | 5-F-2-Pip-CO- | tBuNH- |
| 697 | 2-Quix-CO- | CarCH₂ | Bz | 4-F-2-Pip-CO- | tBuNH- |
| 698 | 2-Quix-CO- | CarCH₂ | Bz | 3-F-2-Pip-CO- | tBuNH- |
| 699 | 2-Quix-CO- | CarCH₂ | Bz | 4,4-diF-2-Pip-CO- | tBuNH- |
| 700 | 2-Quix-CO- | CarCH₂ | Bz | 3-Oxo-6-Mor-CO- | tBuNH- |
| 701 | 2-Quix-CO- | CarCH₂ | Bz | 2-Oxo-4-Pipr-CO- | tBuNH- |
| 702 | Bzc | CarCH₂ | Bz | 2-Azep-CO- | tBuNH- |
| 703 | Bzc | CarCH₂ | Bz | 7-HO-2-Azep-CO- | tBuNH- |
| 704 | Bzc | CarCH₂ | Bz | 6-HO-2-Azep-CO- | tBuNH- |
| 705 | Bzc | CarCH₂ | Bz | 5-HO-2-Azep-CO- | tBuNH- |
| 706 | Bzc | CarCH₂ | Bz | 4-HO-2-Azep-CO- | tBuNH- |
| 707 | Bzc | CarCH₂ | Bz | 3-HO-2-Azep-CO- | tBuNH- |
| 708 | Bzc | CarCH₂ | Bz | 6-Cl-2-Azep-CO- | tBuNH- |
| 709 | Bzc | CarCH₂ | Bz | 5-Cl-2-Azep-CO- | tBuNH- |
| 710 | Bzc | CarCH₂ | Bz | 4-Cl-2-Azep-CO- | tBuNH- |
| 711 | Bzc | CarCH₂ | Bz | 3-Cl-2-Azep-CO- | tBuNH- |
| 712 | Bzc | CarCH₂ | Bz | 6-Br-2-Azep-CO- | tBuNH- |
| 713 | Bzc | CarCH₂ | Bz | 5-Br-2-Azep-CO- | tBuNH- |
| 714 | Bzc | CarCH₂ | Bz | 4-Br-2-Azep-CO- | tBuNH- |
| 715 | Bzc | CarCH₂ | Bz | 3-Br-2-Azep-CO- | tBuNH- |
| 716 | Bzc | CarCH₂ | Bz | 6-F-2-Azep-CO- | tBuNH- |
| 717 | Bzc | CarCH₂ | Bz | 5-F-2-Azep-CO- | tBuNH- |
| 718 | Bzc | CarCH₂ | Bz | 4-F-2-Azep-CO- | tBuNH- |
| 719 | Bzc | CarCH₂ | Bz | 3-F-2-Azep-CO- | tBuNH- |
| 720 | Bzc | CarCH₂ | Bz | 3,3-diF-2-Azep-CO- | tBuNH- |
| 721 | Bzc | CarCH₂ | Bz | 6-Oxo-2-Azep-CO- | tBuNH- |
| 722 | Bzc | CarCH₂ | Bz | 5-Oxo-2-Azep-CO- | tBuNH- |
| 723 | Bzc | CarCH₂ | Bz | 4-Oxo-2-Azep-CO- | tBuNH- |
| 724 | Bzc | CarCH₂ | Bz | 3-Oxo-2-Azep-CO- | tBuNH- |
| 725 | Bzc | CarCH₂ | Bz | 1,4-Diaz-2-Oxo-5-Azep-CO- | tBuNH- |
| 726 | Bzc | CarCH₂ | Bz | 1,4-Diaz-5-Oxo-2-Azep-CO- | tBuNH- |
| 727 | Bzc | CarCH₂ | Bz | 1,4-Oxaz-2-Oxo-5-Azep-CO- | tBuNH- |
| 728 | Bzc | CarCH₂ | Bz | 1,4-Oxaz-7-Oxo-3-Azep-CO- | tBuNH- |
| 729 | Bzc | CarCH₂ | Bz | 1,4-Oxaz-7-oxo-5-Azep-CO- | tBuNH- |
| 730 | Bzc | CarCH₂ | Bz | 1,4-Diaz-7-Oxo-5-Azep-CO- | tBuNH- |
| 731 | Bzc | CarCH₂ | Bz | 6-HO-2-Pip-CO- | tBuNH- |
| 732 | Bzc | CarCH₂ | Bz | 5-HO-2-Pip-CO- | tBuNH- |
| 733 | Bzc | CarCH₂ | Bz | 4-HO-2-Pip-CO- | tBuNH- |
| 734 | Bzc | CarCH₂ | Bz | 3-HO-2-Pip-CO- | tBuNH- |
| 735 | Bzc | CarCH₂ | Bz | 5-Cl-2-Pip-CO- | tBuNH- |
| 736 | Bzc | CarCH₂ | Bz | 4-Cl-2-Pip-CO- | tBuNH- |

TABLE 1-continued

| Cpd. No. | R¹ | R³ | R⁴ | Z | R⁵ |
|---|---|---|---|---|---|
| 737 | Bzc | CarCH₂ | Bz | 3-Cl-2-Pip-CO- | tBuNH- |
| 738 | Bzc | CarCH₂ | Bz | 5-Br-2-Pip-CO- | tBuNH- |
| 739 | Bzc | CarCH₂ | Bz | 4-Br-2-Pip-CO- | tBuNH- |
| 740 | Bzc | CarCH₂ | Bz | 3-Br-2-Pip-CO- | tBuNH- |
| 741 | Bzc | CarCH₂ | Bz | 5-F-2-Pip-CO- | tBuNH- |
| 742 | Bzc | CarCH₂ | Bz | 4-F-2-Pip-CO- | tBuNH- |
| 743 | Bzc | CarCH₂ | Bz | 3-F-2-Pip-CO- | tBuNH- |
| 744 | Bzc | CarCH₂ | Bz | 4,4-diF-2-Pip-CO- | tBuNH- |
| 745 | Bzc | CarCH₂ | Bz | 3-Oxo-6-Mor-CO- | tBuNH- |
| 746 | Bzc | CarCH₂ | Bz | 2-Oxo-4-Pipr-CO- | tBuNH- |
| 747 | Bzc | Me₂NCH₂ | Bz | 4-Cl-Pro- | tBuNH- |
| 748 | Bzc | 2-Car-Et | Bz | 4-Cl-Pro- | tBuNH- |
| 749 | Bzc | CNCH₂ | Bz | 4-Cl-Pro- | tBuNH- |
| 750 | Bzc | iPr | Bz | 4-Cl-Pro- | tBuNH- |
| 751 | Bzc | tBu | Bz | 4-Cl-Pro- | tBuNH- |
| 752 | Bzc | diMeCar-CH₂ | Bz | 4-Cl-Pro- | tBuNH- |
| 753 | Bzc | MorCOCH₂ | Bz | 4-Cl-Pro- | tBuNH- |
| 754 | Bzc | PipCOCH₂ | Bz | 4-Cl-Pro- | tBuNH- |
| 755 | Bzc | 2-NH₂-Et | Bz | 4-Cl-Pro- | tBuNH- |
| 756 | Bzc | 3-NH₂-Pr | Bz | 4-Cl-Pro- | tBuNH- |
| 757 | Bzc | MeCarCH₂ | Bz | 4-Cl-Pro- | tBuNH- |
| 758 | Bzc | EtCarCH₂ | Bz | 4-Cl-Pro- | tBuNH- |
| 759 | Bzc | H | Bz | 4-Cl-Pro- | tBuNH- |
| 760 | Bzc | HOCH₂ | Bz | 4-Cl-Pro- | tBuNH- |
| 761 | Bzc | 4-ThizCH₂ | Bz | 4-Cl-Pro- | tBuNH- |
| 762 | Bzc | 4-ImidCH₂ | Bz | 4-Cl-Pro- | tBuNH- |
| 763 | Bzc | COOH-CH₂ | Bz | 4-Cl-Pro- | tBuNH- |
| 764 | Bzc | 2-COOH-Et | Bz | 4-Cl-Pro- | tBuNH- |
| 765 | Bzc | MeSCH₂ | Bz | 4-Cl-Pro- | tBuNH- |
| 766 | Bzc | SamCH₂ | Bz | 4-Cl-Pro- | tBuNH- |
| 767 | Bzc | Bz | Bz | 4-Cl-Pro- | tBuNH- |
| 768 | Bzc | SimCH₂ | Bz | 4-Cl-Pro- | tBuNH- |
| 769 | Bzc | HiaCH₂ | Bz | 4-Cl-Pro- | tBuNH- |
| 770 | Bzc | 2-Sim-Et | Bz | 4-Cl-Pro- | tBuNH- |
| 771 | Bzc | 2-Hia-Et | Bz | 4-Cl-Pro- | tBuNH- |
| 772 | Bzc | NH₂CH₂ | Bz | 4-Cl-Pro- | tBuNH- |
| 773 | Bzc | MeNHCH₂ | Bz | 4-Cl-Pro- | tBuNH- |
| 774 | 2-Quix-CO- | 2-Car-Et | Bz | 4-Cl-Pro- | tBuNH- |
| 775 | 2-Quix-CO- | CNCH₂ | Bz | 4-Cl-Pro- | tBuNH- |
| 776 | 2-Quix-CO- | iPr | Bz | 4-Cl-Pro- | tBuNH- |
| 777 | 2-Quix-CO- | tBu | Bz | 4-Cl-Pro- | tBuNH- |
| 778 | 2-Quix-CO- | diMeCar-CH₂ | Bz | 4-Cl-Pro- | tBuNH- |
| 779 | 2-Quix-CO- | MorCOCH₂ | Bz | 4-Cl-Pro- | tBuNH- |
| 780 | 2-Quix-CO- | PipCOCH₂ | Bz | 4-Cl-Pro- | tBuNH- |
| 781 | 2-Quix-CO- | 2-NH₂-Et | Bz | 4-Cl-Pro- | tBuNH- |
| 782 | 2-Quix-CO- | 3-NH₂-Pr | Bz | 4-Cl-Pro- | tBuNH- |
| 783 | 2-Quix-CO- | MeCarCH₂ | Bz | 4-Cl-Pro- | tBuNH- |
| 784 | 2-Quix-CO- | EtCarCH₂ | Bz | 4-Cl-Pro- | tBuNH- |
| 785 | 2-Quix-CO- | H | Bz | 4-Cl-Pro- | tBuNH- |
| 786 | 2-Quix-CO- | HOCH₂ | Bz | 4-Cl-Pro- | tBuNH- |
| 787 | 2-Quix-CO- | 4-ThizCH₂ | Bz | 4-Cl-Pro- | tBuNH- |
| 788 | 2-Quix-CO- | 4-ImidCH₂ | Bz | 4-Cl-Pro- | tBuNH- |
| 789 | 2-Quix-CO- | COOH-CH₂ | Bz | 4-Cl-Pro- | tBuNH- |
| 790 | 2-Quix-CO- | 2-COOH-Et | Bz | 4-Cl-Pro- | tBuNH- |
| 791 | 2-Quix-CO- | MeSCH₂ | Bz | 4-Cl-Pro- | tBuNH- |
| 792 | 2-Quix-CO- | SamCH₂ | Bz | 4-Cl-Pro- | tBuNH- |
| 793 | 2-Quix-CO- | Bz | Bz | 4-Cl-Pro- | tBuNH- |
| 794 | 2-Quix-CO- | SimCH₂ | Bz | 4-Cl-Pro- | tBuNH- |
| 795 | 2-Quix-CO- | HiaCH₂ | Bz | 4-Cl-Pro- | tBuNH- |
| 796 | 2-Quix-CO- | 2-Sim-Et | Bz | 4-Cl-Pro- | tBuNH- |
| 797 | 2-Quix-CO- | 2-Hia-Et | Bz | 4-Cl-Pro- | tBuNH- |
| 798 | 2-Quix-CO- | NH₂CH₂ | Bz | 4-Cl-Pro- | tBuNH- |
| 799 | 2-Quix-CO- | MeNHCH₂ | Bz | 4-Cl-Pro- | tBuNH- |
| 800 | 2-Quix-CO- | Me₂NCH₂ | Bz | 4-Cl-Pro- | tBuNH- |
| 801 | 3-Quin-CO- | CarCH₂ | Bz | 4-Cl-Pro- | tBuNH- |
| 802 | 4-Quin-CO- | CarCH₂ | Bz | 4-Cl-Pro- | tBuNH- |
| 803 | 2-Pyr-CO- | CarCH₂ | Bz | 4-Cl-Pro- | tBuNH- |
| 804 | 3-Pyr-CO- | CarCH₂ | Bz | 4-Cl-Pro- | tBuNH- |
| 805 | 4-Pyr-CO- | CarCH₂ | Bz | 4-Cl-Pro- | tBuNH- |
| 806 | 4-MeO-2-Quin-CO- | CarCH₂ | Bz | 4-Cl-Pro- | tBuNH- |
| 807 | 2-Np-CO- | CarCH₂ | Bz | 4-Cl-Pro- | tBuNH- |
| 808 | 1-Np-CO- | CarCH₂ | Bz | 4-Cl-Pro- | tBuNH- |
| 809 | 2-Bfur-CO- | CarCH₂ | Bz | 4-Cl-Pro- | tBuNH- |
| 810 | 3-Bfur-CO- | CarCH₂ | Bz | 4-Cl-Pro- | tBuNH- |
| 811 | 5-Bu-2-Pyr-CO- | CarCH₂ | Bz | 4-Cl-Pro- | tBuNH- |
| 812 | 4-HO-2-Quin-CO- | CarCH₂ | Bz | 4-Cl-Pro- | tBuNH- |

TABLE 1-continued

| Cpd. No. | R¹ | R³ | R⁴ | Z | R⁵ |
|---|---|---|---|---|---|
| 813 | 3-HO-2-Quix-CO- | CarCH₂ | Bz | 4-Cl-Pro- | tBuNH- |
| 814 | 1-Np-Sfo- | CarCH₂ | Bz | 4-Cl-Pro- | tBuNH- |
| 815 | 2-Np-Sfo- | CarCH₂ | Bz | 4-Cl-Pro- | tBuNH- |
| 816 | Boz | CarCH₂ | Bz | 4-Cl-Pro- | tBuNH- |
| 817 | Bz-NHCO- | CarCH₂ | Bz | 4-Cl-Pro- | tBuNH- |
| 818 | Bz-NH-CS- | CarCH₂ | Bz | 4-Cl-Pro- | tBuNH- |
| 819 | 3-Ind-CO- | CarCH₂ | Bz | 4-Cl-Pro- | tBuNH- |
| 820 | 2-Pyrd-CO- | CarCH₂ | Bz | 4-Cl-Pro- | tBuNH- |
| 821 | 2-Pip-CO- | CarCH₂ | Bz | 4-Cl-Pro- | tBuNH- |
| 822 | 2-Thi-CO- | CarCH₂ | Bz | 4-Cl-Pro- | tBuNH- |
| 823 | MeOCOCO- | CarCH₂ | Bz | 4-Cl-Pro- | tBuNH- |
| 824 | PhoAc- | CarCH₂ | Bz | 4-Cl-Pro- | tBuNH- |
| 825 | 3-Bzisox-CO- | CarCH₂ | Bz | 4-Cl-Pro- | tBuNH- |
| 826 | 2-Bzim-CO- | CarCH₂ | Bz | 4-Cl-Pro- | tBuNH- |
| 827 | N-Me-3-Ind-CO- | CarCH₂ | Bz | 4-Cl-Pro- | tBuNH- |
| 828 | 2-Bzthiaz-CO- | CarCH₂ | Bz | 4-Cl-Pro- | tBuNH- |
| 829 | 2-Bzoxaz-CO- | CarCH₂ | Bz | 4-Cl-Pro- | tBuNH- |
| 830 | 5-MeO-2-Ind-CO- | CarCH₂ | Bz | 4-Cl-Pro- | tBuNH- |
| 831 | 5-HO-2-Ind-CO- | CarCH₂ | Bz | 4-Cl-Pro- | tBuNH- |
| 832 | 5-AcO-2-Ind-CO- | CarCH₂ | Bz | 4-Cl-Pro- | tBuNH- |
| 833 | 5-NH₂AcO-2-Ind-CO- | CarCH₂ | Bz | 4-Cl-Pro- | tBuNH- |
| 834 | 5-Bzim-CO- | CarCH₂ | Bz | 4-Cl-Pro- | tBuNH- |
| 835 | (2-NpO)Ac- | CarCH₂ | Bz | 4-Cl-Pro- | tBuNH- |
| 836 | (1-NpO)Ac- | CarCH₂ | Bz | 4-Cl-Pro- | tBuNH- |
| 837 | 1-NpOCO- | CarCH₂ | Bz | 4-Cl-Pro- | tBuNH- |
| 838 | 2-NpOCO- | CarCH₂ | Bz | 4-Cl-Pro- | tBuNH- |
| 839 | (3-PhPho)Ac- | CarCH₂ | Bz | 4-Cl-Pro- | tBuNH- |
| 840 | 2-Quix-CO- | CarCH₂ | Bz | 4-Cl-Pro- | 3-HOPr-NH- |
| 841 | 2-Quix-CO- | CarCH₂ | Bz | 4-Cl-Pro- | BuNH- |
| 842 | 2-Quix-CO- | CarCH₂ | Bz | 4-Cl-Pro- | tBuO- |
| 843 | 2-Quix-CO- | CarCH₂ | Bz | 4-Cl-Pro- | 1,1-diMe-2-HOEt-NH- |
| 844 | Bzc | CarCH₂ | Bz | 4-Cl-Pro- | 3-HOPr-NH- |
| 845 | Bzc | CarCH₂ | Bz | 4-Cl-Pro- | BuNH- |
| 846 | Bzc | CarCH₂ | Bz | 4-Cl-Pro- | tBuO- |
| 847 | Bzc | CarCH₂ | Bz | 4-Cl-Pro- | 1,1-diMe-2-HOEt-NH- |
| 848 | 3-NH₂-PhoAc- | CarCH₂ | Bz | 4-Cl-Pro- | tBuNH- |
| 849 | 2-NH₂-PhoAc- | CarCH₂ | Bz | 4-Cl-Pro- | tBuNH- |
| 850 | 2,3-diNH₂-PhoAc- | CarCH₂ | Bz | 4-Cl-Pro- | tBuNH- |
| 851 | 2,4-diNH₂-PhoAc- | CarCH₂ | Bz | 4-Cl-Pro- | tBuNH- |
| 852 | 4-NH₂-Ph-CO- | CarCH₂ | Bz | 4-Cl-Pro- | tBuNH- |
| 853 | 4-NH₂-Bzc | CarCH₂ | Bz | 4-Cl-Pro- | tBuNH- |
| 854 | 4-Me₂N-PhoAc- | CarCH₂ | Bz | 4-Cl-Pro- | tBuNH- |
| 855 | 4-[Me(Bz)N]-PhoAc- | CarCH₂ | Bz | 4-Cl-Pro- | tBuNH- |
| 856 | 4-Mor-PhoAc- | CarCH₂ | Bz | 4-Cl-Pro- | tBuNH- |
| 857 | 4-[N-Bz-Pipr]-PhoAc- | CarCH₂ | Bz | 4-Cl-Pro- | tBuNH- |
| 858 | 4-MeNH-PhoAc- | CarCH₂ | Bz | 4-Cl-Pro- | tBuNH- |
| 859 | 4-[(4'Me-Bzc)-NH]-PhoAc- | CarCH₂ | Bz | 4-Cl-Pro- | tBuNH- |
| 860 | 4-[tBoc-NH]-PhoAc- | CarCH₂ | Bz | 4-Cl-Pro- | tBuNH- |
| 861 | 4-[tBoc-MeN]-PhoAc- | CarCH₂ | Bz | 4-Cl-Pro- | tBuNH- |
| 862 | 4-[Gly-NH]-PhoAc- | CarCH₂ | Bz | 4-Cl-Pro- | tBuNH- |
| 863 | 4-[Gly-NMe]-PhoAc- | CarCH₂ | Bz | 4-Cl-Pro- | tBuNH- |
| 864 | 4-(N-Me-Gly)NMe-PhoAc- | CarCH₂ | Bz | 4-Cl-Pro- | tBuNH- |
| 865 | 4-[(N-tBoc-Gly)NMe]-PhoAc- | CarCH₂ | Bz | 4-Cl-Pro- | tBuNH- |
| 866 | 4-(N-tBoc-N-Me-Gly)-NMe-PhoAc- | CarCH₂ | Bz | 4-Cl-Pro- | tBuNH- |
| 867 | Boc | CarCH₂ | Bz | 4-Cl-Pro- | tBuNH- |
| 868 | 4-[BrAc-NMe]-PhoAc- | CarCH₂ | Bz | 4-Cl-Pro- | tBuNH- |
| 869 | 4-[(4'-MeO-Bzc)NH]-PhoAc- | CarCH₂ | Bz | 4-Cl-Pro- | tBuNH- |
| 870 | N-Me-4-Pip-O-Ac- | CarCH₂ | Bz | 4-Cl-Pro- | tBuNH- |
| 871 | 4-NH₂-cHxO-Ac- | CarCH₂ | Bz | 4-Cl-Pro- | tBuNH- |
| 872 | 4-NH₂-PhoAc- | CarCH₂ | Bz | 4-Cl-Pro- | 1,1-diMe-2-HOEt-NH- |
| 873 | 3-NH₂-PhoAc- | CarCH₂ | Bz | 4-Cl-Pro- | 1,1-diMe-2-HOEt-NH- |
| 874 | 2-NH₂-PhoAc- | CarCH₂ | Bz | 4-Cl-Pro | 1,1-diMe-2-HOEt-NH- |
| 875 | 2,3-diNH₂-PhoAc- | CarCH₂ | Bz | 4-Cl-Pro- | 1,1-diMe-2-HOEt-NH- |
| 876 | 2,4-diNH₂-PhoAc- | CarCH₂ | Bz | 4-Cl-Pro- | 1,1-diMe-2-HOEt-NH- |
| 877 | 4-NH₂-Ph-CO- | CarCH₂ | Bz | 4-Cl-Pro- | 1,1-diMe-2-HOEt-NH- |
| 878 | 4-NH₂-Bzc | CarCH₂ | Bz | 4-Cl-Pro- | 1,1-diMe-2-HOEt-NH- |
| 879 | 4-Me₂N-PhoAc- | CarCH₂ | Bz | 4-Cl-Pro- | 1,1-diMe-2-HOEt-NH- |
| 880 | 4-[Me(Bz)N]PhoAc- | CarCH₂ | Bz | 4-Cl-Pro- | 1,1-diMe-2-HOEt-NH- |

TABLE 1-continued

| Cpd. No. | R¹ | R³ | R⁴ | Z | R⁵ |
|---|---|---|---|---|---|
| 881 | 4-Mor-PhoAc- | CarCH₂ | Bz | 4-Cl-Pro- | 1,1-diMe-2-HOEt-NH- |
| 882 | 4-[N-Bz-Pipr]-PhoAc- | CarCH₂ | Bz | 4-Cl-Pro- | 1,1-diMe-2-HOEt-NH- |
| 883 | 4-MeNH-PhoAc- | CarCH₂ | Bz | 4-Cl-Pro- | 1,1-diMe-2-HOEt-NH- |
| 884 | 4-[(4'-Me-Bzc)NH]-PhoAc- | CarCH₂ | Bz | 4-Cl-Pro- | 1,1-diMe-2-HOEt-NH- |
| 885 | 4-[Bzc-NH]-PhoAc- | CarCH₂ | Bz | 4-Cl-Pro- | 1,1-diMe-2-HOEt-NH- |
| 886 | 4-[tBoc-NH]-PhoAc- | CarCH₂ | Bz | 4-Cl-Pro- | 1,1-diMe-2-HOEt-NH- |
| 887 | 4-[tBoc-MeN]-PhoAc- | CarCH₂ | Bz | 4-Cl-Pro- | 1,1-diMe-2-HOEt-NH- |
| 888 | 4-[Gly-NH]-PhoAc- | CarCH₂ | Bz | 4-Cl-Pro- | 1,1-diMe-2-HOEt-NH- |
| 889 | 4-[Gly-NMe]-PhoAc- | CarCH₂ | Bz | 4-Cl-Pro- | 1,1-diMe-2-HOEt-NH- |
| 890 | 4-[(N-Me-Gly)-NMe]-PhoAc- | CarCH₂ | Bz | 4-Cl-Pro- | 1,1-diMe-2-HOEt-NH- |
| 891 | 4-[(N-tBoc-Gly)-NMe]-PhoAc- | CarCH₂ | Bz | 4-Cl-Pro- | 1,1-diMe-2-HOEt-NH- |
| 892 | 4-[(N-tBoc-NMe-Gly)NMe]-PhoAc- | CarCH₂ | Bz | 4-Cl-Pro- | 1,1-diMe-2-HOEt-NH- |
| 893 | Boc | CarCH₂ | Bz | 4-Cl-Pro- | 1,1-diMe-2-HOEt-NH- |
| 894 | 4-[(Br-Ac)NMe]-PhoAc- | CarCH₂ | Bz | 4-Cl-Pro- | 1,1-diMe-2-HOEt-NH- |
| 895 | 4-[(4'-MeO-Bzc)-NH]-PhoAc- | CarCH₂ | Bz | 4-Cl-Pro- | 1,1-diMe-2-HOEt-NH- |
| 896 | N-Me-4-PipO-Ac- | CarCH₂ | Bz | 4-Cl-Pro- | 1,1-diMe-2-HOEt-NH- |
| 897 | 4-NH₂-cHxO-Ac- | CarCH₂ | Bz | 4-Cl-Pro- | 1,1-diMe-2-HOEt-NH- |
| 898 | 4-(Mor-Ac)NMe-PhoAc- | CarCH₂ | Bz | 4-Cl-Pro- | 1,1-diMe-2-HOEt-NH- |
| 899 | 4-NH₂-PhoAc- | CarCH₂ | Bz | 4-Cl-Pro- | 1,1-diMe-2-HOPr-NH- |
| 900 | 3-NH₂-PhoAc- | CarCH₂ | Bz | 4-Cl-Pro- | 1,1-diMe-2-HOPr-NH- |
| 901 | 2-NH₂-PhoAc- | CarCH₂ | Bz | 4-Cl-Pro- | 1,1-diMe-2-HOPr-NH- |
| 902 | 2,3-diNH₂-PhoAc- | CarCH₂ | Bz | 4-Cl-Pro- | 1,1-diMe-2-HOPr-NH- |
| 903 | 2,4-diNH₂-PhoAc- | CarCH₂ | Bz | 4-Cl-Pro- | 1,1-diMe-2-HOPr-NH- |
| 904 | 4-NH₂-Ph-CO- | CarCH₂ | Bz | 4-Cl-Pro- | 1,1-diMe-2-HOPr-NH- |
| 905 | 4-NH₂-Bzc- | CarCH₂ | Bz | 4-Cl-Pro- | 1,1-diMe-2-HOPr-NH- |
| 906 | 4-Me₂N-PhoAc- | CarCH₂ | Bz | 4-Cl-Pro- | 1,1-diMe-2-HOPr-NH- |
| 907 | 4-[Me(Bz)N]-PhoAc- | CarCH₂ | Bz | 4-Cl-Pro- | 1,1-diMe-2-HOPr-NH- |
| 908 | 4-Mor-PhoAc- | CarCH₂ | Bz | 4-Cl-Pro- | 1,1-diMe-2-HOPr-NH- |
| 909 | 4-[N-Bz-Pipr]-PhoAc- | CarCH₂ | Bz | 4-Cl-Pro- | 1,1-diMe-2-HOPr-NH- |
| 910 | 4-MeNH-PhoAc- | CarCH₂ | Bz | 4-Cl-Pro- | 1,1-diMe-2-HOPr-NH- |
| 911 | 4-[(4'-Me-Bzc)NH]-PhoAc- | CarCH₂ | Bz | 4-Cl-Pro- | 1,1-diMe-2-HOPr-NH- |
| 912 | 4-[Bzc-NH]-PhoAc- | CarCH₂ | Bz | 4-Cl-Pro- | 1,1-diMe-2-HOPr-NH- |
| 913 | 4-[tBoc-NH]-PhoAc- | CarCH₂ | Bz | 4-Cl-Pro- | 1,1-diMe-2-HOPr-NH- |
| 914 | 4-[tBoc-MeN]-PhoAc- | CarCH₂ | Bz | 4-Cl-Pro- | 1,1-diMe-2-HOPr-NH- |
| 915 | 4-[Gly-NH]-PhoAc- | CarCH₂ | Bz | 4-Cl-Pro- | 1,1-diMe-2-HOPr-NH- |
| 916 | 4-[Gly-NMe]-PhoAc- | CarCH₂ | Bz | 4-Cl-Pro- | 1,1-diMe-2-HOPr-NH- |
| 917 | 4-[N-Me-Gly)NMe]-PhoAc- | CarCH₂ | Bz | 4-Cl-Pro- | 1,1-diMe-2-HOPr-NH- |
| 918 | 4-[(N-tBoc-Gly)-NMe]-PhoAc- | CarCH₂ | Bz | 4-Cl-Pro- | 1,1-diMe-2-HOPr-NH- |
| 919 | 4-[(N-tBoc-NMe-Gly)NMe]-PhoAc- | CarCH₂ | Bz | 4-Cl-Pro- | 1,1-diMe-2-HOPr-NH- |
| 920 | Boc | CarCH₂ | Bz | 4-Cl-Pro- | 1,1-diMe-2-HOPr-NH- |
| 921 | 4-(Br-Ac)NMe-PhoAc- | CarCH₂ | Bz | 4-Cl-Pro- | 1,1-diMe-2-HOPr-NH- |
| 922 | 4-[(4'-MeO-Bzc)-NH]-PhoAc- | CarCH₂ | Bz | 4-Cl-Pro- | 1,1-diMe-2-HOPr-NH- |
| 923 | N-Me-4-PipO-Ac- | CarCH₂ | Bz | 4-Cl-Pro- | 1,1-diMe-2-HOPr-NH- |
| 924 | 4-NH₂-cHxO-Ac- | CarCH₂ | Bz | 4-Cl-Pro- | 1,1-diMe-2-HOPr-NH- |
| 925 | 4-(Mor-Ac)NMe-PhoAc- | CarCH₂ | Bz | 4-Cl-Pro- | 1,1-diMe-2-HOPr-NH- |
| 926 | 2-Quin-CO- | CarCH₂ | Bz | 4-Cl-Pro- | 1,1-diMe-2-HOEt-NH- |
| 927 | 3-Quin-CO- | CarCH₂ | Bz | 4-Cl-Pro- | 1,1-diMe-2-HOEt-NH- |
| 928 | 4-Quin-CO- | CarCH₂ | Bz | 4-Cl-Pro- | 1,1-diMe-2-HOEt-NH- |
| 929 | 2-Pyr-CO- | CarCH₂ | Bz | 4-Cl-Pro- | 1,1-diMe-2-HOEt-NH- |
| 930 | 3-Pyr-CO- | CarCH₂ | Bz | 4-Cl-Pro- | 1,1-diMe-2-HOEt-NH- |
| 931 | 4-Pyr-CO- | CarCH₂ | Bz | 4-Cl-Pro- | 1,1-diMe-2-HOEt-NH- |
| 932 | 4-MeO-2-Quin-CO- | CarCH₂ | Bz | 4-Cl-Pro- | 1,1-diMe-2-HOEt-NH- |
| 933 | 2-Np-CO- | CarCH₂ | Bz | 4-Cl-Pro- | 1,1-diMe-2-HOEt-NH- |
| 934 | 1-Np-CO- | CarCH₂ | Bz | 4-Cl-Pro- | 1,1-diMe-2-HOEt-NH- |
| 935 | 2-Bfur-CO- | CarCH₂ | Bz | 4-Cl-Pro- | 1,1-diMe-2-HOEt-NH- |
| 936 | 3-Bfur-CO- | CarCH₂ | Bz | 4-Cl-Pro- | 1,1-diMe-2-HOEt-NH- |
| 937 | 5-Bu-2-Pyr-CO- | CarCH₂ | Bz | 4-Cl-Pro- | 1,1-diMe-2-HOEt-NH- |

TABLE 1-continued

| Cpd. No. | R¹ | R³ | R⁴ | Z | R⁵ |
|---|---|---|---|---|---|
| 938 | 4-HO-2-Quin-CO- | CarCH₂ | Bz | 4-Cl-Pro- | 1,1-diMe-2-HOEt-NH- |
| 939 | 3-HO-2-Quix-CO- | CarCH₂ | Bz | 4-Cl-Pro- | 1,1-diMe-2-HOEt-NH- |
| 940 | 1-Np-Sfo- | CarCH₂ | Bz | 4-Cl-Pro- | 1,1-diMe-2-HOEt-NH- |
| 941 | 2-Np-Sfo- | CarCH₂ | Bz | 4-Cl-Pro- | 1,1-diMe-2-HOEt-NH- |
| 942 | Boz | CarCH₂ | Bz | 4-Cl-Pro- | 1,1-diMe-2-HOEt-NH- |
| 943 | Bz-NHCO- | CarCH₂ | Bz | 4-Cl-Pro- | 1,1-diMe-2-HOEt-NH- |
| 944 | Bz-NHCS- | CarCH₂ | Bz | 4-Cl-Pro- | 1,1-diMe-2-HOEt-NH- |
| 945 | 2-Ind-CO- | CarCH₂ | Bz | 4-Cl-Pro- | 1,1-diMe-2-HOEt-NH- |
| 946 | 3-Ind-CO- | CarCH₂ | Bz | 4-Cl-Pro- | 1,1-diMe-2-HOEt-NH- |
| 947 | tBoc | CarCH₂ | Bz | 4-Cl-Pro- | 1,1-diMe-2-HOEt-NH- |
| 948 | 2-Pyrd-CO- | CarCH₂ | Bz | 4-Cl-Pro- | 1,1-diMe-2-HOEt-NH- |
| 949 | 2-Pip-CO- | CarCH₂ | Bz | 4-Cl-Pro- | 1,1-diMe-2-HOEt-NH- |
| 950 | 2-Thi-CO- | CarCH₂ | Bz | 4-Cl-Pro- | 1,1-diMe-2-HOEt-NH- |
| 951 | MeOCOCO- | CarCH₂ | Bz | 4-Cl-Pro- | 1,1-diMe-2-HOEt-NH- |
| 952 | PhoAc- | CarCH₂ | Bz | 4-Cl-Pro- | 1,1-diMe-2-HOEt-NH- |
| 953 | MPhoAc- | CarCH₂ | Bz | 4-Cl-Pro- | 1,1-diMe-2-HOEt-NH- |
| 954 | 3-Bzisox-CO- | CarCH₂ | Bz | 4-Cl-Pro- | 1,1-diMe-2-HOEt-NH- |
| 955 | 2-Bzim-CO- | CarCH₂ | Bz | 4-Cl-Pro- | 1,1-diMe-2-HOEt-NH- |
| 956 | N-Me-3-Ind-CO- | CarCH₂ | Bz | 4-Cl-Pro- | 1,1-diMe-2-HOEt-NH- |
| 957 | 2-Bzthiaz-CO- | CarCH₂ | Bz | 4-Cl-Pro- | 1,1-diMe-2-HOEt-NH- |
| 958 | 2-Bzoxaz-CO- | CarCH₂ | Bz | 4-Cl-Pro- | 1,1-diMe-2-HOEt-NH- |
| 959 | 5-MeO-2-Ind-CO- | CarCH₂ | Bz | 4-Cl-Pro- | 1,1-diMe-2-HOEt-NH- |
| 960 | 5-HO-2-Ind-CO- | CarCH₂ | Bz | 4-Cl-Pro- | 1,1-diMe-2-HOEt-NH- |
| 961 | 5-AcO-2-Ind-CO- | CarCH₂ | Bz | 4-Cl-Pro- | 1,1-diMe-2-HOEt-NH- |
| 962 | 5-NH₂AcO-2-Ind-CO- | CarCH₂ | Bz | 4-Cl-Pro- | 1,1-diMe-2-HOEt-NH- |
| 963 | 5-Bzim-CO- | CarCH₂ | Bz | 4-Cl-Pro- | 1,1-diMe-2-HOEt-NH- |
| 964 | (1-NpO)Ac- | CarCH₂ | Bz | 4-Cl-Pro- | 1,1-diMe-2-HOEt-NH- |
| 965 | 1-NpOCO- | CarCH₂ | Bz | 4-Cl-Pro- | 1,1-diMe-2-HOEt-NH- |
| 966 | 2-NpOCO- | CarCH₂ | Bz | 4-Cl-Pro- | 1,1-diMe-2-HOEt-NH- |
| 967 | (3-PhPho)Ac- | CarCH₂ | Bz | 4-Cl-Pro- | 1,1-diMe-2-HOEt-NH- |
| 968 | (2-NpO)Ac- | CarCH₂ | Bz | 4-Cl-Pro- | 1,1-diMe-2-HOEt-NH- |
| 969 | Bzc | CarCH₂ | Bz | 4-Cl-Pro- | 1,1-diMe-2-HOPr-NH- |
| 970 | 2-Quix-CO- | CarCH₂ | Bz | 4-Cl-Pro- | 1,1-diMe-2-HOPr-NH- |
| 971 | 2-Quin-CO- | CarCH₂ | Bz | 4-Cl-Pro- | 1,1-diMe-2-HOPr-NH- |
| 972 | 3-Quin-CO- | CarCH₂ | Bz | 4-Cl-Pro- | 1,1-diMe-2-HOPr-NH- |
| 973 | 4-Quin-CO- | CarCH₂ | Bz | 4-Cl-Pro- | 1,1-diMe-2-HOPr-NH- |
| 974 | 2-Pyr-CO- | CarCH₂ | Bz | 4-Cl-Pro- | 1,1-diMe-2-HOPr-NH- |
| 975 | 3-Pyr-CO- | CarCH₂ | Bz | 4-Cl-Pro- | 1,1-diMe-2-HOPr-NH- |
| 976 | 4-Pyr-CO- | CarCH₂ | Bz | 4-Cl-Pro- | 1,1-diMe-2-HOPr-NH- |
| 977 | 4-MeO-2-Quin-CO- | CarCH₂ | Bz | 4-Cl-Pro- | 1,1-diMe-2-HOPr-NH- |
| 978 | 2-Np-CO- | CarCH₂ | Bz | 4-Cl-Pro- | 1,1-diMe-2-HOPr-NH- |
| 979 | 1-Np-CO- | CarCH₂ | Bz | 4-Cl-Pro- | 1,1-diMe-2-HOPr-NH- |
| 980 | 2-Bfur-CO- | CarCH₂ | Bz | 4-Cl-Pro- | 1,1-diMe-2-HOPr-NH- |
| 981 | 3-Bfur-CO- | CarCH₂ | Bz | 4-Cl-Pro- | 1,1-diMe-2-HOPr-NH- |
| 982 | 5-Bu-2-Pyr-CO- | CarCH₂ | Bz | 4-Cl-Pro- | 1,1-diMe-2-HOPr-NH- |
| 983 | 4-HO-2-Quin-CO- | CarCH₂ | Bz | 4-Cl-Pro- | 1,1-diMe-2-HOPr-NH- |
| 984 | 3-HO-2-Quix-CO- | CarCH₂ | Bz | 4-Cl-Pro- | 1,1-diMe-2-HOPr-NH- |
| 985 | 1-Np-Sfo- | CarCH₂ | Bz | 4-Cl-Pro- | 1,1-diMe-2-HOPr-NH- |
| 986 | 2-Np-Sfo- | CarCH₂ | Bz | 4-Cl-Pro- | 1,1-diMe-2-HOPr-NH- |
| 987 | Boz | CarCH₂ | Bz | 4-Cl-Pro- | 1,1-diMe-2-HOPr-NH- |
| 988 | Bz-NHCO- | CarCH₂ | Bz | 4-Cl-Pro- | 1,1-diMe-2-HOPr-NH- |
| 989 | Bz-NHCS- | CarCH₂ | Bz | 4-Cl-Pro- | 1,1-diMe-2-HOPr-NH- |
| 990 | 2-Ind-CO- | CarCH₂ | Bz | 4-Cl-Pro- | 1,1-diMe-2-HOPr-NH- |
| 991 | 3-Ind-CO- | CarCH₂ | Bz | 4-Cl-Pro- | 1,1-diMe-2-HOPr-NH- |
| 992 | tBoc | CarCH₂ | Bz | 4-Cl-Pro- | 1,1-diMe-2-HOPr-NH- |
| 993 | 2-Pyrd-CO- | CarCH₂ | Bz | 4-Cl-Pro- | 1,1-diMe-2-HOPr-NH- |
| 994 | 2-Pip-CO- | CarCH₂ | Bz | 4-Cl-Pro- | 1,1-diMe-2-HOPr-NH- |
| 995 | 2-Thi-CO- | CarCH₂ | Bz | 4-Cl-Pro- | 1,1-diMe-2-HOPr-NH- |
| 996 | MecCO- | CarCH₂ | Bz | 4-Cl-Pro- | 1,1-diMe-2-HOPr-NH- |
| 997 | PhoAc- | CarCH₂ | Bz | 4-Cl-Pro- | 1,1-diMe-2-HOPr-NH- |
| 998 | MPhoAc- | CarCH₂ | Bz | 4-Cl-Pro- | 1,1-diMe-2-HOPr-NH- |
| 999 | 3-Bzisox-CO- | CarCH₂ | Bz | 4-Cl-Pro- | 1,1-diMe-2-HOPr-NH- |
| 1000 | 2-Bzim-CO- | CarCH₂ | Bz | 4-Cl-Pro- | 1,1-diMe-2-HOPr-NH- |
| 1001 | N-Me-3-Ind-CO- | CarCH₂ | Bz | 4-Cl-Pro- | 1,1-diMe-2-HOPr-NH- |
| 1002 | 2-Bzthiaz-CO- | CarCH₂ | Bz | 4-Cl-Pro- | 1,1-diMe-2-HOPr-NH- |
| 1003 | 2-Bzoxaz-CO- | CarCH₂ | Bz | 4-Cl-Pro- | 1,1-diMe-2-HOPr-NH- |
| 1004 | 5-MeO-2-Ind-CO- | CarCH₂ | Bz | 4-Cl-Pro- | 1,1-diMe-2-HOPr-NH- |
| 1005 | 5-HO-2-Ind-CO- | CarCH₂ | Bz | 4-Cl-Pro- | 1,1-diMe-2-HOPr-NH- |
| 1006 | 5-AcO-2-Ind-CO- | CarCH₂ | Bz | 4-Cl-Pro- | 1,1-diMe-2-HOPr-NH- |
| 1007 | 5-NH₂AcO-2-Ind-CO- | CarCH₂ | Bz | 4-Cl-Pro- | 1,1-diMe-2-HOPr-NH- |
| 1008 | 5-Bzim-CO- | CarCH₂ | Bz | 4-Cl-Pro- | 1,1-diMe-2-HOPr-NH- |
| 1009 | (2-NpO)Ac- | CarCH₂ | Bz | 4-Cl-Pro- | 1,1-diMe-2-HOPr-NH- |
| 1010 | (1-NpO)Ac- | CarCH₂ | Bz | 4-Cl-Pro- | 1,1-diMe-2-HOPr-NH- |

TABLE 1-continued

| Cpd. No. | R¹ | R³ | R⁴ | Z | R⁵ |
|---|---|---|---|---|---|
| 1011 | 1-NpOCO- | CarCH₂ | Bz | 4-Cl-Pro- | 1,1-diMe-2-HOPr-NH- |
| 1012 | 2-NpOCO- | CarCH₂ | Bz | 4-Cl-Pro- | 1,1-diMe-2-HOPr-NH- |
| 1013 | (3-PhPho)Ac- | CarCH₂ | Bz | 4-Cl-Pro- | 1,1-diMe-2-HOPr-NH- |
| 1014 | Bzc | CarCH₂ | 4-Br-Bz | 4-Cl-Pro- | tBuNH- |
| 1015 | 2-Quix-CO- | CarCH₂ | 4-Br-Bz | 4-Cl-Pro- | tBuNH- |
| 1016 | Bzc | CarCH₂ | 4-MeOBz | 4-Cl-Pro- | tBuNH- |
| 1017 | 2-Quix-CO- | CarCH₂ | 4-MeOBz | 4-Cl-Pro- | tBuNH- |
| 1018 | Bzc | CarCH₂ | 4-Me-Bz | 4-Cl-Pro- | tBuNH- |
| 1019 | 2-Quix-CO- | CarCH₂ | 4-Me-Bz | 4-Cl-Pro- | tBuNH- |
| 1020 | Bzc | CarCH₂ | cHxCH₂ | 4-Cl-Pro- | tBuNH- |
| 1021 | 2-Quix-CO- | CarCH₂ | cHxCH₂ | 4-Cl-Pro- | tBuNH- |
| 1022 | Bzc | CarCH₂ | Bz | 3-Br-2-Azet-CO- | tBuNH- |
| 1023 | Bzc | CarCH₂ | Bz | 4-tBuO-Pro- | tBuO- |
| 1024 | Bzc | MeSOCH₂ | Bz | 4-Cl-Pro- | tBuNH- |
| 1025 | Bzc | MeSO₂CH₂ | Bz | 4-Cl-Pro- | tBuNH- |
| 1026 | Bzc | MeOCH₂ | Bz | 4-Cl-Pro- | tBuNH- |
| 1027 | Bzc | MecCH₂CH₂ | Bz | 4-Cl-Pro- | tBuNH- |
| 1028 | Bzc | MecCH₂ | Bz | 4-Cl-Pro- | tBuNH- |
| 1029 | 2-Quix-CO- | MeSOCH₂ | Bz | 4-Cl-Pro- | tBuNH- |
| 1030 | 2-Quix-CO- | MeSO₂CH₂ | Bz | 4-Cl-Pro- | tBuNH- |
| 1031 | 2-Quix-CO- | MeOCH₂ | Bz | 4-Cl-Pro- | tBuNH- |
| 1032 | 2-Quix-CO- | MecCH₂CH₂ | Bz | 4-Cl-Pro- | tBuNH- |
| 1033 | 2-Quix-CO- | MecCH₂ | Bz | 4-Cl-Pro- | tBuNH- |
| 1034 | 2-Quin-CO- | MeSOCH₂ | Bz | 4-Cl-Pro- | tBuNH- |
| 1035 | 2-Quin-CO- | MeSO₂CH₂ | Bz | 4-Cl-Pro- | tBuNH- |
| 1036 | 2-Quin-CO- | MeOCH₂- | Bz | 4-Cl-Pro- | tBuNH- |
| 1037 | 2-Quin-CO- | MecCH₂CH₂ | Bz | 4-Cl-Pro- | tBuNH- |
| 1038 | 2-Quin-CO- | MecCH₂ | Bz | 4-Cl-Pro- | tBuNH- |
| 1039 | 3-Quin-CO- | MeSOCH₂ | Bz | 4-Cl-Pro- | tBuNH- |
| 1040 | 3-Quin-CO- | MeSO₂CH₂ | Bz | 4-Cl-Pro- | tBuNH- |
| 1041 | 3-Quin-CO- | MeOCH₂ | Bz | 4-Cl-Pro- | tBuNH- |
| 1042 | 3-Quin-CO- | MecCH₂CH₂ | Bz | 4-Cl-Pro- | tBuNH- |
| 1043 | 3-Quin-CO- | MecCH₂ | Bz | 4-Cl-Pro- | tBuNH- |
| 1044 | 2-Bfur-CO- | MeSOCH₂ | Bz | 4-Cl-Pro- | tBuNH- |
| 1045 | 2-Bfur-CO- | MeSO₂CH₂ | Bz | 4-Cl-Pro- | tBuNH- |
| 1046 | 2-Bfur-CO- | MeOCH₂ | Bz | 4-Cl-Pro- | tBuNH- |
| 1047 | 2-Bfur-CO- | MecCH₂CH₂ | Bz | 4-Cl-Pro- | tBuNH- |
| 1048 | 2-Bfur-CO- | MecCH₂ | Bz | 4-Cl-Pro- | tBuNH- |
| 1049 | 3-Bfur-CO- | MeSOCH₂ | Bz | 4-Cl-Pro- | tBuNH- |
| 1050 | 3-Bfur-CO- | MeSO₂CH₂ | Bz | 4-Cl-Pro- | tBuNH- |
| 1051 | 3-Bfur-CO- | MeOCH₂ | Bz | 4-Cl-Pro- | tBuNH- |
| 1052 | 3-Bfur-CO- | MecCH₂CH₂ | Bz | 4-Cl-Pro- | tBuNH- |
| 1053 | 3-Bfur-CO- | MecCH₂ | Bz | 4-Cl-Pro- | tBuNH- |
| 1054 | 3-Ind-CO- | MeSOCH₂ | Bz | 4-Cl-Pro- | tBuNH- |
| 1055 | 3-Ind-CO- | MeSO₂CH₂ | Bz | 4-Cl-Pro- | tBuNH- |
| 1056 | 3-Ind-CO- | MeOCH₂ | Bz | 4-Cl-Pro- | tBuNH- |
| 1057 | 3-Ind-CO- | MecCH₂CH₂ | Bz | 4-Cl-Pro- | tBuNH- |
| 1058 | 3-Ind-CO- | MecCH₂ | Bz | 4-Cl-Pro- | tBuNH- |
| 1059 | MPhOAc- | MeSOCH₂ | Bz | 4-Cl-Pro- | tBuNH- |
| 1060 | MPhOAc- | MeSO₂CH₂ | Bz | 4-Cl-Pro- | tBuNH- |
| 1061 | MPhOAc- | MeOCH₂ | Bz | 4-Cl-Pro- | tBuNH- |
| 1062 | MPhOAc- | MecCH₂CH₂ | Bz | 4-Cl-Pro- | tBuNH- |
| 1063 | MPhOAc- | MecCH₂ | Bz | 4-Cl-Pro- | tBuNH- |
| 1064 | 5-NH₂-Ac-O-2-Ind-CO- | MeSOCH₂ | Bz | 4-Cl-Pro- | tBuNH- |
| 1065 | 5-NH₂-Ac-O-2-Ind-CO- | MeSO₂CH₂ | Bz | 4-Cl-Pro- | tBuNH- |
| 1066 | 5-NH₂-Ac-O-2-Ind-CO- | MeOCH₂ | Bz | 4-Cl-Pro- | tBuNH- |
| 1067 | 5-NH₂-Ac-O-2-Ind-CO- | MecCH₂CH₂ | Bz | 4-Cl-Pro- | tBuNH- |
| 1068 | 5-NH₂-Ac-O-2-Ind-CO- | MecCH₂ | Bz | 4-Cl-Pro- | tBuNH- |
| 1069 | 4-NH₂-PhoAc- | MeSOCH₂ | Bz | 4-Cl-Pro- | tBuNH- |
| 1070 | 4-NH₂-PhoAc- | MeSO₂CH₂ | Bz | 4-Cl-Pro- | tBuNH- |
| 1071 | 4-NH₂-PhoAc- | MeOCH₂ | Bz | 4-Cl-Pro- | tBuNH- |
| 1072 | 4-NH₂-PhoAc- | MecCH₂CH₂ | Bz | 4-Cl-Pro- | tBuNH- |
| 1073 | 4-NH₂-PhoAc- | MecCH₂ | Bz | 4-Cl-Pro- | tBuNH- |
| 1074 | 4-[BzcNH]-PhoAc- | MeSOCH₂ | Bz | 4-Cl-Pro- | tBuNH- |
| 1075 | 4-[BzcNH]-PhoAc- | MeSO₂CH₂ | Bz | 4-Cl-Pro- | tBuNH- |

TABLE 1-continued

| Cpd. No. | R¹ | R³ | R⁴ | Z | R⁵ |
|---|---|---|---|---|---|
| 1076 | 4-[BzcNH]-PhoAc- | MeOCH₂ | Bz | 4-Cl-Pro- | tBuNH- |
| 1077 | 4-[BzcNH]-PhoAc- | MecCH₂CH₂ | Bz | 4-Cl-Pro- | tBuNH- |
| 1078 | 4-[BzcNH]-PhoAc- | MecCH₂ | Bz | 4-Cl-Pro- | tBuNH- |
| 1079 | 4-[MorAc-NMe]-Pho-Ac- | MeSOCH₂ | Bz | 4-Cl-Pro- | tBuNH- |
| 1080 | 4-[MorAc-NMe]-Pho-Ac- | MeSO₂CH₂ | Bz | 4-Cl-Pro- | tBuNH- |
| 1081 | 4-[MorAc-NMe]-Pho-Ac- | MeOCH₂ | Bz | 4-Cl-Pro- | tBuNH- |
| 1082 | 4-[MorAc-NMe]-Pho-Ac- | MecCH₂CH₂ | Bz | 4-Cl-Pro- | tBuNH- |
| 1083 | 4-[MorAc-NMe]-Pho-Ac- | MecCH₂ | Bz | 4-Cl-Pro- | tBuNH- |
| 1084 | 4-MeO-Bzc | CarCH₂ | Bz | 4-Cl-Pro- | tBuNH- |
| 1085 | 4-MeO-Bzc | CarCH₂ | Bz | 4-Cl-Pro- | tBuNH- |
| 1086 | Bzc | CarCH₂ | Bz | 4-Br-Pro | tBuNH- |
| 1087 | 2-Quix-CO- | CarCH₂ | Bz | 4-Br-Pro | tBuNH- |
| 1088 | 2-Quin-CO- | CarCH₂ | Bz | 4-Br-Pro | tBuNH- |
| 1089 | 3-Quin-CO- | CarCH₂ | Bz | 4-Br-Pro | tBuNH- |
| 1090 | 4-Quin-CO- | CarCH₂ | Bz | 4-Br-Pro | tBuNH- |
| 1091 | 2-Pyr-CO- | CarCH₂ | Bz | 4-Br-Pro | tBuNH- |
| 1092 | 3-Pyr-CO- | CarCH₂ | Bz | 4-Br-Pro | tBuNH- |
| 1093 | 4-Pyr-CO- | CarCH₂ | Bz | 4-Br-Pro | tBuNH- |
| 1094 | 4-MeO-2-Quin-CO- | CarCH₂ | Bz | 4-Br-Pro | tBuNH- |
| 1095 | 2-Np-CO- | CarCH₂ | Bz | 4-Br-Pro | tBuNH- |
| 1096 | 1-Np-CO- | CarCH₂ | Bz | 4-Br-Pro | tBuNH- |
| 1097 | 2-Bfur-CO- | CarCH₂ | Bz | 4-Br-Pro | tBuNH- |
| 1098 | 3-Bfur-CO- | CarCH₂ | Bz | 4-Br-Pro | tBuNH- |
| 1099 | 5-Bu-2-Pyr-CO- | CarCH₂ | Bz | 4-Br-Pro | tBuNH- |
| 1100 | 4-HO-2-Quin-CO- | CarCH₂ | Bz | 4-Br-Pro | tBuNH- |
| 1101 | 3-HO-2-Quix-CO- | CarCH₂ | Bz | 4-Br-Pro | tBuNH- |
| 1102 | 1-Np-Sfo- | CarCH₂ | Bz | 4-Br-Pro | tBuNH- |
| 1103 | 2-Np-Sfo- | CarCH₂ | Bz | 4-Br-Pro | tBuNH- |
| 1104 | Boz | CarCH₂ | Bz | 4-Br-Pro | tBuNH- |
| 1105 | Bz-NHCO- | CarCH₂ | Bz | 4-Br-Pro | tBuNH- |
| 1106 | Bz-NHCS- | CarCH₂ | Bz | 4-Br-Pro | tBuNH- |
| 1107 | 2-Ind-CO- | CarCH₂ | Bz | 4-Br-Pro | tBuNH- |
| 1108 | 3-Ind-CO- | CarCH₂ | Bz | 4-Br-Pro | tBuNH- |
| 1109 | tBoc | CarCH₂ | Bz | 4-Br-Pro | tBuNH- |
| 1110 | 2-Pyrd-CO- | CarCH₂ | Bz | 4-Br-Pro | tBuNH- |
| 1111 | 2-Pip-CO- | CarCH₂ | Bz | 4-Br-Pro | tBuNH- |
| 1112 | 2-Thi-CO- | CarCH₂ | Bz | 4-Br-Pro | tBuNH- |
| 1113 | MecCO- | CarCH₂ | Bz | 4-Br-Pro | tBuNH- |
| 1114 | Bzc | Me₂NCH₂ | Bz | 4-Br-Pro | tBuNH- |
| 1115 | Bzc | 2-Car-Et | Bz | 4-Br-Pro | tBuNH- |
| 1116 | Bzc | CNCH₂ | Bz | 4-Br-Pro | tBuNH- |
| 1117 | Bzc | iPr | Bz | 4-Br-Pro- | tBuNH- |
| 1118 | Bzc | tBu | Bz | 4-Br-Pro- | tBuNH- |
| 1119 | Bzc | diMe-Car-CH₂ | Bz | 4-Br-Pro- | tBuNH- |
| 1120 | Bzc | MorCOCH₂ | Bz | 4-Br-Pro- | tBuNH- |
| 1121 | Bzc | PipCOCH₂ | Bz | 4-Br-Pro- | tBuNH- |
| 1122 | Bzc | 2-NH₂-Et | Bz | 4-Br-Pro- | tBuNH- |
| 1123 | Bzc | 3-NH₂-Pr | Bz | 4-Br-Pro- | tBuNH- |
| 1124 | Bzc | MeCarCH₂ | Bz | 4-Br-Pro- | tBuNH- |
| 1125 | Bzc | EtCarCH₂ | Bz | 4-Br-Pro- | tBuNH- |
| 1126 | Bzc | H | Bz | 4-Br-Pro- | tBuNH- |
| 1127 | Bzc | HOCH₂ | Bz | 4-Br-Pro- | tBuNH- |
| 1128 | Bzc | 4-ThizCH₂ | Bz | 4-Br-Pro- | tBuNH- |
| 1129 | Bzc | 4-ImidCH₂ | Bz | 4-Br-Pro- | tBuNH- |
| 1130 | Bzc | COOH-CH₂ | Bz | 4-Br-Pro- | tBuNH- |
| 1131 | Bzc | 2-COOH-Et | Bz | 4-Br-Pro- | tBuNH- |
| 1132 | Bzc | MeSCH | Bz | 4-Br-Pro- | tBuNH- |
| 1133 | Bzc | SamCH₂ | Bz | 4-Br-Pro- | tBuNH- |
| 1134 | Bzc | Bz | Bz | 4-Br-Pro- | tBuNH- |
| 1135 | Bzc | SimCH₂ | Bz | 4-Br-Pro- | tBuNH- |
| 1136 | Bzc | HiaCH₂ | Bz | 4-Br-Pro- | tBuNH- |
| 1137 | Bzc | 2-Sim-Et | Bz | 4-Br-Pro- | tBuNH- |
| 1138 | Bzc | 2-Hia-Et | Bz | 4-Br-Pro- | tBuNH- |
| 1139 | Bzc | NH₂CH₂ | Bz | 4-Br-Pro- | tBuNH- |
| 1140 | Bzc | MeNHCH₂ | Bz | 4-Br-Pro- | tBuNH- |
| 1141 | 2-Quix-CO- | 2-Car-Et | Bz | 4-Br-Pro- | tBuNH- |
| 1142 | 2-Quix-CO- | CNCH₂ | Bz | 4-Br-Pro- | tBuNH- |
| 1143 | 2-Quix-CO- | iPr | Bz | 4-Br-Pro- | tBuNH- |
| 1144 | 2-Quix-CO- | tBu | Bz | 4-Br-Pro- | tBuNH- |
| 1145 | 2-Quix-CO- | diMeCar-CH₂ | Bz | 4-Br-Pro- | tBuNH- |
| 1146 | 2-Quix-CO- | MorCOCH₂ | Bz | 4-Br-Pro- | tBuNH- |

TABLE 1-continued

| Cpd. No. | R¹ | R³ | R⁴ | Z | R⁵ |
|---|---|---|---|---|---|
| 1147 | 2-Quix-CO- | PipCOCH₂ | Bz | 4-Br-Pro- | tBuNH- |
| 1148 | 2-Quix-CO- | 2-NH₂-Et | Bz | 4-Br-Pro- | tBuNH- |
| 1149 | 2-Quix-CO- | 3-NH₂-Pr | Bz | 4-Br-Pro- | tBuNH- |
| 1150 | 2-Quix-CO- | MeCarCH₂ | Bz | 4-Br-Pro- | tBuNH- |
| 1151 | 2-Quix-CO- | EtCar-CH | Bz | 4-Br-Pro- | tBuNH- |
| 1152 | 2-Quix-CO- | H | Bz | 4-Br-Pro- | tBuNH- |
| 1153 | 2-Quix-CO- | HOCH₂ | Bz | 4-Br-Pro- | tBuNH- |
| 1154 | 2-Quix-CO- | 4-ThizCH₂ | Bz | 4-Br-Pro- | tBuNH- |
| 1155 | 2-Quix-CO- | 4-ImidCH₂ | Bz | 4-Br-Pro- | tBuNH- |
| 1156 | 2-Quix-CO- | COOH-CH₂ | Bz | 4-Br-Pro- | tBuNH- |
| 1157 | 2-Quix-CO- | 2-COOH-Et | Bz | 4-Br-Pro- | tBuNH- |
| 1158 | 2-Quix-CO- | MeSCH₂ | Bz | 4-Br-Pro- | tBuNH- |
| 1159 | 2-Quix-CO- | SamCH₂ | Bz | 4-Br-Pro- | tBuNH- |
| 1160 | 2-Quix-CO- | Bz | Bz | 4-Br-Pro- | tBuNH- |
| 1161 | 2-Quix-CO- | SimCH₂ | Bz | 4-Br-Pro- | tBuNH- |
| 1162 | 2-Quix-CO- | HiaCH₂ | Bz | 4-Br-Pro- | tBuNH- |
| 1163 | 2-Quix-CO- | 2-Sim-Et | Bz | 4-Br-Pro- | tBuNH- |
| 1164 | 2-Quix-CO- | 2-Hia-Et | Bz | 4-Br-Pro- | tBuNH- |
| 1165 | 2-Quix-CO- | NH₂CH₂ | Bz | 4-Br-Pro- | tBuNH- |
| 1166 | 2-Quix-CO- | MeNHCH₂ | Bz | 4-Br-Pro- | tBuNH- |
| 1167 | 2-Quix-CO- | Me₂NCH₂ | Bz | 4-Br-Pro- | tBuNH- |
| 1168 | 3-Quin-CO- | CarCH₂ | Bz | 4-Br-Pro- | tBuNH- |
| 1169 | 4-Quin-CO- | CarCH₂ | Bz | 4-Br-Pro- | tBuNH- |
| 1170 | 2-Pyr-CO- | CarCH₂ | Bz | 4-Br-Pro- | tBuNH- |
| 1171 | 3-Pyr-CO- | CarCH₂ | Bz | 4-Br-Pro- | tBuNH- |
| 1172 | 4-Pyr-CO- | CarCH₂ | Bz | 4-Br-Pro- | tBuNH- |
| 1173 | 4-MeO-2-Quin-CO- | CarCH₂ | Bz | 4-Br-Pro- | tBuNH- |
| 1174 | 2-Np-CO- | CarCH₂ | Bz | 4-Br-Pro- | tBuNH- |
| 1175 | 1-Np-CO- | CarCH₂ | Bz | 4-Br-Pro- | tBuNH- |
| 1176 | 2-Bfur-CO- | CarCH₂ | Bz | 4-Br-Pro- | tBuNH- |
| 1177 | 3-Bfur-CO- | CarCH₂ | Bz | 4-Br-Pro- | tBuNH- |
| 1178 | 5-Bu-2-Pyr-CO- | CarCH₂ | Bz | 4-Br-Pro- | tBuNH- |
| 1179 | 4-OH-2-Quin-CO- | CarCH₂ | Bz | 4-Br-Pro- | tBuNH- |
| 1180 | 3-OH-2-Quix-CO- | CarCH₂ | Bz | 4-Br-Pro- | tBuNH- |
| 1181 | 1-Np-Sfo- | CarCH₂ | Bz | 4-Br-Pro- | tBuNH- |
| 1182 | 2-Np-Sfo- | CarCH₂ | Bz | 4-Br-Pro- | tBuNH- |
| 1183 | Boz | CarCH₂ | Bz | 4-Br-Pro- | tBuNH- |
| 1184 | Bz-NHCO- | CarCH₂ | Bz | 4-Br-Pro- | tBuNH- |
| 1185 | Bz-NHCS- | CarCH₂ | Bz | 4-Br-Pro- | tBuNH- |
| 1186 | 3-Ind-CO- | CarCH₂ | Bz | 4-Br-Pro- | tBuNH- |
| 1187 | 2-Pyrd-CO- | CarCH₂ | Bz | 4-Br-Pro- | tBuNH- |
| 1188 | 2-Pip-CO- | CarCH₂ | Bz | 4-Br-Pro- | tBuNH- |
| 1189 | 2-Thi-CO- | CarCH₂ | Bz | 4-Br-Pro- | tBuNH- |
| 1190 | MecCO- | CarCH₂ | Bz | 4-Br-Pro- | tBuNH- |
| 1191 | PhoAc- | CarCH₂ | Bz | 4-Br-Pro- | tBuNH- |
| 1192 | 3-Bzisox-CO- | CarCH₂ | Bz | 4-Br-Pro- | tBuNH- |
| 1193 | 2-Bzim-CO- | CarCH₂ | Bz | 4-Br-Pro- | tBuNH- |
| 1194 | N-Me-3-Ind-CO- | CarCH₂ | Bz | 4-Br-Pro- | tBuNH- |
| 1195 | 2-Bzthiaz-CO- | CarCH₂ | Bz | 4-Br-Pro- | tBuNH- |
| 1196 | 2-Bzoxaz-CO- | CarCH₂ | Bz | 4-Br-Pro- | tBuNH- |
| 1197 | 5-MeO-2-Ind-CO- | CarCH₂ | Bz | 4-Br-Pro- | tBuNH- |
| 1198 | 5-HO-2-Ind-CO- | CarCH₂ | Bz | 4-Br-Pro- | tBuNH- |
| 1199 | 5-AcO-2-Ind-CO- | CarCH₂ | Bz | 4-Br-Pro- | tBuNH- |
| 1200 | 5-NH 2AcO-2-Ind-CO- | CarCH₂ | Bz | 4-Br-Pro- | tBuNH- |
| 1201 | 5-Bzim-CO- | CarCH₂ | Bz | 4-Br-Pro- | tBuNH- |
| 1202 | (2-NpO)Ac- | CarCH₂ | Bz | 4-Br-Pro- | tBuNH- |
| 1203 | (1-NpO)Ac- | CarCH₂ | Bz | 4-Br-Pro- | tBuNH- |
| 1204 | 1-NpOCO- | CarCH₂ | Bz | 4-Br-Pro- | tBuNH- |
| 1205 | 2-NpOCO- | CarCH₂ | Bz | 4-Br-Pro- | tBuNH- |
| 1206 | (3-PhPho)Ac- | CarCH₂ | Bz | 4-Br-Pro- | tBuNH- |
| 1207 | 2-Quix-CO- | CarCH₂ | Bz | 4-Br-Pro- | 3-HOPr-NH- |
| 1208 | 2-Quix-CO- | CarCH₂ | Bz | 4-Br-Pro- | BuNH- |
| 1209 | 2-Quix-CO- | CarCH₂ | Bz | 4-Br-Pro- | tBuO- |
| 1210 | 2-Quix-CO- | CarCH₂ | Bz | 4-Br-Pro- | 1,1-diMe-2-HOEt-NH- |
| 1211 | Bzc | CarCH₂ | Bz | 4-Br-Pro- | 3-HOPr-NH- |
| 1212 | Bzc | CarCH₂ | Bz | 4-Br-Pro- | BuNH- |
| 1213 | Bzc | CarCH₂ | Bz | 4-Br-Pro- | tBuO- |
| 1214 | Bzc | CarCH₂ | Bz | 4-Br-Pro- | 1,1-diMe-2-HOEt-NH- |
| 1215 | 3-NH₂-PhoAc- | CarCH₂ | Bz | 4-Br-Pro- | tBuNH- |
| 1216 | 2-NH₂-PhoAc- | CarCH₂ | Bz | 4-Br-Pro- | tBuNH- |
| 1217 | 2,3-diNH₂-PhoAc- | CarCH₂ | Bz | 4-Br-Pro- | tBuNH- |
| 1218 | 2,4-diNH₂-PhoAc- | CarCH₂ | Bz | 4-Br-Pro- | tBuNH- |
| 1219 | 4-NH₂-Ph-CO- | CarCH₂ | Bz | 4-Br-Pro- | tBuNH- |
| 1220 | 4-NH₂-Bzc | CarCH₂ | Bz | 4-Br-Pro- | tBuNH- |
| 1221 | 4-Me₂N-PhoAc- | CarCH₂ | Bz | 4-Br-Pro- | tBuNH- |

TABLE 1-continued

| Cpd. No. | R$^1$ | R$^3$ | R$^4$ | Z | R$^5$ |
|---|---|---|---|---|---|
| 1222 | 4-[Me(Bz)N]-PhoAc- | CarCH$_2$ | Bz | 4-Br-Pro- | tBuNH- |
| 1223 | 4-Mor-PhoAc- | CarCH$_2$ | Bz | 4-Br-Pro- | tBuNH- |
| 1224 | 4-[N-Bz-Pipr]-PhoAc- | CarCH$_2$ | Bz | 4-Br-Pro- | tBuNH- |
| 1225 | 4-MeNH-PhoAc- | CarCH$_2$ | Bz | 4-Br-Pro- | tBuNH- |
| 1226 | 4-[(4'Me-Bzc)-NH]-Pho-Ac- | CarCH$_2$ | Bz | 4-Br-Pro- | tBuNH- |
| 1227 | 4-[tBoc-NH]-PhoAc- | CarCH$_2$ | Bz | 4-Br-Pro- | tBuNH- |
| 1228 | 4-[tBoc-MeN]-PhoAc- | CarCH$_2$ | Bz | 4-Br-Pro- | tBuNH- |
| 1229 | 4-[Gly-NH]-PhoAc- | CarCH$_2$ | Bz | 4-Br-Pro- | tBuNH- |
| 1230 | 4-[Gly-NMe]-PhoAc- | CarCH$_2$ | Bz | 4-Br-Pro- | tBuNH- |
| 1231 | 4-[N-Me-Gly)NMe]-PhoAc- | CarCH$_2$ | Bz | 4-Br-Pro- | tBuNH- |
| 1232 | 4-[(N-tBoc-Gly)-NMe]-PhoAc- | CarCH$_2$ | Bz | 4-Br-Pro- | tBuNH- |
| 1233 | 4-[(N-tBoc-NMe-Gly)NMe]-PhoAc- | CarCH$_2$ | Bz | 4-Br-Pro- | tBuNH- |
| 1234 | 4-[(N-Me-Gly)NMe]-PhoAc- | CarCH$_2$ | Bz | 4-Br-Pro- | tBuNH- |
| 1235 | 4-(Br-Ac)NMe-PhoAc- | CarCH$_2$ | Bz | 4-Br-Pro- | tBuNH- |
| 1236 | 4-[(4'-MeO-Bzc)-NH]-PhoAc- | CarCH$_2$ | Bz | 4-Br-Pro- | tBuNH- |
| 1237 | N-Me-4-PipO-Ac- | CarCH$_2$ | Bz | 4-Br-Pro- | tBuNH- |
| 1238 | 4-NH$_2$-cHxO-Ac- | CarCH$_2$ | Bz | 4-Br-Pro- | tBuNH- |
| 1239 | 4-NH$_2$-PhoAc- | CarCH$_2$ | Bz | 4-Br-Pro- | 1,1-diMe-2-HOEt-NH- |
| 1240 | 3-NH$_2$-PhoAc- | CarCH$_2$ | Bz | 4-Br-Pro- | 1,1-diMe-2-HOEt-NH- |
| 1241 | 2-NH$_2$-PhoAc- | CarCH$_2$ | Bz | 4-Br-Pro- | 1,1-diMe-2-HOEt-NH- |
| 1242 | 2,3-diNH$_2$-PhoAc- | CarCH$_2$ | Bz | 4-Br-Pro- | 1,1-diMe-2-HOEt-NH- |
| 1243 | 2,4-diNH$_2$-PhoAc- | CarCH$_2$ | Bz | 4-Br-Pro- | 1,1-diMe-2-HOEt-NH- |
| 1244 | 4-NH$_2$-Ph-CO- | CarCH$_2$ | Bz | 4-Br-Pro- | 1,1-diMe-2-HOEt-NH- |
| 1245 | 4-NH$_2$-Bzc | CarCH$_2$ | Bz | 4-Br-Pro- | 1,1-diMe-2-HOEt-NH- |
| 1246 | 4-Me$_2$N-PhoAc- | CarCH$_2$ | Bz | 4-Br-Pro- | 1,1-diMe-2-HOEt-NH- |
| 1247 | 4-(Me(Bz)N]- | CarCH$_2$ | Bz | 4-Br-Pro- | 1,1-diMe-2-HOEt-NH- |
| 1248 | 4-Mor-PhoAc- | CarCH$_2$ | Bz | 4-Br-Pro- | 1,1-diMe-2-HOEt-NH- |
| 1249 | 4-[N-Bz-Pipr]-PhoAc- | CarCH$_2$ | Bz | 4-Br-Pro- | 1,1-diMe-2-HOEt-NH- |
| 1250 | 4-[MeNH]-PhoAc- | CarCH$_2$ | Bz | 4-Br-Pro- | 1,1-diMe-2-HOEt-NH- |
| 1251 | 4-[(4'Me-Bzc)-NH]-PhoAc- | CarCH$_2$ | Bz | 4-Br-Pro- | 1,1-diMe-2-HOEt-NH- |
| 1252 | 4-[BzcNH]-PhoAc- | CarCH$_2$ | Bz | 4-Br-Pro- | 1,1-diMe-2-HOEt-NH- |
| 1253 | 4-[tBoc-NH]-PhoAc- | CarCH$_2$ | Bz | 4-Br-Pro- | 1,1-diMe-2-HOEt-NH- |
| 1254 | 4-[tBoc-MeN]-PhoAc- | CarCH$_2$ | Bz | 4-Br-Pro- | 1,1-diMe-2-HOEt-NH- |
| 1255 | 4-[Gly-NH]-PhoAc- | CarCH$_2$ | Bz | 4-Br-Pro- | 1,1-diMe-2-HOEt-NH- |
| 1256 | 4-[Gly-NMe]-PhoAc- | CarCH$_2$ | Bz | 4-Br-Pro- | 1,1-diMe-2-HOEt-NH- |
| 1257 | 4-[(N-Me-Gly)NMe]-PhoAc- | CarCH$_2$ | Bz | 4-Br-Pro- | 1,1-diMe-2-HOEt-NH- |
| 1258 | 4-[(N-tBoc-Gly)NMe]-PhoAc- | CarCH$_2$ | Bz | 4-Br-Pro- | 1,1-diMe-2-HOEt-NH- |
| 1259 | 4-[(N-tBoc-N-Me-Gly)-NMe]-PhoAc- | CarCH$_2$ | Bz | 4-Br-Pro- | 1,1-diMe-2-HOEt-NH- |
| 1260 | Boc | CarCH$_2$ | Bz | 4-Br-Pro- | 1,1-diMe-2-HOEt-NH- |
| 1261 | 4-[BrAc-NMe]-PhoAc- | CarCH$_2$ | Bz | 4-Br-Pro- | 1,1-diMe-2-HOEt-NH- |
| 1262 | 4-[(4'-MeO-Bzc)NH]-PhoAc- | CarCH$_2$ | Bz | 4-Br-Pro- | 1,1-diMe-2-HOEt-NH- |
| 1263 | N-Me-4-PipO-Ac- | CarCH$_2$ | Bz | 4-Br-Pro- | 1,1-diMe-2-HOEt-NH- |
| 1264 | 4-NH$_2$-cHxO-Ac- | CarCH$_2$ | Bz | 4-Br-Pro- | 1,1-diMe-2-HOEt-NH |
| 1265 | 4-(Mor-Ac)NMe-PhoAc- | CarCH$_2$ | Bz | 4-Br-Pro- | 1,1-diMe-2-HOEt-NH |
| 1266 | 4-NH$_2$-PhoAc- | CarCH$_2$ | Bz | 4-Br-Pro- | 1,1-diMe-2-HOPr-NH- |
| 1267 | 3-NH$_2$-PhoAc- | CarCH$_2$ | Bz | 4-Br-Pro- | 1,1-diMe-2-HOPr-NH- |
| 1268 | 2-NH$_2$-PhoAc- | CarCH$_2$ | Bz | 4-Br-Pro- | 1,1-diMe-2-HOPr-NH- |
| 1269 | 2,3-diNH$_2$-PhoAc- | CarCH$_2$ | Bz | 4-Br-Pro- | 1,1-diMe-2-HOPr-NH- |
| 1270 | 2,4-diNH$_2$-PhoAc- | CarCH$_2$ | Bz | 4-Br-Pro- | 1,1-diMe-2-HOPr-NH- |
| 1271 | 4-NH$_2$-Ph-CO- | CarCH$_2$ | Bz | 4-Br-Pro- | 1,1-diMe-2-HOPr-NH- |
| 1272 | 4-NH$_2$-Bzc | CarCH$_2$ | Bz | 4-Br-Pro- | 1,1-diMe-2-HOPr-NH- |
| 1273 | 4-Me$_2$N-PhoAc- | CarCH$_2$ | Bz | 4-Br-Pro- | 1,1-diMe-2-HOPr-NH- |
| 1274 | 4-[Me(Bz)N]-PhoAc- | CarCH$_2$ | Bz | 4-Br-Pro- | 1,1-diMe-2-HOPr-NH- |
| 1275 | 4-Mor-PhoAc- | CarCH$_2$ | Bz | 4-Br-Pro- | 1,1-diMe-2-HOPr-NH- |
| 1276 | 4-[N-Bz-Pipr]-PhoAc- | CarCH$_2$ | Bz | 4-Br-Pro- | 1,1-diMe-2-HOPr-NH- |

TABLE 1-continued

| Cpd. No. | R¹ | R³ | R⁴ | Z | R⁵ |
|---|---|---|---|---|---|
| 1277 | 4-MeNH-PhoAc- | CarCH₂ | Bz | 4-Br-Pro- | 1,1-diMe-2-HOPr-NH- |
| 1278 | 4-[(4'Me-Bzc)-NH]-PhoAc- | CarCH₂ | Bz | 4-Br-Pro- | 1,1-diMe-2-HOPr-NH- |
| 1279 | 4-[BzcNH]-PhoAc- | CarCH₂ | Bz | 4-Br-Pro- | 1,1-diMe-2-HOPr-NH- |
| 1280 | 4-[tBoc-NH]-PhoAc- | CarCH₂ | Bz | 4-Br-Pro- | 1,1-diMe-2-HOPr-NH- |
| 1281 | 4-[tBoc-MeN]-PhoAc- | CarCH₂ | Bz | 4-Br-Pro- | 1,1-diMe-2-HOPr-NH- |
| 1282 | 4-[Gly-NH]-PhoAc- | CarCH₂ | Bz | 4-Br-Pro- | 1,1-diMe-2-HOPr-NH- |
| 1283 | 4-[Gly-NMe]-PhoAc- | CarCH₂ | Bz | 4-Br-Pro- | 1,1-diMe-2-HOPr-NH- |
| 1284 | 4-[N-Me-Gly)NMe]-PhoAc- | CarCH₂ | Bz | 4-Br-Pro- | 1,1-diMe-2-HOPr-NH- |
| 1285 | 4-[(N-tBoc-Gly)-NMe]-Pho-Ac- | CarCH₂ | Bz | 4-Br-Pro- | 1,1-diMe-2-HOPr-NH- |
| 1286 | 4-[(N-tBoc-NMe-Gly)NMe]-PhoAc- | CarCH₂ | Bz | 4-Br-Pro- | 1,1-diMe-2-HOPr-NH- |
| 1287 | Boc | CarCH₂ | Bz | 4-Br-Pro- | 1,1-diMe-2-HOPr-NH- |
| 1288 | 4-[(BrAc)NMe]-PhoAc- | CarCH₂ | Bz | 4-Br-Pro- | 1,1-diMe-2-HOPr-NH- |
| 1289 | 4-[(4'-MeO-Bzc)-NH]-PhoAc- | CarCH₂ | Bz | 4-Br-Pro- | 1,1-diMe-2-HOPr-NH- |
| 1290 | N-Me-4-PipO-Ac- | CarCH₂ | Bz | 4-Br-Pro- | 1,1-diMe-2-HOPr-NH- |
| 1291 | 4-NH₂-cHxO-Ac- | CarCH₂ | Bz | 4-Br-Pro- | 1,1-diMe-2-HOPr-NH- |
| 1292 | 4-[(MorAc)NMe]-PhoAc- | CarCH₂ | Bz | 4-Br-Pro- | 1,1-diMe-2-HOPr-NH- |
| 1293 | 2-Quin-CO- | CarCH₂ | Bz | 4-Br-Pro- | 1,1-diMe-2-HOEt-NH- |
| 1294 | 3-Quin-CO- | CarCH₂ | Bz | 4-Br-Pro- | 1,1-diMe-2-HOEt-NH- |
| 1295 | 4-Quin-CO- | CarCH₂ | Bz | 4-Br-Pro- | 1,1-diMe-2-HOEt-NH- |
| 1296 | 2-Pyr-CO- | CarCH₂ | Bz | 4-Br-Pro- | 1,1-diMe-2-HOEt-NH- |
| 1297 | 3-Pyr-CO- | CarCH₂ | Bz | 4-Br-Pro- | 1,1-diMe-2-HOEt-NH- |
| 1298 | 4-Pyr-CO- | CarCH₂ | Bz | 4-Br-Pro- | 1,1-diMe-2-HOEt-NH- |
| 1299 | 4-MeO-2-Quin-CO- | CarCH₂ | Bz | 4-Br-Pro- | 1,1-diMe-2-HOEt-NH- |
| 1300 | 2-Np-CO- | CarCH₂ | Bz | 4-Br-Pro- | 1,1-diMe-2-HOEt-NH- |
| 1301 | 1-Np-CO- | CarCH₂ | Bz | 4-Br-Pro- | 1,1-diMe-2-HOEt-NH- |
| 1302 | 2-Bfur-CO- | CarCH₂ | Bz | 4-Br-Pro- | 1,1-diMe-2-HOEt-NH- |
| 1303 | 3-Bfur-CO- | CarCH₂ | Bz | 4-Br-Pro- | 1,1-diMe-2-HOEt-NH- |
| 1304 | 5-Bu-2-Pyr-CO- | CarCH₂ | Bz | 4-Br-Pro- | 1,1-diMe-2-HOEt-NH- |
| 1305 | 4-HO-2-Quin-CO- | CarCH₂ | Bz | 4-Br-Pro- | 1,1-diMe-2-HOEt-NH- |
| 1306 | 3-HO-2-Quix-CO- | CarCH₂ | Bz | 4-Br-Pro- | 1,1-diMe-2-HOEt-NH- |
| 1307 | 1-Np-Sfo- | CarCH₂ | Bz | 4-Br-Pro- | 1,1-diMe-2-HOEt-NH- |
| 1308 | 2-Np-Sfo- | CarCH₂ | Bz | 4-Br-Pro- | 1,1-diMe-2-HOEt-NH- |
| 1309 | Boz | CarCH₂ | Bz | 4-Er-Pro- | 1,1-diMe-2-HOEt-NH- |
| 1310 | Bz-NHCO- | CarCH₂ | Bz | 4-Br-Pro- | 1,1-diMe-2-HOEt-NH- |
| 1311 | Bz-NHCS- | CarCH₂ | Bz | 4-Br-Pro- | 1,1-diMe-2-HOEt-NH- |
| 1312 | 2-Ind-CO- | CarCH₂ | Bz | 4-Br-Pro- | 1,1-diMe-2-HOEt-NH- |
| 1313 | 3-Ind-CO- | CarCH₂ | Bz | 4-Br-Pro- | 1,1-diMe-2-HOEt-NH- |
| 1314 | tBoc | CarCH₂ | Bz | 4-Br-Pro- | 1,1-diMe-2-HOEt-NH- |
| 1315 | 2-Pyrd-CO- | CarCH₂ | Bz | 4-Br-Pro- | 1,1-diMe-2-HOEt-NH- |
| 1316 | 2-Pip-CO- | CarCH₂ | Bz | 4-Br-Pro- | 1,1-diMe-2-HOEt-NH- |
| 1317 | 2-Thi-CO- | CarCH₂ | Bz | 4-Br-Pro- | 1,1-diMe-2-HOEt-NH- |
| 1318 | MecCO- | CarCH₂ | Bz | 4-Br-Pro- | 1,1-diMe-2-HOEt-NH- |
| 1319 | PhoAc- | CarCH₂ | Bz | 4-Br-Pro- | 1,1-diMe-2-HOEt-NH- |
| 1320 | MPhoAc- | CarCH₂ | Bz | 4-Br-Pro- | 1,1-diMe-2-HOEt-NH- |
| 1321 | 3-Bzisox-CO- | CarCH₂ | Bz | 4-Br-Pro- | 1,1-diMe-2-HOEt-NH- |
| 1322 | 2-Bzim-CO- | CarCH₂ | Bz | 4-Br-Pro- | 1,1-diMe-2-HOEt-NH- |
| 1323 | N-Me-3-Ind-CO- | CarCH₂ | Bz | 4-Br-Pro- | 1,1-diMe-2-HOEt-NH- |
| 1324 | 2-Bzthiaz-CO- | CarCH₂ | Bz | 4-Br-Pro- | 1,1-diMe-2-HOEt-NH- |
| 1325 | 2-Bzoxaz-CO- | CarCH₂ | Bz | 4-Br-Pro- | 1,1-diMe-2-HOEt-NH- |
| 1326 | 5-MeO-2-Ind-CO- | CarCH₂ | Bz | 4-Br-Pro- | 1,1-diMe-2-HOEt-NH- |
| 1327 | 5-HO-2-Ind-CO- | CarCH₂ | Bz | 4-Br-Pro- | 1,1-diMe-2-HOEt-NH- |
| 1328 | 5-AcO-2-Ind-CO- | CarCH₂ | Bz | 4-Br-Pro- | 1,1-diMe-2-HOEt-NH- |
| 1329 | 5-NH₂AcO-2-Ind-CO- | CarCH₂ | Bz | 4-Br-Pro- | 1,1-diMe-2-HOEt-NH- |
| 1330 | 5-Bzim-CO- | CarCH₂ | Bz | 4-Br-Pro- | 1,1-diMe-2-HOEt-NH- |
| 1331 | (1-NpO)Ac- | CarCH₂ | Bz | 4-Br-Pro- | 1,1-diMe-2-HOEt-NH- |
| 1332 | 1-NpOCO- | CarCH₂ | Bz | 4-Br-Pro- | 1,1-diMe-2-HOEt-NH- |
| 1333 | 2-NpOCO- | CarCH₂ | Bz | 4-Br-Pro- | 1,1-diMe-2-HOEt-NH- |
| 1334 | (3-PhPho)Ac- | CarCH₂ | Bz | 4-Br-Pro- | 1,1-diMe-2-HOEt-NH- |
| 1335 | (2-NpO)Ac- | CarCH₂ | Bz | 4-Br-Pro- | 1,1-diMe-2-HOEt-NH- |
| 1336 | Bzc | CarCH₂ | Bz | 4-Br-Pro- | 1,1-diMe-2-HOPr-NH- |
| 1337 | 2-Quix-CO- | CarCH₂ | Bz | 4-Br-Pro- | 1,1-diMe-2-HOPr-NH- |
| 1338 | 2-Quin-CO- | CarCH₂ | Bz | 4-Br-Pro- | 1,1-diMe-2-HOPr-NH- |
| 1339 | 3-Quin-CO- | CarCH₂ | Bz | 4-Br-Pro- | 1,1-diMe-2-HOPr-NH- |
| 1340 | 4-Quin-CO- | CarCH₂ | Bz | 4-Br-Pro- | 1,1-diMe-2-HOPr-NH- |

TABLE 1-continued

| Cpd. No. | R¹ | R³ | R⁴ | Z | R⁵ |
|---|---|---|---|---|---|
| 1341 | 2-Pyr-CO- | CarCH₂ | Bz | 4-Br-Pro- | 1,1-diMe-2-HOPr-NH- |
| 1342 | 3-Pyr-CO- | CarCH₂ | Bz | 4-Br-Pro- | 1,1-diMe-2-HOPr-NH- |
| 1343 | 4-Pyr-CO- | CarCH₂ | Bz | 4-Br-Pro- | 1,1-diMe-2-HOPr-NH- |
| 1344 | 4-MeO-2-Quin-CO- | CarCH₂ | Bz | 4-Br-Pro- | 1,1-diMe-2-HOPr-NH- |
| 1345 | 2-Np-CO- | CarCH₂ | Bz | 4-Br-Pro- | 1,1-diMe-2-HOPr-NH- |
| 1346 | 1-Np-CO- | CarCH₂ | Bz | 4-Br-Pro- | 1,1-diMe-2-HOPr-NH- |
| 1347 | 2-Bfur-CO- | CarCH₂ | Bz | 4-Br-Pro- | 1,1-diMe-2-HOPr-NH- |
| 1348 | 3-Bfur-CO- | CarCH₂ | Bz | 4-Br-Pro- | 1,1-diMe-2-HOPr-NH- |
| 1349 | 5-Bu-2-Pyr-CO- | CarCH₂ | Bz | 4-Br-Pro- | 1,1-diMe-2-HOPr-NH- |
| 1350 | 4-HO-2-Quin-CO- | CarCH₂ | Bz | 4-Br-Pro- | 1,1-diMe-2-HOPr-NH- |
| 1351 | 3-HO-2-Quix-CO- | CarCH₂ | Bz | 4-Br-Pro- | 1,1-diMe-2-HOPr-NH- |
| 1352 | 1-Np-Sfo- | CarCH₂ | Bz | 4-Br-Pro- | 1,1-diMe-2-HOPr-NH- |
| 1353 | 2-Np-Sfo- | CarCH₂ | Bz | 4-Br-Pro- | 1,1-diMe-2-HOPr-NH- |
| 1354 | Boz | CarCH₂ | Bz | 4-Br-Pro- | 1,1-diMe-2-HOPr-NH- |
| 1355 | Bz-NHCO- | CarCH₂ | Bz | 4-Br-Pro- | 1,1-diMe-2-HOPr-NH- |
| 1356 | Bz-NHCS- | CarCH₂ | Bz | 4-Br-Pro- | 1,1-diMe-2-HOPr-NH- |
| 1357 | 2-Ind-CO- | CarCH₂ | Bz | 4-Br-Pro- | 1,1-diMe-2-HOPr-NH- |
| 1358 | 3-Ind-CO- | CarCH₂ | Bz | 4-Br-Pro- | 1,1-diMe-2-HOPr-NH- |
| 1359 | tBoc | CarCH₂ | Bz | 4-Br-Pro- | 1,1-diMe-2-HOPr-NH- |
| 1360 | 2-Pyrd-CO- | CarCH₂ | Bz | 4-Br-Pro- | 1,1-diMe-2-HOPr-NH- |
| 1361 | 2-Pip-CO- | CarCH₂ | Bz | 4-Br-Pro- | 1,1-diMe-2-HOPr-NH- |
| 1362 | 2-Thi-CO- | CarCH₂ | Bz | 4-Br-Pro- | 1,1-diMe-2-HOPr-NH- |
| 1363 | MecCO- | CarCH₂ | Bz | 4-Br-Pro- | 1,1-diMe-2-HOPr-NH- |
| 1364 | PhoAc- | CarCH₂ | Bz | 4-Br-Pro- | 1,1-diMe-2-HOPr-NH- |
| 1365 | MPhoAc- | CarCH₂ | Bz | 4-Br-Pro- | 1,1-diMe-2-HOPr-NH- |
| 1366 | 3-Bzisox-CO- | CarCH₂ | Bz | 4-Br-Pro- | 1,1-diMe-2-HOPr-NH- |
| 1367 | 2-Bzim-CO- | CarCH₂ | Bz | 4-Br-Pro- | 1,1-diMe-2-HOPr-NH- |
| 1368 | N-Me-3-Ind-CO- | CarCH₂ | Bz | 4-Br-Pro- | 1,1-diMe-2-HOPr-NH- |
| 1369 | 2-Bzthiaz-CO- | CarCH₂ | Bz | 4-Br-Pro- | 1,1-diMe-2-HOPr-NH- |
| 1370 | 2-Bzoxaz-CO- | CarCH₂ | Bz | 4-Br-Pro- | 1,1-diMe-2-HOPr-NH- |
| 1371 | 5-MeO-2-Ind-CO- | CarCH₂ | Bz | 4-Br-Pro- | 1,1-diMe-2-HOPr-NH- |
| 1372 | 5-HO-2-Ind-CO- | CarCH₂ | Bz | 4-Br-Pro- | 1,1-diMe-2-HOPr-NH- |
| 1373 | 5-AcO-2-Ind-CO- | CarCH₂ | Bz | 4-Br-Pro- | 1,1-diMe-2-HOPr-NH- |
| 1374 | 5-NH₂AcO-2-Ind-CO- | CarCH₂ | Bz | 4-Br-Pro- | 1,1-diMe-2-HOPr-NH- |
| 1375 | 5-Bzim-CO- | CarCH₂ | Bz | 4-Br-Pro- | 1,1-diMe-2-HOPr-NH- |
| 1376 | (2-NpO)Ac- | CarCH₂ | Bz | 4-Br-Pro- | 1,1-diMe-2-HOPr-NH- |
| 1377 | (1-NpO)Ac- | CarCH₂ | Bz | 4-Br-Pro- | 1,1-diMe-2-HOPr-NH- |
| 1378 | 1-NpOCO- | CarCH₂ | Bz | 4-Br-Pro- | 1,1-diMe-2-HOPr-NH- |
| 1379 | 2-NpOCO- | CarCH₂ | Bz | 4-Br-Pro- | 1,1-diMe-2-HOPr-NH- |
| 1380 | (3-PhPho)-Ac- | CarCH₂ | Bz | 4-Br-Pro- | 1,1-diMe-2-HOPr-NH- |
| 1381 | Bzc | CarCH₂ | 4-Br-Bz | 4-Br-Pro- | tBuNH- |
| 1382 | 2-Quix-CO- | CarCH₂ | 4-Br-Bz | 4-Br-Pro- | tBuNH- |
| 1383 | Bzc | CarCH₂ | 4-MeOBz | 4-Br-Pro- | tBuNH- |
| 1384 | 2-Quix-CO- | CarCH₂ | 4-MeOBz | 4-Br-Pro- | tBuNH- |
| 1385 | Bzc | CarCH₂ | 4-Me-Bz | 4-Br-Pro- | tBuNH- |
| 1386 | 2-Quix-CO- | CarCH₂ | 4-Me-Bz | 4-Br-Pro- | tBuNH- |
| 1387 | Bzc | CarCH₂ | cHxCH₂- | 4-Br-Pro- | tBuNH- |
| 1388 | 2-Quix-CO- | CarCH₂ | cHxCH₂- | 4-Br-Pro- | tBuNH- |
| 1389 | Bzc | MeSOCH₂ | Bz | 4-Br-Pro- | tBuNH- |
| 1390 | Bzc | MeSO₂CH₂ | Bz | 4-Br-Pro- | tBuNH- |
| 1391 | Bzc | MeOCH₂ | Bz | 4-Br-Pro- | tBuNH- |
| 1392 | Bzc | MecCH₂CH₂ | Bz | 4-Br-Pro- | tBuNH- |
| 1393 | Bzc | MecCH₂ | Bz | 4-Br-Pro- | tBuNH- |
| 1394 | 2-Quix-CO- | MeSOCH₂ | Bz | 4-Br-Pro- | tBuNH- |
| 1395 | 2-Quix-CO- | MeSO₂CH₂ | Bz | 4-Br-Pro- | tBuNH- |
| 1396 | 2-Quix-CO- | MeOCH₂ | Bz | 4-Br-Pro- | tBuNH- |
| 1397 | 2-Quix-CO- | MecCH₂CH₂ | Bz | 4-Br-Pro- | tBuNH- |
| 1398 | 2-Quix-CO- | MecCH₂ | Bz | 4-Br-Pro- | tBuNH- |
| 1399 | 2-Quin-CO- | MeSOCH₂ | Bz | 4-Br-Pro- | tBuNH- |
| 1400 | 2-Quin-CO- | MeSO₂CH₂ | Bz | 4-Br-Pro- | tBuNH- |
| 1401 | 2-Quin-CO- | MeOCH₂ | Bz | 4-Br-Pro- | tBuNH- |
| 1402 | 2-Quin-CO- | MecCH₂CH₂ | Bz | 4-Br-Pro- | tBuNH- |
| 1403 | 2-Quin-CO- | MecCH₂ | Bz | 4-Br-Pro- | tBuNH- |
| 1404 | 3-Quin-CO- | MeSOCH₂ | Bz | 4-Br-Pro- | tBuNH- |
| 1405 | 3-Quin-CO- | MeSO₂CH₂ | Bz | 4-Br-Pro- | tBuNH- |
| 1406 | 3-Quin-CO- | MeOCH₂ | Bz | 4-Br-Pro- | tBuNH- |
| 1407 | 3-Quin-CO- | MecCH₂CH₂ | Bz | 4-Br-Pro- | tBuNH- |
| 1408 | 3-Quin-CO- | MecCH₂ | Bz | 4-Br-Pro- | tBuNH- |
| 1409 | 2-Bfur-CO- | MeSOCH₂ | Bz | 4-Br-Pro- | tBuNH- |
| 1410 | 2-Bfur-CO- | MeSO₂CH₂ | Bz | 4-Br-Pro- | tBuNH- |
| 1411 | 2-Bfur-CO- | MeOCH₂ | Bz | 4-Br-Pro- | tBuNH- |

TABLE 1-continued

| Cpd. No. | R¹ | R³ | R⁴ | Z | R⁵ |
|---|---|---|---|---|---|
| 1412 | 2-Bfur-CO- | MecCH₂CH₂ | Bz | 4-Br-Pro- | tBuNH- |
| 1413 | 2-Bfur-CO- | MecCH₂ | Bz | 4-Br-Pro- | tBuNH- |
| 1414 | 3-Bfur-CO- | MeSOCH₂ | Bz | 4-Br-Pro- | tBuNH- |
| 1415 | 3-Bfur-CO- | MeSO₂CH₂ | Bz | 4-Br-Pro- | tBuNH- |
| 1416 | 3-Bfur-CO- | MeOCH₂ | Bz | 4-Br-Pro- | tBuNH- |
| 1417 | 3-Bfur-CO- | MecCH₂CH₂ | Bz | 4-Br-Pro- | tBuNH- |
| 1418 | 3-Bfur-CO- | MecCH₂ | Bz | 4-Br-Pro- | tBuNH- |
| 1419 | 3-Ind-CO- | MeSOCH₂ | Bz | 4-Br-Pro- | tBuNH- |
| 1420 | 3-Ind-CO- | MeSO₂CH₂ | Bz | 4-Br-Pro- | tBuNH- |
| 1421 | 3-Ind-CO- | MeOCH₂ | Bz | 4-Br-Pro- | tBuNH- |
| 1422 | 3-Ind-CO- | MecCH₂CH₂ | Bz | 4-Br-Pro- | tBuNH- |
| 1423 | 3-Ind-CO- | MecCH₂ | Bz | 4-Br-Pro- | tBuNH- |
| 1424 | MPhOAc- | MeSOCH₂ | Bz | 4-Br-Pro- | tBuNH- |
| 1425 | MPhOAc- | MeSO₂CH₂ | Bz | 4-Br-Pro- | tBuNH- |
| 1426 | MPhOAc- | MeOCH₂ | Bz | 4-Br-Pro- | tBuNH- |
| 1427 | MPhOAc- | MecCH₂CH₂ | Bz | 4-Br-Pro- | tBuNH- |
| 1428 | MPhOAc- | MecCH₂ | Bz | 4-Br-Pro- | tBuNH- |
| 1429 | 5-NH₂-AcO-2-Ind-CO- | MeSOCH₂ | Bz | 4-Br-Pro- | tBuNH- |
| 1430 | 5-NH₂-AcO-2-Ind-CO- | MeSO₂CH₂ | Bz | 4-Br-Pro- | tBuNH- |
| 1431 | 5-NH₂-AcO-2-Ind-CO- | MeOCH₂ | Bz | 4-Br-Pro- | tBuNH- |
| 1432 | 5-NH₂-AcO-2-Ind-CO- | MecCH₂CH₂ | Bz | 4-Br-Pro- | tBuNH- |
| 1433 | 5-NH₂-AcO-2-Ind-CO- | MecCH₂ | Bz | 4-Br-Pro- | tBuNH- |
| 1434 | 4-NH₂-Pho-Ac- | MeSOCH₂ | Bz | 4-Br-Pro- | tBuNH- |
| 1435 | 4-NH₂-Pho-Ac- | MeSO₂CH₂ | Bz | 4-.Br-Pro- | tBuNH- |
| 1436 | 4-NH₂-Pho-Ac- | MeOCH₂ | Bz | 4-Br-Pro- | tBuNH- |
| 1437 | 4-NH₂-PhoAc- | MecCH₂CH₂ | Bz | 4-Br-Pro- | tBuNH- |
| 1438 | 4-NH₂-PhoAc- | MecCH₂ | Bz | 4-Br-Pro- | tBuNH- |
| 1439 | 4-[Bzc-NH]-PhoAc- | MeSOCH₂ | Bz | 4-Br-Pro- | tBuNH- |
| 1440 | 4-[Bzc-NH]-PhoAc- | MeSO₂CH₂ | Bz | 4-Br-Pro- | tBuNH- |
| 1441 | 4-[Bzc-NH]-PhoAc- | MeOCH₂ | Bz | 4-Br-Pro- | tBuNH- |
| 1442 | 4-[Bzc-NH]-PhoAc- | MecCH₂CH₂ | Bz | 4-Br-Pro- | tBuNH- |
| 1443 | 4-[Bzc-NH]-PhoAc- | MecCH₂ | Bz | 4-Br-Pro- | tBuNH- |
| 1444 | 4-[MorAc-NMe]-PhoAc- | MeSOCH₂ | Bz | 4-Br-Pro- | tBuNH- |
| 1445 | 4-[MorAc-NMe]-PhoAc- | MeSO₂CH₂ | Bz | 4-Br-Pro- | tBuNH- |
| 1446 | 4-[MorAc-NMe]-PhoAc- | MeOCH₂ | Bz | 4-Br-Pro- | tBuNH- |
| 1447 | 4-(MorAc-NMe)-Pho-Ac | MecCH₂CH₂ | Bz | 4-Br-Pro- | tBuNH- |
| 1448 | 4-[MorAc-NMe]-PhoAc- | MecCH₂ | Bz | 4-Br-Pro- | tBuNH- |
| 1449 | 4-MeO-Bzc | CarCH₂ | Bz | 4-Br-Pro- | tBuNH- |
| 1450 | Bzc | Me₂NCH₂ | Bz | 4-F-Pro- | tBuNH- |
| 1451 | Bzc | 2-Car-Et | Bz | 4-F-Pro- | tBuNH- |
| 1452 | Bzc | CNCH₂ | Bz | 4-F-Pro- | tBuNH- |
| 1453 | Bzc | iPr | Bz | 4-F-Pro- | tBuNH- |
| 1454 | Bzc | tBu | Bz | 4-F-Pro- | tBuNH- |
| 1455 | Bzc | diMeCarCH₂ | Bz | 4-F-Pro- | tBuNH- |
| 1456 | Bzc | MorCOCH₂ | Bz | 4-F-Pro- | tBuNH- |
| 1457 | Bzc | PipCOCH | Bz | 4-F-Pro- | tBuNH- |
| 1458 | Bzc | 2-NH₂-Et | Bz | 4-F-Pro- | tBuNH- |
| 1459 | Bzc | 3-NH₂-Pr | Bz | 4-F-Pro- | tBuNH- |
| 1460 | Bzc | MeCarCH₂ | Bz | 4-F-Pro- | tBuNH- |
| 1461 | Bzc | EtCarCH₂ | Bz | 4-F-Pro- | tBuNH- |
| 1462 | Bzc | H | Bz | 4-F-Pro- | tBuNH- |
| 1463 | Bzc | HOCH₂ | Bz | 4-F-Pro- | tBuNH- |
| 1464 | Bzc | 4-ThizCH₂ | Bz | 4-F-Pro- | tBuNH- |
| 1465 | Bzc | 4-ImidCH₂ | Bz | 4-F-Pro- | tBuNH- |
| 1466 | Bzc | COOH-CH₂ | Bz | 4-F-Pro- | tBuNH- |
| 1467 | Bzc | 2-COOH-Et | Bz | 4-F-Pro- | tBuNH- |
| 1468 | Bzc | MeSCH₂ | Bz | 4-F-Pro- | tBuNH- |
| 1469 | Bzc | SamCH₂ | Bz | 4-F-Pro- | tBuNH- |

TABLE 1-continued

| Cpd. No. | R¹ | R³ | R⁴ | Z | R⁵ |
|---|---|---|---|---|---|
| 1470 | Bzc | Bz | Bz | 4-F-Pro- | tBuNH- |
| 1471 | Bzc | SimCH₂ | Bz | 4-F-Pro- | tBuNH- |
| 1472 | Bzc | HiaCH₂ | Bz | 4-F-Pro- | tBuNH- |
| 1473 | Bzc | 2-Sim-Et | Bz | 4-F-Pro- | tBuNH- |
| 1474 | Bzc | 2-Hia-Et | Bz | 4-F-Pro- | tBuNH- |
| 1475 | Bzc | NH₂CH₂ | Bz | 4-F-Pro- | tBuNH- |
| 1476 | Bzc | MeNHCH₂ | Bz | 4-F-Pro- | tBuNH- |
| 1477 | 2-Quix-CO- | 2-Car-Et | Bz | 4-F-Pro- | tBuNH- |
| 1478 | 2-Quix-CO- | CNCH₂ | Bz | 4-F-Pro- | tBuNH- |
| 1479 | 2-Quix-CO- | iPr | Bz | 4-F-Pro- | tBuNH- |
| 1480 | 2-Quix-CO- | tBu | Bz | 4-F-Pro- | tBuNH- |
| 1481 | 2-Quix-CO- | diMeCarCH₂ | Bz | 4-F-Pro- | tBuNH- |
| 1482 | 2-Quix-CO- | MorCOCH₂ | Bz | 4-F-Pro- | tBuNH- |
| 1483 | 2-Quix-CO- | PipCOCH₂ | Bz | 4-F-Pro- | tBuNH- |
| 1484 | 2-Quix-CO- | 2-NH₂-Et | Bz | 4-F-Pro- | tBuNH- |
| 1485 | 2-Quix-CO- | 3-NH₂-Pr | Bz | 4-F-Pro- | tBuNH- |
| 1486 | 2-Quix-CO- | MeCarCH₂ | Bz | 4-F-Pro- | tBuNH- |
| 1487 | 2-Quix-CO- | Et-Car-CH₂ | Bz | 4-F-Pro- | tBuNH- |
| 1488 | 2-Quix-CO- | H | Bz | 4-F-Pro- | tBuNH- |
| 1489 | 2-Quix-CO- | HOCH₂ | Bz | 4-F-Pro- | tBuNH- |
| 1490 | 2-Quix-CO- | 4-ThizCH₂ | Bz | 4-F-Pro- | tBuNH- |
| 1491 | 2-Quix-CO- | 4-ImidCH₂ | Bz | 4-F-Pro- | tBuNH- |
| 1492 | 2-Quix-CO- | COOH-CH₂ | Bz | 4-F-Pro- | tBuNH- |
| 1493 | 2-Quix-CO- | 2-COOH-Et | Bz | 4-F-Pro- | tBuNH- |
| 1494 | 2-Quix-CO- | MeSCH₂ | Bz | 4-F-Pro- | tBuNH- |
| 1495 | 2-Quix-CO- | SAMCH₂ | Bz | 4-F-Pro- | tBuNH- |
| 1496 | 2-Quix-CO- | Bz | Bz | 4-F-Pro- | tBuNH- |
| 1497 | 2-Quix-CO- | SimCH₂ | Bz | 4-F-Pro- | tBuNH- |
| 1498 | 2-Quix-CO- | HiaCH₂ | Bz | 4-F-Pro- | tBuNH- |
| 1499 | 2-Quix-CO- | 2-Sim-Et | Bz | 4-F-Pro- | tBuNH- |
| 1500 | 2-Quix-CO- | 2-Hia-Et | Bz | 4-F-Pro- | tBuNH- |
| 1501 | 2-Quix-CO- | NH₂CH₂ | Bz | 4-F-Pro- | tBuNH- |
| 1502 | 2-Quix-CO- | MeNHCH₂ | Bz | 4-F-Pro- | tBuNH- |
| 1503 | 2-Quix-CO- | Me₂NCH₂ | Bz | 4-F-Pro- | tBuNH- |
| 1504 | 3-Quin-CO- | CarCH₂ | Bz | 4-F-Pro- | tBuNH- |
| 1505 | 4-Quin-CO- | CarCH₂ | Bz | 4-F-Pro- | tBuNH- |
| 1506 | 2-Pyr-CO- | CarCH₂ | Bz | 4-F-Pro- | tBuNH- |
| 1507 | 3-Pyr-CO- | CarCH₂ | Bz | 4-F-Pro- | tBuNH- |
| 1508 | 4-Pyr-CO- | CarCH₂ | Bz | 4-F-Pro- | tBuNH- |
| 1509 | 4-MeO-2-Quin-CO- | CarCH₂ | Bz | 4-F-Pro- | tBuNH- |
| 1510 | 2-Np-CO- | CarCH₂ | Bz | 4-F-Pro- | tBuNH- |
| 1511 | 1-Np-CO- | CarCH₂ | Bz | 4-F-Pro- | tBuNH- |
| 1512 | 2-Bfur-CO- | CarCH₂ | Bz | 4-F-Pro- | tBuNH- |
| 1513 | 3-Bfur-CO- | CarCH₂ | Bz | 4-F-Pro- | tBuNH- |
| 1514 | 5-Bu-2-Pyr-CO- | CarCH₂ | Bz | 4-F-Pro- | tBuNH- |
| 1515 | 4-HO-2-Quin-CO- | CarCH₂ | Bz | 4-F-Pro- | tBuNH- |
| 1516 | 3-HO-2-Quix-CO- | CarCH₂ | Bz | 4-F-Pro- | tBuNH- |
| 1517 | 1-Np-Sfo- | CarCH₂ | Bz | 4-F-Pro- | tBuNH- |
| 1518 | 2-Np-Sfo- | CarCH₂ | Bz | 4-F-Pro- | tBuNH- |
| 1519 | Boz | CarCH₂ | Bz | 4-F-Pro- | tBuNH- |
| 1520 | Bz-NHCO- | CarCH₂ | Bz | 4-F-Pro- | tBuNH- |
| 1521 | Bz-NHCS- | CarCH₂ | Bz | 4-F-Pro- | tBuNH- |
| 1522 | 3-Ind-CO- | CarCH₂ | Bz | 4-F-Pro- | tBuNH- |
| 1523 | 2-Pyrd-CO- | CarCH₂ | Bz | 4-F-Pro- | tBuNH- |
| 1524 | 2-Pip-CO- | CarCH₂ | Bz | 4-F-Pro- | tBuNH- |
| 1525 | 2-Thi-CO- | CarCH₂ | Bz | 4-F-Pro- | tBuNH- |
| 1526 | MecCO- | CarCH₂ | Bz | 4-F-Pro- | tBuNH- |
| 1527 | PhoAc- | CarCH₂ | Bz | 4-F-Pro- | tBuNH- |
| 1528 | 3-Bzisox-CO- | CarCH₂ | Bz | 4-F-Pro- | tBuNH- |
| 1529 | 2-Bzim-CO- | CarCH₂ | Bz | 4-F-Pro- | tBuNH- |
| 1530 | N-Me-3-Ind-CO- | CarCH₂ | Bz | 4-F-Pro- | tBuNH- |
| 1531 | 2-Bzthiaz-CO- | CarCH₂ | Bz | 4-F-Pro- | tBuNH- |
| 1532 | 2-Bzoxaz-CO- | CarCH₂ | Bz | 4-F-Pro- | tBuNH- |
| 1533 | 5-MeO-2-Ind-CO- | CarCH₂ | Bz | 4-F-Pro- | tBuNH- |
| 1534 | 5-HO-2-Ind-CO- | CarCH₂ | Bz | 4-F-Pro- | tBuNH- |
| 1535 | 5-AcO-2-Ind-CO- | CarCH₂ | Bz | 4-F-Pro- | tBuNH- |
| 1536 | 5-NH₂AcO-2-Ind-CO- | CarCH₂ | Bz | 4-F-Pro- | tBuNH- |
| 1537 | 5-Bzim-CO- | CarCH₂ | Bz | 4-F-Pro- | tBuNH- |
| 1538 | (2-NpO)Ac- | CarCH₂ | Bz | 4-F-Pro- | tBuNH- |
| 1539 | (1-NpO)Ac- | CarCH₂ | Bz | 4-F-Pro- | tBuNH- |
| 1540 | 1-NpOCO- | CarCH₂ | Bz | 4-F-Pro- | tBuNH- |
| 1541 | 2-NpOCO- | CarCH₂ | Bz | 4-F-Pro- | tBuNH- |
| 1542 | (3-PhPho)Ac- | CarCH₂ | Bz | 4-F-Pro- | tBuNH- |
| 1543 | 2-Quix-CO- | CarCH₂ | Bz | 4-F-Pro- | 3-HO-Pr-NH- |

TABLE 1-continued

| Cpd. No. | R¹ | R³ | R⁴ | Z | R⁵ |
|---|---|---|---|---|---|
| 1544 | 2-Quix-CO- | CarCH₂ | Bz | 4-F-Pro- | BuNH |
| 1545 | 2-Quix-CO- | CarCH₂ | Bz | 4-F-Pro- | tBuO- |
| 1546 | 2-Quix-CO- | CarCH₂ | Bz | 4-F-Pro- | 1,1-diMe-2-HOEt-NH- |
| 1547 | Bzc | CarCH₂ | Bz | 4-F-Pro- | 3-HOPr-NH- |
| 1548 | Bzc | CarCH₂ | Bz | 4-F-Pro- | BuNH- |
| 1549 | Bzc | CarCH₂ | Bz | 4-F-Pro- | tBuO- |
| 1550 | Bzc | CarCH₂ | Bz | 4-F-Pro- | 1,1-diMe-2-HOEt-NH- |
| 1551 | 3-NH₂-PhoAc- | CarCH₂ | Bz | 4-F-Pro- | tBuNH- |
| 1552 | 2-NH₂-PhoAc- | CarCH₂ | Bz | 4-F-Pro- | tBuNH- |
| 1553 | 2,3-diNH₂-PhoAc- | CarCH₂ | Bz | 4-F-Pro- | tBuNH- |
| 1554 | 2,4-diNH₂-PhoAc- | CarCH₂ | Bz | 4-F-Pro- | tBuNH- |
| 1555 | 4-NH₂-Ph-CO- | CarCH₂ | Bz | 4-F-Pro- | tBuNH- |
| 1556 | 4-NH₂-Bzc | CarCH₂ | Bz | 4-F-Pro- | tBuNH- |
| 1557 | 4-Me₂N-PhoAc- | CarCH₂ | Bz | 4-F-Pro- | tBuNH- |
| 1558 | 4-[Me(Bz)N]-PhoAc- | CarCH₂ | Bz | 4-F-Pro- | tBuNH- |
| 1559 | 4-Mor-PhoAc- | CarCH₂ | Bz | 4-FrPro- | tBuNH- |
| 1560 | 4-Bz-Pipr-Pho-Ac- | CarCH₂ | Bz | 4-F-Pro- | tBuNH- |
| 1561 | 4-MeNH-PhoAc- | CarCH₂ | Bz | 4-F-Pro- | tBuNH- |
| 1562 | 4-[(4'Me-Bzc)-NH]-PhoAc- | CarCH₂ | Bz | 4-F-Pro- | tBuNH- |
| 1563 | 4-[tBoc-NH]-PhoAc- | CarCH₂ | Bz | 4-F-Pro- | tBuNH- |
| 1564 | 4-[tBoc-MeN]-PhoAc- | CarCH₂ | Bz | 4-F-Pro- | tBuNH- |
| 1565 | 4-[Gly-NH]-PhoAc- | CarCH₂ | Bz | 4-F-Pro- | tBuNH- |
| 1566 | 4-[Gly-NMe]-PhoAc- | CarCH₂ | Bz | 4-F-Pro- | tBuNH- |
| 1567 | 4-[N-Me-Gly)NMe]-PhoAc- | CarCH₂ | Bz | 4-F-Pro- | tBuNH- |
| 1568 | 4-[(N-tBoc-Gly)-NMe]-PhoAc- | CarCH₂ | Bz | 4-F-Pro- | tBuNH- |
| 1569 | 4-[(N-tBoc-N-Me-Gly)-NMe]-PhoAc- | CarCH₂ | Bz | 4-F-Pro- | tBuNH- |
| 1570 | 4-[N-Me-Gly)NMe]-PhoAc- | CarCH₂ | Bz | 4-F-Pro- | tBuNH- |
| 1571 | 4-[(BrAc)NMe]-Pho-Ac | CarCH₂ | Bz | 4-F-Pro- | tBuNH- |
| 1572 | 4-[(4'-MeO-Bzc)-NH]-PhoAc- | CarCH₂ | Bz | 4-F-Pro- | tBuNH- |
| 1573 | N-Me-4-PipO-Ac- | CarCH₂ | Bz | 4-F-Pro- | tBuNH- |
| 1574 | 4-NH₂-cHxO-Ac- | CarCH₂ | Bz | 4-F-Pro- | tBuNH- |
| 1575 | 4-NH₂-PhoAc- | CarCH₂ | Bz | 4-F-Pro- | 1,1-diMe-2-HOEt-NH- |
| 1576 | 3-NH₂-PhoAc- | CarCH₂ | Bz | 4-F-Pro- | 1,1-diMe-2-HOEt-NH- |
| 1577 | 2-NH₂-PhoAc- | CarCH₂ | Bz | 4-F-Pro- | 1,1-diMe-2-HOEt-NH- |
| 1578 | 2,3-diNH₂-Ac- | CarCH₂ | Bz | 4-F-Pro- | 1,1-diMe-2-HOEt-NH- |
| 1579 | 2,4-diNH₂-PhoAc- | CarCH₂ | Bz | 4-F-Pro- | 1,1-diMe-2-HOEt-NH- |
| 1580 | 4-NH₂-Ph-CO- | CarCH₂ | Bz | 4-F-Pro- | 1,1-diMe-2-HOEt-NH- |
| 1581 | 4-NH₂-Bzc | CarCH₂ | Bz | 4-F-Pro- | 1,1-diMe-2-HOEt-NH- |
| 1582 | 4-Me₂N-PhoAc- | CarCH₂ | Bz | 4-F-Pro- | 1,1-diMe-2-HOEt-NH- |
| 1583 | 4-[Me(Bz)N]- | CarCH₂ | Bz | 4-F-Pro- | 1,1-diMe-2-HOEt-NH- |
| 1584 | 4-Mor-PhoAc- | CarCH₂ | Bz | 4-F-Pro- | 1,1-diMe-2-HOEt-NH- |
| 1585 | 4-[N-Bz-Pipr]PhoAc- | CarCH₂ | Bz | 4-F-Pro- | 1,1-diMe-2-HOEt-NH- |
| 1586 | 4-[MeNH]-PhoAc- | CarCH₂ | Bz | 4-F-Pro- | 1,1-diMe-2-HOEt-NH- |
| 1587 | 4-[(4'Me-Bzc)-NH]-PhoAc- | CarCH₂ | Bz | 4-F-Pro- | 1,1-diMe-2-HOEt-NH- |
| 1588 | 4-[BzcNH]-PhoAc- | CarCH₂ | Bz | 4-F-Pro- | 1,1-diMe-2-HOEt-NH- |
| 1589 | 4-[tBoc-NH]-PhoAc- | CarCH₂ | Bz | 4-F-Pro- | 1,1-diMe-2-HOEt-NH- |
| 1590 | 4-[tBoc-NMe]-PhoAc- | CarCH₂ | Bz | 4-F-Pro- | 1,1-diMe-2-HOEt-NH- |
| 1591 | 4-[Gly-NH]-PhoAc- | CarCH₂ | Bz | 4-F-Pro- | 1,1-diMe-2-HOEt-NH- |
| 1592 | 4-[Gly-NMe]-PhoAc- | CarCH₂ | Bz | 4-F-Pro- | 1,1-diMe-2-HOEt-NH- |
| 1593 | 4-[N-Me-Gly)NMe]-PhoAc- | CarCH₂ | Bz | 4-F-Pro- | 1,1-diMe-2-HOEt-NH- |
| 1594 | 4-[(N-tBoc-Gly)-NMe]-PhoAc- | CarCH₂ | Bz | 4-F-Pro- | 1,1-diMe-2-HOEt-NH- |
| 1595 | 4-[(N-tBoc-N-Me-Gly)-NMe]-Pho-Ac- | CarCH₂ | Bz | 4-F-Pro- | 1,1-diMe-2-HOEt-NH- |
| 1596 | Boc | CarCH₂ | Bz | 4-F-Pro- | 1,1-diMe-2-HOEt-NH- |
| 1597 | 4-[(BrAc)NMe]-PhoAc- | CarCH₂ | Bz | 4-F-Pro- | 1,1-diMe-2-HOEt-NH- |
| 1598 | 4-[(4'-MeO-Bzc)-NH]-PhoAc- | CarCH₂ | Bz | 4-F-Pro- | 1,1-diMe-2-HOEt-NH- |
| 1599 | N-Me-4-PipO-Ac- | CarCH₂ | Bz | 4-F-Pro- | 1,1-diMe-2-HOEt-NH- |
| 1600 | 4-NH₂-cHxO-Ac- | CarCH₂ | Bz | 4-F-Pro- | 1,1-diMe-2-HOEt-NH- |
| 1601 | 4-(Mor-Ac)NMe-PhoAc- | CarCH₂ | Bz | 4-F-Pro- | 1,1-diMe-2-HOEt-NH- |

TABLE 1-continued

| Cpd. No. | R¹ | R³ | R⁴ | Z | R⁵ |
|---|---|---|---|---|---|
| 1602 | 4-NH₂-PhoAc- | CarCH₂ | Bz | 4-F-Pro- | 1,1-diMe-2-HOPr-NH- |
| 1603 | 3-NH₂-PhoAc- | CarCH₂ | Bz | 4-F-Pro- | 1,1-diMe-2-HOPr-NH- |
| 1604 | 2-NH₂-PhoAc- | CarCH₂ | Bz | 4-F-Pro- | 1,1-diMe-2-HOPr-NH- |
| 1605 | 2,3-diNH₂-PhoAc- | CarCH₂ | Bz | 4-F-Pro- | 1,1-diMe-2-HOPr-NH- |
| 1606 | 2,4-diNH₂-PhoAc- | CarCH₂ | Bz | 4-F-Pro- | 1,1-diMe-2-HOPr-NH- |
| 1607 | 4-NH₂-Ph-CO- | CarCH₂ | Bz | 4-F-Pro- | 1,1-diMe-2-HOPr-NH- |
| 1608 | 4-NH₂-Bzc | CarCH₂ | Bz | 4-F-Pro- | 1,1-diMe-2-HOPr-NH- |
| 1609 | 4-Me₂N-PhoAc- | CarCH₂ | Bz | 4-F-Pro- | 1,1-diMe-2-HOPr-NH- |
| 1610 | 4-[Me(Bz)N]-PhoAc- | CarCH₂ | Bz | 4-F-Pro- | 1,1-diMe-2-HOPr-NH- |
| 1611 | 4-Mor-PhoAc- | CarCH₂ | Bz | 4-F-Pro- | 1,1-diMe-2-HOPr-NH- |
| 1612 | 4-[N-Bz-Pipr]-PhoAc- | CarCH₂ | Bz | 4-F-Pro- | 1,1-diMe-2-HOPr-NH- |
| 1613 | 4-MeNH-PhoAc- | CarCH₂ | Bz | 4-F-Pro- | 1,1-diMe-2-HOPr-NH- |
| 1614 | 4-[(4'Me-Bzc)-NH]-PhoAc- | CarCH₂ | Bz | 4-F-Pro- | 1,1-diMe-2-HOPr-NH- |
| 1615 | 4-[BzcNH]-PhoAc- | CarCH₂ | Bz | 4-F-Pro- | 1,1-diMe-2-HOPr-NH- |
| 1616 | 4-[tBoc-NH]-PhoAc- | CarCH₂ | Bz | 4-F-Pro- | 1,1-diMe-2-HOPr-NH- |
| 1617 | 4-[tBoc-MeN]-PhoAc- | CarCH₂ | Bz | 4-F-Pro- | 1,1-diMe-2-HOPr-NH- |
| 1618 | 4-[Gly-NH]-PhoAc- | CarCH₂ | Bz | 4-F-Pro- | 1,1-diMe-2-HOPr-NH- |
| 1619 | 4-[Gly-NMe]-PhoAc- | CarCH₂ | Bz | 4-F-Pro- | 1,1-diMe-2-HOPr-NH- |
| 1620 | 4-[(N-Me-Gly)NMe]-PhoAc- | CarCH₂ | Bz | 4-F-Pro- | 1,1-diMe-2-HOPr-NH- |
| 1621 | 4-[(N-tBoc-Gly)-NMe]-Pho-Ac) | CarCH₂ | Bz | 4-F-Pro- | 1,1-diMe-2-HOPr-NH- |
| 1622 | 4-[(N-tBoc-N-Me-Gly)-NMe]-Pho-Ac- | CarCH₂ | Bz | 4-F-Pro- | 1,1-diMe-2-HOPr-NH- |
| 1623 | Boc | CarCH₂ | Bz | 4-F-Pro- | 1,1-diMe-2-HOPr-NH- |
| 1624 | 4-[(BrAc)NMe]-PhoAc- | CarCH₂ | Bz | 4-F-Pro- | 1,1-diMe-2-HOPr-NH- |
| 1625 | 4-[(4'-MeO-Bzc)NH]-PhoAc- | CarCH₂ | Bz | 4-F-Pro- | 1,1-diMe-2-HOPr-NH- |
| 1626 | N-Me-4-PipO-Ac- | CarCH₂ | Bz | 4-F-Pro- | 1,1-diMe-2-HOPr-NH- |
| 1627 | 4-NH₂-cHxO-Ac- | CarCH₂ | Bz | 4-F-Pro- | 1,1-diMe-2-HOPr-NH- |
| 1628 | 4-[(MorAc)NMe]-PhoAc- | CarCH₂ | Bz | 4-F-Pro- | 1,1-diMe-2-HOPr-NH- |
| 1629 | 2-Quin-CO- | CarCH₂ | Bz | 4-F-Pro- | 1,1-diMe-2-HOEt-NH- |
| 1630 | 3-Quin-CO- | CarCH₂ | Bz | 4-F-Pro- | 1,1-diMe-2-HOEt-NH- |
| 1631 | 4-Quin-CO- | CarCH₂ | Bz | 4-F-Pro- | 1,1-diMe-2-HOEt-NH- |
| 1632 | 2-Pyr-CO- | CarCH₂ | Bz | 4-F-Pro- | 1,1-diMe-2-HOEt-NH- |
| 1633 | 3-Pyr-CO- | CarCH₂ | Bz | 4-F-Pro- | 1,1-diMe-2-HOEt-NH- |
| 1634 | 4-Pyr-CO- | CarCH₂ | Bz | 4-F-Pro- | 1,1-diMe-2-HOEt-NH- |
| 1635 | 4-MeO-2-Quin-CO- | CarCH₂ | Bz | 4-F-Pro- | 1,1-diMe-2-HOEt-NH- |
| 1636 | 2-Np-CO- | CarCH₂ | Bz | 4-F-Pro- | 1,1-diMe-2-HOEt-NH- |
| 1637 | 1-Np-CO- | CarCH₂ | Bz | 4-F-Pro- | 1,1-diMe-2-HOEt-NH- |
| 1638 | 2-Bfur-CO- | CarCH₂ | Bz | 4-F-Pro- | 1,1-diMe-2-HOEt-NH- |
| 1639 | 3-Bfur-CO- | CarCH₂ | Bz | 4-F-Pro- | 1,1-diMe-2-HOEt-NH- |
| 1640 | 5-Bu-2-Pyr-CO- | CarCH₂ | Bz | 4-F-Pro- | 1,1-diMe-2-HOEt-NH- |
| 1641 | 4-OH-2-Quin-CO- | CarCH₂ | Bz | 4-F-Pro- | 1,1-diMe-2-HOEt-NH- |
| 1642 | 3-OH-2-Quix-CO- | CarCH₂ | Bz | 4-F-Pro- | 1,1-diMe-2-HOEt-NH- |
| 1643 | 1-Np-Sfo- | CarCH₂ | Bz | 4-F-Pro- | 1,1-diMe-2-HOEt-NH- |
| 1644 | 2-Np-Sfo- | CarCH₂ | Bz | 4-F-Pro- | 1,1-diMe-2-HOEt-NH- |
| 1645 | Boz | CarCH₂ | Bz | 4-F-Pro- | 1,1-diMe-2-HOEt-NH- |
| 1646 | Bz-NHCO- | CarCH₂ | Bz | 4-F-Pro- | 1,1-diMe-2-HOEt-NH- |
| 1647 | Bz-NHCS- | CarCH₂ | Bz | 4-F-Pro- | 1,1-diMe-2-HOEt-NH- |
| 1648 | 2-Ind-CO- | CarCH₂ | Bz | 4-F-Pro- | 1,1-diMe-2-HOEt-NH- |
| 1649 | 3-Ind-CO- | CarCH₂ | Bz | 4-F-Pro- | 1,1-diMe-2-HOEt-NH- |
| 1650 | tBoc | CarCH₂ | Bz | 4-F-Pro- | 1,1-diMe-2-HOEt-NH- |
| 1651 | 2-Pyrd-CO- | CarCH₂ | Bz | 4-F-Pro- | 1,1-diMe-2-HOEt-NH- |
| 1652 | 2-Pip-CO- | CarCH₂ | Bz | 4-F-Pro- | 1,1-diMe-2-HOEt-NH- |
| 1653 | 2-Thi-CO- | CarCH₂ | Bz | 4-F-Pro- | 1,1-diMe-2-HOEt-NH- |
| 1654 | MecCO- | CarCH₂ | Bz | 4-F-Pro- | 1,1-diMe-2-HOEt-NH- |
| 1655 | PhoAc- | CarCH₂ | Bz | 4-F-Pro- | 1,1-diMe-2-HOEt-NH- |
| 1656 | MPhoAc- | CarCH₂ | Bz | 4-F-Pro- | 1,1-diMe-2-HOEt-NH- |
| 1657 | 3-Bzisox-CO- | CarCH₂ | Bz | 4-F-Pro- | 1,1-diMe-2-HOEt-NH- |
| 1658 | 2-Bzim-CO- | CarCH₂ | Bz | 4-F-Pro- | 1,1-diMe-2-HOEt-NH- |
| 1659 | N-Me-3-Ind-CO- | CarCH₂ | Bz | 4-F-Pro- | 1,1-diMe-2-HOEt-NH- |
| 1660 | 2-Bzthiaz-CO- | CarCH₂ | Bz | 4-F-Pro- | 1,1-diMe-2-HOEt-NH- |
| 1661 | 2-Bzoxaz-CO- | CarCH₂ | Bz | 4-F-Pro- | 1,1-diMe-2-HOEt-NH- |
| 1662 | 5-MeO-2-Ind-CO- | CarCH₂ | Bz | 4-F-Pro- | 1,1-diMe-2-HOEt-NH- |
| 1663 | 5-HO-2-Ind-CO- | CarCH₂ | Bz | 4-F-Pro- | 1,1-diMe-2-HOEt-NH- |
| 1664 | 5-AcO-2-Ind-CO- | CarCH₂ | Bz | 4-F-Pro- | 1,1-diMe-2-HOEt-NH- |
| 1665 | 5-NH₂AcO-2-Ind-CO- | CarCH₂ | Bz | 4-F-Pro- | 1,1-diMe-2-HOEt-NH- |
| 1666 | 5-Bzim-CO- | CarCH₂ | Bz | 4-F-Pro- | 1,1-diMe-2-HOEt-NH- |
| 1667 | (1-NpO)Ac- | CarCH₂ | Bz | 4-F-Pro- | 1,1-diMe-2-HOEt-NH- |
| 1668 | 1-NpOCO- | CarCH₂ | Bz | 4-F-Pro- | 1,1-diMe-2-HOEt-NH- |

TABLE 1-continued

| Cpd. No. | R¹ | R³ | R⁴ | Z | R⁵ |
|---|---|---|---|---|---|
| 1669 | 2-NpOCO- | CarCH₂ | Bz | 4-F-Pro- | 1,1-diMe-2-HOEt-NH- |
| 1670 | (3-PhPho)Ac- | CarCH₂ | Bz | 4-F-Pro- | 1,1-diMe-2-HOEt-NH- |
| 1671 | (2-NpO)Ac- | CarCH₂ | Bz | 4-F-Pro- | 1,1-diMe-2-HOEt-NH- |
| 1672 | Bzc | CarCH₂ | Bz | 4-F-Pro- | 1,1-diMe-2-HOPr-NH- |
| 1673 | 2-Quix-CO- | CarCH₂ | Bz | 4-F-Pro- | 1,1-diMe-2-HOPr-NH- |
| 1674 | 2-Quin-CO- | CarCH₂ | Bz | 4-F-Pro- | 1,1-diMe-2-HOPr-NH- |
| 1675 | 3-Quin-CO- | CarCH₂ | Bz | 4-F-Pro- | 1,1-diMe-2-HOPr-NH- |
| 1676 | 4-Quin-CO- | CarCH₂ | Bz | 4-F-Pro- | 1,1-diMe-2-HOPr-NH- |
| 1677 | 2-Pyr-CO- | CarCH₂ | Bz | 4-F-Pro- | 1,1-diMe-2-HOPr-NH- |
| 1678 | 3-Pyr-CO- | CarCH₂ | Bz | 4-F-Pro- | 1,1-diMe-2-HOPr-NH- |
| 1679 | 4-Pyr-CO- | CarCH₂ | Bz | 4-F-Pro- | 1,1-diMe-2-HOPr-NH- |
| 1680 | 4-MeO-2-Quin-CO- | CarCH₂ | Bz | 4-F-Pro- | 1,1-diMe-2-HOPr-NH- |
| 1681 | 2-Np-CO- | CarCH₂ | Bz | 4-F-Pro- | 1,1-diMe-2-HOPr-NH- |
| 1682 | 1-Np-CO- | CarCH₂ | Bz | 4-F-Pro- | 1,1-diMe-2-HOPr-NH- |
| 1683 | 2-Bfur-CO- | CarCH₂ | Bz | 4-F-Pro- | 1,1-diMe-2-HOPr-NH- |
| 1684 | 3-Bfur-CO- | CarCH₂ | Bz | 4-F-Pro- | 1,1-diMe-2-HOPr-NH- |
| 1685 | 5-Bu-2-Pyr-CO- | CarCH₂ | Bz | 4-F-Pro- | 1,1-diMe-2-HOPr-NH- |
| 1686 | 4-HO-2-Quin-CO- | CarCH₂ | Bz | 4-F-Pro- | 1,1-diMe-2-HOPr-NH- |
| 1687 | 3-HO-2-Quix-CO- | CarCH₂ | Bz | 4-F-Pro- | 1,1-diMe-2-HOPr-NH- |
| 1688 | 1-Np-Sfo- | CarCH₂ | Bz | 4-F-Pro- | 1,1-diMe-2-HOPr-NH- |
| 1689 | 2-Np-Sfo- | CarCH₂ | Bz | 4-F-Pro- | 1,1-diMe-2-HOPr-NH- |
| 1690 | Boz | CarCH₂ | Bz | 4-F-Pro- | 1,1-diMe-2-HOPr-NH- |
| 1691 | Bz-NHCO- | CarCH₂ | Bz | 4-F-Pro- | 1,1-diMe-2-HOPr-NH- |
| 1692 | Bz-NHCS- | CarCH₂ | Bz | 4-F-Pro- | 1,1-diMe-2-HOPr-NH- |
| 1693 | 2-Ind-CO- | CarCH₂ | Bz | 4-F-Pro- | 1,1-diMe-2-HOPr-NH- |
| 1694 | 3-Ind-CO- | CarCH₂ | Bz | 4-F-Pro- | 1,1-diMe-2-HOPr-NH- |
| 1695 | tBoc | CarCH₂ | Bz | 4-F-Pro- | 1,1-diMe-2-HOPr-NH- |
| 1696 | 2-Pyrd-CO- | CarCH₂ | Bz | 4-F-Pro- | 1,1-diMe-2-HOPr-NH- |
| 1697 | 2-Pip-CO- | CarCH₂ | Bz | 4-F-Pro- | 1,1-diMe-2-HOPr-NH- |
| 1698 | 2-Thi-CO- | CarCH₂ | Bz | 4-F-Pro- | 1,1-diMe-2-HOPr-NH- |
| 1699 | MeOCOCO- | CarCH₂ | Bz | 4-F-Pro- | 1,1-diMe-2-HOPr-NH- |
| 1700 | PhoAc- | CarCH₂ | Bz | 4-F-Pro- | 1,1-diMe-2-HOPr-NH- |
| 1701 | MPhoAc- | CarCH₂ | Bz | 4-F-Pro- | 1,1-diMe-2-HOPr-NH- |
| 1702 | 3-Bzisox-CO- | CarCH₂ | Bz | 4-F-Pro- | 1,1-diMe-2-HOPr-NH- |
| 1703 | 2-Bzim-CO- | CarCH₂ | Bz | 4-F-Pro- | 1,1-diMe-2-HOPr-NH- |
| 1704 | N-Me-3-Ind-CO- | CarCH₂ | Bz | 4-F-Pro- | 1,1-diMe-2-HOPr-NH- |
| 1705 | 2-Bzthiaz-CO- | CarCH₂ | Bz | 4-F-Pro- | 1,1-diMe-2-HOPr-NH- |
| 1706 | 2-Bzoxaz-CO- | CarCH₂ | Bz | 4-F-Pro- | 1,1-diMe-2-HOPr-NH- |
| 1707 | 5-MeO-2-Ind-CO- | CarCH₂ | Bz | 4-F-Pro- | 1,1-diMe-2-HOPr-NH- |
| 1708 | 5-HO-2-Ind-CO- | CarCH₂ | Bz | 4-F-Pro- | 1,1-diMe-2-HOPr-NH- |
| 1709 | 5-AcO-2-Ind-CO- | CarCH₂ | Bz | 4-F-Pro- | 1,1-diMe-2-HOPr-NH- |
| 1710 | 5-H₂NAcO-2-Ind-CO- | CarCH₂ | Bz | 4-F-Pro- | 1,1-diMe-2-HOPr-NH- |
| 1711 | 5-Bzim-CO- | CarCH₂ | Bz | 4-F-Pro- | 1,1-diMe-2-HOPr-NH- |
| 1712 | (2-NpO)Ac- | CarCH₂ | Bz | 4-F-Pro- | 1,1-diMe-2-HOPr-NH- |
| 1713 | (1-NpO)Ac- | CarCH₂ | Bz | 4-F-Pro- | 1,1-diMe-2-HOPr-NH- |
| 1714 | 1-NpOCO- | CarCH₂ | Bz | 4-F-Pro- | 1,1-diMe-2-HOPr-NH- |
| 1715 | 2-NpOCO- | CarCH₂ | Bz | 4-F-Pro- | 1,1-diMe-2-HOPr-NH- |
| 1716 | (3-PhPho)-Ac- | CarCH₂ | Bz | 4-F-Pro- | 1,1-diMe-2-HOPr-NH- |
| 1717 | Bzc | CarCH₂ | 4-Br-Bz | 4-F-Pro- | tBuNH- |
| 1718 | 2-Quix-CO- | CarCH₂ | 4-Br-Bz | 4-F-Pro- | tBuNH- |
| 1719 | Bzc | CarCH₂ | 4-MeOBz | 4-F-Pro- | tBuNH- |
| 1720 | 2-Quix-CO- | CarCH₂ | 4-MeOBz | 4-F-Pro- | tBuNH- |
| 1721 | Bzc | CarCH₂ | 4-Me-Bz | 4-F-Pro- | tBuNH- |
| 1722 | 2-Quix-CO- | CarCH₂ | 4-Me-Bz | 4-F-Pro- | tBuNH- |
| 1723 | Bzc | CarCH₂ | cHxCH₂ | 4-F-Pro- | tBuNH- |
| 1724 | 2-Quix-CO- | CarCH₂ | cHxCH₂ | 4-F-Pro- | tBuNH- |
| 1725 | Bzc | MeSOCH₂ | Bz | 4-F-Pro- | tBuNH- |
| 1726 | Bzc | MeSO₂CH₂ | Bz | 4-F-Pro- | tBuNH- |
| 1727 | Bzc | MeOCH₂- | Bz | 4-F-Pro- | tBuNH- |
| 1728 | Bzc | MecCH₂-CH₂ | Bz | 4-F-Pro- | tBuNH- |
| 1729 | Bzc | MecCH₂ | Bz | 4-F-Pro- | tBuNH- |
| 1730 | 2-Quix-CO- | MeSOCH | Bz | 4-F-Pro- | tBuNH- |
| 1731 | 2-Quix-CO- | MeSO₂CH₂ | Bz | 4-F-Pro- | tBuNH- |
| 1732 | 2-Quix-CO- | MeOCH₂ | Bz | 4-F-Pro- | tBuNH- |
| 1733 | 2-Quix-CO- | MecCH₂CH₂ | Bz | 4-F-Pro- | tBuNH- |
| 1734 | 2-Quix-CO- | MecCH₂ | Bz | 4-F-Pro- | tBuNH- |
| 1735 | 2-Quin-CO- | MeSOCH₂ | Bz | 4-F-Pro- | tBuNH- |
| 1736 | 2-Quin-CO- | MeSO₂CH₂ | Bz | 4-F-Pro- | tBuNH- |
| 1737 | 2-Quin-CO- | MeOCH₂ | Bz | 4-F-Pro- | tBuNH- |
| 1738 | 2-Quin-CO- | MecCH₂CH₂ | Bz | 4-F-Pro- | tBuNH- |
| 1739 | 2-Quin-CO- | MecCH₂ | Bz | 4-F-Pro- | tBuNH- |

TABLE 1-continued

| Cpd. No. | R¹ | R³ | R⁴ | Z | R⁵ |
|---|---|---|---|---|---|
| 1740 | 3-Quin-CO- | MeSOCH₂ | Bz | 4-F-Pro- | tBuNH- |
| 1741 | 3-Quin-CO- | MeSO₂CH₂ | Bz | 4-F-Pro- | tBuNH- |
| 1742 | 3-Quin-CO- | MeOCH₂ | Bz | 4-F-Pro- | tBuNH- |
| 1743 | 3-Quin-CO- | MecCH₂CH₂ | Bz | 4-F-Pro- | tBuNH- |
| 1744 | 3-Quin-CO- | MecCH₂ | Bz | 4-F-Pro- | tBuNH- |
| 1745 | 2-Bfur-CO- | MeSOCH₂ | Bz | 4-F-Pro- | tBuNH- |
| 1746 | 2-Bfur-CO- | MeSO₂CH₂ | Bz | 4-F-Pro- | tBuNH- |
| 1747 | 2-Bfur-CO- | MeOCH₂ | Bz | 4-F-Pro- | tBuNH- |
| 1748 | 2-Bfur-CO- | MecCH₂CH₂ | Bz | 4-F-Pro- | tBuNH- |
| 1749 | 2-Bfur-CO- | MecCH₂ | Bz | 4-F-Pro- | tBuNH- |
| 1750 | 3-Bfur-CO- | MeSOCH | Bz | 4-F-Pro- | tBuNH- |
| 1751 | 3-Bfur-CO- | MeSO₂CH₂ | Bz | 4-F-Pro- | tBuNH- |
| 1752 | 3-Bfur-CO- | MeOCH₂ | Bz | 4-F-Pro- | tBuNH- |
| 1753 | 3-Bfur-CO- | MecCH₂CH₂ | Bz | 4-F-Pro- | tBuNH- |
| 1754 | 3-Bfur-CO- | MecCH₂ | Bz | 4-F-Pro- | tBuNH- |
| 1755 | 3-Ind-CO- | MeSOCH₂ | Bz | 4-F-Pro- | tBuNH- |
| 1756 | 3-Ind-CO- | MeSO₂CH₂ | Bz | 4-F-Pro- | tBuNH- |
| 1757 | 3-Ind-CO- | MeOCH₂ | Bz | 4-F-Pro- | tBuNH- |
| 1758 | 3-Ind-CO- | MecCH₂CH₂ | Bz | 4-F-Pro- | tBuNH- |
| 1759 | 3-Ind-CO- | MecCH₂ | Bz | 4-F-Pro- | tBuNH- |
| 1760 | Mph-O-Ac- | MeSOCH₂ | Bz | 4-F-Pro- | tBuNH- |
| 1761 | Mph-O-Ac- | MeSO₂CH₂ | Bz | 4-F-Pro- | tBuNH- |
| 1762 | Mph-O-Ac- | MeOCH₂ | Bz | 4-F-Pro- | tBuNH- |
| 1763 | Mph-O-Ac- | MecCH₂CH₂ | Bz | 4-F-Pro- | tBuNH- |
| 1764 | Mph-O-Ac- | MecCH₂ | Bz | 4-F-Pro- | tBuNH- |
| 1765 | 5-NH₂-AcO-2-Ind-CO- | MeSOCH₂ | Bz | 4-F-Pro- | tBuNH- |
| 1766 | 5-NH₂-AcO-2-Ind-CO- | MeSO₂CH₂ | Bz | 4-F-Pro- | tBuNH- |
| 1767 | 5-NH₂-AcO-2-Ind-CO- | MeOCH₂ | Bz | 4-F-Pro- | tBuNH- |
| 1768 | 5-NH₂-AcO-2-Ind-CO- | MecCH₂CH₂ | Bz | 4-F-Pro- | tBuNH- |
| 1769 | 5-NH₂-AcO-2-Ind-CO- | MecCH₂ | Bz | 4-F-Pro- | tBuNH- |
| 1770 | 4-NH₂-PhoAc- | MeSOCH₂ | Bz | 4-F-Pro- | tBuNH- |
| 1771 | 4-NH₂-PhoAc- | MeSO₂CH₂ | Bz | 4-F-Pro- | tBuNH- |
| 1772 | 4-NH₂-PhoAc- | MeOCH₂ | Bz | 4-F-Pro- | tBuNH- |
| 1773 | 4-NH₂-PhoAc- | MecCH₂CH₂ | Bz | 4-F-Pro- | tBuNH- |
| 1774 | 4-NH₂-PhoAc- | MecCH₂ | Bz | 4-F-Pro- | tBuNH- |
| 1775 | 4-[BzcNH]-PhoAc | MeSOCH₂ | Bz | 4-F-Pro- | tBuNH- |
| 1776 | 4-[BzcNH]-PhoAc | MeSO₂CH₂ | Bz | 4-F-Pro- | tBuNH- |
| 1777 | 4-[BzcNH]-PhoAc | MeOCH₂ | Bz | 4-F-Pro- | tBuNH- |
| 1778 | 4-[BzcNH]-PhoAc | MecCH₂CH₂ | Bz | 4-F-Pro- | tBuNH- |
| 1779 | 4-[BzcNH]-PhoAc | MecCH₂ | Bz | 4-F-Pro- | tBuNH- |
| 1780 | 4-[MorAc-NMe]-PhoAc- | MeSOCH₂ | Bz | 4-F-Pro- | tBuNH- |
| 1781 | 4-[MorAc-NMe]-PhoAc- | MeSO₂CH₂ | Bz | 4-F-Pro- | tBuNH- |
| 1782 | 4-[MorAc-NMe]-PhoAc- | MeOCH₂ | Bz | 4-F-Pro- | tBuNH- |
| 1783 | 4-[MorAc-NMe]-PhoAc- | MecCH₂CH₂ | Bz | 4-F-Pro- | tBuNH- |
| 1784 | 4-[MorAc-NMe]-PhoAc- | MecCH₂ | Bz | 4-F-Pro- | tBuNH- |
| 1785 | 4-MeO-Bzc | CarCH₂ | Bz | 4-F-Pro- | tBuNH- |
| 1786 | Bzc | Me₂NCH₂ | Bz | 4-I-Pro- | tBuNH- |
| 1787 | Bzc | 2-CarEt | Bz | 4-I-Pro- | tBuNH- |
| 1788 | Bzc | CNCH₂ | Bz | 4-I-Pro- | tBuNH- |
| 1789 | Bzc | iPr | Bz | 4-I-Pro- | tBuNH- |
| 1790 | Bzc | tBu | Bz | 4-I-Pro- | tBuNH- |
| 1791 | Bzc | diMeCarCH₂ | Bz | 4-I-Pro- | tBuNH- |
| 1792 | Bzc | MorCOCH₂ | Bz | 4-I-Pro- | tBuNH- |
| 1793 | Bzc | PipCOCH₂ | Bz | 4-I-Pro- | tBuNH- |
| 1794 | Bzc | 2-NH₂-Et | Bz | 4-I-Pro- | tBuNH- |
| 1795 | Bzc | 3-NH₂-Pr | Bz | 4-I-Pro- | tBuNH- |
| 1796 | Bzc | MeCarCH₂ | Bz | 4-I-Pro- | tBuNH- |
| 1797 | Bzc | EtCarCH₂ | Bz | 4-I-Pro- | tBuNH- |
| 1798 | Bzc | H | Bz | 4-I-Pro- | tBuNH- |
| 1799 | Bzc | HOCH₂ | Bz | 4-I-Pro- | tBuNH- |
| 1800 | Bzc | 4-ThizCH₂ | Bz | 4-I-Pro- | tBuNH- |
| 1801 | Bzc | 4-ImidCH₂ | Bz | 4-I-Pro- | tBuNH- |
| 1802 | Bzc | COOH-CH₂ | Bz | 4-I-Pro- | tBuNH- |
| 1803 | Bzc | 2-COOH-Et | Bz | 4-I-Pro- | tBuNH- |
| 1804 | Bzc | MeSCH₂ | Bz | 4-I-Pro- | tBuNH- |
| 1805 | Bzc | SamCH₂ | Bz | 4-I-Pro- | tBuNH- |

TABLE 1-continued

| Cpd. No. | R¹ | R³ | R⁴ | Z | R⁵ |
|---|---|---|---|---|---|
| 1806 | Bzc | Bz | Bz | 4-I-Pro- | tBuNH- |
| 1807 | Bzc | SimCH₂ | Bz | 4-I-Pro- | tBuNH- |
| 1808 | Bzc | HiaCH₂ | Bz | 4-I-Pro- | tBuNH- |
| 1809 | Bzc | 2-Sim-Et | Bz | 4-I-Pro- | tBuNH- |
| 1810 | Bzc | 2-Hia-Et | Bz | 4-I-Pro- | tBuNH- |
| 1811 | Bzc | NH₂CH₂ | Bz | 4-I-Pro- | tBuNH- |
| 1812 | Bzc | MeNHCH₂ | Bz | 4-I-Pro- | tBuNH- |
| 1813 | 2-Quix-CO- | 2-Car-Et | Bz | 4-I-Pro- | tBuNH- |
| 1814 | 2-Quix-CO- | CNCH₂ | Bz | 4-I-Pro- | tBuNH- |
| 1815 | 2-Quix-CO- | iPr | Bz | 4-I-Pro- | tBuNH- |
| 1816 | 2-Quix-CO- | tBu | Bz | 4-I-Pro- | tBuNH- |
| 1817 | 2-Quix-CO- | diMeCarCH₂ | Bz | 4-I-Pro- | tBuNH- |
| 1818 | 2-Quix-CO- | MorCOCH | Bz | 4-I-Pro- | tBuNH- |
| 1819 | 2-Quix-CO- | PipCOCH₂ | Bz | 4-I-Pro- | tBuNH- |
| 1820 | 2-Quix-CO- | 2-NH₂-Et | Bz | 4-I-Pro- | tBuNH- |
| 1821 | 2-Quix-CO- | 3-NH₂-Pr | Bz | 4-I-Pro- | tBuNH- |
| 1822 | 2-Quix-CO- | MeCarCH₂ | Bz | 4-I-Pro- | tBuNH- |
| 1823 | 2-Quix-CO- | EtCarCH₂ | Bz | 4-I-Pro- | tBuNH- |
| 1824 | 2-Quix-CO- | H | Bz | 4-I-Pro- | tBuNH- |
| 1825 | 2-Quix-CO- | HOCH₂ | Bz | 4-I-Pro- | tBuNH- |
| 1826 | 2-Quix-CO- | 4-ThizCH₂ | Bz | 4-I-Pro- | tBuNH- |
| 1827 | 2-Quix-CO- | 4-ImidCH₂ | Bz | 4-I-Pro- | tBuNH- |
| 1828 | 2-Quix-CO- | COOH-CH₂ | Bz | 4-I-Pro- | tBuNH- |
| 1829 | 2-Quix-CO- | 2-COOH-Et | Bz | 4-I-Pro- | tBuNH- |
| 1830 | 2-Quix-CO- | MeSCH₂ | Bz | 4-I-Pro- | tBuNH- |
| 1831 | 2-Quix-CO- | SamCH₂ | Bz | 4-I-Pro- | tBuNH- |
| 1832 | 2-Quix-CO- | Bz | Bz | 4-I-Pro- | tBuNH- |
| 1833 | 2-Quix-CO- | SimCH₂ | Bz | 4-I-Pro- | tBuNH- |
| 1834 | 2-Quix-CO- | HiaCH₂ | Bz | 4-I-Pro- | tBuNH- |
| 1835 | 2-Quix-CO- | 2-Sim-Et | Bz | 4-I-Pro- | tBuNH- |
| 1836 | 2-Quix-CO- | 2-Hia-Et | Bz | 4-I-Pro- | tBuNH- |
| 1837 | 2-Quix-CO- | NH₂CH₂ | Bz | 4-I-Pro- | tBuNH- |
| 1838 | 2-Quix-CO- | MeNHCH₂ | Bz | 4-I-Pro- | tBuNH- |
| 1839 | 2-Quix-CO- | Me₂NCH₂ | Bz | 4-I-Pro- | tBuNH- |
| 1840 | 3-Quin-CO- | CarCH₂ | Bz | 4-I-Pro- | tBuNH- |
| 1841 | 4-Quin-CO- | CarCH₂ | Bz | 4-I-Pro- | tBuNH- |
| 1842 | 2-Pyr-CO- | CarCH₂ | Bz | 4-I-Pro- | tBuNH- |
| 1843 | 3-Pyr-CO- | CarCH₂ | Bz | 4-I-Pro- | tBuNH- |
| 1844 | 4-Pyr-CO- | CarCH₂ | Bz | 4-I-Pro- | tBuNH- |
| 1845 | 4-MeO-2-Quin-CO- | CarCH₂ | Bz | 4-I-Pro- | tBuNH- |
| 1846 | 2-Np-CO- | CarCH₂ | Bz | 4-I-Pro- | tBuNH- |
| 1847 | 1-Np-CO- | CarCH₂ | Bz | 4-I-Pro- | tBuNH- |
| 1848 | 2-Bfur-CO- | CarCH₂ | Bz | 4-I-Pro- | tBuNH- |
| 1849 | 3-Bfur-CO- | CarCH₂ | Bz | 4-I-Pro- | tBuNH- |
| 1850 | 5-Bu-2-Pyr-CO- | CarCH₂ | Bz | 4-I-Pro- | tBuNH- |
| 1851 | 4-HO-2-Quin-CO- | CarCH₂ | Bz | 4-I-Pro- | tBuNH- |
| 1852 | 3-HO-2-Quix-CO- | CarCH₂ | Bz | 4-I-Pro- | tBuNH- |
| 1853 | 1-Np-Sfo- | CarCH₂ | Bz | 4-I-Pro- | tBuNH- |
| 1854 | 2-Np-Sfo- | CarCH₂ | Bz | 4-I-Pro- | tBuNH- |
| 1855 | Boz | CarCH₂ | Bz | 4-I-Pro- | tBuNH- |
| 1856 | Bz-NHCO- | CarCH₂ | Bz | 4-I-Pro- | tBuNH- |
| 1857 | Bz-NHCS- | CarCH₂ | Bz | 4-I-Pro- | tBuNH- |
| 1858 | 3-Ind-CO- | CarCH₂ | Bz | 4-I-Pro- | tBuNH- |
| 1859 | 2-Pyrd-CO- | CarCH₂ | Bz | 4-I-Pro- | tBuNH- |
| 1860 | 2-Pip-CO- | CarCH₂ | Bz | 4-I-Pro- | tBuNH- |
| 1861 | 2-Thi-CO- | CarCH₂ | Bz | 4-I-Pro- | tBuNH- |
| 1862 | MecCO- | CarCH₂ | Bz | 4-I-Pro- | tBuNH- |
| 1863 | PhoAc- | CarCH₂ | Bz | 4-I-Pro- | tBuNH- |
| 1864 | 3-Bzisox-CO- | CarCH₂ | Bz | 4-I-Pro- | tBuNH- |
| 1865 | 2-Bzim-CO- | CarCH₂ | Bz | 4-I-Pro- | tBuNH- |
| 1866 | N-Me-3-Ind-CO- | CarCH₂ | Bz | 4-I-Pro- | tBuNH- |
| 1867 | 2-Bzthiaz-CO- | CarCH₂ | Bz | 4-I-Pro- | tBuNH- |
| 1868 | 2-Bzoxaz-CO- | CarCH₂ | Bz | 4-I-Pro- | tBuNH- |
| 1869 | 5-MeO-2-Ind-CO- | CarCH₂ | Bz | 4-I-Pro- | tBuNH- |
| 1870 | 5-HO-2-Ind-CO- | CarCH₂ | Bz | 4-I-Pro- | tBuNH- |
| 1871 | 5-AcO-2-Ind-CO- | CarCH₂ | Bz | 4-I-Pro- | tBuNH- |
| 1872 | 5-H₂NAcO-2-Ind-CO- | CarCH₂ | Bz | 4-I-Pro- | tBuNH- |
| 1873 | 5-Bzim-CO- | CarCH₂ | Bz | 4-I-Pro- | tBuNH- |
| 1874 | (2-NpO)Ac- | CarCH₂ | Bz | 4-I-Pro- | tBuNH- |
| 1875 | (1-NpO)Ac- | CarCH₂ | Bz | 4-I-Pro- | tBuNH- |
| 1876 | 1-NpOCO- | CarCH₂ | Bz | 4-I-Pro- | tBuNH- |
| 1877 | 2-NpOCO- | CarCH₂ | Bz | 4-I-Pro- | tBuNH- |
| 1878 | (3-PhPho)Ac- | CarCH₂ | Bz | 4-I-Pro- | tBuNH- |
| 1879 | 2-Quix-CO- | CarCH₂ | Bz | 4-I-Pro- | 3-HOPr-NH- |
| 1880 | 2-Quix-CO- | CarCH₂ | Bz | 4-I-Pro- | BuNH- |

TABLE 1-continued

| Cpd. No. | R¹ | R³ | R⁴ | Z | R⁵ |
|---|---|---|---|---|---|
| 1881 | 2-Quix-CO- | CarCH₂ | Bz | 4-I-Pro- | tBuO- |
| 1882 | 2-Quix-CO- | CarCH₂ | Bz | 4-I-Pro- | 1,1-diMe-2-HOEt-NH- |
| 1883 | Bzc | CarCH₂ | Bz | 4-I-Pro- | 3-HOPr-NH- |
| 1884 | Bzc | CarCH₂ | Bz | 4-I-Pro- | BuNH- |
| 1885 | Bzc | CarCH₂ | Bz | 4-I-Pro- | tBuO- |
| 1886 | Bzc | CarCH₂ | Bz | 4-I-Pro- | 1,1-diMe-2-HOEt-NH- |
| 1887 | 3-NH₂-PhoAc- | CarCH₂ | Bz | 4-I-Pro- | tBuNH- |
| 1888 | 2-NH₂-PhoAc- | CarCH₂ | Bz | 4-I-Pro- | tBuNH- |
| 1889 | 2,3-diNH₂-PhoAc- | CarCH₂ | Bz | 4-I-pro- | tBuNH- |
| 1890 | 2,4-diNH₂-PhoAc- | CarCH₂ | Bz | 4-I-Pro- | tBuNH- |
| 1891 | 4-NH₂-Ph-CO- | CarCH₂ | Bz | 4-I-Pro- | tBuNH- |
| 1892 | 4-NH₂-Bzc | CarCH₂ | Bz | 4-I-Pro- | tBuNH- |
| 1893 | 4-Me₂N-PhoAc- | CarCH₂ | Bz | 4-I-Pro- | tBuNH- |
| 1894 | 4-[Me(Bz)N]-PhoAc- | CarCH₂ | Bz | 4-I-Pro- | tBuNH- |
| 1895 | 4-Mor-PhoAc- | CarCH₂ | Bz | 4-I-Pro- | tBuNH- |
| 1896 | 4-[N-Bz-Pipr]-PhoAc- | CarCH₂ | Bz | 4-I-Pro- | tBuNH- |
| 1897 | 4-[MeNH]-PhoAc- | CarCH₂ | Bz | 4-I-Pro- | tBuNH- |
| 1898 | 4-[(4'Me-Bzc)-NH]-PhoAc- | CarCH₂ | Bz | 4-I-Pro- | tBuNH- |
| 1899 | 4-[tBoc-NH]-PhoAc- | CarCH₂ | Bz | 4-I-Pro- | tBuNH- |
| 1900 | 4-[tBoc-NMe]-PhoAc- | CarCH₂ | Bz | 4-I-Pro- | tBuNH- |
| 1901 | 4-[Gly-NH]-PhoAc- | CarCH₂ | Bz | 4-I-Pro- | tBuNH- |
| 1902 | 4-[Gly-NMe]-PhoAc- | CarCH₂ | Bz | 4-I-Pro- | tBuNH- |
| 1903 | 4-[(N-Me-Gly)-NMe]-PhoAc- | CarCH₂ | Bz | 4-I-Pro- | tBuNH- |
| 1904 | 4-[(N-tBoc-Gly)-NMe]-PhoAc- | CarCH₂ | Bz | 4-I-Pro- | tBuNH- |
| 1905 | 4-[(N-tBoc-N-Me-Gly)NMe]-PhoAc- | CarCH₂ | Bz | 4-I-Pro- | tBuNH- |
| 1906 | Boc | CarCH₂ | Bz | 4-I-Pro- | tBuNH- |
| 1907 | 4-[(BrAc)NMe]-PhoAc- | CarCH₂ | Bz | 4-I-Pro- | tBuNH- |
| 1908 | 4-[(4'-MeO-Bzc)NH]-PhoAc- | CarCH₂ | Bz | 4-I-Pro- | tBuNH- |
| 1909 | N-Me-4-PipO-Ac- | CarCH₂ | Bz | 4-I-Pro- | tBuNH- |
| 1910 | 4-NH₂-cHxO-Ac- | CarCH₂ | Bz | 4-I-Pro- | tBuNH- |
| 1911 | 4-NH₂-PhoAc- | CarCH₂ | Bz | 4-I-Pro- | 1,1-diMe-2-HOEt-NH- |
| 1912 | 3-NH₂-PhoAc- | CarCH₂ | Bz | 4-I-Pro- | 1,1-diMe-2-HOEt-NH- |
| 1913 | 2-NH₂-PhoAc- | CarCH₂ | Bz | 4-I-Pro- | 1,1-diMe-2-HOEt-NH- |
| 1914 | 2,3-diNH₂-PhoAc- | CarCH₂ | Bz | 4-I-Pro- | 1,1-diMe-2-HOEt-NH- |
| 1915 | 2,4-diNH₂-PhoAc- | CarCH₂ | Bz | 4-I-Pro- | 1,1-diMe-2-HOEt-NH- |
| 1916 | 4-NH₂-Ph-CO- | CarCH₂ | Bz | 4-I-Pro- | 1,1-diMe-2-HOEt-NH- |
| 1917 | 4-NH₂-Bzc | CarCH₂ | Bz | 4-I-Pro- | 1,1-diMe-2-HOEt-NH- |
| 1918 | 4-Me₂N-PhoAc- | CarCH₂ | Bz | 4-I-Pro- | 1,1-diMe-2-HOEt-NH- |
| 1919 | 4-[Me(Bz)N]- | CarCH₂ | Bz | 4-I-Pro- | 1,1-diMe-2-HOEt-NH- |
| 1920 | 4-Mor-PhoAc- | CarCH₂ | Bz | 4-I-Pro- | 1,1-diMe-2-HOEt-NH- |
| 1921 | 4-[N-Bz-Pipr]-PhoAc- | CarCH₂ | Bz | 4-I-Pro- | 1,1-diMe-2-HOEt-NH- |
| 1922 | 4-[MeNH]-PhoAc- | CarCH₂ | Bz | 4-I-Pro- | 1,1-diMe-2-HOEt-NH- |
| 1923 | 4-[(4'Me-Bzc)-NH]-PhoAc- | CarCH₂ | Bz | 4-I-Pro.- | 1,1-diMe-2-HOEt-NH- |
| 1924 | 4-[BzcNH]-PhoAc- | CarCH₂ | Bz | 4-I-Pro- | 1,1-diMe-2-HOEt-NH- |
| 1925 | 4-(tBoc-NH]-PhoAc- | CarCH₂ | Bz | 4-I-Pro- | 1,1-diMe-2-HOEt-NH- |
| 1926 | 4-[tBoc-NMe]-PhoAc- | CarCH₂ | Bz | 4-I-Pro- | 1,1-diMe-2-HOEt-NH- |
| 1927 | 4-[Gly-NH]-PhoAc- | CarCH₂ | Bz | 4-I-Pro- | 1,1-diMe-2-HOEt-NH- |
| 1928 | 4-[Gly-NMe]-PhoAc- | CarCH₂ | Bz | 4-I-Pro- | 1,1-diMe-2-HOEt-NH- |
| 1929 | Boc | CarCH₂ | Bz | 4-I-Pro- | 1,1-diMe-2-HOEt-NH- |
| 1930 | 4-[(N-tBoc-Gly)NMe]-PhoAc- | CarCH₂ | Bz | 4-I-Pro- | 1,1-diMe-2-HOEt-NH- |
| 1931 | 4-[(N-tBoc-NMe-Gly)NMe]-PhoAc- | CarCH₂ | Bz | 4-I-Pro- | 1,1-diMe-2-HOEt-NH- |
| 1932 | 4-[(N-Me-Gly)-NMe]-PhoAc- | CarCH₂ | Bz | 4-I-Pro- | 1,1-diMe-2-HOEt-NH- |

TABLE 1-continued

| Cpd. No. | R¹ | R³ | R⁴ | Z | R⁵ |
|---|---|---|---|---|---|
| 1933 | 4-[(BrAc)NMe]-PhoAc- | CarCH₂ | Bz | 4-I-Pro- | 1,1-diMe-2-HOEt-NH- |
| 1934 | 4-[(4'-MeO-Bzc)NH]-PhoAc- | CarCH₂ | Bz | 4-I-Pro- | 1,1-diMe-2-HOEt-NH- |
| 1935 | N-Me-4-PipO-Ac- | CarCH₂ | Bz | 4-I-Pro- | 1,1-diMe-2-HOEt-NH- |
| 1936 | 4-NH₂-cHxO-Ac- | CarCH₂ | Bz | 4-I-Pro- | 1,1-diMe-2-HOEt-NH- |
| 1937 | 4-[(MorAc)NMe]-PhoAc- | CarCH₂ | Bz | 4-I-Pro- | 1,1-diMe-2-HOEt-NH- |
| 1938 | 4-NH₂-PhoAc- | CarCH₂ | Bz | 4-I-Pro- | 1,1-diMe-2-HOPr-NH- |
| 1939 | 3-NH₂-PhoAc- | CarCH₂ | Bz | 4-I-Pro- | 1,1-diMe-2-HOPr-NH- |
| 1940 | 2-NH₂-Pho-Ac- | CarCH₂ | Bz | 4-I-Pro- | 1,1-diMe-2-HOPr-NH- |
| 1941 | 2,3-diNH₂-Pho-Ac- | CarCH₂ | Bz | 4-I-Pro- | 1,1-diMe-2-HOPr-NH- |
| 1942 | 2,4-diNH₂-Pho-Ac- | CarCH₂ | Bz | 4-I-Pro- | 1,1-diMe-2-HOPr-NH- |
| 1943 | 4-NH₂-Ph-CO- | CarCH₂ | Bz | 4-I-Pro- | 1,1-diMe-2-HOPr-NH- |
| 1944 | 4-NH₂-Bzc | CarCH₂ | Bz | 4-I-Pro- | 1,1-diMe-2-HOPr-NH- |
| 1945 | 4-Me₂N-PhoAc- | CarCH₂ | Bz | 4-I-Pro- | 1,1-diMe-2-HOPr-NH- |
| 1946 | 4-[Me(Bz)N]-PhoAc- | CarCH₂ | Bz | 4-I-Pro- | 1,1-diMe-2-HOPr-NH- |
| 1947 | 4-Mor-PhoAc- | CarCH₂ | Bz | 4-I-Pro- | 1,1-diMe-2-HOPr-NH- |
| 1948 | 4-Bz-Pipr-Pho-Ac- | CarCH₂ | Bz | 4-I-Pro- | 1,1-diMe-2-HOPr-NH- |
| 1949 | 4-MeNH-PhoAc- | CarCH₂ | Bz | 4-I-Pro- | 1,1-diMe-2-HOPr-NH- |
| 1950 | 4-[(4'-Me-Bzc)-NH]-PhoAc- | CarCH₂ | Bz | 4-I-Pro- | 1,1-diMe-2-HOPr-NH- |
| 1951 | 4-[BzcNH]-PhoAc- | CarCH₂ | Bz | 4-I-Pro- | 1,1-diMe-2-HOPr-NH- |
| 1952 | 4-[tBoc-NH]-Pho-Ac- | CarCH₂ | Bz | 4-I-Pro- | 1,1-diMe-2-HOPr-NH- |
| 1953 | 4-[tBoc-NMe]-PhoAc- | CarCH₂ | Bz | 4-I-Pro- | 1,1-diMe-2-HOPr-NH- |
| 1954 | 4-[Gly-NH]-PhoAc- | CarCH₂ | Bz | 4-I-Pro- | 1,1-diMe-2-HOPr-NH- |
| 1955 | 4-[Gly-NMe]-Pho-Ac- | CarCH₂ | Bz | 4-I-Pro- | 1,1-diMe-2-HOPr-NH- |
| 1956 | 4-(N-Me-Gly)-NMe]-PhoAc- | CarCH₂ | Bz | 4-I-Pro- | 1,1-diMe-2-HOPr-NH- |
| 1957 | 4-[(N-tBoc-Gly)NMe]-PhoAc- | CarCH₂ | Bz | 4-I-Pro- | 1,1-diMe-2-HOPr-NH- |
| 1958 | 4-[(N-tBoc-NMe-Gly)NMe]-PhoAc- | CarCH₂ | Bz | 4-I-Pro- | 1,1-diMe-2-HOPr-NH- |
| 1959 | Boc | CarCH₂ | Bz | 4-I-Pro- | 1,1-diMe-2-HOPr-NH- |
| 1960 | 4-[(BrAc)NMe]-PhoAc- | CarCH₂ | Bz | 4-I-Pro- | 1,1-diMe-2-HOPr-NH- |
| 1961 | 4-[(4'-MeO-Bzc)-NH]-PhoAc- | CarCH₂ | Bz | 4-I-Pro- | 1,1-diMe-2-HOPr-NH- |
| 1962 | N-Me-4-PipO-Ac- | CarCH₂ | Bz | 4-I-Pro- | 1,1-diMe-2-HOPr-NH- |
| 1963 | 4-NH₂-cHxO-Ac- | CarCH₂ | Bz | 4-I-Pro- | 1,1-diMe-2-HOPr-NH- |
| 1964 | 4-[(MorAc)NMe]-PhoAc- | CarCH₂ | Bz | 4-I-Pro- | 1,1-diMe-2-HOPr-NH- |
| 1965 | 2-Quin-CO- | CarCH₂ | Bz | 4-I-Pro- | 1,1-diMe-2-HOEt-NH- |
| 1966 | 3-Quin-CO- | CarCH₂ | Bz | 4-I-Pro- | 1,1-diMe-2-HOEt-NH- |
| 1967 | 4-Quin-CO- | CarCH₂ | Bz | 4-I-Pro- | 1,1-diMe-2-HOEt-NH- |
| 1968 | 2-Pyr-CO- | CarCH₂ | Bz | 4-I-Pro- | 1,1-diMe-2-HOEt-NH- |
| 1969 | 3-Pyr-CO- | CarCH₂ | Bz | 4-I-Pro- | 1,1-diMe-2-HOEt-NH- |
| 1970 | 4-Pyr-CO- | CarCH₂ | Bz | 4-I-Pro- | 1,1-diMe-2-HOEt-NH- |
| 1971 | 4-MeO-2-Quin-CO- | CarCH₂ | Bz | 4-I-Pro- | 1,1-diMe-2-HOEt-NH- |
| 1972 | 2-Np-CO- | CarCH₂ | Bz | 4-I-Pro- | 1,1-diMe-2-HOEt-NH- |
| 1973 | 1-Np-CO- | CarCH₂ | Bz | 4-I-Pro- | 1,1-diMe-2-HOEt-NH- |
| 1974 | 2-Bfur-CO- | CarCH₂ | Bz | 4-I-Pro- | 1,1-diMe-2-HOEt-NH- |
| 1975 | 3-Bfur-CO- | CarCH₂ | Bz | 4-I-Pro- | 1,1-diMe-2-HOEt-NH- |
| 1976 | 5-Bu-2-Pyr-CO- | CarCH₂ | Bz | 4-I-Pro- | 1,1-diMe-2-HOEt-NH- |
| 1977 | 4-HO-2-Quin-CO- | CarCH₂ | Bz | 4-I-Pro- | 1,1-diMe-2-HOEt-NH- |
| 1978 | 3-HO-2-Quix-CO- | CarCH₂ | Bz | 4-I-Pro- | 1,1-diMe-2-HOEt-NH- |
| 1979 | 1-Np-Sfo- | CarCH₂ | Bz | 4-I-Pro- | 1,1-diMe-2-HOEt-NH- |
| 1980 | 2-Np-Sfo- | CarCH₂ | Bz | 4-I-Pro- | 1,1-diMe-2-HOEt-NH- |
| 1981 | Boz | CarCH₂ | Bz | 4-I-Pro- | 1,1-diMe-2-HOEt-NH- |
| 1982 | Bz-NHCO- | CarCH₂ | Bz | 4-I-Pro- | 1,1-diMe-2-HOEt-NH- |
| 1983 | Bz-NHCS- | CarCH₂ | Bz | 4-I-Pro- | 1,1-diMe-2-HOEt-NH- |
| 1984 | 2-Ind-CO- | CarCH₂ | Bz | 4-I-Pro- | 1,1-diMe-2-HOEt-NH- |
| 1985 | 3-Ind-CO- | CarCH₂ | Bz | 4-I-Pro- | 1,1-diMe-2-HOEt-NH- |
| 1986 | tBoc | CarCH₂ | Bz | 4-I-Pro- | 1,1-diMe-2-HOEt-NH- |
| 1987 | 2-Pyrd-CO- | CarCH₂ | Bz | 4-I-Pro- | 1,1-diMe-2-HOEt-NH- |
| 1988 | 2-Pip-CO- | CarCH₂ | Bz | 4-I-Pro- | 1,1-diMe-2-HOEt-NH- |
| 1989 | 2-Thi-CO- | CarCH₂ | Bz | 4-I-Pro- | 1,1-diMe-2-HOEt-NH- |

TABLE 1-continued

| Cpd. No. | R¹ | R³ | R⁴ | Z | R⁵ |
|---|---|---|---|---|---|
| 1990 | MecCO- | CarCH₂ | Bz | 4-I-Pro- | 1,1-diMe-2-HOEt-NH- |
| 1991 | PhoAc- | CarCH₂ | Bz | 4-I-Pro- | 1,1-diMe-2-HOEt-NH- |
| 1992 | MPhoAc- | CarCH₂ | Bz | 4-I-Pro- | 1,1-diMe-2-HOEt-NH- |
| 1993 | 3-Bzisox-CO- | CarCH₂ | Bz | 4-I-Pro- | 1,1-diMe-2-HOEt-NH- |
| 1994 | 2-Bzim-CO- | CarCH₂ | Bz | 4-I-Pro- | 1,1-diMe-2-HOEt-NH- |
| 1995 | N-Me-3-Ind-CO- | CarCH₂ | Bz | 4-I-Pro- | 1,1-diMe-2-HOEt-NH- |
| 1996 | 2-Bzthiaz-CO- | CarCH₂ | Bz | 4-I-Pro- | 1,1-diMe-2-HOEt-NH- |
| 1997 | 2-Bzoxaz-CO- | CarCH₂ | Bz | 4-I-Pro- | 1,1-diMe-2-HOEt-NH- |
| 1998 | 5-MeO-2-Ind-CO- | CarCH₂ | Bz | 4-I-Pro- | 1,1-diMe-2-HOEt-NH- |
| 1999 | 5-HO-2-Ind-CO- | CarCH₂ | Bz | 4-I-Pro- | 1,1-diMe-2-HOEt-NH- |
| 2000 | 5-AcO-2-Ind-CO- | CarCH₂ | Bz | 4-I-Pro- | 1,1-diMe-2-HOEt-NH- |
| 2001 | 5-NH₂AcO-2-Ind-CO- | CarCH₂ | Bz | 4-I-Pro- | 1,1-diMe-2-HOEt-NH- |
| 2002 | 5-Bzim-CO- | CarCH₂ | Bz | 4-I-Pro- | 1,1-diMe-2-HOEt-NH- |
| 2003 | (1-NpO)Ac- | CarCH₂ | Bz | 4-I-Pro- | 1,1-diMe-2-HOEt-NH- |
| 2004 | 1-NpOCO- | CarCH₂ | Bz | 4-I-Pro- | 1,1-diMe-2-HOEt-NH- |
| 2005 | 2-NpOCO- | CarCH₂ | Bz | 4-I-Pro- | 1,1-diMe-2-HOEt-NH- |
| 2006 | (3-PhPho)Ac- | CarCH₂ | Bz | 4-I-Pro- | 1,1-diMe-2-HOEt-NH- |
| 2007 | (2-NpO)Ac- | CarCH₂ | Bz | 4-I-Pro- | 1,1-diMe-2-HOEt-NH- |
| 2008 | Bzc | CarCH₂ | Bz | 4-I-Pro- | 1,1-diMe-2-HOPr-NH- |
| 2009 | 2-Quix-CO- | CarCH₂ | Bz | 4-I-Pro- | 1,1-diMe-2-HOPr-NH- |
| 2010 | 2-Quin-CO- | CarCH₂ | Bz | 4-I-Pro- | 1,1-diMe-2-HOPr-NH- |
| 2011 | 3-Quin-CO- | CarCH₂ | Bz | 4-I-Pro- | 1,1-diMe-2-HOPr-NH- |
| 2012 | 4-Quin-CO- | CarCH₂ | Bz | 4-I-Pro- | 1,1-diMe-2-HOPr-NH- |
| 2013 | 2-Pyr-CO- | CarCH₂ | Bz | 4-I-Pro- | 1,1-diMe-2-HOPr-NH- |
| 2014 | 3-Pyr-CO- | CarCH₂ | Bz | 4-I-Pro- | 1,1-diMe-2-HOPr-NH- |
| 2015 | 4-Pyr-CO- | CarCH₂ | Bz | 4-I-Pro- | 1,1-diMe-2-HOPr-NH- |
| 2016 | 4-MeO-2-Quin-CO- | CarCH₂ | Bz | 4-I-Pro- | 1,1-diMe-2-HOPr-NH- |
| 2017 | 2-Np-CO- | CarCH₂ | Bz | 4-I-Pro- | 1,1-diMe-2-HOPr-NH- |
| 2018 | 1-Np-CO- | CarCH₂ | Bz | 4-I-Pro- | 1,1-diMe-2-HOPr-NH- |
| 2019 | 2-Bfur-CO- | CarCH₂ | Bz | 4-I-Pro- | 1,1-diMe-2-HOPr-NH- |
| 2020 | 3-Bfur-CO- | CarCH₂ | Bz | 4-I-Pro- | 1,1-diMe-2-HOPr-NH- |
| 2021 | 5-Bu-2-Pyr-CO- | CarCH₂ | Bz | 4-I-Pro- | 1,1-diMe-2-HOPr-NH- |
| 2022 | 4-HO-2-Quin-CO- | CarCH₂ | Bz | 4-I-Pro- | 1,1-diMe-2-HOPr-NH- |
| 2023 | 3-HO-2-Quix-CO- | CarCH₂ | Bz | 4-I-Pro- | 1,1-diMe-2-HOPr-NH- |
| 2024 | 1-Np-Sfo- | CarCH₂ | Bz | 4-I-Pro- | 1,1-diMe-2-HOPr-NH- |
| 2025 | 2-Np-Sfo- | CarCH₂ | Bz | 4-I-Pro- | 1,1-diMe-2-HOPr-NH- |
| 2026 | Boz | CarCH₂ | Bz | 4-I-Pro- | 1,1-diMe-2-HOPr-NH- |
| 2027 | Bz-NHCO- | CarCH₂ | Bz | 4-I-Pro- | 1,1-diMe-2-HOPr-NH- |
| 2028 | Bz-NHCS- | CarCH₂ | Bz | 4-I-Pro- | 1,1-diMe-2-HOPr-NH- |
| 2029 | 2-Ind-CO- | CarCH₂ | Bz | 4-I-Pro- | 1,1-diMe-2-HOPr-NH- |
| 2030 | 3-Ind-CO- | CarCH₂ | Bz | 4-I-Pro- | 1,1-diMe-2-HOPr-NH- |
| 2031 | tBoc | CarCH₂ | Bz | 4-I-Pro- | 1,1-diMe-2-HOPr-NH- |
| 2032 | 2-Pyrd-CO- | CarCH₂ | Bz | 4-I-Pro- | 1,1-diMe-2-HOPr-NH- |
| 2033 | 2-Pip-CO- | CarCH₂ | Bz | 4-I-Pro- | 1,1-diMe-2-HOPr-NH- |
| 2034 | 2-Thi-CO- | CarCH₂ | Bz | 4-I-Pro- | 1,1-diMe-2-HOPr-NH- |
| 2035 | MecCO- | CarCH₂ | Bz | 4-I-Pro- | 1,1-diMe-2-HOPr-NH- |
| 2036 | PhoAc- | CarCH₂ | Bz | 4-I-Pro- | 1,1-diMe-2-HOPr-NH- |
| 2037 | MPhoAc- | CarCH₂ | Bz | 4-I-Pro- | 1,1-diMe-2-HOPr-NH- |
| 2038 | 3-Bzisox-CO- | CarCH₂ | Bz | 4-I-Pro- | 1,1-diMe-2-HOPr-NH- |
| 2039 | 2-Bzim-CO- | CarCH₂ | Bz | 4-I-Pro- | 1,1-diMe-2-HOPr-NH- |
| 2040 | N-Me-3-Ind-CO- | CarCH₂ | Bz | 4-I-Pro- | 1,1-diMe-2-HOPr-NH- |
| 2041 | 2-Bzthiaz-CO- | CarCH₂ | Bz | 4-I-Pro- | 1,1-diMe-2-HOPr-NH- |
| 2042 | 2-Bzoxaz-CO- | CarCH₂ | Bz | 4-I-Pro- | 1,1-diMe-2-HOPr-NH- |
| 2043 | 5-MeO-2-Ind-CO- | CarCH₂ | Bz | 4-I-Pro- | 1,1-diMe-2-HOPr-NH- |
| 2044 | 5-HO-2-Ind-CO- | CarCH₂ | Bz | 4-I-Pro- | 1,1-diMe-2-HOPr-NH- |
| 2045 | 5-AcO-2-Ind-CO- | CarCH₂ | Bz | 4-I-Pro- | 1,1-diMe-2-HOPr-NH- |
| 2046 | 5-NH₂AcO-2-Ind-CO- | CarCH₂ | Bz | 4-I-Pro- | 1,1-diMe-2-HOPr-NH- |
| 2047 | 5-Bzim-CO- | CarCH₂ | Bz | 4-I-Pro- | 1,1-diMe-2-HOPr-NH- |
| 2048 | (2-NpO)Ac- | CarCH₂ | Bz | 4-I-Pro- | 1,1-diMe-2-HOPr-NH- |
| 2049 | (1-NpO)Ac- | CarCH₂ | Bz | 4-I-Pro- | 1,1-diMe-2-HOPr-NH- |
| 2050 | 1-NpOCO- | CarCH₂ | Bz | 4-I-Pro- | 1,1-diMe-2-HOPr-NH- |
| 2051 | 2-NpOCO- | CarCH₂ | Bz | 4-I-Pro- | 1,1-diMe-2-HOPr-NH- |
| 2052 | (3-PhPho)Ac- | CarCH₂ | Bz | 4-I-Pro- | 1,1-diMe-2-HOPr-NH- |
| 2053 | Bzc | CarCH₂ | 4-Br-Bz | 4-I-Pro- | tBuNH- |
| 2054 | 2-Quix-CO- | CarCH₂ | 4-Br-Bz | 4-I-Pro- | tBuNH- |
| 2055 | Bzc | CarCH₂ | 4-MeOBz | 4-I-Pro- | tBuNH- |
| 2056 | 2-Quix-CO- | CarCH₂ | 4-MeOBz | 4-I-Pro- | tBuNH- |
| 2057 | Bzc | CarCH₂ | 4-Me-Bz | 4-I-Pro- | tBuNH- |
| 2058 | 2-Quix-CO- | CarCH₂ | 4-Me-Bz | 4-I-Pro- | tBuNH- |
| 2059 | Bzc | CarCH₂ | cHxCH₂- | 4-I-Pro- | tBuNH- |
| 2060 | 2-Quix-CO- | CarCH₂ | cHxCH₂- | 4-I-Pro- | tBuNH- |
| 2061 | Bzc | MeSOCH₂ | Bz | 4-I-Pro- | tBuNH- |
| 2062 | Bzc | MeSO₂- | Bz | 4-I-Pro- | tBuNH- |

TABLE 1-continued

| Cpd. No. | R$^1$ | R$^3$ | R$^4$ | Z | R$^5$ |
|---|---|---|---|---|---|
| 2063 | Bzc | MeOCH$_2$ | Bz | 4-I-Pro- | tBuNH- |
| 2064 | Bzc | MecCH$_2$-CH$_2$ | Bz | 4-I-Pro- | tBuNH- |
| 2065 | Bzc | MecCH$_2$ | Bz | 4-I-Pro- | tBuNH- |
| 2066 | 2-Quix-CO- | MeSO-CH$_2$- | Bz | 4-I-Pro- | tBuNH- |
| 2067 | 2-Quix-CO- | MeSO$_2$-CH$_2$- | Bz | 4-I-Pro- | tBuNH- |
| 2068 | 2-Quix-CO- | MeOCH$_2$ | Bz | 4-I-Pro- | tBuNH- |
| 2069 | 2-Quix-CO- | MecCH$_2$-CH$_2$ | Bz | 4-I-Pro- | tBuNH- |
| 2070 | 2-Quix-CO- | MecCH$_2$ | Bz | 4-I-Pro- | tBuNH- |
| 2071 | 2-Quin-CO- | MeSOCH$_2$ | Bz | 4-I-Pro- | tBuNH- |
| 2072 | 2-Quin-CO- | MeSO$_2$CH$_2$ | Bz | 4-I-Pro- | tBuNH- |
| 2073 | 2-Quin-CO- | MeOCH$_2$ | Bz | 4-I-Pro- | tBuNH- |
| 2074 | 2-Quin-CO- | MecCH$_2$CH$_2$ | Bz | 4-I-Pro- | tBuNH- |
| 2075 | 2-Quin-CO- | MecCH$_2$ | Bz | 4-I-Pro- | tBuNH- |
| 2076 | 3-Quin-CO- | MeSOCH$_2$ | Bz | 4-I-Pro- | tBuNH- |
| 2077 | 3-Quin-CO- | MeSO$_2$CH$_2$ | Bz | 4-I-Pro- | tBuNH- |
| 2078 | 3-Quin-CO- | MeOCH$_2$ | Bz | 4-I-Pro- | tBuNH- |
| 2079 | 3-Quin-CO- | MecCH$_2$CH$_2$ | Bz | 4-I-Pro- | tBuNH- |
| 2080 | 3-Quin-CO- | MecCH$_2$ | Bz | 4-I-Pro- | tBuNH- |
| 2081 | 2-Bfur-CO- | MeSOCH$_2$ | Bz | 4-I-Pro- | tBuNH- |
| 2082 | 2-Bfur-CO- | MeSO$_2$CH$_2$ | Bz | 4-I-Pro- | tBuNH- |
| 2083 | 2-Bfur-CO- | MeOCH$_2$ | Bz | 4-I-Pro- | tBuNH- |
| 2084 | 2-Bfur-CO- | MecCH$_2$CH$_2$ | Bz | 4-I-Pro- | tBuNH- |
| 2085 | 2-Bfur-CO- | MecCH$_2$ | Bz | 4-I-Pro- | tBuNH- |
| 2086 | 3-Bfur-CO- | MeSOCH$_2$ | Bz | 4-I-Pro- | tBuNH- |
| 2087 | 3-Bfur-CO- | MeSO$_2$CH$_2$ | Bz | 4-I-Pro- | tBuNH- |
| 2088 | 3-Bfur-CO- | MeOCH$_2$ | Bz | 4-I-Pro- | tBuNH- |
| 2089 | 3-Bfur-CO- | MecCH$_2$CH$_2$ | Bz | 4-I-Pro- | tBuNH- |
| 2090 | 3-Bfur-CO- | MecCH$_2$ | Bz | 4-I-Pro- | tBuNH- |
| 2091 | 3-Ind-CO- | MeSOCH$_2$ | Bz | 4-I-Pro- | tBuNH- |
| 2092 | 3-Ind-CO- | MeSO$_2$CH$_2$ | Bz | 4-I-Pro- | tBuNH- |
| 2093 | 3-Ind-CO- | MeOCH$_2$ | Bz | 4-I-Pro- | tBuNH- |
| 2094 | 3-Ind-CO- | MecCH$_2$CH$_2$ | Bz | 4-I-Pro- | tBuNH- |
| 2095 | 3-Ind-CO- | MecCH$_2$ | Bz | 4-I-Pro- | tBuNH- |
| 2096 | MPhOAc- | MeSOCH$_2$ | Bz | 4-I-Pro- | tBuNH- |
| 2097 | MPhOAc- | MeSO$_2$CH$_2$ | Bz | 4-I-Pro- | tBuNH- |
| 2098 | MPhOAc- | MeOCH$_2$ | Bz | 4-I-Pro- | tBuNH- |
| 2099 | MPhOAc- | MecCH$_2$CH$_2$ | Bz | 4-I-Pro- | tBuNH- |
| 2100 | MPhOAc- | MecCH$_2$ | Bz | 4-I-Pro- | tBuNH- |
| 2101 | 5-NH$_2$-AcO-2-Ind-CO- | MeSOCH$_2$ | Bz | 4-I-Pro- | tBuNH- |
| 2102 | 5-NH$_2$-AcO-2-Ind-CO- | MeSO$_2$CH$_2$ | Bz | 4-I-Pro- | tBuNH- |
| 2103 | 5-NH$_2$-AcO-2-Ind-CO- | MeOCH$_2$ | Bz | 4-I-Pro- | tBuNH- |
| 2104 | 5-NH$_2$-AcO-2-Ind-CO- | MecCH$_2$CH$_2$ | Bz | 4-I-Pro- | tBuNH- |
| 2105 | 5-NH$_2$-AcO-2-Ind-CO- | MecCH$_2$ | Bz | 4-I-Pro- | tBuNH- |
| 2106 | 4-NH$_2$-PhoAc- | MeSOCH$_2$ | Bz | 4-I-Pro- | tBuNH- |
| 2107 | 4-NH$_2$-PhoAc- | MeSO$_2$CH$_2$ | Bz | 4-I-Pro- | tBuNH- |
| 2108 | 4-NH$_2$-PhoAc- | MeOCH$_2$ | Bz | 4-I-Pro- | tBuNH- |
| 2109 | 4-NH$_2$-PhoAc- | MecCH$_2$CH$_2$ | Bz | 4-I-Pro- | tBuNH- |
| 2110 | 4-NH$_2$-PhoAc- | MecCH$_2$ | Bz | 4-I-Pro- | tBuNH- |
| 2111 | 4-[Bzc-NH]-PhoAc- | MeSOCH$_2$ | Bz | 4-I-Pro- | tBuNH- |
| 2112 | 4-[Bzc-NH]-PhoAc- | MeSO$_2$CH$_2$ | Bz | 4-I-Pro- | tBuNH- |
| 2113 | 4-[Bzc-NH]-PhoAc- | MeOCH$_2$ | Bz | 4-I-Pro- | tBuNH- |
| 2114 | 4-[Bzc-NH]-PhoAc- | MecCH$_2$CH$_2$ | Bz | 4-I-Pro- | tBuNH- |
| 2115 | 4-[Bzc-NH]-PhoAc | MecCH$_2$ | Bz | 4-I-Pro- | tBuNH- |
| 2116 | 4-Mor-Ac-NMe-PhoAc- | MeSOCH$_2$ | Bz | 4-I-Pro- | tBuNH- |
| 2117 | 4-Mor-Ac-NMe-PhoAc- | MeSO$_2$CH$_2$ | Bz | 4-I-Pro- | tBuNH- |
| 2118 | 4-Mor-Ac-NMe-PhoAc- | MeOCH$_2$ | Bz | 4-I-Pro- | tBuNH- |
| 2119 | 4-Mor-Ac-NMe-PhoAc- | MecCH$_2$CH$_2$ | Bz | 4-I-Pro- | tBuNH- |
| 2120 | 4-Mor-Ac-NMe-PhoAc- | MecCH$_2$ | Bz | 4-I-Pro- | tBuNH- |
| 2121 | 4-MeO-Bzc | CarCH$_2$ | Bz | 4-I-Pro- | tBuNH- |
| 2122 | Bzc | Me$_2$NCH$_2$ | Bz | 4,4-diF-Pro- | tBuNH- |
| 2123 | Bzc | 2-Car-Et | Bz | 4,4-diF-Pro- | tBuNH- |

TABLE 1-continued

| Cpd. No. | R¹ | R³ | R⁴ | Z | R⁵ |
|---|---|---|---|---|---|
| 2124 | Bzc | CNCH₂ | Bz | 4,4-diF-Pro- | tBuNH- |
| 2125 | Bzc | iPr | Bz | 4,4-diF-Pro- | tBuNH- |
| 2126 | Bzc | tBu | Bz | 4,4-diF-Pro- | tBuNH- |
| 2127 | Bzc | diMeCar-CH₂ | Bz | 4,4-diF-Pro- | tBuNH- |
| 2128 | Bzc | MorCOCH₂ | Bz | 4,4-diF-Pro- | tBuNH- |
| 2129 | Bzc | PipeCOCH₂ | Bz | 4,4-diF-Pro- | tBuNH- |
| 2130 | Bzc | 2-NH₂-Et | Bz | 4,4-diF-Pro- | tBuNH- |
| 2131 | Bzc | 3-NH₂-Pr | Bz | 4,4-diF-Pro- | tBuNH- |
| 2132 | Bzc | MeCarCH₂ | Bz | 4,4-diF-Pro- | tBuNH- |
| 2133 | Bzc | EtCarCH₂ | Bz | 4,4-diF-Pro- | tBuNH- |
| 2134 | Bzc | H | Bz | 4,4-diF-Pro- | tBuNH- |
| 2135 | Bzc | HOCH₂ | Bz | 4,4-diF-Pro- | tBuNH- |
| 2136 | Bzc | 4-Thiz-CH₂ | Bz | 4,4-diF-Pro- | tBuNH- |
| 2137 | Bzc | 4-Imid-CH₂ | Bz | 4,4-diF-Pro- | tBuNH- |
| 2138 | Bzc | COOH-CH₂ | Bz | 4,4-diF-Pro- | tBuNH- |
| 2139 | Bzc | 2-COOH-Et | Bz | 4,4-diF-Pro- | tBuNH- |
| 2140 | Bzc | MeSCH₂ | Bz | 4,4-diF-Pro- | tBuNH- |
| 2141 | Bzc | SamCH₂ | Bz | 4,4-diF-Pro- | tBuNH- |
| 2142 | Bzc | Bz | Bz | 4,4-diF-Pro- | tBuNH- |
| 2143 | Bzc | SimCH₂ | Bz | 4,4-diF-Pro- | tBuNH- |
| 2144 | Bzc | HiaCH₂ | Bz | 4,4-diF-Pro- | tBuNH- |
| 2145 | Bzc | 2-Sim-Et | Bz | 4,4-diF-Pro- | tBuNH- |
| 2146 | Bzc | 2-Hia-Et | Bz | 4,4-diF-Pro- | tBuNH- |
| 2147 | Bzc | NH₂CH₂ | Bz | 4,4-diF-Pro- | tBuNH- |
| 2148 | Bzc | MeNHCH₂ | Bz | 4,4-diF-Pro- | tBuNH- |
| 2149 | 2-Quix-CO- | 2-Car-Et | Bz | 4,4-diF-Pro- | tBuNH- |
| 2150 | 2-Quix-CO- | CNCH₂ | Bz | 4,4-diF-Pro- | tBuNH- |
| 2151 | 2-Quix-CO- | iPr | Bz | 4,4-diF-Pro- | tBuNH- |
| 2152 | 2-Quix-CO- | tBu | Bz | 4,4-diF-Pro- | tBuNH- |
| 2153 | 2-Quix-CO- | diMeCar-CH₂ | Bz | 4,4-diF-Pro- | tBuNH- |
| 2154 | 2-Quix-CO- | MorCOCH₂ | Bz | 4,4-diF-Pro- | tBuNH- |
| 2155 | 2-Quix-CO- | PipeCOCH₂ | Bz | 4,4-diF-Pro- | tBuNH- |
| 2156 | 2-Quix-CO- | 2-NH₂-Et | Bz | 4,4-diF-Pro- | tBuNH- |
| 2157 | 2-Quix-CO- | 3-NH₂-Pr | Bz | 4,4-diF-Pro- | tBuNH- |
| 2158 | 2-Quix-CO- | MeCarCH₂ | Bz | 4,4-diF-Pro- | tBuNH- |
| 2159 | 2-Quix-CO- | EtCarCH₂ | Bz | 4,4-diF-Pro- | tBuNH- |
| 2160 | 2-Quix-CO- | H | Bz | 4,4-diF-Pro- | tBuNH- |
| 2161 | 2-Quix-CO- | HOCH₂ | Bz | 4,4-diF-Pro- | tBuNH- |
| 2162 | 2-Quix-CO- | 4-Thiz-CH₂ | Bz | 4,4-diF-Pro- | tBuNH- |
| 2163 | 2-Quix-CO- | 4-Imid-CH₂ | Bz | 4,4-diF-Pro- | tBuNH- |
| 2164 | 2-Quix-CO- | COOH-CH₂ | Bz | 4,4-diF-Pro- | tBuNH- |
| 2165 | 2-Quix-CO- | 2-COOH-Et | Bz | 4,4-diF-Pro- | tBuNH- |
| 2166 | 2-Quix-CO- | MeSCH₂ | Bz | 4,4-diF-Pro- | tBuNH- |
| 2167 | 2-Quix-CO- | SamCH | Bz | 4,4-diF-Pro- | tBuNH- |
| 2168 | 2-Quix-CO- | Bz | Bz | 4,4-diF-Pro- | tBuNH- |
| 2169 | 2-Quix-CO- | SimCH₂ | Bz | 4,4-diF-Pro- | tBuNH- |
| 2170 | 2-Quix-CO- | HiaCH₂ | Bz | 4,4-diF-Pro- | tBuNH- |
| 2171 | 2-Quix-CO- | 2-Sim-Et | Bz | 4,4-diF-Pro- | tBuNH- |
| 2172 | 2-Quix-CO- | 2-Hia-Et | Bz | 4,4-diF-Pro- | tBuNH- |
| 2173 | 2-Quix-CO- | NH₂CH₂ | Bz | 4,4-diF-Pro- | tBuNH- |
| 2174 | 2-Quix-CO- | MeNHCH₂ | Bz | 4,4-diF-Pro- | tBuNH- |
| 2175 | 2-Quix-CO- | Me₂NCH₂ | Bz | 4,4-diF-Pro- | tBuNH- |
| 2176 | 3-Quin-CO- | CarCH₂ | Bz | 4,4-diF-Pro- | tBuNH- |
| 2177 | 4-Quin-CO- | CarCH₂ | Bz | 4,4-diF-Pro- | tBuNH- |
| 2178 | 2-Pyr-CO- | CarCH₂ | Bz | 4,4-diF-Pro- | tBuNH- |
| 2179 | 3-Pyr-CO- | CarCH₂ | Bz | 4,4-diF-Pro- | tBuNH- |
| 2180 | 4-Pyr-CO- | CarCH₂ | Bz | 4,4-diF-Pro- | tBuNH- |
| 2181 | 4-MeO-2-Quin-CO- | CarCH₂ | Bz | 4,4-diF-Pro- | tBuNH- |
| 2182 | 2-Np-CO- | CarCH₂ | Bz | 4,4-diF-Pro- | tBuNH- |
| 2183 | 1-Np-CO- | CarCH₂ | Bz | 4,4-diF-Pro- | tBuNH- |
| 2184 | 2-Bfur-CO- | CarCH₂ | Bz | 4,4-diF-Pro- | tBuNH- |
| 2185 | 3-Bfur-CO- | CarCH₂ | Bz | 4,4-diF-Pro- | tBuNH- |
| 2186 | 5-Bu-2-Pyr-CO- | CarCH₂ | Bz | 4,4-diF-Pro- | tBuNH- |
| 2187 | 4-OH-2-Quin-CO- | CarCH₂ | Bz | 4,4-diF-Pro- | tBuNH- |
| 2188 | 3-OH-2-Quix-CO- | CarCH₂ | Bz | 4,4-diF-Pro- | tBuNH- |
| 2189 | 1-Np-Sfo- | CarCH₂ | Bz | 4,4-diF-Pro- | tBuNH- |
| 2190 | 2-Np-Sfo- | CarCH₂ | Bz | 4,4-diF-Pro- | tBuNH- |
| 2191 | Boz | CarCH₂ | Bz | 4,4-diF-Pro- | tBuNH- |
| 2192 | Bz-NHCO- | CarCH₂ | Bz | 4,4-diF-Pro- | tBuNH- |
| 2193 | Bz-NHCS- | CarCH₂ | Bz | 4,4-diF-Pro- | tBuNH- |
| 2194 | 3-Ind-CO- | CarCH₂ | Bz | 4,4-diF-Pro- | tBuNH- |

TABLE 1-continued

| Cpd. No. | R¹ | R³ | R⁴ | Z | R⁵ |
|---|---|---|---|---|---|
| 2195 | 2-Pyrd-CO- | CarCH$_2$ | Bz | 4,4-diF-Pro- | tBuNH- |
| 2196 | 2-Pipe-CO- | CarCH$_2$ | Bz | 4,4-diF-Pro- | tBuNH- |
| 2197 | 2-Thi-CO- | CarCH$_2$ | Bz | 4,4-diF-Pro- | tBuNH- |
| 2198 | MecCO- | CarCH$_2$ | Bz | 4,4-diF-Pro- | tBuNH- |
| 2199 | PhoAc- | CarCH$_2$ | Bz | 4,4-diF-Pro- | tBuNH- |
| 2200 | 3-Bzisox-CO- | CarCH$_2$ | Bz | 4,4-diF-Pro- | tBuNH- |
| 2201 | 2-Bzim-CO- | CarCH$_2$ | Bz | 4,4-diF-Pro- | tBuNH- |
| 2202 | N-Me-3-Ind-CO- | CarCH$_2$ | Bz | 4,4-diF-Pro- | tBuNH- |
| 2203 | 2-Bzthiaz-CO- | CarCH$_2$ | Bz | 4,4-diF-Pro- | tBuNH- |
| 2204 | 2-Bzoxaz-CO- | CarCH$_2$ | Bz | 4,4-diF-Pro- | tBuNH- |
| 2205 | 5-MeO-2-Ind-CO- | CarCH$_2$ | Bz | 4,4-diF-Pro- | tBuNH- |
| 2206 | 5-HO-2-Ind-CO- | CarCH$_2$ | Bz | 4,4-diF-Pro- | tBuNH- |
| 2207 | 5-AcO-2-Ind-CO- | CarCH$_2$ | Bz | 4,4-diF-Pro- | tBuNH- |
| 2208 | 5-H$_2$NAcO-2-Ind-CO- | CarCH$_2$ | Bz | 4,4-diF-Pro- | tBuNH- |
| 2209 | 5-Bzim-CO- | CarCH$_2$ | Bz | 4,4-diF-Pro- | tBuNH- |
| 2210 | (2-NpO)Ac- | CarCH$_2$ | Bz | 4,4-diF-Pro- | tBuNH- |
| 2211 | (1-NpO)Ac- | CarCH$_2$ | Bz | 4,4-diF-Pro- | tBuNH- |
| 2212 | 1-NpOCO- | CarCH$_2$ | Bz | 4,4-diF-Pro- | tBuNH- |
| 2213 | 2-NpOCO- | CarCH$_2$ | Bz | 4,4-diF-Pro- | tBuNH- |
| 2214 | (3-PhPho)Ac- | CarCH$_2$ | Bz | 4,4-diF-Pro- | tBuNH- |
| 2215 | 2-Quix-CO- | CarCH$_2$ | Bz | 4,4-diF-Pro- | 3-HOPr-NH- |
| 2216 | 2-Quix-CO- | CarCH$_2$ | Bz | 4,4-diF-Pro- | BuNH- |
| 2217 | 2-Quix-CO- | CarCH$_2$ | Bz | 4,4-diF-Pro- | tBuO- |
| 2218 | 2-Quix-CO- | CarCH$_2$ | Bz | 4,4-diF-Pro- | 1,1-diMe-2-HOEt-NH- |
| 2219 | Bzc | CarCH$_2$ | Bz | 4,4-diF-Pro- | 3-HOPr-NH- |
| 2220 | Bzc | CarCH$_2$ | Bz | 4,4-diF-Pro- | BuNH- |
| 2221 | Bzc | CarCH$_2$ | Bz | 4,4-diF-Pro- | tBuO- |
| 2222 | Bzc | CarCH$_2$ | Bz | 4,4-diF-Pro- | 1,1-diMe-2-HOEt-NH- |
| 2223 | 3-NH$_2$-PhoAc- | CarCH$_2$ | Bz | 4,4-diF-Pro- | tBuNH- |
| 2224 | 2-NH$_2$-PhoAc- | CarCH$_2$ | Bz | 4,4-diF-Pro- | tBuNH- |
| 2225 | 2,3-diNH$_2$-Pho-Ac- | CarCH$_2$ | Bz | 4,4-diF-Pro- | tBuNH- |
| 2226 | 2,4-diNH$_2$-Pho-Ac- | CarCH$_2$ | Bz | 4,4-diF-Pro- | tBuNH- |
| 2227 | 4-NH$_2$-Ph-CO- | CarCH$_2$ | Bz | 4,4-diF-Pro- | tBuNH- |
| 2228 | 4-NH$_2$-Bzc | CarCH$_2$ | Bz | 4,4-diF-Pro- | tBuNH- |
| 2229 | 4-Me$_2$N-PhoAc- | CarCH$_2$ | Bz | 4,4-diF-Pro- | tBuNH- |
| 2230 | 4-[Me(BzN)]-PhoAc- | CarCH$_2$ | Bz | 4,4-diF-Pro- | tBuNH- |
| 2231 | 4-Mor-PhoAc- | CarCH$_2$ | Bz | 4,4-diF-Pro- | tBuNH- |
| 2232 | 4-[N-Bz-Pipr]-PhoAc- | CarCH$_2$ | Bz | 4,4-diF-Pro- | tBuNH- |
| 2233 | 4-[MeNH]-PhoAc- | CarCH$_2$ | Bz | 4,4-diF-Pro- | tBuNH- |
| 2234 | 4-[(4'-Me-Bzc)-NH]-PhoAc- | CarCH$_2$ | Bz | 4,4-diF-Pro- | tBuNH- |
| 2235 | 4-[tBoc-NH]-Pho-Ac- | CarCH$_2$ | Bz | 4,4-diF-Pro- | tBuNH- |
| 2236 | 4-[tBoc-MeN]-PhoAc- | CarCH$_2$ | Bz | 4,4-diF-Pro- | tBuNH- |
| 2237 | 4-[Gly-NH]-PhoAc- | CarCH$_2$ | Bz | 4,4-diF-Pro- | tBuNH- |
| 2238 | 4-[Gly-NMe]-Pho-Ac- | CarCH$_2$ | Bz | 4,4-diF-Pro- | tBuNH- |
| 2239 | 4-[(N-Me-Gly)-NMe]-Ac- | CarCH$_2$ | Bz | 4,4-diF-Pro- | tBuNH- |
| 2240 | 4-[(N-tBoc-Gly)NMe]-PhoAc- | CarCH$_2$ | Bz | 4,4-diF-Pro- | tBuNH- |
| 2241 | 4-[(N-tBoc-N-Me-Gly)NMe]-PhoAc- | CarCH$_2$ | Bz | 4,4-diF-Pro- | tBuNH- |
| 2242 | Boc | CarCH$_2$ | Bz | 4,4-diF-Pro- | tBuNH- |
| 2243 | 4-[(BrAc)NMe]-PhoAc- | CarCH$_2$ | Bz | 4,4-diF-Pro- | tBuNH- |
| 2244 | 4-[(4'-MeO-Bzc)NH]-PhoAc- | CarCH$_2$ | Bz | 4,4-diF-Pro- | tBuNH- |
| 2245 | N-Me-4-PipO-Ac- | CarCH$_2$ | Bz | 4,4-diF-Pro- | tBuNH- |
| 2246 | 4-NH$_2$-cHxO-Ac- | CarCH$_2$ | Bz | 4,4-diF-Pro- | tBuNH- |
| 2247 | 4-NH$_2$-PhoAc- | CarCH$_2$ | Bz | 4,4-diF-Pro- | 1,1-diMe-2-HOEt-NH |
| 2248 | 3-NH$_2$-PhoAc- | CarCH$_2$ | Bz | 4,4-diF-Pro- | 1,1-diMe-2-HOEt-NH |
| 2249 | 2-NH$_2$-PhoAc- | CarCH$_2$ | Bz | 4,4-diF-Pro- | 1,1-diMe-2-HOEt-NH |

TABLE 1-continued

| Cpd. No. | R¹ | R³ | R⁴ | Z | R⁵ |
|---|---|---|---|---|---|
| 2250 | 2,3-diNH₂-Pho-Ac- | CarCH₂ | Bz | 4,4-diF-Pro- | 1,1-diMe-2-HOEt-NH |
| 2251 | 2,4-diNH₂-Pho-Ac- | CarCH₂ | Bz | 4,4-diF-Pro- | 1,1-diMe-2-HOEt-NH |
| 2252 | 4-NH₂-Ph-CO- | CarCH₂ | Bz | 4,4-diF-Pro- | 1,1-diMe-2-HOEt-NH |
| 2253 | 4-NH₂-Bzc | CarCH₂ | Bz | 4,4-diF-Pro- | 1,1-diMe-2-HOEt-NH |
| 2254 | 4-Me₂N-PhoAc- | CarCH₂ | Bz | 4,4-diF-Pro- | 1,1-diMe-2-HOEt-NH |
| 2255 | 4-[Me(Bz)N]-Pho-Ac- | CarCH₂ | Bz | 4,4-diF-Pro- | 1,1-diMe-2-HOEt-NH |
| 2256 | 4-Mor-PhoAc- | CarCH₂ | Bz | 4,4-diF-Pro- | 1,1-diMe-2-HOEt-NH |
| 2257 | 4-[N-Bz-Pipr]-PhoAc- | CarCH₂ | Bz | 4,4-diF-Pro- | 1,1-diMe-2-HOEt-NH |
| 2258 | 4-[MeNH]-PhoAc- | CarCH₂ | Bz | 4,4-diF-Pro- | 1,1-diMe-2-HOEt-NH |
| 2259 | 4-[(4'-Me-Bzc)-NH]-PhoAc- | CarCH₂ | Bz | 4,4-diF-Pro- | 1,1-diMe-2-HOEt-NH |
| 2260 | 4-[Bzc-NH]-Pho-Ac- | CarCH₂ | Bz | 4,4,-diF-Pro- | 1,1-diMe-2-HOEt-NH |
| 2261 | 4-[t-Boc-NH]-Pho-Ac- | CarCH₂ | Bz | 4,4-diF-Pro- | 1,1-diMe-2-HOEt-NH |
| 2262 | 4-[tBoc-MeN]-PhoAc- | CarCH₂ | Bz | 4,4-diF-Pro- | 1,1-diMe-2-HOEt-NH |
| 2263 | 4-[Gly-NH]-PhoAc- | CarCH₂ | Bz | 4,4-diF-Pro- | 1,1-diMe-2-HOEt-NH |
| 2264 | 4-[Gly-NMe]-Pho-Ac- | CarCH₂ | Bz | 4,4-diF-Pro- | 1,1-diMe-2-HOEt-NH |
| 2265 | 4-[(N-Me-Gly)-NMe]-PhoAc- | CarCH₂ | Bz | 4,4-diF-Pro- | 1,1-diMe-2-HOEt-NH |
| 2266 | 4-[(N-tBoc-Gly)NMe]-PhoAc- | CarCH₂ | Bz | 4,4-diF-Pro- | 1,1-diMe-2-HOEt-NH |
| 2267 | 4-[(N-tBoc-N-Me-Gly)NMe]-PhoAc- | CarCH₂ | Bz | 4,4-diF-Pro- | 1,1-diMe-2-HOEt-NH |
| 2268 | Boc | CarCH₂ | Bz | 4,4-diF-Pro- | 1,1-diMe-2-HOEt-NH |
| 2269 | 4-[(BrAc)NMe]-PhoAc- | CarCH₂ | Bz | 4,4-diF-Pro- | 1,1-diMe-2-HOEt-NH |
| 2270 | 4-[(4'-MeO-Bzc)NH]-PhoAc- | CarCH₂ | Bz | 4,4-diF-Pro- | 1,1-diMe-2-HOEt-NH |
| 2271 | N-Me-4-Pip-O-Ac- | CarCH₂ | Bz | 4,4-diF-Pro- | 1,1-diMe-2-HOEt-NH |
| 2272 | 4-NH₂-cHxO-Ac- | CarCH₂ | Bz | 4,4-diF-Pro- | 1,1-diMe-2-HOEt-NH |
| 2273 | 4-[(MorAc)NMe]-PhoAc- | CarCH₂ | Bz | 4,4-diF-Pro- | I,I-diMe-2-HOEt-NH |
| 2274 | 4-NH₂-PhoAc- | CarCH₂ | Bz | 4,4-diF-Pro- | 1,1-diMe-2-HOPr-NH- |
| 2275 | 3-NH₂-PhoAc- | CarCH₂ | Bz | 4,4-diF-Pro- | 1,1-diMe-2-HOPr-NH- |
| 2276 | 2-NH₂-PhoAc- | CarCH₂ | Bz | 4,4-diF-Pro- | 1,1-diMe-2-HOPr-NH- |
| 2277 | 2,3-diNH₂-Pho-Ac- | CarCH₂ | Bz | 4,4-diF-Pro- | 1,1-diMe-2-HOPr-NH- |
| 2278 | 2,4-diNH₂-Pho-Ac- | CarCH₂ | Bz | 4,4-diF-Pro- | 1,1-diMe-2-HOPr-NH- |
| 2279 | 4-NH₂-Pho-CO- | CarCH₂ | Bz | 4,4-diF-Pro- | 1,1-diMe-2-HOPr-NH- |
| 2280 | 4-NH₂-Bzc | CarCH₂ | Bz | 4,4-diF-Pro- | 1,1-diMe-2-HOPr-NH- |
| 2281 | 4-Me₂N-PhoAc- | CarCH₂ | Bz | 4,4-diF-Pro- | 1,1-diMe-2-HOPr-NH- |
| 2282 | 4-[Me(Bz)N]-Pho-Ac- | CarCH₂ | Bz | 4,4-diF-Pro- | 1,1-diMe-2-HOPr-NH- |
| 2283 | 4-Mor-PhoAc- | CarCH₂ | Bz | 4,4-diF-Pro- | 1,1-diMe-2-HOPr-NH- |
| 2284 | 4-[N-Bz-Pipr]-Pho-Ac- | CarCH₂ | Bz | 4,4-diF-Pro- | 1,1-diMe-2-HOPr-NH- |
| 2285 | 4-MeNH-PhoAc- | CarCH₂ | Bz | 4,4-diF-Pro- | 1,1-diMe-2-HOPr-NH- |
| 2286 | 4-[(4'-Me-Bzc)-NH]-PhoAc- | CarCH₂ | Bz | 4,4-diF-Pro- | 1,1-diMe-2-HOPr-NH- |
| 2287 | 4-[Bzc-NH]-Pho-Ac- | CarCH₂ | Bz | 4,4-diF-Pro- | 1,1-diMe-2-HOPr-NH- |

TABLE 1-continued

| Cpd. No. | R¹ | R³ | R⁴ | Z | R⁵ |
|---|---|---|---|---|---|
| 2288 | 4-[t-Boc-NH]-PhoAc- | CarCH₂ | Bz | 4,4-diF-Pro- | 1,1-diMe-2-HOPr-NH- |
| 2289 | 4-[t-Boc-MeN]-PhoAc- | CarCH₂ | Bz | 4,4-diF-Pro- | 1,1-diMe-2-HOPr-NH- |
| 2290 | 4-[Gly-NH]-Pho-Ac- | CarCH₂ | Bz | 4,4-diF-Pro- | 1,1-diMe-2-HOPr-NH- |
| 2291 | 4-[Gly-NMe]-PhoAc- | CarCH₂ | Bz | 4,4-diF-Pro- | 1,1-diMe-2-HOPr-NH- |
| 2292 | 4-[(N-Me-Gly)-NMe]-PhoAc- | CarCH₂ | Bz | 4,4-diF-Pro- | 1,1-diMe-2-HOPr-NH- |
| 2293 | 4-[(N-tBoc-Gly)NMe]-PhoAc- | CarCH₂ | Bz | 4,4-diF-Pro- | 1,1-diMe-2-HOPr-NH- |
| 2294 | 4-[(N-tBoc-NMe-Gly)NMe]-PhoAc- | CarCH₂ | Bz | 4,4-diF-Pro- | 1,1-diMe-2-HOPr-NH- |
| 2295 | Boc | CarCH₂ | Bz | 4,4-diF-Pro- | 1,1-diMe-2-HOPr-NH- |
| 2296 | 4-[(BrAc)NMe]-PhoAc- | CarCH₂ | Bz | 4,4-diF-Pro- | 1,1-diMe-2-HOPr-NH- |
| 2297 | 4-[(4'-MeO-Bzc)NH]-PhoAc- | CarCH₂ | Bz | 4,4-diF-Pro- | 1,1-diMe-2-HOPr-NH- |
| 2298 | N-Me-4-PipO-Ac- | CarCH₂ | Bz | 4,4-diF-Pro- | 1,1-diMe-2-HOPr-NH- |
| 2299 | 4-NH₂-cHxO-Ac- | CarCH₂ | Bz | 4,4-diF-Pro- | 1,1-diMe-2-HOPr-NH- |
| 2300 | 4-[(MorAc)NMe-PhoAc- | CarCH₂ | Bz | 4,4-diF-Pro- | 1,1-diMe-2-HOPr-NH- |
| 2301 | 2-Quin-CO- | CarCH₂ | Bz | 4,4-diF-Pro- | 1,1-diMe-2-HOEt-NH- |
| 2302 | 3-Quin-CO- | CarCH₂ | Bz | 4,4-diF-Pro- | 1,1-diMe-2-HOEt-NH- |
| 2303 | 4-Quin-CO- | CarCH₂ | Bz | 4,4-diF-Pro- | 1,1-diMe-2-HOEt-NH- |
| 2304 | 2-Pyr-CO- | CarCH₂ | Bz | 4,4-diF-Pro- | 1,1-diMe-2-HOEt-NH- |
| 2305 | 3-Pyr-CO- | CarCH₂ | Bz | 4,4-diF-Pro- | 1,1-diMe-2-HOEt-NH- |
| 2306 | 4-Pyr-CO- | CarCH₂ | Bz | 4,4-diF-Pro- | 1,1-diMe-2-HOEt-NH- |
| 2307 | 4-MeO-2-Quin-CO- | CarCH₂ | Bz | 4,4-diF-Pro- | 1,1-diMe-2-HOEt-NH- |
| 2308 | 2-Np-CO- | CarCH₂ | Bz | 4,4-diF-Pro- | 1,1-diMe-2-HOEt-NH- |
| 2309 | 1-Np-CO- | CarCH₂ | Bz | 4,4-diF-Pro- | 1,1-diMe-2-HOEt-NH- |
| 2310 | 2-Bfur-CO- | CarCH₂ | Bz | 4,4-diF-Pro- | 1,1-diMe-2-HOEt-NH- |
| 2311 | 3-Bfur-CO- | CarCH₂ | Bz | 4,4-diF-Pro- | 1,1-diMe-2-HOEt-NH- |
| 2312 | 5-Bu-2-Pyr-CO- | CarCH₂ | Bz | 4,4-diF-Pro- | 1,1-diMe-2-HOEt-NH- |
| 2313 | 4-HO-2-Quin-CO- | CarCH₂ | Bz | 4,4-diF-Pro- | 1,1-diMe-2-HOEt-NH- |
| 2314 | 3-HO-2-Quix-CO- | CarCH₂ | Bz | 4,4-diF-Pro- | 1,1-diMe-2-HOEt-NH- |
| 2315 | 1-Np-Sfo- | CarCH₂ | Bz | 4,4-diF-Pro- | 1,1-diMe-2-HOEt-NH- |
| 2316 | 2-Np-Sfo- | CarCH₂ | Bz | 4,4-diF-Pro- | 1,1-diMe-2-HOEt-NH- |
| 2317 | Boz | CarCH₂ | Bz | 4,4-diF-Pro- | 1,1-diMe-2-HOEt-NH- |
| 2318 | Bz-NHCO- | CarCH₂ | Bz | 4,4-diF-Pro- | 1,1-diMe-2-HOEt-NH- |
| 2319 | Bz-NHCS- | CarCH₂ | Bz | 4,4-diF-Pro- | 1,1-diMe-2-HOEt-NH- |
| 2320 | 2-Ind-CO- | CarCH₂ | Bz | 4,4-diF-Pro- | 1,1-diMe-2-HOEt-NH- |
| 2321 | 3-Ind-CO- | CarCH₂ | Bz | 4,4-diF-Pro- | 1,1-diMe-2-HOEt-NH- |
| 2322 | tBoc | CarCH₂ | Bz | 4,4-diF-Pro- | 1,1-diMe-2-HOEt-NH- |
| 2323 | 2-Pyrd-CO- | CarCH₂ | Bz | 4,4-diF-Pro- | 1,1-diMe-2-HOEt-NH- |
| 2324 | 2-Pip-CO- | CarCH₂ | Bz | 4,4-diF-Pro- | 1,1-diMe-2-HOEt-NH- |
| 2325 | 2-Thi-CO- | CarCH₂ | Bz | 4,4-diF-Pro- | 1,1-diMe-2-HOEt-NH- |

TABLE 1-continued

| Cpd. No. | R¹ | R³ | R⁴ | Z | R⁵ |
|---|---|---|---|---|---|
| 2326 | MecCO- | CarCH₂ | Bz | 4,4-diF-Pro- | 1,1-diMe-2-HOEt-NH- |
| 2327 | PhoAc | CarCH₂ | Bz | 4,4-diF-Pro- | 1,1-diMe-2-HOEt-NH- |
| 2328 | MPhoAc | CarCH₂ | Bz | 4,4-diF-Pro- | 1,1-diMe-2-HOEt-NH- |
| 2329 | 3-Bzisox-CO- | CarCH₂ | Bz | 4,4-diF-Pro- | 1,1-diMe-2-HOEt-NH- |
| 2330 | 2-Bzim-CO- | CarCH₂ | Bz | 4,4-diF-Pro- | 1,1-diMe-2-HOEt-NH- |
| 2331 | N-Me-3-Ind-CO- | CarCH₂ | Bz | 4,4-diF-Pro- | 1,1-diMe-2-HOEt-NH- |
| 2332 | 2-Bzthiaz-CO- | CarCH₂ | Bz | 4,4-diF-Pro- | 1,1-diMe-2-HOEt-NH- |
| 2333 | 2-Bzoxaz-CO- | CarCH₂ | Bz | 4,4-diF-Pro- | 1,1-diMe-2-HOEt-NH- |
| 2334 | 5-MeO-2-Ind-CO- | CarCH₂ | Bz | 4,4-diF-Pro- | 1,1-diMe-2-HOEt-NH- |
| 2335 | 5-HO-2-Ind-CO- | CarCH₂ | Bz | 4,4-diF-Pro- | 1,1-diMe-2-HOEt-NH- |
| 2336 | 5-AcO-2-Ind-CO- | CarCH₂ | Bz | 4,4-diF-Pro- | 1,1-diMe-2-HOEt-NH- |
| 2337 | 5-H₂NAcO-2-Ind-CO- | CarCH₂ | Bz | 4,4-diF-Pro- | 1,1-diMe-2-HOEt-NH- |
| 2338 | 5-Bzim-CO- | CarCH₂ | Bz | 4,4-diF-Pro- | 1,1-diMe-2-HOEt-NH- |
| 2339 | (1-NpO)Ac- | CarCH₂ | Bz | 4,4-diF-Pro- | 1,1-diMe-2-HOEt-NH- |
| 2340 | 1-NpOCO- | CarCH₂ | Bz | 4,4-diF-Pro- | 1,1-diMe-2-HOEt-NH- |
| 2341 | 2-NpOCO- | CarCH₂ | Bz | 4,4-diF-Pro- | 1,1-diMe-2-HOEt-NH- |
| 2342 | (3-PhPho)Ac- | CarCH₂ | Bz | 4,4-diF-Pro- | 1,1-diMe-2-HOEt-NH- |
| 2343 | (2-NpO)Ac- | CarCH₂ | Bz | 4,4-diF-Pro- | 1,1-diMe-2-HOEt-NH- |
| 2344 | Bzc | CarCH₂ | Bz | 4,4-diF-Pro- | 1,1-diMe-2-HOPr-NH- |
| 2345 | 2-Quix-CO- | CarCH₂ | Bz | 4,4-diF-Pro- | 1,1-diMe-2-HOPr-NH- |
| 2346 | 2-Quin-CO- | CarCH₂ | Bz | 4,4-diF-Pro- | 1,1-diMe-2-HOPr-NH- |
| 2347 | 3-Quin-CO- | CarCH₂ | Bz | 4,4-diF-Pro- | 1,1-diMe-2-HOPr-NH- |
| 2348 | 4-Quin-CO- | CarCH₂ | Bz | 4,4-diF-Pro- | 1,1-diMe-2-HOPr-NH- |
| 2349 | 2-Pyr-CO- | CarCH₂ | Bz | 4,4-diF-Pro- | 1,1-diMe-2-HOPr-NH- |
| 2350 | 3-Pyr-CO- | CarCH₂ | Bz | 4,4-diF-Pro- | 1,1-diMe-2-HOPr-NH- |
| 2351 | 4-Pyr-CO- | CarCH₂ | Bz | 4,4-diF-Pro- | 1,1-diMe-2-HOPr-NH- |
| 2352 | 4-MeO-2-Quin-CO- | CarCH₂ | Bz | 4,4-diF-Pro- | 1,1-diMe-2-HOPr-NH- |
| 2353 | 2-Np-CO- | CarCH₂ | Bz | 4,4-diF-Pro- | 1,1-diMe-2-HOPr-NH- |
| 2354 | 1-Np-CO- | CarCH₂ | Bz | 4,4-diF-Pro- | 1,1-diMe-2-HOPr-NH- |
| 2355 | 2-Bfur-CO- | CarCH₂ | Bz | 4,4-diF-Pro- | 1,1-diMe-2-HOPr-NH- |
| 2356 | 3-Bfur-CO- | CarCH₂ | Bz | 4,4-diF-Pro- | 1,1-diMe-2-HOPr-NH- |
| 2357 | 5-Bu-2-Pyr-CO- | CarCH₂ | Bz | 4,4-diF-Pro- | 1,1-diMe-2-HOPr-NH- |
| 2358 | 4-HO-2-Quin-CO- | CarCH₂ | Bz | 4,4-diF-Pro- | 1,1-diMe-2-HOPr-NH- |
| 2359 | 3-HO-2-Quix-CO- | CarCH₂ | Bz | 4,4-diF-Pro- | 1,1-diMe-2-HOPr-NH- |
| 2360 | 1-Np-Sfo- | CarCH₂ | Bz | 4,4-diF-Pro- | 1,1-diMe-2-HOPr-NH- |
| 2361 | 2-Np-Sfo- | CarCH₂ | Bz | 4,4-diF-Pro- | 1,1-diMe-2-HOPr-NH- |
| 2362 | Boz | CarCH₂ | Bz | 4,4-diF-Pro- | 1,1-diMe-2-HOPr-NH- |
| 2363 | Bz-NHCO- | CarCH₂ | Bz | 4,4-diF-Pro- | 1,1-diMe-2-HOPr-NH- |

TABLE 1-continued

| Cpd. No. | R¹ | R³ | R⁴ | Z | R⁵ |
|---|---|---|---|---|---|
| 2364 | Bz-NHCS- | CarCH₂ | Bz | 4,4-diF-Pro- | 1,1-diMe-2-HOPr-NH- |
| 2365 | 2-Ind-CO- | CarCH₂ | Bz | 4,4-diF-Pro- | 1,1-diMe-2-HOPr-NH- |
| 2366 | 3-Ind-CO- | CarCH₂ | Bz | 4,4-diF-Pro- | 1,1-diMe-2-HOPr-NH- |
| 2367 | tBoc | CarCH₂ | Bz | 4,4-diF-Pro- | 1,1-diMe-2-HOPr-NH- |
| 2368 | 2-Pyrd-CO- | CarCH₂ | Bz | 4,4-diF-Pro- | 1,1-diMe-2-HOPr-NH- |
| 2369 | 2-Pip-CO- | CarCH₂ | Bz | 4,4-diF-Pro- | 1,1-diMe-2-HOPr-NH- |
| 2370 | 2-Thi-CO- | CarCH₂ | Bz | 4,4-diF-Pro- | 1,1-diMe-2-HOPr-NH- |
| 2371 | MecCO- | CarCH₂ | Bz | 4,4-diF-Pro- | 1,1-diMe-2-HOPr-NH- |
| 2372 | PhoAc- | CarCH₂ | Bz | 4,4-diF-Pro- | 1,1-diMe-2-HOPr-NH- |
| 2373 | MPhoAc- | CarCH₂ | Bz | 4,4-diF-Pro- | 1,1-diMe-2-HOPr-NH- |
| 2374 | 3-Bzisox-CO- | CarCH₂ | Bz | 4,4-diF-Pro- | 1,1-diMe-2-HOPr-NH- |
| 2375 | 2-Bzim-CO- | CarCH₂ | Bz | 4,4-diF-Pro- | 1,1-diMe-2-HOPr-NH- |
| 2376 | N-Me-3-Ind-CO- | CarCH₂ | Bz | 4,4-diF-Pro- | 1,1-diMe-2-HOPr-NH- |
| 2377 | 2-Bzthiaz-CO- | CarCH₂ | Bz | 4,4-diF-Pro- | 1,1-diMe-2-HOPr-NH- |
| 2378 | 2-Bzoxaz-CO- | CarCH₂ | Bz | 4,4-diF-Pro- | 1,1-diMe-2-HOPr-NH- |
| 2379 | 5-MeO-2-Ind-CO- | CarCH₂ | Bz | 4,4-diF-Pro- | 1,1-diMe-2-HOPr-NH- |
| 2380 | 5-HO-2-Ind-CO- | CarCH₂ | Bz | 4,4-diF-Pro- | 1,1-diMe-2-HOPr-NH- |
| 2381 | 5-AcO-2-Ind-CO- | CarCH₂ | Bz | 4,4-diF-Pro- | 1,1-diMe-2-HOPr-NH- |
| 2382 | 5-H₂NAcO-2-Ind-CO- | CarCH₂ | Bz | 4,4-diF-Pro- | 1,1-diMe-2-HOPr-NH- |
| 2383 | 5-Bzim-CO- | CarCH₂ | Bz | 4,4-diF-Pro- | 1,1-diMe-2-HOPr-NH- |
| 2384 | (2-NpO)Ac- | CarCH₂ | Bz | 4,4-diF-Pro- | 1,1-diMe-2-HOPr-NH- |
| 2385 | (1-NpO)Ac- | CarCH₂ | Bz | 4,4-diF-Pro- | 1,1-diMe-2-HOPr-NH- |
| 2386 | 1-NpOCO- | CarCH₂ | Bz | 4,4-diF-Pro- | 1,1-diMe-2-HOPr-NH- |
| 2387 | 2-NpOCO- | CarCH₂ | Bz | 4,4-diF-Pro- | 1,1-diMe-2-HOPr-NH- |
| 2388 | (3-PhPho)Ac- | CarCH₂ | Bz | 4,4-diF-Pro- | 1,1-diMe-2-HOPr-NH- |
| 2389 | Bzc | CarCH₂ | 4-Br-Bz | 4,4-diF-Pro- | tBuNH- |
| 2390 | 2-Quix-CO- | CarCH₂ | 4-Br-Bz | 4,4-diF-Pro- | tBuNH- |
| 2391 | Bzc | CarCH₂ | 4-MeOBz | 4,4-diF-Pro- | tBuNH- |
| 2392 | 2-Quix-CO- | CarCH₂ | 4-MeOBz | 4,4-diF-Pro- | tBuNH- |
| 2393 | Bzc | CarCH₂ | 4-Me-Bz | 4,4-diF-Pro- | tBuNH- |
| 2394 | 2-Quix-CO- | CarCH₂ | 4-Me-Bz | 4,4-diF-Pro- | tBuNH- |
| 2395 | Bzc | CarCH₂ | cHxCH₂ | 4,4-diF-Pro- | tBuNH- |
| 2396 | 2-Quix-CO- | CarCH₂ | cHxCH₂ | 4,4-diF-Pro- | tBuNH- |
| 2397 | Bzc | MeSOCH₂ | Bz | 4,4-diF-Pro- | tBuNH- |
| 2398 | Bzc | MeSO₂CH₂ | Bz | 4,4-diF-Pro- | tBuNH- |
| 2399 | Bzc | MeOCH₂ | Bz | 4,4-diF-Pro- | tBuNH- |
| 2400 | Bzc | MecCH₂CH₂ | Bz | 4,4-diF-Pro- | tBuNH- |
| 2401 | Bzc | MecCH₂ | Bz | 4,4-diF-Pro- | tBuNH- |
| 2402 | 2-Quix-CO- | MeSOCH₂ | Bz | 4,4-diF-Pro- | tBuNH- |
| 2403 | 2-Quix-CO- | MeSO₂CH₂ | Bz | 4,4-diF-Pro- | tBuNH- |
| 2404 | 2-Quix-CO- | MeOCH₂ | Bz | 4,4-diF-Pro- | tBuNH- |
| 2405 | 2-Quix-CO- | MecCH₂CH₂ | Bz | 4,4-diF-Pro- | tBuNH- |
| 2406 | 2-Quix-CO- | MecCH₂ | Bz | 4,4-diF-Pro- | tBuNH- |
| 2407 | 2-Quin-CO- | MeSOCH₂ | Bz | 4,4-diF-Pro- | tBuNH- |
| 2408 | 2-Quin-CO- | MeSO₂CH₂ | Bz | 4,4-diF-Pro- | tBuNH- |
| 2409 | 2-Quin-CO- | MeOCH₂ | Bz | 4,4-diF-Pro- | tBuNH- |
| 2410 | 2-Quin-CO- | MecCH₂CH | Bz | 4,4-diF-Pro- | tBuNH- |
| 2411 | 2-Quin-CO- | MecCH₂ | Bz | 4,4-diF-Pro- | tBuNH- |
| 2412 | 3-Quin-CO- | MeSOCH₂ | Bz | 4,4-diF-Pro- | tBuNH- |
| 2413 | 3-Quin-CO- | MeSO₂CH₂ | Bz | 4,4-diF-Pro- | tBuNH- |
| 2414 | 3-Quin-CO- | MeOCH₂ | Bz | 4,4-diF-Pro- | tBuNH- |

TABLE 1-continued

| Cpd. No. | R¹ | R³ | R⁴ | Z | R⁵ |
|---|---|---|---|---|---|
| 2415 | 3-Quin-CO- | MecCH₂CH₂ | Bz | 4,4-diF-Pro- | tBuNH- |
| 2416 | 3-Quin-CO- | MecCH₂ | Bz | 4,4-diF-Pro- | tBuNH- |
| 2417 | 2-Bfur-CO- | MeSOCH₂ | Bz | 4,4-diF-Pro- | tBuNH- |
| 2418 | 2-Bfur-CO- | MeSO₂CH₂ | Bz | 4,4-diF-Pro- | tBuNH- |
| 2419 | 2-Bfur-CO- | MeOCH₂ | Bz | 4,4-diF-Pro- | tBuNH- |
| 2420 | 2-Bfur-CO- | MecCH₂CH₂ | Bz | 4,4-diF-Pro- | tBuNH- |
| 2421 | 2-Bfur-CO- | MecCH₂ | Bz | 4,4-diF-Pro- | tBuNH- |
| 2422 | 3-Bfur-CO- | MeSOCH₂ | Bz | 4,4-diF-Pro- | tBuNH- |
| 2423 | 3-Bfur-CO- | MeSO₂CH₂ | Bz | 4,4-diF-Pro- | tBuNH- |
| 2424 | 3-Bfur-CO- | MeOCH₂ | Bz | 4,4-diF-Pro- | tBuNH- |
| 2425 | 3-Bfur-CO- | MecCH₂CH₂ | Bz | 4,4-diF-Pro- | tBuNH- |
| 2426 | 3-Bfur-CO- | MecCH₂ | Bz | 4,4-diF-Pro- | tBuNH- |
| 2427 | 3-Ind-CO- | MeSOCH₂ | Bz | 4,4-diF-Pro- | tBuNH- |
| 2428 | 3-Ind-CO- | MeSO₂CH₂ | Bz | 4,4-diF-Pro- | tBuNH- |
| 2429 | 3-Ind-CO- | MeOCH₂ | Bz | 4,4-diF-Pro- | tBuNH- |
| 2430 | 3-Ind-CO- | MecCH₂CH₂ | Bz | 4,4-diF-Pro- | tBuNH- |
| 2431 | 3-Ind-CO- | MecCH₂ | Bz | 4,4-diF-Pro- | tBuNH- |
| 2432 | MPhOAc- | MeSOCH₂ | Bz | 4,4-diF-Pro- | tBuNH- |
| 2433 | MPhOAc- | MeSO₂CH₂ | Bz | 4,4-diF-Pro- | tBuNH- |
| 2434 | MPhOAc- | MeOCH₂ | Bz | 4,4-diF-Pro- | tBuNH- |
| 2435 | MPhOAc- | MecCH₂CH₂ | Bz | 4,4-diF-Pro- | tBuNH- |
| 2436 | MPhOAc- | MecCH₂ | Bz | 4,4-diF-Pro- | tBuNH- |
| 2437 | 5-NH₂-AcO-2-Ind-CO- | MeSOCH₂ | Bz | 4,4-diF-Pro- | tBuNH- |
| 2438 | 5-NH₂-AcO-2-Ind-CO- | MeSO₂CH₂ | Bz | 4,4-diF-Pro- | tBuNH- |
| 2439 | 5-NH₂-AcO-2-Ind-CO- | MeOCH₂ | Bz | 4,4-diF-Pro- | tBuNH- |
| 2440 | 5-NH₂-AcO-2-Ind-CO- | MecCH₂CH₂ | Bz | 4,4-diF-Pro- | tBuNH- |
| 2441 | 5-NH₂-AcO-2-Ind-CO- | MecCH₂ | Bz | 4,4-diF-Pro- | tBuNH- |
| 2442 | 4-NH₂-PhoAc- | MeSOCH₂ | Bz | 4,4-diF-Pro- | tBuNH- |
| 2443 | 4-NH₂-PhoAc- | MeSO₂CH₂ | Bz | 4,4-diF-Pro- | tBuNH- |
| 2444 | 4-NH₂-PhoAc- | MeOCH₂ | Bz | 4,4-diF-Pro- | tBuNH- |
| 2445 | 4-NH₂-PhoAc- | MecCH₂CH₂ | Bz | 4,4-diF-Pro- | tBuNH- |
| 2446 | 4-NH₂-PhoAc- | MecCH₂ | Bz | 4,4-diF-Pro- | tBuNH- |
| 2447 | 4-[Bzc-NH]-Pho-Ac- | MeSOCH₂ | Bz | 4,4-diF-Pro- | tBuNH- |
| 2448 | 4-[Bzc-NH]-Pho-Ac- | MeSO₂CH₂ | Bz | 4,4-diF-Pro- | tBuNH- |
| 2449 | 4-[Bzc-NH]-Pho-Ac- | MeOCH₂ | Bz | 4,4-diF-Pro- | tBuNH- |
| 2450 | 4-[Bzc-NH]-Pho-Ac- | MecCH₂CH₂ | Bz | 4,4-diF-Pro- | tBuNH- |
| 2451 | 4-[Bzc-NH]-Pho-Ac- | MecCH₂ | Bz | 4,4-diF-Pro- | tBuNH- |
| 2452 | 4-[(MorAc)-NMe]-PhoAc- | MeSOCH₂ | Bz | 4,4-diF-Pro- | tBuNH- |
| 2453 | 4-[(MorAc)-NMe]-PhoAc- | MeSO₂CH₂ | Bz | 4,4-diF-Pro- | tBuNH- |
| 2454 | 4-[(MorAc)-NMe]-PhoAc- | MeOCH₂ | Bz | 4,4-diF-Pro- | tBuNH- |
| 2455 | 4-[(MorAc)-NMe]-PhoAc- | MecCH₂CH₂ | Bz | 4,4-diF-Pro- | tBuNH- |
| 2456 | 4-Mor-Ac-N-Me-PhoAc- | MecCH₂ | Bz | 4,4-diF-Pro- | tBuNH- |
| 2457 | 4-MeO-Bzc | CarCH₂ | Bz | 4,4-diF-Pro- | tBuNH- |
| 2458 | Bzc | Me₂NCH₂ | Bz | 3-Cl-Pro- | tBuNH- |
| 2459 | Bzc | 2-Car-Et | Bz | 3-Cl-Pro- | tBuNH- |
| 2460 | Bzc | CNCH₂ | Bz | 3-Cl-Pro- | tBuNH- |
| 2461 | Bzc | iPr | Bz | 3-Cl-Pro- | tBuNH- |
| 2462 | Bzc | tBu | Bz | 3-Cl-Pro- | tBuNH- |
| 2463 | Bzc | diMeCarCH₂ | Bz | 3-Cl-Pro- | tBuNH- |
| 2464 | Bzc | MorCOCH₂ | Bz | 3-Cl-Pro- | tBuNH- |
| 2465 | Bzc | PipCOCH₂ | Bz | 3-Cl-Pro- | tBuNH- |
| 2466 | Bzc | 2-NH₂-Et | Bz | 3-Cl-Pro- | tBuNH- |
| 2467 | Bzc | 3-NH₂-Pr | Bz | 3-Cl-Pro- | tBuNH- |
| 2468 | Bzc | MeCarCH₂ | Bz | 3-Cl-Pro- | tBuNH- |
| 2469 | Bzc | EtCarCH₂ | Bz | 3-Cl-Pro- | tBuNH- |
| 2470 | Bzc | H | Bz | 3-Cl-Pro- | tBuNH- |
| 2471 | Bzc | HOCH₂ | Bz | 3-Cl-Pro- | tBuNH- |
| 2472 | Bzc | 4-Thiz-CH₂ | Bz | 3-Cl-Pro- | tBuNH- |
| 2473 | Bzc | 4-Imid-CH₂ | Bz | 3-Cl-Pro- | tBuNH- |
| 2474 | Bzc | COOH-CH₂ | Bz | 3-Cl-Pro- | tBuNH- |
| 2475 | Bzc | 2-COOH-Et | Bz | 3-Cl-Pro- | tBuNH- |
| 2476 | Bzc | MeSCH₂ | Bz | 3-Cl-Pro- | tBuNH- |
| 2477 | Bzc | SamCH₂ | Bz | 3-Cl-Pro- | tBuNH- |
| 2478 | Bzc | Bz | Bz | 3-Cl-Pro- | tBuNH- |
| 2479 | Bzc | SimCH₂ | Bz | 3-Cl-Pro- | tBuNH- |

TABLE 1-continued

| Cpd. No. | R¹ | R³ | R⁴ | Z | R⁵ |
|---|---|---|---|---|---|
| 2480 | Bzc | HiaCH₂ | Bz | 3-Cl-Pro- | tBuNH- |
| 2481 | Bzc | 2-Sim-Et | Bz | 3-Cl-Pro- | tBuNH- |
| 2482 | Bzc | 2-Hia-Et | Bz | 3-Cl-Pro- | tBuNH- |
| 2483 | Bzc | NH₂CH₂ | Bz | 3-Cl-Pro- | tBuNH- |
| 2484 | Bzc | MeNHCH₂ | Bz | 3-Cl-Pro- | tBuNH- |
| 2485 | 2-Quix-CO- | 2-Car-Et | Bz | 3-Cl-Pro- | tBuNH- |
| 2486 | 2-Quix-CO- | CNCH₂ | Bz | 3-Cl-Pro- | tBuNH- |
| 2487 | 2-Quix-CO- | iPr | Bz | 3-Cl-Pro- | tBuNH- |
| 2488 | 2-Quix-CO- | tBu | Bz | 3-Cl-Pro- | tBuNH- |
| 2489 | 2-Quix-CO- | diMeCarCH₂ | Bz | 3-Cl-Pro- | tBuNH- |
| 2490 | 2-Quix-CO- | MorCOCH₂ | Bz | 3-Cl-Pro- | tBuNH- |
| 2491 | 2-Quix-CO- | PipCOCH₂ | Bz | 3-Cl-Pro- | tBuNH- |
| 2492 | 2-Quix-CO- | 2-NH₂-Et | Bz | 3-Cl-Pro- | tBuNH- |
| 2493 | 2-Quix-CO- | 3-NH₂-Pr | Bz | 3-Cl-Pro- | tBuNH- |
| 2494 | 2-Quix-CO- | MeCarCH₂ | Bz | 3-Cl-Pro- | tBuNH- |
| 2495 | 2-Quix-CO- | EtCarCH₂ | Bz | 3-Cl-Pro- | tBuNH- |
| 2496 | 2-Quix-CO- | H | Bz | 3-Cl-Pro- | tBuNH- |
| 2497 | 2-Quix-CO- | HOCH₂ | Bz | 3-Cl-Pro- | tBuNH- |
| 2498 | 2-Quix-CO- | 4-Thiz-CH₂ | Bz | 3-Cl-Pro- | tBuNH- |
| 2499 | 2-Quix-CO- | 4-Imid-CH₂ | Bz | 3-Cl-Pro- | tBuNH- |
| 2500 | 2-Quix-CO- | COOH-CH₂ | Bz | 3-Cl-Pro- | tBuNH- |
| 2501 | 2-Quix-CO- | 2-COOH-Et | Bz | 3-Cl-Pro- | tBuNH- |
| 2502 | 2-Quix-CO- | MeSCH₂ | Bz | 3-Cl-Pro- | tBuNH- |
| 2503 | 2-Quix-CO- | SamCH₂- | Bz | 3-Cl-Pro- | tBuNH- |
| 2504 | 2-Quix-CO- | Bz | Bz | 3-Cl-Pro- | tBuNH- |
| 2505 | 2-Quix-CO- | SimCH₂ | Bz | 3-Cl-Pro- | tBuNH- |
| 2506 | 2-Quix-CO- | HiaCH₂ | Bz | 3-Cl-Pro- | tBuNH- |
| 2507 | 2-Quix-CO- | 2-Sim-Et | Bz | 3-Cl-Pro- | tBuNH- |
| 2508 | 2-Quix-CO- | 2-Hia-Et | Bz | 3-Cl-Pro- | tBuNH- |
| 2509 | 2-Quix-CO- | NH₂CH₂ | Bz | 3-Cl-Pro- | tBuNH- |
| 2510 | 2-Quix-CO- | MeNHCH₂ | Bz | 3-Cl-Pro- | tBuNH- |
| 2511 | 2-Quix-CO- | Me₂NCH₂ | Bz | 3-Cl-Pro- | tBuNH- |
| 2512 | 3-Quin-CO- | CarCH₂ | Bz | 3-Cl-Pro- | tBuNH- |
| 2513 | 4-Quin-CO- | CarCH₂ | Bz | 3-Cl-Pro- | tBuNH- |
| 2514 | 2-Pyr-CO- | CarCH₂ | Bz | 3-Cl-Pro- | tBuNH- |
| 2515 | 3-Pyr-CO- | CarCH₂ | Bz | 3-Cl-Pro- | tBuNH- |
| 2516 | 4-Pyr-CO- | CarCH₂ | Bz | 3-Cl-Pro- | tBuNH- |
| 2517 | 4-MeO-2-Quin-CO- | CarCH₂ | Bz | 3-Cl-Pro- | tBuNH- |
| 2518 | 2-Np-CO- | CarCH₂ | Bz | 3-Cl-Pro- | tBuNH- |
| 2519 | 1-Np-CO- | CarCH₂ | Bz | 3-Cl-Pro- | tBuNH- |
| 2520 | 2-Bfur-CO- | CarCH₂ | Bz | 3-Cl-Pro- | tBuNH- |
| 2521 | 3-Bfur-CO- | CarCH₂ | Bz | 3-Cl-Pro- | tBuNH- |
| 2522 | 5-Bu-2-Pyr-CO- | CarCH₂ | Bz | 3-Cl-Pro- | tBuNH- |
| 2523 | 4-HO-2-Quin-CO- | CarCH₂ | Bz | 3-Cl-Pro- | tBuNH- |
| 2524 | 3-HO-2-Quix-CO- | CarCH₂ | Bz | 3-Cl-Pro- | tBuNH- |
| 2525 | 1-Np-Sfo- | CarCH₂ | Bz | 3-Cl-Pro- | tBuNH- |
| 2526 | 2-Np-Sfo- | CarCH₂ | Bz | 3-Cl-Pro- | tBuNH- |
| 2527 | Boz | CarCH₂ | Bz | 3-Cl-Pro- | tBuNH- |
| 2528 | Bz-NHCO- | CarCH₂ | Bz | 3-Cl-Pro- | tBuNH- |
| 2529 | Bz-NHCS- | CarCH₂ | Bz | 3-Cl-Pro- | tBuNH- |
| 2530 | 3-Ind-CO- | CarCH₂ | Bz | 3-Cl-Pro- | tBuNH- |
| 2531 | 2-Pyrd-CO- | CarCH₂ | Bz | 3-Cl-Pro- | tBuNH- |
| 2532 | 2-Pip-CO- | CarCH₂ | Bz | 3-Cl-Pro- | tBuNH- |
| 2533 | 2-Thi-CO- | CarCH₂ | Bz | 3-Cl-Pro- | tBuNH- |
| 2534 | MecCO- | CarCH₂ | Bz | 3-Cl-Pro- | tBuNH- |
| 2535 | PhoAc- | CarCH₂ | Bz | 3-Cl-Pro- | tBuNH- |
| 2536 | 3-Bzisox-CO- | CarCH₂ | Bz | 3-Cl-Pro- | tBuNH- |
| 2537 | 2-Bzim-CO- | CarCH₂ | Bz | 3-Cl-Pro- | tBuNH- |
| 2538 | N-Me-3-Ind-CO- | CarCH₂ | Bz | 3-Cl-Pro- | tBuNH- |
| 2539 | 2-Bzthiaz-CO- | CarCH₂ | Bz | 3-Cl-Pro- | tBuNH- |
| 2540 | 2-Bzoxaz-CO- | CarCH₂ | Bz | 3-Cl-Pro- | tBuNH- |
| 2541 | 5-MeO-2-Ind-CO- | CarCH₂ | Bz | 3-Cl-Pro- | tBuNH- |
| 2542 | 5-HO-2-Ind-CO- | CarCH₂ | Bz | 3-Cl-Pro- | tBuNH- |
| 2543 | 5-AcO-2-Ind-CO- | CarCH₂ | Bz | 3-Cl-Pro- | tBuNH- |
| 2544 | 5-H₂NAcO-2-Ind-CO- | CarCH₂ | Bz | 3-Cl-Pro- | tBuNH- |
| 2545 | 5-Bzim-CO- | CarCH₂ | Bz | 3-Cl-Pro- | tBuNH- |
| 2546 | (2-NpO)Ac- | CarCH₂ | Bz | 3-Cl-Pro- | tBuNH- |
| 2547 | (1-NpO)Ac- | CarCH₂ | Bz | 3-Cl-Pro- | tBuNH- |
| 2548 | 1-NpOCO- | CarCH₂ | Bz | 3-Cl-Pro- | tBuNH- |
| 2549 | 2-NpOCO- | CarCH₂ | Bz | 3-Cl-Pro- | tBuNH- |
| 2550 | (3-PhPho)Ac- | CarCH₂ | Bz | 3-Cl-Pro- | tBuNH- |
| 2551 | 2-Quix-CO- | CarCH₂ | Bz | 3-Cl-Pro- | 3-HOPr-NH- |
| 2552 | 2-Quix-CO- | CarCH₂ | Bz | 3-Cl-Pro- | BuNH- |
| 2553 | 2-Quix-CO- | CarCH₂ | Bz | 3-Cl-Pro- | tBuO- |

TABLE 1-continued

| Cpd. No. | R¹ | R³ | R⁴ | Z | R⁵ |
|---|---|---|---|---|---|
| 2554 | 2-Quix-CO- | CarCH₂ | Bz | 3-Cl-Pro- | 1,1-diMe-2-HOEt-NH- |
| 2555 | Bzc | CarCH₂ | Bz | 3-Cl-Pro- | 3-HOPr-NH- |
| 2556 | Bzc | CarCH₂ | Bz | 3-Cl-Pro- | BuNH- |
| 2557 | Bzc | CarCH₂ | Bz | 3-Cl-Pro- | tBuO- |
| 2558 | Bzc | CarCH₂ | Bz | 3-Cl-Pro- | 1,1-diMe-2-HOEt-NH- |
| 2559 | 3-NH₂-PhoAc- | CarCH₂ | Bz | 3-Cl-Pro- | tBuNH- |
| 2560 | 2-NH₂-PhoAc- | CarCH₂ | Bz | 3-Cl-Pro- | tBuNH- |
| 2561 | 2,3-diNH₂-Pho-Ac- | CarCH₂ | Bz | 3-Cl-Pro- | tBuNH- |
| 2562 | 2,4-diNH₂-Pho-Ac- | CarCH₂ | Bz | 3-Cl-Pro- | tBuNH- |
| 2563 | 4-NH₂-Ph-CO- | CarCH₂ | Bz | 3-Cl-Pro- | tBuNH- |
| 2564 | 4-NH₂-Bzc | CarCH₂ | Bz | 3-Cl-Pro- | tBuNH- |
| 2565 | 4-Me₂N-PhoAc- | CarCH₂ | Bz | 3-Cl-Pro- | tBuNH- |
| 2566 | 4-[Me(Bz)N]-PhoAc- | CarCH₂ | Bz | 3-Cl-Pro- | tBuNH- |
| 2567 | 4-Mor-PhoAc- | CarCH₂ | Bz | 3-Cl-Pro- | tBuNH- |
| 2568 | 4-[N-Bz-Pipr]-PhoAc- | CarCH₂ | Bz | 3-Cl-Pro- | tBuNH- |
| 2569 | 4-MeNH-PhoAc- | CarCH₂ | Bz | 3-Cl-Pro- | tBuNH- |
| 2570 | 4-[(4'-Me-Bzc)-NH-PhoAc- | CarCH₂ | Bz | 3-Cl-Pro- | tBuNH- |
| 2571 | 4-[tBoc-NH]-Pho-Ac- | CarCH₂ | Bz | 3-Cl-Pro- | tBuNH- |
| 2572 | 4-[tBoc-MeN]-PhoAc- | CarCH₂ | Bz | 3-Cl-Pro- | tBuNH- |
| 2573 | 4-[Gly-NH]-Pho-Ac- | CarCH₂ | Bz | 3-Cl-Pro- | tBuNH- |
| 2574 | 4-[Gly-NMe]-Pho-Ac- | CarCH₂ | Bz | 3-Cl-Pro- | tBuNH- |
| 2575 | 4-[(N-Me-Gly)-NMe]-PhoAc- | CarCH₂ | Bz | 3-Cl-Pro- | tBuNH- |
| 2576 | 4-[(N-tBoc-Gly)NMe]-PhoAc- | CarCH₂ | Bz | 3-Cl-Pro- | tBuNH- |
| 2577 | 4-[(N-tBoc-NMe-Gly)]NMe-PhoAc- | CarCH₂ | Bz | 3-Cl-Pro- | tBuNH- |
| 2578 | Boc | CarCH₂ | Bz | 3-Cl-Pro- | tBuNH- |
| 2579 | 4-[(BrAc)NMe]-PhoAc) | CarCH₂ | Bz | 3-Cl-Pro- | tBuNH- |
| 2580 | 4-[(4'-MeO-Bzc)NH]-PhoAc- | CarCH₂ | Bz | 3-Cl-Pro- | tBuNH- |
| 2581 | N-Me-4-PipO-Ac- | CarCH₂ | Bz | 3-Cl-Pro- | tBuNH- |
| 2582 | 4-NH₂-cHxO-Ac- | CarCH₂ | Bz | 3-Cl-Pro- | tBuNH- |
| 2583 | 4-NH₂-PhoAc- | CarCH₂ | Bz | 3-Cl-Pro- | 1,1-diMe-2-HOEt-NH- |
| 2584 | 3-NH₂-PhoAc- | CarCH₂ | Bz | 3-Cl-Pro- | 1,1-diMe-2-HOEt-NH- |
| 2585 | 2-NH₂-PhoAc- | CarCH₂ | Bz | 3-Cl-Pro- | 1,1-diMe-2-HOEt-NH- |
| 2586 | 2,3-diNH₂-Pho-Ac- | CarCH₂ | Bz | 3-Cl-Pro- | 1,1-diMe-2-HOEt-NH- |
| 2587 | 2,4-diNH₂-Pho-Ac- | CarCH₂ | Bz | 3-Cl-Pro- | 1,1-diMe-2-HOEt-NH- |
| 2588 | 4-NH₂-Ph-CO- | CarCH₂ | Bz | 3-Cl-Pro- | 1,1-diMe-2-HOEt-NH- |
| 2589 | 4-NH₂-Bzc | CarCH₂ | Bz | 3-Cl-Pro- | 1,1-diMe-2-HOEt-NH- |
| 2590 | 4-Me₂N-PhoAc- | CarCH₂ | Bz | 3-Cl-Pro- | 1,1-diMe-2-HOEt-NH- |
| 2591 | 4-[Me(Bz)N]- | CarCH₂ | Bz | 3-Cl-Pro- | 1,1-diMe-2-HOEt-NH- |
| 2592 | 4-Mor-PhoAc- | CarCH₂ | Bz | 3-Cl-Pro- | 1,1-diMe-2-HOEt-NH- |
| 2593 | 4-[N-Bz-Pipr]-PhoAc- | CarCH₂ | Bz | 3-Cl-Pro- | 1,1-diMe-2-HOEt-NH- |
| 2594 | 4-MeNH-PhoAc- | CarCH₂ | Bz | 3-Cl-Pro- | 1,1-diMe-2-HOEt-NH- |
| 2595 | 4-[(4'-Me-Bzc)-NH]-PhoAc- | CarCH₂ | Bz | 3-Cl-Pro- | 1,1-diMe-2-HOEt-NH- |
| 2596 | 4-[Bzc-NH]-Pho-Ac- | CarCH₂ | Bz | 3-Cl-Pro- | 1,1-diMe-2-HOEt-NH- |
| 2597 | 4-[tBoc-NH]-Pho-Ac- | CarCH₂ | Bz | 3-Cl-Pro- | 1,1-diMe-2-HOEt-NH- |

TABLE 1-continued

| Cpd. No. | R¹ | R³ | R⁴ | Z | R⁵ |
|---|---|---|---|---|---|
| 2598 | 4-[tBoc-MeN]-PhoAc- | CarCH₂ | Bz | 3-Cl-Pro- | 1,1-diMe-2-HOEt-NH- |
| 2599 | 4-Gly-NH-Pho-Ac- | CarCH₂ | Bz | 3-Cl-Pro- | 1,1-diMe-2-HOEt-NH- |
| 2600 | 4-[Gly-NMe]-Pho-Ac- | CarCH₂ | Bz | 3-Cl-Pro- | 1,1-diMe-2-HOEt-NH- |
| 2601 | 4-[(N-Me-Gly)-NMe]-PhoAc- | CarCH₂ | Bz | 3-Cl-Pro- | 1,1-diMe-2-HOEt-NH- |
| 2602 | 4-[(N-tBoc-Gly)NMe]-PhoAc- | CarCH₂ | Bz | 3-Cl-Pro- | 1,1-diMe-2-HOEt-NH- |
| 2603 | 4-[(N-tBoc-NMe-Gly)NMe]-PhoAc- | CarCH₂ | Bz | 3-Cl-Pro- | 1,1-diMe-2-HOEt-NH- |
| 2604 | Boc | CarCH₂ | Bz | 3-Cl-Pro- | 1,1-diMe-2-HOEt-NH- |
| 2605 | 4-[(BrAc)NMe]-PhoAc) | CarCH₂ | Bz | 3-Cl-Pro- | 1,1-dime-2-HOEt-NH- |
| 2606 | 4-[(4'-MeO-Bzc)NH]-PhoAc- | CarCH₂ | Bz | 3-Cl-Pro- | 1,1-diMe-2-HOEt-NH- |
| 2607 | N-Me-4-PipO-Ac- | CarCH₂ | Bz | 3-Cl-Pro- | 1,1-diMe-2-HOEt-NH- |
| 2608 | 4-NH₂-cHxO-Ac- | CarCH₂ | Bz | 3-Cl-Pro- | 1,1-diMe-2-HOEt-NH- |
| 2609 | 4-[(MorAc)NMe]-PhoAc- | CarCH₂ | Bz | 3-Cl-Pro- | 1,1-diMe-2-HOEt-NH- |
| 2610 | 4-NH₂-PhoAc- | CarCH₂ | Bz | 3-Cl-Pro- | 1,1-diMe-2-HOPr-NH- |
| 2611 | 3-NH₂-PhoAc- | CarCH₂ | Bz | 3-Cl-Pro- | 1,1-diMe-2-HOPr-NH- |
| 2612 | 2-NH₂-PhoAc- | CarCH₂ | Bz | 3-Cl-Pro- | 1,1-diMe-2-HOPr-NH- |
| 2613 | 2,3-diNH₂-Pho-Ac- | CarCH₂ | Bz | 3-Cl-Pro- | 1,1-diMe-2-HOPr-NH- |
| 2614 | 2,4-diNH₂-Pho-Ac- | CarCH₂ | Bz | 3-Cl-Pro- | 1,1-diMe-2-HOPr-NH- |
| 2615 | 4-NH₂-Ph-CO- | CarCH₂ | Bz | 3-Cl-Pro- | 1,1-diMe-2-HOPr-NH- |
| 2616 | 4-NH₂-Bzc | CarCH₂ | Bz | 3-Cl-Pro- | 1,1-diMe-2-HOPr-NH- |
| 2617 | 4-Me₂N-PhoAc- | CarCH₂ | Bz | 3-Cl-Pro- | 1,1-diMe-2-HOPr-NH- |
| 2618 | 4-[Me(Bz)N]-Pho-Ac- | CarCH₂ | Bz | 3-Cl-Pro- | 1,1-diMe-2-HOPr-NH- |
| 2619 | 4-Mor-PhoAc- | CarCH₂ | Bz | 3-Cl-Pro- | 1,1-diMe-2-HOPr-NH- |
| 2620 | 4-[N-Bz-Pipr]-PhoAc- | CarCH₂ | Bz | 3-Cl-Pro- | 1,1-diMe-2-HOPr-NH- |
| 2621 | 4-MeNH-PhoAc- | CarCH₂ | Bz | 3-Cl-Pro- | 1,1-diMe-2-HOPr-NH- |
| 2622 | 4-[(4'-Me-Bzc)-NH-PhoAc- | CarCH₂ | Bz | 3-Cl-Pro- | 1,1-diMe-2-HOPr-NH- |
| 2623 | (4-[Bzc-NH]-Pho-Ac- | CarCH₂ | Bz | 3-Cl-Pro- | 1,1-diMe-2-HOPr-NH- |
| 2624 | 4-[tBoc-NH]-Pho-Ac- | CarCH₂ | Bz | 3-Cl-Pro- | 1,1-diMe-2-HOPr-NH- |
| 2625 | 4-(tBoc-MeN]-PhoAc- | CarCH₂ | Bz | 3-Cl-Pro- | 1,1-diMe-2-HOPr-NH- |
| 2626 | 4-Gly-NH-Pho-Ac- | CarCH₂ | Bz | 3-Cl-Pro- | 1,1-diMe-2-HOPr-NH- |
| 2627 | 4-[Gly-NMe]-Pho-Ac- | CarCH₂ | Bz | 3-Cl-Pro- | 1,1-diMe-2-HOPr-NH- |
| 2628 | 4-[(N-Me-Gly)NMe]-PhoAc- | CarCH₂ | Bz | 3-Cl-Pro- | 1,1-diMe-2-HOPr-NH- |
| 2629 | 4-[(N-tBoc-Gly)NMe]-PhoAc- | CarCH₂ | Bz | 3-Cl-Pro- | 1,1-diMe-2-HOPr-NH- |
| 2630 | 4-[(N-tBoc-NMe-Gly)NMe]-PhoAc- | CarCH₂ | Bz | 3-Cl-Pro- | 1,1-diMe-2-HOPr-NH- |
| 2631 | Boc | CarCH₂ | Bz | 3-Cl-Pro- | 1,1-diMe-2-HOPr-NH- |
| 2632 | 4-[(BrAc)NMe]-PhoAc- | CarCH₂ | Bz | 3-Cl-Pro- | 1,1-diMe-2-HOPr-NH- |
| 2633 | 4-[(4'-MeO-Bzc)NH]-PhoAc- | CarCH₂ | Bz | 3-Cl-Pro- | 1,1-diMe-2-HOPr-NH- |
| 2634 | N-Me-4-PipO-Ac- | CarCH₂ | Bz | 3-Cl-Pro- | 1,1-diMe-2-HOPr-NH- |
| 2635 | 4-NH₂-cHxO-Ac- | CarCH₂ | Bz | 3-Cl-Pro- | 1,1-diMe-2-HOPr-NH- |

TABLE 1-continued

| Cpd. No. | R¹ | R³ | R⁴ | Z | R⁵ |
|---|---|---|---|---|---|
| 2636 | 4-[(MorAc)NMe]-PhoAc- | CarCH₂ | Bz | 3-Cl-Pro- | 1,1-diMe-2-HOPr-NH- |
| 2637 | 2-Quin-CO- | CarCH₂ | Bz | 3-Cl-Pro- | 1,1-diMe-2-HOEt-NH- |
| 2638 | 3-Quin-CO- | CarCH₂ | Bz | 3-Cl-Pro- | 1,1-diMe-2-HOEt-NH- |
| 2639 | 4-Quin-CO- | CarCH₂ | Bz | 3-Cl-Pro- | 1,1-diMe-2-HOEt-NH- |
| 2640 | 2-Pyr-CO- | CarCH₂ | Bz | 3-Cl-Pro- | 1,1-diMe-2-HOEt-NH- |
| 2641 | 3-Pyr-CO- | CarCH₂ | Bz | 3-Cl-Pro- | 1,1-diMe-2-HOEt-NH- |
| 2642 | 4-Pyr-CO- | CarCH₂ | Bz | 3-Cl-Pro- | 1,1-diMe-2-HOEt-NH- |
| 2643 | 4-MeO-2-Quin-CO- | CarCH₂ | Bz | 3-Cl-Pro- | 1,1-diMe-2-HOEt-NH- |
| 2644 | 2-Np-CO- | CarCH₂ | Bz | 3-Cl-Pro- | 1,1-diMe-2-HOEt-NH- |
| 2645 | 1-Np-CO- | CarCH₂ | Bz | 3-Cl-Pro- | 1,1-diMe-2-HOEt-NH- |
| 2646 | 2-Bfur-CO- | CarCH₂ | Bz | 3-Cl-Pro- | 1,1-diMe-2-HOEt-NH- |
| 2647 | 3-Bfur-CO- | CarCH₂ | Bz | 3-Cl-Pro- | 1,1-diMe-2-HOEt-NH- |
| 2648 | 5-Bu-2-Pyr-CO- | CarCH₂ | Bz | 3-Cl-Pro- | 1,1-diMe-2-HOEt-NH- |
| 2649 | 4-HO-2-Quin-CO- | CarCH₂ | Bz | 3-Cl-Pro- | 1,1-diMe-2-HOEt-NH- |
| 2650 | 3-HO-2-Quix-CO- | CarCH₂ | Bz | 3-Cl-Pro- | 1,1-diMe-2-HOEt-NH- |
| 2651 | 1-Np-Sfo- | CarCH₂ | Bz | 3-Cl-Pro- | 1,1-diMe-2-HOEt-NH- |
| 2652 | 2-Np-Sfo- | CarCH₂ | Bz | 3-Cl-Pro- | 1,1-diMe-2-HOEt-NH- |
| 2653 | Boz | CarCH₂ | Bz | 3-Cl-Pro- | 1,1-diMe-2-HOEt-NH- |
| 2654 | Bz-NHCO- | CarCH₂ | Bz | 3-Cl-Pro- | 1,1-diMe-2-HOEt-NH- |
| 2655 | Bz-NHCS- | CarCH₂ | Bz | 3-Cl-Pro- | 1,1-diMe-2-HOEt-NH- |
| 2656 | 2-Ind-CO- | CarCH₂ | Bz | 3-Cl-Pro- | 1,1-diMe-2-HOEt-NH- |
| 2657 | 3-Ind-CO- | CarCH₂ | Bz | 3-Cl-Pro- | 1,1-diMe-2-HOEt-NH- |
| 2658 | tBoc | CarCH₂ | Bz | 3-Cl-Pro- | 1,1-diMe-2-HOEt-NH- |
| 2659 | 2-Pyrd-CO- | CarCH₂ | Bz | 3-Cl-Pro- | 1,1-diMe-2-HOEt-NH- |
| 2660 | 1-Pip-CO- | CarCH₂ | Bz | 3-Cl-Pro- | 1,1-diMe-2-HOEt-NH- |
| 2661 | 2-Thi-CO- | CarCH₂ | Bz | 3-Cl-Pro- | 1,1-diMe-2-HOEt-NH- |
| 2662 | MecCO- | CarCH₂ | Bz | 3-Cl-Pro- | 1,1-diMe-2-HOEt-NH- |
| 2663 | PhoAc- | CarCH₂ | Bz | 3-Cl-Pro- | 1,1-diMe-2-HOEt-NH- |
| 2664 | MPhoAc- | CarCH₂ | Bz | 3-Cl-Pro- | 1,1-diMe-2-HOEt-NH- |
| 2665 | 3-Bzisox-CO- | CarCH₂ | Bz | 3-Cl-Pro- | 1,1-diMe-2-HOEt-NH- |
| 2666 | 2-Bzim-CO- | CarCH₂ | Bz | 3-Cl-Pro- | 1,1-diMe-2-HOEt-NH- |
| 2667 | N-Me-3-Ind-CO- | CarCH₂ | Bz | 3-Cl-Pro- | 1,1-diMe-2-HOEt-NH- |
| 2668 | 2-Bzthiaz-CO- | CarCH₂ | Bz | 3-Cl-Pro- | 1,1-diMe-2-HOEt-NH- |
| 2669 | 2-Bzoxaz-CO- | CarCH₂ | Bz | 3-Cl-Pro- | 1,1-diMe-2-HOEt-NH- |
| 2670 | 5-MeO-2-Ind-CO- | CarCH₂ | Bz | 3-Cl-Pro- | 1,1-diMe-2-HOEt-NH- |
| 2671 | 5-HO-2-Ind-CO- | CarCH₂ | Bz | 3-Cl-Pro- | 1,1-diMe-2-HOEt-NH- |
| 2672 | 5-AcO-2-Ind-CO- | CarCH₂ | Bz | 3-Cl-Pro- | 1,1-diMe-2-HOEt-NH- |
| 2673 | 5-H₂NAcO-2-Ind-CO- | CarCH₂ | Bz | 3-Cl-Pro- | 1,1-diMe-2-HOEt-NH- |

TABLE 1-continued

| Cpd. No. | R¹ | R³ | R⁴ | Z | R⁵ |
|---|---|---|---|---|---|
| 2674 | 5-Bzim-CO- | CarCH₂ | Bz | 3-Cl-Pro- | 1,1-diMe-2-HOEt-NH- |
| 2675 | (1-NpO)Ac- | CarCH₂ | Bz | 3-Cl-Pro- | 1,1-diMe-2-HOEt-NH- |
| 2676 | 1-NpOCO- | CarCH₂ | Bz | 3-Cl-Pro- | 1,1-diMe-2-HOEt-NH- |
| 2677 | 2-NpOCO- | CarCH₂ | Bz | 3-Cl-Pro- | 1,1-diMe-2-HOEt-NH- |
| 2678 | (3-PhPho)Ac- | CarCH₂ | Bz | 3-Cl-Pro- | 1,1-diMe-2-HOEt-NH- |
| 2679 | (2-NpO)Ac- | CarCH₂ | Bz | 3-Cl-Pro- | 1,1-diMe-2-HOEt-NH- |
| 2680 | Bzc | CarCH₂ | Bz | 3-Cl-Pro- | 1,1-diMe-2-HOPr-NH- |
| 2681 | 2-Quix-CO- | CarCH₂ | Bz | 3-Cl-Pro- | 1,1-diMe-2-HOPr-NH- |
| 2682 | 2-Quin-CO- | CarCH₂ | Bz | 3-Cl-Pro- | 1,1-diMe-2-HOPr-NH- |
| 2683 | 3-Quin-CO- | CarCH₂ | Bz | 3-Cl-Pro- | 1,1-diMe-2-HOPr-NH- |
| 2684 | 4-Quin-CO- | CarCH₂ | Bz | 3-Cl-Pro- | 1,1-diMe-2-HOPr-NH- |
| 2685 | 2-Pyr-CO- | CarCH₂ | Bz | 3-Cl-Pro- | 1,1-diMe-2-HOPr-NH- |
| 2686 | 3-Pyr-CO- | CarCH₂ | Bz | 3-Cl-Pro- | 1,1-diMe-2-HOPr-NH- |
| 2687 | 4-Pyr-CO- | CarCH₂ | Bz | 3-Cl-Pro- | 1,1-diMe-2-HOPr-NH- |
| 2688 | 4-MeO-2-Quin-CO- | CarCH₂ | Bz | 3-Cl-Pro- | 1,1-diMe-2-HOPr-NH- |
| 2689 | 2-Np-CO- | CarCH₂ | Bz | 3-Cl-Pro- | 1,1-diMe-2-HOPr-NH- |
| 2690 | 1-Np-CO- | CarCH₂ | Bz | 3-Cl-Pro- | 1,1-diMe-2-HOPr-NH- |
| 2691 | 2-Bfur-CO- | CarCH₂ | Bz | 3-Cl-Pro- | 1,1-diMe-2-HOPr-NH- |
| 2692 | 3-Bfur-CO- | CarCH₂ | Bz | 3-Cl-Pro- | 1,1-diMe-2-HOPr-NH- |
| 2693 | 5-Bu-2-Pyr-CO- | CarCH₂ | Bz | 3-Cl-Pro- | 1,1-diMe-2-HOPr-NH- |
| 2694 | 4-HO-2-Quin-CO- | CarCH₂ | Bz | 3-Cl-Pro- | 1,1-diMe-2-HOPr-NH- |
| 2695 | 3-HO-2-Quix-CO- | CarCH₂ | Bz | 3-Cl-Pro- | 1,1-diMe-2-HOPr-NH- |
| 2696 | 1-Np-Sfo- | CarCH₂ | Bz | 3-Cl-Pro- | 1,1-diMe-2-HOPr-NH- |
| 2697 | 2-Np-Sfo- | CarCH₂ | Bz | 3-Cl-Pro- | 1,1-diMe-2-HOPr-NH- |
| 2698 | Boz | CarCH₂ | Bz | 3-Cl-Pro- | 1,1-diMe-2-HOPr-NH- |
| 2699 | Bz-NHCO- | CarCH₂ | Bz | 3-Cl-Pro- | 1,1-diMe-2-HOPr-NH- |
| 2700 | Bz-NHCS- | CarCH₂ | Bz | 3-Cl-Pro- | 1,1-diMe-2-HOPr-NH- |
| 2701 | 2-Ind-CO- | CarCH₂ | Bz | 3-Cl-Pro- | 1,1-diMe-2-HOPr-NH- |
| 2702 | 3-Ind-CO- | CarCH₂ | Bz | 3-Cl-Pro- | 1,1-diMe-2-HOPr-NH- |
| 2703 | tBoc | CarCH₂ | Bz | 3-Cl-Pro- | 1,1-diMe-2-HOPr-NH- |
| 2704 | 2-Pyrd-CO- | CarCH₂ | Bz | 3-Cl-Pro- | 1,1-diMe-2-HOPr-NH- |
| 2705 | 2-Pip-CO- | CarCH₂ | Bz | 3-Cl-Pro- | 1,1-diMe-2-HOPr-NH- |
| 2706 | 2-Thi-CO- | CarCH₂ | Bz | 3-Cl-Pro- | 1,1-diMe-2-HOPr-NH- |
| 2707 | MecCO- | CarCH₂ | Bz | 3-Cl-Pro- | 1,1-diMe-2-HOPr-NH- |
| 2708 | PhoAc- | CarCH₂ | Bz | 3-Cl-Pro- | 1,1-diMe-2-HOPr-NH- |
| 2709 | MPhoAc- | CarCH₂ | Bz | 3-Cl-Pro- | 1,1-diMe-2-HOPr-NH- |
| 2710 | 3-Bzisox-CO- | CarCH₂ | Bz | 3-Cl-Pro- | 1,1-diMe-2-HOPr-NH- |
| 2711 | 2-Bzim-CO- | CarCH₂ | Bz | 3-Cl-Pro- | 1,1-diMe-2-HOPr-NH- |

TABLE 1-continued

| Cpd. No. | R¹ | R³ | R⁴ | Z | R⁵ |
|---|---|---|---|---|---|
| 2712 | N-Me-3-Ind-CO- | CarCH₂ | Bz | 3-Cl-Pro- | 1,1-diMe-2-HOPr-NH- |
| 2713 | 2-Bzthiaz-CO- | CarCH₂ | Bz | 3-Cl-Pro- | 1,1-diMe-2-HOPr-NH- |
| 2714 | 2-Bzoxaz-CO- | CarCH₂ | Bz | 3-Cl-Pro- | 1,1-diMe-2-HOPr-NH- |
| 2715 | 5-MeO-2-Ind-CO- | CarCH₂ | Bz | 3-Cl-Pro- | 1,1-diMe-2-HOPr-NH- |
| 2716 | 5-HO-2-Ind-CO- | CarCH₂ | Bz | 3-Cl-Pro- | 1,1-diMe-2-HOPr-NH- |
| 2717 | 5-AcO-2-Ind-CO- | CarCH₂ | Bz | 3-Cl-Pro- | 1,1-diMe-2-HOPr-NH- |
| 2718 | 5-H₂NAcO-2-Ind-CO- | CarCH₂ | Bz | 3-Cl-Pro- | 1,1-diMe-2-HOPr-NH- |
| 2719 | 5-Bzim-CO- | CarCH₂ | Bz | 3-Cl-Pro- | 1,1-diMe-2-HOPr-NH- |
| 2720 | (2-NpO)Ac- | CarCH₂ | Bz | 3-Cl-Pro- | 1,1-diMe-2-HOPr-NH- |
| 2721 | (1-NpO)Ac- | CarCH₂ | Bz | 3-Cl-Pro- | 1,1-diMe-2-HOPr-NH- |
| 2722 | 1-NpOCO- | CarCH₂ | Bz | 3-Cl-Pro- | 1,1-diMe-2-HOPr-NH- |
| 2723 | 2-NpOCO- | CarCH₂ | Bz | 3-Cl-Pro- | 1,1-diMe-2-HOPr-NH- |
| 2724 | (3-PhPho)Ac- | CarCH₂ | Bz | 3-Cl-Pro- | 1,1-diMe-2-HOPr-NH- |
| 2725 | Bzc | CarCH₂ | 3-Cl-Bz | 3-Cl-Pro- | tBuNH- |
| 2726 | 2-Quix-CO- | CarCH₂ | 3-Cl-Bz | 3-Cl-Pro- | tBuNH- |
| 2727 | Bzc | CarCH₂ | 4-MeOBz | 3-Cl-Pro- | tBuNH- |
| 2728 | 2-Quix-CO- | CarCH₂ | 4-MeOBz | 3-Cl-Pro- | tBuNH- |
| 2729 | Bzc | CarCH₂ | 4-Me-Bz | 3-Cl-Pro- | tBuNH- |
| 2730 | 2-Quix-CO- | CarCH₂ | 4-Me-Bz | 3-Cl-Pro- | tBuNH- |
| 2731 | Bzc | CarCH₂ | cHxCH₂ | 3-Cl-Pro- | tBuNH- |
| 2732 | 2-Quix-CO- | CarCH₂ | cHxCH₂ | 3-Cl-Pro- | tBuNH- |
| 2733 | Bzc | MeSOCH₂ | Bz | 3-Cl-Pro- | tBuNH- |
| 2734 | Bzc | MeSO₂CH₂ | Bz | 3-Cl-Pro- | tBuNH- |
| 2735 | Bzc | MeOCH₂- | Bz | 3-Cl-Pro- | tBuNH- |
| 2736 | Bzc | MecCH₂CH₂ | Bz | 3-Cl-Pro- | tBuNH- |
| 2737 | Bzc | MecCH₂ | Bz | 3-Cl-Pro- | tBuNH- |
| 2738 | 2-Quix-CO- | MeSOCH₂- | Bz | 3-Cl-Pro- | tBuNH- |
| 2739 | 2-Quix-CO- | MeSO₂CH₂- | Bz | 3-Cl-Pro- | tBuNH- |
| 2740 | 2-Quix-CO- | MeOCH₂ | Bz | 3-Cl-Pro- | tBuNH- |
| 2741 | 2-Quix-CO- | MecCH₂CH₂ | Bz | 3-Cl-Pro- | tBuNH- |
| 2742 | 2-Quix-CO- | MecCH₂ | Bz | 3-Cl-Pro- | tBuNH- |
| 2743 | 2-Quin-CO- | MeSOCH₂ | Bz | 3-Cl-Pro- | tBuNH- |
| 2744 | 2-Quin-CO- | MeSO₂CH₂ | Bz | 3-Cl-Pro- | tBuNH- |
| 2745 | 2-Quin-CO- | MeOCH₂- | Bz | 3-Cl-Pro- | tBuNH- |
| 2746 | 2-Quin-CO- | MecCH₂CH₂ | Bz | 3-Cl-Pro- | tBuNH- |
| 2747 | 2-Quin-CO- | MecCH₂ | Bz | 3-Cl-Pro- | tBuNH- |
| 2748 | 3-Quin-CO- | MeSOCH₂ | Bz | 3-Cl-Pro- | tBuNH- |
| 2749 | 3-Quin-CO- | MeSO₂CH₂ | Bz | 3-Cl-Pro- | tBuNH- |
| 2750 | 3-Quin-CO- | MeOCH₂- | Bz | 3-Cl-Pro- | tBuNH- |
| 2751 | 3-Quin-CO- | MecCH₂CH₂ | Bz | 3-Cl-Pro- | tBuNH- |
| 2752 | 3-Quin-CO- | MecCH₂- | Bz | 3-Cl-Pro- | tBuNH- |
| 2753 | 2-Bfur-CO- | MeSOCH₂- | Bz | 3-Cl-Pro- | tBuNH- |
| 2754 | 2-Bfur-CO- | MeSO₂CH₂ | Bz | 3-Cl-Pro- | tBuNH- |
| 2755 | 2-Bfur-CO- | MeOCH₂ | Bz | 3-Cl-Pro- | tBuNH- |
| 2756 | 2-Bfur-CO- | MecCH₂CH₂ | Bz | 3-Cl-Pro- | tBuNH- |
| 2757 | 2-Bfur-CO- | MecCH₂ | Bz | 3-Cl-Pro- | tBuNH- |
| 2758 | 3-Bfur-CO- | MeSOCH₂ | Bz | 3-Cl-Pro- | tBuNH- |
| 2759 | 3-Bfur-CO- | MeSO₂CH₂ | Bz | 3-Cl-Pro- | tBuNH- |
| 2760 | 3-Bfur-CO- | MeOCH₂ | Bz | 3-Cl-Pro- | tBuNH- |
| 2761 | 3-Bfur-CO- | MecCH₂CH₂ | Bz | 3-Cl-Pro- | tBuNH- |
| 2762 | 3-Bfur-CO- | MecCH₂ | Bz | 3-Cl-Pro- | tBuNH- |
| 2763 | 3-Ind-CO- | MeSOCH₂ | Bz | 3-Cl-Pro- | tBuNH- |
| 2764 | 3-Ind-CO- | MeSO₂CH₂ | Bz | 3-Cl-Pro- | tBuNH- |
| 2765 | 3-Ind-CO- | MeOCH₂ | Bz | 3-Cl-Pro- | tBuNH- |
| 2766 | 3-Ind-CO- | MecCH₂CH₂ | Bz | 3-Cl-Pro- | tBuNH- |
| 2767 | 3-Ind-CO- | MecCH₂ | Bz | 3-Cl-Pro- | tBuNH- |
| 2768 | Mph-O-Ac- | MeSOCH₂ | Bz | 3-Cl-Pro- | tBuNH- |
| 2769 | Mph-O-Ac- | MeSO₂CH₂ | Bz | 3-Cl-Pro- | tBuNH- |
| 2770 | Mph-O-Ac- | MeOCH₂ | Bz | 3-Cl-Pro- | tBuNH- |
| 2771 | Mph-O-Ac- | MecCH₂CH₂ | Bz | 3-Cl-Pro- | tBuNH- |
| 2772 | Mph-O-Ac- | MecCH₂ | Bz | 3-Cl-Pro- | tBuNH- |
| 2773 | 5-NH₂-AcO-2-Ind-CO- | MeSOCH₂ | Bz | 3-Cl-Pro- | tBuNH- |

TABLE 1-continued

| Cpd. No. | R¹ | R³ | R⁴ | Z | R⁵ |
|---|---|---|---|---|---|
| 2774 | 5-NH₂-AcO-2-Ind-CO- | MeSO₂CH₂ | Bz | 3-Cl-Pro- | tBuNH- |
| 2775 | 5-NH₂-AcO-2-Ind-CO- | MeOCH₂ | Bz | 3-Cl-Pro- | tBuNH- |
| 2776 | 5-NH₂-AcO-2-Ind-CO- | MecCH₂CH₂ | Bz | 3-Cl-Pro- | tBuNH- |
| 2777 | 5-NH₂-AcO-2-Ind-CO- | MecCH₂ | Bz | 3-Cl-Pro- | tBuNH- |
| 2778 | 4-NH₂-PhoAc- | MeSOCH₂ | Bz | 3-Cl-Pro- | tBuNH- |
| 2779 | 4-NH₂-PhoAc- | MeSO₂CH₂ | Bz | 3-Cl-Pro- | tBuNH- |
| 2780 | 4-NH₂-PhoAc- | MeOCH₂ | Bz | 3-Cl-Pro- | tBuNH- |
| 2781 | 4-NH₂-PhoAc- | MecCH₂CH₂ | Bz | 3-Cl-Pro- | tBuNH- |
| 2782 | 4-NH₂-PhoAc- | MecCH₂ | Bz | 3-Cl-Pro- | tBuNH- |
| 2783 | 4-[Bzc-NH]-Pho-Ac- | MeSOCH₂ | Bz | 3-Cl-Pro- | tBuNH- |
| 2784 | 4-[Bzc-NH]-Pho-Ac- | MeSO₂CH₂ | Bz | 3-Cl-Pro- | tBuNH- |
| 2785 | 4-[Bzc-NH]-Pho-Ac- | MeOCH₂ | Bz | 3-Cl-Pro- | tBuNH- |
| 2786 | 4-[Bzc-NH]-Pho-Ac- | MecCH₂CH₂ | Bz | 3-Cl-Pro- | tBuNH- |
| 2787 | 4-[Bzc-NH]-Pho-Ac- | MecCH₂ | Bz | 3-Cl-Pro- | tBuNH- |
| 2788 | 4-[(MorAc)-NMe]-PhoAc- | MeSOCH₂ | Bz | 3-Cl-Pro- | tBuNH- |
| 2789 | 4-[(MorAc)-NMe]-PhoAc- | MeSO₂CH₂ | Bz | 3-Cl-Pro- | tBuNH- |
| 2790 | 4-[(MorAc)-NMe]-PhoAc- | MeOCH₂ | Bz | 3-Cl-Pro- | tBuNH- |
| 2791 | 4-[(MorAc)-NMe]-PhoAc- | MecCH₂CH₂ | Bz | 3-Cl-Pro- | tBuNH- |
| 2792 | 4-[(MorAc)-NMe]-PhoAc-NMe-PhoAc- | MecCH₂ | Bz | 3-Cl-Pro- | tBuNH- |
| 2793 | 4-MeO-Bzc- | CarCH₂ | Bz | 3-Cl-Pro- | tBuNH- |
| 2794 | Bzc | Me₂NCH₂ | Bz | 3-Br-Pro- | tBuNH- |
| 2795 | Bzc | 2-Car-Et | Bz | 3-Br-Pro- | tBuNH- |
| 2796 | Bzc | CNCH₂ | Bz | 3-Br-Pro- | tBuNH- |
| 2797 | Bzc | iPr | Bz | 3-Br-Pro- | tBuNH- |
| 2798 | Bzc | tBu | Bz | 3-Br-Pro- | tBuNH- |
| 2799 | Bzc | diMeCarCH₂ | Bz | 3-Br-Pro- | tBuNH- |
| 2800 | Bzc | MorCOCH₂ | Bz | 3-Br-Pro- | tBuNH- |
| 2801 | Bzc | PipCOCH₂ | Bz | 3-Br-Pro- | tBuNH- |
| 2802 | Bzc | 2-NH₂-Et | Bz | 3-Br-Pro- | tBuNH- |
| 2803 | Bzc | 3-NH₂-Pr | Bz | 3-Br-Pro- | tBuNH- |
| 2804 | Bzc | MeCarCH₂ | Bz | 3-Br-Pro- | tBuNH- |
| 2805 | Bzc | EtCarCH₂ | Bz | 3-Br-Pro- | tBuNH- |
| 2806 | Bzc | H | Bz | 3-Br-Pro- | tBuNH- |
| 2807 | Bzc | HOCH₂ | Bz | 3-Br-Pro- | tBuNH- |
| 2808 | Bzc | 4-Thiz-CH₂ | Bz | 3-Br-Pro- | tBuNH- |
| 2809 | Bzc | 4-Imid-CH₂ | Bz | 3-Br-Pro- | tBuNH- |
| 2810 | Bzc | COOH-CH₂ | Bz | 3-Br-Pro- | tBuNH- |
| 2811 | Bzc | 2-COOH-Et | Bz | 3-Br-Pro- | tBuNH- |
| 2812 | Bzc | MeSCH₂ | Bz | 3-Br-Pro- | tBuNH- |
| 2813 | Bzc | SamCH₂ | Bz | 3-Br-Pro- | tBuNH- |
| 2814 | Bzc | Bz | Bz | 3-Br-Pro- | tBuNH- |
| 2815 | Bzc | Sim-CH₂ | Bz | 3-Br-Pro- | tBuNH- |
| 2816 | Bzc | Hia-CH₂ | Bz | 3-Br-Pro- | tBuNH- |
| 2817 | Bzc | 2-SimEt | Bz | 3-Br-Pro- | tBuNH- |
| 2818 | Bzc | 2-HiaEt | Bz | 3-Br-Pro- | tBuNH- |
| 2819 | Bzc | NH₂CH₂ | Bz | 3-Br-Pro- | tBuNH- |
| 2820 | Bzc | MeNHCH₂ | Bz | 3-Br-Pro- | tBuNH- |
| 2821 | 2-Quix-CO- | 2-Car-Et | Bz | 3-Br-Pro- | tBuNH- |
| 2822 | 2-Quix-CO- | CNCH₂ | Bz | 3-Br-Pro- | tBuNH- |
| 2823 | 2-Quix-CO- | iPr | Bz | 3-Br-Pro- | tBuNH- |
| 2824 | 2-Quix-CO- | tBu | Bz | 3-Br-Pro- | tBuNH- |
| 2825 | 2-Quix-CO- | diMeCarCH₂ | Bz | 3-Br-Pro- | tBuNH- |
| 2826 | 2-Quix-CO- | MorCOCH₂ | Bz | 3-Br-Pro- | tBuNH- |
| 2827 | 2-Quix-CO- | PipCOCH₂ | Bz | 3-Br-Pro- | tBuNH- |
| 2828 | 2-Quix-CO- | 2-NH₂-Et | Bz | 3-Br-Pro- | tBuNH- |
| 2829 | 2-Quix-CO- | 3-NH₂-Pr | Bz | 3-Br-Pro- | tBuNH- |
| 2830 | 2-Quix-CO- | MeCarCH₂ | Bz | 3-Br-Pro- | tBuNH- |
| 2831 | 2-Quix-CO- | EtCarCH₂ | Bz | 3-Br-Pro- | tBuNH- |
| 2832 | 2-Quix-CO- | H | Bz | 3-Br-Pro- | tBuNH- |
| 2833 | 2-Quix-CO- | HOCH₂ | Bz | 3-Br-Pro- | tBuNH- |
| 2834 | 2-Quix-CO- | 4-Thiz-CH₂ | Bz | 3-Br-Pro- | tBuNH- |
| 2835 | 2-Quix-CO- | 4-Imid-CH₂ | Bz | 3-Br-Pro- | tBuNH- |
| 2836 | 2-Quix-CO- | COOH-CH₂ | Bz | 3-Br-Pro- | tBuNH- |
| 2837 | 2-Quix-CO- | 2-COOH-Et | Bz | 3-Br-Pro- | tBuNH- |
| 2838 | 2-Quix-CO- | MeSCH₂ | Bz | 3-Br-Pro- | tBuNH- |
| 2839 | 2-Quix-CO- | SamCH₂ | Bz | 3-Br-Pro- | tBuNH- |

TABLE 1-continued

| Cpd. No. | R¹ | R³ | R⁴ | Z | R⁵ |
|---|---|---|---|---|---|
| 2840 | 2-Quix-CO- | Bz | Bz | 3-Br-Pro- | tBuNH- |
| 2841 | 2-Quix-CO- | Sim-CH₂ | Bz | 3-Br-Pro- | tBuNH- |
| 2842 | 2-Quix-CO- | Hia-CH₂ | Bz | 3-Br-Pro- | tBuNH- |
| 2843 | 2-Quix-CO- | 2-SimEt | Bz | 3-Br-Pro- | tBuNH- |
| 2844 | 2-Quix-CO- | 2-HiaEt | Bz | 3-Br-Pro- | tBuNH- |
| 2845 | 2-Quix-CO- | NH₂CH₂ | Bz | 3-Br-Pro- | tBuNH- |
| 2846 | 2-Quix-CO- | MeNHCH₂ | Bz | 3-Br-Pro- | tBuNH- |
| 2847 | 2-Quix-CO- | Me₂NCH₂ | Bz | 3-Br-Pro- | tBuNH- |
| 2848 | 3-Quin-CO- | CarCH₂ | Bz | 3-Br-Pro- | tBuNH- |
| 2849 | 4-Quin-CO- | CarCH₂ | Bz | 3-Br-Pro- | tBuNH- |
| 2850 | 2-Pyr-CO- | CarCH₂ | Bz | 3-Br-Pro- | tBuNH- |
| 2851 | 3-Pyr-CO- | CarCH₂ | Bz | 3-Br-Pro- | tBuNH- |
| 2852 | 4-Pyr-CO- | CarCH₂ | Bz | 3-Br-Pro- | tBuNH- |
| 2853 | 4-MeO-2-Quin-CO- | CarCH₂ | Bz | 3-Br-Pro- | tBuNH- |
| 2854 | 2-Np-CO- | CarCH₂ | Bz | 3-Br-Pro- | tBuNH- |
| 2855 | 1-Np-CO- | CarCH₂ | Bz | 3-Br-Pro- | tBuNH- |
| 2856 | 2-Bfur-CO- | CarCH₂ | Bz | 3-Br-Pro- | tBuNH- |
| 2857 | 3-Bfur-CO- | CarCH₂ | Bz | 3-Br-Pro- | tBuNH- |
| 2858 | 5-Bu-2-Pyr-CO- | CarCH₂ | Bz | 3-Br-Pro- | tBuNH- |
| 2859 | 4-HO-2-Quin-CO- | CarCH₂ | Bz | 3-Br-Pro- | tBuNH- |
| 2860 | 3-HO-2-Quix-CO- | CarCH₂ | Bz | 3-Br-Pro- | tBuNH- |
| 2861 | 1-Np-Sfo- | CarCH₂ | Bz | 3-Br-Pro- | tBuNH- |
| 2862 | 2-Np-Sfo- | CarCH₂ | Bz | 3-Br-Pro- | tBuNH- |
| 2863 | Boz | CarCH₂ | Bz | 3-Br-Pro- | tBuNH- |
| 2864 | Bz-NHCO- | CarCH₂ | Bz | 3-Br-Pro- | tBuNH- |
| 2865 | Bz-NHCS- | CarCH₂ | Bz | 3-Br-Pro- | tBuNH- |
| 2866 | 3-Ind-CO- | CarCH₂ | Bz | 3-Br-Pro- | tBuNH- |
| 2867 | 2-Pyrd-CO- | CarCH₂ | Bz | 3-Br-Pro- | tBuNH- |
| 2868 | 2-Pip-CO- | CarCH₂ | Bz | 3-Br-Pro- | tBuNH- |
| 2869 | 2-Thi-CO- | CarCH₂ | Bz | 3-Br-Pro- | tBuNH- |
| 2870 | MecCO- | CarCH₂ | Bz | 3-Br-Pro- | tBuNH- |
| 2871 | PhoAc- | CarCH₂ | Bz | 3-Br-Pro- | tBuNH- |
| 2872 | 3-Bzisox-CO- | CarCH₂ | Bz | 3-Br-Pro- | tBuNH- |
| 2873 | 2-Bzim-CO- | CarCH₂ | Bz | 3-Br-Pro- | tBuNH- |
| 2874 | N-Me-3-Ind-CO- | CarCH₂ | Bz | 3-Br-Pro- | tBuNH- |
| 2875 | 2-Bzthiaz-CO- | CarCH₂ | Bz | 3-Br-Pro- | tBuNH- |
| 2876 | 2-Bzoxaz-CO- | CarCH₂ | Bz | 3-Br-Pro- | tBuNH- |
| 2877 | 5-MeO-2-Ind-CO- | CarCH₂ | Bz | 3-Br-Pro- | tBuNH- |
| 2878 | 5-HO-2-Ind-CO- | CarCH₂ | Bz | 3-Br-Pro- | tBuNH- |
| 2879 | 5-AcO-2-Ind-CO- | CarCH₂ | Bz | 3-Br-Pro- | tBuNH- |
| 2880 | 2-H₂NAcO-2-Ind-CO- | CarCH₂ | Bz | 3-Br-Pro- | tBuNH- |
| 2881 | 5-Bzim-CO- | CarCH₂ | Bz | 3-Br-Pro- | tBuNH- |
| 2882 | (2-NpO)Ac- | CarCH₂ | Bz | 3-Br-Pro- | tBuNH- |
| 2883 | (1-NpO)Ac- | CarCH₂ | Bz | 3-Br-Pro- | tBuNH- |
| 2884 | 1-NpOCO- | CarCH₂ | Bz | 3-Br-Pro- | tBuNH- |
| 2885 | 2-NpOCO- | CarCH₂ | Bz | 3-Br-Pro- | tBuNH- |
| 2886 | (3-PhPho)Ac- | CarCH₂ | Bz | 3-Br-Pro- | tBuNH- |
| 2887 | 2-Quix-CO- | CarCH₂ | Bz | 3-Br-Pro- | 3-HOPr-NH- |
| 2888 | 2-Quix-CO- | CarCH₂ | Bz | 3-Br-Pro- | BU-NH- |
| 2889 | 2-Quix-CO- | CarCH₂ | Bz | 3-Br-Pro- | tBuO- |
| 2890 | 2-Quix-CO- | CarCH₂ | Bz | 3-Br-Pro- | 1,1-diMe-2-HOEt-NH- |
| 2891 | Bzc | CarCH₂ | Bz | 3-Br-Pro- | 3-HOPr-NH- |
| 2892 | Bzc | CarCH₂ | Bz | 3-Br-Pro- | Bu-NH- |
| 2893 | Bzc | CarCH₂ | Bz | 3-Br-Pro- | tBuO- |
| 2894 | Bzc | CarCH₂ | Bz | 3-Br-Pro- | 1,1-diMe-2-HOEt-NH- |
| 2895 | 3-NH₂-PhoAc- | CarCH₂ | Bz | 3-Br-Pro- | tBuNH- |
| 2896 | 2-NH₂-PhoAc- | CarCH₂ | Bz | 3-Br-Pro- | tBuNH- |
| 2897 | 2,3-diNH₂-Pho-Ac- | CarCH₂ | Bz | 3-Br-Pro- | tBuNH- |
| 2898 | 2,4-diNH₂-Pho-Ac- | CarCH₂ | Bz | 3-Br-Pro- | tBuNH- |
| 2899 | 4-NH₂-Ph-CO- | CarCH₂ | Bz | 3-Br-Pro- | tBuNH- |
| 2900 | 4-NH₂-Bzc | CarCH₂ | Bz | 3-Br-Pro- | tBuNH- |
| 2901 | 4-Me₂N-PhoAc- | CarCH₂ | Bz | 3-Br-Pro- | tBuNH- |
| 2902 | 4-[Me(Bz)N]-PhoAc- | CarCH₂ | Bz | 3-Br-Pro- | tBuNH- |
| 2903 | 4-Mor-PhoAc- | CarCH₂ | Bz | 3-Br-Pro- | tBuNH- |
| 2904 | 4-[N-Bz-Pipr]-PhoAc- | CarCH₂ | Bz | 3-Br-Pro- | tBuNH- |
| 2905 | 4-MeNH-PhoAc- | CarCH₂ | Bz | 3-Br-Pro- | tBuNH- |
| 2906 | 4-[(4'-Me-Bzc)-NH]-PhoAc- | CarCH₂ | Bz | 3-Br-Pro- | tBuNH- |

TABLE 1-continued

| Cpd. No. | R¹ | R³ | R⁴ | Z | R⁵ |
|---|---|---|---|---|---|
| 2907 | 4-[tBoc-NH]-Pho-Ac- | CarCH₂ | Bz | 3-Br-Pro- | tBuNH- |
| 2908 | 4-[tBoc-MeN]-Pho-Ac- | CarCH₂ | Bz | 3-Br-Pro- | tBuNH- |
| 2909 | 4-Gly-NH-PhoAc- | CarCH₂ | Bz | 3-Br-Pro- | tBuNH- |
| 2910 | 4-[Gly-NMe]-Pho-Ac- | CarCH₂ | Bz | 3-Br-Pro- | tBuNH- |
| 2911 | 4-[(N-Me-Gly)NMe]-PhoAc- | CarCH₂ | Bz | 3-Br-Pro- | tBuNH- |
| 2912 | 4-[(N-tBoc-Gly)NMe]-PhoAc- | CarCH₂ | Bz | 3-Br-Pro- | tBuNH- |
| 2913 | 4-[(N-tBoc-NMe-Gly)NMe]-PhoAc- | CarCH₂ | Bz | 3-Br-Pro- | tBuNH- |
| 2914 | Boc | CarCH₂ | Bz | 3-Br-Pro- | tBuNH- |
| 2915 | 4-[(BrAc)NMe]-PhoAc- | CarCH₂ | Bz | 3-Br-Pro- | tBuNH- |
| 2916 | 4-[(4'-MeO-Bzc)NH]-PhoAc- | CarCH₂ | Bz | 3-Br-Pro- | tBuNH- |
| 2917 | N-Me-4-PipO-Ac- | CarCH₂ | Bz | 3-Br-Pro- | tBuNH- |
| 2918 | 4-NH₂-cHxO-Ac- | CarCH₂ | Bz | 3-Br-Pro- | tBuNH- |
| 2919 | 4-NH₂-PhoAc- | CarCH₂ | Bz | 3-Br-Pro- | 1,1-diMe-2-HOEt-NH- |
| 2920 | 3-NH₂-PhoAc- | CarCH₂ | Bz | 3-Br-Pro- | 1,1-diMe-2-HOEt-NH- |
| 2921 | 2-NH₂-PhoAc- | CarCH₂ | Bz | 3-Br-Pro- | 1,1-diMe-2-HOEt-NH- |
| 2922 | 2,3-diNH₂-Pho-Ac- | CarCH₂ | Bz | 3-Br-Pro- | 1,1-diMe-2-HOEt-NH- |
| 2922 | 2,4-diNH₂-Pho-Ac- | CarCH₂ | Bz | 3-Br-Pro- | 1,1-diMe-2-HOEt-NH- |
| 2924 | 4-NH₂-Ph-CO- | CarCH₂ | Bz | 3-Br-Pro- | 1,1-diMe-2-HOEt-NH- |
| 2925 | 4-NH₂-Bzc | CarCH₂ | Bz | 3-Br-Pro- | 1,1-diMe-2-HOEt-NH- |
| 2926 | 4-Me₂N-PhoAc- | CarCH₂ | Bz | 3-Br-Pro- | 1,1-diMe-2-HOEt-NH- |
| 2927 | 4-[Me(Bz)N]-Pho-Ac- | CarCH₂ | Bz | 3-Br-Pro- | 1,1-diMe-2-HOEt-NH- |
| 2928 | 4-Mor-PhoAc- | CarCH₂ | Bz | 3-Br-Pro- | 1,1-diMe-2-HOEt-NH- |
| 2929 | 4-[N-Bz-Pipr]-PhoAc- | CarCH₂ | Bz | 3-Br-Pro- | 1,1-diMe-2-HOEt-NH- |
| 2930 | 4-MeNH-PhoAc- | CarCH₂ | Bz | 3-Br-Pro- | 1,1-diMe-2-HOEt-NH- |
| 2931 | 4-[(4'-Me-Bzc)-NH]-PhoAc- | CarCH₂ | Bz | 3-Br-Pro- | 1,1-diMe-2-HOEt-NH- |
| 2932 | 4-[Bzc-NH]-Pho-Ac- | CarCH₂ | Bz | 3-Br-Pro- | 1,1-diMe-2-HOEt-NH- |
| 2933 | 4-(tBoc-NH]-Pho-Ac- | CarCH₂ | Bz | 3-Br-Pro- | 1,1-diMe-2-HOEt-NH- |
| 2934 | 4-[tBoc-MeN]-PhoAc- | CarCH₂ | Bz | 3-Br-Pro- | 1,1-diMe-2-HOEt-NH- |
| 2935 | 4-Gly-NH-Pho-Ac- | CarCH₂ | Bz | 3-Br-Pro- | 1,1-diMe-2-HOEt-NH- |
| 2936 | 4-[Gly-NMe]-Pho-Ac- | CarCH₂ | Bz | 3-Br-Pro- | 1,1-diMe-2-HOEt-NH- |
| 2937 | 4-[(N-Me-Gly)NMe]-PhoAc- | CarCH₂ | Bz | 3-Br-Pro- | 1,1-diMe-2-HOEt-NH- |
| 2938 | 4-[(N-tBoc-Gly)NMe]-PhoAc- | CarCH₂ | Bz | 3-Br-Pro- | 1,1-diMe-2-HOEt-NH- |
| 2939 | 4-[(N-tBoc-NMe-Gly)NMe]-PhoAc- | CarCH₂ | Bz | 3-Br-Pro- | 1,1-diMe-2-HOEt-NH- |
| 2940 | Boc | CarCH₂ | Bz | 3-Br-Pro- | 1,1-diMe-2-HOEt-NH- |
| 2941 | 4-[(BrAc)NMe]-PhoAc- | CarCH₂ | Bz | 3-Br-Pro- | 1,1-diMe-2-HOEt-NH- |
| 2942 | 4-[(4'-MeO-Bzc)NH]-PhoAc- | CarCH₂ | Bz | 3-Br-Pro- | 1,1-diMe-2-HOEt-NH- |
| 2943 | N-Me-4-Pip-O-Ac- | CarCH₂ | Bz | 3-Br-Pro- | 1,1-diMe-2-HOEt-NH- |
| 2944 | 4-NH₂-cHxO-Ac- | CarCH₂ | Bz | 3-Br-Pro- | 1,1-diMe-2-HOEt-NH- |
| 2945 | 4-[(MorAc)NMe]-PhoAc- | CarCH₂ | Bz | 3-Br-Pro- | 1,1-diMe-2-HOEt-NH- |
| 2946 | 4-NH₂-PhoAc- | CarCH₂ | Bz | 3-Br-Pro- | 1,1-diMe-2-HOPr-NH- |
| 2947 | 3-NH₂-PhoAc- | CarCH₂ | Bz | 3-Br-Pro- | 1,1-diMe-2-HOPr-NH- |

TABLE 1-continued

| Cpd. No. | R¹ | R³ | R⁴ | Z | R⁵ |
|---|---|---|---|---|---|
| 2948 | 2-NH₂-PhoAc- | CarCH₂ | Bz | 3-Br-Pro- | 1,1-diMe-2-HOPr-NH- |
| 2949 | 2,3-diNH₂-Pho-Ac- | CarCH₂ | Bz | 3-Br-Pro- | 1,1-diMe-2-HOPr-NH- |
| 2950 | 2,4-diNH₂-Pho-Ac- | CarCH₂ | Bz | 3-Br-Pro- | 1,1-diMe-2-HOPr-NH- |
| 2951 | 4-NH₂-Ph-CO- | CarCH₂ | Bz | 3-Br-Pro- | 1,1-diMe-2-HOPr-NH- |
| 2952 | 4-NH₂-Bzc | CarCH₂ | Bz | 3-Br-Pro- | 1,1-diMe-2-HOPr-NH- |
| 2953 | 4-Me₂N-PhoAc- | CarCH₂ | Bz | 3-Br-Pro- | 1,1-diMe-2-HOPr-NH- |
| 2954 | 4-[Me(Bz)N]-PhoAc- | CarCH₂ | Bz | 3-Br-Pro- | 1,1-diMe-2-HOPr-NH- |
| 2955 | 4-Mor-PhoAc- | CarCH₂ | Bz | 3-Br-Pro- | 1,1-diMe-2-HOPr-NH- |
| 2956 | 4-[N-Bz-Pipr]-PhoAc- | CarCH₂ | Bz | 3-Br-Pro- | 1,1-diMe-2-HOPr-NH- |
| 2957 | 4-MeNH-PhoAc- | CarCH₂ | Bz | 3-Br-Pro- | 1,1-diMe-2-HOPr-NH- |
| 2958 | 4-[(4'-Me-Bzc)-NH]-PhoAc- | CarCH₂ | Bz | 3-Br-Pro- | 1,1-diMe-2-HOPr-NH- |
| 2959 | 4-[Bzc-NH]-PhoAc- | CarCH₂ | Bz | 3-Br-Pro- | 1,1-diMe-2-HOPr-NH- |
| 2960 | 4-[tBoc-NH]-Pho-Ac- | CarCH₂ | Bz | 3-Br-Pro- | 1,1-diMe-2-HOPr-NH- |
| 2961 | 4-[tBoc-MeN]-Pho-Ac- | CarCH₂ | Bz | 3-Br-Pro- | 1,1-diMe-2-HOPr-NH- |
| 2962 | 4-Gly-NH-PhoAc- | CarCH₂ | Bz | 3-Br-Pro- | 1,1-diMe-2-HOPr-NH- |
| 2963 | 4-[Gly-NMe]-Pho-Ac- | CarCH₂ | Bz | 3-Br-Pro- | 1,1-diMe-2-HOPr-NH- |
| 2964 | 4-[(N-Me-Gly)NMe]-PhoAc- | CarCH₂ | Bz | 3-Br-Pro- | 1,1-diMe-2-HOPr-NH- |
| 2965 | 4-[(N-tBoc-Gly)NMe]-PhoAc- | CarCH₂ | Bz | 3-Br-Pro- | 1,1-diMe-2-HOPr-NH- |
| 2966 | 4-[(N-tBoc-NMe-Gly)NMe]-PhoAc- | CarCH₂ | Bz | 3-Br-Pro- | 1,1-diMe-2-HOPr-NH- |
| 2967 | Boc | CarCH₂ | Bz | 3-Br-Pro- | 1,1-diMe-2-HOPr-NH- |
| 2968 | 4-[(BrAc)NMe]-PhoAc- | CarCH₂ | Bz | 3-Br-Pro- | 1,1-diMe-2-HOPr-NH- |
| 2969 | 4-[(4'-MeO-Bzc)NH]-PhoAc- | CarCH₂ | Bz | 3-Br-Pro- | 1,1-diMe-2-HOPr-NH- |
| 2970 | N-Me-4-PipO-Ac- | CarCH₂ | Bz | 3-Br-Pro- | 1,1-diMe-2-HOPr-NH- |
| 2971 | 4-NH₂-cHxO-Ac- | CarCH₂ | Bz | 3-Br-Pro- | 1,1-diMe-2-HOPr-NH- |
| 2972 | 4-[(MorAc)NMe]-PhoAc- | CarCH₂ | Bz | 3-Br-Pro- | 1,1-diMe-2-HOPr-NH- |
| 2973 | 2-Quin-CO- | CarCH₂ | Bz | 3-Br-Pro- | 1,1-diMe-2-HOEt-NH- |
| 2974 | 3-Quin-CO- | CarCH₂ | Bz | 3-Br-Pro- | 1,1-diMe-2-HOEt-NH- |
| 2975 | 4-Quin-CO- | CarCH₂ | Bz | 3-Br-Pro- | 1,1-diMe-2-HOEt-NH- |
| 2976 | 2-Pyr-CO- | CarCH₂ | Bz | 3-Br-Pro- | 1,1-diMe-2-HOEt-NH- |
| 2977 | 3-Pyr-CO- | CarCH₂ | Bz | 3-Br-Pro- | 1,1-diMe-2-HOEt-NH- |
| 2978 | 4-Pyr-CO- | CarCH₂ | Bz | 3-Br-Pro- | 1,1-diMe-2-HOEt-NH- |
| 2979 | 4-MeO-2-Quin-CO- | CarCH₂ | Bz | 3-Br-Pro- | 1,1-diMe-2-HOEt-NH- |
| 2980 | 2-Np-CO- | CarCH₂ | Bz | 3-Br-Pro- | 1,1-diMe-2-HOEt-NH- |
| 2981 | 1-Np-CO- | CarCH₂ | Bz | 3-Br-Pro- | 1,1-diMe-2-HOEt-NH- |
| 2982 | 2-Bfur-CO- | CarCH₂ | Bz | 3-Br-Pro- | 1,1-diMe-2-HOEt-NH- |
| 2983 | 3-Bfur-CO- | CarCH₂ | Bz | 3-Br-Pro- | 1,1-diMe-2-HOEt-NH- |
| 2984 | 5-Bu-2-Pyr-CO- | CarCH₂ | Bz | 3-Br-Pro- | 1,1-diMe-2-HOEt-NH- |
| 2985 | 4-HO-2-Quin-CO- | CarCH₂ | Bz | 3-Br-Pro- | 1,1-diMe-2-HOEt-NH- |

TABLE 1-continued

| Cpd. No. | R¹ | R³ | R⁴ | Z | R⁵ |
|---|---|---|---|---|---|
| 2986 | 3-HO-2-Quix-CO- | CarCH₂ | Bz | 3-Br-Pro- | 1,1-diMe-2-HOEt-NH- |
| 2987 | 1-Np-Sfo- | CarCH₂ | Bz | 3-Br-Pro- | 1,1-diMe-2-HOEt-NH- |
| 2988 | 2-Np-Sfo- | CarCH₂ | Bz | 3-Br-Pro- | 1,1-diMe-2-HOEt-NH- |
| 2989 | Boz | CarCH₂ | Bz | 3-Br-Pro- | 1,1-diMe-2-HOEt-NH- |
| 2990 | Bz-NHCO- | CarCH₂ | Bz | 3-Br-Pro- | 1,1-diMe-2-HOEt-NH- |
| 2991 | Bz-NHCS- | CarCH₂ | Bz | 3-Br-Pro- | 1,1-diMe-2-HOEt-NH- |
| 2992 | 2-Ind-CO- | CarCH₂ | Bz | 3-Br-Pro- | 1,1-diMe-2-HOEt-NH- |
| 2993 | 3-Ind-CO- | CarCH₂ | Bz | 3-Br-Pro- | 1,1-diMe-2-HOEt-NH- |
| 2994 | tBoc | CarCH₂ | Bz | 3-Br-Pro- | 1,1-diMe-2-HOEt-NH- |
| 2995 | 2-Pyrd-CO- | CarCH₂ | Bz | 3-Br-Pro- | 1,1-diMe-2-HOEt-NH- |
| 2996 | 2-Pip-CO- | CarCH₂ | Bz | 3-Br-Pro- | 1,1-diMe-2-HOEt-NH- |
| 2997 | 2-Thi-CO- | CarCH₂ | Bz | 3-Br-Pro- | 1,1-diMe-2-HOEt-NH- |
| 2998 | MecCO- | CarCH₂ | Bz | 3-Br-Pro- | 1,1-diMe-2-HOEt-NH- |
| 2999 | PhoAc- | CarCH₂ | Bz | 3-Br-Pro- | 1,1-diMe-2-HOEt-NH- |
| 3000 | MPhoAc- | CarCH₂ | Bz | 3-Br-Pro- | 1,1-diMe-2-HOEt-NH- |
| 3001 | 3-Bzisox-CO- | CarCH₂ | Bz | 3-Br-Pro- | 1,1-diMe-2-HOEt-NH- |
| 3002 | 2-Bzim-CO- | CarCH₂ | Bz | 3-Br-Pro- | 1,1-diMe-2-HOEt-NH- |
| 3003 | N-Me-3-Ind-CO- | CarCH₂ | Bz | 3-Br-Pro- | 1,1-diMe-2-HOEt-NH- |
| 3004 | 2-Bzthiaz-CO- | CarCH₂ | Bz | 3-Br-Pro- | 1,1-diMe-2-HOEt-NH- |
| 3005 | 2-Bzoxaz-CO- | CarCH₂ | Bz | 3-Br-Pro- | 1,1-diMe-2-HOEt-NH- |
| 3006 | 5-MeO-2-Ind-CO- | CarCH₂ | Bz | 3-Br-Pro- | 1,1-diMe-2-HOEt-NH- |
| 3007 | 5-HO-2-Ind-CO- | CarCH₂ | Bz | 3-Br-Pro- | 1,1-diMe-2-HOEt-NH- |
| 3008 | 5-AcO-2-Ind-CO- | CarCH₂ | Bz | 3-Br-Pro- | 1,1-diMe-2-HOEt-NH- |
| 3009 | 5-H₂NAcO-2-Ind-CO- | CarCH₂ | Bz | 3-Br-Pro- | 1,1-diMe-2-HOEt-NH- |
| 3010 | 5-Bzim-CO- | CarCH₂ | Bz | 3-Br-Pro- | 1,1-diMe-2-HOEt-NH- |
| 3011 | (1-NpO)Ac- | CarCH₂ | Bz | 3-Br-Pro- | 1,1-diMe-2-HOEt-NH- |
| 3012 | 1-NpOCO- | CarCH₂ | Bz | 3-Br-Pro- | 1,1-diMe-2-HOEt-NH- |
| 3013 | 2-NpOCO- | CarCH₂ | Bz | 3-Br-Pro- | 1,1-diMe-2-HOEt-NH- |
| 3014 | (3-PhPho)Ac- | CarCH₂ | Bz | 3-Br-Pro- | 1,1-diMe-2-HOEt-NH- |
| 3015 | (2-NpO)Ac- | CarCH₂ | Bz | 3-Br-Pro- | 1,1-diMe-2-HOEt-NH- |
| 3016 | Bzc | CarCH₂ | Bz | 3-Br-Pro- | 1,1-diMe-2-HOPr-NH- |
| 3017 | 2-Quix-CO- | CarCH₂ | Bz | 3-Br-Pro- | 1,1-diMe-2-HOPr-NH- |
| 3018 | 2-Quin-CO- | CarCH₂ | Bz | 3-Br-Pro- | 1,1-diMe-2-HOPr-NH- |
| 3019 | 3-Quin-CO- | CarCH₂ | Bz | 3-Br-Pro- | 1,1-diMe-2-HOPr-NH- |
| 3020 | 4-Quin-CO- | CarCH₂ | Bz | 3-Br-Pro- | 1,1-diMe-2-HOPr-NH- |
| 3021 | 2-Pyr-CO- | CarCH₂ | Bz | 3-Br-Pro- | 1,1-diMe-2-HOPr-NH- |
| 3022 | 3-Pyr-CO- | CarCH₂ | Bz | 3-Br-Pro- | 1,1-diMe-2-HOPr-NH- |
| 3023 | 4-Pyr-CO- | CarCH₂ | Bz | 3-Br-Pro- | 1,1-diMe-2-HOPr-NH- |

TABLE 1-continued

| Cpd. No. | R¹ | R³ | R⁴ | Z | R⁵ |
|---|---|---|---|---|---|
| 3024 | 4-MeO-2-Quin-CO- | CarCH₂ | Bz | 3-Br-Pro- | 1,1-diMe-2-HOPr-NH- |
| 3025 | 2-Np-CO- | CarCH₂ | Bz | 3-Br-Pro- | 1,1-diMe-2-HOPr-NH- |
| 3026 | 1-Np-CO- | CarCH₂ | Bz | 3-Br-Pro- | 1,1-diMe-2-HOPr-NH- |
| 3027 | 2-Bfur-CO- | CarCH₂ | Bz | 3-Br-Pro- | 1,1-diMe-2-HOPr-NH- |
| 3028 | 3-Bfur-CO- | CarCH₂ | Bz | 3-Br-Pro- | 1,1-diMe-2-HOPr-NH- |
| 3029 | 5-Bu-2-Pyr-CO- | CarCH₂ | Bz | 3-Br-Pro- | 1,1-diMe-2-HOPr-NH- |
| 3030 | 4-HO-2-Quin-CO- | CarCH₂ | Bz | 3-Br-Pro- | 1,1-diMe-2-HOPr-NH- |
| 3031 | 3-HO-2-Quix-CO- | CarCH₂ | Bz | 3-Br-Pro- | 1,1-diMe-2-HOPr-NH- |
| 3032 | 1-Np-Sfo- | CarCH₂ | Bz | 3-Br-Pro- | 1,1-diMe-2-HOPr-NH- |
| 3033 | 2-Np-Sfo- | CarCH₂ | Bz | 3-Br-Pro- | 1,1-diMe-2-HOPr-NH- |
| 3034 | Boz | CarCH₂ | Bz | 3-Br-Pro- | 1,1-diMe-2-HOPr-NH- |
| 3035 | Bz-NHCO- | CarCH₂ | Bz | 3-Br-Pro- | 1,1-diMe-2-HOPr-NH- |
| 3036 | Bz-NHCS- | CarCH₂ | Bz | 3-Br-Pro- | 1,1-diMe-2-HOPr-NH- |
| 3037 | 2-Ind-CO- | CarCH₂ | Bz | 3-Br-Pro- | 1,1-diMe-2-HOPr-NH- |
| 3038 | 3-Ind-CO- | CarCH₂ | Bz | 3-Br-Pro- | 1,1-diMe-2-HOPr-NH- |
| 3039 | tBoc | CarCH₂ | Bz | 3-Br-Pro- | 1,1-diMe-2-HOPr-NH- |
| 3040 | 2-Pyrd-CO- | CarCH₂ | Bz | 3-Br-Pro- | 1,1-diMe-2-HOPr-NH- |
| 3041 | 2-Pip-CO- | CarCH₂ | Bz | 3-Br-Pro- | 1,1-diMe-2-HOPr-NH- |
| 3042 | 2-Thi-CO- | CarCH₂ | Bz | 3-Br-Pro- | 1,1-diMe-2-HOPr-NH- |
| 3043 | MecCO- | CarCH₂ | Bz | 3-Br-Pro- | 1,1-diMe-2-HOPr-NH- |
| 3044 | PhoAc- | CarCH₂ | Bz | 3-Br-Pro- | 1,1-diMe-2-HOPr-NH- |
| 3045 | MPhoAc | CarCH₂ | Bz | 3-Br-Pro- | 1,1-diMe-2-HOPr-NH- |
| 3046 | 3-Bzisox-CO- | CarCH₂ | Bz | 3-Br-Pro- | 1,1-diMe-2-HOPr-NH- |
| 3047 | 2-Bzim-CO- | CarCH₂ | Bz | 3-Br-Pro- | 1,1-diMe-2-HOPr-NH- |
| 3048 | N-Me-3-Ind-CO- | CarCH₂ | Bz | 3-Br-Pro- | 1,1-diMe-2-HOPr-NH- |
| 3049 | 2-Bzthiaz-CO- | CarCH₂ | Bz | 3-Br-Pro- | 1,1-diMe-2-HOPr-NH- |
| 3050 | 2-Bzoxaz-CO- | CarCH₂ | Bz | 3-Br-Pro- | 1,1-diMe-2-HOPr-NH- |
| 3051 | 5-MeO-2-Ind-CO- | CarCH₂ | Bz | 3-Br-Pro- | 1,1-diMe-2-HOPr-NH- |
| 3052 | 5-HO-2-Ind-CO- | CarCH₂ | Bz | 3-Br-Pro- | 1,1-diMe-2-HOPr-NH- |
| 3053 | 5-AcO-2-Ind-CO- | CarCH₂ | Bz | 3-Br-Pro- | 1,1-diMe-2-HOPr-NH- |
| 3054 | 5-H₂NAcO-2-Ind-CO- | CarCH₂ | Bz | 3-Br-Pro- | 1,1-diMe-2-HOPr-NH- |
| 3055 | 5-Bzim-CO- | CarCH₂ | Bz | 3-Br-Pro- | 1,1-diMe-2-HOPr-NH- |
| 3056 | (2-NpO)Ac- | CarCH₂ | Bz | 3-Br-Pro- | 1,1-diMe-2-HOPr-NH- |
| 3057 | (1-NpO)Ac- | CarCH₂ | Bz | 3-Br-Pro- | 1,1-diMe-2-HOPr-NH- |
| 3058 | 1-NpOCO- | CarCH₂ | Bz | 3-Br-Pro- | 1,1-diMe-2-HOPr-NH- |
| 3059 | 2-NpOCO- | CarCH₂ | Bz | 3-Br-Pro- | 1,1-diMe-2-HOPr-NH- |
| 3060 | (3-PhPho)Ac- | CarCH₂ | Bz | 3-Br-Pro- | 1,1-diMe-2-HOPr-NH- |
| 3061 | Bzc | CarCH₂ | 3-Cl-Bz | 3-Br-Pro- | tBuNH- |
| 3062 | 2-Quix-CO- | CarCH₂ | 3-Cl-Bz | 3-Br-Pro- | tBuNH- |

TABLE 1-continued

| Cpd. No. | R¹ | R³ | R⁴ | Z | R⁵ |
|---|---|---|---|---|---|
| 3063 | Bzc | CarCH₂ | 4-MeOBz | 3-Br-Pro- | tBuNH- |
| 3064 | 2-Quix-CO- | CarCH₂ | 4-MeOBz | 3-Br-Pro- | tBuNH- |
| 3065 | Bzc | CarCH₂ | 4-Me-Bz | 3-Br-Pro- | tBuNH- |
| 3066 | 2-Quix-CO- | CarCH₂ | 4-Me-Bz | 3-Br-Pro- | tBuNH- |
| 3067 | Bzc | CarCH₂ | cHxCH₂- | 3-Br-Pro- | tBuNH- |
| 3068 | 2-Quix-CO- | CarCH₂ | cHxCH₂- | 3-Br-Pro- | tBuNH- |
| 3069 | Bzc | MeSOCH₂ | Bz | 3-Br-Pro- | tBuNH- |
| 3070 | Bzc | MeSO₂CH₂ | Bz | 3-Br-Pro- | tBuNH- |
| 3071 | Bzc | MeOCH₂- | Bz | 3-Br-Pro- | tBuNH- |
| 3072 | Bzc | MecCH₂CH₂ | Bz | 3-Br-Pro- | tBuNH- |
| 3073 | Bzc | MecCH₂ | Bz | 3-Br-Pro- | tBuNH- |
| 3074 | 2-Quix-CO- | MeSOCH₂- | Bz | 3-Br-Pro- | tBuNH- |
| 3075 | 2-Quix-CO- | MeSO₂CH₂- | Bz | 3-Br-Pro- | tBuNH- |
| 3076 | 2-Quix-CO- | MeOCH₂ | Bz | 3-Br-Pro- | tBuNH- |
| 3077 | 2-Quix-CO- | MecCH₂CH₂ | Bz | 3-Br-Pro- | tBuNH- |
| 3078 | 2-Quix-CO- | MecCH₂ | Bz | 3-Br-Pro- | tBuNH- |
| 3079 | 2-Quin-CO- | MeSOCH₂ | Bz | 3-Br-Pro- | tBuNH- |
| 3080 | 2-Quin-CO- | MeSO₂CH₂ | Bz | 3-Br-Pro- | tBuNH- |
| 3081 | 2-Quin-CO- | MeOCH₂- | Bz | 3-Br-Pro- | tBuNH- |
| 3082 | 2-Quin-CO- | MecCH₂CH₂ | Bz | 3-Br-Pro- | tBuNH- |
| 3083 | 2-Quin-CO- | MecCH₂ | Bz | 3-Br-Pro- | tBuNH- |
| 3084 | 3-Quin-CO- | MeSOCH₂ | Bz | 3-Br-Pro- | tBuNH- |
| 3085 | 3-Quin-CO- | MeSO₂CH₂ | Bz | 3-Br-Pro- | tBuNH- |
| 3086 | 3-Quin-CO- | MeOCH₂- | Bz | 3-Br-Pro- | tBuNH- |
| 3087 | 3-Quin-CO- | MecCH₂CH₂ | Bz | 3-Br-Pro- | tBuNH- |
| 3088 | 3-Quin-CO- | MecCH₂- | Bz | 3-Br-Pro- | tBuNH- |
| 3089 | 2-Bfur-CO- | MeSOCH₂- | Bz | 3-Br-Pro- | tBuNH- |
| 3090 | 2-Bfur-CO- | MeSO₂CH₂ | Bz | 3-Br-Pro- | tBuNH- |
| 3091 | 2-Bfur-CO- | MeOCH₂ | Bz | 3-Br-Pro- | tBuNH- |
| 3092 | 2-Bfur-CO- | MecCH₂CH₂ | Bz | 3-Br-Pro- | tBuNH- |
| 3093 | 2-Bfur-CO- | MecCH₂ | Bz | 3-Br-Pro- | tBuNH- |
| 3094 | 3-Bfur-CO- | MeSOCH₂ | Bz | 3-Br-Pro- | tBuNH- |
| 3095 | 3-Bfur-CO- | MeSO₂CH₂ | Bz | 3-Br-Pro- | tBuNH- |
| 3096 | 3-Bfur-CO- | MeOCH₂ | Bz | 3-Br-Pro- | tBuNH- |
| 3097 | 3-Bfur-CO- | MecCH₂CH₂ | Bz | 3-Br-Pro- | tBuNH- |
| 3098 | 3-Bfur-CO- | MecCH₂ | Bz | 3-Br-Pro- | tBuNH- |
| 3099 | 3-Ind-CO- | MeSOCH₂ | Bz | 3-Br-Pro- | tBuNH- |
| 3100 | 3-Ind-CO- | MeSO₂CH₂ | Bz | 3-Br-Pro- | tBuNH- |
| 3101 | 3-Ind-CO- | MeOCH₂ | Bz | 3-Br-Pro- | tBuNH- |
| 3102 | 3-Ind-CO- | MecCH₂CH₂ | Bz | 3-Br-Pro- | tBuNH- |
| 3103 | 3-Ind-CO- | MecCH₂ | Bz | 3-Br-Pro- | tBuNH- |
| 3104 | MPhOAc- | MeSOCH₂ | Bz | 3-Br-Pro- | tBuNH- |
| 3105 | MPhOAc- | MeSO₂CH₂ | Bz | 3-Br-Pro- | tBuNH- |
| 3106 | MPhOAc- | MeOCH₂ | Bz | 3-Br-Pro- | tBuNH- |
| 3107 | MPhOAc- | MecCH₂CH₂ | Bz | 3-Br-Pro- | tBuNH- |
| 3108 | MPhOAc- | MecCH₂ | Bz | 3-Br-Pro- | tBuNH- |
| 3109 | 5-NH₂-AcO-2-Ind-CO- | MeSOCH₂ | Bz | 3-Br-Pro- | tBuNH- |
| 3110 | 5-NH₂-AcO-2-Ind-CO- | MeSO₂CH₂ | Bz | 3-Br-Pro- | tBuNH- |
| 3111 | 5-NH₂-AcO-2-Ind-CO- | MeOCH₂ | Bz | 3-Br-Pro- | tBuNH- |
| 3112 | 5-NH₂-AcO-2-Ind-CO- | MecCH₂CH₂ | Bz | 3-Br-Pro- | tBuNH- |
| 3113 | 5-NH₂-AcO-2-Ind-CO- | MecCH₂ | Bz | 3-Br-Pro- | tBuNH- |
| 3114 | 4-NH₂-Pho-Ac- | MeSOCH₂ | Bz | 3-Br-Pro- | tBuNH- |
| 3115 | 4-NH₂-Pho-Ac- | MeSO₂CH₂ | Bz | 3-Br-Pro- | tBuNH- |
| 3116 | 4-NH₂-Pho-Ac- | MeOCH₂ | Bz | 3-Br-Pro- | tBuNH- |
| 3117 | 4-NH₂-Pho-Ac- | MecCH₂CH₂ | Bz | 3-Br-Pro- | tBuNH- |
| 3118 | 4-NH₂-Pho-Ac- | MecCH₂ | Bz | 3-Br-Pro- | tBuNH- |
| 3119 | 4-[Bzc-NH]-PhoAc | MeSOCH₂ | Bz | 3-Br-Pro- | tBuNH- |
| 3120 | 4-[Bzc-NH]-PhoAc | MeSO₂CH₂ | Bz | 3-Br-Pro- | tBuNH- |
| 3121 | 4-[Bzc-NH]-PhoAc | MeOCH₂ | Bz | 3-Br-Pro- | tBuNH- |
| 3122 | 4-[Bzc-NH]-PhoAc | MecCH₂CH₂ | Bz | 3-Br-Pro- | tBuNH- |
| 3123 | 4-[Bzc-NH]-PhoAc | MecCH₂ | Bz | 3-Br-Pro- | tBuNH- |

TABLE 1-continued

| Cpd. No. | $R^1$ | $R^3$ | $R^4$ | Z | $R^5$ |
|---|---|---|---|---|---|
| 3124 | 4-[(MorAc)-NMe]-PhoAc | MeSOCH$_2$ | Bz | 3-Br-Pro- | tBuNH- |
| 3125 | 4-[(MorAc)-NMe]-PhoAc | MeSO$_2$CH$_2$ | Bz | 3-Br-Pro- | tBuNH- |
| 3126 | 4-[(MorAc)-NMe]-PhoAc | MeOCH$_2$ | Bz | 3-Br-Pro- | tBuNH- |
| 3127 | 4-[(MorAc)-NMe]-PhoAc | MecCH$_2$CH$_2$ | Bz | 3-Br-Pro- | tBuNH- |
| 3128 | 4-[(MorAc)-NMe]-PhoAc | MecCH$_2$ | Bz | 3-Br-Pro- | tBuNH- |
| 3129 | 4-MeO-Bzc | CarCH$_2$ | Bz | 3-Br-Pro- | tBuNH- |
| 3130 | Bzc | Me$_2$NCH$_2$ | Bz | 3-I-Pro- | tBuNH- |
| 3131 | Bzc | 2-Car-Et | Bz | 3-I-Pro- | tBuNH- |
| 3132 | Bzc | CNCH$_2$ | Bz | 3-I-Pro- | tBuNH- |
| 3233 | Bzc | iPr | Bz | 3-I-Pro- | tBuNH- |
| 3134 | Bzc | tBu | Bz | 3-I-Pro- | tBuNH- |
| 3135 | Bzc | diMeCarCH$_2$ | Bz | 3-I-Pro- | tBuNH- |
| 3136 | Bzc | MorCOCH$_2$ | Bz | 3-I-Pro- | tBuNH- |
| 3137 | Bzc | PipCOCH$_2$ | Bz | 3-I-Pro- | tBuNH- |
| 3138 | Bzc | 2-NH$_2$-Et | Bz | 3-I-Pro- | tBuNH- |
| 3139 | Bzc | 3-NH$_2$-Pr | Bz | 3-I-Pro- | tBuNH- |
| 3140 | Bzc | MeCarCH$_2$ | Bz | 3-I-Pro- | tBuNH- |
| 3141 | Bzc | EtCarCH$_2$ | Bz | 3-I-Pro- | tBuNH- |
| 3142 | Bzc | H | Bz | 3-I-Pro- | tBuNH- |
| 3143 | Bzc | HOCH$_2$ | Bz | 3-I-Pro- | tBuNH- |
| 3144 | Bzc | 4-Thiz-CH$_2$ | Bz | 3-I-Pro- | tBuNH- |
| 3145 | Bzc | 4-Imid-CH$_2$ | Bz | 3-I-Pro- | tBuNH- |
| 3146 | Bzc | COOH-CH$_2$ | Bz | 3-I-Pro- | tBuNH- |
| 3147 | Bzc | 2-COOH-Et | Bz | 3-I-Pro- | tBuNH- |
| 3148 | Bzc | MeSCH$_2$ | Bz | 3-I-Pro- | tBuNH- |
| 3149 | Bzc | SamCH$_2$ | Bz | 3-I-Pro- | tBuNH- |
| 3150 | Bzc | Bz | Bz | 3-I-Pro- | tBuNH- |
| 3151 | Bzc | SimCH$_2$ | Bz | 3-I-Pro- | tBuNH- |
| 3152 | Bzc | HiaCH$_2$ | Bz | 3-I-Pro- | tBuNH- |
| 3153 | Bzc | 2-Sim-Et | Bz | 3-I-Pro- | tBuNH- |
| 3154 | Bzc | 2-Hia-Et- | Bz | 3-I-Pro- | tBuNH- |
| 3155 | Bzc | NH$_2$CH$_2$ | Bz | 3-I-Pro- | tBuNH- |
| 3156 | Bzc | MeNHCH$_2$ | Bz | 3-I-Pro- | tBuNH- |
| 3157 | 2-Quix-CO- | 2-Car-Et | Bz | 3-I-Pro- | tBuNH- |
| 3158 | 2-Quix-CO- | CNCH$_2$ | Bz | 3-I-Pro- | tBuNH- |
| 3159 | 2-Quix-CO- | iPr | Bz | 3-I-Pro- | tBuNH- |
| 3160 | 2-Quix-CO- | tBu | Bz | 3-I-Pro- | tBuNH- |
| 3161 | 2-Quix-CO- | diMeCarCH$_2$ | Bz | 3-I-Pro- | tBuNH- |
| 3162 | 2-Quix-CO- | MorCOCH$_2$ | Bz | 3-I-Pro- | tBuNH- |
| 3163 | 2-Quix-CO- | PipCOCH$_2$ | Bz | 3-I-Pro- | tBuNH- |
| 3164 | 2-Quix-CO- | 2-NH$_2$-Et | Bz | 3-I-Pro- | tBuNH- |
| 3165 | 2-Quix-CO- | 3-NH$_2$-Pr | Bz | 3-I-Pro- | tBuNH- |
| 3166 | 2-Quix-CO- | MeCarCH$_2$ | Bz | 3-I-Pro- | tBuNH- |
| 3167 | 2-Quix-CO- | EtCarCH$_2$ | Bz | 3-I-Pro- | tBuNH- |
| 3168 | 2-Quix-CO- | H | Bz | 3-I-Pro- | tBuNH- |
| 3169 | 2-Quix-CO- | HOCH$_2$ | Bz | 3-I-Pro- | tBuNH- |
| 3170 | 2-Quix-CO- | 4-Thiz-CH$_2$ | Bz | 3-I-Pro- | tBuNH- |
| 3171 | 2-Quix-CO- | 4-Imid-CH$_2$ | Bz | 3-I-Pro- | tBuNH- |
| 3172 | 2-Quix-CO- | COOH-CH$_2$ | Bz | 3-I-Pro- | tBuNH- |
| 3173 | 2-Quix-CO- | 2-COOH-Et | Bz | 3-I-Pro- | tBuNH- |
| 3174 | 2-Quix-CO- | MeSCH$_2$ | Bz | 3-I-Pro- | tBuNH- |
| 3175 | 2-Quix-CO- | SamCH$_2$ | Bz | 3-I-Pro- | tBuNH- |
| 3176 | 2-Quix-CO- | Bz | Bz | 3-I-Pro- | tBuNH- |
| 3177 | 2-Quix-CO- | SimCH$_2$ | Bz | 3-I-Pro- | tBuNH- |
| 3178 | 2-Quix-CO- | HiaCH$_2$ | Bz | 3-I-Pro- | tBuNH- |
| 3179 | 2-Quix-CO- | 2-Sim-Et | Bz | 3-I-Pro- | tBuNH- |
| 3180 | 2-Quix-CO- | 2-Hia-Et | Bz | 3-I-Pro- | tBuNH- |
| 3181 | 2-Quix-CO- | NH$_2$CH | Bz | 3-I-Pro- | tBuNH- |
| 3182 | 2-Quix-CO- | MeNHCH$_2$ | Bz | 3-I-Pro- | tBuNH- |
| 3183 | 2-Quix-CO- | Me$_2$NCH$_2$ | Bz | 3-I-Pro- | tBuNH- |
| 3184 | 3-Quin-CO- | CarCH$_2$ | Bz | 3-I-Pro- | tBuNH- |
| 3185 | 4-Quin-CO- | CarCH$_2$ | Bz | 3-I-Pro- | tBuNH- |
| 3186 | 2-Pyr-CO- | CarCH$_2$ | Bz | 3-I-Pro- | tBuNH- |
| 3187 | 3-Pyr-CO- | CarCH$_2$ | Bz | 3-I-Pro- | tBuNH- |
| 3188 | 4-Pyr-CO- | CarCH$_2$ | Bz | 3-I-Pro- | tBuNH- |
| 3189 | 4-MeO-2-Quin-CO- | CarCH$_2$ | Bz | 3-I-Pro- | tBuNH- |
| 3190 | 2-Np-CO- | CarCH$_2$ | Bz | 3-I-Pro- | tBuNH- |
| 3191 | 1-Np-CO- | CarCH$_2$ | Bz | 3-I-Pro- | tBuNH- |
| 3192 | 2-Bfur-CO- | CarCH$_2$ | Bz | 3-I-Pro- | tBuNH- |
| 3193 | 3-Bfur-CO- | CarCH$_2$ | Bz | 3-I-Pro- | tBuNH- |

TABLE 1-continued

| Cpd. No. | R¹ | R³ | R⁴ | Z | R⁵ |
|---|---|---|---|---|---|
| 3194 | 5-Bu-2-Pyr-CO- | CarCH₂ | Bz | 3-I-Pro- | tBuNH- |
| 3195 | 4-HO-2-Quin-CO- | CarCH₂ | Bz | 3-I-Pro- | tBuNH- |
| 3196 | 3-HO-2-Quix-CO- | CarCH₂ | Bz | 3-I-Pro- | tBuNH- |
| 3197 | 1-Np-Sfo- | CarCH₂ | Bz | 3-I-Pro- | tBuNH- |
| 3198 | 2-Np-Sfo- | CarCH₂ | Bz | 3-I-Pro- | tBuNH- |
| 3199 | Boz | CarCH₂ | Bz | 3-I-Pro- | tBuNH- |
| 3200 | Bz-NHCO- | CarCH₂ | Bz | 3-I-Pro- | tBuNH- |
| 3201 | Bz-NHCS- | CarCH₂ | Bz | 3-I-Pro- | tBuNH- |
| 3202 | 3-Ind-CO- | CarCH₂ | Bz | 3-I-Pro- | tBuNH- |
| 3203 | 2-Pyrd-CO- | CarCH₂ | Bz | 3-I-Pro- | tBuNH- |
| 3204 | 2-Pip-CO- | CarCH₂ | Bz | 3-I-Pro- | tBuNH- |
| 3205 | 2-Thi-CO- | CarCH₂ | Bz | 3-I-Pro- | tBuNH- |
| 3206 | MecCO- | CarCH₂ | Bz | 3-I-Pro- | tBuNH- |
| 3207 | PhoAc- | CarCH₂ | Bz | 3-I-Pro- | tBuNH- |
| 3208 | 3-Bzisox-CO- | CarCH₂ | Bz | 3-I-Pro- | tBuNH- |
| 3209 | 2-Bzim-CO- | CarCH₂ | Bz | 3-I-Pro- | tBuNH- |
| 3210 | N-Me-3-Ind-CO- | CarCH₂ | Bz | 3-I-Pro- | tBuNH- |
| 3211 | 2-Bzthiaz-CO- | CarCH₂ | Bz | 3-I-Pro- | tBuNH- |
| 3212 | 2-Bzoxaz-CO- | CarCH₂ | Bz | 3-I-Pro- | tBuNH- |
| 3213 | 5-MeO-2-Ind-CO- | CarCH₂ | Bz | 3-I-Pro- | tBuNH- |
| 3214 | 5-HO-2-Ind-CO- | CarCH₂ | Bz | 3-I-Pro- | tBuNH- |
| 3215 | 5-AcO-2-Ind-CO- | CarCH₂ | Bz | 3-I-Pro- | tBuNH- |
| 3216 | 5-H₂NAcO-2-Ind-CO- | CarCH₂ | Bz | 3-I-Pro- | tBuNH- |
| 3217 | 5-Bzim-CO- | CarCH₂ | Bz | 3-I-Pro- | tBuNH- |
| 3218 | (2-NpO)Ac- | CarCH₂ | Bz | 3-I-Pro- | tBuNH- |
| 3219 | (1-NpO)Ac- | CarCH₂ | Bz | 3-I-Pro- | tBuNH- |
| 3220 | 1-NpOCO- | CarCH₂ | Bz | 3-I-Pro- | tBuNH- |
| 3221 | 2-NpOCO- | CarCH₂ | Bz | 3-I-Pro- | tBuNH- |
| 3222 | (3-PhPho)Ac- | CarCH₂ | Bz | 3-I-Pro- | tBuNH- |
| 3223 | 2-Quix-CO- | CarCH₂ | Bz | 3-I-Pro- | 3-HOPr-NH- |
| 3224 | 2-Quix-CO- | CarCH₂ | Bz | 3-I-Pro- | BuNH- |
| 3225 | 2-Quix-CO- | CarCH₂ | Bz | 3-I-Pro- | tBuO- |
| 3226 | 2-Quix-CO- | CarCH₂ | Bz | 3-I-Pro- | 1,1-diMe-2-HOEt-NH- |
| 3227 | Bzc | CarCH₂ | Bz | 3-I-Pro- | 3-HOPr-NH- |
| 3228 | Bzc | CarCH₂ | Bz | 3-I-Pro- | BuNH- |
| 3229 | Bzc | CarCH₂ | Bz | 3-I-Pro- | tBuO- |
| 3230 | Bzc | CarCH₂ | Bz | 3-I-Pro- | 1,1-diMe-2-HOEt-NH- |
| 3231 | 3-NH₂-PhoAc- | CarCH₂ | Bz | 3-I-Pro- | tBuNH- |
| 3232 | 2-NH₂-PhoAc- | CarCH₂ | Bz | 3-I-Pro- | tBuNH- |
| 3233 | 2,3-diNH₂-Pho-Ac- | CarCH₂ | Bz | 3-I-Pro- | tBuNH- |
| 3234 | 2,4-diNH₂-Pho-Ac- | CarCH₂ | Bz | 3-I-Pro- | tBuNH- |
| 3235 | 4-NH₂-Ph-CO- | CarCH₂ | Bz | 3-I-Pro- | tBuNH- |
| 3236 | 4-NH₂-Bzc | CarCH₂ | Bz | 3-I-Pro- | tBuNH- |
| 3237 | 4-Me₂N-PhoAc- | CarCH₂ | Bz | 3-I-Pro- | tBuNH- |
| 3238 | 4-[Me(Bz)N]-PhoAc- | CarCH₂ | Bz | 3-I-Pro- | tBuNH- |
| 3239 | 4-Mor-PhoAc- | CarCH₂ | Bz | 3-I-Pro- | tBuNH- |
| 3240 | 4-[N-Bz-Pipr]-PhoAc- | CarCH₂ | Bz | 3-I-Pro- | tBuNH- |
| 3241 | 4-MeNH-PhoAc- | CarCH₂ | Bz | 3-I-Pro- | tBuNH- |
| 3242 | 4-[(4'-Me-Bzc)-NH]-PhoAc- | CarCH₂ | Bz | 3-I-Pro- | tBuNH- |
| 3243 | 4-[tBoc-NH]-PhoAc- | CarCH₂ | Bz | 3-I-Pro- | tBuNH- |
| 3244 | 4-[tBoc-MeN]-PhoAc- | CarCH₂ | Bz | 3-I-Pro- | tBuNH- |
| 3245 | 4-[Gly-NH]-PhoAc- | CarCH₂ | Bz | 3-I-Pro- | tBuNH- |
| 3246 | 4-[Gly-NMe]-PhoAc- | CarCH₂ | Bz | 3-I-Pro- | tBuNH- |
| 3247 | 4-[(N-Me-Gly)-NMe]-PhoAc- | CarCH₂ | Bz | 3-I-Pro- | tBuNH- |
| 3248 | 4-[(N-tBoc-Gly)NMe]-PhoAc- | CarCH₂ | Bz | 3-I-Pro- | tBuNH- |
| 3249 | 4-[(N-tBoc-NMe-Gly)NMe]-PhoAc- | CarCH₂ | Bz | 3-I-Pro- | tBuNH- |
| 3250 | 4-[(N-Me-Gly)-NMe]-PhoAc- | CarCH₂ | Bz | 3-I-Pro- | tBuNH- |
| 3251 | 4-[(BrAc)NMe]-PhoAc- | CarCH₂ | Bz | 3-I-Pro- | tBuNH- |

TABLE 1-continued

| Cpd. No. | R¹ | R³ | R⁴ | Z | R⁵ |
|---|---|---|---|---|---|
| 3252 | 4-[(4'-MeO-Bzc)NH]-PhoAc- | CarCH₂ | Bz | 3-I-Pro- | tBuNH- |
| 3253 | N-Me-4-PipO-Ac- | CarCH₂ | Bz | 3-I-Pro- | tBuNH- |
| 3254 | 4-NH₂-cHxO-Ac- | CarCH₂ | Bz | 3-I-Pro- | tBuNH- |
| 3255 | 4-NH₂-PhoAc- | CarCH₂ | Bz | 3-I-Pro- | 1,1-diMe-2-HOEt-NH- |
| 3256 | 3-NH₂-PhoAc- | CarCH₂ | Bz | 3-I-Pro- | 1,1-diMe-2-HOEt-NH- |
| 3257 | 2-NH₂-PhoAc- | CarCH₂ | Bz | 3-I-Pro- | 1,1-diMe-2-HOEt-NH- |
| 3258 | 2,3-diNH₂-Pho-Ac- | CarCH₂ | Bz | 3-I-Pro- | 1,1-diMe-2-HOEt-NH- |
| 3259 | 2,4-diNH₂-Ac-Pho- | CarCH₂ | Bz | 3-I-Pro- | 1,1-diMe-2-HOEt-NH- |
| 3260 | 4-NH₂-Ph-CO- | CarCH₂ | Bz | 3-I-Pro- | 1,1-diMe-2-HOEt-NH- |
| 3261 | 4-NH₂-Bzc | CarCH₂ | Bz | 3-I-Pro- | 1,1-diMe-2-HOEt-NH- |
| 3262 | 4-Me₂N-PhoAc- | CarCH₂ | Bz | 3-I-Pro- | 1,1-diMe-2-HOEt-NH- |
| 3263 | 4-[Me(Bz)N]-PhoAc- | CarCH₂ | Bz | 3-I-Pro- | 1,1-diMe-2-HOEt-NH- |
| 3264 | 4-Mor-PhoAc- | CarCH₂ | Bz | 3-I-Pro- | 1,1-diMe-2-HOEt-NH- |
| 3265 | 4-[N-Bz-Pipr]-PhoAc- | CarCH₂ | Bz | 3-Z-Pro- | 1,1-diMe-2-HOEt-NH- |
| 3266 | 4-MeNH-PhoAc- | CarCH₂ | Bz | 3-I-Pro- | 1,1-diMe-2-HOEt-NH- |
| 3267 | 4-[(4'-Me-Bzc)-NH]-PhoAc- | CarCH₂ | Bz | 3-I-Pro- | 1,1-diMe-2-HOEt-NH- |
| 3268 | 4-[Bzc-NH]-Pho-Ac- | CarCH₂ | Bz | 3-I-Pro- | 1,1-diMe-2-HOEt-NH- |
| 3269 | 4-[tBoc-NH]-Pho-Ac- | CarCH₂ | Bz | 3-I-Pro- | 1,1-diMe-2-HOEt-NH- |
| 3270 | 4-[tBoc-MeN]-Pho-Ac- | CarCH₂ | Bz | 3-I-Pro- | 1,1-diMe-2-HOEt-NH- |
| 3271 | 4-[Gly-NH]-Pho-Ac- | CarCH₂ | Bz | 3-I-Pro- | 1,1-diMe-2-HOEt-NH- |
| 3272 | 4-[Gly-NMe]-Pho-Ac- | CarCH₂ | Bz | 3-I-Pro- | 1,1-diMe-2-HOEt-NH- |
| 3273 | 4-[(N-Me-Gly)-NMe]-PhoAc- | CarCH₂ | Bz | 3-I-Pro- | 1,1-diMe-2-HOEt-NH- |
| 3274 | 4-[(N-tBoc-Gly)NMe]-PhoAc- | CarCH₂ | Bz | 3-I-Pro- | 1,1-diMe-2-HOEt-NH- |
| 3275 | 4-[(N-tBoc-NMe-Gly)NMe]-PhoAc- | CarCH₂ | Bz | 3-I-Pro- | 1,1-diMe-2-HOEt-NH- |
| 3276 | 4-[(N-Me-Gly)-NMe]-PhoAc- | CarCH₂ | Bz | 3-I-Pro- | 1,1-diMe-2-HOEt-NH- |
| 3277 | 4-[(BrAc)NMe]-PhoAc- | CarCH₂ | Bz | 3-I-Pro- | 1,1-diMe-2-HOEt-NH- |
| 3278 | 4-[(4'-MeO-Bzc)NH]-PhoAc- | CarCH₂ | Bz | 3-I-Pro- | 1,1-diMe-2-HOEt-NH- |
| 3279 | N-Me-4-PipO-Ac- | CarCH₂ | Bz | 3-I-Pro- | 1,1-diMe-2-HOEt-NH- |
| 3280 | 4-NH₂-cHxO-Ac- | CarCH₂ | Bz | 3-I-Pro- | 1,1-diMe-2-HOEt-NH- |
| 3281 | 4-[(MorAc)NMe]-PhoAc- | CarCH₂ | Bz | 3-I-Pro- | 1,1-diMe-2-HOEt-NH- |
| 3282 | 4-NH₂-PhoAc- | CarCH₂ | Bz | 3-I-Pro- | 1,1-diMe-2-HOPr-NH- |
| 3283 | 3-NH₂-PhoAc- | CarCH₂ | Bz | 3-I-Pro- | 1,1-diMe-2-HOPr-NH- |
| 3284 | 2-NH₂-PhoAc- | CarCH₂ | Bz | 3-I-Pro- | 1,1-diMe-2-HOPr-NH- |
| 3285 | 2,3-diNH₂-Pho-Ac- | CarCH₂ | Bz | 3-I-Pro- | 1,1-diMe-2-HOPr-NH- |
| 3286 | 2,4-diNH₂-Pho-Ac- | CarCH₂ | Bz | 3-I-Pro- | 1,1-diMe-2-HOPr-NH- |
| 3287 | 4-NH₂-Ph-CO- | CarCH₂ | Bz | 3-I-Pro- | 1,1-diMe-2-HOPr-NH- |
| 3288 | 4-NH₂-Bzc | CarCH₂ | Bz | 3-I-Pro- | 1,1-diMe-2-HOPr-NH- |
| 3289 | 4-Me₂N-PhoAc- | CarCH₂ | Bz | 3-I-Pro- | 1,1-diMe-2-HOPr-NH- |
| 3290 | 4-[Me(Bz)N]-Pho-Ac- | CarCH₂ | Bz | 3-I-Pro- | 1,1-diMe-2-HOPr-NH- |

TABLE 1-continued

| Cpd. No. | R¹ | R³ | R⁴ | Z | R⁵ |
|---|---|---|---|---|---|
| 3291 | 4-Mor-PhoAc- | CarCH₂ | Bz | 3-I-Pro- | 1,1-diMe-2-HOPr-NH- |
| 3292 | 4-[N-Bz-Pipr]-PhoAc- | CarCH₂ | Bz | 3-I-Pro- | 1,1-diMe-2-HOPr-NH- |
| 3293 | 4-MeNH-PhoAc- | CarCH₂ | Bz | 3-I-Pro- | 1,1-diMe-2-HOPr-NH- |
| 3294 | 4-[(4'-Me-Bzc)-NH]-PhoAc- | CarCH₂ | Bz | 3-I-Pro- | 1,1-diMe-2-HOPr-NH- |
| 3295 | 4-(Bzc-NH]-PhoAc- | CarCH₂ | Bz | 3-I-Pro- | 1,1-diMe-2-HOPr-NH- |
| 3296 | 4-[tBoc-NH]-PhoAc- | CarCH₂ | Bz | 3-I-Pro- | 1,1-diMe-2-HOPr-NH- |
| 3297 | 4-[tBoc-MeN]-PhoAc- | CarCH₂ | Bz | 3-I-Pro- | 1,1-diMe-2-HOPr-NH- |
| 3298 | 4-Gly-NH-PhoAc- | CarCH₂ | Bz | 3-I-Pro- | 1,1-diMe-2-HOPr-NH- |
| 3299 | 4-[Gly-NMe]-PhoAc- | CarCH₂ | Bz | 3-I-Pro- | 1,1-diMe-2-HOPr-NH- |
| 3300 | 4-[(N-Me-Gly)-NMe]-PhoAc- | CarCH₂ | Bz | 3-I-Pro- | 1,1-diMe-2-HOPr-NH- |
| 3301 | 4-[(N-tBoc-Gly)NMe]-PhoAc- | CarCH₂ | Bz | 3-I-Pro- | 1,1-diMe-2-HOPr-NH- |
| 3302 | 4-[(N-tBoc-NMe-Gly)NMe]-PhoAc- | CarCH₂ | Bz | 3-I-Pro- | 1,1-diMe-2-HOPr-NH- |
| 3303 | 4-[(N-Me-Gly)-NMe]-PhoAc- | CarCH₂ | Bz | 3-I-Pro- | 1,1-diMe-2-HOPr-NH- |
| 3304 | 4-[(BrAc)NMe]-PhoAc- | CarCH₂ | Bz | 3-I-Pro- | 1,1-diMe-2-HOPr-NH- |
| 3305 | 4-[(4'-MeO-Bzc)NH]-PhoAc- | CarCH₂ | Bz | 3-I-Pro- | 1,1-diMe-2-HOPr-NH- |
| 3306 | N-Me-4-PipO-Ac- | CarCH₂ | Bz | 3-I-Pro- | 1,1-diMe-2-HOPr-NH- |
| 3307 | 4-NH₂-cHxO-Ac- | CarCH₂ | Bz | 3-I-Pro- | 1,1-diMe-2-HOPr-NH- |
| 3308 | 4-[(MorAc)NMe]-PhoAc- | CarCH₂ | Bz | 3-I-Pro- | 1,1-diMe-2-HOPr-NH- |
| 3309 | 2-Quin-CO- | CarCH₂ | Bz | 3-I-Pro- | 1,1-diMe-2-HOEt-NH- |
| 3310 | 3-Quin-CO- | CarCH₂ | Bz | 3-I-Pro- | 1,1-diMe-2-HOEt-NH- |
| 3311 | 4-Quin-CO- | CarCH₂ | Bz | 3-I-Pro- | 1,1-diMe-2-HOEt-NH- |
| 3312 | 2-Pyr-CO- | CarCH₂ | Bz | 3-I-Pro- | 1,1-diMe-2-HOEt-NH- |
| 3313 | 3-Pyr-CO- | CarCH₂ | Bz | 3-I-Pro- | 1,1-diMe-2-HOEt-NH- |
| 3314 | 4-Pyr-CO- | CarCH₂ | Bz | 3-I-Pro- | 1,1-diMe-2-HOEt-NH- |
| 3315 | 4-MeO-2-Quin-CO- | CarCH₂ | Bz | 3-I-Pro- | 1,1-diMe-2-HOEt-NH- |
| 3316 | 2-Np-CO- | CarCH₂ | Bz | 3-I-Pro- | 1,1-diMe-2-HOEt-NH- |
| 3317 | 1-Np-CO- | CarCH₂ | Bz | 3-I-Pro- | 1,1-diMe-2-HOEt-NH- |
| 3318 | 2-Bfur-CO- | CarCH₂ | Bz | 3-I-Pro- | 1,1-diMe-2-HOEt-NH- |
| 3319 | 3-Bfur-CO- | CarCH₂ | Bz | 3-I-Pro- | 1,1-diMe-2-HOEt-NH- |
| 3320 | 5-Bu-2-Pyr-CO- | CarCH₂ | Bz | 3-I-Pro- | 1,1-diMe-2-HOEt-NH- |
| 3321 | 4-HO-2-Quin-CO- | CarCH₂ | Bz | 3-I-Pro- | 1,1-diMe-2-HOEt-NH- |
| 3322 | 3-HO-2-Quix-CO- | CarCH₂ | Bz | 3-I-Pro- | 1,1-diMe-2-HOEt-NH- |
| 3323 | 1-Np-Sfo- | CarCH₂ | Bz | 3-I-Pro- | 1,1-diMe-2-HOEt-NH- |
| 3324 | 2-Np-Sfo- | CarCH₂ | Bz | 3-I-Pro- | 1,1-diMe-2-HOEt-NH- |
| 3325 | Boz | CarCH₂ | Bz | 3-I-Pro- | 1,1-diMe-2-HOEt-NH- |
| 3326 | Bz-NHCO- | CarCH₂ | Bz | 3-I-Pro- | 1,1-diMe-2-HOEt-NH- |
| 3327 | Bz-NHCS- | CarCH₂ | Bz | 3-I-Pro- | 1,1-diMe-2-HOEt-NH- |
| 3328 | 2-Ind-CO- | CarCH₂ | Bz | 3-I-Pro- | 1,1-diMe-2-HOEt-NH- |

TABLE 1-continued

| Cpd. No. | R¹ | R³ | R⁴ | Z | R⁵ |
|---|---|---|---|---|---|
| 3329 | 3-Ind-CO- | CarCH₂ | Bz | 3-I-Pro- | 1,1-diMe-2-HOEt-NH- |
| 3330 | tBoc | CarCH₂ | Bz | 3-I-Pro- | 1,1-diMe-2-HOEt-NH- |
| 3331 | 2-Pyrd-CO- | CarCH₂ | Bz | 3-I-Pro- | 1,1-diMe-2-HOEt-NH- |
| 3332 | 2-Pip-CO- | CarCH₂ | Bz | 3-I-Pro- | 1,1-diMe-2-HOEt-NH- |
| 3333 | 2-Thi-CO- | CarCH₂ | Bz | 3-I-Pro- | 1,1-diMe-2-HOEt-NH- |
| 3334 | MecCO- | CarCH₂ | Bz | 3-I-Pro- | 1,1-diMe-2-HOEt-NH- |
| 3335 | PhoAc- | CarCH₂ | Bz | 3-I-Pro- | 1,1-diMe-2-HOEt-NH- |
| 3336 | MPhoAc- | CarCH₂ | Bz | 3-I-Pro- | 1,1-diMe-2-HOEt-NH- |
| 3337 | 3-Bzisox-CO- | CarCH₂ | Bz | 3-I-Pro- | 1,1-diMe-2-HOEt-NH- |
| 3338 | 2-Bzim-CO- | CarCH₂ | Bz | 3-I-Pro- | 1,1-diMe-2-HOEt-NH- |
| 3339 | N-Me-3-Ind-CO- | CarCH₂ | Bz | 3-I-Pro- | 1,1-diMe-2-HOEt-NH- |
| 3340 | 2-Bzthiaz-CO- | CarCH₂ | Bz | 3-I-Pro- | 1,1-diMe-2-HOEt-NH- |
| 3341 | 2-Bzoxaz-CO- | CarCH₂ | Bz | 3-I-Pro- | 1,1-diMe-2-HOEt-NH- |
| 3342 | 5-MeO-2-Ind-CO- | CarCH₂ | Bz | 3-I-Pro- | 1,1-diMe-2-HOEt-NH- |
| 3343 | 5-HO-2-Ind-CO- | CarCH₂ | Bz | 3-I-Pro- | 1,1-diMe-2-HOEt-NH- |
| 3344 | 5-AcO-2-Ind-CO- | CarCH₂ | Bz | 3-I-Pro- | 1,1-dime-2-HOEt-NH- |
| 3345 | 5-H₂NAcO-2-Ind-CO- | CarCH₂ | Bz | 3-I-Pro- | 1,1-diMe-2-HOEt-NH- |
| 3346 | 5-Bzim-CO- | CarCH₂ | Bz | 3-I-Pro- | 1,1-diMe-2-HOEt-NH- |
| 3347 | (1-NpO)Ac- | CarCH₂ | Bz | 3-I-Pro- | 1,1-diMe-2-HOEt-NH- |
| 3348 | 1-NpOCO- | CarCH₂ | Bz | 3-I-Pro- | 1,1-diMe-2-HOEt-NH- |
| 3349 | 2-NpOCO- | CarCH₂ | Bz | 3-I-Pro- | 1,1-diMe-2-HOEt-NH- |
| 3350 | (3-PhPho)Ac- | CarCH₂ | Bz | 3-I-Pro- | 1,1-diMe-2-HOEt-NH- |
| 3351 | (2-NpO)Ac- | CarCH₂ | Bz | 3-I-Pro- | 1,1-diMe-2-HOEt-NH- |
| 3352 | Bzc | CarCH₂ | Bz | 3-I-Pro- | 1,1-diMe-2-HOPr-NH- |
| 3353 | 2-Quix-CO- | CarCH₂ | Bz | 3-I-Pro- | 1,1-diMe-2-HOPr-NH- |
| 3354 | 2-Quin-CO- | CarCH₂ | Bz | 3-I-Pro- | 1,1-diMe-2-HOPr-NH- |
| 3355 | 3-Quin-CO- | CarCH₂ | Bz | 3-I-Pro- | 1,1-diMe-2-HOPr-NH- |
| 3356 | 4-Quin-CO- | CarCH₂ | Bz | 3-I-Pro- | 1,1-diMe-2-HOPr-NH- |
| 3357 | 2-Pyr-CO- | CarCH₂ | Bz | 3-I-Pro- | 1,1-diMe-2-HOPr-NH- |
| 3358 | 3-Pyr-CO- | CarCH₂ | Bz | 3-I-Pro- | 1,1-diMe-2-HOPr-NH- |
| 3359 | 4-Pyr-CO- | CarCH₂ | Bz | 3-I-Pro- | 1,1-diMe-2-HOPr-NH- |
| 3360 | 4-MeO-2-Quin-CO- | CarCH₂ | Bz | 3-I-Pro- | 1,1-diMe-2-HOPr-NH- |
| 3361 | 2-Np-CO- | CarCH₂ | Bz | 3-I-Pro- | 1,1-diMe-2-HOPr-NH- |
| 3362 | 1-Np-CO- | CarCH₂ | Bz | 3-I-Pro- | 1,1-diMe-2-HOPr-NH- |
| 3363 | 2-Bfur-CO- | CarCH₂ | Bz | 3-I-Pro- | 1,1-diMe-2-HOPr-NH- |
| 3364 | 3-Bfur-CO- | CarCH₂ | Bz | 3-I-Pro- | 1,1-diMe-2-HOPr-NH- |
| 3365 | 5-Bu-2-Pyr-CO- | CarCH₂ | Bz | 3-I-Pro- | 1,1-diMe-2-HOPr-NH- |
| 3366 | 4-HO-2-Quin-CO- | CarCH₂ | Bz | 3-I-Pro- | 1,1-diMe-2-HOPr-NH- |

TABLE 1-continued

| Cpd. No. | R¹ | R³ | R⁴ | Z | R⁵ |
|---|---|---|---|---|---|
| 3367 | 3-HO-2-Quix-CO- | CarCH₂ | Bz | 3-I-Pro- | 1,1-diMe-2-HOPr-NH- |
| 3368 | 1-Np-Sfo- | CarCH₂ | Bz | 3-I-Pro- | 1,1-diMe-2-HOPr-NH- |
| 3369 | 2-Np-Sfo- | CarCH₂ | Bz | 3-I-Pro- | 1,1-diMe-2-HOPr-NH- |
| 3370 | Boz | CarCH₂ | Bz | 3-I-Pro- | 1,1-diMe-2-HOPr-NH- |
| 3371 | Bz-NHCO- | CarCH₂ | Bz | 3-I-Pro- | 1,1-diMe-2-HOPr-NH- |
| 3372 | Bz-NHCS- | CarCH₂ | Bz | 3-I-Pro- | 1,1-diMe-2-HOPr-NH- |
| 3373 | 2-Ind-CO- | CarCH₂ | Bz | 3-I-Pro- | 1,1-diMe-2-HOPr-NH- |
| 3374 | 3-Ind-CO- | CarCH₂ | Bz | 3-I-Pro- | 1,1-diMe-2-HOPr-NH- |
| 3375 | tBoc | CarCH₂ | Bz | 3-I-Pro- | 1,1-diMe-2-HOPr-NH- |
| 3376 | 2-Pyrd-CO- | CarCH₂ | Bz | 3-I-Pro- | 1,1-diMe-2-HOPr-NH- |
| 3377 | 2-Pip-CO- | CarCH₂ | Bz | 3-I-Pro- | 1,1-diMe-2-HOPr-NH- |
| 3378 | 2-Thi-CO- | CarCH₂ | Bz | 3-I-Pro- | 1,1-diMe-2-HOPr-NH- |
| 3379 | MecCO- | CarCH₂ | Bz | 3-I-Pro- | 1,1-diMe-2-HOPr-NH- |
| 3380 | PhoAc- | CarCH₂ | Bz | 3-I-Pro- | 1,1-diMe-2-HOPr-NH- |
| 3381 | MPhoAc- | CarCH₂ | Bz | 3-I-Pro- | 1,1-diMe-2-HOPr-NH- |
| 3382 | 3-Bzisox-CO- | CarCH₂ | Bz | 3-I-Pro- | 1,1-diMe-2-HOPr-NH- |
| 3383 | 2-Bzim-CO- | CarCH₂ | Bz | 3-I-Pro- | 1,1-diMe-2-HOPr-NH- |
| 3384 | N-Me-3-Ind-CO- | CarCH₂ | Bz | 3-I-Pro- | 1,1-diMe-2-HOPr-NH- |
| 3385 | 2-Bzthiaz-CO- | CarCH₂ | Bz | 3-I-Pro- | 1,1-diMe-2-HOPr-NH- |
| 3386 | 2-Bzoxaz-CO- | CarCH₂ | Bz | 3-I-Pro- | 1,1-diMe-2-HOPr-NH- |
| 3387 | 5-MeO-2-Ind-CO- | CarCH₂ | Bz | 3-I-Pro- | 1,1-diMe-2-HOPr-NH- |
| 3388 | 5-HO-2-Ind-CO- | CarCH₂ | Bz | 3-I-Pro- | 1,1-diMe-2-HOPr-NH- |
| 3389 | 5-AcO-2-Ind-CO- | CarCH₂ | Bz | 3-I-Pro- | 1,1-diMe-2-HOPr-NH- |
| 3390 | 5-H₂NAcO-2-Ind-CO- | CarCH₂ | Bz | 3-I-Pro- | 1,1-diMe-2-HOPr-NH- |
| 3391 | 5-Bzim-CO- | CarCH₂ | Bz | 3-I-Pro- | 1,1-diMe-2-HOPr-NH- |
| 3392 | (2-NpO)Ac- | CarCH₂ | Bz | 3-I-Pro- | 1,1-diMe-2-HOPr-NH- |
| 3393 | (1-NpO)Ac- | CarCH₂ | Bz | 3-I-Pro- | 1,1-diMe-2-HOPr-NH- |
| 3394 | 1-NpOCO- | CarCH₂ | Bz | 3-I-Pro- | 1,1-diMe-2-HOPr-NH- |
| 3395 | 2-NpOCO- | CarCH₂ | Bz | 3-I-Pro- | 1,1-diMe-2-HOPr-NH- |
| 3396 | (3-PhPho)Ac- | CarCH₂ | Bz | 3-I-Pro- | 1,1-diMe-2-HOPr-NH- |
| 3397 | Bzc | CarCH₂ | 4-Br-Bz | 3-I-Pro- | tBuNH- |
| 3398 | 2-Quix-CO- | CarCH₂ | 4-Br-Bz | 3-I-Pro- | tBuNH- |
| 3399 | Bzc | CarCH₂ | 4-MeOBz | 3-I-Pro- | tBuNH- |
| 3400 | 2-Quix-CO- | CarCH₂ | 4-MeOBz | 3-I-Pro- | tBuNH- |
| 3401 | Bzc | CarCH₂ | 4-Me-Bz | 3-I-Pro- | tBuNH- |
| 3402 | 2-Quix-CO- | CarCH₂ | 4-Me-Bz | 3-I-Pro- | tBuNH- |
| 3403 | Bzc | CarCH₂ | cHxCH₂ | 3-I-Pro- | tBuNH- |
| 3404 | 2-Quix-CO- | CarCH₂ | cHxCH₂ | 3-I-Pro- | tBuNH- |
| 3405 | Bzc | MeSOCH₂ | Bz | 3-I-Pro- | tBuNH- |
| 3406 | Bzc | MeSO₂CH₂ | Bz | 3-I-Pro- | tBuNH- |
| 3407 | Bzc | MeOCH₂ | Bz | 3-I-Pro- | tBuNH- |
| 3408 | Bzc | MecCH₂CH₂ | Bz | 3-I-Pro- | tBuNH- |
| 3409 | Bzc | MecCH₂ | Bz | 3-I-Pro- | tBuNH- |
| 3410 | 2-Quix-CO- | MeSOCH₂ | Bz | 3-I-Pro- | tBuNH- |
| 3411 | 2-Quix-CO- | MeSO₂CH₂ | Bz | 3-I-Pro- | tBuNH- |
| 3412 | 2-Quix-CO- | MeOCH₂ | Bz | 3-I-Pro- | tBuNH- |

TABLE 1-continued

| Cpd. No. | R¹ | R³ | R⁴ | Z | R⁵ |
|---|---|---|---|---|---|
| 3413 | 2-Quix-CO- | MecCH₂CH₂ | Bz | 3-I-Pro- | tBuNH- |
| 3414 | 2-Quix-CO- | MecCH₂ | Bz | 3-I-Pro- | tBuNH- |
| 3415 | 2-Quin-CO- | MeSOCH₂ | Bz | 3-I-Pro- | tBuNH- |
| 3416 | 2-Quin-CO- | MeSO₂CH₂ | Bz | 3-I-Pro- | tBuNH- |
| 3417 | 2-Quin-CO- | MeOCH₂ | Bz | 3-I-Pro- | tBuNH- |
| 3418 | 2-Quin-CO- | MecCH₂CH₂ | Bz | 3-I-Pro- | tBuNH- |
| 3419 | 2-Quin-CO- | MecCH₂ | Bz | 3-I-Pro- | tBuNH- |
| 3420 | 3-Quin-CO- | MeSOCH₂ | Bz | 3-I-Pro- | tBuNH- |
| 3421 | 3-Quin-CO- | MeSO₂CH₂ | Bz | 3-I-Pro- | tBuNH- |
| 3422 | 3-Quin-CO- | MeOCH₂ | Bz | 3-I-Pro- | tBuNH- |
| 3423 | 3-Quin-CO- | MecCH₂CH₂ | Bz | 3-I-Pro- | tBuNH- |
| 3424 | 3-Quin-CO- | MecCH₂ | Bz | 3-I-Pro- | tBuNH- |
| 3425 | 2-Bfur-CO- | MeSOCH₂ | Bz | 3-I-Pro- | tBuNH- |
| 3426 | 2-Bfur-CO- | MeSO₂CH₂ | Bz | 3-I-Pro- | tBuNH- |
| 3427 | 2-Bfur-CO- | MeOCH₂ | Bz | 3-I-Pro- | tBuNH- |
| 3428 | 2-Bfur-CO- | MecCH₂CH₂ | Bz | 3-I-Pro- | tBuNH- |
| 3429 | 2-Bfur-CO- | MecCH | Bz | 3-I-Pro- | tBuNH- |
| 3430 | 3-Bfur-CO- | MeSOCH₂ | Bz | 3-I-Pro- | tBuNH- |
| 3431 | 3-Bfur-CO- | MeSO₂CH₂ | Bz | 3-I-Pro- | tBuNH- |
| 3432 | 3-Bfur-CO- | MeOCH₂ | Bz | 3-I-Pro- | tBuNH- |
| 3433 | 3-Bfur-CO- | MecCH₂CH₂ | Bz | 3-I-Pro- | tBuNH- |
| 3434 | 3-Bfur-CO- | MecCH₂ | Bz | 3-I-Pro- | tBuNH- |
| 3435 | 3-Ind-CO- | MeSOCH₂ | Bz | 3-I-Pro- | tBuNH- |
| 3436 | 3-Ind-CO- | MeSO₂CH₂ | Bz | 3-I-Pro- | tBuNH- |
| 3437 | 3-Ind-CO- | MeOCH₂ | Bz | 3-I-Pro- | tBuNH- |
| 3438 | 3-Ind-CO- | MecCH₂CH₂ | Bz | 3-I-Pro- | tBuNH- |
| 3439 | 3-Ind-CO- | MecCH₂ | Bz | 3-I-Pro- | tBuNH- |
| 3440 | MPhOAc- | MeSOCH₂ | Bz | 3-I-Pro- | tBuNH- |
| 3441 | MPhOAc- | MeSO₂CH₂ | Bz | 3-I-Pro- | tBuNH- |
| 3442 | MPhOAc- | MeOCH₂ | Bz | 3-I-Pro- | tBuNH- |
| 3443 | MPhOAc- | MecCH₂CH₂ | Bz | 3-I-Pro- | tBuNH- |
| 3444 | MPhOAc- | MecCH₂ | Bz | 3-I-Pro- | tBuNH- |
| 3445 | 5-NH₂-AcO-2-Ind-CO- | MeSOCH₂ | Bz | 3-I-Pro- | tBuNH- |
| 3446 | 5-NH₂-AcO-2-Ind-CO- | MeSO₂CH₂ | Bz | 3-I-Pro- | tBuNH- |
| 3447 | 5-NH₂-AcO-2-Ind-CO- | MeOCH₂ | Bz | 3-I-Pro- | tBuNH- |
| 3448 | 5-NH₂-AcO-2-Ind-CO- | MecCH₂CH₂ | Bz | 3-I-Pro- | tBuNH- |
| 3449 | 5-NH₂-AcO-2-Ind-CO- | MecCH₂ | Bz | 3-I-Pro- | tBuNH- |
| 3450 | 4-NH₂-PhoAc- | MeSOCH₂ | Bz | 3-I-Pro- | tBuNH- |
| 3451 | 4-NH₂-PhoAc- | MeSO₂CH₂ | Bz | 3-I-Pro- | tBuNH- |
| 3452 | 4-NH₂-PhoAc- | MeOCH₂ | Bz | 3-I-Pro- | tBuNH- |
| 3453 | 4-NH₂-PhoAc- | MecCH₂CH₂ | Bz | 3-I-Pro- | tBuNH- |
| 3454 | 4-NH₂-PhoAc- | MecCH₂ | Bz | 3-I-Pro- | tBuNH- |
| 3455 | 4-[Bzc-NH]-Pho-Ac- | MeSOCH₂ | Bz | 3-I-Pro- | tBuNH- |
| 3456 | 4-[Bzc-NH]-Pho-Ac- | MeSO₂CH₂ | Bz | 3-I-Pro- | tBuNH- |
| 3457 | 4-[Bzc-NH]-Pho-Ac- | MeOCH₂ | Bz | 3-I-Pro- | tBuNH- |
| 3458 | 4-[Bzc-NH]-Pho-Ac- | MecCH₂CH₂ | Bz | 3-I-Pro- | tBuNH- |
| 3459 | 4-[Bzc-NH]-Pho-Ac- | MecCH₂ | Bz | 3-I-Pro- | tBuNH- |
| 3460 | 4-[(MorAc)NMe]-PhoAc- | MeSOCH₂ | Bz | 3-I-Pro- | tBuNH- |
| 3461 | 4-[(MorAc)NMe]PhoAc- | MeSO₂CH₂ | Bz | 3-I-Pro- | tBuNH- |
| 3462 | 4-[(MorAc)NMe]PhoAc- | MeOCH₂ | Bz | 3-I-Pro- | tBuNH- |
| 3463 | 4-[(MorAc)NMe]PhoAc- | MecCH₂CH₂ | Bz | 3-I-Pro- | tBuNH- |
| 3464 | 4-[(MorAc)NMe]PhoAc- | MecCH₂ | Bz | 3-I-Pro- | tBuNH- |
| 3465 | 4-MeO-Bzc | CarCH₂ | Bz | 3-I-Pro- | tBuNH- |
| 3466 | Bzc | Me₂NCH₂ | Bz | 3-F-Pro- | tBuNH- |
| 3467 | Bzc | 2-Car-Et | Bz | 3-F-Pro- | tBuNH- |
| 3468 | Bzc | CNCH₂ | Bz | 3-F-Pro- | tBuNH- |
| 3469 | Bzc | iPr | Bz | 3-F-Pro- | tBuNH- |
| 3470 | Bzc | tBu | Bz | 3-F-Pro- | tBuNH- |
| 3471 | Bzc | diMeCarCH₂ | Bz | 3-F-Pro- | tBuNH- |
| 3472 | Bzc | MorCOCH₂ | Bz | 3-F-Pro- | tBuNH- |
| 3473 | Bzc | PipCOCH₂ | Bz | 3-F-Pro- | tBuNH- |

TABLE 1-continued

| Cpd. No. | R¹ | R³ | R⁴ | Z | R⁵ |
|---|---|---|---|---|---|
| 3474 | Bzc | 2-NH₂-Et | Bz | 3-F-Pro- | tBuNH- |
| 3475 | Bzc | 3-NH₂-Pr | Bz | 3-F-Pro- | tBuNH- |
| 3476 | Bzc | MeCarCH₂ | Bz | 3-F-Pro- | tBuNH- |
| 3477 | Bzc | EtCarCH₂ | Bz | 3-F-Pro- | tBuNH- |
| 3478 | Bzc | H | Bz | 3-F-Pro- | tBuNH- |
| 3479 | Bzc | HOCH₂ | Bz | 3-F-Pro- | tBuNH- |
| 3480 | Bzc | 4-Thiz-CH₂ | Bz | 3-F-Pro- | tBuNH- |
| 3481 | Bzc | 4-Imid-CH₂ | Bz | 3-F-Pro- | tBuNH- |
| 3482 | Bzc | COOH-CH₂ | Bz | 3-F-Pro- | tBuNH- |
| 3483 | Bzc | 2-COOH-Et | Bz | 3-F-Pro- | tBuNH- |
| 3484 | Bzc | MeSCH₂ | Bz | 3-F-Pro- | tBuNH- |
| 3485 | Bzc | SamCH₂ | Bz | 3-F-Pro- | tBuNH- |
| 3486 | Bzc | Bz | Bz | 3-F-Pro- | tBuNH- |
| 3487 | Bzc | SimCH₂ | Bz | 3-F-Pro- | tBuNH- |
| 3488 | Bzc | HiaCH₂ | Bz | 3-F-Pro- | tBuNH- |
| 3489 | Bzc | 2-Sim-Et | Bz | 3-F-Pro- | tBuNH- |
| 3490 | Bzc | 2-Hia-Et | Bz | 3-F-Pro- | tBuNH- |
| 3491 | Bzc | NH₂CH₂ | Bz | 3-F-Pro- | tBuNH- |
| 3492 | Bzc | MeNHCH₂ | Bz | 3-F-Pro- | tBuNH- |
| 3493 | 2-Quix-CO- | 2-Car-Et | Bz | 3-F-Pro- | tBuNH- |
| 3494 | 2-Quix-CO- | CNCH₂ | Bz | 3-F-Pro- | tBuNH- |
| 3495 | 2-Quix-CO- | iPr | Bz | 3-F-Pro- | tBuNH- |
| 3496 | 2-Quix-CO- | tBu | Bz | 3-F-Pro- | tBuNH- |
| 3497 | 2-Quix-CO- | diMeCarCH₂ | Bz | 3-F-Pro- | tBuNH- |
| 3498 | 2-Quix-CO- | MorCOCH₂ | Bz | 3-F-Pro- | tBuNH- |
| 3499 | 2-Quix-CO- | PipCOCH₂ | Bz | 3-F-Pro- | tBuNH- |
| 3500 | 2-Quix-CO- | 2-NH₂-Et | Bz | 3-F-Pro- | tBuNH- |
| 3501 | 2-Quix-CO- | 3-NH₂-Pr | Bz | 3-F-Pro- | tBuNH- |
| 3502 | 2-Quix-CO- | MeCarCH₂ | Bz | 3-F-Pro- | tBuNH- |
| 3503 | 2-Quix-CO- | EtCarCH₂ | Bz | 3-F-Pro- | tBuNH- |
| 3504 | 2-Quix-CO- | H | Bz | 3-F-Pro- | tBuNH- |
| 3505 | 2-Quix-CO- | HOCH₂ | Bz | 3-F-Pro- | tBuNH- |
| 3506 | 2-Quix-CO- | 4-Thiz-CH₂ | Bz | 3-F-Pro- | tBuNH- |
| 3507 | 2-Quix-CO- | 4-Imid-CH₂ | Bz | 3-F-Pro- | tBuNH- |
| 3508 | 2-Quix-CO- | COOH-CH₂ | Bz | 3-F-Pro- | tBuNH- |
| 3509 | 2-Quix-CO- | 2-COOH-Et | Bz | 3-F-Pro- | tBuNH- |
| 3510 | 2-Quix-CO- | MeSCH₂ | Bz | 3-F-Pro- | tBuNH- |
| 3511 | 2-Quix-CO- | SamCH₂ | Bz | 3-F-Pro- | tBuNH- |
| 3512 | 2-Quix-CO- | Bz | Bz | 3-F-Pro- | tBuNH- |
| 3513 | 2-Quix-CO- | SimCH₂ | Bz | 3-F-Pro- | tBuNH- |
| 3514 | 2-Quix-CO- | HiaCH₂ | Bz | 3-F-Pro- | tBuNH- |
| 3515 | 2-Quix-CO- | 2-Sim-Et | Bz | 3-F-Pro- | tBuNH- |
| 3516 | 2-Quix-CO- | 2-Hia-Et | Bz | 3-F-Pro- | tBuNH- |
| 3517 | 2-Quix-CO- | NH₂CH₂ | Bz | 3-F-Pro- | tBuNH- |
| 3518 | 2-Quix-CO- | MeNHCH₂ | Bz | 3-F-Pro- | tBuNH- |
| 3519 | 2-Quix-CO- | Me₂NCH₂ | Bz | 3-F-Pro- | tBuNH- |
| 3520 | 3-Quin-CO- | CarCH₂ | Bz | 3-F-Pro- | tBuNH- |
| 3521 | 4-Quin-CO- | CarCH₂ | Bz | 3-F-Pro- | tBuNH- |
| 3522 | 2-Pyr-CO- | CarCH₂ | Bz | 3-F-Pro- | tBuNH- |
| 3523 | 3-Pyr-CO- | CarCH₂ | Bz | 3-F-Pro- | tBuNH- |
| 3524 | 4-Pyr-CO- | CarCH₂ | Bz | 3-F-Pro- | tBuNH- |
| 3525 | 4-MeO-2-Quin-CO- | CarCH₂ | Bz | 3-F-Pro- | tBuNH- |
| 3526 | 2-Np-CO- | CarCH₂ | Bz | 3-F-Pro- | tBuNH- |
| 3527 | 1-Np-CO- | CarCH₂ | Bz | 3-F-Pro- | tBuNH- |
| 3528 | 2-Bfur-CO- | CarCH₂ | Bz | 3-F-Pro- | tBuNH- |
| 3529 | 3-Bfur-CO- | CarCH₂ | Bz | 3-F-Pro- | tBuNH- |
| 3530 | 5-Bu-2-Pyr-CO- | CarCH₂ | Bz | 3-F-Pro- | tBuNH- |
| 3531 | 4-HO-2-Quin-CO- | CarCH₂ | Bz | 3-F-Pro- | tBuNH- |
| 3532 | 3-HO-2-Quix-CO- | CarCH₂ | Bz | 3-F-Pro- | tBuNH- |
| 3533 | 1-Np-Sfo- | CarCH₂ | Bz | 3-F-Pro- | tBuNH- |
| 3534 | 2-Np-Sfo- | CarCH₂ | Bz | 3-F-Pro- | tBuNH- |
| 3535 | Boz | CarCH₂ | Bz | 3-F-Pro | tBuNH- |
| 3536 | Bz-NHCO- | CarCH₂ | Bz | 3-F-Pro- | tBuNH- |
| 3537 | Bz-NHCS- | CarCH₂ | Bz | 3-F-Pro- | tBuNH- |
| 3538 | 3-Ind-CO- | CarCH₂ | Bz | 3-F-Pro- | tBuNH- |
| 3539 | 2-Pyrd-CO- | CarCH₂ | Bz | 3-F-Pro- | tBuNH- |
| 3540 | 2-Pip-CO- | CarCH₂ | Bz | 3-F-Pro- | tBuNH- |
| 3541 | 2-Thi-CO- | CarCH₂ | Bz | 3-F-Pro- | tBuNH- |
| 3542 | MecCO- | CarCH₂ | Bz | 3-F-Pro- | tBuNH- |
| 3543 | PhoAc- | CarCH₂ | Bz | 3-F-Pro- | tBuNH- |
| 3544 | 3-Bzisox-CO- | CarCH₂ | Bz | 3-F-Pro- | tBuNH- |
| 3545 | 2-Bzim-CO- | CarCH₂ | Bz | 3-F-Pro- | tBuNH- |
| 3546 | N-Me-3-Ind-CO- | CarCH₂ | Bz | 3-F-Pro- | tBuNH- |
| 3547 | 2-Bzthiaz-CO- | CarCH₂ | Bz | 3-F-Pro- | tBuNH- |
| 3548 | 2-Bzoxaz-CO- | CarCH₂ | Bz | 3-F-Pro- | tBuNH- |
| 3549 | 5-MeO-2-Ind-CO- | CarCH₂ | Bz | 3-F-Pro- | tBuNH- |

TABLE 1-continued

| Cpd. No. | R$^1$ | R$^3$ | R$^4$ | Z | R$^5$ |
|---|---|---|---|---|---|
| 3550 | 5-HO-2-Ind-CO- | CarCH$_2$ | Bz | 3-F-Pro- | tBuNH- |
| 3551 | 5-AcO-2-Ind-CO- | CarCH$_2$ | Bz | 3-F-Pro- | tBuNH- |
| 3552 | 5-H$_2$NAcO-2-Ind-CO- | CarCH$_2$ | Bz | 3-F-Pro- | tBuNH- |
| 3553 | 5-Bzim-CO- | CarCH$_2$ | Bz | 3-F-Pro- | tBuNH- |
| 3554 | (2-NpO)Ac- | CarCH$_2$ | Bz | 3-F-Pro- | tBuNH- |
| 3555 | (1-NpO)Ac- | CarCH$_2$ | Bz | 3-F-Pro- | tBuNH- |
| 3556 | 1-NpOCO- | CarCH$_2$ | Bz | 3-F-Pro- | tBuNH- |
| 3557 | 2-NpOCO- | CarCH$_2$ | Bz | 3-F-Pro- | tBuNH- |
| 3558 | (3-PhPho)Ac- | CarCH$_2$ | Bz | 3-F-Pro- | tBuNH- |
| 3559 | 2-Quix-CO- | CarCH$_2$ | Bz | 3-F-Pro- | 3-HOPr-NH- |
| 3560 | 2-Quix-CO- | CarCH$_2$ | Bz | 3-F-Pro- | BuNH- |
| 3561 | 2-Quix-CO- | CarCH$_2$ | Bz | 3-F-Pro- | tBuO- |
| 3562 | 2-Quix-CO- | CarCH$_2$ | Bz | 3-F-Pro- | 1,1-diMe-2-HOEt-NH- |
| 3563 | Bzc | CarCH$_2$ | Bz | 3-F-Pro- | 3-HOPr-NH- |
| 3564 | Bzc | CarCH$_2$ | Bz | 3-F-Pro- | BuNH- |
| 3565 | Bzc | CarCH$_2$ | Bz | 3-F-Pro- | tBuO- |
| 3566 | Bzc | CarCH$_2$ | Bz | 3-F-Pro- | 1,1-diMe-2-HOEt-NH- |
| 3567 | 3-NH$_2$-PhoAc- | CarCH$_2$ | Bz | 3-F-Pro- | tBuNH- |
| 3568 | 2-NH$_2$-PhoAc- | CarCH$_2$ | Bz | 3-F-Pro- | tBuNH- |
| 3569 | 2,3-diNH$_2$-Pho-Ac- | CarCH$_2$ | Bz | 3-F-Pro- | tBuNH- |
| 3570 | 2,4-diNH$_2$-Pho-Ac- | CarCH$_2$ | Bz | 3-F-Pro- | tBuNH- |
| 3571 | 4-NH$_2$-Ph-CO- | CarCH$_2$ | Bz | 3-F-Pro- | tBuNH- |
| 3572 | 4-NH$_2$-Bzc | CarCH$_2$ | Bz | 3-F-Pro- | tBuNH- |
| 3573 | 4-Me$_2$N-PhoAc- | CarCH$_2$ | Bz | 3-F-Pro- | tBuNH- |
| 3574 | 4-[Me(Bz)N]-PhoAc- | CarCH$_2$ | Bz | 3-F-Pro- | tBuNH- |
| 3575 | 4-Mor-PhoAc- | CarCH$_2$ | Bz | 3-F-Pro- | tBuNH- |
| 3576 | 4-[N-Bz-Pipr]-PhoAc- | CarCH$_2$ | Bz | 3-F-Pro- | tBuNH- |
| 3577 | 4-MeNH-PhoAc- | CarCH$_2$ | Bz | 3-F-Pro- | tBuNH- |
| 3578 | 4-[(4'-Me-Bzc)-NH]-PhoAc- | CarCH$_2$ | Bz | 3-F-Pro- | tBuNH- |
| 3579 | 4-[tBoc-NH]-Pho-Ac- | CarCH$_2$ | Bz | 3-F-Pro- | tBuNH- |
| 3580 | 4-(tBoc-MeN]-Pho-Ac- | CarCH$_2$ | Bz | 3-F-Pro- | tBuNH- |
| 3581 | 4-Gly-NH-Pho-Ac- | CarCH$_2$ | Bz | 3-F-Pro- | tBuNH- |
| 3582 | 4-[Gly-NMe]-Pho-Ac- | CarCH$_2$ | Bz | 3-F-Pro- | tBuNH- |
| 3583 | 4-[(N-Me-Gly)NMe]-PhoAc- | CarCH$_2$ | Bz | 3-F-Pro- | tBuNH- |
| 3584 | 4-[(N-tBoc-Gly)NMe]-PhoAc- | CarCH$_2$ | Bz | 3-F-Pro- | tBuNH- |
| 3585 | 4-[(N-tBoc-NMe-Gly)NMe]-PhoAc- | CarCH$_2$ | Bz | 3-F-Pro- | tBuNH- |
| 3586 | Boc | CarCH$_2$ | Bz | 3-F-Pro- | tBuNH- |
| 3587 | 4-[(BrAc)NMe]-PhoAc- | CarCH$_2$ | Bz | 3-F-Pro- | tBuNH- |
| 3588 | 4-[(4'-MeO-Bzc)NH]-PhoAc- | CarCH$_2$ | Bz | 3-F-Pro- | tBuNH- |
| 3589 | N-Me-4-PipO-Ac- | CarCH$_2$ | Bz | 3-F-Pro- | tBuNH- |
| 3590 | 4-NH$_2$-cHxO-Ac- | CarCH$_2$ | Bz | 3-F-Pro- | tBuNH- |
| 3591 | 4-NH$_2$-PhoAc- | CarCH$_2$ | Bz | 3-F-Pro- | 1,1-diMe-2-HOEt-NH- |
| 3592 | 3-NH$_2$-PhoAc- | CarCH$_2$ | Bz | 3-F-Pro- | 1,1-diMe-2-HOEt-NH- |
| 3593 | 2-NH$_2$-PhoAc- | CarCH$_2$ | Bz | 3-F-Pro- | 1,1-diMe-2-HOEt-NH- |
| 3594 | 2,3-diNH$_2$-Pho-Ac- | CarCH$_2$ | Bz | 3-F-Pro- | 1,1-diMe-2-HOEt-NH- |
| 3595 | 2,4-diNH$_2$-Pho-Ac- | CarCH$_2$ | Bz | 3-F-Pro- | 1,1-diMe-2-HOEt-NH- |
| 3596 | 4-NH$_2$-Ph-CO- | CarCH$_2$ | Bz | 3-F-Pro- | 1,1-diMe-2-HOEt-NH- |
| 3597 | 4-NH$_2$-Bzc | CarCH$_2$ | Bz | 3-F-Pro- | 1,1-diMe-2-HOEt-NH- |
| 3598 | 4-Me$_2$N-PhoAc- | CarCH$_2$ | Bz | 3-F-Pro- | 1,1-diMe-2-HOEt-NH- |
| 3599 | 4-Me-Bzc | CarCH$_2$ | Bz | 3-F-Pro- | 1,1-diMe-2-HOEt-NH- |
| 3600 | 4-Mor-PhoAc- | CarCH$_2$ | Bz | 3-F-Pro- | 1,1-diMe-2-HOEt-NH- |

TABLE 1-continued

| Cpd. No. | R¹ | R³ | R⁴ | Z | R⁵ |
|---|---|---|---|---|---|
| 3601 | 4-(N-Bz-Pipr]-PhoAc- | CarCH₂ | Bz | 3-F-Pro- | 1,1-diMe-2-HOEt-NH- |
| 3602 | 4-MeNH-PhoAc- | CarCH₂ | Bz | 3-F-Pro- | 1,1-diMe-2-HOEt-NH- |
| 3603 | 4-[(4'-Me-Bzc)-NH]-PhoAc- | CarCH₂ | Bz | 3-F-Pro- | 1,1-diMe-2-HOEt-NH- |
| 3604 | 4-[Bzc-NH]-Pho-Ac- | CarCH₂ | Bz | 3-F-Pro- | 1,1-diMe-2-HOEt-NH- |
| 3605 | 4-[tBoc-NH]-Pho-Ac- | CarCH₂ | Bz | 3-F-Pro- | 1,1-diMe-2-HOEt-NH- |
| 3606 | 4-[tBoc-MeN]-PhoAc- | CarCH₂ | Bz | 3-F-Pro- | 1,1-diMe-2-HOEt-NH- |
| 3607 | 4-Gly-NH-Pho-Ac- | CarCH₂ | Bz | 3-F-Pro- | 1,1-diMe-2-HOEt-NH- |
| 3608 | 4-[Gly-NMe]-Pho-Ac- | CarCH₂ | Bz | 3-F-Pro- | 1,1-diMe-2-HOEt-NH- |
| 3609 | 4-[(N-Me-Gly)NMe]-PhoAc- | CarCH₂ | Bz | 3-F-Pro- | 1,1-diMe-2-HOEt-NH- |
| 3610 | 4-[(N-tBoc-Gly)NMe]-PhoAc- | CarCH₂ | Bz | 3-F-Pro- | 1,1-diMe-2-HOEt-NH- |
| 3611 | 4-[(N-tBoc-NMe-Gly)NMe]-PhoAc- | CarCH₂ | Bz | 3-F-Pro- | 1,1-diMe-2-HOEt-NH- |
| 3612 | 4-[(N-Me-Gly)NMe]-PhoAc- | CarCH₂ | Bz | 3-F-Pro- | 1,1-diMe-2-HOEt-NH- |
| 3613 | 4-[(BrAc)NMe]-PhoAc- | CarCH₂ | Bz | 3-F-Pro- | 1,1-diMe-2-HOEt-NH- |
| 3614 | 4-[(4'-MeO-Bzc)NH]-PhoAc- | CarCH₂ | Bz | 3-F-Pro- | 1,1-diMe-2-HOEt-NH- |
| 3615 | N-Me-4-PipO-Ac- | CarCH₂ | Bz | 3-F-Pro- | 1,1-diMe-2-HOEt-NH- |
| 3616 | 4-NH₂-cHxO-Ac- | CarCH₂ | Bz | 3-F-Pro- | 1,1-diMe-2-HOEt-NH- |
| 3617 | 4-[(MorAc)NMe]-PhoAc- | CarCH₂ | Bz | 3-F-Pro- | 1,1-diMe-2-HOEt-NH- |
| 3618 | 4-NH₂-PhoAc- | CarCH₂ | Bz | 3-F-Pro- | 1,1-diMe-2-HOPr-NH- |
| 3619 | 3-NH₂-PhoAc- | CarCH₂ | Bz | 3-F-Pro- | 1,1-diMe-2-HOPr-NH- |
| 3620 | 2-NH₂-PhoAc- | CarCH₂ | Bz | 3-F-Pro- | 1,1-diMe-2-HOPr-NH- |
| 3621 | 2,3-diNH₂-Pho-Ac- | CarCH₂ | Bz | 3-F-Pro- | 1,1-diMe-2-HOPr-NH- |
| 3622 | 2,4-diNH₂-Pho-Ac- | CarCH₂ | Bz | 3-F-Pro- | 1,1-diMe-2-HOPr-NH- |
| 3623 | 4-NH₂-Ph-CO- | CarCH₂ | Bz | 3-F-Pro- | 1,1-diMe-2-HOPr-NH- |
| 3624 | 4-NH₂-Bzc | CarCH₂ | Bz | 3-F-Pro- | 1,1-diMe-2-HOPr-NH- |
| 3625 | 4-Me₂N-PhoAc- | CarCH₂ | Bz | 3-F-Pro- | 1,1-diMe-2-HOPr-NH- |
| 3626 | 4-[Me(Bz)N]-PhoAc- | CarCH₂ | Bz | 3-F-Pro- | 1,1-diMe-2-HOPr-NH- |
| 3627 | 4-Mor-PhoAc- | CarCH₂ | Bz | 3-F-Pro- | 1,1-diMe-2-HOPr-NH- |
| 3628 | 4-[N-Bz-Pipr]-PhoAc- | CarCH₂ | Bz | 3-F-Pro- | 1,1-diMe-2-HOPr-NH- |
| 3629 | 4-MeNH-PhoAc- | CarCH₂ | Bz | 3-F-Pro- | 1,1-diMe-2-HOPr-NH- |
| 3630 | 4-[(4'-Me-Bzc)-NH]-PhoAc- | CarCH₂ | Bz | 3-F-Pro- | 1,1-diMe-2-HOPr-NH- |
| 3631 | 4-[Bzc-NH]-Pho-Ac- | CarCH₂ | Bz | 3-F-Pro- | 1,1-diMe-2-HOPr-NH- |
| 3632 | 4-[tBoc-NH]-Pho-Ac- | CarCH₂ | Bz | 3-F-Pro- | 1,1-diMe-2-HOPr-NH- |
| 3633 | 4-[tBoc-MeN]-PhoAc) | CarCH₂ | Bz | 3-F-Pro- | 1,1-diMe-2-HOPr-NH- |
| 3634 | 4-Gly-NH-Pho-Ac- | CarCH₂ | Bz | 3-F-Pro- | 1,1-diMe-2-HOPr-NH- |
| 3635 | 4-[Gly-NMe]-Pho-Ac- | CarCH₂ | Bz | 3-F-Pro- | 1,1-diMe-2-HOPr-NH- |
| 3636 | 4-[(N-Me-Gly)NMe]-Ac- | CarCH₂ | Bz | 3-F-Pro- | 1,1-diMe-2-HOPr-NH- |
| 3637 | 4-[(N-tBoc-Gly)NMe]-PhoAc- | CarCH₂ | Bz | 3-F-Pro- | 1,1-diMe-2-HOPr-NH- |
| 3638 | 4-[(N-tBoc-NMe-Gly)NMe]-PhoAc- | CarCH₂ | Bz | 3-F-Pro- | 1,1-diMe-2-HOPr-NH- |

TABLE 1-continued

| Cpd. No. | R¹ | R³ | R⁴ | Z | R⁵ |
|---|---|---|---|---|---|
| 3639 | Boc | CarCH₂ | Bz | 3-F-Pro- | 1,1-diMe-2-HOPr-NH- |
| 3640 | 4-[(BrAc)NMe]-PhoAc- | CarCH₂ | Bz | 3-F-Pro- | 1,1-diMe-2-HOPr-NH- |
| 3641 | 4-[(4'-MeO-Bzc)NH]-PhoAc- | CarCH₂ | Bz | 3-F-Pro- | 1,1-diMe-2-HOPr-NH- |
| 3642 | N-Me-4-PipO-Ac- | CarCH₂ | Bz | 3-F-Pro- | 1,1-diMe-2-HOPr-NH- |
| 3643 | 4-NH₂-cHxO-Ac- | CarCH₂ | Bz | 3-F-Pro- | 1,1-diMe-2-HOPr-NH- |
| 3644 | 4-[(MorAc)NMe]-PhoAc- | CarCH₂ | Bz | 3-F-Pro- | 1,1-diMe-2-HOPr-NH- |
| 3645 | 2-Quin-CO- | CarCH₂ | Bz | 3-F-Pro- | 1,1-diMe-2-HOEt-NH- |
| 3646 | 3-Quin-CO- | CarCH₂ | Bz | 3-F-Pro- | 1,1-diMe-2-HOEt-NH- |
| 3647 | 4-Quin-CO- | CarCH₂ | Bz | 3-F-Pro- | 1,1-diMe-2-HOEt-NH- |
| 3648 | 2-Pyr-CO- | CarCH₂ | Bz | 3-F-Pro- | 1,1-diMe-2-HOEt-NH- |
| 3649 | 3-Pyr-CO- | CarCH₂ | Bz | 3-F-Pro- | 1,1-diMe-2-HOEt-NH- |
| 3650 | 4-Pyr-CO- | CarCH₂ | Bz | 3-F-Pro- | 1,1-diMe-2-HOEt-NH- |
| 3651 | 4-MeO-2-Quin-CO- | CarCH₂ | Bz | 3-F-Pro- | 1,1-diMe-2-HOEt-NH- |
| 3652 | 2-Np-CO- | CarCH₂ | Bz | 3-F-Pro- | 1,1-diMe-2-HOEt-NH- |
| 3653 | 1-Np-CO- | CarCH₂ | Bz | 3-F-Pro- | 1,1-diMe-2-HOEt-NH- |
| 3654 | 2-Bfur-CO- | CarCH₂ | Bz | 3-F-Pro- | 1,1-diMe-2-HOEt-NH- |
| 3655 | 3-Bfur-CO- | CarCH₂ | Bz | 3-F-Pro- | 1,1-diMe-2-HOEt-NH- |
| 3656 | 5-Bu-2-Pyr-CO- | CarCH₂ | Bz | 3-F-Pro- | 1,1-diMe-2-HOEt-NH- |
| 3657 | 4-HO-2-Quin-CO- | CarCH₂ | Bz | 3-F-Pro- | 1,1-diMe-2-HOEt-NH- |
| 3658 | 3-HO-2-Quin-CO- | CarCH₂ | Bz | 3-F-Pro- | 1,1-diMe-2-HOEt-NH- |
| 3659 | 1-Np-Sfo- | CarCH₂ | Bz | 3-F-Pro- | 1,1-diMe-2-HOEt-NH- |
| 3660 | 2-Np-Sfo- | CarCH₂ | Bz | 3-F-Pro- | 1,1-diMe-2-HOEt-NH- |
| 3661 | Boz | CarCH₂ | Bz | 3-F-Pro- | 1,1-diMe-2-HOEt-NH- |
| 3662 | Bz-NHCO- | CarCH₂ | Bz | 3-F-Pro- | 1,1-diMe-2-HOEt-NH- |
| 3663 | Bz-NHCS- | CarCH₂ | Bz | 3-F-Pro- | 1,1-diMe-2-HOEt-NH- |
| 3664 | 2-Ind-CO- | CarCH₂ | Bz | 3-F-Pro- | 1,1-diMe-2-HOEt-NH- |
| 3665 | 3-Ind-CO- | CarCH₂ | Bz | 3-F-Pro- | 1,1-diMe-2-HOEt-NH- |
| 3666 | tBoc | CarCH₂ | Bz | 3-F-Pro- | 1,1-diMe-2-HOEt-NH- |
| 3667 | 2-Pyrd-CO- | CarCH₂ | Bz | 3-F-Pro- | 1,1-diMe-2-HOEt-NH- |
| 3668 | 2-Pip-CO- | CarCH₂ | Bz | 3-F-Pro- | 1,1-diMe-2-HOEt-NH- |
| 3669 | 2-Thi-CO- | CarCH₂ | Bz | 3-F-Pro- | 1,1-diMe-2-HOEt-NH- |
| 3670 | MecCO- | CarCH₂ | Bz | 3-F-Pro- | 1,1-diMe-2-HOEt-NH- |
| 3671 | PhoAc- | CarCH₂ | Bz | 3-F-Pro- | 1,1-diMe-2-HOEt-NH- |
| 3672 | MPhoAc- | CarCH₂ | Bz | 3-F-Pro- | 1,1-diMe-2-HOEt-NH- |
| 3673 | 3-Bzisox-CO- | CarCH₂ | Bz | 3-F-Pro- | 1,1-diMe-2-HOEt-NH- |
| 3674 | 2-Bzim-CO- | CarCH₂ | Bz | 3-F-Pro- | 1,1-diMe-2-HOEt-NH- |
| 3675 | N-Me-3-Ind-CO- | CarCH₂ | Bz | 3-F-Pro- | 1,1-diMe-2-HOEt-NH- |
| 3676 | 2-Bzthiaz-CO- | CarCH₂ | Bz | 3-F-Pro- | 1,1-diMe-2-HOEt-NH- |

TABLE 1-continued

| Cpd. No. | R¹ | R³ | R⁴ | Z | R⁵ |
|---|---|---|---|---|---|
| 3677 | 2-Bzoxaz-CO- | CarCH₂ | Bz | 3-F-Pro- | 1,1-diMe-2-HOEt-NH- |
| 3678 | 5-MeO-2-Ind-CO- | CarCH₂ | Bz | 3-F-Pro- | 1,1-diMe-2-HOEt-NH- |
| 3679 | 5-HO-2-Ind-CO- | CarCH₂ | Bz | 3-F-Pro- | 1,1-diMe-2-HOEt-NH- |
| 3680 | 5-AcO-2-Ind-CO- | CarCH₂ | Bz | 3-F-Pro- | 1,1-diMe-2-HOEt-NH- |
| 3681 | 5-H₂NAcO-2-Ind-CO- | CarCH₂ | Bz | 3-F-Pro- | 1,1-diMe-2-HOEt-NH- |
| 3682 | 5-Bzim-CO- | CarCH₂ | Bz | 3-F-Pro- | 1,1-diMe-2-HOEt-NH- |
| 3683 | (1-NpO)Ac- | CarCH₂ | Bz | 3-F-Pro- | 1,1-diMe-2-HOEt-NH- |
| 3684 | 1-NpOCO- | CarCH₂ | Bz | 3-F-Pro- | 1,1-diMe-2-HOEt-NH- |
| 3685 | 2-NpOCO- | CarCH₂ | Bz | 3-F-Pro- | 1,1-diMe-2-HOEt-NH- |
| 3686 | (3-PhPho)Ac- | CarCH₂ | Bz | 3-F-Pro- | 1,1-diMe-2-HOEt-NH- |
| 3687 | (2-NpO)Ac- | CarCH₂ | Bz | 3-F-Pro- | 1,1-diMe-2-HOEt-NH- |
| 3688 | Bzc | CarCH₂ | Bz | 3-F-Pro- | 1,1-diMe-2-HOPr-NH- |
| 3689 | 2-Quix-CO- | CarCH₂ | Bz | 3-F-Pro- | 1,1-diMe-2-HOPr-NH- |
| 3690 | 2-Quin-CO- | CarCH₂ | Bz | 3-F-Pro- | 1,1-diMe-2-HOPr-NH- |
| 3691 | 3-Quin-CO- | CarCH₂ | Bz | 3-F-Pro- | 1,1-diMe-2-HOPr-NH- |
| 3692 | 4-Quin-CO- | CarCH₂ | Bz | 3-F-Pro- | 1,1-diMe-2-HOPr-NH- |
| 3693 | 2-Pyr-CO- | CarCH₂ | Bz | 3-F-Pro- | 1,1-diMe-2-HOPr-NH- |
| 3694 | 3-Pyr-CO- | CarCH₂ | Bz | 3-F-Pro- | 1,1-diMe-2-HOPr-NH- |
| 3695 | 4-Pyr-CO- | CarCH₂ | Bz | 3-F-Pro- | 1,1-diMe-2-HOPr-NH- |
| 3696 | 4-MeO-2-Quin-CO- | CarCH | Bz | 3-F-Pro- | 1,1-diMe-2-HOPr-NH- |
| 3697 | 2-Np-CO- | CarCH₂ | Bz | 3-F-Pro- | 1,1-diMe-2-HOPr-NH- |
| 3698 | 1-Np-CO- | CarCH₂ | Bz | 3-F-Pro- | 1,1-diMe-2-HOPr-NH- |
| 3699 | 2-Bfur-CO- | CarCH₂ | Bz | 3-F-Pro- | 1,1-diMe-2-HOPr-NH- |
| 3700 | 3-Bfur-CO- | CarCH₂ | Bz | 3-F-Pro- | 1,1-diMe-2-HOPr-NH- |
| 3701 | 5-Bu-2-Pyr-CO- | CarCH₂ | Bz | 3-F-Pro- | 1,1-diMe-2-HOPr-NH- |
| 3702 | 4-HO-2-Quin-CO- | CarCH₂ | Bz | 3-F-Pro- | 1,1-diMe-2-HOPr-NH- |
| 3703 | 3-HO-2-Quix-CO- | CarCH₂ | Bz | 3-F-Pro- | 1,1-diMe-2-HOPr-NH- |
| 3704 | 1-Np-Sfo- | CarCH₂ | Bz | 3-F-Pro- | 1,1-diMe-2-HOPr-NH- |
| 3705 | 2-Np-Sfo- | CarCH₂ | Bz | 3-F-Pro- | 1,1-diMe-2-HOPr-NH- |
| 3706 | Boz | CarCH₂ | Bz | 3-F-Pro- | 1,1-diMe-2-HOPr-NH- |
| 3707 | Bz-NHCO- | CarCH₂ | Bz | 3-F-Pro- | 1,1-diMe-2-HOPr-NH- |
| 3708 | Bz-NHCS- | CarCH₂ | Bz | 3-F-Pro- | 1,1-diMe-2-HOPr-NH- |
| 3709 | 2-Ind-CO- | CarCH₂ | Bz | 3-F-Pro- | 1,1-diMe-2-HOPr-NH- |
| 3710 | 3-Ind-CO- | CarCH₂ | Bz | 3-F-Pro- | 1,1-diMe-2-HOPr-NH- |
| 3711 | tBoc | CarCH₂ | Bz | 3-F-Pro- | 1,1-diMe-2-HOPr-NH- |
| 3712 | 2-Pyrd-CO- | CarCH₂ | Bz | 3-F-Pro- | 1,1-diMe-2-HOPr-NH- |
| 3713 | 2-Pip-CO- | CarCH₂ | Bz | 3-F-Pro- | 1,1-diMe-2-HOPr-NH- |
| 3714 | 2-Thi-CO- | CarCH₂ | Bz | 3-F-Pro- | 1,1-diMe-2-HOPr-NH- |

TABLE 1-continued

| Cpd. No. | R¹ | R³ | R⁴ | Z | R⁵ |
|---|---|---|---|---|---|
| 3715 | MecCO- | CarCH₂ | Bz | 3-F-Pro- | 1,1-diMe-2-HOPr-NH- |
| 3716 | PhoAc- | CarCH₂ | Bz | 3-F-Pro- | 1,1-diMe-2-HOPr-NH- |
| 3717 | MPhoAc- | CarCH₂ | Bz | 3-F-Pro- | 1,1-diMe-2-HOPr-NH- |
| 3718 | 3-Bzisox-CO- | CarCH₂ | Bz | 3-F-Pro- | 1,1-diMe-2-HOPr-NH- |
| 3719 | 2-Bzim-CO- | CarCH₂ | Bz | 3-F-Pro- | 1,1-diMe-2-HOPr-NH- |
| 3720 | N-Me-3-Ind-CO- | CarCH₂ | Bz | 3-F-Pro- | 1,1-diMe-2-HOPr-NH- |
| 3721 | 2-Bzthiaz-CO- | CarCH₂ | Bz | 3-F-Pro- | 1,1-diMe-2-HOPr-NH- |
| 3722 | 2-Bzoxaz-CO- | CarCH₂ | Bz | 3-F-Pro- | 1,1-diMe-2-HOPr-NH- |
| 3723 | 5-MeO-2-Ind-CO- | CarCH₂ | Bz | 3-F-Pro- | 1,1-diMe-2-HOPr-NH- |
| 3724 | 5-HO-2-Ind-CO- | CarCH₂ | Bz | 3-F-Pro- | 1,1-diMe-2-HOPr-NH- |
| 3725 | 5-AcO-2-Ind-CO- | CarCH₂ | Bz | 3-F-Pro- | 1,1-diMe-2-HOPr-NH- |
| 3726 | 5-H₂NAcO-2-Ind-CO- | CarCH₂ | Bz | 3-F-Pro- | 1,1-diMe-2-HOPr-NH- |
| 3727 | 5-Bzim-CO- | CarCH₂ | Bz | 3-F-Pro- | 1,1-diMe-2-HOPr-NH- |
| 3728 | (2-NpO)Ac- | CarCH₂ | Bz | 3-F-Pro- | 1,1-diMe-2-HOPr-NH- |
| 3729 | (1-NpO)Ac- | CarCH₂ | Bz | 3-F-Pro- | 1,1-diMe-2-HOPr-NH- |
| 3730 | 1-NpOCO- | CarCH₂ | Bz | 3-F-Pro- | 1,1-diMe-2-HOPr-NH- |
| 3731 | 2-NpOCO- | CarCH₂ | Bz | 3-F-Pro- | 1,1-diMe-2-HOPr-NH- |
| 3732 | (3-PhPho)Ac- | CarCH₂ | Bz | 3-F-Pro- | 1,1-diMe-2-HOPr-NH- |
| 3733 | Bzc | CarCH₂ | 4-Br-Bz | 3-F-Pro- | tBuNH- |
| 3734 | 2-Quix-CO- | CarCH₂ | 4-Br-Bz | 3-F-Pro- | tBuNH- |
| 3735 | Bzc | CarCH₂ | 4-MeOBz | 3-F-Pro- | tBuNH- |
| 3736 | 2-Quix-CO- | CarCH₂ | 4-MeOBz | 3-F-Pro- | tBuNH- |
| 3737 | Bzc | CarCH₂ | 4-Me-Bz | 3-F-Pro- | tBuNH- |
| 3738 | 2-Quix-CO- | CarCH₂ | 4-Me-Bz | 3-F-Pro- | tBuNH- |
| 3739 | Bzc | CarCH₂ | CHxCH₂ | 3-F-Pro- | tBuNH- |
| 3740 | 2-Quix-CO- | CarCH₂ | CHxCH₂ | 3-F-Pro- | tBuNH- |
| 3741 | Bzc | MeSOCH₂ | Bz | 3-F-Pro- | tBuNH- |
| 3742 | Bzc | MeSO₂CH₂ | Bz | 3-F-Pro- | tBuNH- |
| 3743 | Bzc | MeOCH₂ | Bz | 3-F-Pro- | tBuNH- |
| 3744 | Bzc | MecCH₂CH₂ | Bz | 3-F-Pro- | tBuNH- |
| 3745 | Bzc | MecCH₂ | Bz | 3-F-Pro- | tBuNH- |
| 3746 | 2-Quix-CO- | MeSOCH₂ | Bz | 3-F-Pro- | tBuNH- |
| 3747 | 2-Quix-CO- | MeSO₂CH₂ | Bz | 3-F-Pro- | tBuNH- |
| 3748 | 2-Quix-CO- | MeOCH₂ | Bz | 3-F-Pro- | tBuNH- |
| 3749 | 2-Quix-CO- | MecCH₂CH₂ | Bz | 3-F-Pro- | tBuNH- |
| 3750 | 2-Quix-CO- | MecCH₂ | Bz | 3-F-Pro- | tBuNH- |
| 3751 | 2-Quin-CO- | MeSOCH₂ | Bz | 3-F-Pro- | tBuNH- |
| 3752 | 2-Quin-CO- | MeSO₂CH₂ | Bz | 3-F-Pro- | tBuNH- |
| 3753 | 2-Quin-CO- | MeOCH₂ | Bz | 3-F-Pro- | tBuNH- |
| 3754 | 2-Quin-CO- | MecCH₂CH₂ | Bz | 3-F-Pro- | tBuNH- |
| 3755 | 2-Quin-CO- | MecCH₂ | Bz | 3-F-Pro- | tBuNH- |
| 3756 | 3-Quin-CO- | MeSOCH₂ | Bz | 3-F-Pro- | tBuNH- |
| 3757 | 3-Quin-CO- | MeSO₂CH₂ | Bz | 3-F-Pro- | tBuNH- |
| 3758 | 3-Quin-CO- | MeOCH₂ | Bz | 3-F-Pro- | tBuNH- |
| 3759 | 3-Quin-CO- | MecCH₂CH₂ | Bz | 3-F-Pro- | tBuNH- |
| 3760 | 3-Quin-CO- | MecCH₂ | Bz | 3-F-Pro- | tBuNH- |
| 3761 | 2-Bfur-CO- | MeSOCH₂ | Bz | 3-F-Pro- | tBuNH- |
| 3762 | 2-Bfur-CO- | MeSO₂CH₂ | Bz | 3-F-Pro- | tBuNH- |
| 3763 | 2-Bfur-CO- | MeOCH₂ | Bz | 3-F-Pro- | tBuNH- |
| 3764 | 2-Bfur-CO- | MecCH₂CH₂ | Bz | 3-F-Pro- | tBuNH- |
| 3765 | 2-Bfur-CO- | MecCH₂ | Bz | 3-F-Pro- | tBuNH- |
| 3766 | 3-Bfur-CO- | MeSOCH₂ | Bz | 3-F-Pro- | tBuNH- |
| 3767 | 3-Bfur-CO- | MeSO₂CH₂ | Bz | 3-F-Pro- | tBuNH- |
| 3768 | 3-Bfur-CO- | MeOCH₂ | Bz | 3-F-Pro- | tBuNH- |
| 3769 | 3-Bfur-CO- | MecCH₂CH₂ | Bz | 3-F-Pro- | tBuNH- |
| 3770 | 3-Bfur-CO- | MecCH₂ | Bz | 3-F-Pro- | tBuNH- |
| 3771 | 3-Ind-CO- | MeSOCH₂ | Bz | 3-F-Pro- | tBuNH- |
| 3772 | 3-Ind-CO- | MeSO₂CH₂ | Bz | 3-F-Pro- | tBuNH- |

TABLE 1-continued

| Cpd. No. | R¹ | R³ | R⁴ | Z | R⁵ |
|---|---|---|---|---|---|
| 3773 | 3-Ind-CO- | MeOCH₂ | Bz | 3-F-Pro- | tBuNH- |
| 3774 | 3-Ind-CO- | MecCH₂CH₂ | Bz | 3-F-Pro- | tBuNH- |
| 3775 | 3-Ind-CO- | MecCH₂ | Bz | 3-F-Pro- | tBuNH- |
| 3776 | MPhOAc- | MeSOCH₂ | Bz | 3-F-Pro- | tBuNH- |
| 3777 | MPhOAc- | MeSO₂CH₂ | Bz | 3-F-Pro- | tBuNH- |
| 3778 | MPhOAc- | MeOCH₂ | Bz | 3-F-Pro- | tBuNH- |
| 3779 | MPhOAc- | MecCH₂CH₂ | Bz | 3-F-Pro- | tBuNH- |
| 3780 | MPhOAc- | MecCH₂ | Bz | 3-F-Pro- | tBuNH- |
| 3781 | 5-NH₂-AcO-2-Ind-CO- | MeSOCH₂ | Bz | 3-F-Pro- | tBuNH- |
| 3782 | 5-NH₂-AcO-2-Ind-CO- | MeSO₂CH₂ | Bz | 3-F-Pro- | tBuNH- |
| 3783 | 5-NH₂-AcO-2-Ind-CO- | MeOCH₂ | Bz | 3-F-Pro- | tBuNH- |
| 3784 | 5-NH₂-AcO-2-Ind-CO- | MecCH₂CH₂ | Bz | 3-F-Pro- | tBuNH- |
| 3785 | 5-NH₂-AcO-2-Ind-CO- | MecCH₂ | Bz | 3-F-Pro- | tBuNH- |
| 3786 | 4-NH₂-PhoAc- | MeSOCH₂ | Bz | 3-F-Pro- | tBuNH- |
| 3787 | 4-NH₂-PhoAc- | MeSO₂CH₂ | Bz | 3-F-Pro- | tBuNH- |
| 3788 | 4-NH₂-PhoAc- | MeOCH₂ | Bz | 3-F-Pro- | tBuNH- |
| 3789 | 4-NH₂-PhoAc- | MecCH₂CH₂ | Bz | 3-F-Pro- | tBuNH- |
| 3790 | 4-NH₂-PhoAc- | MecCH₂ | Bz | 3-F-Pro- | tBuNH- |
| 3791 | 4-[Bzc-NH]-PhoAc- | MeSOCH₂ | Bz | 3-F-Pro- | tBuNH- |
| 3792 | 4-(Bzc-NH)-PhoAc- | MeSO₂CH₂ | Bz | 3-F-Pro- | tBuNH- |
| 3793 | 4-(Bzc-NH)-PhoAc- | MeOCH₂ | Bz | 3-F-Pro- | tBuNH- |
| 3794 | 4-[Bzc-NH]-PhoAc- | MecCH₂CH₂ | Bz | 3-F-Pro- | tBuNH- |
| 3795 | 4-[Bzc-NH]-PhoAc- | MecCH₂ | Bz | 3-F-Pro- | tBuNH- |
| 3796 | 4-[(MorAc)NMe]-PhoAc- | MeSOCH₂ | Bz | 3-F-Pro- | tBuNH- |
| 3797 | 4-[(MorAc)NMe]-PhoAc- | MeSO₂CH₂ | Bz | 3-F-Pro- | tBuNH- |
| 3798 | 4-[(MorAc)NMe]-PhoAc- | MeOCH₂ | Bz | 3-F-Pro- | tBuNH- |
| 3799 | 4-[(MorAc)NMe]-PhoAc- | MecCH₂CH₂ | Bz | 3-F-Pro- | tBuNH- |
| 3800 | 4-[(MorAc)NMe]-PhoAc- | MecCH₂ | Bz | 3-F-Pro- | tBuNH- |
| 3801 | 4-MeO-Bzc | CarCH₂ | Bz | 3-F-Pro- | tBuNH- |
| 3802 | Bzc | Me₂NCH₂ | Bz | 3-F-Pro- | tBuNH- |
| 3803 | Bzc | 2-Car-Et | Bz | 3,3-diF-Pro- | tBuNH- |
| 3804 | Bzc | CNCH₂ | Bz | 3,3-diF-Pro- | tBuNH- |
| 3805 | Bzc | iPr | Bz | 3,3-diF-Pro- | tBuNH- |
| 3806 | Bzc | tBu | Bz | 3,3-diF-Pro- | tBuNH- |
| 3807 | Bzc | diMeCarCH₂ | Bz | 3,3-diF-Pro- | tBuNH- |
| 3808 | Bzc | MorCOCH₂ | Bz | 3,3-diF-Pro- | tBuNH- |
| 3809 | Bzc | PipCOCH₂ | Bz | 3,3-diF-Pro- | tBuNH- |
| 3810 | Bzc | 2-NH₂-Et | Bz | 3,3-diF-Pro- | tBuNH- |
| 3811 | Bzc | 3-NH₂-Pr | Bz | 3,3-diF-Pro- | tBuNH- |
| 3812 | Bzc | MeCarCH₂ | Bz | 3,3-diF-Pro- | tBuNH- |
| 3813 | Bzc | Et-Car-CH₂ | Bz | 3,3-diF-Pro- | tBuNH- |
| 3814 | Bzc | H | Bz | 3,3-diF-Pro- | tBuNH- |
| 3815 | Bzc | HOCH₂ | Bz | 3,3-diF-Pro- | tBuNH- |
| 3816 | Bzc | 4-Thiz-CH₂ | Bz | 3,3-diF-Pro- | tBuNH- |
| 3817 | Bzc | 4-Imid-CH₂ | Bz | 3,3-diF-Pro- | tBuNH- |
| 3818 | Bzc | COOH-CH₂ | Bz | 3,3-diF-Pro- | tBuNH- |
| 3819 | Bzc | 2-COOH-Et | Bz | 3,3-diF-Pro- | tBuNH- |
| 3820 | Bzc | MeSCH₂ | Bz | 3,3-diF-Pro- | tBuNH- |
| 3821 | Bzc | SamCH₂ | Bz | 3,3-diF-Pro- | tBuNH- |
| 3822 | Bzc | Bz | Bz | 3,3-diF-Pro- | tBuNH- |
| 3823 | Bzc | SimCH₂ | Bz | 3,3-diF-Pro- | tBuNH- |
| 3824 | Bzc | HiaCH₂ | Bz | 3,3-diF-Pro- | tBuNH- |
| 3825 | Bzc | 2-Sim-Et | Bz | 3,3-diF-Pro- | tBuNH- |
| 3826 | Bzc | 2-Hia-Et | Bz | 3,3-diF-Pro- | tBuNH- |
| 3827 | Bzc | NH₂CH₂ | Bz | 3,3-diF-Pro- | tBuNH- |
| 3828 | Bzc | MeNHCH₂ | Bz | 3,3-diF-Pro- | tBuNH- |
| 3829 | 2-Quix-CO- | 2-Car-Ft | Bz | 3,3-diF-Pro- | tBuNH- |
| 3830 | 2-Quix-CO- | CNCH₂ | Bz | 3,3-diF-Pro- | tBuNH- |
| 3831 | 2-Quix-CO- | iPr | Bz | 3,3-diF-Pro- | tBuNH- |
| 3832 | 2-Quix-CO- | tBu | Bz | 3,3-diF-Pro- | tBuNH- |
| 3833 | 2-Quix-CO- | diMeCarCH₂ | Bz | 3,3-diF-Pro- | tBuNH- |

TABLE 1-continued

| Cpd. No. | R¹ | R³ | R⁴ | Z | R⁵ |
|---|---|---|---|---|---|
| 3834 | 2-Quix-CO- | MorCOCH₂ | Bz | 3,3-diF-Pro- | tBuNH- |
| 3835 | 2-Quix-CO- | PipCOCH₂ | Bz | 3,3-diF-Pro- | tBuNH- |
| 3836 | 2-Quix-CO- | 2-NH₂-Et | Bz | 3,3-diF-Pro- | tBuNH- |
| 3837 | 2-Quix-CO- | 3-NH₂-Pr | Bz | 3,3-diF-Pro- | tBuNH- |
| 3838 | 2-Quix-CO- | MeCarCH₂ | Bz | 3,3-diF-Pro- | tBuNH- |
| 3839 | 2-Quix-CO- | EtCarCH₂ | Bz | 3,3-diF-Pro- | tBuNH- |
| 3840 | 2-Quix-CO- | H | Bz | 3,3-diF-Pro- | tBuNH- |
| 3841 | 2-Quix-CO- | HOCH₂ | Bz | 3,3-diF-Pro- | tBuNH- |
| 3842 | 2-Quix-CO- | 4-Thiz-CH₂ | Bz | 3,3-diF-Pro- | tBuNH- |
| 3843 | 2-Quix-CO- | 4-Imid-CH₂ | Bz | 3,3-diF-Pro- | tBuNH- |
| 3844 | 2-Quix-CO- | COOH-CH₂ | Bz | 3,3-diF-Pro- | tBuNH- |
| 3845 | 2-Quix-CO- | 2-COOH-Et | Bz | 3,3-diF-Pro- | tBuNH- |
| 3846 | 2-Quix-CO- | MeSCH₂ | Bz | 3,3-diF-Pro- | tBuNH- |
| 3847 | 2-Quix-CO- | SamCH₂ | Bz | 3,3-diF-Pro- | tBuNH- |
| 3848 | 2-Quix-CO- | Bz | Bz | 3,3-diF-Pro- | tBuNH- |
| 3849 | 2-Quix-CO- | Sim-CH₂ | Bz | 3,3-diF-Pro- | tBuNH- |
| 3850 | 2-Quix-CO- | Hia-CH₂ | Bz | 3,3-diF-Pro- | tBuNH- |
| 3851 | 2-Quix-CO- | 2-SimEt | Bz | 3,3-diF-Pro- | tBuNH- |
| 3852 | 2-Quix-CO- | 2-HiaEt | Bz | 3,3-diF-Pro- | tBuNH- |
| 3853 | 2-Quix-CO- | NH₂CH₂ | Bz | 3,3-diF-Pro- | tBuNH- |
| 3854 | 2-Quix-CO- | MeNHCH₂ | Bz | 3,3-diF-Pro- | tBuNH- |
| 3855 | 2-Quix-CO- | Me₂NCH₂ | Bz | 3,3-diF-Pro- | tBuNH- |
| 3856 | 3-Quin-CO- | CarCH₂ | Bz | 3,3-diF-Pro- | tBuNH- |
| 3857 | 4-Quin-CO- | CarCH₂ | Bz | 3,3-diF-Pro- | tBuNH- |
| 3858 | 2-Pyr-CO- | CarCH₂ | Bz | 3,3-diF-Pro- | tBuNH- |
| 3859 | 3-Pyr-CO- | CarCH₂ | Bz | 3,3-diF-Pro- | tBuNH- |
| 3860 | 4-Pyr-CO- | CarCH₂ | Bz | 3,3-diF-Pro- | tBuNH- |
| 3861 | 4-MeO-2-Quin-CO- | CarCH₂ | Bz | 3,3-diF-Pro- | tBuNH- |
| 3862 | 2-Np-CO- | CarCH₂ | Bz | 3,3-diF-Pro- | tBuNH- |
| 3863 | 1-Np-CO- | CarCH₂ | Bz | 3,3-diF-Pro- | tBuNH- |
| 3864 | 2-Bfur-CO- | CarCH₂ | Bz | 3,3-diF-Pro- | tBuNH- |
| 3865 | 3-Bfur-CO- | CarCH₂ | Bz | 3,3-diF-Pro- | tBuNH- |
| 3866 | 5-Bu-2-Pyr-CO- | CarCH₂ | Bz | 3,3-diF-Pro- | tBuNH- |
| 3867 | 4-HO-2-Quin-CO- | CarCH₂ | Bz | 3,3-diF-Pro- | tBuNH- |
| 3868 | 3-HO-2-Quix-CO- | CarCH₂ | Bz | 3,3-diF-Pro- | tBuNH- |
| 3869 | 1-Np-Sfo- | CarCH₂ | Bz | 3,3-diF-Pro- | tBuNH- |
| 3870 | 2-Np-Sfo- | CarCH₂ | Bz | 3,3-diF-Pro- | tBuNH- |
| 3871 | Boz | CarCH₂ | Bz | 3,3-diF-Pro- | tBuNH- |
| 3872 | Bz-NHCO- | CarCH₂ | Bz | 3,3-diF-Pro- | tBuNH- |
| 3873 | Bz-NHCS- | CarCH₂ | Bz | 3,3-diF-Pro- | tBuNH- |
| 3874 | 3-Ind-CO- | CarCH₂ | Bz | 3,3-diF-Pro- | tBuNH- |
| 3875 | 2-Pyrd-CO- | CarCH₂ | Bz | 3,3-diF-Pro- | tBuNH- |
| 3876 | 2-Pip-CO- | CarCH₂ | Bz | 3,3-diF-Pro- | tBuNH- |
| 3877 | 2-Thi-CO- | CarCH₂ | Bz | 3,3-diF-Pro- | tBuNH- |
| 3878 | MecCO- | CarCH₂ | Bz | 3,3-diF-Pro- | tBuNH- |
| 3879 | PhoAc- | CarCH₂ | Bz | 3,3-diF-Pro- | tBuNH- |
| 3880 | 3-Bzisox-CO- | CarCH₂ | Bz | 3,3-diF-Pro- | tBuNH- |
| 3881 | 2-Bzim-CO- | CarCH₂ | Bz | 3,3-diF-Pro- | tBuNH- |
| 3882 | N-Me-3-Ind-CO- | CarCH₂ | Bz | 3,3-diF-Pro- | tBuNH- |
| 3883 | 2-Bzthiaz-CO- | CarCH₂ | Bz | 3,3-diF-Pro- | tBuNH- |
| 3884 | 2-Bzoxaz-CO- | CarCH₂ | Bz | 3,3-diF-Pro- | tBuNH- |
| 3885 | 5-MeO-2-Ind-CO- | CarCH₂ | Bz | 3,3-diF-Pro- | tBuNH- |
| 3886 | 5-HO-2-Ind-CO- | CarCH₂ | Bz | 3,3-diF-Pro- | tBuNH- |
| 3887 | 5-AcO-2-Ind-CO- | CarCH₂ | Bz | 3,3-diF-Pro- | tBuNH- |
| 3888 | 5-H₂NAcO-2-Ind-CO- | CarCH₂ | Bz | 3,3-diF-Pro- | tBuNH- |
| 3889 | 5-Bzim-CO- | CarCH₂ | Bz | 3,3-diF-Pro- | tBuNH- |
| 3890 | (2-NpO)Ac- | CarCH₂ | Bz | 3,3-diF-Pro- | tBuNH- |
| 3891 | (1-NpO)Ac- | CarCH₂ | Bz | 3,3-diF-Pro- | tBuNH- |
| 3892 | 1-NpOCO- | CarCH₂ | Bz | 3,3-diF-Pro- | tBuNH- |
| 3893 | 2-NpOCO- | CarCH₂ | Bz | 3,3-diF-Pro- | tBuNH- |
| 3894 | (3-PhPho)Ac- | CarCH₂ | Bz | 3,3-diF-Pro- | tBuNH- |
| 3895 | 2-Quix-CO- | CarCH₂ | Bz | 3,3-diF-Pro- | 3-HOPr-NH- |
| 3896 | 2-Quix-CO- | CarCH₂ | Bz | 3,3-diF-Pro- | BuNH- |
| 3897 | 2-Quix-CO- | CarCH₂ | Bz | 3,3-diF-Pro- | tBuO- |
| 3898 | 2-Quix-CO- | CarCH₂ | Bz | 3,3-diF-Pro- | 1,1-diMe-2-HOEt-NH- |
| 3899 | Bzc | CarCH₂ | Bz | 3,3-diF-Pro- | 3-HOPr-NH- |
| 3900 | Bzc | CarCH₂ | Bz | 3,3-diF-Pro- | BuNH- |
| 3901 | Bzc | CarCH₂ | Bz | 3,3-diF-Pro- | tBuO- |
| 3902 | Bzc | CarCH₂ | Bz | 3,3-diF-Pro- | 1,1-diMe-2-HOEt-NH- |
| 3903 | 3-NH₂-PhoAc- | CarCH₂ | Bz | 3,3-diF-Pro- | tBuNH- |
| 3904 | 2-NH₂-PhoAc- | CarCH₂ | Bz | 3,3-diF-Pro- | tBuNH- |

TABLE 1-continued

| Cpd. No. | R¹ | R³ | R⁴ | Z | R⁵ |
|---|---|---|---|---|---|
| 3905 | 2,3-diNH₂-Pho-Ac- | CarCH₂ | Bz | 3,3-diF-Pro- | tBuNH- |
| 3906 | 2,4-diNH₂-Pho-Ac- | CarCH₂ | Bz | 3,3-diF-Pro- | tBuNH- |
| 3907 | 4-NH₂-Ph-CO- | CarCH₂ | Bz | 3,3-diF-Pro- | tBuNH- |
| 3908 | 4-NH₂-Bzc | CarCH₂ | Bz | 3,3-diF-Pro- | tBuNH- |
| 3909 | 4-Me₂N-PhoAc- | CarCH₂ | Bz | 3,3-diF-Pro- | tBuNH- |
| 3910 | 4-[Me(Bz)N]-PhoAc- | CarCH₂ | Bz | 3,3-diF-Pro- | tBuNH- |
| 3911 | 4-Mor-PhoAc- | CarCH₂ | Bz | 3,3-diF-Pro- | tBuNH- |
| 3912 | 4-(N-Bz-Pipr]-PhoAc- | CarCH₂ | Bz | 3,3-diF-Pro- | tBuNH- |
| 3913 | 4-MeNH-PhoAc- | CarCH₂ | Bz | 3,3-diF-Pro- | tBuNH- |
| 3914 | 4-[(4'-Me-Bzc)-NH-PhoAc- | CarCH₂ | Bz | 3,3-diF-Pro- | tBuNH- |
| 3915 | 4-[tBoc-NH]-Pho-Ac- | CarCH₂ | Bz | 3,3-diF-Pro- | tBuNH- |
| 3916 | 4-[tBoc-MeN]-PhoAc- | CarCH₂ | Bz | 3,3-diF-Pro- | tBuNH- |
| 3917 | 4-[Gly-NH]-Pho-Ac- | CarCH₂ | Bz | 3,3-diF-Pro- | tBuNH- |
| 3918 | 4-[Gly-NMe]-Pho-Ac- | CarCH₂ | Bz | 3,3-diF-Pro- | tBuNH- |
| 3919 | 4-[(N-Me-Gly)-NMe]-PhoAc- | CarCH₂ | Bz | 3,3-diF-Pro- | tBuNH- |
| 3920 | 4-[(N-tBoc-Gly)NMe]-PhoAc- | CarCH₂ | Bz | 3,3-diF-Pro- | tBuNH- |
| 3921 | 4-[(N-tBoc-NMe-Gly)NMe]-PhoAc- | CarCH₂ | Bz | 3,3-diF-Pro- | tBuNH- |
| 3922 | Boc | CarCH₂ | Bz | 3,3-diF-Pro- | tBuNH- |
| 3923 | 4-[(BrAc)NMe]-PhoAc- | CarCH₂ | Bz | 3,3-diF-Pro- | tBuNH- |
| 3924 | 4-[(4'-MeO-Bzc) NH]-PhoAc- | CarCH₂ | Bz | 3,3-diF-Pro- | tBuNH- |
| 3925 | N-Me-4-PipO-Ac- | CarCH₂ | Bz | 3,3-diF-Pro- | tBuNH- |
| 3926 | 4-NH₂-cHxO-Ac- | CarCH₂ | Bz | 3,3-diF-Pro- | tBuNH- |
| 3927 | 4-NH₂-PhoAc- | CarCH₂ | Bz | 3,3-diF-Pro- | 1,1-diMe-2-HOEt-NH- |
| 3928 | 3-NH₂-PhoAc- | CarCH₂ | Bz | 3,3-diF-Pro- | 1,1-diMe-2-HOEt-NH- |
| 3929 | 2-NH₂-PhoAc- | CarCH₂ | Bz | 3,3-diF-Pro- | 1,1-diMe-2-HOEt-NH- |
| 3930 | 2,3-diNH₂-Pho-Ac- | CarCH₂ | Bz | 3,3-diF-Pro- | 1,1-diMe-2-HOEt-NH- |
| 3931 | 2,4-diNH₂-Pho-Ac- | CarCH₂ | Bz | 3,3-diF-Pro- | 1,1-diMe-2-HOEt-NH- |
| 3932 | 4-NH₂-Ph-CO- | CarCH₂ | Bz | 3,3-diF-Pro- | 1,1-diMe-2-HOEt-NH- |
| 3933 | 4-NH₂-Bzc | CarCH₂ | Bz | 3,3-diF-Pro- | 1,1-diMe-2-HOEt-NH- |
| 3934 | 4-Me₂N-PhoAc- | CarCH₂ | Bz | 3,3-diF-Pro- | 1,1-diMe-2-HOEt-NH- |
| 3935 | 4-[Me(Bz)N]-PhoAc- | CarCH₂ | Bz | 3,3-diF-Pro- | 1,1-diMe-2-HOEt-NH- |
| 3936 | 4-Mor-PhoAc- | CarCH₂ | Bz | 3,3-diF-Pro- | 1,1-diMe-2-HOEt-NH- |
| 3937 | 4-[N-Bz-Pipr]-PhoAc- | CarCH₂ | Bz | 3,3-diF-Pro- | 1,1-diMe-2-HOEt-NH- |
| 3938 | 4-MeNH-PhoAc- | CarCH₂ | Bz | 3,3-diF-Pro- | 1,1-diMe-2-HOEt-NH- |
| 3939 | 4-[(4'-Me-Bzc)-NH-PhoAc- | CarCH₂ | Bz | 3,3-diF-Pro- | 1,1-diMe-2-HOEt-NH- |
| 3940 | 4-[Bzc-NH]-Pho-Ac- | CarCH₂ | Bz | 3,3-diF-Pro- | 1,1-diMe-2-HOEt-NH- |
| 3941 | 4-[tBoc-NH]-PhoAc- | CarCH₂ | Bz | 3,3-diF-Pro- | 1,1-diMe-2-HOEt-NH- |
| 3942 | 4-[tBoc-MeN]-PhoAc- | CarCH₂ | Bz | 3,3-diF-Pro- | 1,1-diMe-2-HOEt-NH- |
| 3943 | 4-Gly-NH-Pho-Ac- | CarCH₂ | Bz | 3,3-diF-Pro- | 1,1-diMe-2-HOEt-NH- |
| 3944 | 4-[Gly-NMe]-Pho-Ac- | CarCH₂ | Bz | 3,3-diF-Pro- | 1,1-diMe-2-HOEt-NH- |
| 3945 | 4-[(N-Me-Gly)-NMe]-PhoAc- | CarCH₂ | Bz | 3,3-diF-Pro- | 1,1-diMe-2-HOEt-NH- |
| 3946 | 4-[(N-tBoc-Gly)NMe]-PhoAc- | CarCH₂ | Bz | 3,3-diF-Pro- | 1,1-diMe-2-HOEt-NH- |

TABLE 1-continued

| Cpd. No. | R¹ | R³ | R⁴ | Z | R⁵ |
|---|---|---|---|---|---|
| 3947 | 4-[(N-tBoc-NMe-Gly)NMe]-PhoAc- | CarCH₂ | Bz | 3,3-diF-Pro- | 1,1-diMe-2-HOEt-NH- |
| 3948 | Boc | CarCH₂ | Bz | 3,3-diF-Pro- | 1,1-diMe-2-HOEt-NH- |
| 3949 | 4-[(BrAc)NMe]-PhoAc- | CarCH₂ | Bz | 3,3-diF-Pro- | 1,1-diMe-2-HOEt-NH- |
| 3950 | 4-[(4'-MeO-Bzc)NH]-PhoAc- | CarCH₂ | Bz | 3,3-diF-Pro- | 1,1-diMe-2-HOEt-NH- |
| 3951 | N-Me-4-PipO-Ac- | CarCH₂ | Bz | 3,3-diF-Pro- | 1,1-dime-2-HOEt-NH- |
| 3952 | 4-NH₂-cHxO-Ac- | CarCH₂ | Bz | 3,3-diF-Pro- | 1,1-diMe-2-HOEt-NH- |
| 3953 | 4-[(Mor-Ac)NMe]-PhoAc- | CarCH₂ | Bz | 3,3-diF-Pro- | 1,1-diMe-2-HOEt-NH- |
| 3954 | 4-NH₂-PhoAc- | CarCH₂ | Bz | 3,3-diF-Pro- | 1,1-diMe-2-HOPr-NH- |
| 3955 | 3-NH₂-PhoAc- | CarCH₂ | Bz | 3,3-diF-Pro- | 1,1-diMe-2-HOPr-NH- |
| 3956 | 3-NH₂-PhoAc- | CarCH₂ | Bz | 3,3-diF-Pro- | 1,1-diMe-2-HOPr-NH- |
| 3957 | 2,3-diNH₂-Pho-Ac- | CarCH₂ | Bz | 3,3-diF-Pro- | 1,1-diMe-2-HOPr-NH- |
| 3958 | 2,4-diNH₂-Pho-Ac- | CarCH₂ | Bz | 3,3-diF-Pro- | 1,1-diMe-2-HOPr-NH- |
| 3959 | 4-NH₂-Ph-CO- | CarCH₂ | Bz | 3,3-diF-Pro- | 1,1-diMe-2-HOPr-NH- |
| 3960 | 4-NH₂-Bzc | CarCH₂ | Bz | 3,3-diF-Pro- | 1,1-diMe-2-HOPr-NH- |
| 3961 | 4-Me₂N-PhoAc- | CarCH₂ | Bz | 3,3-diF-Pro- | 1,1-diMe-2-HOPr-NH- |
| 3962 | 4-[Me(Bz)N]-Pho-Ac- | CarCH₂ | Bz | 3,3-diF-Pro- | 1,1-diMe-2-HOPr-NH- |
| 3963 | 4-Mor-PhoAc- | CarCH₂ | Bz | 3,3-diF-Pro- | 1,1-diMe-2-HOPr-NH- |
| 3964 | 4-[N-Bz-Pipr]-PhoAc- | CarCH₂ | Bz | 3,3-diF-Pro- | 1,1-diMe-2-HOPr-NH- |
| 3965 | 4-MeNH-PhoAc- | CarCH₂ | Bz | 3,3-diF-Pro- | 1,1-diMe-2-HOPr-NH- |
| 3966 | 4-[(4'-Me-Bzc)-NH]-PhoAc- | CarCH₂ | Bz | 3,3-diF-Pro- | 1,1-diMe-2-HOPr-NH- |
| 3967 | 4-[Bzc-NH]-Pho-Ac- | CarCH₂ | Bz | 3,3-diF-Pro- | 1,1-diMe-2-HOPr-NH- |
| 3968 | 4-[tBoc-NH]-Pho-Ac- | CarCH₂ | Bz | 3,3-diF-Pro- | 1,1-diMe-2-HOPr-NH- |
| 3969 | 4-[tBoc-MeN]-PhoAc- | CarCH₂ | Bz | 3,3-diF-Pro- | 1,1-diMe-2-HOPr-NH- |
| 3970 | 4-Gly-NH-Pho-Ac- | CarCH₂ | Bz | 3,3-diF-Pro- | 1,1-diMe-2-HOPr-NH- |
| 3971 | 4-[Gly-NMe]-Pho-Ac- | CarCH₂ | Bz | 3,3-diF-Pro- | 1,1-diMe-2-HOPr-NH- |
| 3972 | 4-[(N-Me-Gly)-NMe]-PhoAc- | CarCH₂ | Bz | 3,3-diF-Pro- | 1,1-diMe-2-HOPr-NH- |
| 3973 | 4-[(N-tBoc-Gly)NMe]-PhoAc- | CarCH₂ | Bz | 3,3-diF-Pro- | 1,1-diMe-2-HOPr-NH- |
| 3974 | 4-[(N-tBoc-NMe-Gly)NMe]-PhoAc- | CarCH₂ | Bz | 3,3-diF-Pro- | 1,1-diMe-2-HOPr-NH- |
| 3975 | Boc | CarCH₂ | Bz | 3,3-diF-Pro- | 1,1-diMe-2-HOPr-NH- |
| 3976 | 4-[(BrAc)NMe]-PhoAc- | CarCH₂ | Bz | 3,3-diF-Pro- | 1,1-diMe-2-HOPr-NH- |
| 3977 | 4-[(4'-MeO-Bzc)NH]-PhoAc- | CarCH₂ | Bz | 3,3-diF-Pro- | 1,1-diMe-2-HOPr-NH- |
| 3978 | N-Me-4-PipO-Ac- | CarCH₂ | Bz | 3,3-diF-Pro- | 1,1-diMe-2-HOPr-NH- |
| 3979 | 4-NH₂-cHxO-Ac- | CarCH₂ | Bz | 3,3-diF-Pro- | 1,1-diMe-2-HOPr-NH- |
| 3980 | 4-[(MorAc)NMe]-PhoAc- | CarCH₂ | Bz | 3,3-diF-Pro- | 1,1-diMe-2-HOPr-NH- |
| 3981 | 2-Quin-CO- | CarCH₂ | Bz | 3,3-diF-Pro- | 1,1-diMe-2-HOEt-NH- |
| 3982 | 3-Quin-CO- | CarCH₂ | Bz | 3,3-diF-Pro- | 1,1-diMe-2-HOEt-NH- |
| 3983 | 4-Quin-CO- | CarCH₂ | Bz | 3,3-diF-Pro- | 1,1-diMe-2-HOEt-NH- |
| 3984 | 2-Pyr-CO- | CarCH₂ | Bz | 3,3-diF-Pro- | 1,1-diMe-2-HOEt-NH- |

TABLE 1-continued

| Cpd. No. | R¹ | R³ | R⁴ | Z | R⁵ |
|---|---|---|---|---|---|
| 3985 | 3-Pyr-CO- | CarCH₂ | Bz | 3,3-diF-Pro- | 1,1-diMe-2-HOEt-NH- |
| 3986 | 4-Pyr-CO- | CarCH₂ | Bz | 3,3-diF-Pro- | 1,1-diMe-2-HOEt-NH- |
| 3987 | 4-MeO-2-Quin-CO- | CarCH₂ | Bz | 3,3-diF-Pro- | 1,1-diMe-2-HOEt-NH- |
| 3988 | 2-Np-CO- | CarCH₂ | Bz | 3,3-diF-Pro- | 1,1-diMe-2-HOEt-NH- |
| 3989 | 1-Np-CO- | CarCH₂ | Bz | 3,3-diF-Pro- | 1,1-diMe-2-HOEt-NH- |
| 3990 | 2-Bfur-CO- | CarCH₂ | Bz | 3,3-diF-Pro- | 1,1-diMe-2-HOEt-NH- |
| 3991 | 3-Bfur-CO- | CarCH₂ | Bz | 3,3-diF-Pro- | 1,1-diMe-2-HOEt-NH- |
| 3992 | 5-Bu-2-Pyr-CO- | CarCH₂ | Bz | 3,3-diF-Pro- | 1,1-diMe-2-HOEt-NH- |
| 3993 | 4-HO-2-Quin-CO- | CarCH₂ | Bz | 3,3-diF-Pro- | 1,1-diMe-2-HOEt-NH- |
| 3994 | 3-HO-2-Quix-CO- | CarCH₂ | Bz | 3,3-diF-Pro- | 1,1-diMe-2-HOEt-NH- |
| 3995 | 1-Np-Sfo- | CarCH₂ | Bz | 3,3-diF-Pro- | 1,1-diMe-2-HOEt-NH- |
| 3996 | 2-Np-Sfo- | CarCH₂ | Bz | 3,3-diF-Pro- | 1,1-diMe-2-HOEt-NH- |
| 3997 | Boz | CarCH₂ | Bz | 3,3-diF-Pro- | 1,1-diMe-2-HOEt-NH- |
| 3998 | Bz-NHCO- | CarCH₂ | Bz | 3,3-diF-Pro- | 1,1-diMe-2-HOEt-NH- |
| 3999 | Bz-NHCS- | CarCH₂ | Bz | 3,3-diF-Pro- | 1,1-diMe-2-HOEt-NH- |
| 4000 | 2-Ind-CO- | CarCH₂ | Bz | 3,3-diF-Pro- | 1,1-diMe-2-HOEt-NH- |
| 4001 | 3-Ind-CO- | CarCH₂ | Bz | 3,3-diF-Pro- | 1,1-diMe-2-HOEt-NH- |
| 4002 | tBoc | CarCH₂ | Bz | 3,3-diF-Pro- | 1,1-diMe-2-HOEt-NH- |
| 4003 | 2-Pyrd-CO- | CarCH₂ | Bz | 3,3-diF-Pro- | 1,1-diMe-2-HOEt-NH- |
| 4004 | 2-Pip-CO- | CarCH₂ | Bz | 3,3-diF-Pro- | 1,1-diMe-2-HOEt-NH- |
| 4005 | 2-Thi-CO- | CarCH₂ | Bz | 3,3-diF-Pro- | 1,1-diMe-2-HOEt-NH- |
| 4006 | MeOCOCO- | CarCH₂ | Bz | 3,3-diF-Pro- | 1,1-diMe-2-HOEt-NH- |
| 4007 | PhoAc- | CarCH₂ | Bz | 3,3-diF-Pro- | 1,1-diMe-2-HOEt-NH- |
| 4008 | MPhoAc- | CarCH₂ | Bz | 3,3-diF-Pro- | 1,1-diMe-2-HOEt-NH- |
| 4009 | 3-Bzisox-CO- | CarCH₂ | Bz | 3,3-diF-Pro- | 1,1-diMe-2-HOEt-NH- |
| 4010 | 2-Bzim-CO- | CarCH₂ | Bz | 3,3-diF-Pro- | 1,1-diMe-2-HOEt-NH- |
| 4011 | N-Me-Ind-CO- | CarCH₂ | Bz | 3,3-diF-Pro- | 1,1-diMe-2-HOEt-NH- |
| 4012 | 2-Bzthiaz-CO- | CarCH₂ | Bz | 3,3-diF-Pro- | 1,1-diMe-2-HOEt-NH- |
| 4013 | 2-Bzoxaz-CO- | CarCH₂ | Bz | 3,3-diF-Pro- | 1,1-diMe-2-HOEt-NH- |
| 4014 | 4-MeO-2-Ind-CO- | CarCH₂ | Bz | 3,3-diF-Pro- | 1,1-diMe-2-HOEt-NH- |
| 4015 | 5-HO-2-Ind-CO- | CarCH₂ | Bz | 3,3-diF-Pro- | 1,1-diMe-2-HOEt-NH- |
| 4016 | 5-AcO-2-Ind-CO- | CarCH₂ | Bz | 3,3-diF-Pro- | 1,1-diMe-2-HOEt-NH- |
| 4017 | 5-H₂NAcO-2-Ind-CO- | CarCH₂ | Bz | 3,3-diF-Pro- | 1,1-diMe-2-HOEt-NH- |
| 4018 | 5-Bzim-CO- | CarCH₂ | Bz | 3,3-diF-Pro- | 1,1-diMe-2-HOEt-NH- |
| 4019 | (1-NpO)Ac- | CarCH₂ | Bz | 3,3-diF-Pro- | 1,1-diMe-2-HOEt-NH- |
| 4020 | 1-NpOCO- | CarCH₂ | Bz | 3,3-diF-Pro- | 1,1-diMe-2-HOEt-NH- |
| 4021 | 2-NpOCO- | CarCH₂ | Bz | 3,3-diF-Pro- | 1,1-diMe-2-HOEt-NH- |
| 4022 | (3-PhPho)Ac- | CarCH₂ | Bz | 3,3-diF-Pro- | 1,1-diMe-2-HOEt-NH- |

TABLE 1-continued

| Cpd. No. | R¹ | R³ | R⁴ | Z | R⁵ |
|---|---|---|---|---|---|
| 4023 | (2-NpO)Ac- | CarCH₂ | Bz | 3,3-diF-Pro- | 1,1-diMe-2-HOEt-NH- |
| 4024 | Bzc | CarCH₂ | Bz | 3,3-diF-Pro- | 1,1-diMe-2-HOPr-NH- |
| 4025 | 2-Quix-CO- | CarCH₂ | Bz | 3,3-diF-Pro- | 1,1-diMe-2-HOPr-NH- |
| 4026 | 2-Quin-CO- | CarCH₂ | Bz | 3,3-diF-Pro- | 1,1-diMe-2-HOPr-NH- |
| 4027 | 3-Quin-CO- | CarCH₂ | Bz | 3,3-diF-Pro- | 1,1-diMe-2-HOPr-NH- |
| 4028 | 4-Quin-CO- | CarCH₂ | Bz | 3,3-diF-Pro- | 1,1-diMe-2-HOPr-NH- |
| 4029 | 2-Pyr-CO- | CarCH₂ | Bz | 3,3-diF-Pro- | 1,1-diMe-2-HOPr-NH- |
| 4030 | 3-Pyr-CO- | CarCH₂ | Bz | 3,3-diF-Pro- | 1,1-diMe-2-HOPr-NH- |
| 4031 | 4-Pyr-CO- | CarCH₂ | Bz | 3,3-diF-Pro- | 1,1-diMe-2-HOPr-NH- |
| 4032 | 4-MeO-2-Quin-CO- | CarCH₂ | Bz | 3,3-diF-Pro- | 1,1-diMe-2-HOPr-NH- |
| 4033 | 2-Np-CO- | CarCH₂ | Bz | 3,3-diF-Pro- | 1,1-diMe-2-HOPr-NH- |
| 4034 | 1-Np-CO- | CarCH₂ | Bz | 3,3-diF-Pro- | 1,1-diMe-2-HOPr-NH- |
| 4035 | 2-Bfur-CO- | CarCH₂ | Bz | 3,3-diF-Pro- | 1,1-diMe-2-HOPr-NH- |
| 4036 | 3-Bfur-CO- | CarCH₂ | Bz | 3,3-diF-Pro- | 1,1-diMe-2-HOPr-NH- |
| 4037 | 5-Bu-2-Pyr-CO- | CarCH₂ | Bz | 3,3-diF-Pro- | 1,1-diMe-2-HOPr-NH- |
| 4038 | 4-HO-2-Quin-CO- | CarCH₂ | Bz | 3,3-diF-Pro- | 1,1-diMe-2-HOPr-NH- |
| 4039 | 3-HO-2-Quix-CO- | CarCH₂ | Bz | 3,3-diF-Pro- | 1,1-diMe-2-HOPr-NH- |
| 4040 | 1-Np-Sfo- | CarCH₂ | Bz | 3,3-diF-Pro- | 1,1-diMe-2-HOPr-NH- |
| 4041 | 2-Np-Sfo- | CarCH₂ | Bz | 3,3-diF-Pro- | 1,1-diMe-2-HOPr-NH- |
| 4042 | Boz | CarCH₂ | Bz | 3,3-diF-Pro- | 1,1-diMe-2-HOPr-NH- |
| 4043 | Bz-NHCO- | CarCH₂ | Bz | 3,3-diF-Pro- | 1,1-diMe-2-HOPr-NH- |
| 4044 | Bz-NHCS- | CarCH₂ | Bz | 3,3-diF-Pro- | 1,1-diMe-2-HOPr-NH- |
| 4045 | 2-Ind-CO- | CarCH₂ | Bz | 3,3-diF-Pro- | 1,1-diMe-2-HOPr-NH- |
| 4046 | 3-Ind-CO- | CarCH₂ | Bz | 3,3-diF-Pro- | 1,1-diMe-2-HOPr-NH- |
| 4047 | tBoc | CarCH₂ | Bz | 3,3-diF-Pro- | 1,1-diMe-2-HOPr-NH- |
| 4048 | 2-Pyrd-CO- | CarCH₂ | Bz | 3,3-diF-Pro- | 1,1-diMe-2-HOPr-NH- |
| 4049 | 2-Pip-CO- | CarCH₂ | Bz | 3,3-diF-Pro- | 1,1-diMe-2-HOPr-NH- |
| 4050 | 2-Thi-CO- | CarCH₂ | Bz | 3,3-diF-Pro- | 1,1-diMe-2-HOPr-NH- |
| 4051 | MeOCOCO- | CarCH₂ | Bz | 3,3-diF-Pro- | 1,1-diMe-2-HOPr-NH- |
| 4052 | PhoAc- | CarCH₂ | Bz | 3,3-diF-Pro- | 1,1-diMe-2-HOPr-NH- |
| 4053 | MPhoAc- | CarCH₂ | Bz | 3,3-diF-Pro- | 1,1-diMe-2-HOPr-NH- |
| 4054 | 3-Bzisox-CO- | CarCH₂ | Bz | 3,3-diF-Pro- | 1,1-diMe-2-HOPr-NH- |
| 4055 | 2-Bzim-CO- | CarCH₂ | Bz | 3,3-diF-Pro- | 1,1-diMe-2-HOPr-NH- |
| 4056 | N-Me-Ind-CO- | CarCH₂ | Bz | 3,3-diF-Pro- | 1,1-diMe-2-HOPr-NH- |
| 4057 | 2-Bzthiaz-CO- | CarCH₂ | Bz | 3,3-diF-Pro- | 1,1-diMe-2-HOPr-NH- |
| 4058 | 2-Bzoxaz-CO- | CarCH₂ | Bz | 3,3-diF-Pro- | 1,1-diMe-2-HOPr-NH- |
| 4059 | 5-MeO-2-Ind-CO- | CarCH₂ | Bz | 3,3-diF-Pro- | 1,1-diMe-2-HOPr-NH- |
| 4060 | 5-HO-2-Ind-CO- | CarCH₂ | Bz | 3,3-diF-Pro- | 1,1-diMe-2-HOPr-NH- |

TABLE 1-continued

| Cpd. No. | R¹ | R³ | R⁴ | Z | R⁵ |
|---|---|---|---|---|---|
| 4061 | 5-AcO-2-Ind-CO- | CarCH₂ | Bz | 3,3-diF-Pro- | 1,1-diMe-2-HOPr-NH- |
| 4062 | 5-H₂NAcO-2-Ind-CO- | CarCH₂ | Bz | 3,3-diF-Pro- | 1,1-diMe-2-HOPr-NH- |
| 4063 | 5-Bzim-CO- | CarCH₂ | Bz | 3,3-diF-Pro- | 1,1-diMe-2-HOPr-NH- |
| 4064 | 2-NpO)Ac- | CarCH₂ | Bz | 3,3-diF-Pro- | 1,1-diMe-2-HOPr-NH- |
| 4065 | (1-NpO)Ac- | CarCH₂ | Bz | 3,3-diF-Pro- | 1,1-diMe-2-HOPr-NH- |
| 4066 | 1-NpOCO- | CarCH₂ | Bz | 3,3-diF-Pro- | 1,1-diMe-2-HOPr-NH- |
| 4067 | 2-NpOCO- | CarCH₂ | Bz | 3,3-diF-Pro- | 1,1-diMe-2-HOPr-NH- |
| 4068 | (3-PhPho)Ac- | CarCH₂ | Bz | 3,3-diF-Pro- | 1,1-diMe-2-HOPr-NH- |
| 4069 | Bzc | CarCH₂ | 4-Br-Bz | 3,3-diF-Pro- | tBuNH- |
| 4070 | 2-Quix-CO- | CarCH₂ | 4-Br-Bz | 3,3-diF-Pro- | tBuNH- |
| 4071 | Bzc | CarCH₂ | 4-MeOBz | 3,3-diF-Pro- | tBuNH- |
| 4072 | 2-Quix-CO- | CarCH₂ | 4-MeOBz | 3,3-diF-Pro- | tBuNH- |
| 4073 | Bzc | CarCH₂ | 4-Me-Bz | 3,3-diF-Pro- | tBuNH- |
| 4074 | 2-Quix-CO- | CarCH₂ | 4-Me-Bz | 3,3-diF-Pro- | tBuNH- |
| 4075 | Bzc | CarCH₂ | CHxCH₂ | 3,3-diF-Pro- | tBuNH- |
| 4076 | 2-Quix-CO- | CarCH₂ | CHxCH₂ | 3,3-diF-Pro- | tBuNH- |
| 4077 | Bzc | MeSOCH₂ | Bz | 3,3-diF-Pro- | tBuNH- |
| 4078 | Bzc | MeSO₂CH₂ | Bz | 3,3-diF-Pro- | tBuNH- |
| 4079 | Bzc | MeOCH₂ | Bz | 3,3-diF-Pro- | tBuNH- |
| 4080 | Bzc | MecCH₂CH₂ | Bz | 3,3-diF-Pro- | tBuNH- |
| 4081 | Bzc | MecCH₂ | Bz | 3,3-diF-Pro- | tBuNH- |
| 4082 | 2-Quix-CO- | MeSOCH₂ | Bz | 3,3-diF-Pro- | tBuNH- |
| 4083 | 2-Quix-CO- | MeSO₂CH₂ | Bz | 3,3-diF-Pro- | tBuNH- |
| 4084 | 2-Quix-CO- | MeOCH₂ | Bz | 3,3-diF-Pro- | tBuNH- |
| 4085 | 2-Quix-CO- | MecCH₂CH₂ | Bz | 3,3-diF-Pro- | tBuNH- |
| 4086 | 2-Quix-CO- | MecCH₂ | Bz | 3,3-diF-Pro- | tBuNH- |
| 4087 | 2-Quin-CO- | MeSOCH₂ | Bz | 3,3-diF-Pro- | tBuNH- |
| 4088 | 2-Quin-CO- | MeSO₂CH₂ | Bz | 3,3-diF-Pro- | tBuNH- |
| 4089 | 2-Quin-CO- | MeOCH₂- | Bz | 3,3-diF-Pro- | tBuNH- |
| 4090 | 2-Quin-CO- | MecCH₂CH₂ | Bz | 3,3-diF-Pro- | tBuNH- |
| 4091 | 2-Quin-CO- | MecCH₂ | Bz | 3,3-diF-Pro- | tBuNH- |
| 4092 | 3-Quin-CO- | MeSOCH₂ | Bz | 3,3-diF-Pro- | tBuNH- |
| 4093 | 3-Quin-CO- | MeSO₂CH₂ | Bz | 3,3-diF-Pro- | tBuNH- |
| 4094 | 3-Quin-CO- | MeOCH₂- | Bz | 3,3-diF-Pro- | tBuNH- |
| 4095 | 3-Quin-CO- | MecCH₂CH₂ | Bz | 3,3-diF-Pro- | tBuNH- |
| 4096 | 3-Quin-CO- | MecCH₂- | Bz | 3,3-diF-Pro- | tBuNH- |
| 4097 | 2-Bfur-CO- | MeSOCH₂- | Bz | 3,3-diF-Pro- | tBuNH- |
| 4098 | 2-Bfur-CO- | MeSO₂CH₂ | Bz | 3,3-diF-Pro- | tBuNH- |
| 4099 | 2-Bfur-CO- | MeOCH₂ | Bz | 3,3-diF-Pro- | tBuNH- |
| 4100 | 2-Bfur-CO- | MecCH₂CH₂ | Bz | 3,3-diF-Pro- | tBuNH- |
| 4101 | 2-Bfur-CO- | MecCH₂ | Bz | 3,3-diF-Pro- | tBuNH- |
| 4102 | 3-Bfur-CO- | MeSOCH₂ | Bz | 3,3-diF-Pro- | tBuNH- |
| 4103 | 3-Bfur-CO- | MeSO₂CH₂ | Bz | 3,3-diF-Pro- | tBuNH- |
| 4104 | 3-Bfur-CO- | MeOCH₂ | Bz | 3,3-diF-Pro- | tBuNH- |
| 4105 | 3-Bfur-CO- | MecCH₂CH₂ | Bz | 3,3-diF-Pro- | tBuNH- |
| 4106 | 3-Bfur-CO- | MecCH₂ | Bz | 3,3-diF-Pro- | tBuNH- |
| 4107 | 3-Ind-CO- | MeSOCH₂ | Bz | 3,3-diF-Pro- | tBuNH- |
| 4108 | 3-Ind-CO- | MeSO₂CH₂ | Bz | 3,3-diF-Pro- | tBuNH- |
| 4109 | 3-Ind-CO- | MeOCH₂ | Bz | 3,3-diF-Pro- | tBuNH- |
| 4110 | 3-Ind-CO- | MecCH₂CH₂ | Bz | 3,3-diF-Pro- | tBuNH- |
| 4111 | 3-Ind-CO- | MecCH₂ | Bz | 3,3-diF-Pro- | tBuNH- |
| 4112 | MPhOAc- | MeSOCH₂ | Bz | 3,3-diF-Pro- | tBuNH- |
| 4113 | MPhOAc- | MeSO₂CH₂ | Bz | 3,3-diF-Pro- | tBuNH- |
| 4114 | MPhOAc- | MeOCH₂ | Bz | 3,3-diF-Pro- | tBuNH- |
| 4115 | MPhOAc- | MecCH₂CH₂ | Bz | 3,3-diF-Pro- | tBuNH- |
| 4116 | MPhOAc- | MecCH₂ | Bz | 3,3-diF-Pro- | tBuNH- |
| 4117 | 5-NH₂-AcO-2-Ind-CO- | MeSOCH₂ | Bz | 3,3-diF-Pro- | tBuNH- |
| 4118 | 5-NH₂-AcO-2-Ind-CO- | MeSO₂CH₂ | Bz | 3,3-diF-Pro- | tBuNH- |
| 4119 | 5-NH₂-AcO-2-Ind-CO- | MeOCH₂ | Bz | 3,3-diF-Pro- | tBuNH- |
| 4120 | 5-NH₂-AcO-2-Ind-CO- | MecCH₂CH₂ | Bz | 3,3-diF-Pro- | tBuNH- |
| 4121 | 5-NH₂-AcO-2-Ind-CO- | MecCH₂ | Bz | 3,3-diF-Pro- | tBuNH- |
| 4122 | 4-NH₂-PhoAc- | MeSOCH₂ | Bz | 3,3-diF-Pro- | tBuNH- |
| 4123 | 4-NH₂-PhoAc- | MeSO₂CH₂ | Bz | 3,3-diF-Pro- | tBuNH- |

TABLE 1-continued

| Cpd. No. | R¹ | R³ | R⁴ | Z | R⁵ |
|---|---|---|---|---|---|
| 4124 | 4-NH₂-PhoAc- | MeOCH₂ | Bz | 3,3-diF-Pro- | tBuNH- |
| 4125 | 4-NH₂-PhoAc- | MecCH₂CH₂ | Bz | 3,3-diF-Pro- | tBuNH- |
| 4126 | 4-NH₂-PhoAc- | MecCH₂ | Bz | 3,3-diF-Pro- | tBuNH- |
| 4127 | 4-[Bzc-NH]-PhoAc- | MeSOCH₂ | Bz | 3,3-diF-Pro- | tBuNH- |
| 4128 | 4-[Bzc-NH]-PhoAc- | MeSO₂CH₂ | Bz | 3,3-diF-Pro- | tBuNH- |
| 4129 | 4-[Bzc-NH]-PhoAc- | MeOCH₂ | Bz | 3,3-diF-Pro- | tBuNH- |
| 4130 | 4-[Bzc-NH]-PhoAc- | MecCH₂CH₂ | Bz | 3,3-diF-Pro- | tBuNH- |
| 4131 | 4-[Bzc-NH]-PhoAc- | MecCH₂ | Bz | 3,3-diF-Pro- | tBuNH- |
| 4132 | 4-[(MorAc)NMe]-PhoAc- | MeSOCH₂ | Bz | 3,3-diF-Pro- | tBuNH- |
| 4133 | 4-[(MorAc)NMe]-PhoAc- | MeSO₂CH₂ | Bz | 3,3-diF-Pro- | tBuNH- |
| 4134 | 4-[(MorAc)NMe]-PhoAc- | MeOCH₂ | Bz | 3,3-diF-Pro- | tBuNH- |
| 4135 | 4-[(MorAc)NMe]-PhoAc- | MecCH₂CH₂ | Bz | 3,3-diF-Pro- | tBuNH- |
| 4136 | 4-[(MorAc)NMe]-PhoAc- | MecCH₂ | Bz | 3,3-diF-Pro- | tBuNH- |
| 4137 | 4-MeO-Bzc | CarCH₂ | Bz | 3,3-diF-Pro- | tBuNH- |
| 4138 | 7-MeO-2-Bfur-CO- | CarCH₂ | Bz | Pro | tBuNH- |
| 4139 | 6-NO₂-2-Quix-CO- | CarCH₂ | Bz | Pro | tBuNH- |
| 4140 | 6-NH₂-2-Quix-CO- | CarCH₂ | Bz | Pro | tBuNH- |
| 4141 | 5-F-2-Ind-CO- | CarCH₂ | Bz | Pro | tBuNH- |
| 4142 | 1-Me-3-Inda-CO- | CarCH₂ | Bz | Pro | tBuNH- |
| 4143 | 4-[Mor-CO-Pipr-Ac-NMe]PhoAc- | CarCH₂ | Bz | Pro | tBuNH- |
| 4144 | 2-Quix-Me | CarCH₂ | Bz | Pro | tBuNH- |
| 4145 | 4-[Pro-NMe]PhoAc | CarCH₂ | Bz | Pro | tBuNH- |
| 4146 | 4-[tBoc-Pro-NMe]-PhoAc- | CarCH₂ | Bz | Pro | tBuNH- |
| 4147 | 4-[Bz-Pipr-Ac-NH)-PhoAc- | CarCH₂ | Bz | Pro | tBuNH- |
| 4148 | 4-[(MorEt-NH)-Ac-NH]PhoAc- | CarCH₂ | Bz | Pro | tBuNH- |
| 4149 | 4-[(MorAc-NH)]-PhoAc- | CarCH₂ | Bz | Pro | tBuNH- |
| 4150 | 4-[Bzc-NH]-cHxO-Ac- | CarCH₂ | Bz | Pro | tBuNH- |
| 4151 | N-Bzc-4-PipO-Ac- | CarCH₂ | Bz | Pro | tBuNH- |
| 4152 | 4-PipO-Ac | CarCH₂ | Bz | Pro | tBuNH- |
| 4153 | 4-[Bz(Bz)N]-cHxO-Ac- | CarCH₂ | Bz | Pro | tBuNH- |
| 4154 | N-Bz-4-PipO-Ac- | CarCH₂ | Bz | Pro | tBuNH- |
| 4155 | 4-[Glu(Me)N]-PhoAc- | | | | |
| 4156 | 4-[(2-Bza-4-Bzc-Byr)-NMe]-PhoAc- | CarCH₂ | Bz | Pro | tBuNH- |
| 4157 | 4-[(3-MorPr-NH-Ac)-NMe]PhoAc | CarCH₂ | Bz | Pro | tBuNH- |
| 4158 | 4-[(3-Me₂N-Pr-NH-Ac)-NMe]-PhoAc- | CarCH₂ | Bz | Pro | tBuNH- |
| 4159 | 4-[(2-HOEt-NH-Ac)-NMe]-PhoAc- | CarCH₂ | Bz | Pro | tBuNH- |
| 4160 | 4-[2-MorEt-NMe]-PhoAc- | CarCH₂ | Bz | Pro | tBuNH- |
| 4161 | 4-[(3-Me₂N-Pr-NH)-CO-NMe]-PhoAc- | CarCH₂ | Bz | Pro | tBuNH- |
| 4162 | 4-[(Mor-CO)-NMe]-Pho-Ac- | CarCH₂ | Bz | Pro | tBuNH- |
| 4163 | 4-[(4-NO₂-Pho)-CO-NMe]-PhoAc- | CarCH₂ | Bz | Pro | tBuNH- |
| 4164 | 4-[N-Bz-Pipr-Ac-NMe]PhoAc- | CarCH₂ | Bz | Pro | tBuNH- |
| 4165 | 4-[Ph(Me)N-Ac-NMe]PhoAc- | CarCH₂ | Bz | Pro | tBuNH- |
| 4166 | 4-[(iPn-NH-Ac)-NMe]PhoAc- | CarCH₂ | Bz | Pro | tBuNH- |
| 4167 | 2-(Bzc-NH)-PhoAc- | CarCH₂ | Bz | Pro | tBuNH- |
| 4168 | 3-(Bzc-NH)-PhoAc- | CarCH₂ | Bz | Pro | tBuNH- |

TABLE 1-continued

| Cpd. No. | R¹ | R³ | R⁴ | Z | R⁵ |
|---|---|---|---|---|---|
| 4169 | 4-[(Me₂N-Ac)-NMe]-PhoAc- | CarCH₂ | Bz | Pro | tBuNH- |
| 4170 | 4-(Bzc-NMe)-PhoAc- | CarCH₂ | Bz | Pro | tBuNH- |
| 4171 | 7-MeO-2-Bfur-CO- | CarCH₂ | Bz | 4-Cl-Pro | tBuNH- |
| 4172 | 6-NO₂-2-Quix-CO- | CarCH₂ | Bz | 4-Cl-Pro | tBuNH- |
| 4173 | 6-NH₂-2-Quix-CO- | CarCH₂ | Bz | 4-Cl-Pro | tBuNH- |
| 4174 | 5-F-2-Ind-CO- | CarCH₂ | Bz | 4-Cl-Pro | tBuNH- |
| 4175 | 1-Me-3-Inda-CO- | CarCH₂ | Bz | 4-Cl-Pro | tBuNH- |
| 4176 | 4-[(Mor-CO-Pipr-Ac)-NMe]-PhoAc- | CarCH₂ | Bz | 4-Cl-Pro | tBuNH- |
| 4177 | 2-Quix-Me | CarCH₂ | Bz | 4-Cl-Pro | tBuNH- |
| 4178 | 4-Pro-NMe]-PhoAc- | CarCH₂ | Bz | 4-Cl-Pro | tBuNH- |
| 4179 | 4-[(tBoc-Pro)-NMe]-PhoAc- | CarCH₂ | Bz | 4-Cl-Pro | tBuNH- |
| 4180 | 4-[(Bz-Pipr-Ac)-NH]-PhoAc- | CarCH | Bz | 4-Cl-Pro | tBuNH- |
| 4181 | 4-[(MorEt-NH-Ac)-NH]PhoAc- | CarCH₂ | Bz | 4-Cl-Pro | tBuNH- |
| 4182 | 4-[(MorAc)-NH]-PhoAc- | CarCH₂ | Bz | 4-Cl-Pro | tBuNH- |
| 4183 | 4-[Bzc-NH]-cHxO-Ac- | CarCH₂ | Bz | 4-Cl-Pro | tBuNH- |
| 4184 | N-Bzc-4-PipO-Ac- | CarCH₂ | Bz | 4-Cl-Pro | tBuNH- |
| 4185 | 4-PipO-Ac- | CarCH₂ | Bz | 4-Cl-Pro | tBuNH- |
| 4186 | 4-[Bz(Bz)N]-cHxO-Ac- | CarCH₂ | Bz | 4-Cl-Pro | tBuNH- |
| 4187 | N-Bz-4-PipO-Ac- | CarCH₂ | Bz | 4-Cl-Pro | tBuNH- |
| 4188 | 4-[Glu(Me)N]-PhoAc- | CarCH₂ | Bz | 4-Cl-Pro | tBuNH- |
| 4189 | 4-[(2-Bza-4-Bzc-Byr)-NMe]-PhoAc- | CarCH₂ | Bz | 4-Cl-Pro | tBuNH- |
| 4190 | 4-[(3-MorPr-NH-Ac)-NMe]-PhoAc- | CarCH₂ | Bz | 4-Cl-Pro | tBuNH- |
| 4191 | 4-[(3-Me₂N-Pr-NH-Ac)-NMe]-PhoAc- | CarCH₂ | Bz | 4-Cl-Pro | tBuNH- |
| 4192 | 4-[(2-HOEt-NH-Ac)-NMe]PhoAc | CarCH₂ | Bz | 4-Cl-Pro | tBuNH- |
| 4193 | 4-[(2-MorEt)-NMe]-PhoAc- | CarCH₂ | Bz | 4-Cl-Pro | tBuNH- |
| 4194 | 4-[(3-Me₂N-Pr-NH-CO)-NMe]-PhoAc- | CarCH₂ | Bz | 4-Cl-Pro | tBuNH- |
| 4195 | 4-[(Mor-CO)-NMe]-PhoAc- | CarCH₂ | Bz | 4-Cl-Pro | tBuNH- |
| 4196 | 4-[(4-NO₂-Pho-CO)-NMe]-PhoAc- | CarCH₂ | Bz | 4-Cl-Pro | tBuNH- |
| 4197 | 4-[(N-Bz-Pipr-Ac)-NMe]-PhoAc- | CarCH₂ | Bz | 4-Cl-Pro | tBuNH- |
| 4198 | 4-[(Ph(Me)N-Ac-NMe]-PhoAc- | CarCH₂ | Bz | 4-Cl-Pro | tBuNH- |
| 4199 | 4-[(iPn-NH-Ac)-NMe]-PhoAc- | CarCH₂ | Bz | 4-Cl-Pro | tBuNH- |
| 4200 | 2-Bzc-NH-PhoAc- | CarCH₂ | Bz | 4-Cl-Pro | tBuNH- |
| 4201 | 3-Bzc-NH-PhoAc- | CarCH₂ | Bz | 4-Cl-Pro | tBuNH- |
| 4202 | 4-[Me₂N-Ac-NMe]-PhoAc- | CarCH₂ | Bz | 4-Cl-Pro | tBuNH- |
| 4203 | 4-(Bzc-NMe]-PhoAc- | CarCH₂ | Bz | 4-Cl-Pro | tBuNH- |
| 4204 | 7-MeO-2-Bfur-CO- | CarCH₂ | Bz | 4-HO-Pro | tBuNH- |
| 4205 | 6-NO₂-2-Quix-CO- | CarCH₂ | Bz | 4-HO-Pro | tBuNH- |
| 4206 | 6-NH₂-2-Quix-CO- | CarCH₂ | Bz | 4-HO-Pro | tBuNH- |
| 4207 | 5-F-2-Ind-CO- | CarCH₂ | Bz | 4-HO-Pro | tBuNH- |
| 4208 | 1-Me-3-Inda-CO- | CarCH₂ | Bz | 4-HO-Pro | tBuNH- |
| 4209 | 4-[(Mor-CO-Pipr-Ac)NMe]-PhoAc- | CarCH₂ | Bz | 4-HO-Pro | tBuNH- |
| 4210 | 2-Quix-Me- | CarCH₂ | Bz | 4-HO-Pro | tBuNH- |
| 4211 | 4-[(Pro-NMe]-PhoAc- | CarCH₂ | Bz | 4-HO-Pro | tBuNH- |
| 4212 | 4-[(tBoc-Pro)-NMe]-PhoAc- | CarCH₂ | Bz | 4-HO-Pro | tBuNH- |

TABLE 1-continued

| Cpd. No. | R¹ | R³ | R⁴ | Z | R⁵ |
|---|---|---|---|---|---|
| 4213 | 4-[(Bz-Pipr-Ac)-NH]-PhoAc- | CarCH₂ | Bz | 4-HO-Pro | tBuNH- |
| 4214 | 4-[(MorEt-NH-Ac)-NH]-PhoAc- | CarCH₂ | Bz | 4-HO-Pro | tBuNH- |
| 4215 | 4-[(Mor-Ac)-NH]-PhoAc- | CarCH₂ | Bz | 4-HO-Pro | tBuNH- |
| 4216 | 4-[Bzc-NH]-cHxO-Ac- | CarCH₂ | Bz | 4-HO-Pro | tBuNH- |
| 4217 | N-Bzc-4-PipO-Ac- | CarCH₂ | Bz | 4-HO-Pro | tBuNH- |
| 4218 | 4-PipO-Ac- | CarCH₂ | Bz | 4-HO-Pro | tBuNH- |
| 4219 | 4-Bz(Bz)N]-cHx-O-Ac- | CarCH₂ | Bz | 4-HO-Pro | tBuNH- |
| 4220 | N-Bz-4-PipO-Ac- | CarCH₂ | Bz | 4-HO-Pro | tBuNH- |
| 4221 | 4-[Glu(Me)N]-PhoAc- | CarCH₂ | Bz | 4-HO-Pro | tBuNH- |
| 4222 | 4-[(2-Bza-4-Bzc-Byr)-NMe]PhoAc- | CarCH₂ | Bz | 4-HO-Pro | tBuNH- |
| 4223 | 4-[(3-MorPr-NH-Ac)-NMe]-PhoAc- | CarCH₂ | Bz | 4-HO-Pro | tBuNH- |
| 4224 | 4-[(3-Me₂N-Pr-NH-Ac)-NMe]-PhoAc- | CarCH₂ | Bz | 4-HO-Pro | tBuNH- |
| 4225 | 4-[(2-HOEt-NH-Ac)-NMe]-PhoAc- | CarCH₂ | Bz | 4-HO-Pro | tBuNH- |
| 4226 | 4-[(2-MorEt)-NMe]-PhoAc- | CarCH₂ | Bz | 4-HO-Pro | tBuNH- |
| 4227 | 4-[(3-Me₂N-Pr-NH-CO)-NMe]-PhoAc- | CarCH₂ | Bz | 4-HO-Pro | tBuNH- |
| 4228 | 4-[(Mor-CO-NMe]-PhoAc- | CarCH₂ | Bz | 4-HO-Pro | tBuNH- |
| 4229 | 4-[(4-NO₂-Pho-CO)-NMe]-PhoAc- | CarCH₂ | Bz | 4-HO-Pro | tBuNH- |
| 4230 | 4-[(N-Bz-Pipr-Ac)-NMe]-PhoAc- | CarCH₂ | Bz | 4-HO-Pro | tBuNH- |
| 4231 | 4-[(Ph(Me)N-Ac)-NMe]-PhoAc- | CarCH₂ | Bz | 4-HO-Pro | tBuNH- |
| 4232 | 4-[(iPn-NH-Ac)-NMe]-PhoAc- | CarCH₂ | Bz | 4-HO-Pro | tBuNH- |
| 4233 | 2-Bzc-NH-PhoAc- | CarCH₂ | Bz | 4-HO-Pro | tBuNH- |
| 4234 | 3-Bzc-NH-PhoAc- | CarCH₂ | Bz | 4-HO-Pro | tBuNH- |
| 4235 | 4-[(Me₂N-Ac)-NMe]-PhoAc- | CarCH₂ | Bz | 4-HO-Pro | tBuNH- |
| 4236 | 4-[Bzc-NMe]-PhoAc- | CarCH₂ | Bz | 4-HO-Pro | tBuNH- |
| 4237 | 7-MeO-2-Bfur-CO- | CarCH₂ | Bz | 3-Cl-Pro | tBuNH- |
| 4238 | 6-NO₂-2-Quix-CO- | CarCH₂ | Bz | 3-Cl-Pro | tBuNH- |
| 4239 | 6-NH₂-2-Quix-CO- | CarCH₂ | Bz | 3-Cl-Pro | tBuNH- |
| 4240 | 5-F-2-Ind-CO- | CarCH₂ | Bz | 3-Cl-Pro | tBuNH- |
| 4241 | 1-Me-3-Inda-CO- | CarCH₂ | Bz | 3-Cl-Pro | tBuNH- |
| 4242 | 4-[(Mor-CO-Pipr-Ac)-NMe]-PhoAc- | CarCH₂ | Bz | 3-Cl-Pro | tBuNH- |
| 4243 | 2-Quix-Me | CarCH₂ | Bz | 3-Cl-Pro | tBuNH- |
| 4244 | 4-[Pro-NMe]-PhoAc- | CarCH₂ | Bz | 3-Cl-Pro | tBuNH- |
| 4245 | 4-[(tBoc-Pro)-NMe]-PhoAc- | CarCH₂ | Bz | 3-Cl-Pro | tBuNH- |
| 4246 | 4-Bz-Pipr-Ac-NH]-PhoAc- | CarCH₂ | Bz | 3-Cl-Pro | tBuNH- |
| 4247 | 4-[(MorEt-NH-Ac)-NH]-PhoAc- | CarCH₂ | Bz | 3-Cl-Pro | tBuNH- |
| 4248 | 4-[Mor-Ac-NH]-PhoAc- | CarCH₂ | Bz | 3-Cl-Pro | tBuNH- |
| 4249 | 4-[Bzc-NH]-cHxO-Ac- | CarCH₂ | Bz | 3-Cl-Pro | tBuNH- |
| 4250 | N-Bzc-4-PipO-Ac- | CarCH₂ | Bz | 3-Cl-Pro | tBuNH- |
| 4251 | 4-PipO-Ac- | CarCH₂ | Bz | 3-Cl-Pro | tBuNH- |
| 4252 | 4-[Bz(Bz)N]-cHx-O-Ac- | CarCH₂ | Bz | 3-Cl-Pro | tBuNH- |
| 4253 | N-Bz-4-PipO-Ac- | CarCH₂ | Bz | 3-Cl-Pro | tBuNH- |
| 4254 | 4-[Glu(Me)N]-PhoAc- | CarCH₂ | Bz | 3-Cl-Pro | tBuNH- |
| 4255 | 4-[(2-Bzc-4-Bzc-Byr)-NMe]-PhoAc- | CarCH₂ | Bz | 3-Cl-Pro | tBuNH- |
| 4256 | 4-[(3-MorPr-NH)-Ac-NMe]-PhoAc- | CarCH₂ | Bz | 3-Cl-Pro | tBuNH- |

TABLE 1-continued

| Cpd. No. | R¹ | R³ | R⁴ | Z | R⁵ |
|---|---|---|---|---|---|
| 4257 | 4-[(3-Me₂N-Pr-NH-Ac)-NMe]-PhoAc- | CarCH₂ | Bz | 3-Cl-Pro | tBuNH- |
| 4258 | 4-[(2-HOEt-NH-Ac)-NMe]-PhoAc- | CarCH₂ | Bz | 3-Cl-Pro | tBuNH- |
| 4259 | 4-[(2-MorEt)-NMe]-PhoAc- | CarCH₂ | Bz | 3-Cl-Pro | tBuNH- |
| 4260 | 4-[(3-Me₂N-Pr-NH-CO)-NMe]-PhoAc- | CarCH₂ | Bz | 3-Cl-Pro | tBuNH- |
| 4261 | 4-[(Mor-CO)-NMe]-PhoAc- | CarCH₂ | Bz | 3-Cl-Pro | tBuNH- |
| 4262 | 4-[(4-NO₂-Pro-CO)-NMe]-PhoAc- | CarCH₂ | Bz | 3-Cl-Pro | tBuNH- |
| 4263 | 4-[(N-Bz-Pipr-Ac)-NMe]-PhoAc- | CarCH₂ | Bz | 3-Cl-Pro | tBuNH- |
| 4264 | 4-[(Ph(Me)N-Ac)-NMe]-PhoAc- | CarCH₂ | Bz | 3-Cl-Pro | tBuNH- |
| 4265 | 4-[(iPn-NH-Ac)-NMe]-PhoAc- | CarCH₂ | Bz | 3-Cl-Pro | tBuNH- |
| 4266 | 2-[Bzc-NH]-PhoAc- | CarCH₂ | Bz | 3-Cl-Pro | tBuNH- |
| 4267 | 3-[Bzc-NH]-PhoAc- | CarCH₂ | Bz | 3-Cl-Pro | tBuNH- |
| 4268 | 4-[(Me₂N-Ac)-NMe]-PhoAc- | CarCH₂ | Bz | 3-Cl-Pro | tBuNH- |
| 4269 | 4-[(Bzc-NMe]-PhoAc- | CarCH₂ | Bz | 3-Cl-Pro | tBuNH- |
| 4270 | 7-MeO-2-Bfur-CO- | CarCH₂ | Bz | 3-HO-Pro | tBuNH- |
| 4271 | 6-NO₂-2-Quix-CO- | CarCH₂ | Bz | 3-HO-Pro | tBuNH- |
| 4272 | 6-NH₂-2-Quix-CO- | CarCH₂ | Bz | 3-HO-Pro | tBuNH- |
| 4273 | 5-F-2-Ind-CO- | CarCH₂ | Bz | 3-HO-Pro | tBuNH- |
| 4274 | 1-Me-3-Inda-CO- | CarCH₂ | Bz | 3-HO-Pro | tBuNH- |
| 4275 | 4-[(Mor-CO-Pipr-Ac)-NMe]-PhoAc- | CarCH₂ | Bz | 3-HO-Pro | tBuNH- |
| 4276 | 2-Quix-Me- | CarCH₂ | Bz | 3-HO-Pro | tBuNH- |
| 4277 | 4-(Pro-NMe]PhoAc- | CarCH₂ | Bz | 3-HO-Pro | tBuNH- |
| 4278 | 4-[(tBoc-Pro)-NMe]-PhoAc- | CarCH₂ | Bz | 3-HO-Pro | tBuNH- |
| 4279 | 4-[(Bz-Pipr-Ac)-NH]-PhoAc- | CarCH₂ | Bz | 3-HO-Pro | tBuNH- |
| 4280 | 4-[(MorEt-NH-Ac)-NH]-PhoAc- | CarCH₂ | Bz | 3-HO-Pro | tBuNH- |
| 4281 | 4-[(Mor-Ac-NH]Pho-Ac- | CarCH₂ | Bz | 3-HO-Pro | tBuNH- |
| 4282 | 4-Bzc-NH-cHxO-Ac- | CarCH₂ | Bz | 3-HO-Pro | tBuNH- |
| 4283 | N-Bzc-4-PipO-Ac- | CarCH₂ | Bz | 3-HO-Pro | tBuNH- |
| 4284 | 4-PipO-Ac- | CarCH₂ | Bz | 3-HO-Pro | tBuNH- |
| 4285 | 4-[Bz(Bz)N]-cHxO-Ac- | CarCH₂ | Bz | 3-HO-Pro | tBuNH- |
| 4286 | N-Bz-4-PipO-Ac- | CarCH₂ | Bz | 3-HO-Pro | tBuNH- |
| 4287 | 4-Glu(Me)N]-PhoAc- | CarCH₂ | Bz | 3-HO-Pro | tBuNH- |
| 4288 | 4-[(2-Bzc-4-Bzc-Byr)-NMe]-PhoAc- | CarCH₂ | Bz | 3-HO-Pro | tBuNH- |
| 4289 | 4-[(3-MorPr-NH-Ac)-NMe]-PhoAc- | CarCH₂ | Bz | 3-HO-Pro | tBuNH- |
| 4290 | 4-[(3-Me₂N-Pr-NH-Ac)-NMe]-PhoAc- | CarCH₂ | Bz | 3-HO-Pro | tBuNH- |
| 4291 | 4-[(2-HOEt-NH-Ac)-NMe]-PhoAc- | CarCH₂ | Bz | 3-HO-Pro | tBuNH- |
| 4292 | 4-[(2-MorEt)-NMe]- | CarCH₂ | Bz | 3-HO-Pro | tBuNH- |
| 4293 | 4-[(3-Me₂N-Pr-NH-CO)-NMe]-PhoAc- | CarCH₂ | Bz | 3-HO-Pro | tBuNH- |
| 4294 | 4-[(Mor-CO)-NMe]-PhoAc- | CarCH₂ | Bz | 3-HO-Pro | tBuNH- |
| 4295 | 4-[(4-NO₂-Pro-CO)-NMe]-PhoAc- | CarCH₂ | Bz | 3-HO-Pro | tBuNH- |
| 4296 | 4-[(N-Bz-Pipr-Ac-NMe]-PhoAc- | CarCH₂ | Bz | 3-HO-Pro | tBuNH- |
| 4297 | 4-[(Ph(Me)N-Ac)-NMe]-PhoAc- | CarCH₂ | Bz | 3-HO-Pro | tBuNH- |
| 4298 | 4-[(iPn-NH-Ac)-NMe]-PhoAc- | CarCH₂ | Bz | 3-HO-Pro | tBuNH- |
| 4299 | 2-[Bzc-NH]-PhoAc- | CarCH₂ | Bz | 3-HO-Pro | tBuNH- |
| 4300 | 3-[Bzc-NH]-PhoAc | CarCH₂ | Bz | 3-HO-Pro | tBuNH- |
| 4301 | 4-[(Me₂N-Ac)-NMe]-PhoAc- | CarCH₂ | Bz | 3-HO-Pro | tBuNH- |
| 4302 | 4-[Bzc-NMe]-PhoAc- | CarCH₂ | Bz | 3-HO-Pro | tBuNH- |
| 4303 | 7-MeO-2-Bfur-CO- | CarCH₂ | Bz | Pro | 1,1-diMe-2-HOEt-NH- |

TABLE 1-continued

| Cpd. No. | R¹ | R³ | R⁴ | Z | R⁵ |
|---|---|---|---|---|---|
| 4304 | 6-NO₂-2-Quix-CO- | CarCH₂ | Bz | Pro | 1,1-diMe-2-HOEt-NH- |
| 4305 | 6-NH₂-2-Quix-CO- | CarCH₂ | Bz | Pro | 1,1-diMe-2-HOEt-NH- |
| 4306 | 5-F-2-Ind-CO- | CarCH₂ | Bz | Pro | 1,1-diMe-2-HOEt-NH- |
| 4307 | 1-Me-3-Inda-CO- | CarCH₂ | Bz | Pro | 1,1-diMe-2-HOEt-NH- |
| 4308 | 4-[(Mor-CO-Pipr-Ac)-NMe)PhoAc- | CarCH₂ | Bz | Pro | 1,1-diMe-2-HOEt-NH- |
| 4309 | 2-Quix-Me- | CarCH₂ | Bz | Pro | 1,1-diMe-2-HOEt-NH- |
| 4310 | 4-[Pro-NMe]PhoAc- | CarCH₂ | Bz | Pro | 1,1-diMe-2-HOEt-NH- |
| 4311 | 4-[(tBoc-Pro)-NMe]-PhoAc- | CarCH₂ | Bz | Pro | 1,1-diMe-2-HOEt-NH- |
| 4312 | 4-[(Bz-Pipr-Ac-NH]-PhoAc- | CarCH₂ | Bz | Pro | 1,1-diMe-2-HOEt-NH- |
| 4313 | 4-[(MorEt-NH-Ac)-NH]-PhoAc- | CarCH₂ | Bz | Pro | 1,1-diMe-2-HOEt-NH- |
| 4314 | 4-[Mor-Ac-NH]-PhoAc- | CarCH₂ | Bz | Pro | 1,1-diMe-2-HOEt-NH- |
| 4315 | 4-[Bzc-NH]-cHxO-Ac- | CarCH₂ | Bz | Pro | 1,1-diMe-2-HOEt-NH- |
| 4316 | N-Bzc-4-PipO-Ac- | CarCH₂ | Bz | Pro | 1,1-diMe-2-HOEt-NH- |
| 4317 | 4-PipO-Ac- | CarCH₂ | Bz | Pro | 1,1-diMe-2-HOEt-NH- |
| 4318 | 4-[Bz(Bz)N]-cHxO-Ac- | CarCH₂ | Bz | Pro | 1,1-diMe-2-HOEt-NH- |
| 4319 | N-Bz-4-PipO-Ac- | CarCH₂ | Bz | Pro | 1,1-diMe-2-HOEt-NH- |
| 4320 | 4-[(Glu(Me)N]-PhoAc- | CarCH₂ | Bz | Pro | 1,1-diMe-2-HOEt-NH- |
| 4321 | 4-[2-Bzc-4-Bzc-Byr)-NMe]-PhoAc- | CarCH₂ | Bz | Pro | 1,1-diMe-2-HOEt-NH- |
| 4322 | 4-[(3-MorPr-NH-Ac)-NMe]-PhoAc- | CarCH₂ | Bz | Pro | 1,1-diMe-2-HOEt-NH- |
| 4323 | 4-[(3-Me₂N-Pr-NH-Ac)-NMe]-PhoAc- | CarCH₂ | Bz | Pro | 1,1-diMe-2-HOEt-NH- |
| 4324 | 4-[(2-HOEt-NH-Ac)-NMe]-PhoAc- | CarCH₂ | Bz | Pro | 1,1-diMe-2-HOEt-NH- |
| 4325 | 4-[(2-MorEt-NMe]-Pho-Ac- | CarCH₂ | Bz | Pro | 1,1-diMe-2-HOEt-NH- |
| 4326 | 4-[(3-Me₂N-Pr-NH-CO)-NMe]-PhoAc- | CarCH₂ | Bz | Pro | 1,1-diMe-2-HOEt-NH- |
| 4327 | 4-[(Mor-CO)-NMe]-PhoAc- | CarCH₂ | Bz | Pro | 1,1-diMe-2-HOEt-NH- |
| 4328 | 4-[(4-NO₂-Pro-CO)-NMe]-PhoAc- | CarCH₂ | Bz | Pro | 1,1-diMe-2-HOEt-NH- |
| 4329 | 4-[(N-Bz-Pipr-Ac)-NMe]-PhoAc- | CarCH₂ | Bz | Pro | 1,1-diMe-2-HOEt-NH- |
| 4330 | 4-(Ph(Me)N-Ac)-NMe]-PhoAc- | CarCH₂ | Bz | Pro | 1,1-diMe-2-HOEt-NH- |
| 4331 | 4-[(iPn-NH-Ac)-NMe]-PhoAc- | CarCH₂ | Bz | Pro | 1,1-diMe-2-HOEt-NH- |
| 4332 | 2-[Bzc-NH]-PhoAc- | CarCH₂ | Bz | Pro | 1,1-diMe-2-HOEt-NH- |
| 4333 | 3-[Bzc-NH]-PhoAc- | CarCH₂ | Bz | Pro | 1,1-diMe-2-HOEt-NH- |
| 4334 | 4-[(Me₂N-Ac)-NMe]-PhoAc- | CarCH₂ | Bz | Pro | 1,1-diMe-2-HOEt-NH- |
| 4335 | 4-[Bzc-NMe]PhoAc- | CarCH₂ | Bz | Pro | 1,1-diMe-2-HOEt-NH- |
| 4336 | 7-MeO-2-Bfur-CO- | CarCH₂ | Bz | 3,4-Deh-Pro | tBuNH- |
| 4337 | 6-NO₂-2-Quix-CO- | CarCH₂ | Bz | 3,4-Deh-Pro | tBuNH- |
| 4338 | 6-NH₂-2-Quix-CO- | CarCH₂ | Bz | 3,4-Deh-Pro | tBuNH- |
| 4339 | 5-F-2-Ind-CO- | CarCH₂ | Bz | 3,4-Deh-Pro | tBuNH- |
| 4340 | 1-Me-3-Inda-CO- | CarCH₂ | Bz | 3,4-Deh-Pro | tBuNH- |
| 4341 | 4-[(Mor-CO-Pipr-Ac)-NMe]-PhoAc- | CarCH₂ | Bz | 3,4-Deh-Pro | tBuNH- |
| 4342 | 2-Quix-Me- | CarCH₂ | Bz | 3,4-Deh-Pro | tBuNH- |
| 4343 | 4-[Pro-NMe]PhoAc- | CarCH₂ | Bz | 3,4-Deh-Pro | tBuNH- |
| 4344 | 4-[(tBoc-Pro)-NMe]-PhoAc- | CarCH₂ | Bz | 3,4-Deh-Pro | tBuNH- |
| 4345 | 4-[(Bz-Pipr-Ac)-NH]-PhoAc- | CarCH₂ | Bz | 3,4-Deh-Pro | tBuNH- |
| 4346 | 4-[(MorEt-NH-Ac)-NH]-PhoAc- | CarCH₂ | Bz | 3,4-Deh-Pro | tBuNH- |
| 4347 | 4-[(MorAc)-NH]-PhoAc- | CarCH₂ | Bz | 3,4-Deh-Pro | tBuNH- |
| 4348 | 4-[Bzc-NH]-cHxO-Ac | CarCH₂ | Bz | 3,4-Deh-Pro | tBuNH- |
| 4349 | N-Bzc-4-PipO-Ac- | CarCH₂ | Bz | 3,4-Deh-Pro | tBuNH- |
| 4350 | 4-PipO-Ac- | CarCH₂ | Bz | 3,4-Deh-Pro | tBuNH- |
| 4351 | 4-[Bz(Bz)N]-cHxO-Ac- | CarCH₂ | Bz | 3,4-Deh-Pro | tBuNH- |
| 4352 | N-Bz-4-PipO-Ac- | CarCH₂ | Bz | 3,4-Deh-Pro | tBuNH- |

TABLE 1-continued

| Cpd. No. | R¹ | R³ | R⁴ | Z | R⁵ |
|---|---|---|---|---|---|
| 4353 | 4-[(Glu(Me)N]-PhoAc- | CarCH₂ | Bz | 3,4-Deh-Pro | tBuNH- |
| 4354 | 4-[(2-Bzc-4-Bzc-Byr)-NMe]-PhoAc- | CarCH₂ | Bz | 3,4-Deh-Pro | tBuNH- |
| 4355 | 4-[(3-MorPr-NH-Ac)-NMe]-PhoAc- | CarCH₂ | Bz | 3,4-Deh-Pro | tBuNH- |
| 4356 | 4-[(3-Me₂N-Pr-NH-Ac)-NMe]-PhoAc- | CarCH₂ | Bz | 3,4-Deh-Pro | tBuNH- |
| 4357 | 4-[(2-HOEt-NH-Ac)-NMe]-PhoAc- | CarCH₂ | Bz | 3,4-Deh-Pro | tBuNH- |
| 4358 | 4-[(2-MorEt)--PhoAc- | CarCH₂ | Bz | 3,4-Deh-Pro | tBuNH- |
| 4359 | 4-[(3-Me₂N-Pr-NH-CO)-NMe]-PhoAc- | CarCH₂ | Bz | 3,4-Deh-Pro | tBuNH- |
| 4360 | 4-[(Mor-CO)-NMe]-PhoAc- | CarCH₂ | Bz | 3,4-Deh-Pro | tBuNH- |
| 4361 | 4-[(4-NO₂-Pro-CO-NMe]-PhoAc- | CarCH₂ | Bz | 3,4-Deh-Pro | tBuNH- |
| 4362 | 4-[(N-Bz-Pipr-Ac)-NMe]-PhoAc- | CarCH₂ | Bz | 3,4-Deh-Pro | tBuNH- |
| 4363 | 4-[(Ph(Me)N-Ac)-NMe]-PhoAc- | CarCH₂ | Bz | 3,4-Deh-Pro | tBuNH- |
| 4364 | 4-[(iPn-NH-Ac)-NMe]-PhoAc- | CarCH₂ | Bz | 3,4-Deh-Pro | tBuNH- |
| 4365 | 2-[Bzc-NH]-PhoAc- | CarCH₂ | Bz | 3,4-Deh-Pro | tBuNH- |
| 4366 | 3-[Bzc-NH]-PhoAc- | CarCH₂ | Bz | 3,4-Deh-Pro | tBuNH- |
| 4367 | 4-[(Me₂N-Ac)-NMe]-PhoAc- | CarCH₂ | Bz | 3,4-Deh-Pro | tBuNH- |
| 4368 | 4-(Bzc-NMe]-PhoAc- | CarCH₂ | Bz | 3,4-Deh-Pro | tBuNH- |
| 4369 | Bzc | CarCH₂ | Bz | 3,4-Deh-Pro | tBuNH- |
| 4370 | Bzc | CarCH₂ | Bz | Pro | 1,1,-diMe-2-HOEt-NH- |
| 4371 | Bzc | 2-ThfO-CH₂ | Bz | 4-Cl-Pro | tBuNH- |
| 4372 | Bzc | MeS(O)CH₂-CH₂ | Bz | 4-Cl-Pro | tBuNH- |
| 4373 | Bzc | diMeOP(O)-CH₂ | Bz | 4-Cl-Pro | tBuNH- |
| 4374 | 1-Me-2-Ind-CO- | CarCH₂ | Bz | Pro | tBuNH- |
| 4375 | 1-Me-2-Ind-CO- | CarCH₂ | Bz | 4-Cl-Pro | tBuNH- |
| 4376 | 1-Me-2-Ind-CO- | CarCH₂ | Bz | 4-HO-Pro | tBuNH- |
| 4377 | 1-Me-2-Ind-CO- | CarCH₂ | Bz | 3-Cl-Pro | tBuNH- |
| 4378 | 1-Me-2-Ind-CO- | CarCH₂ | Bz | 3-HO-Pro | tBuNH- |
| 4379 | 1-Me-2-Ind-CO- | CarCH₂ | Bz | Pro | 1,1-diMe-2-HOEt-NH- |
| 4380 | 1-Me-2-Ind-CO- | CarCH₂ | Bz | 3,4-Deh-Pro | tBuNH- |
| 4381 | Bzc | MeSO₂-CH₂CH₂ | Bz | 4-Cl-Pro | tBuNH- |
| 4382 | 2-Quix-CO- | MeSO₂-CH₂CH₂ | Bz | 4-Cl-Pro | tBuNH- |
| 4383 | 2-Quin-CO- | MeSO₂-CH₂CH₂ | Bz | 4-Cl-Pro | tBuNH- |
| 4384 | 3-Quin-CO- | MeSO₂-CH₂CH₂ | Bz | 4-Cl-Pro | tBuNH- |
| 4385 | 4-Quin-CO- | MeSO₂-CH₂CH₂ | Bz | 4-Cl-Pro | tBuNH- |
| 4386 | 2-Bfur-CO- | MeSO₂CH₂CH₂ | Bz | 4-Cl-Pro | tBuNH- |
| 4387 | 3-Bfur-CO- | MeSO₂CH₂CH₂ | Bz | 4-Cl-Pro | tBuNH- |
| 4388 | 2-Ind-CO- | MeSO₂CH₂CH₂ | Bz | 4-Cl-Pro | tBuNH- |
| 4389 | tBoc | MeSO₂CH₂CH₂ | Bz | 4-Cl-Pro | tBuNH- |
| 4390 | PhoAc- | MeSO₂CH₂CH₂ | Bz | 4-Cl-Pro | tBuNH- |
| 4391 | 4-MPhOAc- | MeSO₂CH₂CH₂ | Bz | 4-Cl-Pro | tBuNH- |
| 4392 | 3-Bzisox-CO- | MeSO₂CH₂CH₂ | Bz | 4-Cl-Pro | tBuNH- |
| 4393 | 5-H₂N-AcO-2-Ind-CO- | MeSO₂CH₂CH | Bz | 4-Cl-Pro | tBuNH- |
| 4394 | 4-NH₂-Pho-Ac- | MeSO₂CH₂CH₂ | Bz | 4-Cl-Pro | tBuNH- |
| 4395 | 4-NH₂-Bzc | MeSO₂CH₂CH₂ | Bz | 4-Cl-Pro | tBuNH- |
| 4396 | 4-Me₂N-Pho-Ac- | MeSO₂CH₂CH₂ | Bz | 4-Cl-Pro | tBuNH- |
| 4397 | 4-MeNH-PhoAc- | MeSO₂CH₂CH₂ | Bz | 4-Cl-Pro | tBuNH- |
| 4398 | 4-[Bzc-NH]-PhoAc- | MeSO₂CH₂CH₂ | Bz | 4-Cl-Pro | tBuNH- |
| 4399 | 4-[Gly-NH]-PhoAc- | MeSO₂CH₂CH₂ | Bz | 4-Cl-Pro | tBuNH- |

TABLE 1-continued

| Cpd. No. | R¹ | R³ | R⁴ | Z | R⁵ |
|---|---|---|---|---|---|
| 4400 | 4-[Gly-NMe]-PhoAc- | MeSO₂CH₂CH₂ | Bz | 4-Cl-Pro | tBuNH- |
| 4401 | 4-[Sar-NMe]-PhoAc- | MeSO₂CH₂CH₂ | Bz | 4-Cl-Pro | tBuNH- |
| 4402 | 4-[(MorAc)-NMe]-PhoAc- | MeSO₂CH₂CH₂ | Bz | 4-Cl-Pro | tBuNH- |
| 4403 | 7-MeO-2-Bfur-CO- | MeSO₂CH₂CH₂ | Bz | 4-Cl-Pro | tBuNH- |
| 4404 | 6-NO₂-2-Quix-CO- | MeSO₂CH₂CH₂ | Bz | 4-Cl-Pro | tBuNH- |
| 4405 | 6-NH₂-2-Quix-CO- | MeSO₂CH₂CH₂ | Bz | 4-Cl-Pro | tBuNH- |
| 4406 | 5-F-2-Ind-CO- | MeSO₂CH₂CH₂ | Bz | 4-Cl-Pro | tBuNH- |
| 4407 | 1-Me-3-Inda-CO- | MeSO₂CH₂CH₂ | Bz | 4-Cl-Pro | tBuNH- |
| 4408 | 4-[(Mor-CO-Pipr-Ac)-NMe]-PhoAc- | MeSO₂CH₂CH₂ | Bz | 4-Cl-Pro | tBuNH- |
| 4409 | 4-[(N-tBoc-Pro)-NMe]-PhoAc- | MeSO₂CH₂CH₂ | Bz | 4-Cl-Pro | tBuNH- |
| 4410 | 4-[(Bz-Pipr-Ac)-NH)-PhoAc- | MeSO₂CH₂CH₂ | Bz | 4-Cl-Pro | tBuNH- |
| 4411 | 4-[(MorEt-NH-Ac)-NH]-PhoAc- | MeSO₂CH₂CH₂ | Bz | 4-Cl-Pro | tBuNH- |
| 4412 | 4-[MorAc-NH]-PhoAc- | MeSO₂CH₂CH₂ | Bz | 4-Cl-Pro | tBuNH- |
| 4413 | 4-[Bzc-NH]-cHxO-Ac- | MeSO₂CH₂CH₂ | Bz | 4-Cl-Pro | tBuNH- |
| 4414 | N-Bzc-4-PipO-Ac- | MeSO₂CH₂CH₂ | Bz | 4-Cl-Pro | tBuNH- |
| 4415 | 4-[(2-MorEt)-NMe]-PhoAc- | MeSO₂CH₂CH₂ | Bz | 4-Cl-Pro | tBuNH- |
| 4416 | 4-[(3-Me₂N-Pr-NH-CO)-NMe]-PhoAc- | MeSO₂CH₂CH₂ | Bz | 4-Cl-Pro | tBuNH- |
| 4417 | 4-[(Mor-CO-NMe]-PhoAc- | MeSO₂CH₂CH₂ | Bz | 4-Cl-Pro | tBuNH- |
| 4418 | 4-[(4-NO₂-Pho-CO)NMe]-PhoAc | MeSO₂CH₂CH₂ | Bz | 4-Cl-Pro | tBuNH- |
| 4419 | 4-[(N-Bz-Pipr-Ac)-NMe]-PhoAc- | MeSO₂CH₂CH₂ | Bz | 4-Cl-Pro | tBuNH- |
| 4420 | 2-NH₂-PhoAc- | MeSO₂CH₂CH₂ | Bz | 4-Cl-Pro | tBuNH- |
| 4421 | 3-NH₂-PhoAc- | MeSO₂CH₂CH₂ | Bz | 4-Cl-Pro | tBuNH- |
| 4422 | 1-Me-2-Ind-CO- | MeSO₂CH₂CH₂ | Bz | 4-Cl-Pro | tBuNH- |
| 4423 | Bzc | OH₂= | Bz | 4-Cl-Pro | tBuNH- |
| 4424 | Bzc | NH₂CO₂CH₂ | Bz | 4-Cl-Pro | tBuNH- |
| 4425 | 2-Quix-CO- | NH₂CO₂CH₂ | Bz | 4-Cl-Pro | tBuNH- |
| 4426 | 2-Quin-CO- | NH₂CO₂CH₂ | Bz | 4-Cl-Pro | tBuNH- |
| 4427 | 3-Quin-CO- | NH₂CO₂CH₂ | Bz | 4-Cl-Pro | tBuNH- |
| 4428 | 4-Quin-CO- | NH₂CO₂CH₂ | Bz | 4-Cl-Pro | tBuNH- |
| 4429 | 2-Bfur-CO- | NH₂CO₂CH₂ | Bz | 4-Cl-Pro | tBuNH- |
| 4430 | 3-Bfur-CO- | NH₂CO₂CH₂ | Bz | 4-Cl-Pro | tBuNH- |
| 4431 | 2-Ind-CO- | NH₂CO₂CH₂ | Bz | 4-Cl-Pro | tBuNH- |
| 4432 | tBoc | NH₂CO₂CH₂ | Bz | 4-Cl-Pro | tBuNH- |
| 4433 | PhoAc- | NH₂CO₂CH₂ | Bz | 4-Cl-Pro | tBuNH- |
| 4434 | 4-MPhOAc- | NH₂CO₂CH₂ | Bz | 4-Cl-Pro | tBuNH- |
| 4435 | 3-Bzisox-CO- | NH₂CO₂CH₂ | Bz | 4-Cl-Pro | tBuNH- |
| 4436 | 5-H₂N-AcO-2-Ind-CO- | NH₂CO₂CH₂ | Bz | 4-Cl-Pro | tBuNH- |
| 4437 | 4-NH₂-PhoAc- | NH₂CO₂CH₂ | Bz | 4-Cl-Pro | tBuNH- |
| 4438 | 4-NH₂-Bzc | NH₂CO₂CH₂ | Bz | 4-Cl-Pro | tBuNH- |
| 4439 | 4-Me₂N-PhoAc | NH₂CO₂CH₂ | Bz | 4-Cl-Pro | tBuNH- |
| 4440 | 4-MeNH-PhoAc- | NH₂CO₂CH₂ | Bz | 4-Cl-Pro | tBuNH- |
| 4441 | 4-[Bzc-NH]-PhoAc- | NH₂CO₂CH₂ | Bz | 4-Cl-Pro | tBuNH- |
| 4442 | 4-[Gly-NH]-PhoAc- | NH₂CO₂CH₂ | Bz | 4-Cl-Pro | tBuNH- |
| 4443 | 4-[Gly-NMe]-PhoAc- | NH₂CO₂CH₂ | Bz | 4-Cl-Pro | tBuNH- |
| 4444 | 4-[Sar-NMe]-PhoAc- | NH₂CO₂CH₂ | Bz | 4-Cl-Pro | tBuNH- |
| 4445 | 4-[(MorAc)-NMe]-PhoAc- | NH₂CO₂CH₂ | Bz | 4-Cl-Pro | tBuNH- |
| 4446 | 7-MeO-2-Bfur-CO- | NH₂CO₂CH₂ | Bz | 4-Cl-Pro | tBuNH- |
| 4447 | 6-NO₂-2-Quix-CO- | NH₂CO₂CH₂ | Bz | 4-Cl-Pro | tBuNH- |

TABLE 1-continued

| Cpd. No. | R¹ | R³ | R⁴ | Z | R⁵ |
|---|---|---|---|---|---|
| 4448 | 6-NH₂-2-Quix-CO- | NH₂CO₂CH₂ | Bz | 4-Cl-Pro | tBuNH- |
| 4449 | 5-F-2-Ind-CO- | NH₂CO₂CH₂ | Bz | 4-Cl-Pro | tBuNH- |
| 4450 | 1-Me-3-Inda-CO- | NH₂CO₂CH₂ | Bz | 4-Cl-Pro | tBuNH- |
| 4451 | 4-[(Mor-CO-Pipr-Ac)-NMe]-PhoAc- | NH₂CO₂CH₂ | Bz | 4-Cl-Pro | tBuNH- |
| 4452 | 4-[(N-tBoc-Pro)-NMe]-PhoAc- | NH₂CO₂CH₂ | Bz | 4-Cl-Pro | tBuNH- |
| 4453 | 4-[(Bz-Pipr-Ac)-NH]-PhoAc- | NH₂CO₂CH₂ | Bz | 4-Cl-Pro | tBuNH- |
| 4454 | 4-[(MorEt-NH-Ac)-NH]-PhoAc- | NH₂CO₂CH₂ | Bz | 4-Cl-Pro | tBuNH- |
| 4455 | 4-[MorAc-NH]-PhoAc- | NH₂CO₂CH₂ | Bz | 4-Cl-Pro | tBuNH- |
| 4456 | 4-[Bzc-NH]-cHxO-Ac- | NH₂CO₂CH₂ | Bz | 4-Cl-Pro | tBuNH- |
| 4457 | N-Bzc-4-PipO-Ac- | NH₂CO₂CH₂ | Bz | 4-Cl-Pro | tBuNH- |
| 4458 | 4-[(2-MorEt)-NMe]-PhoAc- | NH₂CO₂CH₂ | Bz | 4-Cl-Pro | tBuNH- |
| 4459 | 4-[(3-Me₂N-Pr-NH-CO)-NMe]-PhoAc- | NH₂CO₂CH₂ | Bz | 4-Cl-Pro | tBuNH- |
| 4460 | 4-[(Mor-CO)-NMe]-PhoAc- | NH₂CO₂CH₂ | Bz | 4-Cl-Pro | tBuNH- |
| 4461 | 4-[(4-NO₂-Pho-CO)-NMe]-PhoAc- | NH₂CO₂CH₂ | Bz | 4-Cl-Pro | tBuNH- |
| 4462 | 4-[(N-Bz-Pipr-Ac)-NMe]-PhoAc- | NH₂CO₂CH₂ | Bz | 4-Cl-Pro | tBuNH- |
| 4463 | 2-NH₂-PhoAc- | NH₂CO₂CH₂ | Bz | 4-Cl-Pro | tBuNH- |
| 4464 | 3-NH₂-PhoAc- | NH₂CO₂CH₂ | Bz | 4-Cl-Pro | tBuNH- |
| 4465 | 1-Me-2-Ind-CO- | NH₂CO₂CH₂ | Bz | 4-Cl-Pro | tBuNH- |
| 4466 | Bzc | NH₂SO₂CH₂CH₂ | Bz | 4-Cl-Pro | tBuNH- |
| 4467 | 2-Quix-CO- | NH₂SO₂CH₂CH₂ | Bz | 4-Cl-Pro | tBuNH- |
| 4468 | 2-Quin-CO- | NH₂SO₂CH₂CH₂ | Bz | 4-Cl-Pro | tBuNH- |
| 4469 | 3-Quin-CO- | NH₂SO₂CH₂CH₂ | Bz | 4-Cl-Pro | tBuNH- |
| 4470 | 4-Quin-CO- | NH₂SO₂CH₂CH₂ | Bz | 4-Cl-Pro | tBuNH- |
| 4471 | 2-Bfur-CO- | NH₂SO₂CH₂CH₂ | Bz | 4-Cl-Pro | tBuNH- |
| 4472 | 3-Bfur-CO- | NH₂SO₂CH₂CH₂ | Bz | 4-Cl-Pro | tBuNH- |
| 4473 | 2-Ind-CO- | NH₂SO₂CH₂CH₂ | Bz | 4-Cl-Pro | tBuNH- |
| 4474 | tBoc | NH₂SO₂CH₂CH₂ | Bz | 4-Cl-Pro | tBuNH- |
| 4475 | PhoAc- | NH₂SO₂CH₂CH₂ | Bz | 4-Cl-Pro | tBuNH- |
| 4476 | 4-MPhOAc- | NH₂SO₂CH₂CH₂ | Bz | 4-Cl-Pro | tBuNH- |
| 4477 | 3-Bzisox-CO- | NH₂SO₂CH₂CH₂ | Bz | 4-Cl-Pro | tBuNH- |
| 4478 | 5-H₂N-AcO-2-Ind-CO- | NH₂SO₂CH₂CH₂ | Bz | 4-Cl-Pro | tBuNH- |
| 4479 | 4-NH₂-PhoAc- | NH₂SO₂CH₂CH₂ | Bz | 4-Cl-Pro | tBuNH- |
| 4480 | 4-NH₂-Bzc | NH₂SO₂CH₂CH₂ | Bz | 4-Cl-Pro | tBuNH- |
| 4481 | 4-Me₂N-Pho-Ac- | NH₂SO₂CH₂CH₂ | Bz | 4-Cl-Pro | tBuNH- |
| 4482 | 4-MeNH-PhoAc- | NH₂SO₂CH₂CH₂ | Bz | 4-Cl-Pro | tBuNH- |
| 4483 | 4-[Bzc-NH]-PhoAc- | NH₂SO₂CH₂CH₂ | Bz | 4-Cl-Pro | tBuNH- |
| 4484 | 4-[Gly-NH]-PhoAc- | NH₂SO₂CH₂CH₂ | Bz | 4-Cl-Pro | tBuNH- |
| 4485 | 4-[Gly-NMe]-PhoAc- | NH₂SO₂CH₂CH₂ | Bz | 4-Cl-Pro | tBuNH- |
| 4486 | 4-[Sar-NMe]-PhoAc- | NH₂SO₂CH₂CH₂ | Bz | 4-Cl-Pro | tBuNH- |
| 4487 | 4-[(MorAc)-NMe]-PhoAc- | NH₂SO₂CH₂CH₂ | Bz | 4-Cl-Pro | tBuNH- |
| 4488 | 7-MeO-2-Bfur-CO- | NH₂SO₂CH₂CH₂ | Bz | 4-Cl-Pro | tBuNH- |
| 4489 | 6-NO₂-2-Quix-CO- | NH₂SO₂CH₂CH₂ | Bz | 4-Cl-Pro | tBuNH- |
| 4490 | 6-NH₂-2-Quix-CO- | NH₂SO₂CH₂CH₂ | Bz | 4-Cl-Pro | tBuNH- |
| 4491 | 5-F-2-Ind-CO- | NH₂SO₂CH₂CH₂ | Bz | 4-Cl-Pro | tBuNH- |
| 4492 | 1-Me-3-Inda-CO- | NH₂SO₂CH₂CH₂ | Bz | 4-Cl-Pro | tBuNH- |
| 4493 | 4-[(Mor-CO-Pipr-Ac)-NMe]-PhoAc- | NH₂SO₂CH₂CH₂ | Bz | 4-Cl-Pro | tBuNH- |
| 4494 | 4-[(N-tBoc-Pro-NMe]-PhoAc- | NH₂SO₂CH₂CH₂ | Bz | 4-Cl-Pro | tBuNH- |
| 4495 | 4-[(Bz-Pipr-Ac)-NH]-PhoAc- | NH₂SO₂CH₂CH₂ | Bz | 4-Cl-Pro | tBuNH- |

TABLE 1-continued

| Cpd. No. | R¹ | R³ | R⁴ | Z | R⁵ |
|---|---|---|---|---|---|
| 4496 | 4-[(MorEt-NH-Ac)-NH]-PhoAc- | NH₂SO₂CH₂CH₂ | Bz | 4-Cl-Pro | tBuNH- |
| 4497 | 4-[(MorAc)-NH]-PhoAc- | NH₂SO₂CH₂CH₂ | Bz | 4-Cl-Pro | tBuNH- |
| 4498 | 4-Bzc-NH-cHx-O-Ac- | NH₂SO₂CH₂CH₂ | Bz | 4-Cl-Pro | tBuNH- |
| 4499 | N-Bzc-4-PipO-Ac- | NH₂SO₂CH₂CH₂ | Bz | 4-Cl-Pro | tBuNH- |
| 4500 | 4-[(2-MorEt)-NMe]-PhoAc- | NH₂SO₂CH₂CH₂ | Bz | 4-Cl-Pro | tBuNH- |
| 4501 | 4-[(3-Me₂N-Pr-NH-CO)-NMe]-PhoAc- | NH₂SO₂CH₂CH₂ | Bz | 4-Cl-Pro | tBuNH- |
| 4502 | 4-[(Mor-CO)-NMe]-PhoAc- | NH₂SO₂CH₂CH₂ | Bz | 4-Cl-Pro | tBuNH- |
| 4503 | 4-[(4-NO₂-Pho-CO)-NMe]-PhoAc- | NH₂SO₂CH₂CH₂ | Bz | 4-Cl-Pro | tBuNH- |
| 4504 | 4-[(N-Bz-Pipr-Ac)-NMe]-PhoAc- | NH₂SO₂CH₂CH₂ | Bz | 4-Cl-Pro | tBuNH- |
| 4505 | 2-NH₂-PhoAc- | NH₂SO₂CH₂CH₂ | Bz | 4-Cl-Pro | tBuNH- |
| 4506 | 3-NH₂-PhoAc- | NH₂SO₂CH₂CH₂ | Bz | 4-Cl-Pro | tBuNH- |
| 4507 | 1-Me-2-Ind-CO- | NH₂SO₂CH₂CH₂ | Bz | 4-Cl-Pro | tBuNH- |
| 4508 | Bzc | NH₂SO₂CH₂CH₂ | Bz | 4-Cl-Pro | 1,1-diMe-2-HOEt-NH- |
| 4509 | 2-Quix-CO- | NH₂SO₂CH₂CH₂ | Bz | 4-Cl-Pro | 1,1-diMe-2-HOEt-NH- |
| 4510 | 2-Quin-CO- | NH₂SO₂CH₂CH₂ | Bz | 4-Cl-Pro | 1,1-diMe-2-HOEt-NH- |
| 4511 | 3-Quin-CO- | NH₂SO₂CH₂CH₂ | Bz | 4-Cl-Pro | 1,1-diMe-2-HOEt-NH- |
| 4512 | 4-Quin-CO- | NH₂SO₂CH₂CH₂ | Bz | 4-Cl-Pro | 1,1-diMe-2-HOEt-NH- |
| 4513 | 2-Bfur-CO- | NH₂SO₂CH₂CH₂ | Bz | 4-Cl-Pro | 1,1-diMe-2-HOEt-NH- |
| 4514 | 3-Bfur-CO- | NH₂SO₂CH₂CH₂ | Bz | 4-Cl-Pro | 1,1-diMe-2-HOEt-NH- |
| 4515 | 2-Ind-CO- | NH₂SO₂CH₂CH₂ | Bz | 4-Cl-Pro | 1,1-diMe-2-HOEt-NH- |
| 4516 | tBoc | NH₂SO₂CH₂CH₂ | Bz | 4-Cl-Pro | 1,1-diMe-2-HOEt-NH- |
| 4517 | PhoAc- | NH₂SO₂CH₂CH₂ | Bz | 4-Cl-Pro | 1,1-diMe-2-HOEt-NH- |
| 4518 | 4-MPhOAc- | NH₂SO₂CH₂CH₂ | Bz | 4-Cl-Pro | 1,1-diMe-2-HOEt-NH- |
| 4519 | 3-Bzisox-CO- | NH₂SO₂CH₂CH₂ | Bz | 4-Cl-Pro | 1,1-diMe-2-HOEt-NH- |
| 4520 | 5-H₂N-AcO-2-Ind-CO- | NH₂SO₂CH₂CH₂ | Bz | 4-Cl-Pro | 1,1-diMe-2-HOEt-NH- |
| 4521 | 4-NH₂-PhoAc- | NH₂SO₂CH₂CH₂ | Bz | 4-Cl-Pro | 1,1-diMe-2-HOEt-NH- |
| 4522 | 4-NH₂-Bzc | NH₂SO₂CH₂CH₂ | Bz | 4-Cl-Pro | 1,1-diMe-2-HOEt-NH- |
| 4523 | 4-Me₂N-PhoAc- | NH₂SO₂CH₂CH₂ | Bz | 4-Cl-Pro | 1,1-diMe-2-HOEt-NH- |
| 4524 | 4-MeNH-PhoAc- | NH₂SO₂CH₂CH₂ | Bz | 4-Cl-Pro | 1,1-diMe-2-HOEt-NH- |
| 4525 | 4-[Bzc-NH]-PhoAc- | NH₂SO₂CH₂CH₂ | Bz | 4-Cl-Pro | 1,1-diMe-2-HOEt-NH- |
| 4526 | 4-[Gly-NH]PhoAc- | NH₂SO₂CH₂CH₂ | Bz | 4-Cl-Pro | 1,1-diMe-2-HOEt-NH- |
| 4527 | 4-[Gly-NMe]-PhoAc- | NH₂SO₂CH₂CH₂ | Bz | 4-Cl-Pro | 1,1-diMe-2-HOEt-NH- |
| 4528 | 4-[Sar-NMe]-PhoAc- | NH₂SO₂CH₂CH₂ | Bz | 4-Cl-Pro | 1,1-diMe-2-HOEt-NH- |
| 4529 | 4-[(MorAc-NMe]-PhoAc- | NH₂SO₂CH₂CH₂ | Bz | 4-Cl-Pro | 1,1-diMe-2-HOEt-NH- |
| 4530 | 7-MeO-2-Bfur-CO- | NH₂SO₂CH₂CH₂ | Bz | 4-Cl-Pro | 1,1-diMe-2-HOEt-NH- |
| 4531 | 6-NO₂-2-Quix-CO- | NH₂SO₂CH₂CH₂ | Bz | 4-Cl-Pro | 1,1-diMe-2-HOEt-NH- |
| 4532 | 6-NH₂-2-Quix-CO- | NH₂SO₂CH₂CH₂ | Bz | 4-Cl-Pro | 1,1-diMe-2-2-HOEt-NH- |
| 4533 | 5-F-2-Ind-CO- | NH₂SO₂CH₂CH₂ | Bz | 4-Cl-Pro | 1,1-diMe-2-HOEt-NH- |
| 4534 | 1-Me-3-Inda-CO- | NH₂SO₂CH₂CH₂ | Bz | 4-Cl-Pro | 1,1-diMe-2-HOEt-NH- |

TABLE 1-continued

| Cpd. No. | R¹ | R³ | R⁴ | Z | R⁵ |
|---|---|---|---|---|---|
| 4535 | 4-[(Mor-CO-Pipr-Ac)-NMe]-PhoAc- | NH₂SO₂CH₂CH₂ | Bz | 4-Cl-Pro | 1,1-diMe-2-HOEt-NH- |
| 4536 | 4-[(N-tBoc-Pro-NMe)PhoAc | NH₂SO₂CH₂CH₂ | Bz | 4-Cl-Pro | 1,1-diMe-2-HOEt-NH- |
| 4537 | 4-[(Bz-Pipr-Ac-NH]-PhoAc- | NH₂SO₂CH₂CH₂ | Bz | 4-Cl-Pro | 1,1-diMe-2-HOEt-NH- |
| 4538 | 4-[(MorEt-NH-Ac-NH)PhoAc- | NH₂SO₂CH₂CH₂ | Bz | 4-Cl-Pro | 1,1-diMe-2-HOEt-NH- |
| 4539 | 4-[MorAc-NH]-PhoAc- | NH₂SO₂CH₂CH₂ | Bz | 4-Cl-Pro | 1,1-diMe-2-HOEt-NH- |
| 4540 | 4-[Bzc-NH]-cHxO-Ac- | NH₂SO₂CH₂CH₂ | Bz | 4-Cl-Pro | 1,1-diMe-2-HOEt-NH- |
| 4541 | N-Bzc-4-Pip-O-Ac- | NH₂SO₂CH₂CH₂ | Bz | 4-Cl-Pro | 1,1-diMe-2-HOEt-NH- |
| 4542 | 4-[(2-MorEt)-NMe]-PhoAc- | NH₂SO₂CH₂CH₂ | Bz | 4-Cl-Pro | 1,1-diMe-2-HOEt-NH- |
| 4543 | 4-[(3-Me₂N-Pr-NH-CO)-NMe]-PhoAc- | NH₂SO₂CH₂CH₂ | Bz | 4-Cl-Pro | 1,1-diMe-2-HOEt-NH- |
| 4544 | 4-[(Mor-CO-NMe]-PhoAc- | NH₂SO₂CH₂CH₂ | Bz | 4-Cl-Pro | 1,1-diMe-2-HOEt-NH- |
| 4545 | 4-[(4-NO₂-Pho-CO)-NMe]-PhoAc- | NH₂SO₂CH₂CH₂ | Bz | 4-Cl-Pro | 1,1-diMe-2-HOEt-NH- |
| 4546 | 4-[(N-Bz-Pipr-Ac)-NMe]-PhoAc- | NH₂SO₂CH₂CH₂ | Bz | 4-Cl-Pro | 1,1-diMe-2-HOEt-NH- |
| 4547 | 2-NH₂-PhoAc- | NH₂SO₂CH₂CH₂ | Bz | 4-Cl-Pro | 1,1-diMe-2-HOEt-NH- |
| 4548 | 3-NH₂-PhoAc- | NH₂SO₂CH₂CH₂ | Bz | 4-Cl-Pro | 1,1-diMe-2-HOEt-NH- |
| 4549 | 1-Me-2-Ind-CO- | NH₂SO₂CH₂CH₂ | Bz | 4-Cl-Pro | 1,1-diMe-2-HOEt-NH- |
| 4550 | 2-Quin-CO- | CarCH₂ | Bz | 2-Pip-CO- | t-BuO- |
| 4551 | Bzc | MeSCH₂CH₂ | Bz | 4-Cl-Pro | tBuNH- |
| 4552 | 2-Quix-CO- | MeSCH₂CH₂ | Bz | 4-Cl-Pro | tBuNH- |
| 4553 | 2-Quin-CO- | MeSCH₂CH₂ | Bz | 4-Cl-Pro | tBuNH- |
| 4554 | 3-Quin-CO- | MeSCH₂CH₂ | Bz | 4-Cl-Pro | tBuNH- |
| 4555 | 4-Quin-CO- | MeSCH₂CH₂ | Bz | 4-Cl-Pro | tBuNH- |
| 4556 | 2-Bfur-CO- | MeSCH₂CH₂ | Bz | 4-Cl-Pro | tBuNH- |
| 4557 | 3-Bfur-CO- | MeSCH₂CH₂ | Bz | 4-Cl-Pro | tBuNH- |
| 4558 | 2-Ind-CO- | MeSCH₂CH₂ | Bz | 4-Cl-Pro | tBuNH- |
| 4559 | tBoc | MeSCH₂CH₂ | Bz | 4-Cl-Pro | tBuNH- |
| 4560 | PhoAc- | MeSCH₂CH₂ | Bz | 4-Cl-Pro | tBuNH- |
| 4561 | 4-MPhOAc- | MeSCH₂CH₂ | Bz | 4-Cl-Pro | tBuNH- |
| 4562 | 3-Bzisox-CO- | MeSCH₂CH₂ | Bz | 4-Cl-Pro | tBuNH- |
| 4563 | 5-H₂N-AcO-2-Ind-CO- | MeSCH₂CH₂ | Bz | 4-Cl-Pro | tBuNH- |
| 4564 | 4-NH₂-PhoAc- | MeSCH₂CH₂ | Bz | 4-Cl-Pro | tBuNH- |
| 4565 | 4-NH₂-Bzc | MeSCH₂CH₂ | Bz | 4-Cl-Pro | tBuNH- |
| 4566 | 4-Me₂N-PhoAc- | MeSCH₂CH₂ | Bz | 4-Cl-Pro | tBuNH- |
| 4567 | 4-MeNH-PhoAc- | MeSCH₂CH₂ | Bz | 4-Cl-Pro | tBuNH- |
| 4568 | 4-[Bzc-NH]-PhoAc- | MeSCH₂CH₂ | Bz | 4-Cl-Pro | tBuNH- |
| 4569 | 4-[Gly-NH]PhoAc- | MeSCH₂CH₂ | Bz | 4-Cl-Pro | tBuNH- |
| 4570 | 4-[Gly-NMe]PhoAc- | MeSCH₂CH₂ | Bz | 4-Cl-Pro | tBuNH- |
| 4571 | 4-Sar-NMe]PhoAc- | MeSCH₂CH₂ | Bz | 4-Cl-Pro | tBuNH- |
| 4572 | 4-[(MorAc)-NMe]-PhoAc- | MeSCH₂CH₂ | Bz | 4-Cl-Pro | tBuNH- |
| 4573 | 7-MeO-2-Bfur-CO- | MeSCH₂CH₂ | Bz | 4-Cl-Pro | tBuNH- |
| 4574 | 6-NO₂-2-Quix-CO- | MeSCH₂CH₂ | Bz | 4-Cl-Pro | tBuNH- |
| 4575 | 6-NH₂-2-Quix-CO- | MeSCH₂CH₂ | Bz | 4-Cl-Pro | tBuNH- |
| 4576 | 5-F-2-Ind-CO- | MeSCH₂CH₂ | Bz | 4-Cl-Pro | tBuNH- |
| 4577 | 1-Me-3-Inda-CO- | MeSCH₂CH₂ | Bz | 4-Cl-Pro | tBuNH- |
| 4578 | 4-[(Mor-CO-Pipr-Ac)-NMe]PhoAc- | MeSCH₂CH₂ | Bz | 4-Cl-Pro | tBuNH- |
| 4579 | 4-[(N-tBoc-Pro-NMe]PhoAc- | MeSCH₂CH₂ | Bz | 4-Cl-Pro | tBuNH- |
| 4580 | 4-[(Bz-Pipr-Ac)-NH]PhoAc- | MeSCH₂CH₂ | Bz | 4-Cl-Pro | tBuNH- |
| 4581 | 4-[(MorEt-NH-Ac)-NH]PhoAc- | MeSCH₂CH₂ | Bz | 4-Cl-Pro | tBuNH- |
| 4582 | 4-[Mor-Ac-NH]-PhoAc- | MeSCH₂CH₂ | Bz | 4-Cl-Pro | tBuNH- |
| 4583 | 4-[Bzc-NH]-cHx-O-Ac- | MeSCH₂CH₂ | Bz | 4-Cl-Pro | tBuNH- |
| 4584 | N-Bzc-4-PipO-Ac- | MeSCH₂CH₂ | Bz | 4-Cl-Pro | tBuNH- |
| 4585 | 4-[(2-MorEt)-NMe]-PhoAc- | MeSCH₂CH₂ | Bz | 4-Cl-Pro | tBuNH- |

TABLE 1-continued

| Cpd. No. | R¹ | R³ | R⁴ | Z | R⁵ |
|---|---|---|---|---|---|
| 4586 | 4-[(3-Me₂N-Pr-NH-CO)-NMe]PhoAc- | MeSCH₂CH₂ | Bz | 4-Cl-Pro | tBuNH- |
| 4587 | 4-[(Mor-CO-NMe]-PhoAc- | MeSCH₂CH₂ | Bz | 4-Cl-Pro | tBuNH- |
| 4588 | 4-[(4-NO₂-Pho-CO)-NMe]PhoAc- | MeSCH₂CH₂ | Bz | 4-Cl-Pro | tBuNH- |
| 4589 | 4-[(N-Bz-Pipr-Ac)-NMe]PhoAc- | MeSCH₂CH₂ | Bz | 4-Cl-Pro | tBuNH- |
| 4590 | 2-NH₂-PhoAc- | MeSCH₂CH₂ | Bz | 4-Cl-Pro | tBuNH- |
| 4591 | 3-NH₂-PhoAc- | MeSCH₂CH₂ | Bz | 4-Cl-Pro | tBuNH- |
| 4592 | 1-Me-2-Ind-CO- | MeSCH₂CH₂ | Bz | 4-Cl-Pro | tBuNH- |
| 4593 | Bzc | MeSCH₂CH₂ | Bz | 4-Cl-Pro | 1,1-diMe-2-HOEt-NH- |
| 4594 | 2-Quix-CO- | MeSCH₂CH₂ | Bz | 4-Cl-Pro | 1,1-diMe-2-HOEt-NH- |
| 4595 | 2-Quin-CO- | MeSCH₂CH₂ | Bz | 4-Cl-Pro | 1,1-diMe-2-HOEt-NH- |
| 4596 | 3-Quin-CO- | MeSCH₂CH₂ | Bz | 4-Cl-Pro | 1,1-diMe-2-HOEt-NH- |
| 4597 | 4-Quin-CO- | MeSCH₂CH₂ | Bz | 4-Cl-Pro | 1,1-diMe-2-HOEt-NH- |
| 4598 | 2-Bfur-CO- | MeSCH₂CH₂ | Bz | 4-Cl-Pro | 1,1-diMe-2-HOEt-NH- |
| 4599 | 3-Bfur-CO- | MeSCH₂CH₂ | Bz | 4-Cl-Pro | 1,1-diMe-2-HOEt-NH- |
| 4600 | 2-Ind-CO- | MeSCH₂CH₂ | Bz | 4-Cl-Pro | 1,1-diMe-2-HOEt-NH- |
| 4601 | tBoc | MeSCH₂CH₂ | Bz | 4-Cl-Pro | 1,1-diMe-2-HOEt-NH- |
| 4602 | PhoAc- | MeSCH₂CH₂ | Bz | 4-Cl-Pro | 1,1-diMe-2-HOEt-NH- |
| 4603 | 4-MPhOAc- | MeSCH₂CH₂ | Bz | 4-Cl-Pro | 1,1-diMe-2-HOEt-NH- |
| 4604 | 3-Bzisox-CO- | MeSCH₂CH₂ | Bz | 4-Cl-Pro | 1,1-diMe-2-HOEt-NH- |
| 4605 | 5-H₂N-AcO-2-Ind-CO- | MeSCH₂CH₂ | Bz | 4-Cl-Pro | 1,1-diMe-2-HOEt-NH- |
| 4606 | 4-NH₂-PhoAc- | MeSCH₂CH₂ | Bz | 4-Cl-Pro | 1,1-diMe-2-HOEt-NH- |
| 4607 | 4-NH₂-Bzc | MeSCH₂CH₂ | Bz | 4-Cl-Pro | 1,1-diMe-2-HOEt-NH- |
| 4608 | 4-Me₂N-PhoAc- | MeSCH₂CH₂ | Bz | 4-Cl-Pro | 1,1-diMe-2-HOEt-NH- |
| 4609 | 4-MeNH-PhoAc- | MeSCH₂CH₂ | Bz | 4-Cl-Pro | 1,1-diMe-2-HOEt-NH- |
| 4610 | 4-[Bzc-NH]-PhoAc- | MeSCH₂CH₂ | Bz | 4-Cl-Pro | 1,1-dime-2-HOEt-NH- |
| 4611 | 4-[Gly-NH]PhoAc- | MeSCH₂CH₂ | Bz | 4-Cl-Pro | 1,1-diMe-2-HOEt-NH- |
| 4612 | 4-[Gly-NMe]-PhoAc- | MeSCH₂CH₂ | Bz | 4-Cl-Pro | 1,1-diMe-2-HOEt-NH- |
| 4613 | 4-[Sar-NMe]-PhoAc- | MeSCH₂CH₂ | Bz | 4-Cl-Pro | 1,1-diMe-2-HOEt-NH- |
| 4614 | 4-[Mor-Ac-NMe]-PhoAc- | MeSCH₂CH₂ | Bz | 4-Cl-Pro | 1,1-diMe-2-HOEt-NH- |
| 4615 | 7-MeO-2-Bfur-CO- | MeSCH₂CH₂ | Bz | 4-Cl-Pro | 1,1-diMe-2-HOEt-NH- |
| 4616 | 6-NO₂-2-Quix-CO- | MeSCH₂CH₂ | Bz | 4-Cl-Pro | 1,1-diMe-2-HOEt-NH- |
| 4617 | 6-NH₂-2-Quix-CO- | MeSCH₂CH₂ | Bz | 4-Cl-Pro | 1,1-diMe-2-HOEt-NH- |
| 4618 | 5-F-2-Ind-CO- | MeSCH₂CH₂ | Bz | 4-Cl-Pro | 1,1-diMe-2-HOEt-NH- |
| 4619 | 1-Me-3-Inda-CO- | MeSCH₂CH₂ | Bz | 4-Cl-Pro | 1,1-diMe-2-HOEt-NH- |
| 4620 | 4-[(Mor-CO-Pipr-Ac-NMe)PhoAc- | MeSCH₂CH₂ | Bz | 4-Cl-Pro | 1,1-diMe-2-HOEt-NH- |
| 4621 | 4-[(N-tBoc-Pro)-NMe]PhoAc- | MeSCH₂CH₂ | Bz | 4-Cl-Pro | 1,1-diMe-2-HOEt-NH- |
| 4622 | 4-[(Bz-Pipr-Ac)-NH)PhoAc- | MeSCH₂CH₂ | Bz | 4-Cl-Pro | 1,1-diMe-2-HOEt-NH- |
| 4623 | 4-[(MorEt-NH-Ac)-NH]PhoAc- | MeSCH₂CH₂ | Bz | 4-Cl-Pro | 1,1-diMe-2-HOEt-NH- |
| 4624 | 4-[Mor-Ac-NH]-PhoA- | MeSCH₂CH₂ | Bz | 4-Cl-Pro | 1,1-diMe-2-HOEt-NH- |

TABLE 1-continued

| Cpd. No. | R¹ | R³ | R⁴ | Z | R⁵ |
|---|---|---|---|---|---|
| 4625 | 4-[Bzc-NH]-cHxO-Ac- | MeSCH₂CH₂ | Bz | 4-Cl-Pro | 1,1-diMe-2-HOEt-NH- |
| 4626 | N-Bzc-4-PipO-Ac- | MeSCH₂CH₂ | Bz | 4-Cl-Pro | 1,1-diMe-2-HOEt-NH- |
| 4627 | 4-[(2-MorEt)-NMe]-PhoAc- | MeSCH₂CH₂ | Bz | 4-Cl-Pro | 1,1-diMe-2-HOEt-NH- |
| 4628 | 4-[(3-Me₂N-Pr-NH-CO)-NMe]PhoAc- | MeSCH₂CH₂ | Bz | 4-Cl-Pro | 1,1-diMe-2-HOEt-NH- |
| 4629 | 4-[Mor-CO-NMe]-PhoAc- | MeSCH₂CH₂ | Bz | 4-Cl-Pro | 1,1-diMe-2-HOEt-NH- |
| 4630 | 4-[(4-NO₂-Pho-CO)NMe]PhoAc- | MeSCH₂CH₂ | Bz | 4-Cl-Pro | 1,1-diMe-2-HOEt-NH- |
| 4631 | 4-[(N-Bz-Pipr-Ac)-NMe]PhoAc- | MeSCH₂CH₂ | Bz | 4-Cl-Pro | 1,1-diMe-2-HOEt-NH- |
| 4632 | 2-NH₂-PhoAc- | MeSCH₂CH₂ | Bz | 4-Cl-Pro | 1,1-diMe-2-HOEt-NH- |
| 4633 | 3-NH₂-PhoAc- | MeSCH₂CH₂ | Bz | 4-Cl-Pro | 1,1-diMe-2-HOEt-NH- |
| 4634 | 1-Me-2-Ind-CO- | MeSCH₂CH₂ | Bz | 4-Cl-Pro | 1,1-diMe-2-HOEt-NH- |
| 4635 | 4-[(N-tBoc-N-Me-Gly)-NMe]PhoAc- | CarCH₂ | Bz | Pro | tBuNH- |
| 4636 | Bzc | CarCH₂ | Bz | 4-[F-BuO]Pro | tBuNH- |
| 4637 | 4-[(BrAc)-NMe]-PhoAc- | CarCH₂ | Bz | Pro | tBuNH- |
| 4638 | 4-MeO-Bzc | CarCH₂ | Bz | Pro | tBuNH- |
| 4639 | Bzc | CNCH₂ | Bz | 2,5-Oxazo-3-Oxo-bicyclo[2.2.1]heptane | |
| 4640 | 7-MeO-2-Bfur-CO- | CarCH₂ | Bz | 4-Br-Pro | tBuNH- |
| 4641 | 7-MeO-2-Bfur-CO- | CarCH₂ | Bz | 3-Br-Pro | tBuNH- |
| 4642 | 7-MeO-2-Bfur-CO- | CarCH₂ | Bz | 4-F-Pro | tBuNH- |
| 4643 | 7-MeO-2-Bfur-CO- | CarCH₂ | Bz | 3-F-Pro | tBuNH- |
| 4644 | 7-MeO-2-Bfur-CO- | CarCH₂ | Bz | 4,4-di-F-Pro | tBuNH- |
| 4645 | 7-MeO-2-Bfur-CO- | CarCH₂ | Bz | 4,4-diMeO-Pro | tBuNH- |
| 4646 | 7-MeO-2-Bfur-CO- | CarCH₂ | Bz | 4-MeO-Imin-Pro | tBuNH- |
| 4647 | 7-MeO-2-Bfur-CO- | CarCH₂ | Bz | 4-CN-Pro | tBuNH- |
| 4648 | 7-MeO-2-Bfur-CO- | CarCH₂ | Bz | 4-Mec-Pro | tBuNH- |
| 4649 | 7-MeO-2-Bfur-CO- | CarCH₂ | Bz | 4-COOH-Pro | tBuNH- |
| 4650 | 7-MeO-2-Bfur-CO- | CarCH₂ | Bz | 4-I-Pro | tBuNH- |
| 4651 | 7-MeO-2-Bfur-CO- | CarCH₂ | Bz | 3-I-Pro | tBuNH- |
| 4652 | 7-MeO-2-Bfur-CO- | CarCH₂ | Bz | 4-Oxo-Pro | tBuNH- |
| 4653 | 7-MeO-2-Bfur-CO- | CarCH₂ | Bz | 3-Oxo-Pro | tBuNH- |
| 4654 | 6-NH₂-2-Quix-CO- | CarCH₂ | Bz | 4-Br-Pro | tBuNH- |
| 4655 | 6-NH₂-2-Quix-CO- | CarCH₂ | Bz | 3-Br-Pro | tBuNH- |
| 4656 | 6-NH₂-2-Quix-CO- | CarCH₂ | Bz | 4-F-Pro | tBuNH- |
| 4657 | 6-NH₂-2-Quix-CO- | CarCH₂ | Bz | 3-F-Pro | tBuNH- |
| 4658 | 6-NH₂-2-Quix-CO- | CarCH₂ | Bz | 4,4-di-F-Pro | tBuNH- |
| 4659 | 6-NH₂-Quix-CO- | CarCH₂ | Bz | 4,4-diMeO-Pro | tBuNH- |
| 4660 | 6-NH₂-2-Quix-CO- | CarCH₂ | Bz | 4-MeO-Imin-Pro | tBuNH- |
| 4661 | 6-NH₂-2-Quix-CO- | CarCH₂ | Bz | 4-CN-Pro | tBuNH- |
| 4662 | 6-NH₂-2-Quix-CO- | CarCH₂ | Bz | 4-Mec-Pro | tBuNH- |
| 4663 | 6-NH₂-2-Quix-CO- | CarCH₂ | Bz | 4-COOH-Pro | tBuNH- |
| 4664 | 6-NH₂-2-Quix-CO- | CarCH₂ | Bz | 4-I-Pro | tBuNH- |
| 4665 | 6-NH₂-2-Quix-CO- | CarCH₂ | Bz | 3-I-Pro | tBuNH- |
| 4666 | 6-NH₂-2-Quix-CO- | CarCH₂ | Bz | 4-Oxo-Pro | tBuNH- |
| 4667 | 6-NH₂-2-Quix-CO- | CarCH₂ | Bz | 3-Oxo-Pro | tBuNH- |
| 4668 | 1-Me-3-Inda-CO- | CarCH₂ | Bz | 4-Br-Pro | tBuNH- |
| 4669 | 1-Me-3-Inda-CO- | CarCH₂ | Bz | 3-Br-Pro | tBuNH- |
| 4670 | 1-Me-3-Inda-CO- | CarCH₂ | Bz | 4-F-Pro | tBuNH- |
| 4671 | 1-Me-3-Inda-CO- | CarCH₂ | Bz | 3-F-Pro | tBuNH- |
| 4672 | 1-Me-3-Inda-CO- | CarCH₂ | Bz | 4,4-di-F-Pro | tBuNH- |
| 4673 | 1-Me-3-Inda-CO- | CarCH₂ | Bz | 4,4-diMeO-Pro | tBuNH- |

TABLE 1-continued

| Cpd. No. | R¹ | R³ | R⁴ | Z | R⁵ |
|---|---|---|---|---|---|
| 4674 | 1-Me-3-Inda-CO- | CarCH₂ | Bz | 4-MeO-Imi-Pro | tBuNH- |
| 4675 | 1-Me-3-Inda-CO- | CarCH₂ | Bz | 4-CN-Pro | tBuNH- |
| 4676 | 1-Me-3-Inda-CO- | CarCH₂ | Bz | 4-Mec-Pro | tBuNH- |
| 4677 | 1-Me-3-Inda-CO- | CarCH₂ | Bz | 4-COOH-Pro | tBuNH- |
| 4678 | 1-Me-3-Inda-CO- | CarCH₂ | Bz | 4-I-Pro | tBuNH- |
| 4679 | 1-Me-3-Inda-CO- | CarCH₂ | Bz | 3-I-Pro | tBuNH- |
| 4680 | 1-Me-3-Inda-CO- | CarCH₂ | Bz | 4-Oxo-Pro | tBuNH- |
| 4681 | 1-Me-3-Inda-CO- | CarCH₂ | Bz | 3-Oxo-Pro | tBuNH- |
| 4682 | H | CarCH₂ | Bz | Pro | tBuNH- |
| 4683 | H | CarCH₂ | Bz | 4-Cl-Pro | tBuNH- |
| 4684 | H | CarCH₂ | Bz | 3-Cl-Pro | tBuNH- |
| 4685 | H | CarCH₂ | Bz | 4-HO-Pro | tBuNH- |
| 4686 | H | CarCH₂ | Bz | 3-HO-Pro | tBuNH- |
| 4687 | H | CarCH₂ | Bz | 4-Br-Pro | tBuNH- |
| 4688 | H | CarCH₂ | Bz | 3-Br-Pro | tBuNH- |
| 4689 | H | CarCH₂ | Bz | 4-F-Pro | tBuNH- |
| 4690 | H | CarCH₂ | Bz | 3-F-Pro | tBuNH- |
| 4691 | H | CarCH₂ | Bz | 4,4-di-F-Pro | tBuNH- |
| 4692 | H | CarCH₂ | Bz | 4,4-diMeO-Pro | tBuNH- |
| 4693 | H | CarCH₂ | Bz | 4-MeoImin-Pro | tBuNH- |
| 4694 | H | CarCH₂ | Bz | 4-CN-Pro | tBuNH- |
| 4695 | H | CarCH₂ | Bz | 4-Mec-Pro | tBuNH- |
| 4696 | H | CarCH₂ | Bz | 4-COOH-Pro | tBuNH- |
| 4697 | H | CarCH₂ | Bz | 3,4-Deh-Pro | tBuNH- |
| 4698 | H | CarCH₂ | Bz | 4-I-Pro | tBuNH- |
| 4699 | H | CarCH₂ | Bz | 3-I-Pro | tBuNH- |
| 4700 | H | CarCH₂ | Bz | 3-Oxo-Pro | tBuNH- |
| 4701 | H | CarCH₂ | Bz | 4-Oxo-Pro | tBuNH- |
| 4702 | Bz | CarCH₂ | Bz | Pro | tBuNH- |
| 4703 | 5-F-2-Ind-CO- | CarCH₂ | Bz | 4-Oxo-Pro | tBuNH- |
| 4704 | 4-[Mor-CO-Pipr-Ac)-NMe)PhoAc- | CarCH₂ | Bz | 4-Oxo-Pro | tBuNH- |
| 4705 | 2-Quix-Me- | CarCH₂ | Bz | 4-Oxo-Pro | tBuNH- |
| 4706 | 4-[Pro-NMe]-PhoAc- | CarCH₂ | Bz | 4-Oxo-Pro | tBuNH- |
| 4707 | 4-[(tBoc-Pro)-NMe]-PhoAc | CarCH₂ | Bz | 4-Oxo-Pro | tBuNH- |
| 4708 | 4-[(Bz-Pipr-Ac)-NH]PhoAc- | CarCH₂ | Bz | 4-Oxo-Pro | tBuNH- |
| 4709 | 4-[(MorEt-NH-Ac)-NH]PhoAc- | CarCH₂ | Bz | 4-Oxo-Pro | tBuNH- |
| 4710 | 4-[(Mor-Ac-NH]-PhoAc- | CarCH₂ | Bz | 4-Oxo-Pro | tBuNH- |
| 4711 | 4-[Bzc-NH]-cHxO-Ac- | CarCH₂ | Bz | 4-Oxo-Pro | tBuNH- |
| 4712 | N-Bzc-4-PipO-Ac- | CarCH₂ | Bz | 4-Oxo-Pro | tBuNH- |
| 4713 | 4-PipO-Ac- | CarCH₂ | Bz | 4-Oxo-Pro | tBuNH- |
| 4714 | 4-N,N-Bz₂-cHx-O-Ac- | CarCH₂ | Bz | 4-Oxo-Pro | tBuNH- |
| 4715 | N-Bz-4-PipO-Ac- | CarCH₂ | Bz | 4-Oxo-Pro | tBuNH- |
| 4716 | 4-[Glu(Me)N]Pho-Ac- | CarCH₂ | Bz | 4-Oxo-Pro | tBuNH- |
| 4717 | 4-[(2-Bza-4-Bzc-Byr)-NMe]PhoAc- | CarCH₂ | Bz | 4-Oxo-Pro | tBuNH- |
| 4718 | 4-[(3-MorPr-NH-Ac)-NMe]PhoAc- | CarCH₂ | Bz | 4-Oxo-Pro | tBuNH- |
| 4719 | 4-[(3-Me₂N-Pr-NH-Ac)-NMe]PhoAc- | CarCH₂ | Bz | 4-Oxo-Pro | tBuNH- |
| 4720 | 4-[(2-HOEt-NH-Ac)-NMe]PhoAc- | CarCH₂ | Bz | 4-Oxo-Pro | tBuNH- |
| 4721 | 4-[(2-MorEt)-NMe]PhoAc- | CarCH₂ | Bz | 4-Oxo-Pro | tBuNH- |
| 4722 | 4-[(3-Me₂N-Pr-NH-CO)-NMe]PhoAc- | CarCH₂ | Bz | 4-Oxo-Pro | tBuNH- |
| 4723 | 4-[(Mor-CO-NMe]Pho-Ac- | CarCH₂ | Bz | 4-Oxo-Pro | tBuNH- |
| 4724 | 4-[(4-NO₂-Pho-CO-NMe)PhoAc- | CarCH₂ | Bz | 4-Oxo-Pro | tBuNH- |
| 4725 | 4-[(N-Bz-Pipr-Ac)-NMe]PhoAc- | CarCH₂ | Bz | 4-Oxo-Pro | tBuNH- |
| 4726 | 4-[(N-Ph-N-Me-Ac)-NMe]PhoAc- | CarCH₂ | Bz | 4-Oxo-Pro | tBuNH- |
| 4727 | 4-[(iPn-NH-Ac)-NMe]PhoAc- | CarCH₂ | Bz | 4-Oxo-Pro | tBuNH- |
| 4728 | 1-Me-2-Ind-CO- | CarCH₂ | Bz | 4-Oxo-Pro | tBuNH- |
| 4729 | 2-[Bzc-NH]PhoAc- | CarCH₂ | Bz | 4-Oxo-Pro | tBuNH- |

TABLE 1-continued

| Cpd. No. | R¹ | R³ | R⁴ | Z | R⁵ |
|---|---|---|---|---|---|
| 4730 | 3-[Bzc-NH]PhoAc- | CarCH$_2$ | Bz | 4-Oxo-Pro | tBuNH- |
| 4731 | 4-[(Me$_2$N-Ac)-NMe]PhoAc- | CarCH$_2$ | Bz | 4-Oxo-Pro | tBuNH- |
| 4732 | 4-[(Bzc-NMe]-PhoAc- | CarCH$_2$ | Bz | 4-Oxo-Pro | tBuNH- |

TABLE 2

| Cpd. No. | R¹ | R³ | R⁴ | Z | R⁵ |
|---|---|---|---|---|---|
| 2-1 | Bzc | CarCH$_2$ | Bz | Pro | tBuNH- |
| 2-2 | 2-Quix-CO- | CarCH$_2$ | Bz | Pro | tBuNH- |
| 2-3 | 2-Quin-CO- | CarCH$_2$ | Bz | Pro | tBuNH- |
| 2-4 | 3-Quin-CO- | CarCH$_2$ | Bz | Pro | tBuNH- |
| 2-5 | 4-Quin-CO- | CarCH$_2$ | Bz | Pro | tBuNH- |
| 2-6 | 2-Bfur-CO- | CarCH$_2$ | Bz | Pro | tBuNH- |
| 2-7 | 3-Bfur-CO- | CarCH$_2$ | Bz | Pro | tBuNH- |
| 2-8 | 2-Ind-CO- | CarCH$_2$ | Bz | Pro | tBuNH- |
| 2-9 | tBoc | CarCH$_2$ | Bz | Pro | tBuNH- |
| 2-10 | PhoAc- | CarCH$_2$ | Bz | Pro | tBuNH- |
| 2-11 | 4-MPhOAc- | CarCH$_2$ | Bz | Pro | tBuNH- |
| 2-12 | 3-Bzisox-CO- | CarCH$_2$ | Bz | Pro | tBuNH- |
| 2-13 | 5-H$_2$N-AcO-2-Ind-CO- | CarCH$_2$ | Bz | Pro | tBuNH- |
| 2-14 | 4-NH$_2$-Pho-Ac- | CarCH$_2$ | Bz | Pro | tBuNH- |
| 2-15 | 4-NH$_2$-Bzc | CarCH$_2$ | Bz | Pro | tBuNH- |
| 2-16 | 4-Me$_3$N-Pho-Ac- | CarCH$_2$ | Bz | Pro | tBuNH- |
| 2-17 | 4-MeNH-Pho-Ac- | CarCH$_2$ | Bz | Pro | tBuNH- |
| 2-18 | 4-[Bzc-NH]-PhoAc- | CarCH$_2$ | Bz | Pro | tBuNH- |
| 2-19 | 4-[Gly-NH]-PhoAc- | CarCH$_2$ | Bz | Pro | tBuNH- |
| 2-20 | 4-[Gly-NMe]-PhoAc- | CarCH$_2$ | Bz | Pro | tBuNH- |
| 2-21 | 4-[Sar-NMe]-PhoAc- | CarCH$_2$ | Bz | Pro | tBuNH- |
| 2-22 | 4-[MorAc-NMe]-PhoAc- | CarCH$_2$ | Bz | Pro | tBuNH- |
| 2-23 | 7-MeO-2-Bfur-CO- | CarCH$_2$ | Bz | Pro | tBuNH- |
| 2-24 | 6-NO$_2$-2-Quix-CO- | CarCH$_2$ | Bz | Pro | tBuNH- |
| 2-25 | 6-NH$_2$-2-Quix-CO- | CarCH$_2$ | Bz | Pro | tBuNH- |
| 2-26 | 5-F-2-Ind-CO- | CarCH$_2$ | Bz | Pro | tBuNH- |
| 2-27 | 1-Me-3-Inda-CO- | CarCH$_2$ | Bz | Pro | tBuNH- |
| 2-28 | 4-[(Mor-CO-Pipr-Ac)-NMe]PhoAc- | CarCH$_2$ | Bz | Pro | tBuNH- |
| 2-29 | 4-[(N-tBoc-Pro-NMe]PhoAc- | CarCH$_2$ | Bz | Pro | tBuNH- |
| 2-30 | 4-[(Bz-Pipr-Ac)-NH]-PhoAc- | CarCH$_2$ | Bz | Pro | tBuNH- |
| 2-31 | 4-[(MorEt-NH-Ac)-NH]PhoAc- | CarCH$_2$ | Bz | Pro | tBuNH- |
| 2-32 | 4-[(Mor-Ac)NH]-PhoAc- | CarCH$_2$ | Bz | Pro | tBuNH- |
| 2-33 | 4-[Bzc-NH]-cHxO-Ac- | CarCH$_2$ | Bz | Pro | tBuNH- |
| 2-34 | N-Bzc-PipO-Ac- | CarCH$_2$ | Bz | Pro | tBuNH- |
| 2-35 | 4-[Me(2-MorEt)-N]-PhoAc- | CarCH$_2$ | Bz | Pro | tBuNH- |
| 2-36 | 4-[(3-Me$_2$N-Pr-NH-CO)-NMe]PhoAc- | CarCH$_2$ | Bz | Pro | tBuNH- |
| 2-37 | 4-[(Mor-CO)-NMe]PhoAc- | CarCH$_2$ | Bz | Pro | tBuNH- |
| 2-38 | 4-[(4-NO$_2$-Pho-CO)-NMe]PhoAc- | CarCH$_2$ | Bz | Pro | tBuNH- |
| 2-39 | 4-[(N-Bz-Pipr-Ac)-NMe]-PhoAc- | CarCH$_2$ | Bz | Pro | tBuNH- |
| 2-40 | 2-NH$_2$-PhoAc- | CarCH$_2$ | Bz | Pro | tBuNH- |

TABLE 2-continued

| Cpd. No. | R¹ | R³ | R⁴ | Z | R⁵ |
|---|---|---|---|---|---|
| 2-41 | 3-NH₂-PhoAc- | CarCH₂ | Bz | Pro | tBuNH- |
| 2-42 | 1-Me-2-Ind-CO- | CarCH₂ | Bz | Pro | tBuNH- |
| 2-43 | Bz | CarCH₂ | Bz | Pro | tBuNH- |
| 2-44 | Bzc | CarCH₂ | Bz | 4-Cl-Pro | tBuNH- |
| 2-45 | 2-Quix-CO- | CarCH₂ | Bz | 4-Cl-Pro | tBuNH- |
| 2-46 | 2-Quin-CO- | CarCH₂ | Bz | 4-Cl-Pro | tBuNH- |
| 2-47 | 3-Quin-CO- | CarCH₂ | Bz | 4-Cl-Pro | tBuNH- |
| 2-48 | 4-Quin-CO- | CarCH₂ | Bz | 4-Cl-Pro | tBuNH- |
| 2-49 | 2-Bfur-CO- | CarCH₂ | Bz | 4-Cl-Pro | tBuNH- |
| 2-50 | 3-Bfur-CO- | CarCH₂ | Bz | 4-Cl-Pro | tBuNH- |
| 2-51 | 2-Ind-CO- | CarCH₂ | Bz | 4-Cl-Pro | tBuNH- |
| 2-52 | tBoc | CarCH₂ | Bz | 4-Cl-Pro | tBuNH- |
| 2-53 | PhoAc- | CarCH₂ | Bz | 4-Cl-Pro | tBuNH- |
| 2-54 | 4-MPhOAc- | CarCH₂ | Bz | 4-Cl-Pro | tBuNH- |
| 2-55 | 3-Bzisox-CO- | CarCH₂ | Bz | 4-Cl-Pro | tBuNH- |
| 2-56 | 5-H₂N-AcO-2-Ind-CO- | CarCH₂ | Bz | 4-Cl-Pro | tBuNH- |
| 2-57 | 4-NH₂-PhoAc- | CarCH₂ | Bz | 4-Cl-Pro | tBuNH- |
| 2-58 | 4-NH₂-Bzc | CarCH₂ | Bz | 4-Cl-Pro | tBuNH- |
| 2-59 | 4-Me₂N-PhoAc- | CarCH₂ | Bz | 4-Cl-Pro | tBuNH- |
| 2-60 | 4-MeNH-PhoAc- | CarCH₂ | Bz | 4-Cl-Pro | tBuNH- |
| 2-61 | 4-[Bzc-NH]PhoAc- | CarCH₂ | Bz | 4-Cl-Pro | tBuNH- |
| 2-62 | 4-[Gly-NH]PhoAc- | CarCH₂ | Bz | 4-Cl-Pro | tBuNH- |
| 2-63 | 4-[Gly-NMe]PhoAc- | CarCH₂ | Bz | 4-Cl-Pro | tBuNH- |
| 2-64 | 4-[Sar-NMe]PhoAc- | CarCH₂ | Bz | 4-Cl-Pro | tBuNH- |
| 2-65 | 4-[(Mor-Ac)-NMe]-PhoAc- | CarCH₂ | Bz | 4-Cl-Pro | tBuNH- |
| 2-66 | 7-MeO-2-Bfur-CO- | CarCH₂ | Bz | 4-Cl-Pro | tBuNH- |
| 2-67 | 6-NO₂-2-Quix-CO- | CarCH₂ | Bz | 4-Cl-Pro | tBuNH- |
| 2-68 | 6-NH₂-2-Quix-CO- | CarCH₂ | Bz | 4-Cl-Pro | tBuNH- |
| 2-69 | 5-F-2-Ind-CO- | CarCH₂ | Bz | 4-Cl-Pro | tBuNH- |
| 2-70 | 1-Me-3-Inda-CO- | CarCH₂ | Bz | 4-Cl-Pro | tBuNH- |
| 2-71 | 4-[(Mor-CO-Pipr-Ac)-NMe]PhoAc- | CarCH₂ | Bz | 4-Cl-Pro | tBuNH- |
| 2-72 | 4-[(N-tBoc-Pro)-NMe]PhoAc- | CarCH₂ | Bz | 4-Cl-Pro | tBuNH- |
| 2-73 | Bzc | CarCH₂ | Bz | 3-Cl-Pro | tBuNH- |
| 2-74 | 2-Quix-CO- | CarCH₂ | Bz | 3-Cl-Pro | tBuNH- |
| 2-75 | 2-Quin-CO- | CarCH₂ | Bz | 3-Cl-Pro | tBuNH- |
| 2-76 | 3-Quin-CO- | CarCH₂ | Bz | 3-Cl-Pro | tBuNH- |
| 2-77 | 4-Quin-CO- | CarCH₂ | Bz | 3-Cl-Pro | tBuNH- |
| 2-78 | 2-Bfur-CO- | CarCH₂ | Bz | 3-Cl-Pro | tBuNH- |
| 2-79 | 3-Bfur-CO- | CarCH₂ | Bz | 3-Cl-Pro | tBuNH- |
| 2-80 | 2-Ind-CO- | CarCH₂ | Bz | 3-Cl-Pro | tBuNH- |
| 2-81 | tBoc | CarCH₂ | Bz | 3-Cl-Pro | tBuNH- |
| 2-82 | PhoAc- | CarCH₂ | Bz | 3-Cl-Pro | tBuNH- |
| 2-83 | 4-MPhOAc- | CarCH₂ | Bz | 3-Cl-Pro | tBuNH- |
| 2-84 | 3-Bzisox-CO- | CarCH₂ | Bz | 3-Cl-Pro | tBuNH- |
| 2-85 | 5-H₂N-AcO-2-Ind-CO- | CarCH₂ | Bz | 3-Cl-Pro | tBuNH- |
| 2-86 | 4-NH₂-PhoAc- | CarCH₂ | Bz | 3-Cl-Pro | tBuNH- |
| 2-87 | 4-NH₂-Bzc | CarCH₂ | Bz | 3-Cl-Pro | tBuNH- |
| 2-88 | 4-Me₂N-PhoAc- | CarCH₂ | Bz | 3-Cl-Pro | tBuNH- |
| 2-89 | 4-MeNH-PhoAc- | CarCH₂ | Bz | 3-Cl-Pro | tBuNH- |
| 2-90 | 4-[Bzc-NH]-PhoAc- | CarCH₂ | Bz | 3-Cl-Pro | tBuNH- |
| 2-91 | 4-[Gly-NH]PloAc- | CarCH₂ | Bz | 3-Cl-Pro | tBuNH- |
| 2-92 | 4-[Gly-NMe]PhoAc- | CarCH₂ | Bz | 3-Cl-Pro | tBuNH- |
| 2-93 | 4-[Sar-NMe]PhoAc- | CarCH₂ | Bz | 3-Cl-Pro | tBuNH- |
| 2-94 | 4-[(Mor-Ac)-NMe]-PhoAc- | CarCH₂ | Bz | 3-Cl-Pro | tBuNH- |
| 2-95 | 7-MeO-2-Bfur-CO- | CarCH₂ | Bz | 3-Cl-Pro | tBuNH- |
| 2-96 | 6-NO₂-2-Quix-CO- | CarCH₂ | Bz | 3-Cl-Pro | tBuNH- |
| 2-97 | 6-NH₂-2-Quix-CO- | CarCH₂ | Bz | 3-Cl-Pro | tBuNH- |
| 2-98 | 5-F-2-Ind-CO- | CarCH₂ | Bz | 3-Cl-Pro | tBuNH- |
| 2-99 | 1-Me-3-Inda-CO- | CarCH₂ | Bz | 3-Cl-Pro | tBuNH- |
| 2-100 | 4-[(Mor-CO-Pipr-Ac)-NMe]PhoAc- | CarCH₂ | Bz | 3-Cl-Pro | tBuNH- |
| 2-101 | 4-[(N-tBoc-Pro)-NMe]PhoAc- | CarCH₂ | Bz | 3-Cl-Pro | tBuNH- |
| 2-102 | 4-[(Bz-Pipr-Ac)-NH]-PhoAc- | CarCH₂ | Bz | 3-Cl-Pro | tBuNH- |
| 2-103 | 4-[(MorEt-NH-Ac)-NH]PhoAc- | CarCH₂ | Bz | 3-Cl-Pro | tBuNH- |
| 2-104 | 4-[(Mor-Ac)NH]-PhoAc- | CarCH₂ | Bz | 3-Cl-Pro | tBuNH- |
| 2-105 | 4-[Bzc-NH]-cHxO- | CarCH₂ | Bz | 3-Cl-Pro | tBuNH- |

TABLE 2-continued

| Cpd. No. | R¹ | R³ | R⁴ | Z | R⁵ |
|---|---|---|---|---|---|
| 2-106 | Ac-N-Bzc-PipO-Ac- | CarCH₂ | Bz | 3-Cl-Pro | tBuNH- |
| 2-107 | 4-[Me(2-MorEt)N]-PhoAc- | CarCH₂ | Bz | 3-Cl-Pro | tBuNH- |
| 2-108 | 4-[(3-Me₂N-Pr-NH-CO)-NMe]PhoAc- | CarCH₂ | Bz | 3-Cl-Pro | tBuNH- |
| 2-109 | 4-[(Mor-CO)-NMe]-PhoAc- | CarCH₂ | Bz | 3-Cl-Pro | tBuNH- |
| 2-110 | 4-[(4-NO₂-Pho-CO)-NMe]PhoAc- | CarCH₂ | Bz | 3-Cl-Pro | tBuNH- |
| 2-111 | 4-[(N-Bz-Pipr-Ac)-NMe]-PhoAc- | CarCH₂ | Bz | 3-Cl-Pro | tBuNH- |
| 2-112 | 2-NH₂-PhoAc- | CarCH₂ | Bz | 3-Cl-Pro | tBuNH- |
| 2-113 | 3-NH₂-PhoAc- | CarCH₂ | Bz | 3-Cl-Pro | tBuNH- |
| 2-114 | 1-Me-2-Ind-CO | CarCH₂ | Bz | 3-Cl-Pro | tBuNH- |
| 2-115 | Bzc | CarCH₂ | Bz | 4-Oxo-Pro | tBuNH- |
| 2-116 | 2-Quix-CO- | CarCH₂ | Bz | 4-Oxo-Pro | tBuNH- |
| 2-117 | 2-Quin-CO- | CarCH₂ | Bz | 4-Oxo-Pro | tBuNH- |
| 2-118 | 3-Quin-CO- | CarCH₂ | Bz | 4-Oxo-Pro | tBuNH- |
| 2-119 | 4-Quin-CO- | CarCH₂ | Bz | 4-Oxo-Pro | tBuNH- |
| 2-120 | 2-Bfur-CO- | CarCH₂ | Bz | 4-Oxo-Pro | tBuNH- |
| 2-121 | 3-Bfur-CO- | CarCH₂ | Bz | 4-Oxo-Pro | tBuNH- |
| 2-122 | 2-Ind-CO- | CarCH₂ | Bz | 4-Oxo-Pro | tBuNH- |
| 2-123 | tBoc | CarCH₂ | Bz | 4-Oxo-Pro | tBuNH- |
| 2-124 | PhoAc- | CarCH₂ | Bz | 4-Oxo-Pro | tBuNH- |
| 2-125 | 4-MPhOAc- | CarCH₂ | Bz | 4-Oxo-Pro | tBuNH- |
| 2-126 | 3-Bzisox-CO- | CarCH₂ | Bz | 4-Oxo-Pro | tBuNH- |
| 2-127 | 5-H₂N-AcO-2-Ind-CO- | CarCH₂ | Bz | 4-Oxo-Pro | tBuNH- |
| 2-128 | 4-NH₂-PhoAc- | CarCH₂ | Bz | 4-Oxo-Pro | tBuNH- |
| 2-129 | 4-NH₂-Bzc | CarCH₂ | Bz | 4-Oxo-Pro | tBuNH- |
| 2-130 | 4-Me₂N-PhoAc- | CarCH₂ | Bz | 4-Oxo-Pro | tBuNH- |
| 2-131 | 4-MeNH-PhoAc- | CarCH₂ | Bz | 4-Oxo-Pro | tBuNH- |
| 2-132 | 4-[Bzc-NH]-PhoAc- | CarCH₂ | Bz | 4-Oxo-Pro | tBuNH- |
| 2-133 | 4-[Gly-NH]PhoAc- | CarCH₂ | Bz | 4-Oxo-Pro | tBuNH- |
| 2-134 | 4-[Gly-NMe]PhoAc- | CarCH₂ | Bz | 4-Oxo-Pro | tBuNH- |
| 2-135 | 4-[Sar-NMe]PhoAc- | CarCH₂ | Bz | 4-Oxo-Pro | tBuNH- |
| 2-136 | 4-[(Mor-Ac)-NMe]-PhoAc- | CarCH₂ | Bz | 4-Oxo-Pro | tBuNH- |
| 2-137 | 7-MeO-2-Bfur-CO- | CarCH₂ | Bz | 4-Oxo-Pro | tBuNH- |
| 2-138 | 6-NO₂-2-Quix-CO- | CarCH₂ | Bz | 4-Oxo-Pro | tBuNH- |
| 2-139 | 6-NH₂-2-Quix-CO- | CarCH₂ | Bz | 4-Oxo-Pro | tBuNH- |
| 2-140 | 5-F-2-Ind-CO- | CarCH₂ | Bz | 4-Oxo-Pro | tBuNH- |
| 2-141 | 1-Me-3-Inda-CO- | CarCH₂ | Bz | 4-Oxo-Pro | tBuNH- |
| 2-142 | 4-[(Mor-CO-Pipr-Ac)-NMe]PhoAc- | CarCH₂ | Bz | 4-Oxo-Pro | tBuNH- |
| 2-143 | 4-[(N-tBoc-Pro)-NMe]PhoAc- | CarCH₂ | Bz | 4-Oxo-Pro | tBuNH- |
| 2-144 | 4-[(Bz-Pipr-Ac)-NH]PhoAc- | CarCH₂ | Bz | 4-Oxo-Pro | tBuNH- |
| 2-145 | 4-[(MorEt-NH-Ac)-NH]PhoAc- | CarCH₂ | Bz | 4-Oxo-Pro | tBuNH- |
| 2-146 | 4-[(Mor-Ac)NH]-PhoAc- | CarCH₂ | Bz | 4-Oxo-Pro | tBuNH- |
| 2-147 | 4-[Bzc-NH]-cHxO-Ac- | CarCH₂ | Bz | 4-Oxo-Pro | tBuNH- |
| 2-148 | N-Bzc-PipO-Ac- | CarCH₂ | Bz | 4-Oxo-Pro | tBuNH- |
| 2-149 | 4-[Me(2-MorEt)N]-PhoAc- | CarCH₂ | Bz | 4-Oxo-Pro | tBuNH- |
| 2-150 | 4-[(3-Me₂N-Pr-NH-CO)-NMe]PhoAc- | CarCH₂ | Bz | 4-Oxo-Pro | tBuNH- |
| 2-151 | 4-[(Mor-CO)-NMe]-PhoAc- | CarCH₂ | Bz | 4-Oxo-Pro | tBuNH- |
| 2-152 | 4-[(4-NO₂-Pho-CO)-NMe]-PhoAc- | CarCH₂ | Bz | 4-Oxo-Pro | tBuNH- |
| 2-153 | 4-[(N-Bz-Pipr-Ac)-NMe]-PhoAc- | CarCH₂ | Bz | 4-Oxo-Pro | tBuNH- |
| 2-154 | 2-NH₂-PhoAc- | CarCH₂ | Bz | 4-Oxo-Pro | tBuNH- |
| 2-155 | 3-NH₂-PhoAc- | CarCH₂ | Bz | 4-Oxo-Pro | tBuNH- |
| 2-156 | 1-Me-2-Ind-CO- | CarCH₂ | Bz | 4-Oxo-Pro | tBuNH- |
| 2-157 | Bzc | CarCH₂ | Bz | 4-HO-Pro | tBuNH- |
| 2-158 | 2-Quix-CO- | CarCH₂ | Bz | 4-HO-Pro | tBuNH- |
| 2-159 | 2-Quin-CO- | CarCH₂ | Bz | 4-HO-Pro | tBuNH- |
| 2-160 | 3-Quin-CO- | CarCH₂ | Bz | 4-HO-Pro | tBuNH- |
| 2-161 | 4-Quin-CO- | CarCH₂ | Bz | 4-HO-Pro | tBuNH- |
| 2-162 | 2-Bfur-CO- | CarCH₂ | Bz | 4-HO-Pro | tBuNH- |

TABLE 2-continued

| Cpd. No. | R¹ | R³ | R⁴ | Z | R⁵ |
|---|---|---|---|---|---|
| 2-163 | 3-Bfur-CO- | CarCH₂ | Bz | 4-HO-Pro | tBuNH- |
| 2-164 | 2-Ind-CO- | CarCH₂ | Bz | 4-HO-Pro | tBuNH- |
| 2-165 | tBoc | CarCH₂ | Bz | 4-HO-Pro | tBuNH- |
| 2-166 | PhoAc- | CarCH₂ | Bz | 4-HO-Pro | tBuNH- |
| 2-167 | 4-MPhOAc- | CarCH₂ | Bz | 4-HO-Pro | tBuNH- |
| 2-168 | 3-Bzisox-CO- | CarCH₂ | Bz | 4-HO-Pro | tBuNH- |
| 2-169 | 5-H₂N-AcO-2-Ind-CO- | CarCH₂ | Bz | 4-HO-Pro | tBuNH- |
| 2-170 | 4-NH₂-PhoAc- | CarCH₂ | Bz | 4-HO-Pro | tBuNH- |
| 2-171 | 4-NH₂-Bzc | CarCH₂ | Bz | 4-HO-Pro | tBuNH- |
| 2-172 | 4-Me₂N-PhoAc- | CarCH₂ | Bz | 4-HO-Pro | tBuNH- |
| 2-173 | 4-MeNH-PhoAc- | CarCH₂ | Bz | 4-HO-Pro | tBuNH- |
| 2-174 | 4-[Bzc-NH]-PhoAc- | CarCH₂ | Bz | 4-HO-Pro | tBuNH- |
| 2-175 | 4-[Gly-NH]PhoAc- | CarCH₂ | Bz | 4-HO-Pro | tBuNH- |
| 2-176 | 4-[Gly-NMe]PhoAc- | CarCH₂ | Bz | 4-HO-Pro | tBuNH- |
| 2-177 | 4-[Sar-NMe]PhoAc- | CarCH₂ | Bz | 4-HO-Pro | tBuNH- |
| 2-178 | 4-[(Mor-Ac)-NMe]-PhoAc- | CarCH₂ | Bz | 4-HO-Pro | tBuNH- |
| 2-179 | 7-MeO-2-Bfur-CO- | CarCH₂ | Bz | 4-HO-Pro | tBuNH- |
| 2-180 | 6-NO₂-2-Quix-CO- | CarCH₂ | Bz | 4-HO-Pro | tBuNH- |
| 2-181 | 6-NH₂-2-Quix-CO- | CarCH₂ | Bz | 4-HO-Pro | tBuNH- |
| 2-182 | 5-F-2-Ind-CO- | CarCH₂ | Bz | 4-HO-Pro | tBuNH- |
| 2-183 | 1-Me-3-Inda-CO- | CarCH₂ | Bz | 4-HO-Pro | tBuNH- |
| 2-184 | 4-[(Mor-CO-Pipr-Ac)-NMe]PhoAc- | CarCH₂ | Bz | 4-HO-Pro | tBuNH- |
| 2-185 | 4-[(N-tBoc-Pro)-NMe]-PhoAc- | CarCH₂ | Bz | 4-HO-Pro | tBuNH- |
| 2-186 | 4-[(Bz-Pipr-Ac)-NH]-PhoAc- | CarCH₂ | Bz | 4-HO-Pro | tBuNH- |
| 2-187 | 4-[(MorEt-NH-Ac)-NH]PhoAc- | CarCH₂ | Bz | 4-HO-Pro | tBuNH- |
| 2-188 | 4-[(Mor-Ac)NH]-PhoAc- | CarCH₂ | Bz | 4-HO-Pro | tBuNH- |
| 2-189 | 4-[Bzc-NH]-cHxO-Ac- | CarCH₂ | Bz | 4-HO-Pro | tBuNH- |
| 2-190 | N-Bzc-PipO-Ac- | CarCH₂ | Bz | 4-HO-Pro | tBuNH- |
| 2-191 | 4-[Me(2-MorEt)N]-PhoAc- | CarCH₂ | Bz | 4-HO-Pro | tBuNH- |
| 2-192 | 4-[(3-Me₂N-Pr-NH-CO)-NMe]PhoAc- | CarCH₂ | Bz | 4-HO-Pro | tBuNH- |
| 2-193 | 4-[(Mor-CO)-NMe]-PhoAc- | CarCH₂ | Bz | 4-HO-Pro | tBuNH- |
| 2-194 | 4-[(4-NO₂-Pho-CO)-NMe]PhoAc- | CarCH₂ | Bz | 4-HO-Pro | tBuNH- |
| 2-195 | 4-[(N-Bz-Pipr-Ac)-NMe]-PhoAc- | CarCH₂ | Bz | 4-HO-Pro | tBuNH- |
| 2-196 | 2-NH₂-PhoAc- | CarCH₂ | Bz | 4-HO-Pro | tBuNH- |
| 2-197 | 3-NH₂-PhoAc- | CarCH₂ | Bz | 4-HO-Pro | tBuNH- |
| 2-198 | 1-Me-2-Ind-CO- | CarCH₂ | Bz | 4-HO-Pro | tBuNH- |
| 2-199 | Bzc | CarCH₂ | Bz | 3-HO-Pro | tBuNH- |
| 2-200 | 2-Quix-CO- | CarCH₂ | Bz | 3-HO-Pro | tBuNH- |
| 2-201 | 2-Quin-CO- | CarCH₂ | Bz | 3-HO-Pro | tBuNH- |
| 2-202 | 3-Quin-CO- | CarCH₂ | Bz | 3-HO-Pro | tBuNH- |
| 2-203 | 4-Quin-CO- | CarCH₂ | Bz | 3-HO-Pro | tBuNH- |
| 2-204 | 2-Bfur-CO- | CarCH₂ | Bz | 3-HO-Pro | tBuNH- |
| 2-205 | 3-Bfur-CO- | CarCH₂ | Bz | 3-HO-Pro | tBuNH- |
| 2-206 | 2-Ind-CO- | CarCH₂ | Bz | 3-HO-Pro | tBuNH- |
| 2-207 | tBoc | CarCH₂ | Bz | 3-HO-Pro | tBuNH- |
| 2-208 | PhoAc- | CarCH₂ | Bz | 3-HO-Pro | tBuNH- |
| 2-209 | 4-MPhOAc- | CarCH₂ | Bz | 3-HO-Pro | tBuNH- |
| 2-210 | 3-Bzisox-CO- | CarCH₂ | Bz | 3-HO-Pro | tBuNH- |
| 2-211 | 5-H₂N-AcO-2-Ind-CO- | CarCH₂ | Bz | 3-HO-Pro | tBuNH- |
| 2-212 | 4-NH₂-PhoAc- | CarCH₂ | Bz | 3-HO-Pro | tBuNH- |
| 2-213 | 4-NH₂-Bzc | CarCH₂ | Bz | 3-HO-Pro | tBuNH- |
| 2-214 | 4-Me₂N-PhoAc- | CarCH₂ | Bz | 3-HO-Pro | tBuNH- |
| 2-215 | 4-MeNH-PhoAc- | CarCH₂ | Bz | 3-HO-Pro | tBuNH- |
| 2-216 | 4-[Bzc-NH]-PhoAc- | CarCH₂ | Bz | 3-HO-Pro | tBuNH- |
| 2-217 | 4-[Gly-NH]PhoAc- | CarCH₂ | Bz | 3-HO-Pro | tBuNH- |
| 2-218 | 4-[Gly-NMe]PhoAc- | CarCH₂ | Bz | 3-HO-Pro | tBuNH- |
| 2-219 | 4-[Sar-NMe]PhoAc- | CarCH₂ | Bz | 3-HO-Pro | tBuNH- |
| 2-220 | 4-[(Mor-Ac)-NMe]-PhoAc- | CarCH₂ | Bz | 3-HO-Pro | tBuNH- |
| 2-221 | 7-MeO-2-Bfur-CO- | CarCH₂ | Bz | 3-HO-Pro | tBuNH- |
| 2-222 | 6-NO₂-2-Quix-CO- | CarCH₂ | Bz | 3-HO-Pro | tBuNH- |
| 2-223 | 6-NH₂-2-Quix-CO- | CarCH₂ | Bz | 3-HO-Pro | tBuNH- |

TABLE 2-continued

| Cpd. No. | R¹ | R³ | R⁴ | Z | R⁵ |
|---|---|---|---|---|---|
| 2-224 | 5-F-2-Ind-CO- | CarCH₂ | Bz | 3-HO-Pro | tBuNH- |
| 2-225 | 1-Me-3-Inda-CO- | CarCH₂ | Bz | 3-HO-Pro | tBuNH- |
| 2-226 | 4-[(Mor-CO-Pipr-Ac)-NMe]PhoAc- | CarCH₂ | Bz | 3-HO-Pro | tBuNH- |
| 2-227 | 4-[(N-tBoc-Pro)-NMe]PhoAc- | CarCH₂ | Bz | 3-HO-Pro | tBuNH- |
| 2-228 | 4-[(Bz-Pipr-Ac)-NH]PhoAc- | CarCH₂ | Bz | 3-HO-Pro | tBuNH- |
| 2-229 | 4-[(MorEt-NH-Ac)-NH]PhoAc- | CarCH₂ | Bz | 3-HO-Pro | tBuNH- |
| 2-230 | 4-[(Mor-Ac)NH]-PhoAc- | CarCH₂ | Bz | 3-HO-Pro | tBuNH- |
| 2-231 | 4-[Bzc-NH]-cHxO-Ac- | CarCH₂ | Bz | 3-HO-Pro | tBuNH- |
| 2-232 | N-Bzc-PipO-Ac- | CarCH₂ | Bz | 3-HO-Pro | tBuNH- |
| 2-233 | 4-[Me(2-MorEt)N]-PhoAc- | CarCH₂ | Bz | 3-HO-Pro | tBuNH- |
| 2-234 | 4-[(3-Me₂N-Pr-NH-CO)-NMe]PhoAc- | CarCH₂ | Bz | 3-HO-Pro | tBuNH- |
| 2-235 | 4-[(Mor-CO)-NMe]-PhoAc- | CarCH₂ | Bz | 3-HO-Pro | tBuNH- |
| 2-236 | 4-[(4-NO₂-Pho-CO)-NMe]PhoAc- | CarCH₂ | Bz | 3-HO-Pro | tBuNH- |
| 2-237 | 4-[(N-Bz-Pipr-Ac)-NMe]PhoAc- | CarCH₂ | Bz | 3-HO-Pro | tBuNH- |
| 2-238 | 2-NH₂-PhoAc- | CarCH₂ | Bz | 3-HO-Pro | tBuNH- |
| 2-239 | 3-NH₂-PhoAc- | CarCH₂ | Bz | 3-HO-Pro | tBuNH- |
| 2-240 | 1-Me-2-Ind-CO- | CarCH₂ | Bz | 3-HO-Pro | tBuNH- |
| 2-241 | Bzc | CarCH₂ | Bz | 4-F-Pro | tBuNH- |
| 2-242 | 2-Quix-CO- | CarCH₂ | Bz | 4-F-Pro | tBuNH- |
| 2-243 | 2-Quin-CO- | CarCH₂ | Bz | 4-F-Pro | tBuNH- |
| 2-244 | 3-Quin-CO- | CarCH₂ | Bz | 4-F-Pro | tBuNH- |
| 2-245 | 4-Quin-CO- | CarCH₂ | Bz | 4-F-Pro | tBuNH- |
| 2-246 | 2-Bfur-CO- | CarCH₂ | Bz | 4-F-Pro | tBuNH- |
| 2-247 | 3-Bfur-CO- | CarCH₂ | Bz | 4-F-Pro | tBuNH- |
| 2-248 | 2-Ind-CO- | CarCH₂ | Bz | 4-F-Pro | tBuNH- |
| 2-249 | tBoc | CarCH₂ | Bz | 4-F-Pro | tBuNH- |
| 2-250 | PhoAc- | CarCH₂ | Bz | 4-F-Pro | tBuNH- |
| 2-251 | 4-MPhOAc- | CarCH₂ | Bz | 4-F-Pro | tBuNH- |
| 2-252 | 3-Bzisox-CO- | CarCH₂ | Bz | 4-F-Pro | tBuNH- |
| 2-253 | 5-H₂N-AcO-2-Ind-CO- | CarCH₂ | Bz | 4-F-Pro | tBuNH- |
| 2-254 | 4-NH₂-PhoAc- | CarCH₂ | Bz | 4-F-Pro | tBuNH- |
| 2-255 | 4-NH₂-Bzc | CarCH₂ | Bz | 4-F-Pro | tBuNH- |
| 2-256 | 4-Me₂N-PhoAc- | CarCH₂ | Bz | 4-F-Pro | tBuNH- |
| 2-257 | 4-MeNH-PhoAc- | CarCH₂ | Bz | 4-F-Pro | tBuNH- |
| 2-258 | 4-[Bzc-NH]-PhoAc- | CarCH₂ | Bz | 4-F-Pro | tBuNH- |
| 2-259 | 4-[Gly-NH]PhoAc- | CarCH₂ | Bz | 4-F-Pro | tBuNH- |
| 2-260 | 4-[Gly-NMe]PhoAc- | CarCH₂ | Bz | 4-F-Pro | tBuNH- |
| 2-261 | 4-[Sar-NMe]PhoAc- | CarCH₂ | Bz | 4-F-Pro | tBuNH- |
| 2-262 | 4-[(Mor-Ac)-NMe]-PhoAc- | CarCH₂ | Bz | 4-F-Pro | tBuNH- |
| 2-263 | 7-MeO-2-Bfur-CO- | CarCH₂ | Bz | 4-F-Pro | tBuNH- |
| 2-264 | 6-NO₂-2-Quix-CO- | CarCH₂ | Bz | 4-F-Pro | tBuNH- |
| 2-265 | 6-NH₂-2-Quix-CO- | CarCH₂ | Bz | 4-F-Pro | tBuNH- |
| 2-266 | 5-F-2-Ind-CO- | CarCH₂ | Bz | 4-F-Pro | tBuNH- |
| 2-267 | 1-Me-3-Inda-CO- | CarCH₂ | Bz | 4-F-Pro | tBuNH- |
| 2-268 | 4-[(Mor-CO-Pipr-Ac)-NMe]PhoAc- | CarCH₂ | Bz | 4-F-Pro | tBuNH- |
| 2-269 | 4-[(N-tBoc-Pro)-NMe]PhoAc- | CarCH₂ | Bz | 4-F-Pro | tBuNH- |
| 2-270 | 4-[(Bz-Pipr-Ac)-NH]PhoAc- | CarCH₂ | Bz | 4-F-Pro | tBuNH- |
| 2-271 | 4-[(MorEt-NH-Ac)-NH]PhoAc- | CarCH₂ | Bz | 4-F-Pro | tBuNH- |
| 2-272 | 4-[(Mor-Ac)NH]-PhoAc- | CarCH₂ | Bz | 4-F-Pro | tBuNH- |
| 2-273 | 4-[Bzc-NH]-cHxO-Ac- | CarCH₂ | Bz | 4-F-Pro | tBuNH- |
| 2-274 | N-Bzc-PipO-Ac- | CarCH₂ | Bz | 4-F-Pro | |
| 2-275 | 4-[Me(2-MorEt)N]-PhoAc- | CarCH₂ | Bz | 4-F-Pro | tBuNH- |
| 2-276 | 4-[(3-Me₂N-Pr-NH-CO)-NMe]PhoAc- | CarCH₂ | Bz | 4-F-Pro | tBuNH- |
| 2-277 | 4-[(Mor-CO)-NMe]-PhoAc- | CarCH₂ | Bz | 4-F-Pro | tBuNH- |

TABLE 2-continued

| Cpd. No. | R¹ | R³ | R⁴ | Z | R⁵ |
|---|---|---|---|---|---|
| 2-278 | 4-[(4-NO₂-Pho-CO)-NMe]PhoAc- | CarCH₂ | Bz | 4-F-Pro | tBuNH- |
| 2-279 | 4-[(N-Bz-Pipr-Ac)-NMe]PhoAc- | CarCH₂ | Bz | 4-F-Pro | tBuNH- |
| 2-280 | 2-NH₂-PhoAc- | CarCH₂ | Bz | 4-F-Pro | tBuNH- |
| 2-281 | 3-NH₂-PhoAc- | CarCH₂ | Bz | 4-F-Pro | tBuNH- |
| 2-282 | 1-Me-2-Ind-CO- | CarCH₂ | Bz | 4-F-Pro | tBuNH- |
| 2-283 | Bzc | CarCH₂ | Bz | 4-Br-Pro | tBuNH- |
| 2-284 | 2-Quix-CO- | CarCH₂ | Bz | 4-Br-Pro | tBuNH- |
| 2-285 | 2-Quin-CO- | CarCH₂ | Bz | 4-Br-Pro | tBuNH- |
| 2-286 | 3-Quin-CO- | CarCH₂ | Bz | 4-Br-Pro | tBuNH- |
| 2-287 | 4-Quin-CO- | CarCH₂ | Bz | 4-Br-Pro | tBuNH- |
| 2-288 | 2-Bfur-CO- | CarCH₂ | Bz | 4-Br-Pro | tBuNH- |
| 2-289 | 3-Bfur-CO- | CarCH₂ | Bz | 4-Br-Pro | tBuNH- |
| 2-290 | 2-Ind-CO- | CarCH₂ | Bz | 4-Br-Pro | tBuNH- |
| 2-291 | tBoc | CarCH₂ | Bz | 4-Br-Pro | tBuNH- |
| 2-292 | PhoAc- | CarCH₂ | Bz | 4-Br-Pro | tBuNH- |
| 2-293 | 4-MPhOAc- | CarCH₂ | Bz | 4-Br-Pro | tBuNH- |
| 2-294 | 3-Bzisox-CO- | CarCH₂ | Bz | 4-Br-Pro | tBuNH- |
| 2-295 | 5-H₂N-AcO-2-Ind-CO- | CarCH₂ | Bz | 4-Br-Pro | tBuNH- |
| 2-296 | 4-NH₂-PhoAc- | CarCH₂ | Bz | 4-Br-Pro | tBuNH- |
| 2-297 | 4-NH₂-Bzc | CarCH₂ | Bz | 4-Br-Pro | tBuNH- |
| 2-298 | 4-Me₂N-PhoAc- | CarCH₂ | Bz | 4-Br-Pro | tBuNH- |
| 2-299 | 4-MeNH-PhoAc- | CarCH₂ | Bz | 4-Br-Pro | tBuNH- |
| 2-300 | 4-[Bzc-NH]PhoAc- | CarCH₂ | Bz | 4-Br-Pro | tBuNH- |
| 2-301 | 4-[Gly-NH]PhoAc- | CarCH₂ | Bz | 4-Br-Pro | tBuNH- |
| 2-302 | 4-[Gly-NMe]PhoAc- | CarCH₂ | Bz | 4-Br-Pro | tBuNH- |
| 2-303 | 4-[Sar-NMe]PhoAc- | CarCH₂ | Bz | 4-Br-Pro | tBuNH- |
| 2-304 | 4-[(Mor-Ac)-NMe]-PhoAc- | CarCH₂ | Bz | 4-Br-Pro | tBuNH- |
| 2-305 | 7-MeO-2-Bfur-CO- | CarCH₂ | Bz | 4-Br-Pro | tBuNH- |
| 2-306 | 6-NO₂-2-Quix-CO- | CarCH₂ | Bz | 4-Br-Pro | tBuNH- |
| 2-307 | 6-NH₂-2-Quix-CO- | CarCH₂ | Bz | 4-Br-Pro | tBuNH- |
| 2-308 | 5-F-2-Ind-CO- | CarCH₂ | Bz | 4-Br-Pro | tBuNH- |
| 2-309 | 1-Me-3-Inda-CO- | CarCH₂ | Bz | 4-Br-Pro | tBuNH- |
| 2-310 | 4-[(Mor-CO-Pipr-Ac)-NMe]PhoAc- | CarCH₂ | Bz | 4-Br-Pro | tBuNH- |
| 2-311 | 4-[(N-tBoc-Pro)-NMe]PhoAc- | CarCH₂ | Bz | 4-Br-Pro | tBuNH- |
| 2-312 | 4-[(Bz-Pipr-Ac)-NH]-PhoAc- | CarCH₂ | Bz | 4-Br-Pro | tBuNH- |
| 2-313 | 4-[(MorEt-NH-Ac)-NH]PhoAc- | CarCH₂ | Bz | 4-Br-Pro | tBuNH- |
| 2-314 | 4-[(Mor-Ac)NH]-PhoAc- | CarCH₂ | Bz | 4-Br-Pro | tBuNH- |
| 2-315 | 4-[Bzc-NH]-cHxO-Ac- | CarCH₂ | Bz | 4-Br-Pro | tBuNH- |
| 2-316 | N-Bzc-PipO-Ac- | CarCH₂ | Bz | 4-Br-Pro | tBuNH- |
| 2-317 | 4-[Me(2-MorEt)N]-PhoAc- | CarCH₂ | Bz | 4-Br-Pro | tBuNH- |
| 2-318 | 4-[(3-Me₂N-Pr-NH-CO)-NMe]PhoAc- | CarCH₂ | Bz | 4-Br-Pro | tBuNH- |
| 2-319 | 4-[(Mor-CO)-NMe]-PhoAc- | CarCH₂ | Bz | 4-Br-Pro | tBuNH- |
| 2-320 | 4-[(4-NO₂-Pho-CO)-NMe]PhoAc- | CarCH₂ | Bz | 4-Br-Pro | tBuNH- |
| 2-321 | 4-[(N-Bz-Pipr-Ac)-NMe]PhoAc- | CarCH₂ | Bz | 4-Br-Pro | tBuNH- |
| 2-322 | 2-NH₂-PhoAc- | CarCH₂ | Bz | 4-Br-Pro | tBuNH- |
| 2-323 | 3-NH₂-PhoAc- | CarCH₂ | Bz | 4-Br-Pro | tBuNH- |
| 2-324 | 1-Me-2-Ind-CO- | CarCH₂ | Bz | 4-Br-Pro | tBuNH- |
| 2-325 | Bzc | CarCH₂ | Bz | 4,4-Di-F-Pro | tBuNH- |
| 2-326 | 2-Quix-CO- | CarCH₂ | Bz | 4,4-Di-F-Pro | tBuNH- |
| 2-327 | 2-Quin-CO- | CarCH₂ | Bz | 4,4-Di-F-Pro | tBuNH- |
| 2-328 | 3-Quin-CO- | CarCH₂ | Bz | 4,4-Di-F-Pro | tBuNH- |
| 2-329 | 4-Quin-CO- | CarCH₂ | Bz | 4,4-Di-F-Pro | tBuNH- |
| 2-330 | 2-Bfur-CO- | CarCH₂ | Bz | 4,4-Di-F-Pro | tBuNH- |
| 2-331 | 3-Bfur-CO- | CarCH₂ | Bz | 4,4-Di-F-Pro | tBuNH- |
| 2-332 | 2-Ind-CO- | CarCH₂ | Bz | 4,4-Di-F-Pro | tBuNH- |
| 2-333 | tBoc | CarCH₂ | Bz | 4,4-Di-F-Pro | tBuNH- |
| 2-334 | PhoAc- | CarCH₂ | Bz | 4,4-Di-F-Pro | tBuNH- |
| 2-335 | 4-MPhOAc- | CarCH₂ | Bz | 4,4-Di-F-Pro | tBuNH- |
| 2-336 | 3-Bzisox-CO- | CarCH₂ | Bz | 4,4-Di-F-Pro | tBuNH- |
| 2-337 | 5-H₂N-AcO-2-Ind-CO- | CarCH₂ | Bz | 4,4-Di-F-Pro | tBuNH- |

TABLE 2-continued

| Cpd. No. | R¹ | R³ | R⁴ | Z | R⁵ |
|---|---|---|---|---|---|
| 2-338 | 4-NH₂-PhoAc- | CarCH₂ | Bz | 4,4-Di-F-Pro | tBuNH- |
| 2-339 | 4-NH₂-Bzc | CarCH₂ | Bz | 4,4-Di-F-Pro | tBuNH- |
| 2-340 | 4-Me₂N-PhoAc- | CarCH₂ | Bz | 4,4-Di-F-Pro | tBuNH- |
| 2-341 | 4-MeNH-PhoAc- | CarCH₂ | Bz | 4,4-Di-F-Pro | tBuNH- |
| 2-342 | 4-[Bzc-NH]PhoAc- | CarCH₂ | Bz | 4,4-Di-F-Pro | tBuNH- |
| 2-343 | 4-[Gly-NH]PhoAc- | CarCH₂ | Bz | 4,4-Di-F-Pro | tBuNH- |
| 2-344 | 4-[Gly-NMe]PhoAc- | CarCH₂ | Bz | 4,4-Di-F-Pro | tBuNH- |
| 2-345 | 4-[Sar-NMe]PhoAc- | CarCH₂ | Bz | 4,4-Di-F-Pro | tBuNH- |
| 2-346 | 4-[(Mor-Ac)-NMe]-PhoAc- | CarCH₂ | Bz | 4,4-Di-F-Pro | tBuNH- |
| 2-347 | 7-MeO-2-Bfur-CO- | CarCH₂ | Bz | 4,4-Di-F-Pro | tBuNH- |
| 2-348 | 6-NO₂-2-Quix-CO- | CarCH₂ | Bz | 4,4-Di-F-Pro | tBuNH- |
| 2-349 | 6-NH₂-2-Quix-CO- | CarCH₂ | Bz | 4,4-Di-F-Pro | tBuNH- |
| 2-350 | 5-F-2-Ind-CO- | CarCH₂ | Bz | 4,4-Di-F-Pro | tBuNH- |
| 2-351 | 1-Me-3-Inda-CO- | CarCH₂ | Bz | 4,4-Di-F-Pro | tBuNH- |
| 2-352 | 4-[(Mor-CO-Pipr-Ac)-NMe]PhoAc- | CarCH₂ | Bz | 4,4-Di-F-Pro | tBuNH- |
| 2-353 | 4-[(N-tBoc-Pro)-NMe]PhoAc- | CarCH₂ | Bz | 4,4-Di-F-Pro | tBuNH- |
| 2-354 | 4-[(Bz-Pipr-Ac)-NH]-PhoAc- | CarCH₂ | Bz | 4,4-Di-F-Pro | tBuNH- |
| 2-355 | 4-[(MorEt-NH-Ac)-NH]PhoAc- | CarCH₂ | Bz | 4,4-Di-F-Pro | tBuNH- |
| 2-356 | 4-[(Mor-Ac)NH]-PhoAc- | CarCH₂ | Bz | 4,4-Di-F-Pro | tBuNH- |
| 2-357 | 4-[Bzc-NH]-cHxO-Ac- | CarCH₂ | Bz | 4,4-Di-F-Pro | tBuNH- |
| 2-358 | N-Bzc-PipO-Ac- | CarCH₂ | Bz | 4,4-Di-F-Pro | tBuNH- |
| 2-359 | 4-[Me(2-MorEt)N]-PhoAc- | CarCH₂ | Bz | 4,4-Di-F-Pro | tBuNH- |
| 2-360 | 4-[(3-Me₂N-Pr-NH-CO)NMe]PhoAc- | CarCH₂ | Bz | 4,4-Di-F-Pro | tBuNH- |
| 2-361 | 4-[(Mor-CO)-NMe]-PhoAc- | CarCH₂ | Bz | 4,4-Di-F-Pro | tBuNH- |
| 2-362 | 4-[4-NO₂-Pho-CO)-NMe]PhoAc- | CarCH₂ | Bz | 4,4-Di-F-Pro | tBuNH- |
| 2-363 | 4-[(N-Bz-Pipr-Ac)-NMe]PhoAc- | CarCH₂ | Bz | 4,4-Di-F-Pro | tBuNH- |
| 2-364 | 2-NH₂-PhoAc- | CarCH₂ | Bz | 4,4-Di-F-Pro | tBuNH- |
| 2-365 | 3-NH₂-PhoAc- | CarCH₂ | Bz | 4,4-Di-F-Pro | tBuNH- |
| 2-366 | 1-Me-2-Ind-CO- | CarCH₂ | Bz | 4,4-Di-F-Pro | tBuNH- |
| 2-367 | Bzc | CarCH₂ | Bz | 4-I-Pro | tBuNH- |
| 2-368 | 2-Quix-CO- | CarCH₂ | Bz | 4-I-Pro | tBuNH- |
| 2-369 | 2-Quin-CO- | CarCH₂ | Bz | 4-I-Pro | tBuNH- |
| 2-370 | 3-Quin-CO- | CarCH₂ | Bz | 4-I-Pro | tBuNH- |
| 2-371 | 4-Quin-CO- | CarCH₂ | Bz | 4-I-Pro | tBuNH- |
| 2-372 | 2-Bfur-CO- | CarCH₂ | Bz | 4-I-Pro | tBuNH- |
| 2-373 | 3-Bfur-CO- | CarCH₂ | Bz | 4-I-Pro | tBuNH- |
| 2-374 | 2-Ind-CO- | CarCH₂ | Bz | 4-I-Pro | tBuNH- |
| 2-375 | tBoc | CarCH₂ | Bz | 4-I-Pro | tBuNH- |
| 2-376 | PhoAc- | CarCH₂ | Bz | 4-I-Pro | tBuNH- |
| 2-377 | 4-MPhOAc- | CarCH₂ | Bz | 4-I-Pro | tBuNH- |
| 2-378 | 3-Bzisox-CO- | CarCH₂ | Bz | 4-I-Pro | tBuNH- |
| 2-379 | 5-H₂N-AcO-2-Ind-CO- | CarCH₂ | Bz | 4-I-Pro | tBuNH- |
| 2-380 | 4-NH₂-PhoAc- | CarCH₂ | Bz | 4-I-Pro | tBuNH- |
| 2-381 | 4-NH₂-Bzc | CarCH₂ | Bz | 4-I-Pro | tBuNH- |
| 2-382 | 4-Me₂N-PhoAc- | CarCH₂ | Bz | 4-I-Pro | tBuNH- |
| 2-383 | 4-MeNH-PhoAc- | CarCH₂ | Bz | 4-I-Pro | tBuNH- |
| 2-384 | 4-[Bzc-NH]-PhoAc- | CarCH₂ | Bz | 4-I-Pro | tBuNH- |
| 2-385 | 4-[Gly-NH]PhoAc- | CarCH₂ | Bz | 4-I-Pro | tBuNH- |
| 2-386 | 4-[Gly-NMe]PhoAc- | CarCH₂ | Bz | 4-I-Pro | tBuNH- |
| 2-387 | 4-[Sar-NMe]PhoAc- | CarCH₂ | Bz | 4-I-Pro | tBuNH- |
| 2-388 | 4-[(Mor-Ac)-NMe]-PhoAc- | CarCH₂ | Bz | 4-I-Pro | tBuNH- |
| 2-389 | 7-MeO-2-Bfur-CO- | CarCH₂ | Bz | 4-I-Pro | tBuNH- |
| 2-390 | 6-NO₂-2-Quix-CO- | CarCH₂ | Bz | 4-I-Pro | tBuNH- |
| 2-391 | 6-NH₂-2-Quix-CO- | CarCH₂ | Bz | 4-I-Pro | tBuNH- |
| 2-392 | 5-F-2-Ind-CO- | CarCH₂ | Bz | 4-I-Pro | tBuNH- |
| 2-393 | 1-Me-3-Inda-CO- | CarCH₂ | Bz | 4-I-Pro | tBuNH- |
| 2-394 | 4-[(Mor-CO-Pipr-Ac)-NMe]PhoAc- | CarCH₂ | Bz | 4-I-Pro | tBuNH- |
| 2-395 | 4-[(N-tBoc-Pro)-NMe]PhoAc- | CarCH₂ | Bz | 4-I-Pro | tBuNH- |
| 2-396 | 4-[(Bz-Pipr-Ac)-NH]PhoAc- | CarCH₂ | Bz | 4-I-Pro | tBuNH- |

TABLE 2-continued

| Cpd. No. | R¹ | R³ | R⁴ | Z | R⁵ |
|---|---|---|---|---|---|
| 2-397 | 4-[(MorEt-NH-Ac)-NH]PhoAc- | CarCH₂ | Bz | 4-I-Pro | tBuNH- |
| 2-398 | 4-[(Mor-Ac)NH]-PhoAc- | CarCH₂ | Bz | 4-I-Pro | tBuNH- |
| 2-399 | 4-[Bzc-NH]-cHxO-Ac- | CarCH₂ | Bz | 4-I-Pro | tBuNH- |
| 2-400 | N-Bzc-PipO-Ac- | CarCH₂ | Bz | 4-I-Pro | tBuNH- |
| 2-401 | 4-[Me(2-MorEt)N]-PhoAc- | CarCH₂ | Bz | 4-I-Pro | tBuNH- |
| 2-402 | 4-[(3-Me₂N-Pr-NH-CO)-NMe]PhoAc- | CarCH₂ | Bz | 4-I-Pro | tBuNH- |
| 2-403 | 4-[(Mor-CO)-NMe]-PhoAc- | CarCH₂ | Bz | 4-I-Pro | tBuNH- |
| 2-404 | 4-[(4-NO₂-Pho-CO)-NMe]PhoAc- | CarCH₂ | Bz | 4-I-Pro | tBuNH- |
| 2-405 | 4-[(N-Bz-Pipr-Ac)-NMe]-PhoAc- | CarCH₂ | Bz | 4-I-Pro | tBuNH- |
| 2-406 | 2-NH₂-PhoAc- | CarCH₂ | Bz | 4-I-Pro | tBuNH- |
| 2-407 | 3-NH₂-PhoAc- | CarCH₂ | Bz | 4-I-Pro | tBuNH- |
| 2-408 | 1-Me-2-Ind-CO- | CarCH₂ | Bz | 4-I-Pro | tBuNH- |

Of the compounds exemplified above, preferred compounds are Compounds No. 1–29, 33–36, 55–69, 83–98, 125–149, 153–157, 162, 163, 167–171, 176, 177, 181–185, 190, 191, 195–199, 204, 205, 209–213, 218, 219, 223–227, 232, 233, 237–241, 242, 246, 247, 251–255, 260, 261, 265–269, 274, 275, 279–283, 288–310, 316–388, 392–427, 430–439, 478–502, 506–540, 544–578, 582–616, 619–679, 686–701, 747–800, 801–815, 819–931, 933–937, 940, 941, 945, 946, 951–966, 969–976, 978–982, 985, 986, 990, 991, 997–1007, 1009–1099, 1107, 1108, 1115, 1130–1133, 1135, 1141, 1156–1159, 1161, 1168, 1173–1178, 1191–1200, 1202–1294, 1300–1304, 1312, 1313, 1319–1329, 1331–1339, 1345–1349, 1357, 1358, 1364–1374, 1376–1449, 1451, 1466, 1467–1469, 1471, 1473, 1477, 1492–1495, 1497, 1504, 1510–1514, 1522, 1528–1536, 1538–1630, 1636–1640, 1655–1665, 1667–1675, 1681–1685, 1693, 1694, 1700–1710, 1712–1722, 1725–1785, 1787, 1802–1805, 1807, 1809, 1813, 1828–1831, 1833, 1835, 1840, 1846–1850, 1858, 1864–1966, 1972–1976, 1984, 1985, 1991–2001, 2003–2011, 2016–2021, 2029, 2030, 2036–2046, 2048–2058, 2061–2121, 2123, 2138–2141, 2141, 2143, 2149, 2164–2167, 2169–2172, 2176, 2181–2186, 2194, 2199–2302, 2308–2312, 2320, 2321, 2327–2337, 2339–2347, 2352–2357, 2365, 2366, 2372–2382 2384–2457, 2459, 2474–2477, 2479–2482, 2500–2503, 2505–2508, 2512, 2517–2522, 2535–2638, 2646–2648, 2656, 2657, 2663–2673, 2675–2683, 2689–2693, 2701, 2702, 2708–2718, 2710–2793, 2795, 2810–2813, 2815–2818, 2836 2839, 2841–2844, 2848, 2853–2858, 2866, 2871–2880, 2882–2974, 2929–2984, 2992, 2993, 2999–3009, 3011–3019, 3024–3029, 3037, 3038, 3044–3129, 3131, 3146–3149, 3151–3154, 3172–3175, 3177–3184, 3189–3194, 3202, 3207–3310, 3315–3320, 3328, 3329, 3335–3355, 3360–3365, 3373, 3374, 338–3390, 3392–3465, 3467, 3482–3485, 3487–3490, 3508–3511, 3513–3516, 3520, 3525–3530, 3538, 3539, 3543–3552, 3554–3646, 3652–3656, 3664, 3665, 3671–3681, 3683–3691, 3696–3701, 3709, 3710, 3716–3801, 3803, 3818–3821, 3823–3826, 3844–3847, 3849–3852, 3856, 3861–3866, 3874, 3875, 3879–3982, 3987–3992, 4000, 4001, 4007–4017, 4019–4027, 4032–4037, 4045, 4046, 4052–4062 4064–4143, 4146–4151, 4156–4165, 4167–4177, 4179–4184, 4186, 4187, 4189–4198, 4200–4209, 4212–4217, 4219, 4220, 4222–4224, 4226–4231, 4233–4242, 4245–4250, 4252, 4253, 4255–4257, 4259, 4275, 4382, 4405, 4425, 4467, 4530, 4552, 4640–4681, 2—2, 2–23, 2–45 and 2–66.

More preferred compounds are Compounds No. 1, 2, 4, 5, 6, 9, 14, 15, 17, 19, 28, 29, 33, 41, 42, 46, 55, 56, 60, 69, 70, 74, 83, 84, 88, 97, 98, 102, 111, 112, 116, 125, 126, 130, 139, 140, 144, 148, 149, 153, 162, 163, 167, 176, 177, 181, 190, 191, 195, 204, 205, 209, 218, 219, 223, 232, 233, 237, 246, 247, 251, 260, 261, 265, 274, 275, 279, 288–350, 354–388, 392–426, 430–439, 478–502, 506–540, 544–578, 582–615, 619–629, 630–656, 657, 658, 663–666, 686, 690–692, 702–703, 708–711, 731, 735–737, 747, 749–751, 760, 763–766, 768–771, 774, 789–792, 794–797, 801, 806, 807, 809–811, 819, 824–833, 840–927, 932, 933, 935–937, 945, 952–962, 964, 968–972, 977, 980, 982, 990, 991, 997–1007, 1014–1024, 1029, 1030, 1034, 1035, 1039, 1040, 1044, 1045, 1049, 1050, 1054, 1055, 1059, 1060, 1064, 1065, 1069, 1070, 1074, 1075, 1079, 1080, 1084–1089, 1095–1098, 1107, 1108, 1130–1133, 1135–1138, 1156–1159, 1161–1164, 1168, 1173–1177, 1191–1200, 1202–1294, 1299–1303, 1312, 1313, 1319–1329, 1331–1339, 1344–1348, 1357, 1358, 1364–1374, 1376–1386, 1389, 1390, 1394, 1395, 1399, 1400, 1404, 1405, 1409, 1410, 1414, 1415, 1419, 1420, 1424, 1425, 1429, 1430, 1434, 1435, 1439, 1440, 1444, 1445, 1449, 1466–1469, 1471–1474, 1492–1495, 1497–1500, 1504, 1509–1513, 1522, 1522–1536, 1538–1630, 1635–1639, 1655–1665, 1667–1675, 1680–1684, 1693, 1694, 1700–1710, 1712–1726, 1730, 1731, 1735, 1736, 1740, 1741, 1745, 1746, 1750, 1751, 1755, 1756, 1760, 1761, 1765, 1766, 1770, 1771, 1775, 1776, 1780, 1781, 1785, 1802–1805, 1807–1810, 1828–1831, 1833–1836, 1840, 1845–1849, 1863–1872, 1874–1966, 1971–1975, 1984, 1985, 1991–2001, 2003–2011, 2016–2020, 2029, 2030, 2036–2046, 2048–2062, 2006, 2067, 2071, 2072, 2076, 2077, 2081, 2082, 2086, 2087, 2091, 2092, 2096, 2097, 2101, 2102, 2106, 2107, 2111, 2112, 2116, 2117, 2121, 2138–2141, 2143–2146, 2164–2167, 2169–2172, 2176, 2181–2185, 2194, 2199–2208, 2210–2302, 2307–2311, 2320, 2321, 2327–2337, 2339–2347, 2352–2356, 2365, 2366, 2372–2382, 2384–2394, 2397, 2398, 2402, 2403, 2407, 2408, 2412, 2413, 2417, 2418, 2422, 2423, 2427, 2428, 2432, 2433, 2437, 2438, 2442, 2443, 2447, 2448, 2452, 2453, 2457, 2474–2477, 2479–2482, 2500–2503, 2505–2508, 2512, 2517–2521, 2535–2544, 2546–2647, 2656, 2657, 2663–2673, 2675–2683, 2688–2692, 2701, 2702, 2708–2718, 2720–2730, 2733, 2734, 2738, 2739, 2743, 2744, 2748, 2749, 2753, 2754, 2758, 2759, 2763, 2764, 2768, 2769, 2773, 2774, 2778, 2779, 2783, 2784, 2788, 2789, 2793, 2810–2813, 2815–2818, 2836–2839, 2841–2844, 2848, 2853–2857, 2866, 2871–2880, 2882–2974, 2979–2983, 2992, 2993, 2999–3009, 3011–3019, 3024–3028, 3037, 3038, 3044–3054, 3056–3070, 3074, 3075, 3079, 3080, 3084, 3085, 3089, 3090, 3094, 3095, 3099, 3100, 3104, 3105, 3109, 3110, 3114, 3115, 3119, 3120, 3124, 3125, 3129, 3146–3149, 3151–3154, 3172–3175, 3177–3180, 3189–3193, 3202, 3207–3216, 3218–3310, 3315–3319, 3328, 3329, 3335–3345, 3347–3355, 3360–3364, 3373, 3374, 3380–3390, 3392–3402, 3405, 3406, 3410, 3411, 3415, 3416, 3420, 3421, 3425, 3426, 3430, 3431, 3435, 3436, 3440, 3441, 3445, 3446, 3450, 3451, 3455, 3456, 3460, 3461, 3465, 3482–3485, 3487–3490, 3508–3511, 3513–3516, 3520, 3525–3529, 3538, 3543–3552, 3554–3646, 3652–3655, 3664, 3665, 3671–3681, 3683–3691, 3696–3700, 3709, 3710, 3716–3726, 3728–3738, 3741, 3742, 3746, 3747, 3751, 3752, 3756, 3757, 3761, 3762, 3766, 3767, 3771, 3772, 3776, 3777, 3781, 3782, 3786, 3787, 3791, 3792, 3796, 3797, 3801, 3818–3821, 3823–3826, 3844–3847, 3849–3852, 3856, 3861–3865, 3874, 3875, 3879–3888, 3890–3982, 3987–3991, 4000, 4001, 4007–4017, 4019–4027, 4032–4036, 4045, 4046, 4052–4062, 4064–4076, 4077, 4078, 4082, 4083, 4087, 4088, 4092, 4093, 4097, 4098, 4102, 4103, 4107, 4108, 4112, 4113, 4117, 4118, 4122, 4123, 4127, 4128, 4132, 4133, 4138, 4140–4142, 4171, 4173–4175, 4240, 4206–4208, 4237, 4239–4241, 4382, 4396, 4403, 4405–4407, 4425, 4446, 4448–4450, 4467, 4488, 4490–4492, 4552, 4573, 4575–4577, 4640, 4642, 4644, 4652, 4654, 4656, 4658, 4666, 4668, 4670, 4672, 4680, 2—2, 2–23, 2–45 and 2–66.

Still more preferred compounds are Compounds No. 1, 2, 6, 14, 15, 19, 28, 29, 33, 41, 42, 46, 55, 56, 60, 69, 70, 74, 83, 84, 88, 97, 98, 102, 125, 126, 130, 139, 140, 144, 148, 149, 153, 162, 163, 167, 176, 177, 181, 190, 191, 195, 204, 205, 209, 218, 219, 223, 232, 233, 237, 238, 246, 247, 251, 260, 261, 265, 274, 275, 279, 288–290, 294–296, 299–301, 326–328, 337–339, 364–366, 375–377, 402–404, 413–415, 478–480, 489–491, 516–518, 527–529, 554–556, 565–567, 592–594, 603–605, 630–637, 641, 646–648, 650, 657, 658, 663–666, 686, 690–692, 747, 749, 760, 763–766, 768–773, 775, 781, 789–792, 794–800, 801–802, 806, 809–811, 819, 825–833, 840–858, 862–867, 869, 872–883, 888–893, 899–906, 910–920, 926–928, 932, 935–937, 945–946, 952–962, 969–973, 977, 980–982, 990–991, 997–1007, 1014–1021, 1029, 1030, 1034, 1035, 1039, 1040, 1044, 1045, 1064, 1065, 1069, 1070, 1074, 1075, 1079, 1080, 1084–1089, 1095, 1097, 1107, 1130–1133, 1156–1159, 1168, 1174, 1176, 1194, 1197–1200, 1202–1294, 1300, 1302, 1312, 1320, 1326–1329, 1331–1339, 1345, 1347, 1357, 1365, 1371–1374, 1376–1386, 1389, 1390, 1394, 1395, 1399, 1400, 1404, 1405, 1409, 1410, 1425, 1425, 1429, 1430, 1434, 1435, 1439, 1440, 1444, 1445, 1449, 1466–1469, 1492–1495, 1504, 1510, 1512, 1530, 1533–1536, 1538–1630, 1636, 1638, 1656, 1662–1665, 1667–1675, 1681, 1683, 1693, 1701, 1707–1710, 1712–1726, 1730, 1731, 1735, 1736, 1740, 1741, 1745, 1746, 1760, 1761, 1765, 1766, 1770, 1771, 1775, 1776, 1780, 1781, 1785, 1802–1805, 1828–1831, 1840, 1846, 1848, 1869–1872, 1874–1966, 1972, 1974, 1984, 1992, 1998–2001, 2003–2011, 2017, 2019, 2029, 2037, 2043–2046, 2048–2062, 2066, 2067, 2071, 2072, 2076, 2077, 2081, 2082, 2096, 2097, 2101, 2102, 2106, 2107, 2111, 2112, 2116, 2117, 2121, 2138–2141, 2164–2167, 2176, 2182, 2184, 2205–2208, 2210–2302, 2308, 2310, 2320, 2328, 2334–2337, 2339–2347, 2353, 2355, 2365, 2373, 2379–2382, 2384–2394, 2397, 2398, 2402, 2403, 2407, 2408, 2412, 2413, 2417, 2418, 2432, 2433, 2437, 2438, 2442, 2443, 2447, 2448, 2452, 2453, 2457, 2474–2477, 2500–2503, 2512, 2518, 2520, 2541–2544, 2544, 2646, 2656, 2664, 2670–2673, 2675–2683, 2689, 2691, 2701, 2709, 2715–2718, 2720–2730, 2733, 2734, 2738, 2739, 2743, 2744, 2748, 2749, 2753, 2754, 2768, 2769, 2773, 2774, 2778, 2779, 2783, 2784, 2788, 2789, 2793, 2810–2813, 2836–2839, 2848, 2854, 2856, 2872, 2877–2880, 2882–2974, 2980, 2982, 2992, 3000, 3006–3009, 3011–3019, 3025, 3027, 3037, 3045, 3051–3054, 3056–3070, 3074, 3075, 3079, 3080, 3084, 3085, 3089, 3090, 3104, 3105, 3109, 3110, 3114, 3115, 3119, 3120, 3124, 3125, 3129, 3146–3149, 3172–3175, 3190, 3192, 3213–3216, 3218–3310, 3316, 3318, 3328, 3336, 3342–3345, 3347–3355, 3361, 3363, 3373, 3381, 3387–3390, 3392–3402, 3405, 3406, 3410, 3411, 3415, 3416, 3420, 3421, 3425, 3426, 3440, 3441, 3445, 3446, 3450, 3451, 3455, 3456, 3460, 3461, 3465, 3482–3485, 3508–3511, 3520, 3526, 3528, 3564, 3549–3552, 3554–3646, 3652, 3654, 3664, 3672, 3678–3681, 3683–3691, 3697, 3699, 3709, 3717, 3723–3726, 3728–3738, 3741, 3742, 3746, 3747, 3751, 3752, 3756, 3757, 3761, 3762, 3776, 3777, 3781, 3782, 3686, 3787, 3791, 3792, 3796, 3797, 3801, 3818–3821, 3844–3847, 3856, 3862, 3864, 3875, 3885–3888, 3890–3982, 3988, 3990, 4000, 4008, 4014–4017, 4019–4027, 4033, 4035, 4045, 4053, 4059–4062, 4064–4076, 4077, 4078, 4082, 4083, 4087, 4088, 4092, 4093, 4097, 4098, 4112, 4113, 4117, 4118, 4122, 4123, 4127, 4128, 4132, 4133, 4138, 4140, 4142, 4147, 4172, 4173, 4175, 4204, 4206, 4208, 4237, 4239, 4241, 4382, 4396, 4403, 4405, 4407, 4425, 4446, 4448, 4450, 4467, 4488, 4490, 4492, 4552, 4573, 4575, 4577, 4577, 4644, 4652, 4658, 4667, 4670, 4672, 4680, 2—2, 2–23, 2–45 and 2–66.

The most preferred compounds are Compounds No.:

299. 1-{3-[$N^2$-(2-Quinoxalinecarbonyl)-L-asparaginyl]amino-2-hydroxy-4-phenylbutyryl}-N-t-butyl-4-chloro-L-prolinamide;

527. 1-{3-[$N^2$-(4-Aminophenoxyacetyl)-L-asparaginyl]amino-2-hydroxy-4-phenylbutyryl]-4-chloro-N-t-butyl-L-prolinamide;

565. 1-[{3-[$N^2$-(4-Benzyloxycarbonylaminophenoxy)acetyl-L-asparaginyl]amino-2-hydroxy-4-phenylbutyryl}-4-chloro-N-t-butyl-L-prolinamide;

630. 1-{3-[$N^2$-(4-Aminophenoxyacetyl)-L-asparaginyl) amino-2-hydroxy-4-phenylbutyryl}-N-t-butyl-L-prolinamide;

637. 1-[3-{$N^2$-[4-(N,N-Dimethylamino)phenoxyacetyl]-L-asparaginyl}amino-2-hydroxy-4-phenylbutyryl]-N-t-butyl-L-prolinamide;

641. 1-[3-{$N^2$-[4-(Methylamino)phenoxyacetyl]-L-asparaginyl}amino-2-hydroxy-4-phenylbutyryl]-N-t-butyl-L-prolinamide;

643. 1-[3-{$N^2$-[4-(Benzyloxycarbonylamino)phenoxyacetyl]-L-asparaginyl}amino-2-hydroxy-4-phenylbutyryl]-N-t-butyl-L-prolinamide;

4147. 1-{3-($N^2$-(7-Methoxy-2-benzofurancarbonyl)-L-asparaginyl]amino-2-hydroxy-4-phenylbutyryl}-4-chloro-N-t-butyl-L-prolinamide;

4173.  1-{3-[N²-(6-Amino-2-quinoxalinecarbonyl)-L-asparaginyl]amino-2-hydroxy-4-phenylbutyryl}-4-chloro-N-t-butyl-L-prolinamide;

4175.  1-{3-[N²-(1-Methylindazol-3-ylcarbonyl)-L-asparaginyl]amino-2-hydroxy-4-phenylbutyryl}-4-chloro-N-t-butyl-L-prolinamide;

and pharmaceutically acceptable salts and esters thereof.

The compounds of the present invention can be prepared by a variety of methods well known in the art for the preparation of oligopeptides, which generally consist in building the oligopeptide from smaller peptides and/or amino-acids.

Thus, in general terms, the present invention provides a process for preparing a compound of formula (I) which comprises reacting at least two peptides and/or amino-acids or reactive derivatives thereof, and, if necessary, removing protecting groups, to form said compound of formula (I).

In more detail, the peptide derivatives of the present invention may be prepared by the following Reaction Schemes A and B:

Reaction Scheme A:

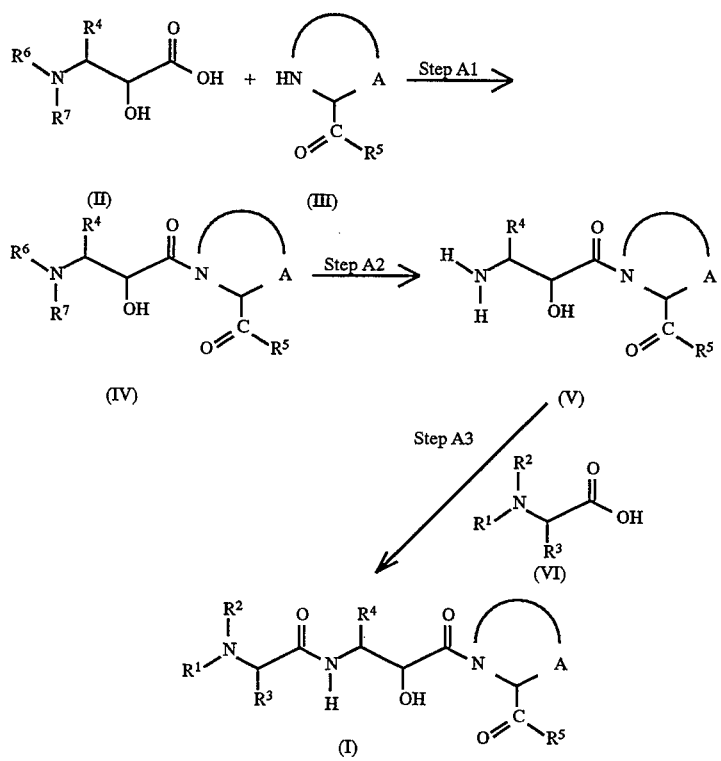

Reaction Scheme B:

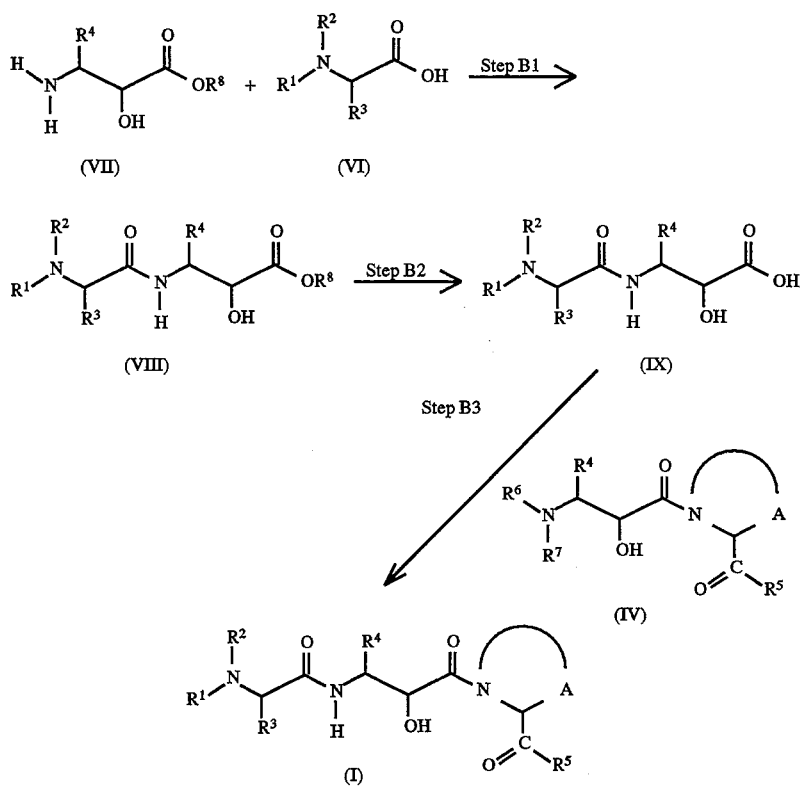

In the above formulae, $R^1$, $R^2$, $R^3$, $R^4$, A and $R^5$ are as defined above. $R^6$ and $R^7$ each represents an amino-protecting group, or, where $R^6$ represents a normal amino-protecting group, $R^7$ represents a hydrogen atom. Alternatively, $R^6$ and $R^7$ together may represent an arylmethylene group, in which the aryl part is substituted with a lower alkyl, lower alkoxy, hydroxy or heterocyclyl group, all of which may be as defined and exemplified above. There is no particular limitation upon the nature of the amino-protecting group represented by $R^6$, and any such group conventionally used as an amino-protecting group may equally be here. Preferred examples of such amino-protecting groups include:

the aliphatic acyl groups defined and exemplified above;

aromatic acyl groups, including arylcarbonyl groups (such as the benzoyl, α-naphthoyl and β-naphthoyl groups), halogenated arylcarbonyl groups (such as the 2-bromobenzoyl and 4-chlorobenzoyl groups), lower alkyl-substituted arylcarbonyl groups (such as the 2,4,6-trimethylbenzoyl and 4-toluoyl groups), lower alkoxy-substituted arylcarbonyl groups (such as the 4-anisolyl group), nitrated arylcarbonyl groups (such as the 4-nitrobenzoyl and 2-nitrobenzoyl groups), lower alkoxycarbonyl-substituted arylcarbonyl groups [such as the 2-(methoxycarbonyl)benzoyl group] and aryl-substituted arylcarbonyl groups (such as the 4-phenylbenzoyl group);

alkoxycarbonyl groups, including the lower alkoxycarbonyl groups (such as the methoxycarbonyl, ethoxycarbonyl, t-butoxycarbonyl and isobutoxycarbonyl groups), lower alkoxycarbonyl groups substituted with a halogen atom or a with tri(lower alkyl)silyl group (such as the 2,2,2-trichloroethoxycarbonyl and 2-trimethylsilylethoxycarbonyl groups);

alkenyloxycarbonyl groups, such as the vinyloxycarbonyl and allyloxycarbonyl groups;

aralkyloxycarbonyl groups, which may be as defined and exemplified above, but in which the aryl ring is preferably unsubstituted or is substituted by 1 or 2 lower alkoxy or nitro groups, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups;

silyl groups, including the tri(lower alkyl)silyl groups (such as the trimethylsilyl, triethylsilyl, isopropyldimethylsilyl, t-butyldimethylsilyl, methyldiisopropylsilyl, methyldi-t-butylsilyl and triisopropylsilyl groups); and tri-substituted silyl groups substituted with 1 or 2 aryl groups and, correspondingly, 2 or 1 alkyl groups (such as the diphenylmethylsilyl, diphenylbutylsilyl, diphenylisopropylsilyl and phenyldiisopropylsilyl groups).

In the case of the above protecting groups represented by $R^6$, $R^7$ preferably represents a hydrogen atom.

Alternatively, $R^6$ and $R^7$ may each represent an aralkyl group, such as those defined and exemplified above. As a further alternative, $R^6$ and $R^7$ may together form a substituted methylene group capable of forming a Schiff's base such as a N,N-dimethylaminomethylene, benzylidene, 4-methoxybenzylidene, 4-nitrobenzylidene, salicylidene, 5-chlorosalicylidene, diphenylmethylene or (5-chloro-2-hydroxyphenyl)phenylmethylene group.

More preferably, $R^6$ represents an alkoxycarbonyl, aralkyloxycarbonyl or arylmethyl group, and most preferably a t-butoxycarbonyl, benzyloxycarbonyl, 4-methoxybenzyloxycarbonyl or benzyl group. In these cases, $R^7$ preferably represents a hydrogen atom.

R⁸ represents a hydrogen atom or a carboxy-protecting group. Examples of such groups include the lower alkyl groups, halogenated lower alkyl groups and aralkyl groups defined and exemplified above; preferably a lower alkyl or aralkyl group.

Step A1

In Step A1 of Reaction Scheme A, a compound of formula (II) or a reactive derivative thereof is reacted with an amino compound of formula (III) to produce a compound of formula (IV).

This reaction can be carried out according to conventional procedures for peptide synthesis, for example, using the azide method, the active ester method, the mixed anhydride method or the condensing method.

Azide method:

In the azide method, the reaction is carried out by treating an amino acid or its ester derivative with hydrazine in an inert Solvent at about room temperature to produce hydrazide, reacting the hydrazide with a nitrous acid compound to convert it to an azide compound and subsequently reacting the azide compound with an amine compound of formula (III).

Examples of nitrous acid compounds which may be used include: alkali metal nitrites, such as sodium nitrite; and alkyl nitrites, such as isoamyl nitrite.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, especially fatty acid amides, such as dimethylformamide or dimethylacetamide; sulfoxides, such as dimethyl sulfoxide; and pyrrolidones, such as N-methylpyrrolidone.

The last two reactions in this step, that is production of the azide compound and its reaction with the amine of formula (III), are normally carried out without isolation of the intermediate azide compound. The reactions can take place over a wide range of temperatures, and the precise reaction temperature is not critical to the invention. In general, we find it convenient to employ a temperature of from −50° to 0° C. in the first part of this reaction and from −10° C. to 10° C. in the second part. The time required for the reactions may also vary widely, depending on many factors, notably the reaction temperature and the nature of the reagents and solvent employed. However, provided that the reaction is effected under the preferred conditions outlined above, a period of from 5 minutes to 1 hour in the first of these reactions and from 10 hours to 5 days in the second will usually suffice.

Active ester method:

In the active ester method, the reaction is carried out by reacting an amino acid with a reagent to prepare an active ester, and subsequently reacting this with an amine compound of formula (III).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride or chloroform; ethers, such as diethyl ether or tetrahydrofuran; and amides, such as dimethylformamide or dimethylacetamide.

Examples of the reagents used for the preparation of the active ester include: N-hydroxy compounds, such as N-hydroxysuccinimide, 1-hydroxybenzotriazole and N-hydroxy-5-norbornene-2,3-dicarboxyimide. The reaction for preparing the active ester is preferably carried out in the presence of a condensing agent, such as dicyclohexyl carbodiimide (DCC). The coupling reaction is normally and preferably carried out in the presence of a condensing agent, such as 1,1'-oxalyldiimidazole, 2,2'-dipyridyl disulfide, N,N'-disuccinimidyl carbonate, diphenylphosphoryl azide (DPPA), diethylphosphoryl cyanide (DEPC), N,N'-bis(2-oxo-3-oxazolidinyl)phosphinic chloride (BOP-Cl), N,N'-carbonyldiimidazole, N,N'-disuccinimidyl oxalate (DSO), N,N'-diphthalimide oxalate (DPO), N,N'-bis(norbornenyl succinimidyl) oxalate (BNO), 1,1'-bis(benzotriazolyl) oxalate (BBTO), 1,1'-bis(6-chlorobenzotriazolyl) oxalate (BCTO), 1,1'-bis(6-trifluoromethylbenzotriazolyl) oxalate (BTBO) or tris-pyrrolidino-phosphonium hexafluorophosphate (PyBrOP).

The reaction can take place over a wide range of temperatures, and the precise reaction temperature is not critical to the invention. The time required for the reaction may also vary widely, depending on many factors, notably the reaction temperature and the nature of the reagents and solvent employed. In general, the preferred reaction temperature ranges from −10° to 25° C. for the preparation of the active ester and is about room temperature in the coupling reaction of the active ester with the amine. The time required for each reaction is normally from 30 minutes to 10 hours.

Mixed anhydride method:

In the mixed anhydride method, the reaction is carried out by producing a mixed anhydride of the amino acid of formula (II) and then reacting the resulting anhydride with an amine of formula (III).

The preparation of the mixed anhydride may be carried out by reacting the amino acid with a lower alkyl haloformate, such as ethyl chloroformate or isobutyl chloroformate, a di(lower alkyl)phosphoryl cyanide, such as diethylphosphoryl cyanide (DEPC), or a diphenylphosphoryl azide (DPPA). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether or tetrahydrofuran; and amides, such as dimethylformamide or dimethylacetamide.

The reaction is preferably carried out in the presence of an organic amine such as triethylamine or N-methylmorpholine. The reaction can take place over a wide range of temperatures, and the precise reaction temperature is not critical to the invention. In general, we find it convenient to carry out the reaction at a temperature of from −10° C. and 25° C. The time required for the reaction may also vary widely, depending on many factors, notably the reaction temperature and the nature of the reagents and solvent employed. However, provided that the reaction is effected under the preferred conditions outlined above, a period of from 30 minutes to 5 hours will usually suffice.

The reaction of the resulting mixed anhydride with the amine of formula (III) is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether or tetrahydrofuran; and amides, such as dimethylformamide or dimethylacetamide. The reaction can take place over a wide range of temperatures, and the precise reaction temperature is not critical to the invention. In general, we find it convenient to carry out the reaction at a temperature of from 0° C. to room temperature. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

Condensing method:

In the condensing method, the amino acid of formula (II) is reacted directly with the amine of formula (III) in the presence of a condensing agent, such as dicyclohexyl carbodiimide or carbodiimidazole. This condensation reaction is essentially the same as that described above in the preparation of the active ester and may be carried out using the same reagents and under the same reaction conditions.

Step A2

In Step A2, a compound of formula (V) is prepared by removing the amino-protecting group or groups from the compound of formula (IV).

Where the amino-protecting group is a silyl group, it can normally be removed by treatment with a compound capable of forming a fluoride anion, for example, tetrabutylammonium fluoride or potassium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as diethyl ether, tetrahydrofuran or dioxane.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents and solvent employed. However, provided that the reaction is effected under the preferred conditions outlined above, a period of from 10 to 18 hours will usually suffice.

Where the amino-protecting is an alkoxycarbonyl group, such as a t-butyloxycarbonyl group, it can be removed by treatment with an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide or dimethylacetamide; ethers, such as diethyl ether, diisopropyl ether, tetrahydrofuran, dioxane, dimethoxyethane or diethylene glycol dimethyl ether; alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether; and halogenated hydrocarbons, especially halogenated aliphatic hydrocarbons, such as methylene chloride, chloroform or trichloroethane.

The nature of the acid used in this reaction is not particularly critical, and any acid commonly used in this type of reaction may equally be used here. Preferred examples include: inorganic acids, such as hydrochloric acid; organic acids, such as trifluoroacetic acid; and Lewis acids, such as boron trifluoride etherate.

The reaction can take place over a wide range of temperatures, and the precise reaction temperature is not critical to the invention. In general, we find it convenient to carry out the reaction at a temperature of from 0° C. to 30° C. The time required for the reaction may also vary widely, depending on many factors, notably the reaction temperature and the nature of the reagents and solvent employed. However, provided that the reaction is effected under the preferred conditions outlined above, a period of from 20 minutes to 1 hour will usually suffice.

Where the amino-protecting group is an aliphatic acyl group, an aromatic acyl group or a substituted methylene group capable of forming a Schiff's base, it can be removed by treatment with an acid or base in the presence of an aqueous solvent.

The nature of the acid used is not particularly critical, and any acid commonly used in this type of reaction may equally be used here. Preferred examples include inorganic acids, such as hydrochloric acid, sulfuric acid, phosphoric acid or hydrobromic acid. There is likewise no particular limitation upon the nature of the base used, provided that it has no adverse effect on other parts of the compound. Preferred examples of bases which may be used include: alkali metal alkoxides, such as sodium methoxide; alkali metal carbonates, such as sodium carbonate or potassium carbonate; alkali metal hydroxides, such as sodium hydroxide or potassium hydroxide; and ammonia, for example aqueous ammonia or concentrated methanolic ammonia.

Hydrolysis using a base may sometimes be accompanied by isomerization.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent, although the solvent is preferably aqueous. Examples of suitable solvents include: water; organic solvents, such as alcohols (for example methanol, ethanol or propanol) and ethers (for example tetrahydrofuran or dioxane); and mixtures of water and one or more of these organic solvents.

The reaction can take place over a wide range of temperatures, and the precise reaction temperature is not critical to the invention. In general, we find it convenient to carry out the reaction at a temperature of from 0° to 150° C. in order to reduce side reactions. The time required for the reaction may also vary widely, depending on many factors, notably the reaction temperature and the nature of the reagents, base and solvent employed. However, provided that the reaction is effected under the preferred conditions outlined above, a period of from 1 to 10 hours will usually suffice.

Where the amino-protecting group is an aralkyloxycarbonyl group, it can be removed by reduction in an inert solvent in the presence of a catalyst.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethoxyethane or diethylene glycol dimethyl ether; and alcohols, such as methanol, ethanol, propanol, isopropanol, butanol, isobutanol, t-butanol, isoamyl alcohol, diethylene glycol, glycerine, octanol, cyclohexanol or ethylene glycol monomethyl ether.

The nature of the catalyst used is also not critical, and any catalyst commonly used for catalytic reduction may equally be employed here. Examples of catalysts which may be used in the catalytic reduction include: palladium on charcoal and palladium black.

The reaction is carried out in the presence of hydrogen, preferably in an atmosphere of hydrogen, suitably at a pressure of from 1 to 10 atmospheres, although the exact hydrogen pressure is not critical.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents and solvent employed. However, provided that the reaction is effected under the preferred conditions outlined above, a period of from 1 to 8 hours will usually suffice.

Where the amino-protecting group is an arylmethyl group, it can be removed: by contacting the protected compound with a reducing reagent in a solvent; or, and preferably, by catalytic reduction at room temperature in the presence of a catalyst; or by using an oxidizing reagent.

In the case of deprotection by means of catalytic reduction, the reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or isopropanol; ethers, such as diethyl ether, tetrahydrofuran or dioxane; aromatic hydrocarbons, such as toluene, benzene or xylene; aliphatic hydrocarbons, such as hexane or cyclohexane; esters, such as ethyl acetate or propyl acetate; aliphatic acids, such as formic acid or acetic acid; mixtures of one or more of these organic solvents and water; and mixtures of one or more aliphatic acids and one or more alcohols.

There is also no particular limitation upon the nature of the catalyst used, and any catalyst commonly used in catalytic reduction reactions may equally be employed here. Preferred examples of such catalysts include: palladium black, palladium on charcoal, Raney nickel, platinum oxide, platinum black, rhodium on alumina, triphenylphosphine-rhodium chloride and palladium on barium sulfate.

The reaction is carried out in the presence of hydrogen, preferably in an atmosphere of hydrogen, suitably at a pressure of from 1 to 10 atmospheres, although the exact hydrogen pressure is not critical.

The reaction can take place over a wide range of temperatures, and the precise reaction temperature is not critical to the invention. In general, we find it convenient to carry out the reaction at a temperature of from 0° C. to 100° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours will usually suffice.

In the case of oxidative deprotection, the reaction is normally and preferably effected in the presence of a solvent, preferably an aqueous organic solvent. There is no particular restriction on the nature of the solvent to be employed, provided that it has no adverse effect on the reaction or on the reagents involved and that it can dissolve the reagents, at least to some extent. Examples of suitable solvents include: ketones, such as acetone; halogenated hydrocarbons, such as methylene chloride, chloroform or carbon tetrachloride; nitriles, such as acetonitrile; ethers, such as diethyl ether, tetrahydrofuran or dioxane; amides, such as dimethylformamide, dimethylacetamide or hexamethylphosphoric triamide; and sulfoxides, such as dimethyl sulfoxide.

There is also no particular limitation upon the nature of the oxidizing reagent, and any conventional oxidizing agent may be used. Preferred examples include: potassium persulfate, sodium persulfate, ammonium cerium nitrate (CAN) and 2,3-dichloro-5,6-dicyano-p-benzoquinone (DDQ).

The reaction can take place over a wide range of temperatures, and the precise reaction temperature is not critical to the invention. In general, we find it convenient to carry out the reaction at a temperature of from 0° C. to 150° C. The time required for the reaction may also vary widely, depending on many factors, notably the reaction temperature and the nature of the reagents, catalyst and solvent employed. However, provided that the reaction is effected under the preferred conditions outlined above, a period of from 10 minutes to 24 hours will usually suffice.

Where the amino-protecting group is a diarylmethyl group, it can be removed in a similar manner to that described above for the deprotection of an arylmethyl group.

Where the amino-protecting group is an alkenyloxycarbonyl group, it can normally be removed by treatment with a base in a similar manner to that described above for the deprotecting reaction used when the amino-protecting group is an aliphatic acyl, aromatic acyl or alkoxycarbonyl group, or a substituted methylene group capable of forming a Schiff's base.

Where the amino-protecting group is an allyloxycarbonyl group, it can be removed particularly simply by using palladium and triphenylphosphine or nickel tetracarbonyl, which has the advantage that side reactions can be suppressed.

Step A3

In Step A3, the compound of formula (I) of the present invention can be prepared by reacting the compound of formula (V) with a compound of formula (VI) or with a reactive derivative thereof. This reaction is essentially the same as that described in Step A1, and may be carried out using the same reagents and reaction conditions.

Reaction Scheme B provides an alternative method of preparing the compound of formula (I) of the present invention.

Step B1

In Step B1, a compound of formula (VIII) is prepared by reacting an amino-acid compound of formula (VII) with a compound of formula (VI) or with a reactive derivative thereof. This reaction is essentially the same as that described in Step A1, and may be carried out using the same reagents and reaction conditions.

Step B2

In Step B2, a compound of formula (IX) is prepared by removing the carboxy-protecting group from the compound of formula (VIII).

Although the deprotecting reaction employed will depend upon the nature of the protecting group, it can be carried out by methods well known in this field, for example as follows.

Where the carboxy-protecting group is a lower alkyl group, it can be removed by treatment with an acid or base.

There is no particular limitation on the nature of the acid employed in this reaction, although we generally find it convenient to use hydrochloric acid, sulfuric acid, phosphoric acid or hydrobromic acid.

There is likewise no particular limitation upon the nature of the base used, provided that it has no adverse effect upon the other parts of the compound. Suitable bases include, for example: alkali metal carbonates, such as sodium carbonate or potassium carbonate; alkali metal hydroxides, such as sodium hydroxide or potassium hydroxide; and concentrated methanolic ammonia.

Hydrolysis by a base may sometimes be accompanied by isomerization.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent, and any solvent commonly used for hydrolysis reactions may equally be used here. Examples of suitable solvents include: water; and mixtures of water and one or more organic solvents, such as alcohols (for example methanol, ethanol or propanol) or ethers (for example tetrahydrofuran or dioxane).

The reaction can take place over a wide range of temperatures, and the precise reaction temperature is not critical to the invention. In general, we find it convenient to carry out the reaction at a temperature of from 0° C. to 150° C. in order to reduce side reactions. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

Where the carboxy-protecting group is a diaryl-substituted methyl group, such as a diphenylmethyl group, it can normally be removed by treatment with an acid. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include aromatic hydrocarbons, such as anisole. Suitable acids include fluorinated organic acids, such as trifluoroacetic acid.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 10 hours will usually suffice.

Where the carboxy-protecting group is an arylmethyl or halogenated lower alkyl group, it can normally be removed by contacting the protected compound with a reducing reagent. The preferred reducing agent will depend on the nature of the group to be removed.

For example, where the carboxy-protecting group is a halogenated lower alkyl group, it can preferably be removed by using zinc and acetic acid; where the carboxy-protecting group is an arylmethyl group, it can be removed by catalytic reduction in the presence of a catalyst such as palladium on charcoal or platinum, or using an alkali metal sulfide, such as potassium sulfide or sodium sulfide.

These reactions are normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; aliphatic acids, such as acetic acid; and mixtures of one or more of these organic solvents and water.

The reaction can take place over a wide range of temperatures, and the precise reaction temperature is not critical to the invention. In general, we find it convenient to carry out the reaction at a temperature of from 0° C. to about room temperature. The time required for the reaction may also vary widely, depending on many factors, notably the reaction temperature and the nature of the reagents, the reducing agent and solvent employed. However, provided that the reaction is effected under the preferred conditions outlined above, a period of from 5 minutes to 12 hours will usually suffice.

Step B3

In Step B3 of Reaction Scheme B, the compound of formula (I) of the present invention is prepared by reacting a compound of formula (IX) with a compound of formula (IV) or with a reactive derivative thereof. This reaction is essentially the same as that described in Step A1, and may be carried out using the same reagents and reaction conditions.

If desired, where the amino group of the compound of formula (VI) is protected, after completion of the reaction in Step A3 or B3, the amino-protecting group may be removed to afford the compound of formula (I) of the present invention having a free amino group. Where some compounds in these methods have a protected group, by repeating Step A2 (for deprotection) and/or Step A3 (for elongation of peptide chain), other compounds of formula (I) of the present invention may be prepared.

In each of the steps described above, the product of each reaction can be recovered from the reaction mixture by conventional means after completion of the reaction. An example of one such recovery technique comprises: neutralizing the reaction mixture; if insoluble materials exist, removing them, e.g. by filtration; adding a water-immiscible organic solvent; washing the mixture with water; and distilling off the solvent. The desired compound obtained can, if necessary, be further purified by conventional means, for example, by recrystallization, reprecipitation or the various chromatography techniques, notably column chromatography or preparative thin layer chromatography.

The starting compounds used in these reactions are either known or can readily be prepared by well-known methods. For example, the compounds of formulae (II) and (VI) may be synthesized by the method described by R. Heranz et al. in Synthesis, 703–706 (1989) and by M. T. Reetz et al. in Tetrahedron Letters, 29, 3295–3298 (1988).

The biological activity of the compounds of the present invention is illustrated by the following Experiments.

EXPERIMENT 1

Assay of The Inhibition of HIV Pol Protease

The ability of the compounds of the present invention to inhibit the activity of the HIV pol protease may be demonstrated by assaying the activity of the HIV pol protease in the presence of the test compound, and using a synthetic substrate. The HIV pol protease may be expressed in *E. coli* for this purpose. The $K_i$, that is the dissociation constant of the enzyme-inhibitor complex, measured according to the equation $$K_i = \frac{[E][I]}{[EI]}$$

[in which [E] is the concentration of enzyme, [I] is the concentration of inhibitor and [EI] is the concentration of E+I], is a measure of the activity of the compounds of the invention.

a) Construction of the expression vector

Using the appropriate restriction enzymes, the sequence between the ClaI site in the gag region and the EcoRI site in the pol region was excised from clone BH10. The BH10 clone [Flossie Wong-Staal et al., Nature (1985), 313, 277–284] contains the main part of the HTLV IIIB provirus. The fragment obtained was cloned into plasmid pBR322 at the corresponding restriction sites (ClaI-EcoRI), with deletion of the existing fragment in pBR322 at that location.

The sequence between the BamHI and ClaI sites in the pBR322 plasmid produced above, upstream of the ClaI to EcoRI fragment, was excised using the appropriate restriction enzymes, and the cleaved plasmid was then ligated with a synthetic nucleotide sequence, designated TE-1. The fragment TE-1 is known and is described in, for example, European Patent Publication No. 498,680.

The BglII to BamHI fragment of the T7 promoter region [Barbara A. Moffatt et al., J. Mol. Biol. (1986), 189, 113–130] was then inserted into the BamHI site of the resulting plasmid, with the result that it was positioned upstream of the TE-1 sequence.

In order to enhance expression of the gag and pol regions, a frame shift mutation was then introduced into the plasmid in the following manner. The plasmid was digested with BglII, and the recessed 3' ends were filled in using the Klenow fragment. The resulting blunt ends of the linearized plasmid were then religated with T4 DNA ligase to give the expression vector, pT7HIV.GP(–), containing a part of both of the HIV gag and pol regions.

b) Expression in *Escherichia coli* pT7HIV.GP(–), prepared as described above, was then introduced into an *E. coli* host containing the T7 polymerase gene [(DE-3) Barbara A. Moffatt et al., J. Mol. Biol. (1986), 189, 113–130] using standard procedures. The resulting transformant was incubated at 37° C. in M9CA-10% LB medium [9 parts M9CA medium (Na$_2$HPO$_4$.12H$_2$, 42 mM; KH$_2$PO$_4$, 22 mM; NaCl, 8.6 mM; NH$_4$Cl, 18.7 mM; Casamino acids, 2.0 g/l; MgSO$_4$, 2 mM; CaCl$_2$, 0.1 mM; glucose, 0.2% w/v) and 1 part LB medium (Bacto-tryptone, 10 g/l; Bacto-yeast extract, 5 g/l; NaCl, 10 g/l)], containing 200 μg/ml of ampicillin, until the absorbancy at 600 nm reached 2.

0.4 mM of isopropylthio-β-D-galactoside was then added to the culture medium, after which incubation was continued for a further 3 hours.

At the end of this time, the bacterial cells were collected and preserved at –80° C.

c) Purification of the enzyme

Expression of the plasmid pT7HIV.GP(–) by the *E. coli* host results in the formation of a polyprotein which includes the HIV protease. The polyprotein is digested by the cells in order to produce the HIV protease.

The bacterial cells in 2 liters of culture medium were pelleted, and these pelleted cells were then re-suspended in 60 ml of Buffer A:

Buffer A 50 mM tris HCl (pH 7.5), 1 mM dithiothreitol, 0.7% w/v lysozyme,

10 μg/ml aprotinin, 5 mM ethylenediaminetetraacetic acid,

10 μg/ml benzamide, 1 mM fluorophenylmethylsulfonic acid,

10% v/v glycerin;

and allowed to stand for 10 minutes at 0° C. Triton X-100™ (0.1% w/v) was added to the suspension and the suspension was then allowed to stand for a further 10 minutes at 0° C.

The suspension was then frozen and thawed four times. 0.1 mg DNase and 10 mM magnesium chloride were then added to the suspension so as to decompose any DNA present.

The suspension was then centrifuged at 10,000×g for 15 minutes, and the supernatant obtained was run on a DEAE Sephadex™ A25 chromatography column (50 mm inner diameter by 200 mm) equilibrated with Buffer B. Buffer B was also used as the eluent.

Buffer B:

50 mM HEPES (N-2-hydroxyethylpiperazine-N'-2-ethanesulfonic acid) (pH 7.8), 1 mM dithiothreitol, 10 μg/ml aprotinin, 5 mM ethylenediaminetetraacetic acid, 10 μg/ml benzamide, 1 mM fluorophenylmethylsulfonic acid, 10% glycerin.

Biologically active fractions were collected from the column. Proteins were precipitated by the addition of ammonium sulfate to a final concentration of 60% w/v. The precipitate was then dissolved in 2 ml of Buffer C:

Buffer C:

50 mM tris HCl (pH 7.5), 1 mM dithiothreitol, 1 mM ethylenediaminetetraacetic acid, 200 mM sodium chloride;

and the resulting solution was then run on a TSK G2000™ gel filtration column (7.5 mm inner diameter by 600 mm; To-So Co., Tokyo, Japan), eluted with Buffer C at a flow rate of 0.5 ml/min.

Biologically active fractions obtained from this column were collected and were then concentrated to half of their original volume using a 10 kD ultra-filter. The resulting enzyme solutions were stored at –80° C.

d) Activity assay

A reaction mixture containing 1 mM or 1.5 mM of the substrate TE-2, having the structure described in European Patent Publication No. 498,680, 1 μl of the desired concentration of the compound to be tested (dissolved in dimethyl sulfoxide comprising 20% v/v water), 2 μl of the enzyme solution prepared as described in step (c), above, and buffer solution [50 mM tris HCl (pH 6.0), 0.25M sodium chloride, 0.1 mM ethylenediaminetetraacetic acid, 0.1 mM Triton X-100] to form 10 μl in total, was incubated for 30 minutes at 37° C.

The reaction was Stopped by the addition of 250 μl of a 0.1% w/v solution of aqueous trifluoroacetic acid and 10% v/v acetonitrile. The reaction mixture was then subjected to Sep-pak light™ chromatography (Waters Co., Milford, Mass., USA), and the fractions passing through the column were collected.

The substrate TE-2 is decomposed by the HIV protease to form a shortened peptide of four amino acids, (TE-3; having the structure described in European Patent Publication No. 498,680). The amount of TE-3 formed was assayed quantitatively using a high performance liquid chromatography (HPLC) column [ODS-120T (Trade Mark), 4.6 mm in inner diameter ×250 mm, To-So Co.] using a mixture of 9% acetonitrile-0.05% trifluoroacetic acid as the eluting solvent.

The $K_i$ in nM was calculated according to the method of Michaelis-Menten using the equation given above.

TABLE 3

| Example No. | $K_i$ (nM) |
|---|---|
| 4 | 56 |
| 1 | 8 |
| 14 | 4.7 |
| 17 | 18.5 |
| 21 | 37 |
| 20 | 49 |
| 16 | 14 |
| 18 | 30 |
| Ro31-8959 | 58 |

Ro 31-8959 is 3-t-butylaminocarbonyl-2-{(2R, 3S)-3-[(N-2'-quinolinecarbonyl-L-asparaginyl)amino]-2-hydroxy-4-phenylbutyl}-(3S, 4aS, 8aS)-decahydroisoquinoline, and has the formula:

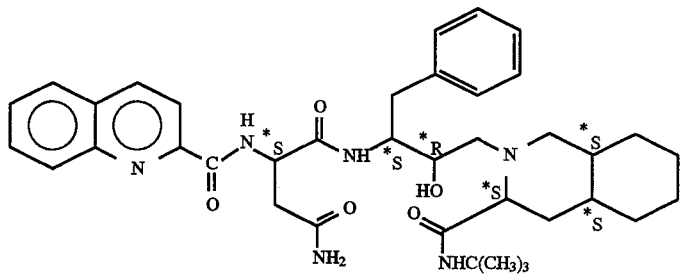

RO 31-8959

EXPERIMENT 2

Inhibition of the Release of Virus from Molt 4 Cells Chronically Infected with HIV (Molt 4/HTLV IIIB)

A Molt 4 cell line chronically infected with HIV, that is with HTLVIIIB, was established (Molt 4/HTLVIIIB). The cells were washed twice with growth medium (RPMI-1640 medium containing 10% v/v heat-inactivated fetal calf serum). The washed cells were then inoculated into growth medium at a density of 2×10⁵ cells/ml, in the presence of selected concentrations of test compounds, at 37° C., and cultured under an atmosphere of 5% carbon dioxide.

After 48 hours, the test cultures were spun down at 1000×g for 3 minutes, and the supernatant was collected. Polyethylene glycol 6000 was added to the supernatant to a final concentration of 10% w/v, and the resulting solution was left to stand for 6 hours on ice. Virions precipitated by this procedure were subsequently obtained as a pellet by centrifuging the treated supernatants for 30 minutes at 10000×g. The amount of HIV antigen in the pellets was then determined using a commercial enzyme immunoassay (EIA) system [HIV antigen EIA kit, available from Abbot].

$IC_{50}$ (the minimum concentration of test compound sufficient to reduce the amount of HIV antigen production by 50%, as determined by the EIA system) was used as a measure of anti-HIV activity.

The results are shown in Table 4.

TABLE 4

| Compound | $IC_{50}$ μg/ml |
|---|---|
| Compound of Example 14 | 0.39 |
| Ro 31-8959 | >20.0 |

From these results, it can be seen that the novel peptide derivatives of the present invention have an excellent inhibiting activity against protease originating in the human immunodeficiency virus (HIV), and in addition have no toxicity. Therefore, the compounds are useful as therapeutic agents for the treatment and prophylaxis of human acquired immune deficiency syndrome.

The compounds of the present invention may be administered by oral administration and may be formulated in an appropriate fashion for such a route of administration, for example as tablets, capsules, granules, powders or syrups; or they may be administered by the parenteral route, for example as injections or suppositories.

These preparations can be prepared according to any conventional means by adding such additives as vehicles, binders, disintegrators, lubricants, stabilizers or corrigents. The daily dosage will vary depending on the age, body weight and symptoms of the patients, however, for an adult human patient, a dose of from 0.1 to 100 mg/kg per day is recommended, and this may be administered as a single dose or divided into several doses.

The invention is further illustrated by the following non-limiting Examples, which illustrate the preparation of certain of the compounds of the present invention. The preparation of some of the starting materials used is illustrated in the subsequent Preparations.

EXAMPLE 1

(4S)-1-[(2S,3S)-3-(N²-Benzyloxycarbonyl-L-asparaginyl)amino-2-hydroxy-4-phenylbutyryl]-N-t-butyl-4-chloro-L-prolinamide 680 mg (2.23 mmol) of (4S)-1-t-butoxycarbonyl-N-t-butyl-4-chloro-L-prolinamide (prepared as described in Preparation 2) were treated with 10 ml of a 4N solution of hydrogen chloride in dioxane, in order to eliminate the t-butoxycarbonyl group and give (4S)-N-t-butyl-4-chloro-L-prolinamide hydrochloride. The whole of the hydrochloride thus obtained and 880 mg (1.99 mmol) of (2S,3S)-3-(N²-benzyloxycarbonyl-L-asparaginyl)amino-2-hydroxy-4-phenylbutyric acid (prepared as described in Preparation 1) were dissolved in 5 ml of dimethylformamide, and the solution was cooled with ice. 420 mg (2.58 mmol) of diethyl cyanophosphate, followed by 640 mg (6.40 mmol) of triethylamine, were then added to the ice-cooled mixture, and the mixture was stirred for 3 hours. At the end of this time, the reaction mixture was concentrated by evaporation under reduced pressure, and the residue was mixed with a 10% w/v aqueous solution of citric acid and then extracted with ethyl acetate. The organic extract was washed with a 10% w/v aqueous solution of sodium hydrogencarbonate and with a saturated aqueous solution of sodium chloride, in that order, after which it was dried over anhydrous sodium sulfate. The solvent was then removed by distillation under reduced pressure, and the residue was purified by preparative thin layer chromatography using a 10:1 by volume mixture of methylene chloride and methanol as the developing solvent, to give 850 mg of the title compound as a colorless powder, melting at 107°–109° C.

Elemental analysis: Calculated for $C_{31}H_{40}N_5O_7Cl.\frac{1}{2}H_2O$ (molecular weight: 639.16): C, 58.26%; H, 6.46%; N, 10.96%; Cl, 5.55%. Found: C, 58.35%; H, 6.56%; N, 10.93%; Cl, 5.46%.

Mass spectrum (m/z): 612(M⁺–17), 577, 514, 493, 477, 398, 368, 318, 91 (base peak).

Infrared Absorption Spectrum (KBr), $v_{max}$ cm⁻¹: 3331, 1700, 1667, 1530, 1455, 1267, 1228.

Nuclear Magnetic Resonance Spectrum (270 MHz, CD₃OD) δ ppm: 1.31, 1.34 (together 9H, each singlet); 2.05–2.08 (1H, multiplet); 2.37–2.46 (1H, multiplet); 2.60–2.70 (1H, multiplet); 2.73–2.97 (3H, multiplet); 3.72 (1H, doublet of doublets, J=2.9 & 7.3 Hz); 4.30–4.45 (5H, multiplet); 5.08 (2H, singlet); 7.10–7.40 (10H, multiplet).

EXAMPLE 2

1-[(2S,3S)-3-(N²-Benzyloxycarbonyl-L-asparaginyl) amino-2-hydroxy-4-phenylbutyryl]-N-t-butyl-4-oxo-L-prolinamide A procedure similar to that described in Example 1 was repeated, except that (2S,3S)-3-(N²-benzyloxycarbonyl-L-asparaginyl)amino-2-hydroxy-4-phenylbutyric acid (prepared as described in Preparation 1) and 1-t-butoxycarbonyl-N-t-butyl-4-oxo-L-prolinamide (prepared as described in Preparation 3) were used as starting materials, in relative proportions similar to those used in that Example, to obtain the title compound as colorless powdery crystals, melting at 116°–120° C.

Elemental analysis: Calculated for $C_{31}H_{39}N_5O_8.\frac{1}{2}H_2O$ (molecular weight: 618.69 ): C, 60.18%; H, 6.52%; N, 11.32%. Found: C, 59.92%; H, 6.63%; N, 11.27%.

Mass spectrum (m/z): 609 (M⁺), 592, 574, 501, 493, 448, 401, 368, 351, 290, 108 (base peak).

Infrared Absorption Spectrum (KBr), $v_{max}$ cm⁻¹: 3338, 1767, 1665, 1535, 1455, 1394, 1367, 1323, 1261, 1226, 1187, 1112, 1050.

Nuclear Magnetic Resonance Spectrum (270 MHz, CD₃OD) δ ppm: 1.31 (9H, singlet); 2.41–2.92 (6H, multiplet); 4.18–4.52 (6H, multiplet); 5.08 (2H, singlet); 7.12–7.36 (10H, multiplet).

EXAMPLE 3

(4S)-1-[(2S,3S)-3-(N²-Benzyloxycarbonyl-L-asparaginyl)amino-2-hydroxy-4-phenylbutyryl]-N-t-butyl-4-hydroxy-L-prolinamide A procedure similar to that described in Example 1 was repeated, except that (2S,3S)-3-(N²-benzyloxy-carbonyl-L-asparaginyl)amino-2-hydroxy-4-phenylbutyric acid (prepared as described in Preparation 1) and (4S)-1-benzyloxycarbonyl-N-t-butyl-4-hydroxy-L-prolinamide (prepared as described in Preparation 4) were used as starting materials, in relative proportions similar to those used in that Example, to obtain the title compound as colorless powdery crystals, melting at 113°–115° C.

Elemental analysis: Calculated for $C_{31}H_{40}N_5O_8.H_2O$ (molecular weight: 628.71): C, 59.22%; H, 6.73%; N, 11.14%. Found: C, 59.61%; H, 6.82%; N, 11.37%.

Mass spectrum (m/z): 594(M⁺–16), 576, 522, 495, 477, 450, 404, 386, 343, 290, 86 (base peak).

Infrared Absorption Spectrum (KBr), $v_{max}$ cm⁻¹: 3327, 1660, 1534 1499, 1455, 1394, 1367, 1326, 1266, 1227, 1110, 1090, 1054.

Nuclear Magnetic Resonance Spectrum (270 MHz, CD₃OD) δ ppm: 1.31, 1.34 (together 9H, each singlet); 1.90 (1H, doublet of triplets J=3.4 & 13.2 Hz); 2.30–2.41 (2H, multiplet); 2.63 (1H, doublet of doublets, J=5.9 & 15.6 Hz); 3.78 (1H, doublet of doublets, J=4.4 & 10.8 Hz); 3.87 (1H, doublet of doublets, J=2.5 & 10.8 Hz); 4.28 4.47 (5H, multiplet); 5.07 (2H, singlet); 7.09–7.36 (10H, multiplet).

EXAMPLE 4

(4R)-1-[(2S,3S)-3-(N²-Benzyloxycarbonyl-L-asparaginyl)amino-2-hydroxy-4-phenylbutyryl]-N-t-butyl-4-hydroxy-L-prolinamide A procedure similar to that described in Example 1 was repeated, except that (2S,3S)-3-(N²-benzyloxycarbonyl-L-asparaginyl)amino-2-hydroxy-4-phenylbutyric acid (prepared as described in Preparation 1) and (4R)-1-t-butoxycarbonyl-N-t-butyl-4-hydroxy-L-prolinamide (prepared as described in Preparation 5) were used as starting materials, in relative proportions similar to those used in that Example, to obtain the title compound as colorless powdery crystals, melting at 115°–120° C.

Elemental analysis: Calculated for $C_{31}H_{40}N_5O_8.\frac{1}{2}H_2O$ (molecular weight: 619.70): C, 60.08%; H, 6.67%; N, 11.30%. Found: C, 60.01%; H, 7.00%; N, 11.22%.

Mass spectrum (m/z): 594(M⁺–16), 576, 522, 495, 450, 403, 386, 343, 108, (base peak).

Infrared Absorption Spectrum (KBr), $v_{max}$ cm⁻¹: 3337, 1669, 1536 (shoulder), 1455, 1393, 1366, 1331, 1258, 1229.

Nuclear Magnetic Resonance Spectrum (270 MHz, CD₃OD) δ ppm: 1.32 (9H, singlet); 2.02–2.20 (2H, multiplet); 2.46 (1H, doublet of doublets, J=15.1 & 7.8 Hz); 2.62 (1H, doublet of doublets, J=15.1 a 5.9 Hz); 2.77–2.84 (2H, multiplet); 3.76–3.78 (2H, multiplet); 4.26–4.33 (1H, multiplet); 4.43–4.54 (4H, multiplet); 5.08 (2H, singlet); 7.08–7.36 (10H, multiplet).

EXAMPLE 5

(4S)-1-[(2S,3S)-3-(N²-Benzyloxycarbonyl-L-asparaginyl)amino-2-hydroxy-4-phenylbutyryl]-N-t-butyl-4-morpholino-L-prolinamide A procedure similar to that described in Example 1 was repeated, except that (2S,3S)-3-(N²-benzyloxycarbonyl- L-asparaginyl)amino-2-hydroxy-4-phenylbutyric acid (prepared as described in Preparation 1) and (4S)-1-t-butoxycarbonyl-N-t-butyl-4-morpholino-L-prolinamide (prepared as described in Preparation 6) were used as starting materials, in relative proportions similar to those used in that Example, to obtain the title compound as colorless powdery crystals, melting at 115°–117° C.

Elemental analysis: Calculated for $C_{35}H_{48}N_6O_8 \cdot \frac{3}{4}H_2O$ (molecular weight: 694.32): C, 60.55%; H, 7.18%; N, 12.10%. Found: C, 60.59%; H, 7.14%; N, 12.14%.

Mass spectrum (m/z): 680(M$^+$), 663, 632, 620, 572, 563, 529, 499, 472, 450, 429, 415, 385, 341, 310, 108 (base peak).

Infrared Absorption Spectrum (KBr), $v_{max}$ cm$^{-1}$: 3330, 1672, 1536, 1454, 1393, 1367, 1311, 1268, 1228, 1158, 1118, 1089, 1048.

Nuclear Magnetic Resonance Spectrum (270 MHz, CD$_3$OD) δ ppm: 1.31 (9H, singlet); 1.78 (quartet, J=10.7 Hz); 2.37–2.65 (7H, multiplet); 2.71–2.90 (2H, multiplet); 3.44 (1H, triplet, J=9.8 Hz); 3.67–3.71 (4H, multiplet); 4.11–4.17 (1H, multiplet); 4.28–4.36 (2H, multiplet); 4.41–4.46 (2H, multiplet); 5.08 (2H, singlet); 7.09–7.36 (10H, multiplet).

EXAMPLE 6 t-Butyl ester of (4R)-1-[(2S,3S)-3-(N$^2$-benzyloxy-carbonyl-L-asparaginyl)amino-2-hydroxy-4-phenylbutyryl]-4-t-butoxy-L-proline A procedure similar to that described in Example 1 was repeated, except that (2S,3S)-3-(N$^2$-benzyloxycarbonyl-L-asparaginyl)amino-2-hydroxy-4-phenylbutyric acid (prepared as described in Preparation 1) and the t-butyl ester of (4R)-4-t-butoxy-L-proline (prepared as described in Preparation 7) were used as starting materials, in relative proportions similar to those used in that Example, to obtain the title compound as colorless powdery crystals, melting at 100°–102° C.

Elemental analysis: Calculated for $C_{35}H_{48}N_4O_9$ (molecular weight: 668.80): C, 62.86%; H, 7.23%; N, 8.38%. Found: C, 62.60%; H, 7.53%; N, 8.09%.

EXAMPLE 7

(4S)-1-[(2S,3S)-3-(N$^2$-Benzyloxycarbonyl-L-asparaginyl)amino-2-hydroxy-4-phenylbutyryl]-4-bromo-N-t-butyl-L-prolinamide A procedure similar to that described in Example 1 was repeated, except that (2S,3S)-3-(N$^2$-benzyloxycarbonyl-L-asparaginyl)amino-2-hydroxy-4-phenylbutyric acid (prepared as described in Preparation 1) and (4S)-N-t-butoxycarbonyl-4-bromo-N-t-butyl-L-prolinamide (prepared as described in Preparation 8) were used as starting materials, in relative proportions similar to those used in that Example, to obtain the title compound as colorless powdery crystals, melting at 100°–105° C.

Elemental analysis: Calculated for $C_{31}H_{40}N_5O_9Br \cdot \frac{1}{2}H_2O$ (molecular weight: 683.61): C, 54.47%; H, 6.04%; N, 10.24%; Br, 11.69%. Found: C, 54.61%; H, 6.10%; N, 10.10%; Br, 11.31%.

Mass spectrum (m/z): 674 (M$^+$+1), 594, 494, 476, 426, 398, 368, 350, 274, 249, 210, 148, 91 (base peak).

Infrared Absorption Spectrum (KBr), $v_{max}$ cm$^{-1}$: 3331, 1668, 1527, 1455, 1393, 1366, 1318, 1250, 1227, 1157, 1112, 1051, 1029.

Nuclear Magnetic Resonance Spectrum (270 MHz, CD$_3$OD) δ ppm: 1.31 (9H, singlet); 2.18 (1H, doublet of triplets, J=12.7 & 9.3 Hz); 2.41 (1H, doublet of doublets, J=7.8 & 15.1 Hz); 2.61 (1H, doublet of doublets, J=5.9 & 15, 1 Hz); 2.72–2.84 (2H, multiplet); 2.90–2.96 (1H, multiplet); 3.78 (1H, doublet of doublets, J=1.9 & 7.8 Hz); 4.26–4.45 (5H, multiplet); 5.07 (2H, singlet); 7.10–7.36 (10H, multiplet).

EXAMPLE 8

(1S,4S)-5-[(2S,3S)-3-(N$^2$-Benzyloxycarbonyl-L-asparaginyl)amino-2-hydroxy-4-phenylbutyryl]-2,5-oxazabicyclo[2.2.1]heptan-3-one A procedure similar to that described in Example 1 was repeated, except that (2S,3S)-3-(N$^2$-benzyloxy-carbonyl-L-asparaginyl)amino-2-hydroxy-4-phenylbutyric acid (prepared as described in Preparation 1) and (1S,4S)-5-t-butoxycarbonyl-2,5-oxazabicyclo[2.2.1]heptan-3-one (prepared as described in Preparation 9) were used as starting materials, in relative proportions similar to those used in that Example, to obtain the title compound as colorless powdery crystals, melting at 147°–152° C.

Elemental analysis: Calculated for $C_{27}H_{30}N_4O_8 \cdot 2H_2O$ (molecular weight: 574.59): C, 56.44%; H, 5.96%; N, 9.75%. Found: C, 56.45%; H, 5.89%; N, 9.80%.

EXAMPLE 9

(1S,4S)-5-[(2S,3S)-3-(N$^2$-Benzyloxycarbonyl-L-asparaginyl)amino-2-hydroxy-4-phenylbutyryl]-2-t-butyl-2,5-diazabicyclo[2.2.1]heptan-3-one A procedure similar to that described in Example 1 was repeated, except that (2S,3S)-3-([2-benzyloxycarbonyl-L-asparaginyl)amino-2-hydroxy-4-phenylbutyric acid (prepared as described in Preparation 1) and (1S,4S)-5-t-butoxycarbonyl-2-t-butyl-2,5-diazabicyclo[2.2.1]heptan-3-one (prepared as described in Preparation 10) were used as starting materials, in relative proportions similar to those used in that Example, to obtain the title compound as colorless powdery crystals, melting at 112°–115° C.

Elemental analysis: Calculated for $C_{31}H_{39}N_5O_7 \cdot \frac{1}{2}H_2O$ (molecular weight: 602.70): C, 61.78%; H, 6.69%; N, 11.62%. Found: C, 61.78%; H, 6.85%; N, 11.51%.

EXAMPLE 10

(4S)-1-[(2S,3S)-3-(N$^2$-Benzyloxycarbonyl-L-asparaginyl)amino-2-hydroxy-4-phenylbutyryl]-N-t-butyl-4-phenylthio-L-prolinamide A procedure similar to that described in Example 1 was repeated, except that (2S,3S)-3-(N$^2$-benzyloxycarbonyl-L-asparaginyl)amino-2-hydroxy-4-phenylbutyric acid (prepared as described in Preparation 1) and (4S)-N-t-butoxycarbonyl-4-phenylthio-L-proline t-butylamide (prepared as described in Preparation 11) were used as starting materials, in relative proportions similar to those used in that Example, to obtain the title compound as colorless powdery crystals, melting at 96°–98° C.

Elemental analysis: Calculated for $C_{37}H_{45}N_5O_7S \cdot \frac{1}{2}H_2O$ (molecular weight: 712.87): C, 62.34%; H, 6.50%; N, 9.82%; S, 4.50%. Found: C, 62.45%; H, 6.45%; N, 9.70%; S, 4.46%.

Mass spectrum (m/z): 686 (M$^+$–1), 587, 577, 522, 495, 478, 435, 382, 365, 336, 178 (base peak).

Infrared Absorption Spectrum (KBr) $v_{max}$ cm$^{-1}$: 3332, 1668, 1585, 1529, 1454, 1393, 1366, 1264, 1227.

Nuclear Magnetic Resonance Spectrum (270 MHz, CD$_3$OD) δ ppm: 1.31, 1.33 (together 9H, each singlet); 1.80–1.90 (1H, multiplet); 2.36–2.45 (1H, multiplet); 2.48–2.65 (2H, multiplet); 2.69–2.79 (1H, multiplet); 2.88–2.95 (1H, multiplet); 3.51 (1H, triplet, J=10.3 Hz); 3.68–3.76 (1H, multiplet); 4.18–4.45 (5H, multiplet); 5.08 (2H, singlet); 7.10–7.49 (15H, multiplet).

EXAMPLE 11

(3R)-1-[(2S,3S)-3-(N$^2$-Benzyloxycarbonyl-L-asparaginyl)amino-2-hydroxy-4-phenylbutyryl]-N-t-butyl-3-hydroxy-L-prolinamide 1.5 ml of a 4N solution of hydrogen chloride in dioxane were added to a solution of 50 mg (0.13 mmol) of (3 R)-1-t-butoxycarbonyl-N-t-butyl-3-t-butyldimethylsilyloxy-L-prolinamide (prepared as described in Preparation 12) in 0.5 ml of methanol, and the mixture was stirred at room temperature for 1 hour. The solvent was removed by distillation under reduced pressure, and the resulting residue was mixed with benzene. The excess hydrogen chloride was then removed by distillation as an azeotrope with the benzene. The resulting residue was dried in vacuo for 2 hours and the whole of the resulting (3E)-N-t-butyl-3-t-butyldimethylsilyloxy-L-prolinamide hydrochloride was reacted with 55 mg (0.13 mmol) of (2S,3S)-3-(N$^2$-benzyloxycarbonyl-L-asparaginyl)amino-2-hydroxy-4-phenylbutyric acid (prepared as described in Preparation 1) following a procedure similar to that described in Example 1, to obtain 33 mg of the title compound as a white powder, melting at 109°–112° C.

Elemental analysis: Calculated for C$_{31}$H$_{41}$N$_5$O$_8$.½H$_2$O (molecular weight: 620.69): C, 59.98%; H, 6.82%; N, 11.28%. Found: C, 60.15%; H, 7.02%; N, 11.05%.

EXAMPLE 12

(3S)-1-[(2S,3S)-3-(N$^2$-Benzyloxycarbonyl-L-asparaginyl)amino-2-hydroxy-4-phenylbutyryl]-N-t-butyl-3-chloro-L-prolinamide The silyl group of (3R)-1-t-butoxycarbonyl-N-t-butyl-3-t-butyldimethylsilyloxy-L-prolinamide (prepared as described in Preparation 12) was eliminated following a procedure similar to that described in Preparation 13(a), to give (3E)-1-t-butoxycarbonyl-N-t-butyl-3-hydroxy-L-prolinamide, and then the resulting hydroxyl group was converted to a chloro group in a similar manner to that described in Preparation 2, to give (3 R)-1-t-butoxycarbonyl-N-t-butyl-3-chloro-L-prolinamide. The t-butoxycarbonyl group was then removed following a procedure similar to that described in Example 11, and the resulting (3R)-N-t-butyl-3-chloro-L-prolinamide was condensed with (2R,3S)-3-(N$^2$-benzyloxycarbonyl-L-asparaginyl)amino-2-hydroxy-4-phenylbutyric acid (prepared as described in Preparation 1) following a procedure similar to that described in Example 1, to give the title compound as a white powder, melting at 102°–104° C.

Elemental analysis: Calculated for C$_{31}$H$_{40}$N$_5$O$_7$Cl.H$_2$O (molecular weight: 648.14): C, 57.44%; H, 6.53%; N, 10.81. Found: C, 57.44%; H, 6.36%; N, 10.43.

Infrared Absorption Spectrum (KBr), $v_{max}$ cm$^{-1}$: 3331, 1671, 1537.

Nuclear Magnetic Resonance Spectrum (CDCl$_3$: CD$_3$OD=5:1 by volume, 270 MHz), δ ppm: 1.30 (9H, singlet); 2.15–2.28 (1H, multiplet); 2.40–2.85 (5H, multiplet); 3.75–3.92 (2H, multiplet); 4.21–4.48 (3H, multiplet); 4.60–4.72 (2H, multiplet); 5.09 (2H, singlet); 7.12–7.40 (10H, multiplet).

EXAMPLE 13

(3S)-1-[(2S,3S)-3-(N$^2$-Benzyloxycarbonyl-L-asparaginyl)amino-2-hydroxy-4-phenylbutyryl]-N-t-butyl-3-hydroxy-L-prolinamide Following a procedure similar to that described in Example 11, 28 mg (0.10 mmol) of (3 S)-1-t-butoxycarbonyl-N-t-butyl-3-hydroxy-L-prolinamide (prepared as described in Preparation 13) was deprotected to remove the t-butoxycarbonyl group. The resulting (3S)-N-t-butyl-3-hydroxy-L-prolinamide was then condensed with 52 mg (0.12 mmol) of (2S,3S)-3-(N$^2$-benzyloxycarbonyl-L-asparaginyl)amino-2-hydroxy-4-phenylbutyric acid (prepared as described in Preparation 1), to give 40 mg of the title compound as a white powder, melting at 111°–113° C.

Elemental analysis: Calculated for C$_{31}$H$_{41}$N$_5$O$_8$.0.75H$_2$O (molecular weight: 625.19): C, 59.55%; H, 6.85%; N, 11.20%. Found: C, 59.73%; H, 6.86%; N, 10.82%.

Mass spectrum (m/z): 594 (M$^+$–17), 494, 450, 403, 386, 290, 244, 187, 153, 127, 86, 58.

Infrared Absorption Spectrum (KBr), $v_{max}$ cm$^{-1}$: 332, 1668, 1535.

Nuclear Magnetic Resonance Spectrum (CDCl$_3$: CD$_3$OD=5:1 by volume, 270 MHz), δ ppm: 1.31 (9H, singlet); 1.89–2.01 (1H, multiplet); 2.20–2.33 (1H, multiplet); 2.49–2.60 (2H, multiplet); 2.75–2.95 (2H, multiplet); 3.68–3.85 (2H, multiplet); 4.17–4.51 (5H, multiplet); 6.08 (2H, singlet); 7.11–7.40 (10H, multiplet).

EXAMPLE 14

(4S)-1-{(2S,3S)-3-[N$^2$-(2-Quinoxalinecarbonyl)-L-asparaginyl]amino-2-hydroxy-4-phenylbutyryl}-N-t-butyl-4-chloro-L-prolinamide 0.6 ml of 1N aqueous hydrochloric acid was added to a solution of 300 mg (0.48 mmol) of (4S)-1-[(2S,3S)-3-(N$^2$-benzyloxycarbonyl-L-asparaginyl)amino-2-hydroxy-4-phenylbutyryl]-N-t-butyl-4-chloro-L-prolinamide (prepared as described in Example 1) in methanol, and a stream of hydrogen was bubbled through the mixture at atmospheric pressure for 3 hours in the presence of 60 mg of 10% w/w palladium-on-charcoal, to remove the benzyloxycarbonyl group. The whole of the resulting (4S)-1-[(2S,3S)-3--asparaginylamino-2-hydroxy-4-phenylbutyryl]-N-t-butyl-4-chloroprolinamide hydrochloride and 99 mg (0.57 mmol) of 2-quinoxalinecarboxylic acid were dissolved in 5 ml of dimethylformamide, and 93 mg (0.57 mmol) of diethyl cyanophosphate and 144 mg (1.44 mmol) of triethylamine under ice-cooling were added to this solution. The resulting mixture was stirred for 3 hours, after which it was concentrated by evaporation under reduced pressure. The residue was mixed with a 10% w/v aqueous solution of sodium hydrogencarbonate and then extracted with ethyl acetate. The organic extract was washed with a saturated aqueous solution of sodium chloride and then dried over anhydrous sodium sulfate. The solvent was removed by distillation under reduced pressure, and the resulting residue was purified by preparative thin layer chromatography, using a 10:1 by volume mixture of methylene chloride and methanol as the developing solvent, to give 140 mg of the title compound as a colorless powder, melting at 132°–134° C.

Elemental analysis: Calculated for $C_{32}H_{38}N_7O_6Cl \cdot \frac{1}{2}H_2O$ (molecular weight: 661.16): C, 58.13%; H, 5.94%; N, 14.83%; Cl, 5.36%. Found: C, 58.25%; H, 6.07%; N, 14.67%; Cl, 5.31%.

Mass spectrum (m/z): 651 ($M^+$), 634, 615, 598, 562, 535, 525, 498, 449, 403, 390, 340, 290, 271 (base peak).

Infrared Absorption Spectrum (KBr) $v_{max}$ $cm^{-1}$: 3338, 1669—vs, 1522, 1493, 1455, 1408, 1393, 1455, 1408, 1393, 1366, 1268, 1226, 1206, 1127.

Nuclear Magnetic Resonance Spectrum ($CD_3OD$, 270 MHz), δ ppm: 1.27, 1.36 (together 9H, each singlet); 2.08–2.13 (1H, multiplet); 2.70–2.80 (4H, multiplet); 2.83–2.96 (1H, multiplet); 3.72–3.78 (1H, multiplet); 4.34–4.45 (5H, multiplet); 4.91 (1H, triplet, J=6.4 Hz); 6.86 (1H, triplet, J=7.3 Hz); 7.02 (2H, triplet, J=7.3 Hz); 7.23 (2H, doublet, J=7.3 Hz); 7.93–8.01 (2H, multiplet); 8.18–8.25 (2H, multiplet); 9.49 (1H, singlet).

EXAMPLE 15

1-[(2S,3S)-3-($N^2$-Butoxycarbonyl-L-asparaginyl) amino-2-hydroxy-4-phenylbutyryl]-N-t-butyl-L-prolinamide 15(a) (2S,3S)-3-(N,N-Dibenzylamino)-2-hydroxy-4-phenylbutyric acid 800 ml of a 1:1 by volume mixture of concentrated aqueous hydrochloric acid and methanol were added to 30.5 g (86 mmol) of (2S, 3S)-3-(N, N-dibenzylamino)-2-hydroxy-4-phenylbutyronitrile [synthesized by the procedure described by M. T. Reetz et al. in Tetrahedron Letters, 29,No. 27, 3295–3298 (1988)], and the resulting mixture was heated under reflux for 1 hour. As the reaction proceeded, the solid substance dissolved. The reaction mixture was then concentrated by evaporation under reduced pressure to one quarter of its original volume, after which it was neutralized with 1N aqueous sodium hydroxide to a pH value of 6–7. The mixture was again concentrated by evaporation under reduced pressure. Water was then added to the resulting residue, and the crystalline substance which then separated was filtered off. This substance was dissolved in 130 ml of a 9:1 by volume mixture of a 1N aqueous solution of sodium hydroxide (129 mmol) and methanol, and the resulting solution was stirred for 3 hours. At the end of this time, the reaction mixture was made acid by the addition of a 10% w/v aqueous solution of citric acid and was then concentrated by evaporation under reduced pressure. Ice-water was then added, and the mixture was extracted with diethyl ether. The organic extract was washed with a 10% w/v aqueous solution of citric acid and with a saturated aqueous solution of sodium chloride and dried over anhydrous sodium sulfate. Insoluble matter was removed by filtration, and 17.1 g (95 mmol) of dicyclohexylamine were added to the ethereal solution; the product which then separated was washed well with diethyl ether. The resulting crystalline substance was partitioned between a 10% w/v aqueous solution of citric acid and diethyl ether. The organic layer was washed with water and with a saturated aqueous sodium chloride, in that order, after which it was dried over anhydrous sodium sulfate. After filtration, the filtrate was concentrated by evaporation under reduced pressure, and hexane was added to the residue, to afford 27.7 g (yield 86%) of the title compound as an amorphous powder, melting at 61°–65 ° C.

15(b) 1-[(2S,3S)-3-(N,N-Dibenzylamino)-2-hydroxy-4-phenylbutyryl]-N-t-butyl-L-prolinamide 11.1 g (41.1 mmol) of 1-t-butoxycarbonyl-N-t-butyl-L-prolinamide were treated with a 4N solution of hydrogen chloride in dioxane in order to remove the t-butoxycarbonyl group and give N-t-butyl-L-prolinamide hydrochloride.

14.0 g (37.0 mmol) of (2S, 3S)-3-(N, N-dibenzylamino)-2-hydroxy-4-phenylbutyric acid [prepared as described in step (a) above] and the whole of the N-t-butyl-L-prolinamide hydrochloride were suspended in 250 ml of methylene chloride, and 6.7 g (41.1 mmol) of diethyl cyanophosphate and 11.2 g (110.9 mmol) of triethylamine were slowly added dropwise to the suspension. The mixture was then stirred for 5 hours. At the end of this time, the reaction mixture was washed with a 10% w/v aqueous solution of citric acid, with a 10% w/v aqueous solution of sodium hydrogencarbonate and with a saturated aqueous solution of sodium chloride, in that order. The mixture was then dried over anhydrous sodium sulfate, after which the solvent was removed by distillation under reduced pressure, and the resulting residue was recrystallized from hexane, to give 16.6 g of the title compound as colorless crystals, melting at 122°–123° C.

Elemental analysis: Calculated for $C_{33}H_{41}N_3O_3$ (molecular weight: 527.71): C, 75.11%; H, 7.83%; N, 7.96%. Found: C, 74.98%; H, 7.81%; N, 7.92%.

15(c) 1-[(2S,3S)-3-Amino-2-hydroxy-4-phenylbutyryl]-N-t-butyl-L-prolinamide

A solution of 22.0 g (41.7 mmol) of (2S,3S)-3-(N,N dibenzylamino)-2-hydroxy-4-phenylbutyryl-N-t-butyl-L-prolinamide [prepared as described in step (b) above] in 200 ml of a 4.4% v/v methanolic solution of formic acid was stirred at room temperature for 4 hours in the presence of 2.2 g of palladium black and in an atmosphere of hydrogen. The atmosphere was replaced with nitrogen, and then the catalyst was filtered off. The filtrate was then concentrated by evaporation under reduced pressure. The resulting residue was diluted with a saturated aqueous solution of sodium hydrogencarbonate and then extracted with methylene chloride. The organic extract was dried over anhydrous sodium sulfate, and the solvent was removed by distillation under reduced pressure. The residue was recrystallized from benzene, to give 12.7 g of the title compound as colorless crystals, melting at 159°–161° C.

Elemental analysis: Calculated for $C_{19}H_{29}N_3O_3$ (molecular weight: 347.46): C, 65.68%; H, 8.41%; N, 12.09%. Found: C, 65.79%; H, 8.44%; N, 12.05%.

15(d) 1-[(2S,3S)-3-($N^2$-t-Butoxycarbonyl-L-asparaginyl) amino-2-hydroxy-4-phenylbutyryl]-N-t-butyl-L-prolinamide 15.5 g (43.9 mmol) of the p-nitrophenyl ester of $N^2$-t-butoxycarbonyl-L-asparagine and 7.33 g (72.3 mmol) of triethylamine were added, whilst ice-cooling, to a solution of 12.7 g (36.6 mmol) of 1-[(2S,3 S)-3-amino-2-hydroxy-4-phenylbutyryl]-N-t-butyl-L-prolinamide [prepared as described in step (c) above] in 100 ml of dimethylformamide, and the mixture was stirred overnight at room temperature. At the end of this time, the reaction mixture was poured into ice-water, after which it was extracted with methylene chloride. The organic extract was then washed with a 1N aqueous solution of sodium hydroxide, with a 10% w/v aqueous solution of citric acid and with a saturated aqueous solution of sodium chloride, in that order. The extract was then dried over anhydrous sodium sulfate, after which the solvent was removed by distillation under reduced pressure. The residue was recrystallized from a mixture of methylene chloride and hexane, to give 17.6 g of the title compound as a colorless powder, melting at 113°–115° C.

Elemental analysis: Calculated for $C_{28}H_{43}N_5O_7 \cdot H_2O$ (molecular weight: 579.70): C, 58.01%; H, 7.83%; N, 12.08%. Found: C, 58.25%; H, 7.77%; N, 11.76%.

EXAMPLE 16

1-[(2S,3S)-3-{$N^2$-[4-(Benzyloxycarbonylamino) phenoxyacetyl]-L-asparaginyl}amino-2-hydroxy-4-phenylbutyryl]-N-t-butyl-L-prolinamide Following a procedure similar to that described in Example 14, but using 99.8 mg (0.33 mmol) of 4-(benzyloxycarbonylamino)phenoxyacetic acid (prepared as described in Preparation 15) and 150 mg (0.30 mmol) of 1-[(2S,3S)-3-(L-asparaginylamino)-2-hydroxy-4-phenylbutyryl]-N-t-butyl-L-prolinamide hydrochloride {prepared by treating 1-[(2S,3S)-3-($N^2$-t-butoxycarbonyl-L-asparaginyl)amino-2-hydroxy-4-phenylbutyryl]-N-t-butyl-L-prolinamide, the compound prepared as described in Example 15, with a 4N solution of hydrogen chloride in dioxane), 164 mg of the title compound were obtained as a white powder, melting at 103°–105° C.

Elemental analysis: Calculated for $C_{39}H_{48}N_6O_9 \cdot \frac{1}{2}H_2O$ (molecular weight: 753.83): C, 62.13%; H, 6.55%; N, 11.15%. Found: C, 62.06%; H, 6.52%; N, 11.21%.

Mass spectrum (m/z): 593, 327, 300, 273, 228, 192, 166, 108, 91, 70.

Infrared Absorption Spectrum (KBr), $v_{max}$ cm$^{-1}$: 3325, 1672, 1512.

Nuclear Magnetic Resonance Spectrum (270 MHz, $CD_3OD$) δ ppm: 1.30 (9H, singlet); 1.85–2.20 (4H, multiplet); 2.55–2.68 (2H, multiplet); 2.75 (1H, doublet of doublets, J=9.8 & 14.2 Hz); 2.88 (1H, doublet of doublets, J=4.4 & 14.2 Hz); 3.68–3.78 (2H, multiplet); 4.31–4.46 (5H, multiplet); 4.67–4.75 (1H, multiplet); 5.16 (2H, singlet); 6.88–6.93 (2H, multiplet); 7.08–7.42 (2H, multiplet).

EXAMPLE 17

1-{(2S,3S)-3-[$N^2$-(4-Aminophenoxyacetyl)-L-asparaginyl)amino-2-hydroxy-4-phenylbutyryl]-N-t-butyl-L-prolinamide hydrochloride 0.16 ml (0.16 mmol) of 1N aqueous hydrochloric acid was added to a solution of 105 mg (0.14 mmol) of 1-[(2S,3S)-3-{$N^2$-[4-(benzyloxycarbonylamino)phenoxyacetyl]-L-asparaginyl}amino-2-hydroxy-4-phenylbutyryl]-N-t-butyl-L-prolinamide (prepared as described in Example 16) in 5 ml of methanol, and the mixture was stirred for 2.5 hours in the presence of 70 mg of palladium on charcoal and under an atmosphere of hydrogen. At the end of this time, the catalyst was removed by filtration, and then the solvent was removed by distillation under reduced pressure. The resulting residue was mixed with benzene and the mixture was dehydrated by azeotropic distillation. This operation was repeated a second time, and then the residue was triturated with diethyl ether, to give 89 mg of the title compound as a red-brown powder, melting at 165°–168° C.

Elemental analysis: Calculated for $C_{31}H_{42}N_6O_7 \cdot HCl \cdot 2.3H_2O$ (molecular weight: 688.60): C, 54.07%; H, 6.97%; N, 12.21%. Found: C, 54.12%; H, 6.72%; N, 12.16%.

Mass spectrum (m/z): 610 (M$^+$), 593, 493, 396, 263, 228, 171, 108, 70.

Infrared Absorption Spectrum (KBr) $v_{max}$ cm$^{-1}$: 328, 1668, 1537, 1509.

Nuclear Magnetic Resonance Spectrum (270 MHz, $CD_3OD$) δ ppm: 1.31 (9H, singlet); 1.85–2.22 (4H, multiplet); 2.56–2.70 (2H, multiplet); 2.75 (1H, doublet of doublets, J =10.3 & 14.2 Hz); 2.90 (1H, doublet of doublets, J=3.9 & 14.2 Hz); 3.70–3.80 (2H, multiplet); 4.32–4.45 (3H, multiplet); 4.54 (2H, singlet); 4.70–4.76 (1H, multiplet); 7.07–7.37 (9H, multiplet).

EXAMPLE 18

1-[(2S,3S)-3-{$N^2$-[4-(Glycylamino)phenoxyacetyl]-L-asparaginyl}amino-2-hydroxy-4-phenylbutyryl]-N-t-butyl-L-prolinamide hydrochloride 25.5 mg (0.093 mmol) of the succinimide ester of t-butoxycarbonylglycine and 26.0 μl (0.187 mmol) of triethylamine were added to a solution of 55 mg (0.085 mmol) of 1-{(2S,3S)-3-$N^2$-(4-aminophenoxyacetyl)-L-asparaginyl)amino-2-hydroxy-4-phenylbutyryl}-N-t-butyl-L-prolinamide hydrochloride (prepared as described in Example 17) in 1 ml of dimethylformamide, and the mixture was stirred at room temperature for 2 days. At the end of this time, the reaction mixture was freed from the solvent by distillation under reduced pressure, and the residue was diluted with ethyl acetate. The resulting organic solution was washed with a 5% w/v aqueous solution of citric acid, with a 5% w/v aqueous solution of sodium hydrogencarbonate and with a saturated aqueous solution of sodium chloride, in that order, after which it was dried over anhydrous sodium sulfate. The solvent was then removed by distillation under reduced pressure, and the resulting residue was purified by preparative thin layer chromatography, using a 7:1 by volume mixture of methylene chloride and methanol as the developing solvent, to give 22 mg of 1-[(2S,3S)-3-{$N^2$-[4-(N-t-butoxycarbonylglycine)-phenoxyacetyl]-L-asparaginyl}amino-2-hydroxy-4-phenylbutyryl]-N-t-butyl-L-prolinamide, as a white powder. The whole of this product (22 mg) was dissolved in 0.5 ml of methanol, and 2 ml of a 4N solution of hydrogen chloride in dioxane were added to the resulting solution. The mixture was then stirred at room temperature for 30 minutes. At the end of this time, the solvent was removed by distillation under reduced pressure, and the residue was mixed with benzene. An excess of hydrogen chloride was removed by azeotropic distillation, and the residue was dissolved in water and then lyophilized. 19 mg of the title compound were obtained as a white powder, melting at 156°–159° C.

Elemental analysis: Calculated for $C33H_{45}N_7O_8 \cdot HCl \cdot 2.5H_2O$ (molecular weight: 749.25): C, 52.90%; H, 6.86%; N, 13.09%. Found: C, 52.82%; H, 6.61%; N, 12.84%.

Mass spectrum (m/z): 593, 493, 396, 327, 256, 228, 166, 120, 108, 70.

Infrared Absorption Spectrum (KBr), $v_{max}$ cm$^{-1}$: 3304, 1669, 1544, 1509.

Nuclear Magnetic Resonance Spectrum ($D_2O$, 270 MHz), δ ppm: 1.10 (9H, singlet); 1.64–1.98 (3H, multiplet); 2.02–2.16 (1H, multiplet); 2.27–2.58 (3H, multiplet); 2.71 (1H, doublet of doublets, J=3.4 & 14.2 Hz); 3.48–3.67 (2H, multiplet); 3.79 (2H, singlet); 4.13–4.30 (2H, multiplet); 4.35–4.45 (3H, multiplet); 4.49–4.54 (1H, multiplet); 6.77–6.85 (2H, multiplet); 6.95–7.14 (5H, multiplet); 7.20–7.28 (2H, multiplet).

EXAMPLE 19

1-[(2S,3S)-3-{N²-[4-(N-Benzyloxycarbonyl-N-methylamino)phenoxyacetyl]-L-asparaginyl}amino-2-hydroxy-4-phenylbutyryl]-N-t-butyl-L-prolinamide Following a procedure similar to that described in Example 14, but using 70 mg (0.22 mmol) of 4-(N-benzyloxycarbonyl-N-methylamino)phenoxyacetic acid (prepared as described in Preparation 17) and 100 mg (0.20 mmol) of 1-[(2S,3S)-3-(L-asparaginylamino)-2-hydroxy-4-phenylbutyryl-N-t-butyl-L-prolinamide hydrochloride as starting materials, 97 mg of the title compound were obtained as a white powder, melting at 98°–100° C.

Elemental analysis: Calculated for $C_{40}H_{50}N_6O_9 \cdot 0.5H_2O$ (molecular weight: 767.86): C, 62.56%; H, 6.70%; N, 10.95%. Found: C, 62.61%; H, 6.62%; N, 10.84%.

Mass spectrum (m/z): 741 (M⁺–17), 641, 501, 411, 314, 256, 228, 171, 155, 120, 91, 70.

Infrared Absorption Spectrum (KBr), $v_{max}$ cm⁻¹: 3339, 1679, 1511.

Nuclear Magnetic Resonance Spectrum (270 MHz, CD₃OD) δ ppm: 1.30 (9H, singlet); 1.85–2.21 (4H, multiplet); 2.52–2.69 (2H, multiplet); 2.75 (1H, doublet of doublets, J=10.3 & 14.2 Hz); 2.87 (1H, doublet of doublets, J=4.4 & 14.2 Hz); 3.26 (3H, singlet); 3.69–3.78 (2H, multiplet); 4.35–4.44 (3H, multiplet); 4.47–4.52 (2H, multiplet); 4.70–4.77 (2H, multiplet); 5.10 (2H, singlet); 6.94–7.00 (2H, multiplet); 7.05–7.35 (12H, multiplet).

EXAMPLE 20

1-[(2S,3S)-3-{N²-[4-(Methylamino)phenoxyacetyl]-L-asparaginyl}amino-2-hydroxy-4-phenylbutyryl]-N-t-butyl-L-prolinamide hydrochloride Following a procedure similar to that described in Example 17, but using 68 mg (0.090 mmol) of 1-[(2S,3S)-3-{N₂-[4-(N-benzyloxycarbonyl-N-methylamino)phenoxyacetyl]-Lasparaginyl}amino-2-hydroxy-4-phenylbutyryl]-N-t-butyl-L-prolinamide (prepared as described in Example 19) as a starting material, 57 mg of the title compound were obtained as a pale red-brown powder, melting at 151°–154° C.

Elemental analysis: Calculated for $C_{32}H_{44}N_6O_7HCl \cdot 3H_2O$ (molecular weight: 715.23): C, 53.73%; H, 7.05%; N, 11.75%. Found: C, 53.86%; H, 6.82%; N, 11.07%.

Mass spectrum (m/z): 624 (M⁺), 607, 508, 410, 327, 277, 228, 180, 171, 122, 70.

Infrared Absorption Spectrum (KBr), $v_{max}$ cm⁻¹: 3311, 1672, 1511.

Nuclear Magnetic Resonance Spectrum (270 MHz, CD₃OD) δ ppm: 1.31 (9H, singlet); 1.88–2.25 (4H, multiplet); 2.53–2.94 (4H, multiplet); 3.04 (3H, singlet); 3.70–3.79 (2H, multiplet); 4.33–4.46 (3H, multiplet); 4.53–4.59 (2H, multiplet); 4.70–4.77 (1H, multiplet); 7.07–7.30 (7H, multiplet); 7.40–7.48 (2H, multiplet).

EXAMPLE 21

1-[(2S,3S)-3-{N²-[4-(N,N-Dimethylamino)phenoxyacetyl]-L-asparaginyl}amino-2-hydroxy-4-phenylbutyryl]-N-t-butyl-L-prolinamide 0.15 ml of a 1N aqueous solution of lithium hydroxide was added to a solution of 30 mg (0.13 mmol) of ethyl 4-(N,N-dimethylamino)phenoxyacetate (prepared as described in Preparation 18) in 1 ml of methanol, and the mixture was stirred at room temperature for 1 hour. At the end of this time, the solvent was removed by distillation under reduced pressure, the resulting residue was mixed with benzene and the mixture was dehydrated by azeotropic distillation. This operation was repeated a further time, and then the residue was dried in vacuo for 2 hours, to give 26 mg of lithium 4-(N,N-dimethylamino)phenoxyacetate.

A procedure similar to that described in Example 14 was then repeated, but using the whole of this lithium salt and 60 mg (0.12 mmol) of 1-[(2S,3S)-3-(L-asparaginylamino)-2-hydroxy-4-phenylbutyryl]-N-t-butyl-L-prolinamide hydrochloride as starting materials, to obtain 40 mg of the title compound as a pale reddish white powder, melting at 102°–104° C.

Elemental analysis: Calculated for $C_{33}H_{46}N_6O_7 \cdot 0.5H_2O$ (molecular weight: 638.75): C, 61.19%; H, 7.31%; N, 12.98%. Found: C, 61.37%; H, 7.24%; N, 12.83%.

Mass spectrum (m/z): 638 (M⁺), 621, 522, 424, 291, 256, 228, 171, 136, 120, 70.

Infrared Absorption Spectrum (KBr), $v_{max}$ cm⁻¹: 3333, 1672, 1514.

Nuclear Magnetic Resonance Spectrum (270MHz, CD₃OD) δ ppm: 1.31 (9H, singlet); 1.86–2.24 (4H, multiplet); 2.55–2.93 (10H, multiplet); 3.69–3.77 (2H, multiplet); 4.32–4.45 (5H, multiplet); 4.69–4.76 (1H, multiplet); 6.77–6.93 (4H, multiplet); 7.06–7.29 (5H, multiplet).

EXAMPLE 22

1-{(2S,3S)-3-[N²-{4-[N-(t-Butoxycarbonylsarcosyl)-N-methylamino]phenoxyacetyl}-L-asparaginyl]amino-2-hydroxy-4-phenylbutyryl}-N-t-butyl-L-prolinamide Following a procedure similar to that described in Example 14, but using 120 mg (0.34 mmol) of 4-[N-(t-butoxycarbonylsarcosyl)-N-methyl]aminophenoxyacetic acid (prepared as described in Preparation 19) and 154 mg (0.31 mmol) of 1-[(2S,3S)-3-(L-asparaginylamino)-2-hydroxy-4-phenylbutyryl]-N-t-butyl-L-prolinamide hydrochloride as starting materials, 130 mg of the title compound were obtained as a white powder, melting at 127°–120° C.

Elemental analysis: Calculated for $C_{40}H_{57}N_7O_{10} \cdot 0.5H_2O$ (molecular weight: 804.92): C, 59.68%; H, 7.26%; N, 12.18%. Found: C, 59.98%; H, 7.46%; N, 11.81%.

Mass spectrum (m/z): 679 (M⁺116), 624, 607, 578, 481, 428, 410, 350, 70 (base).

Infrared Absorption Spectrum (KBr), $v_{max}$ cm⁻¹: 3336, 1678, 1510, 1391, 1245, 1153.

Nuclear Magnetic Resonance Spectrum (CDCl₃, 270 MHz), δ ppm: 1.31 (9H, singlet); 1.44 (9H, singlet); 1.92–2.35 (4H, multiplet); 2.52–2.80 (4H, multiplet); 2.88 (3H, singlet); 3.23 (3H, singlet); 3.62–3.72 (4H, multiplet); 4.07 (1H, triplet); 4.44 (5H, broad singlet); 4.73 (2H, broad singlet); 5.57 (1H, broad singlet); 6.09 (1H, broad singlet); 6.47 (1H, broad singlet); 6.95–7.00 (2H, multiplet); 7.12–7.23 (6H, multiplet); 7.45–7.52 (1H, multiplet).

EXAMPLE 23

1-[(2S,3S)-3-{N²-[4-(N-Sarcosyl-N-methylamino) phenoxyacetyl]-L-asparaginyl}amino-2-hydroxy-4-phenylbutyryl]-N-t-butyl-L-prolinamide hydrochloride Following a procedure similar to that described in Example 18, but using 100 mg (0.13 mmol) of 1-{(2S,3S)-3-[N²-{4-[N-(t-butoxycarbonylsarcosyl)-N-methylamino]phenoxyacetyl}-L-asparaginyl]amino-2-hydroxy-4-phenylbutyryl}-N-t-butyl-L-prolinamide (prepared as described in Example 22), removing the t-butoxycarbonyl group by a procedure similar to that described in the first part of Example 1, and then lyophilizing the product, 70 mg of the title compound were obtained as a white powder, melting at 138°–147° C.

Elemental analysis: Calculated for $C_{35}H_{49}N_7O_8HCl.3.5H_2O$ (molecular weight: 795.32): C, 52.85%; H, 7.22%; N, 12.33%. Found: C, 52.84%; H, 7.03%; N, 12.18%.

EXAMPLE 24

1-{(2S,3S)-3-[N²-{4-[N-(t-Butoxycarbonylglycyl)-N-methyl]aminophenoxyacetyl}-L-asparaginyl]amino-2-hydroxy-4-phenylbutyryl}-N-t-butyl-L-prolinamide Following a procedure similar to that described in Example 14, but using 90 mg (0.27 mmol) of 4-[N-(t-butoxycarbonylglycyl)-N-methyl]aminophenoxyacetic acid (prepared as described in Preparation 20) and 125 mg (0.25 mmol) of 1-[(2S,3S)-3-(L-asparaginylamino)-2-hydroxy-4-phenylbutyryl]-N-t-butyl-L-prolinamide hydrochloride as starting materials, 100 mg of the title compound were obtained as a white powder, melting at
118°–123° C.

Elemental analysis: Calculated for $C_{39}H_{55}N_7O_{10}.H_2O$ (molecular weight: 799.90): C, 58.56%; H, 7.31%; N, 12.26%. Found: C, 58.16%; H, 7.08%; N, 12.14%.

Mass spectrum (m/z): 680 (M⁺−100), 664, 624, 607, 564, 507, 444, 434, 378, 327, 70 (base).

Infrared Absorption Spectrum (KBr), $v_{max}$ cm⁻¹: 3336 1668, 1509, 1454, 1393, 1247.

Nuclear Magnetic Resonance Spectrum (CDCl₃, 270 MHz), δ ppm: 1.30 (9H, singlet); 1.39 (9H, singlet); 1.87–2.04 (2H, multiplet); 2.12–2.18 (1H, multiplet); 2.31–2.38 (1H, multiplet); 2.45–2.52 (1H, multiplet); 2.67–2.82 (3H, multiplet); 3.25 (3H, singlet); 3.56–3.64 (2H, multiplet); 3.66–3.68 (2H, multiplet); 4.03–4.06 (1H, multiplet); 4.45–4.50 (5H, multiplet); 4.69–4.75 (2H, multiplet); 5.47 (1H, broad singlet); 5.65 (1H, broad singlet); 6.23 (1H, broad singlet); 6.51 (1H, broad singlet); 6.95 (2H, doublet, J=9.24 Hz); 7.12–7.28 (6H, multiplet); 7.43–7.45 (1H, multiplet).

EXAMPLE 25

1-[(2S,3S)-3-{N²-[4-(N-Glycyl-N-methylamino) phenoxyacetyl]-L-asparaginyl}amino-2-hydroxy-4-phenylbutyryl]-N-t-butyl-L-prolinamide hydrochloride A procedure similar to that described in Example 18 was repeated, except that 70 mg (0.09 mmol) of 1-{(2S,3 S)-3-[N²-{4-[N-(t-butoxycarbonylglycyl)-N-methyl]aminophenoxyacetyl}-L-asparaginyl]amino-2-hydroxy-4-phenylbutyryl}-N-t-butyl-L-prolinamide (prepared as described in Example 24) were used as a starting material, and that the t-butoxycarbonyl group was then removed, as described in Example 1(a), after which the product was lyophilized, to obtain 64 mg of the title compound as a hygroscopic white powder.

Mass spectrum (m/z): 664 (M⁺−17).

Elemental analysis: Calculated for $C_{34}H_{47}N_7O_8HCl.4.5H_2O$ (molecular weight: 799.31): C, 51.09%; H, 7.19%; N, 12.27%. Found: C, 50.87%; H, 6.86%; N, 11.83%.

EXAMPLE 26

(4S)-1-[(2S,3S)-{3-[N²-(4-Benzyloxycarbonylaminophenoxy)acetyl-L-asparaginyl]amino-2-hydroxy-4-phenylbutyryl}-4-chloro-N-t-butyl-L-prolinamide Following a procedure similar to that described in Example 14, but using 115 mg (0.38 mmol) of 4-(N-benzyl- oxycarbonyl)aminophenoxyacetic acid (prepared as described in Preparation 15) and 169 mg (0.32 mmol) of (4S)-[(2S,3S)-3-L-asparaginylamino-2-hydroxy-4-phenylbutyryl]-4-chloro-N-t-butyl-L-prolinamide hydrochloride, 160 mg of the title compound, melting at 113°–115° C., were obtained.

Elemental analysis: Calculated for $C_{39}H_{47}N_6O_9Cl.0.5H_2O$ (molecular weight: 788.28): C, 59.42%; H, 6.14%; N, 10.66%. Found: C, 59.61%; H, 6.17%; N, 10.52%.

Mass spectrum (m/z): 627, 591, 518, 491, 422, 397, 300, 262, 243, 205, 120, 108, 91, 79, 58.

Infrared Absorption Spectrum (KBr), $v_{max}$ cm⁻¹: 3321, 1668, 1512.

Nuclear Magnetic Resonance Spectrum (270MHz, CD₃OD) δ ppm: 1.30 (9H, singlet); 2.04–2.18 (1H, multiplet); 2.51–2.97 (5H, multiplet); 3.64–3.78 (1H, multiplet); 4.18–4.48 (2H, multiplet); 4.66–4.76 (1H, multiplet); 5.16 (2H, singlet); 6.86–6.95 (2H, multiplet); 7.07–7.42 (12H, multiplet).

EXAMPLE 27

(4S)-1-{(2S,3S)-3-[N²-(4-Aminophenoxyacetyl)-L-asparaginyl]amino-2-hydroxy-4-phenylbutyryl]-4-chloro-N-t-butyl-L-prolinamide hydrochloride Following a procedure similar to that described in Example 17, but using 100 mg (0.13 mmol) of (4S)-1-[(2S,3S)-{3-[N²-(4-benzyloxycarbonylaminophenoxy)acetyl-L-asparaginyl]amino-2-hydroxy-4-phenylbutyryl}-4-chloro-N-t-butyl-L-prolinamide (prepared as described in Example 26), 71 mg of the title compound were obtained as a red-brown powder, melting at 157°–160° C.

Elemental analysis: Calculated for $C_{31}H_{41}N_6O_7Cl.3.5H_2O.HCl$ (molecular weight: 744.66): C, 50.00%; H, 6.63%; N, 11.29%. Found: C, 49.70%; H, 6.29%; N, 11.28%.

Mass spectrum (m/z): 644 (M⁺), 627, 591, 491, 396, 263, 205, 166, 108, 91, 68, 44.

Infrared Absorption Spectrum (KBr), $v_{max}$ cm⁻¹: 3327, 1665, 1534, 1509.

Nuclear Magnetic Resonance Spectrum (270 MHz, CD$_3$OD) δ ppm: 1.31 (9H, singlet); 2.05–2.18 (1H, multiplet); 2.53–3.01 (5H, multiplet); 3.70–3.78 (1H, multiplet); 4.21–4.58 (7H, multiplet); 4.67–4.78 (1H, multiplet); 7.05–7.15 (2H, multiplet); 7.20–7.35 (7H, multiplet).

EXAMPLE 28

(1S,4S)-5-[(2S,3S)-3-(N-Benzyloxycarbonyl-3-cyano-L-alanyl)amino-2-hydroxy-4-phenylbutyryl]-2,5-oxazobicyclo[2.2.1]heptan-3-one Following a procedure similar to that described in Example 1, but using 42.5 mg (0.1 mmol) of (2S,3S)-3-(N-benzyloxycarbonyl-3-cyano-L-alanyl)amino-2-hydroxy-4-phenylbutyric acid and 21.3 mg of (1S,4S)-5-t-butoxy-carbonyl-2,5-oxazobicyclo[2.2.1]heptan-3-one (prepared as described in Preparation 9), 26 mg of the title compound were obtained as a colorless powder, melting at 105°–110° C.

Elemental analysis: Calculated for C$_{27}$H$_{28}$N$_4$O$_7$·½H$_2$O (molecular weight: 529.56): C, 61.24%; H, 5.52%; N, 10.58%. Found: C, 61.55%; H, 5.72%; N, 10.31%.

EXAMPLE 29

1-{(2S,3S)-3-[N$^2$-(4-Methoxybenzyloxycarbonyl)-L-asparaginyl]amino-2-hydroxy-4-phenylbutyryl}-N-t-butyl-L-prolinamide 67 mg (0.33 mmol) of 4-methoxybenzyloxycarbonyl azide and 92 μl (0.66 mmol) of triethylamine were added, whilst ice-cooling, to a solution of 150 mg (0.30 mmol) of (2S,3S)-3-L-asparaginylamino-2-hydroxy-4-phenylbutyryl-N-t-butyl-L-prolinamide hydrochloride in 2 ml of dimethylformamide, and the resulting mixture was stirred at 4° C. for 14 hours. At the end of this time, the reaction mixture was concentrated by evaporation under reduced pressure, and the concentrate was mixed with a 10% w/v aqueous solution of sodium hydrogencarbonate, after which the mixture was extracted with ethyl acetate. The extract was washed with a saturated aqueous solution of sodium chloride and dried over anhydrous sodium sulfate. The solvent was then removed by distillation under reduced pressure, and the residue was purified by preparative thin layer chromatography, using a 10:1 by volume mixture of methylene chloride and methanol as the developing solvent, to give 105 mg of the title compound as a colorless powder, melting at 95°–97° C.

Elemental analysis: Calculated for C$_{32}$H$_{43}$N$_5$O$_8$·0.5H$_2$O (molecular weight: 634.71): C, 60 55%; H, 6.99%; N, 11.03%. Found: C, 60.33%; H, 7.00%; N, 10.86%.

Mass spectrum (m/z): 608 (M$^+$−17), 564, 487. 444, 387, 344, 327, 290, 228, 171, 121, 91, 70.

Infrared Absorption Spectrum (KBr), ν$_{max}$ cm$^{-1}$: 3331, 1671, 1516.

Nuclear Magnetic Resonance Spectrum (CDCl$_3$, 270 MHz), δ ppm: 1.30 (9H, singlet); 1.82–2.32 (4H, multiplet); 2.50–2.81 (4H, multiplet); 3.57 3.66 (2H, multiplet); 3.79 (3H, singlet); 4.35–4.50 (4H, multiplet); 5.01 (2H, singlet); 5.63 (1H, broad singlet); 6.09 (1H, broad singlet); 6.19 (1H, broad doublet, J=7.3 Hz); 6.57 (1H, singlet); 6.87 (2H, doublet, J=8.6 Hz); 7.10–7.30 (8H, multiplet); 7.50 (1H, broad doublet, J=7.9 Hz).

EXAMPLE 30

1-[(2S,3S)-3-{N$^2$-[4-(N-Bromoacetyl-N-methylamino)phenoxy]acetyl-L-asparaginyl}amino-2-hydroxy-4-phenylbutyryl]-N-t-butyl-L-prolinamide 0.59 ml (7.2 mmol) of bromoacetyl chloride and 1.6 ml (11.7 mmol) of triethylamine were added, whilst ice-cooling, to a solution of 3.0 g (4.5 mmol) of 1-[(2S,3S)-3-{N$^2$-[4-(methylamino)phenoxyacetyl]-L-asparaginyl}amino-2-hydroxy-4-phenylbutyryl]-N-t-butyl-L-prolinamide hydrochloride (prepared as described in Example 20) in 10 ml of dimethylformamide, and the resulting mixture was stirred for 1 day. At the end of this time, the reaction mixture was neutralized by the addition of 1N aqueous hydrochloric acid. It was then concentrated by evaporation under reduced pressure, and the concentrate was diluted with ethyl acetate. The resulting diluted solution was washed with 1N aqueous hydrochloric acid, with a 5% w/v aqueous solution of sodium hydrogencarbonate and with a saturated aqueous solution of sodium chloride, in that order. It was then dried over anhydrous sodium sulfate. The solvent was removed by distillation under reduced pressure, and the residue was purified by column chromatography, using a 1:15 by volume mixture of methanol and methylene chloride as the eluent, to give 2.3 g of the title compound as a colorless powder, melting at 116°–122° C.

Elemental analysis: Calculated for C$_{34}$H$_{45}$N$_6$O$_8$Br (molecular weight: 745.65): C, 54.77%; H, 6.08%; N, 11.27%; Br, 10.70%. Found: C, 54.95%; H, 6.30%; N, 11.80%; Br, 10.85%.

Mass spectrum (m/z): 717 (M$^+$−28), 665, 607, 534, 468, 438, 387, 335, 70 (base).

Infrared Absorption Spectrum (KBr), ν$_{max}$ cm$^{-1}$: 3332, 1671, 1510, 1454.

Nuclear Magnetic Resonance Spectrum (CDCl$_3$, 270 MHz), δ ppm: 1.30–1.32 (9H, multiplet); 1.88–2.05 (2H, multiplet); 2.14–2.21 (1H, multiplet); 2.30–2.38 (1H, multiplet); 2.55 (1H, doublet of doublets, J=6.6 & 15.2 Hz); 2.72–2.82 (3H, multiplet); 3.28 (3H, singlet); 3.67 (2H, triplet, J=6.6 Hz); 3.83 (2H, singlet); 3.98–4.07 (1H, multiplet); 4.42–4.48 (5H, multiplet); 4.72–4.78 (1H, multiplet); 5.42 (1H, broad singlet); 5.95 (1H, broad singlet); 6.44 (1H, broad singlet); 6.99 (2H, doublet, J=9.2 Hz); 7.13–7.24 (7H, multiplet); 7.42 (1H, doublet, J=7.9 Hz); 8.15 (1H, doublet, J=7.2 Hz).

EXAMPLE 31

1-{(2S,3S)-3-[N$^2$-(3-Aminophenoxy)acetyl-L-asparaginyl]amino-2-hydroxy-4-phenylbutyryl}-N-t-butyl-L-prolinamide Following a procedure similar to that described in Example 17, but using 0.28 g (0.38 mmol) of 1-{(2S,3S)-3-[N$^2$-(3-benzyloxycarbonylaminophenoxy)acetyl-L-asparaginyl]amino2-hydroxy-4-phenylbutyryl}-N-t-butyl-L-prolinamide (prepared as described in Example 33), 0.17 g of the title compound were obtained as a colorless powder, melting at 108°–114° C.

Elemental analysis: Calculated for C$_{31}$H$_{42}$N$_6$O$_7$·H$_2$O (molecular weight: 628.71): C, 59.21%; H, 7.05%; N, 13.37%. Found: C, 59.37%; H, 6.99%; N, 13.41%.

Mass spectrum (m/z): 611 (M$^+$+1), 594, 494, 396, 70 (base).

Infrared Absorption Spectrum (KBr), ν$_{max}$ cm$^{-1}$: 3352, 1668, 1524, 1495, 1455, 1189, 1161.

Nuclear Magnetic Resonance Spectrum (CD₃OD, 270 MHz), δ ppm: 1.31, 1.33 (together 9H, each singlet); 1.89–2.20 (4H, multiplet); 2.61–2.93 (4H, multiplet); 3.73–3.77 (2H, multiplet); 4.36–4.46 (3H, multiplet); 4.54 (2H, singlet); 4.70–4.78 (1H, multiplet); 6.86–6.92 (2H, multiplet); 7.10–7.39 (7H, multiplet).

EXAMPLE 32

1-{(2S,3S)-3-[N²-{4-[N-(N,N-Dimethylaminoacetyl)-N-methylamino]phenoxy}acetyl-L-asparaginyl]amino-2-hydroxy-4-phenylbutyryl}-N-t-butyl-L-prolinamide Following a procedure similar to that described in Example 38, but using 100 mg (0.13 mmol) of 1-[(2S,3S)-3-{N²-[4-(N-bromoacetyl-N-methylamino)phenoxy]acetyl-L-asparaginyl}amino-2-hydroxy-4-phenylbutyryl]-N-t-butyl-L-prolinamide (prepared as described in Example 30) and 0.12 ml (1.3 mmol) of dimethylamine, 90 mg of the title compound were obtained as a colorless powder, melting at 129°–135° C.

Elemental analysis: Calculated for $C_{36}H_{51}N_7O_8 \cdot 5/2H_2O$ (molecular weight: 754.864): C, 57.28%; H, 7.48%; N, 12.99%. Found: C, 57.31%; H, 7.31%; N, 13.31%.

EXAMPLE 33

1-{(2S,3S)-3-[N²-(3-Benzyloxycarbonylaminophenoxy)acetyl-L-asparaginyl]amino-2-hydroxy-4-phenylbutyryl}-N-t-butyl-L-prolinamide Following a procedure similar to that described in Example 14, but using 0.45 g (0.91 mmol) of 1-[(2S,3S)-3-L-asparaginylamino-2-hydroxy-4-phenylbutyryl]-N-t-butyl-L-prolinamide hydrochloride and 0.30 g (1.00 mmol) of 3-benzyloxycarbonylaminophenoxyacetic acid, 0.34 g of the title compound were obtained as a colorless powder, melting at 107°–117° C.

Elemental analysis: Calculated for $C_{39}H_{48}N_6O_9 \cdot \frac{1}{2}H_2O$ (molecular weight: 753.83): C, 62.13%; H, 6.55%; N, 11.15%. Found: C, 62.21%; H, 6.65%; N, 10.92%.

Mass spectrum (m/z): 593 (M⁺⁻151), 575, 520, 493, 476, 428, 396, 70 (base).

Infrared Absorption Spectrum (KBr), $v_{max}$ cm⁻¹: 3320, 1671, 1609, 1538, 1223.

Nuclear Magnetic Resonance Spectrum (CDCl₃, 270 MHz), δ ppm: 1.27 (9H, singlet); 1.84–1.99 (2H, multiplet); 2.04–2.32 (2H, multiplet); 2.56 (1H, doublet of doublets, J=6.6 & 14.5 Hz); 2.69–2.77 (3H, multiplet); 3.60–3.68 (2H, multiplet); 4.18–4.27 (1H, multiplet); 4.44 (5H, singlet-like); 4.68–4.78 (1H, multiplet); 5.18 (2H, singlet); 5.68 (1H, broad singlet); 6.13 (1H, broad singlet); 6.47–6.50 (1H, multiplet); 6.58–6.61 (1H, multiplet); 7.07–7.24 (8H, multiplet); 7.34–7.38 (5H, multiplet); 7.47–7.50 (1H, multiplet).

EXAMPLE 34

1(2S,3S)-3-[N²-(2-Benzyloxycarbonylaminophenoxy)acetyl-L-asparaginyl]amino-2-hydroxy-4-phenylbutyryl}-N-t-butyl-L-prolinamide Following a procedure similar to that described in Example 14, but using 0.45 g (0.91 mmol) of 1-[(2S,3S)-L-asparaginylamino-2-hydroxy-4-phenylbutyryl]-N-t-butyl-L-prolinamide hydrochloride and 0.30 g (1.00 mmol) of 2-benzyloxycarbonylaminophenoxyacetic acid, 0.42 g of the title compound was obtained as a colorless powder, melting at 100°–105° C.

Elemental analysis: Calculated for $C_{39}H_{48}N_6O_9 \cdot 2/3H_2O$ (molecular weight: 756.83): C, 61.89%; H, 6.57%; N, 11.11%. Found: C, 61.95%; H, 6.49%; N, 11.25%.

EXAMPLE 35

1-{(2S,3S)-3-[N²-(2-Aminophenoxy)acetyl-L-asparaginyl]amino-2-hydroxy-4-phenylbutyryl}-N-t-butyl-L-prolinamide Following a procedure similar to that described in Example 17, but using 0.25 g (0.34 mmol) of 1-{(2S,3S)-3-[N²-(2-benzyloxycarbonylaminophenoxy)acetyl-L-asparaginyl]amino-2-hydroxy-4-phenylbutyryl]-N-t-butyl-L-prolinamide (prepared as described in Example 34), and then purifying the product by preparative thin layer chromatography, using a 1:8 by volume mixture of methanol and methylene chloride as the developing solvent, 60 mg of the title compound were obtained as a colorless powder, melting at 107°–114° C.

Elemental analysis: Calculated for $C_{31}H_{42}N_6O_7 \cdot H_2O$ (molecular weight: 628.71): C, 59.22%; H, 7.05%; N, 13.36%. Found: C, 59.04%; H, 7.04%; N, 13.20%.

Mass spectrum (m/z): 611 (M⁺+1), 594, 494, 463, 397, 70 (base).

Infrared Absorption Spectrum (KBr), $v_{max}$ cm⁻¹: 3344, 1668, 1507, 1455, 1213.

Nuclear Magnetic Resonance Spectrum (CD₃OD, 270 MHz), δ ppm: 1.30, 1.32 (together 9H, each singlet); 1.89–1.98 (2H, multiplet); 2.01–2.20 (2H, multiplet); 2.58–2.70 (2H, multiplet); 2.77–2.87 (2H, multiplet); 3.72–3.76 (2H, multiplet); 4.34–4.44 (3H, multiplet); 4.48–4.56 (2H, multiplet); 4.73 (1H, triplet, J=6.6 Hz); 6.65–6.71 (1H, multiplet); 6.80–6.81 (2H, multiplet); 7.10–7.29 (6H, multiplet).

EXAMPLE 36

(4S)-1-[(2S,3S)-3-(N²-Benzyloxycarbonyl-L-asparaginyl)amino-2-hydroxy-4-phenylbutyryl]-4-fluoro-N-t-butyl-L-prolinamide Following a procedure similar to that described in Example 1, but using 222 mg (0,5 mmol) of (2S,3S)-3-(N²-benzyloxycarbonyl-L-asparaginyl)amino-2-hydroxy-4-phenylbutyric acid and 144 mg (0.5 mmol) of (4S)-N-t-butoxycarbonyl-4-fluoro-N-t-butyl-L-prolinamide, 120 mg of the title compound were obtained as a colorless powder, melting at 95°–100° C.

Elemental analysis: Calculated for $C_{31}H_{40}N_5O_7 \cdot \frac{1}{2}H_2O$ (molecular weight: 622.70): C, 59.80%; H, 6.64%; N, 11.25%; F, 3.05%. Found: C, 60.08%; H, 7.01%; N, 10.88%; F, 2.67%.

Mass spectrum (m/z): 596 (M⁺−17), 576, 514, 497, 452, 406, 368, 318, 290, 246, 210, 189, 147, 91 (base peak).

Infrared Absorption Spectrum (KBr), $v_{max}$ cm⁻¹: 3328, 1668, 1531, 1455, 1394, 1366, 1326, 1263, 1227, 1109, 1047.

Nuclear Magnetic Resonance Spectrum (CD₃OD, 270 MHz), δ ppm: 1.29 (9H, singlet); 2.28–2.66 (4H, multiplet); 2.80–3.03 (2H, multiplet); 3.72–4.80 (6H, multiplet); 5.07 (2H, singlet); 5.27 (1H, doublet-like, J=53.2 Hz); 7.10–7.35 (10H, multiplet).

EXAMPLE 37

1-[(2S,3S)-3-(N²-Benzyloxycarbonyl-L-asparaginyl)
amino-2-hydroxy-4-phenylbutyryl]-4-(4-
fluorobutoxy)-N-t-butyl-L-prolinamide Following a procedure similar to that described in Example 1, but using 222 mg (0.5 mmol) of (2S,3S)-3-(N²-benzyloxycarbonyl-L-asparaginyl)amino-2-hydroxy-4-phenylbutyric acid and 180 mg (0.5 mmol) of N-t-butoxycarbonyl-4-fluorobutoxy-N-t-butyl-L-prolinamine, 180 mg of the title compound were obtained as a colorless powder, melting at 68°–71° C.

Elemental analysis: Calculated for $C_{35}H_{48}N_5O_8F.H_2O$ (molecular weight: 703.82): C, 59.73%; H, 7.16%; N, 9.95%; F, 2.70%. Found: C, 60.05%; H, 7.53%; N, 9.67%; F, 2.34%.

EXAMPLE 38

1-[(2S,3S)-3-{N²-[4-(N-Morpholinoacetyl-N-
methylamino)phenoxy]acetyl-L-asparaginyl}amino-
2-hydroxy-4-phenylbutyryl]-N-t-butyl-L-
prolinamide acetate 0.11 ml (1.3 mmol) of morpholine was added to 100 mg (0.13 mmol) of 1-[(2S,3S)-3-{N²-[4-(N-bromoacetyl-N-methylamino)phenoxy]acetyl-L-asparaginyl}amino-2-hydroxy-4-phenylbutyryl]-N-t-butyl-L-prolinamide (prepared as described in Example 30), and the resulting mixture was allowed to stand for 4 days. At the end of this time, the reaction mixture was diluted with chloroform, and the diluted solution was washed with water. The solvent was then removed by distillation under reduced pressure, and the residue was purified by preparative thin layer chromatography, using a 16:4:1 by volume mixture of chloroform, methanol and 32% v/v aqueous acetic acid. The product was triturated with diethyl ether, to obtain 49 mg of the title compound as a colorless powder, melting at 114°–122° C.

Elemental analysis: Calculated for $C_{38}H_{53}N_7O_9.CH_3COOH.\frac{1}{3}H_2O$ (molecular weight: 817.92): C, 58.73%; H, 7.11%; N, 11.98%. Found: C, 58.76%; H, 7.15%; N, 12.40%.

Mass spectrum (m/z): 444 (M⁺–307), 427, 344, 327, 100 (base).

Infrared Absorption Spectrum (KBr), $v_{max}$ cm⁻¹: 3332, 1668, 1510, 1454, 1228, 1116.

Nuclear Magnetic Resonance Spectrum (CD₃OD, 270 MHz), δ ppm: 1.30, 1.32 (together 9H, each singlet); 1.90–1.98 (2H, multiplet); 2.05–2.21 (2H, multiplet); 2.37 (4H, triplet, J=4.6 Hz); 2.62–2.91 (8H, multiplet); 3.20 (3H, singlet); 3.60–3.66 (6H, multiplet); 3.73–3.76 (2H, multiplet); 4.35–4.43 (3H, multiplet); 4.54 (2H, singlet); 4.73 (1H, triplet, J=6.6 Hz); 7.05–7.28 (9H, multiplet).

EXAMPLE 39

1-{(2S,3S)-3-[N²-{4-[N-(Isopentylamino)acetyl-N-
methylamino]phenoxy}acetyl-n-asparaginyl]-amino-
2-hydroxy-4-phenylbutyryl}-N-t-butyl-L-
prolinamide acetate Following a procedure similar to that described in Example 38, but using 100 mg (0.13mmol) of 1-[(2S,3S)-3-{N²-[4-(N-bromoacetyl-N-methylamino)phenoxy]acetyl-L-asparaginyl}amino-2-hydroxy-4-phenylbutyryl]-N-t-butyl-L-prolinamide (prepared as described in Example 30 and 0.14 ml (1.3 mmol) of isoamylamine, 39 mg of the title compound were obtained as a colorless powder, melting at 96°–104° C.

Elemental analysis: Calculated for $C_{39}H_{57}N_7O_8.CH_3COOH.\frac{1}{3}H_2O$ (molecular weight: 817.96): C, 60.20%; H, 7.60%; N, 11.99%. Found: C, 60.22%; H, 7.53%; N, 12.33%.

Mass spectrum (m/z): 734 (M⁺–17), 607, 444, 389, 327, 307, 100 (base).

Infrared Absorption Spectrum (KBr), $v_{max}$ cm⁻¹: 3327, 1667, 1510, 1454.

Nuclear Magnetic Resonance Spectrum (CDCl₃, 270 MHz), δ ppm: 0.88 (6H, doublet, J=6.6 Hz); 1.30 (9H, singlet); 1.44–1.63 (3H, multiplet); 1.90–2.35 (7H, multiplet); 2.49–2.60 (1H, multiplet); 2.65–2.83 (5H, multiplet); 3.27 (7H, singlet); 3.30–3.38 (2H, multiplet); 3.63–3.70 (2H, multiplet); 4.35–4.55 (5H, multiplet); 4.68–4.78 (1H, multiplet); 6.05 (br 1H, singlet); 6.41–6.55 (2H, multiplet); 6.95–7.01 (2H, multiplet); 7.13–7.30 (8H, multiplet); 7.43 (1H, broad doublet, J=8.6 Hz); 7.99 (1H, doublet, J=7.3 Hz).

EXAMPLE 40

1-{(2S,3S)-3-[N²-{4-[N-(N-Methyl-N-phenylamino)
acetyl-N-methylamino]phenoxy}acetyl-L-
asparaginyl]-amino-2-hydroxy-4-phenylbutyryl}-N-
t-butyl-L-prolinamide Following a procedure similar to that described in Example 38, but using 100 mg (0.13 mmol) of 1-[(2S,3S)-3-{N²-[4-(N-bromoacetyl-N-methylamino)phenoxy]acetyl-L-asparaginyl}amino-2-hydroxy-4-phenylbutyryl]-N-t-butyl-L-prolinamide (prepared as described in Example 30) and 0.14 ml (1.3 mmol) of N-methylaniline, and then purifying the product by preparative thin layer chromatography, using a 1:8 by volume mixture of methanol and methylene chloride as the developing solvent, 43 mg of the title compound were obtained as a colorless powder, melting at 107°–112° C.

Elemental analysis: Calculated for $C_{41}H_{53}N_7O_8.\frac{1}{2}H_2O$ (molecular weight: 780.90): C, 63.06%; H, 6.97%; N, 12.56%. Found: C, 63.01%; H, 6.98%; N, 12.34%.

Mass spectrum (m/z): 444 (M⁺–327), 424, 344, 327, 310, 120 (base).

Infrared Absorption Spectrum (KBr), $v_{max}$ cm⁻¹: 3335, 1672, 1601, 1509, 1453, 1246, 1223.

Nuclear Magnetic Resonance Spectrum (CDCl₃, 270 MHz), δ ppm: 1.29, 1.32 (together 9H, each singlet); 1.89–2.01 (2H, multiplet); 2.14–2.37 (2H, multiplet); 2.55 (1H, doublet of doublets, J=6.6 & 14.5 Hz); 2.69–2.82 (3H, multiplet); 2.92 (3H, singlet); 3.23 (3H, singlet); 3.49 (1H, singlet); 3.67 (2H, triplet, J=6.6 Hz); 3.82 (2H, singlet); 4.44–4.48 (5H, multiplet); 4.71–4.72 (1H, multiplet); 5.87 (1H, broad); 6.43 (1H, singlet); 6.55 (doublet, J=8.58 Hz 2H, ); 6.69 (1H, triplet, J=7.3 Hz); 7.00 (2H, doublet, J=9.2 Hz); 7.19–7.26 (12H, multiplet).

EXAMPLE 41

1-{(2S,3S)-3-[N²-{4-[N-(4-Benzylpiperazinyl-1-acetyl)-N-methylamino]phenoxy}acetyl-L-asparaginyl]amino-2-hydroxy-4-phenylbutyryl}-N-t-butyl-L-prolinamide acetate Following a procedure similar to that described in Example 38, but using 100 mg (0.13 mmol) of 1-[(2S,3S)-3-{N²-[4-bromoacetyl-N-methylamino)phenoxy]acetyl-L-asparaginyl}amino-2-hydroxy-4-phenylbutyryl]-N-t-butyl-L-prolinamide (prepared as described in Example 30) and 0.23 ml (1.3 mmol) of 1-benzylpiperazine, 74 mg of the title compound were obtained as a colorless powder, melting at 109°–114° C.

Elemental analysis: Calculated for $C_{45}H_{60}N_8O_8 \cdot CH_3COOH$ (molecular weight: 901.05): C, 62.65%; H, 7.16%; N, 12.44%. Found: C, 62.72%; H, 6.85%; N, 12.94%.

Mass spectrum (m/z): 723 (M⁺–117), 677, 607, 494, 427, 396, 354, 327, 189 (base).

Infrared Absorption Spectrum (KBr), $v_{max}$ cm⁻¹: 3328, 1668, 1510, 1455, 1227.

Nuclear Magnetic Resonance Spectrum (CDCl₃, 270 MHz), δ ppm: 1.30 (9H, singlet); 1.88–2.38 (7H, multiplet); 2.48–2.93 (12H, multiplet); 3.21 (3H, singlet); 3.28–3.38 (2H, multiplet); 3.59–3.70 (4H, multiplet); 4.39–4.50 (5H, multiplet); 4.68–4.77 (1H, multiplet); 5.80 (1H, broad singlet); 6.09 (1H, broad singlet); 6.40–6.48 (1H, multiplet); 6.92–6.98 (2H, multiplet); 7.09–7.41 (13H, multiplet); 8.17 (1H, doublet, J=7.3 Hz).

EXAMPLE 42

1-[(2S,3S)-3-{N²-[4-(N-p-Nitrophenoxycarbonyl-N-methylamino)phenoxy]acetyl-L-asparaginyl}amino-2-hydroxy-4-phenylbutyryl]-N-t-butyl-L-prolinamide Following a procedure similar to that described in Example 30, but using 500 mg (0.76 mmol) of 1-{(2S,3S)-3-[N²-(p-methylaminophenoxy)acetyl-L-asparaginyl]amino-2-hydroxy-4-phenylbutyryl}-N-t-butyl-L-prolinamide hydrochloride (prepared as described in Example 20) and 236 mg (1.13 mmol) of 4-nitrophenoxycarbonyl chloride, 121 mg of the title compound were obtained as a colorless powder, melting at 116°–119° C.

Elemental analysis: Calculated for $C_{39}H_{47}N_7O_{11} \cdot H_2O$ (molecular weight: 807.84): C, 57.98%; H, 6.11%; N, 12.14%. Found: C, 58.20%; H, 6.10%; N, 12.14%.

Mass spectrum (m/z): 607, 508, 444, 427, 373, 345, 327, 256, 228, 207, 139, 122, 70.

Infrared Absorption Spectrum (KBr), $v_{max}$ cm⁻¹: 3339, 1733, 1675, 1513.

Nuclear Magnetic Resonance Spectrum (CDCl₃, 270 MHz), δ ppm: 1.29, (9H, singlet); 1.81–2.30 (4H, multiplet); 2.56 (1H, doublet of doublets, J=6.6, 18.2 Hz); 2.65–2.80 (3H, multiplet); 3.32–3.45 (3H, multiplet); 3.60–3.70 (2H, multiplet); 4.39–4.50 (5H, multiplet); 4.70–4.79 (1H, multiplet); 5.74 (1H, broad singlet); 6.25 (1H, broad singlet); 6.48 (1H, broad singlet); 6.96 (1H, doublet, J=8.6 Hz); 7.06–7.30 (9H, multiplet); 7.53 (1H, broad doublet, J=8.6 Hz); 8.05–8.28 (3H, multiplet).

EXAMPLE 43

1-[(2S,3S)-3-{N²-[4-(N-Morpholinocarbonyl-N-methylamino)phenoxy]acetyl-L-asparaginyl}amino-2-hydroxy-4-phenylbutyryl]-N-t-butyl-L-prolinamide A solution of 47 mg (0.060 mmol) of 1-[(2S,3S)-3-{N²-[4-(p-N-nitrophenoxycarbonyl-N-methylamino)phenoxy]acetyl-L-asparaginyl}amino-2-hydroxy-4-phenylbutyryl]-N-t-butyl-L-prolinamide (prepared as described in Example 42) dissolved in 0.5 ml of morpholine was allowed to stand at room temperature for 6 days. At the end of this time, the reaction mixture was freed from an excess of morpholine by distillation under reduced pressure, and the residue was diluted with chloroform and then washed with water. The organic layer was dried over anhydrous sodium sulfate and the solvent was removed by distillation under reduced pressure. The residue was purified by preparative thin layer chromatography, using a 8:1 by volume mixture of methylene chloride and methanol as the developing solvent, to give 30 mg of the title compound as a colorless powder, melting at 112°–114° C.

Elemental analysis: Calculated for $C_{37}H_{51}N_7O_9 \cdot 1.2H_2O$ (molecular weight: 759.45): C, 58.51%; H, 7.09%; N, 12.91%. Found: C, 58.77%; H, 6.90%; N, 12.43%.

Mass spectrum (m/z): 720 (M⁺–17), 620, 523, 493, 427, 390, 328, 293, 256, 228, 171, 114, 70.

Infrared Absorption Spectrum (KBr), $v_{max}$ cm⁻¹: 3328, 1675, 1508.

Nuclear Magnetic Resonance Spectrum (CDCl₃, 270 MHz), δ ppm: 1.29, (9H, singlet); 1.85–2.32 (4H, multiplet); 2.53–2.85 (4H, multiplet); 3.13–3.22 (7H, multiplet); 3.43–3.50 (4H, multiplet); 3.62–3.72 (2H, multiplet); 4.35–4.50 (5H, multiplet); 4.70–4.80 (1H, multiplet); 5.80 (1H, broad singlet); 6.37 (1H, broad singlet); 6.52 (1H, broad singlet); 6.90 (2H, doublet, J=9.2 Hz); 7.04–7.25 (7H, multiplet); 7.58 (1H, doublet, J=8.6 Hz); 8.06 (1H, doublet, J=7.3 Hz).

EXAMPLE 44

1-[(2S, 3S)-3-{N²-[4-{N-[N-(3-Dimethylaminopropyl)-aminocarbonyl]-N-methylamino}phenoxyacetyl-L-asparaginyl}amino-2-hydroxy-4-phenylbutyryl]-N-t-butyl-L-prolinamide acetate Following a procedure similar to that described in Example 43, but using 50 mg (0.063 mmol) of 1-[(2S,3S)-3-{N²-[4-(N-p-nitrophenoxycarbonyl-N-methylamino)phenoxy]acetyl-L-asparaginyl}amino-2-hydroxy-4-phenylbutyryl]-N-t-butyl-L-prolinamide (prepared as described in Example 42) and 0.80 ml of 3-dimethylaminopropylamine, and then purifying the product by preparative thin layer chromatography, using a 16:4:1 by volume mixture of chloroform, methanol and 33% v/v aqueous acetic acid as the developing solvent, 9 mg of the title compound were obtained as a colorless powder, melting at 113°–116° C.

Elemental analysis: Calculated for $C_{38}H_{56}N_8O_8 \cdot C_2H_4O_2 \cdot 2H_2O$ (molecular weight: 788.92): C, 56.59%; H, 7.60%; N, 13.20%. Found: C, 56.01%; H, 7.42%; N, 13.00%.

Infrared Absorption Spectrum (KBr), $v_{max}$ cm⁻¹: 3334, 1672, 1576, 1532.

Nuclear Magnetic Resonance Spectrum (CDCl₃: CD₃OD=5:1 by volume, 270 MHz), δ ppm: 1.32 (9H, singlet); 1.70–1.80 (1H, multiplet); 1.90–2.15 (12H, multiplet); 2.48–2.85 (6H, multiplet); 3.15–3.25 (5H, multiplet); 3.65–3.78 (2H, multiplet); 4.30–4.52 (5H, multiplet); 4.67–4.75 (1H, multiplet); 6.98–7.08 (2H, multiplet); 7.11–7.29 (5H, multiplet); 7.45–7.51 (2H, multiplet).

EXAMPLE 45

1-{(2S, 3S)-3-[$N^2$-{4-[N-(2-Morpholinoethyl)-N-methylamino]phenoxy}acetyl-L-asparaginyl]amino-2-hydroxy-4-phenylbutyryl}-N-t-butyl-L-prolinamide 1-[(2S,3S)-3-{$N^2$-[4-(2-bromoethylamino)phenoxy]-acetyl-L-asparaginyl}amino-2-hydroxy-4-phenylbutyryl]-N-t-butyl-L-prolinamide was prepared by reacting 500 mg of 1-{(2S,3S)-3-[$N^2$-(p-methylaminophenoxy)acetyl-L-asparaginyl]amino-2-hydroxy-4-phenylbutyryl}-N-t-butyl-L-prolinamide hydrochloride (prepared as described in of 1-{(2S,3S)-3-[$N^2$-(p-methylaminophenoxy)acetyl-L-asparaginyl]amino-2-hydroxy-4-phenylbutyryl}-N-t-butyl-L-prolinamide hydrochloride (prepared as described in Example 20) with 0.65 ml of 1,2-dibromoethane in the presence of sodium carbonate at a temperature of 70° C.

Following a procedure similar to that described in Example 38, but using the 1-[(2S,3S)-3-{N-[4-(2-bromoethylamino)phenoxy]acetyl-L-asparaginyl}amino-2-hydroxy-4-phenylbutyryl]-N-t-butyl-L-prolinamide prepared as described above and morpholine as starting materials, in relative proportions similar to those used in that Example, and then purifying the product by preparative thin layer chromatography, using a 1:8 by volume mixture of methanol and methylene chloride as the developing solvent, 10 mg of the title compound were obtained as a colorless powder, melting at 85°–95° C.

Elemental analysis: Calculated for $C_{38}H_{55}N_7O_8 \cdot 6/5H_2O$ (molecular weight: 759.50). C, 60.09%; H, 7.62%; N, 12.91%. Found: C, 60.00%; H, 7.11%; N, 12.70%.

Mass spectrum (m/z): 737 ($M^+$), 720, 620, 444, 390, 327, 100 (base).

Infrared Absorption Spectrum (KBr), $v_{max}$ cm$^{-1}$: 3332, 1671, 1512, 1454, 1231, 1117.

Nuclear Magnetic Resonance Spectrum (CDCl$_3$, 270 MHz), δ ppm: 130 (9H, singlet); 1.80–2.80 (14H, multiplet); 2.90 (3H, singlet); 3.37–3.45 (2H, multiplet); 3.63–3.75 (6H, multiplet); 4.39–4.51 (5H, multiplet); 4.69–4.79 (1H, multiplet); 5.43 (1H, broad singlet); 5.95 (1H, singlet); 6.49–6.55 (1H, multiplet); 6.67–6.74 (2H, multiplet); 6.83–6.90 (2H, multiplet); 7.05–7.26 (5H, multiplet); 7.40 (1H, doublet, J=8.6 Hz); 8.02 (1H, doublet, J=7.3 Hz).

EXAMPLE 46

1-[(2S,3S)-3-{$N^2$-[4-{N-[N-(2-Hydroxyethyl)amino]acetyl-N-methylamino}phenoxy]acetyl-L-asparaginyl}-amino-2-hydroxy-4-phenylbutyryl]-N-t-butyl-L-prolinamide acetate Following a procedure similar to that described in Example 38, but using 80 mg (0.11 mmol) of 1-[(2S,3S)-3-{$N^2$-[4-bromoacetyl-N-methylamino)phenoxy]acetyl-L-asparaginyl}amino-2-hydroxy-4-phenylbutyryl]-N-t-butyl-L-prolinamide (prepared as described in Example 30) and 1 ml of 2-aminoethanol, 40 mg of the title compound were obtained as a colorless powder, melting at 96°–106° C.

Elemental analysis: Calculated for $C_{36}H_{51}N_7O_9 \cdot \frac{1}{2}CH_3COOH \cdot 3/2H_2O$ (molecular weight: 842.93): C, 55.57%; H, 7.18%; N, 11.63%. Found: C, 55.56%; H, 6.88%; N, 11.98%.

EXAMPLE 47

1-[(2S,3S)-3-{$N^2$-[4-{N-[3-(N,N-Dimethylamino)propyl]aminoacetyl-N-methylamino}phenoxy]acetyl-L-asparaginyl}amino-2-hydroxy-4-phenylbutyryl]-N-t-butyl-L-prolinamide acetate Following a procedure similar to that described in Example 38, but using 80 mg (0.11 mmol) of 1-[(2S,3S)-3-{$N^2$-[4-bromoacetyl-N-methylamino)phenoxy]acetyl-L-asparaginyl}amino-2-hydroxy-4-phenylbutyryl]-N-t-butyl-L-prolinamide (prepared as described in Example 30) and 1 ml of N,N-dimethylaminopropylamine, 20 mg of the title compound were obtained as a colorless powder, melting at 108°–116° C.

Elemental analysis: Calculated for $C_{39}H_{58}N_8O_8 \cdot 2CH_3COOH \cdot H_2O$ (molecular weight: 905.04): 108°–116° C. C, 57.06%; H, 7.35%; N, 10.83%. Found: C, 52.98%; H, 7.17%; N, 12.22%.

Mass spectrum (m/z): 749 ($M^+$–17), 607, 504, 419, 355, 322, 58 (base).

Infrared Absorption Spectrum (KBr), $v_{max}$ cm$^{-1}$: 3330, 1672, 1543, 1510, 1455, 1401, 227.

Nuclear Magnetic Resonance Spectrum (CDCl$_3$, 270 MHz), δ ppm: 1.30 (9H, multiplet); 1.80–2.31 (10H, multiplet); 2.45–2.90 (14H, multiplet); 3.22–3.34 (5H, multiplet); 3.64–3.72 (2H, multiplet); 4.38–4.56 (5H, multiplet); 4.70–4.78 (1H, multiplet); 6.11–6.18 (1H, multiplet); 6.58–6.69 (2H, multiplet); 6.92–7.00 (2H, multiplet); 7.10–7.29 (8H, multiplet); 7.41 (1H, doublet, J=8.6 Hz); 7.99 (1H, doublet, J=7.9 Hz).

EXAMPLE 48

1-[(2S, 3S)-3-{$N^2$-[4-{N-[N-(3-Morpholinopropyl)amino]acetyl-N-methylamino}phenoxy]acetyl-L-asparaginyl}amino-2-hydroxy-4-phenylbutyryl-N-t-butyl-L-prolinamide acetate Following a procedure similar to that described in Example 38, but using 80 mg (0.11 mmol) of 1-[(2S,3S)-3-{$N^2$-[4-bromoacetyl-N-methylamino)phenoxy]acetyl-L-asparaginyl}amino-2-hydroxy-4-phenylbutyl]-N-t-butyl-L-prolinamide (prepared as described in Example 30) and 1 ml of 4-(3-aminopropyl)morpholine, 30 mg, of the title compound were obtained as a colorless powder, melting at 102°–106° C.

Elemental analysis: Calculated for $C_{41}H_{60}N_8O_9 \cdot CH_3COOH \cdot H_2O$ (molecular weight: 887.02): C, 58.22%; H, 7.50%; N, 12.63%. Found: C, 58.00%; H, 7.29%; N, 12.77%.

EXAMPLE 49

1-{(2S,3S)-3-[$N^2$-{4-[N-(N-Benzyloxycarbonyl-γ-benzyl-L-glutaminyl)-N-methylamino]phenoxy}acetyl-L-asparaginyl]amino-2-hydroxy-4-phenylbutyryl}-N-t-butyl-L-prolinamide 0.15 ml (1.08 mmol) of triethylamine and 0.25 g (0.54 mmol) of bromo-tris-pyrrolidine-phosphonium hexafluorophosphate were added, whilst ice-cooling, to a solution of 300 mg (0.45 mmol) of 1-{(2S,3S)-3-[N²-(p-methylaminophenoxy)acetyl-L-asparaginyl]amino-2-hydroxy-4-phenylbutylryl}-N-t-butyl-L-prolinamide hydrochloride (prepared as described in Example 20) and 200 mg (0.54 mmol) of γ-benzyl N^α-benzyloxycarbonyl-L-glutamate in 5 ml of dimethylformamide, and the resulting mixture was stirred for 1 day. At the end of this time, the mixture was neutralized by the addition of 1N aqueous hydrochloric acid, and then the reaction mixture was concentrated by evaporation under reduced pressure. The resulting concentrate was diluted with ethyl acetate. The diluted solution was washed with 1N aqueous hydrochloric acid, with a 5% w/v aqueous solution of sodium hydrogencarbonate and with a saturated aqueous solution of sodium chloride, in that order, and then the solvent was removed by distillation under reduced pressure. The residue was purified by preparative thin layer chromatography, using a 7.5:1 by volume mixture of methylene chloride and methanol as the developing solvent, and the product was triturated with hexane, to give 136 mg of the title compound as a colorless powder, melting at 85°–91° C.

Elemental analysis: Calculated for $C_{52}H_{63}N_7O_{12}.H_2O$ (molecular weight: 996.10): C, 62.70%; H, 6.58%; N, 9.84%. Found: C, 62.90%; H, 6.49%; N, 9.42%.

EXAMPLE 50

1-[(2S,3S)-3-{N²-[4-(N-L-Glutaminyl-N-methylamino)-phenoxy]acetyl-L-asparaginyl}amino-2-hydroxy-4-phenylbutyryl]-N-t-butyl-L-prolinamide hydrochloride Following a procedure similar to that described in Example 17, but using 80 mg (0.08 mmol) of 1-{(2S,3S)-1-{(2S,3S)-3-[N²-{4-[N-(N-benzyloxycarbonyl-γ-benzyl-L-glutaminyl)-N-methylamino]phen-oxy}acetyl-L-asparaginyl]amino-2-hydroxy-4-phenylbutyryl}-N-t-butyl-L-prolinamide (prepared as described in Example 49), 45 mg of the title compound were obtained as a colorless powder, melting at 106°–123° C.

Elemental analysis: Calculated for $C_{37}H_{51}N_7O_{10}.4/3HCl.3.2H_2O$ (molecular weight: 860.11): C, 51.66%; H, 6.77%; N, 11.40%; Cl, 5.50%. Found: C, 51.40%; H, 6.68%; N, 11.38%; Cl, 5.31%.

EXAMPLE 51

1-[(2S,3S)-3-(N²-Benzyloxycarbonyl-L-asparaginyl)amino-2-hydroxy-4-phenylbutyryl]-N-t-butyl-3,4-dehydro-L-prolinamide Following a procedure similar to that described in Example 1, but using 330 mg (0.75 mmol) of (2S,3S)-3-(N²-benzyloxycarbonyl-L-asparaginyl)amino-2-hydroxy-4-phenylbutyric acid and 200 mg (0.75 mmol) of N-t-butoxy-carbonyl-3,4-dehydro-N-t-butyl-L-prolinamide, 260 mg of melting point 106°–110° C.

Elemental analysis: Calculated for $C_{31}H_{39}N_5O_7.\frac{1}{2}H_2O$ (molecular weight: 602.70): C, 61.78%; H, 6.69%; N, 11.62%. Found: C, 61.68%; H, 6.77%; N, 11.59%.

Mass spectrum (m/z): 593 (M⁺), 576, 494, 477, 426, 386, 343, 290, 246, 226, 169, 158, 108, 68 (base peak).

Infrared Absorption Spectrum (KBr), $v_{max}$ cm⁻¹: 3328, 1668, 1620, 1532, 1455, 1393, 1366, 1322, 1246, 1227, 1156, 1112, 1087, 1052, 1029.

Nuclear Magnetic Resonance Spectrum (270 MHz, CD₃OD) δ ppm: 1.32, 1.33 (together 9H, each singlet); 2.40–2.47 (1H, multiplet); 2.55–2.64 (2H, multiplet); 2.79–2.95 (2H, multiplet); 4.15–4.60 (6H, multiplet); 5.08 (2H, singlet); 5.79 (1H, multiplet); 6.02 (1H, multiplet); 7.10–7.35 (9H, multiplet).

EXAMPLE 52

(4R)-1-[(2S,3S)-3-(N²-Benzyloxycarbonyl-L-asparaginyl)amino-2-hydroxy-4-phenylbutyryl]-4-chloro-N-t-butyl-L-prolinamide Following a procedure similar to that described in Example 1, but using 146 mg (0.33 mmol) of (2S,3S)-3-(N²-benzyloxycarbonyl-L-asparaginyl)amino-2-hydroxy-4-phenylbutyric acid and 100 mg (0.33 mmol) of (4R)-N-t-butoxycarbonyl-4-chloro-N-t-butyl-L-prolinamide, 50 mg of the title compound were obtained as a colorless powder, melting at 103°–107° C.

Elemental analysis: Calculated for $C_{31}H_{40}N_5O_7Cl.\frac{1}{2}H_2O$ (molecular weight: 639.16): C, 58.26%; H, 6.46%; N, 10.96%; Cl, 5.55%. Found: C, 57.93%; H, 6.29%; N, 10.60%; Cl, 5.25%.

Mass spectrum (m/z): 630 (M⁺), 577, 513, 493, 475, 398, 368, 351, 290, 262, 205, 163, 91 (base peak).

Infrared Absorption Spectrum (KBr), $v_{max}$ cm⁻¹: 3328, 1668, 1536, 1499, 1455, 1392, 1367, 1321, 1256, 1227, 1157, 1114, 1051, 1028.

Nuclear Magnetic Resonance Spectrum (270 MHz, CD₃OD) δ ppm: 1.32 (9H, singlet); 2.35–2.47 (1H, multiplet); 2.58–2.65 (1H, multiplet); 2.75–2.86 (2H, multiplet); 4.01–4.09 (2H, multiplet); 4.23–4.34 (1H, multiplet); 4.44–4.47 (2H, multiplet); 4.62 (1H, triplet, J=8.0 Hz); 4.72 (1H, singlet); 5.08 (2H, singlet); 7.11–7.35 (10H, multiplet).

EXAMPLE 53

1-[(2S,3S)-3-(N²-Benzyloxycarbonyl-L-asparaginyl)amino-2-hydroxy-4-phenylbutyryl]-N-t-butyl-L-pyroglutamamide Following a procedure similar to that described in Example 14, 4.78 g (12.7 mmol) of (2S,3S)-3-(N,N-dibenzylamino)-2-hydroxy-4-phenylbutyric acid was condensed with 4.19 g (12.7 mmol) of the α-t-butyl amide of γ-benzyl L-glutamate, to give 6.53 g of the α-t-butylamide of γ-benzyl N-[(2S,3S)-3-(N,N-dibenzylamino)-2-hydroxy-4-phenylbutyryl]-L-glutamate. 1.00 g (1.54 mmol) of this compound was debenzylated by reduction in a similar manner to that described in Example 15(c) and was then acylated using 0.66 g (1.69 mmol) of the p-nitrophenyl ester of N²-benzyl oxycarbonyl-L-asparagine in a similar manner to that described in Example 15(d) to give 0.57 g of the α-t-butylamide of (2S,3S)-3-(N²-benzyloxycarbonyl-L-asparaginyl)amino-2-hydroxy-4-phenylbutyryl-L-glutamic acid. 100 mg (0.16 mmol) of this compound and 2.1 mg (0.018 mmol) of 4-dimethylaminopyridine were dissolved in 5 ml of dimethylformamide and 34 mg (0.18 mmol) of 1-ethyl-3-(3-dimethylaminopropyl)carbodiimide hydrochloride were then added to the resulting solution, whilst ice-cooling. The resulting mixture was then stirred at room temperature for 24 hours, after which the solvent was removed by distillation under reduced pressure. The residue was dissolved in ethyl acetate and the resulting solution was washed with a 5% w/v aqueous solution of citric acid and dried over anhydrous sodium sulfate. The organic solvent was removed by distillation under reduced pressure, and the residue was purified by preparative thin layer chromatography, using a 7.5:1 by volume mixture of methylene chloride and methanol as the developing solvent, to give 14 mg of the title compound as a colorless powder, melting at 121°–124° C.

Elemental analysis: Calculated for $C_{31}H_{39}N_5O_8 \cdot 1.25H_2O$ (molecular weight: 632.14):

Elemental analysis: Calculated for $C_{31}H_{39}N_5O_8 \cdot 1.25H_2O$ (molecular weight: 632.14): C, 58.90%; H, 6.62%; N, 11.08%. Found: C, 58.79%; H, 6.28%; N, 11.07%.

EXAMPLE 54

1-{(2S,3S)-3-{$N^2$-(1-Benzyl-4-piperidyloxy)acetyl-L-asparaginyl]amino-2-hydroxy-4-phenylbutyryl}-N-t-butyl-L-prolinamide Following a procedure similar to that described in Example 14, but using 0.46 g (0.92 mmol) of 1-[(2S,3S)-3-L-asparaginylamino-2-hydroxy-4-phenylbutyryl]-N-t-butyl-L-prolinamide hydrochloride and 0.29 g (1.0 mmol) of 1-benzyl-4-piperidyloxyacetic acid hydrochloride, 310 mg of the title compound were obtained as a colorless powder, melting at 94°–103° C.

Elemental analysis: Calculated for $C_{37}H_{52}N_6O_7 \cdot \frac{2}{3}H_2O$ (molecular weight: 704.85): C, 63.05%; H, 7.63%; N, 11.92%. Found: C, 63.20%; H, 7.67%; N, 11.90%.

EXAMPLE 55

1-{(2S,3S)-3-[$N^2$-(4-N,N-Dibenzylaminocyclohexyloxy)acetyl-L-asparaginyl]amino-2-hydroxy-4-phenylbutyryl}-N-t-butyl-L-prolinamide Following a procedure similar to that described in Example 14, but using 0.22 g (0.45 mmol) of 1-[(2S,3S)-3-L-asparaginylamino-2-hydroxy-4-phenylbutyryl]-N-t-butyl-L-prolinamide hydrochloride and 0.19 g (0.49 mmol) of 4-(N,N-dibenzylamino)cyclohexyloxyacetic acid hydrochloride, 0.12 g of the title compound were obtained as a colorless powder, melting at 98°–103° C.

Elemental analysis: Calculated for $C_{45}H_{60}N_6O_7 \cdot \frac{2}{3}H_2O$ (molecular weight: 808.99): C, 66.81%; H, 7.64%; N, 10.39%. Found: C, 66.67%; H, 7.50%; N, 10.51%.

EXAMPLE 56

1-{(2S,3S)-3-[$N^2$-(4-Piperidyloxy)acetyl-L-asparaginyl]amino-2-hydroxy-4-phenylbutyryl}-N-t-butyl-L-prolinamide hydrochloride Following a procedure similar to that described in Example 17, but using 200 mg (0.29 mmol) of 1-{(2S,3S)-3-{$N^2$-(1-benzylpiperid-4-yloxy)acetyl-L-asparaginyl]amino-2-hydroxy-4-phenylbutyryl}-N-t-butyl-L-prolinamide (prepared as described in Example 54), 160 mg of the title compound were obtained as a colorless powder, melting at 140°–148° C.

Elemental analysis: Calculated for $C_{30}H_{46}N_6O_7 \cdot 5/4HCl \cdot 3/2H_2O$ (molecular weight: 675.32): C, 53.35%; H, 7.50%; N, 12.46%; Cl, 6.56%. Found: C, 53.59%; H, 7.32%; N, 12.43%; Cl, 6.52%.

EXAMPLE 57

1-{(2S,3S)-3-[$N^2$-(1-Benzyloxycarbonylpiperid-4-yl-oxy)acetyl-L-asparaginyl]amino-2-hydroxy-4-phenyl-butyryl}-N-t-butyl-L-prolinamide Following a procedure similar to that described in Example 30, but using 120 mg (0.19 mmol) of 1-{(2S,3S)-3-[$N^2$-(4-piperidyloxy)acetyl-L-asparaginyl]amino-2-hydroxy-4-phenylbutyryl}-N-t-butyl-L-prolinamide hydrochloride (prepared as described in Example 56) and 0.03 ml (0.21 mmol) of benzyloxycarbonyl chloride, 110 mg of the title compound were obtained as a colorless powder, melting at 98°–104° C.

Elemental analysis: Calculated for $C_{38}H_{52}N_6O_9 \cdot H_2O$ (molecular weight: 754.86): C, 60.46%; H, 7.21%; N, 11.13%. Found: C, 60.67%; H, 6.92%; N, 11.03%.

Mass spectrum (m/z): 736, 719, 619, 575, 511, 501, 444, 389, 348, 327, 91 (base).

infrared Absorption Spectrum (KBr), $v_{max}$ cm$^{-1}$: 3338, 1675, 1525, 1454, 1229, 1110.

Nuclear Magnetic Resonance Spectrum (CDCl$_3$, 270 MHz), δ ppm: 1.30 (9H, singlet); 1.55–2.38 (10H, multiplet); 2.45–2.83 (4H, multiplet); 3.21–3.33 (2H, multiplet); 3.43–4.00 (6H, multiplet); 4.36–4.51 (2H, multiplet); 4.61–4.84 (1H, multiplet); 5.13 (2H, singlet); 5.35–5.44 (1H, multiplet); 5.83–5.93 (1H, multiplet); 6.42–6.51 (1H, multiplet); 7.13–7.50 (11H, multiplet); 8.05 (1H, doublet, J=7.3 Hz).

EXAMPLE 58

1-{(2S,3S)-3-[$N^2$-(4-Aminocyclohexyloxy)acetyl-L-asparaginyl]amino-2-hydroxy-4-phenylbutyryl}-N-t-butyl-L-prolinamide hydrochloride Following a procedure similar to that described in Example 17, but using 80 mg (0.1 mmol) of 1-{(2S,3S)-3-[$N^2$-(4-N,N-dibenzylaminocyclohexyloxy)acetyl-L-asparaginyl]amino-2-hydroxy-4-phenylbutyryl}-N-t-butyl-L-prolinamide (prepared as described in Example 55), 65 mg of the title compound were obtained as a colorless powder, melting at 143°–146° C.

Elemental analysis: Calculated for $C_{31}H_{48}N_6O_7 \cdot 7/6HCl \cdot 3/2H_2O$ (molecular weight: 686.31): C, 54.25%; H, 7.66%; N, 12.25%; Cl, 6.03%. Found: C, 54.51%; H, 7.24%; N, 11.22%; Cl, 5.87%.

EXAMPLE 59

1-[(2S,3S)-3-{$N^2$-[4-(N-Benzyloxycarbonylamino)-cyclohexyloxy]acetyl-L-asparaginyl}amino-2-hydroxy-4-phenylbutyryl]-N-t-butyl-L-prolinamide Following a procedure similar to that described in Example 30, but using 40 mg (61.2 µmol) of 1-{(2S,3S)-3-[$N^2$-(4-aminocyclohexyloxy)acetyl-L-asparaginyl]amino-2-hydroxy-4-phenylbutyryl}-N-t-butyl-L-prolinamide hydrochloride (prepared as described in Example 58) and 0.01 ml (67.3 µmol) of benzyloxycarbonyl chloride, 22 mg of the title compound were obtained as a colorless powder, melting at 109°–114° C.

Elemental analysis: Calculated for $C_{39}H_{54}N_6O_9 \cdot H_2O$ (molecular weight: 768.89): C, 60.92%; H, 7.34%; N, 10.93%. Found: C, 60.92%; H, 7.13%; N, 10.85%.

Mass spectrum (m/z): 633 (M$^+$–117), 525, 499, 444, 417, 373, 327, 70 (base).

Infrared Absorption Spectrum (KBr), $v_{max}$ cm$^{-1}$: 3328, 1672, 1527, 1455, 1261, 1227, 1110.

Nuclear Magnetic Resonance Spectrum (CDCl$_3$, 270 MHz), δ ppm: 1.08–1.49 (13H, multiplet); 1.82–2.38 (8H, multiplet); 2.55 (1H, doublet of doublets, J=6.6 & 14.5 Hz); 2.62–2.83 (3H, multiplet); 3.19–3.20 (1H, multiplet); 3.42–3.73 (3H, multiplet); 3.86–3.99 (2H, multiplet); 4.37–4.52 (3H, multiplet); 4.61–4.85 (2H, multiplet); 5.09 (2H, singlet); 5.62–5.73 (1H, multiplet); 6.16 (1H, broad singlet); 6.56 (1H, singlet); 7.10–7.40 (11H, multiplet); 7.53 (1H, doublet, J=7.9 Hz); 7.91 (1H, doublet, J=7.9 Hz).

EXAMPLE 60

1-[(2S,3S)-3-{N$^2$-[4-(2-Morpholinoacetamido) phenoxy]acetyl-L-asparaginyl}amino-2-hydroxy-4-phenylbutyryl]-N-t-butyl-L-prolinamide Following a procedure similar to that described in Example 38, but using 100 mg (0.137 mmol) of 1-[(2S, 3S)-3-[N$^2$-(4-bromoacetamidophenoxy)acetyl-L-asparaginyl]amino-2-hydroxy-4-phenylbutyryl]-N-t-butyl-L-prolinamide and 1 ml of morpholine, 70 mg of the title compound were obtained as a colorless powder, melting at 121°–127° C.

Elemental analysis: Calculated for C$_{37}$H$_{51}$N$_7$O$_9$.½H$_2$O (molecular weight: 746.84): C, 59.50%; H, 7.02%; N, 13.13%. Found: C, 59.34%; H, 7.19%; N, 13.02%.

Mass spectrum (m/z): 721 (M$^+$–16), 720, 620, 523, 493, 428, 391, 348, 327, 100 (base).

Infrared Absorption Spectrum (KBr), $v_{max}$ cm$^{-1}$: 3327, 1674, 1512, 1454, 1224, 1116.

Nuclear Magnetic Resonance Spectrum (CDCl$_3$, 270 MHz), δ ppm: 1.29 (9H, singlet); 1.83–2.30 (4H, multiplet); 2.51–2.81 (8H, multiplet); 3.13 (2H, singlet); 3.60–3.82 (6H, multiplet); 4.18–4.50 (5H, multiplet); 4.69–4.79 (1H, multiplet); 5.79 (1H, broad singlet); 6.30 (1H, broad singlet); 6.56 (1H, singlet); 6.86–6.94 (2H, multiplet); 7.05–7.35 (6H, multiplet); 7.46–7.58 (3H, multiplet); 8.00 (1H, doublet, J=7.3 Hz).

EXAMPLE 61

1-{(2S,3S)-3-[N$^2$-{4-[N-(2-Morpholinoethyl) aminoacetyl]aminophenoxy}acetyl-L-asparaginyl] amino-2-hydroxy-4-phenylbutyryl}-N-t-butyl-L-prolinamide Following a procedure similar to that described in Example 38, but using 100 mg (0.137 mmol) of 1-{(2S, 3S)-3-[N$^2$-(4-bromoacetamidophenoxy)acetyl-L-asparaginyl]amino-2-hydroxy-4-phenylbutyryl}-N-t-butyl-L-prolinamide and 1 ml of 4-(2-aminoethyl) morpholine, 17 mg of the title compound were obtained as a colorless powder, melting at 123°–132° C.

Elemental analysis: Calculated for C$_{39}$H$_{56}$N$_8$O$_9$.H$_2$O (molecular weight: 798.92): C, 58.63%; H, 7.32%; N, 14.03%. Found: C, 58.43%; H, 7.33%; N, 13.68%.

Mass spectrum (m/z): 593 (M$^+$–187), 428, 427, 336, 327, 100 (base).

Infrared Absorption Spectrum (KBr), $v_{max}$ cm$^{-1}$: 3321, 1672, 1510, 1455, 1225, 1117.

Nuclear Magnetic Resonance Spectrum (CDCl$_3$, 270 MHz), δ ppm: 1.29 (9H, singlet); 1.83–2.84 (16H, multiplet); 3.42 (2H, singlet); 3.60–3.75 (6H, multiplet); 4.35–4.52 (5H, multiplet); 4.69–4.80 (1H, multiplet); 5.69 (1H, broad singlet); 6.24 (1H, broad singlet); 6.50–6.58 (1H, multiplet); 6.84–6.93 (2H, multiplet); 7.08–7.39 (7H, multiplet); 7.48–7.57 (3H, multiplet); 8.00 (1H, doublet, J=7.3 Hz).

EXAMPLE 62

1-[(2S,3S)-3-{N$^2$-[4-(4-Benzylpiperazin-1-yl)-acetamidophenoxy]acetyl-L-asparaginyl}amino-2-hydroxy-4-phenylbutyryl]-N-t-butyl-L-prolinamide Following a procedure similar to that described in Example 38, but using 100 mg (0.137 mmol) of 1-{(2S, 3S)-3-[N$^2$-(4-bromoacetamidophenoxy)acetyl-L-asparaginyl]amino-2-hydroxy-4-phenylbutyryl}-N-t-butyl-L-prolinamide and 1 ml of 1-benzylpiperazine, 60 mg of the title compound were obtained as a colorless powder, melting at 119°–127° C.

Elemental analysis: Calculated for C$_{44}$H$_{58}$N$_8$O$_8$.½H$_2$O (molecular weight: 853.98): C, 63.21%; H, 7.11%; N, 13.41%. Found: C, 63.36%; H, 7.11%; N, 13.32%.

Mass spectrum (m/z): 479 (M$^+$–347), 444, 427, 382, 364, 327, 325, 70 (base).

Infrared Absorption Spectrum (KBr), $v_{max}$ cm$^{-1}$: 3327, 1675, 1515, 1455, 1225.

Nuclear Magnetic Resonance Spectrum (CDCl$_3$, 270 MHz), δ ppm: 1.29 (9H, singlet); 1.83–2.31 (4H, multiplet); 2.45–2.79 (12H, multiplet); 3.12 (2H, singlet); 3.51–3.72 (4H, multiplet); 4.19–4.51 (5H, multiplet); 4.70–4.80 (1H, multiplet); 5.76)1H, broad singlet); 6.27 (1H, broad singlet); 6.58 (1H, singlet); 6.85–6.95 (2H, multiplet); 7.07–7.37 (11H, multiplet); 7.43–7.57 (3H, multiplet); 8.00 (1H, doublet, J=7.9 Hz).

EXAMPLE 63

1-{(2S,3S)-3-[N$^2$-{4-[N-(N-t-Butoxycarbonyl-L-prolyl)-N-methylamino]phenoxy}acetyl-L-asparaginyl]-amino-2-hydroxy-4-phenylbutyryl{-N-t-butyl-L-prolinamide Following a procedure similar to that described in Example 49, but using 300 mg (0.45 mmol) of 1-{(2S, 3S)-3-[N$^2$-(p-methylaminophenoxy)acetyl-L-asparaginyl]amino-2-hydroxy-4-phenylbutyryl}-N-t-butyl-L-prolinamide hydrochloride (prepared as described in Example 20) and 20 mg of 1-t-butoxycarbonyl-L-proline, 85 mg of the title compound were obtained as a colorless powder, melting at 116°–125° C.

Elemental analysis: Calculated for C$_{42}$H$_{59}$N$_7$O$_{10}$.3/2H$_2$O (molecular weight: 848.97): C, 59.42%; H, 7.18%; N, 11.55%. Found: C, 59.37%; H, 7.31%; N, 11.26%.

Mass spectrum (m/z): 607 (M$^+$–214), 541, 474, 429, 377, 327, 304, 70 (base).

Infrared Absorption Spectrum (KBr), $v_{max}$ cm$^{-1}$: 3335, 2975, 1675, 1510, 1454, 1395, 1367, 1247, 1228, 1164, 1123.

Nuclear Magnetic Resonance Spectrum (CDCl$_3$, 270 MHz), δ ppm: 1.30 (9H, singlet); 1.37–1.52 (9H, multiplet); 1.63–2.36 (8H, multiplet); 2.57–2.85 (4H, multiplet); 3.21–3.28 (3H, multiplet); 3.30–3.37 (5H, multiplet); 4.07–4.28 (1H, multiplet); 4.40–4.52 (5H, multiplet); 4.70–4.80 (1H, multiplet); 5.70–5.90 (1H, multiplet); 6.25–6.36 (1H, multiplet); 6.47–6.56 (1H, multiplet); 6.93–7.02 (2H, multiplet); 7.10–7.35 (6H, multiplet); 7.51–7.59 (1H, multiplet); 8.01–8.20 (1H, multiplet).

EXAMPLE 64

1-[(2S,3S)-3-{N²-[4-(N-Methyl-N-propylamino)
phenoxy]-acetyl-L-asparaginyl}amino-2-hydroxy-4-
phenylbutyryl]-N-t-butyl-L-prolinamide
hydrochloride 50 mg (0.06 mmol) of 1-{(2S,3S)-3-[N²-{4-[N-(N-t-butoxycarbonyl-L-prolyl)-N-methylamino]phenoxy}acetyl-L-asparaginyl]amino-2-hydroxy-4-phenylbutyryl{-N-t-butyl-L-prolinamide (prepared as described in Example 63) were treated with a 4N solution of hydrogen chloride in dioxane, to eliminate the t-butoxycarbonyl group and thus obtain 39 mg of the title compound as a colorless powder, melting at 150°–156° C.

Elemental analysis: Calculated for $C_{37}H_{51}N_7O_8 \cdot 3/2HCl \cdot 3/2H_2O$ (molecular weight: 803.56): C, 55.30%; H, 6.96%; N, 12.20%; Cl, 6.62%. Found: C, 55.16%; H, 6.74%; N, 11.74%; Cl, 6.31%.

EXAMPLE 65

(4S)-1-[(2S,3S)-3-(N²-t-Butoxycarbonyl-L-asparaginyl)amino-2-hydroxy-4-phenylbutyryl]-4-chloro-N-t-butyl-L-prolinamide 4.4 ml (31.4 mmol) of triethylamine were added, whilst ice-cooling, to a solution of 6.0 g (15.7 mmol) of (4S)-1-[(2S,3S)-3-amino-2-hydroxy-4-phenylbutyryl]-4-chloro-N-t-butyl-L-prolinamide [prepared as described in Preparation 21(b)] and 10.6 g (30.0 mmol) of the p-nitrophenyl ester of N²-t-butoxycarbonyl-L-asparagine in 50 ml of dimethylformamide, and the resulting mixture was stirred for 3 days. At the end of this time, the reaction mixture was freed from the solvent by distillation under reduced pressure, and the residue was diluted with methylene chloride. The diluted solution was washed with a 5% w/v aqueous solution of citric acid, with a 1N aqueous solution of sodium hydroxide and with a saturated aqueous solution of sodium chloride, in that order, after which it was concentrated by evaporation under reduced pressure. The residue thus obtained was purified by column chromatography, using a 1:30 by volume mixture of methanol and methylene chloride as the eluent, to give 7.6 g of the title compound as a colorless powder, melting at 126°–132° C.

Elemental analysis: Calculated for $C_{28}H_{42}N_5O_7 \cdot \frac{1}{2}H_2O$ (molecular weight: 605.12): C, 55.57%; H, 7.16%; N, 11.57%; Cl, 5.86%. Found: C, 55.77%; H, 6.93%; N, 11.72%; Cl, 6.03%.

EXAMPLE 66

(4S)-1-[(2S,3S)-3-(N-Benzyloxycarbonyl-L-methionyl)-amino-2-hydroxy-4-phenylbutyryl]-4-chloro-N-t-butyl-L-prolinamide 51 μl (0.31 mmol) of 93% diethyl cyanophosphate and 72 μl (0.52 mmol) of triethylamine were added, whilst ice-cooling, to a solution of 100 mg (0.26 mmol) of (4S)-1-[(2S,3S)-3-amino-2-hydroxy-4-phenylbutyryl]-4-chloro-N-t-butyl-L-prolinamide [prepared as described in Preparation 21(b)] and 74 m9 (0.26 mmol) of N-benzyl-oxycarbonyl-L-methionine in 2 ml of dimethylformamide, and the resulting mixture was stirred for 1 day. At the end of this time, the reaction mixture was concentrated by distillation under reduced pressure, and the concentrate was diluted with ethyl acetate. The diluted solution was washed with a 5% w/v aqueous solution of citric acid and a 5% w/v aqueous solution of sodium carbonate, in that order, after which it was dried over anhydrous sodium sulfate. The solvent was then removed by distillation under reduced pressure, and the residue was purified by preparative thin layer chromatography, using a 8:1 by volume mixture of methylene chloride and methanol as the developing solvent, to give 161 mg of the title compound as a colorless powder, melting at 81°–88° C.

Elemental analysis: Calculated for $C_{32}H_{43}N_4O_6ClS \cdot \frac{1}{2}H_2O$ (molecular weight: 656.23): C, 58.57%; H, 6.76%; N, 8.54%; Cl, 5.40%; S, 4.89%. Found: C, 58.34%; H, 6.59%; N, 8.42%; Cl, 5.35%; S, 4.75%.

Mass spectrum (m/z): 646, 610, 572, 510, 464, 415, 368, 340, 307, 91 (base).

Infrared Absorption Spectrum (KBr), $v_{max}$ cm$^{-1}$: 3320, 1656, 1531, 1455, 1229.

Nuclear Magnetic Resonance Spectrum (CD$_3$OD, 270 MHz), δ ppm: 1.27–1.37 (9H, multiplet); 1.67–1.88 (2H, multiplet); 1.98–2.04 (3H, multiplet); 2.07–2.15 (1H, multiplet); 2.28–2.44 (2H, multiplet); 2.68–2.99 (3H, multiplet); 3.76 (1H, doublet of doublets, J=7.4, 10.2 Hz); 4.09–4.42 (6H, multiplet); 5.04–5.13 (2H, multiplet); 7.11–7.40 (10H, multiplet).

EXAMPLE 67

1-[(2S,3S)-3-(N²-Quinoxalin-2-ylmethyl-L-asparaginyl)-amino-2-hydroxy-4-phenylbutyryl]-N-t-butyl-L-prolinamide 50 μl (0.36 mmol) of triethylamine and 27 mg (0.42 mmol) of sodium cyanoborohydride were added, whilst ice-cooling, to a solution of 300 mg (0.60 mmol) of 1-[3-(L-asparaginyl)amino-2-hydroxy-4-phenylbutyryl]-N-t-butyl-L-prolinamide hydrochloride and 115 mg (0.72 mmol) of 2-formylquinoxaline in 3 ml of methanol, and the resulting mixture was stirred at room temperature for 20 hours. The progress of reaction was then stopped by adding 0.60 ml of 1N aqueous hydrochloric acid, and the solvent was removed by distillation under reduced pressure. The resulting residue was extracted with ethyl acetate. The organic extract was then washed with a 5% w/v aqueous solution of sodium hydrogencarbonate and with a saturated aqueous solution of sodium chloride, in that order, after which it was dried over anhydrous sodium sulfate. The solvent was then removed by distillation under reduced pressure, and the residue was purified by preparative thin layer chromatography, using a 16:4:1 by volume mixture of chloroform, methanol and 33% v/v aqueous acetic acid as the developing solvent, to give 76 mg of the title compound as a yellow powder, melting at 116°–119° C.

Elemental analysis: Calculated for $C_{32}H_{41}N_7O_5 \cdot 1.25H_2O$ (molecular weight: 626.22): C, 61.37%; H, 7.00%; N, 15.66%. Found: C, 61.64%; H, 7.41%; N, 15.02%.

Mass spectrum (m/z): 590, 503, 429, 327, 228, 163, 133, 70.

Infrared Absorption Spectrum (KBr), $v_{max}$ cm$^{-1}$: 3338, 1668, 1513.

Nuclear Magnetic Resonance Spectrum (CDCl$_3$, 270 MHz), δ ppm: 1.29 (9H, singlet); 1.826–2.45 (6H, multiplet); 2.58–2.82 (2H, multiplet); 2.99–3.14 (1H, multiplet); 3.20–3.80 (7H, multiplet); 4.40–4.51 (3H, multiplet); 5.78 (1H, broad doublet, J=8.6 Hz); 6.22 (1H, broad doublet, J=8.6 Hz); 6.44–6.60 (5H, multiplet); 7.08–7.29 (5H, multiplet); 7.90 (1H, doublet, J=9.2 Hz).

EXAMPLE 68

1-[(26I S,3S)-3-(N²-Benzyloxycarbonyl-L-
asparaginyl)-amino-2-hydroxy-4-phenylbutyryl]-N-
t-butyl-L-azetidine-26-carboxamide Following a procedure similar to that described in Example 1, but using 443 mg (1.0 mmol) of (2S,3S)-3-(N²-benzyloxycarbonyl-L-asparaginyl)amino-2-hydroxy-4-phenylbutyric acid and 256 mg (1.0 mmol) of 1-t-butoxycarbonyl-N-t-butyl-L-azetidine-2-carboxamide, 150 mg of the title compound were obtained as a colorless powder, melting at 109°–110° C.

Elemental analysis: Calculated for $C_{30}H_{39}N_5O_7 \cdot H_2O$ (molecular weight: 599.69): C, 60.09%; H, 6.89%; N, 11.68%. Found: C, 60.34%; H, 6.73%; N, 11.91%.

Mass spectrum (m/z): 581 ($M^+$), 564, 549, 490, 465, 430, 374, 368, 316, 290, 242, 214, 157, 128, 108 (base peak).

Infrared Absorption Spectrum (KBr), $v_{max}$ cm$^{-1}$: 3305, 1668, 1540, 1498, 1455, 1394, 1367, 1323, 1263, 1228, 1122, 1053, 1029.

Nuclear Magnetic Resonance Spectrum (270 MHz, CD$_3$OD) δ ppm: 1.33, 1.36 (together 9H, each singlet); 2.06–2.35 (1H, multiplet); 2.40–2.50 (2H, multiplet); 2.55–2.65 (1H, multiplet); 2.75–2.97 (2H, multiplet); 3.80–4.05 (1H, multiplet); 4.10–4.19 (1H, multiplet); 4.24–4.33 (3H, multiplet); 4.42–4.46 (1H, multiplet); 5.07 (2H, singlet); 7.12–7.35 (10H, multiplet).

EXAMPLE 69 t-Butyl 1-{(2S,3S)-3-[N²-(2-quinolinecarbonyl)-L-
asparaginyl]amino-2-hydroxy-4-phenylbutyryl}-L-
pipecolinate 69(a) t-Butyl 1-[(2S,3S)-3-benzyloxycarbonylamino-2-hydroxy-4-phenylbutyryl]-L-pipecolinate 210 mg (1.2 mmol) of diethyl cyanophosphate and 223 mg (2.2 mmol) of triethylamine were added, whilst ice-cooling, to a solution of 329 mg (1.0 mmol) of (2S,3S)-3-benzyloxycarbonylamino-2-hydroxy-4-phenylbutyric acid and 222 mg (1.0 mmol) of t-butyl L-pipecolinate hydrochloride in 10 ml of dimethylformamide, and the resulting mixture was stirred for 3 hours. At the end of this time, it was worked-up in a similar manner to that described in Example 1, to give 230 mg of the title compound as a colorless syrup.

Mass spectrum (m/z): 497 ($M^+$).

69(b) t-Butyl 1-[(2S,3S)-3-(N²-benzyloxycarbonyl-L-asparaginyl)amino-2-hydroxy-4-phenylbutyryl-L-pipecolinate A solution of the whole (0.46 mmol) of the t-butyl 1-[(2S,3S)-3-benzyloxycarbonylamino-2-hydroxy-4-phenylbutyryl]-L-pipecolinate [prepared as described in step (a) above] dissolved in 10 ml of ethanol was agitated in an atmosphere of hydrogen and in the presence of 0.46 ml of 1N aqueous hydrochloric acid and 50 mg of 10% w/w palladium-on-charcoal. After 5 hours, the catalyst was filtered off and the filtrate was concentrated by evaporation under reduced pressure, to give t-butyl 1-[(2S,3S)-3-amino-2-hydroxy-4-phenylbutyryl]-L-pipecolinate. The whole of the compound thus obtained and 267 mg (0.69 mmol) of p-nitrophenyl N-benzyloxycarbonyl-L-asparaginate were dissolved in 5 ml of dimethylformamide. 50 mg (0.5 mmol) of triethylamine were then added, whilst ice-cooling, to the solution, and the resulting mixture was worked-up in a similar manner to that described in Example 15, to give 60 mg of the title compound as a colorless powder.

69 (c) t-Butyl 1-{(2S, 3S)-3-[N²-(2-quinoline-carbonyl)-L-asparaginyl)amino-2-hydroxy-4-phenyl-butyryl}-L-pipecolinate A solution of 50 mg (0.08 mmol) of t-butyl 1-[(2S,3S)-3-(N²-benzyloxycarbonyl-h-asparaginyl)amino-2-hydroxy-4-phenylbutyryl-L-pipecolinate [prepared as described in step (b) above] in 5 ml of methanol was agitated for 3 hours in an atmosphere of hydrogen and in the presence of 0.08 ml of 1N aqueous hydrochloric acid and 10 mg of 10% palladium-on-charcoal to eliminate the benzyloxycarbonyl group. At the end of this time, the catalyst was filtered off, and the filtrate was concentrated to dryness by evaporation under reduced pressure. The solid residue and 20 mg (0.12 mmol) of quinaldic acid were dissolved in 3 ml of dimethylformamide, and 20 mg (0.12 mmol) of diethyl cyanophosphate and 40 mg (0.40 mmol) of triethylamine were added, whilst ice-cooling, to the solution. The resulting mixture was then stirred for 3 hours, after which it was worked-up in a similar manner to that described in Example 14, to give 29 mg of the title compound as a colorless powder, melting at 86°–88° C.

Elemental analysis: Calculated for $C_{34}H_{41}N_5O_7 \cdot 3.5H_2O$ (molecular weight: 694.76): C, 58.77%; H, 6.966%; N, 10.08%. Found: C, 58.83%; H, 6.626%; N, 8.95%.

Nuclear Magnetic Resonance Spectrum (CDCl$_3$, 270 MHz), δ ppm: 1.31 1.51 (6H, multiplet); 1.6–1.87 (2H, multiplet); 2.70–3.07 (2H, multiplet); 4.10–4.29 (2H, multiplet); 4.30–4.60 (1H, multiplet); 4.9–5.1 (1H, multiplet); 5.3–5.47 (2H, multiplet); 6.26–6.46 (1H, multiplet); 6.93–7.21 (2H, multiplet); 7.27 (2H, singlet); 7.60–7.66 (1H, multiplet); 7.75–7.80 (1H, multiplet); 7.86–7.9 (1H, multiplet); 8.17–8.33 (2H, multiplet); 9.2–9.32 (1H, multiplet).

EXAMPLE 70

(4S)-1-{(2S,3S)-3-[2(S)-Benzyloxycarbonylamino-
4-sulfamoylbutyryl]amino-2-hydroxy-4-
phenylbutyryl}-4-chloro-N-t-butyl-L-prolinamide Following a procedure similar to that described in Example 66, but using 122 mg (0.32 mmol) of (4S)-1-[(2 S,3S)-3-amino-2-hydroxy-4-phenylbutyryl]-4-chloro-N-t-butyl-L-prolinamide [prepared as described in Preparation 21(b)] and 100 mg (0.32 mmol) of (S)-2-benzyloxycarbonylamino-4-sulfamoylbutyric acid, 169 mg of the title compound were obtained as a colorless powder, melting at 115°–122° C.

Elemental analysis: Calculated for $C_{31}H_{42}N_5O_8ClS \cdot \frac{1}{4}H_2O$ (molecular weight: 684.71): C, 54.37%; H, 6.26%; N, 10.23%; Cl, 5.18%; S, 4.68%. Found: C, 54.49%; H, 6.68%; N, 10.17%; Cl, 5.58%; S, 4.63%.

Mass spectrum (m/z): 643 ($M^+$–36), 544, 536, 472, 436, 435, 368, 340, 323, 91 (base).

Infrared Absorption Spectrum (KBr), $v_{max}$ cm$^{-1}$: 3337, 1668, 1531, 1455, 1393, 1366, 1331, 1229, 1151.

Nuclear Magnetic Resonance Spectrum (CD$_3$OD, 270 MHz), δ ppm: 1.32 (9H, singlet); 1.93–2.18 (3H, multiplet); 2.66–2.88 (2H, multiplet); 2.94–3.07 (3H, multiplet); 3.60–3.69 (1H, multiplet); 4.13–4.21 (1H, multiplet); 4.28–4.42 (5H, multiplet); 5.08 (2H, singlet); 7.116–7.39 (10H, multiplet).

EXAMPLE 71

(4S)-1-[(26S,3S)-3-(N-Benzyloxycarbonyl-L-seryl) amino-2-hydroxy-4-phenylbutyryl]-4-chloro-N-t-butyl-L-prolinamide Following a procedure similar to that described in Example 66, but using 100 mg (0.26 mmol) of (4S)-1-[(2S,3S)-3-amino-2-hydroxy-4-phenylbutyryl]-4-chloro-N-t-butyl-L-prolinamide [prepared as described in Preparation 21(b)] and 62 mg (0.26 mmol) of N-benzyloxycarbonyl-L-serine, 84 mg of the title compound were obtained as a colorless powder, melting at 98°–103° C.

Elemental analysis: Calculated for $C_{30}H_{39}N_4O_7 \cdot \frac{1}{3}H_2O$ (molecular weight: 609.11): C, 59.15%; H, 6.56%; N, 9.20%; Cl, 5.82%. Found: C, 59.20%; H, 6.44%; N, 9.23%; Cl, 6.21%.

Mass spectrum (m/z): 603 ($M^+$+1), 566, 503, 466, 458, 399, 371, 342, 341, 91 (base).

Infrared Absorption Spectrum (KBr), $v_{max}$ cm$^{-1}$: 3401, 3328, 1664, 1531, 1499, 1455, 1267, 1226.

Nuclear Magnetic Resonance Spectrum (CD$_3$OD, 270 MHz), δ ppm: 1.31 (9H, singlet); 2.02–2.17 (1H, multiplet); 2.67–2.85 (2H, multiplet); 2.94–3.02 (1H, multiplet); 3.56–3.80 (3H, multiplet); 4.08–4.15 (1H, multiplet); 4.32–4.45 (5H, multiplet); 5.08 (2H, singlet); 7.11–7.40 (10H, multiplet).

EXAMPLE 72

(4S)-1-[(26S,3S)-3-(N$^\alpha$-Benzyloxycarbonyl-L-3-carbamoyloxyalanyl)amino-2-hydroxy-4-phenylbutyryl]-4-chloro-N-t-butyl-L-prolinamide Following a procedure similar to that described in Example 66, but using 135 mg (0.35 mmol) of (4S)-1-[(2S,3S)-3-amino-2-hydroxy-4-phenylbutyryl]-4-chloro-N-t-butyl-L-prolinamide [prepared as described in Preparation 21(b)] and 100 mg (0.35 mmol) of N$^\alpha$-benzyloxycarbonyl-L-3-carbamoyloxyalanine, 20 mg of the title compound were obtained as a colorless powder, melting at 102°–108° C.

Elemental analysis: Calculated for $C_{31}H_{40}N_5O_8Cl \cdot H_2O$ (molecular weight: 664.14): C, 56.06%; H, 6.37%; N, 10.55%; Cl, 5.34%. Found: C, 56.00%; H, 6.20%; N, 10.55%; Cl, 5.70%.

Mass spectrum (m/z): 503 ($M^+$–142), 488, 451, 410, 406, 377, 330, 314, 91 (base).

Infrared Absorption Spectrum (KBr), $v_{max}$ cm$^{-1}$: 3329, 1721, 1667, 1529, 1499, 1455, 1394, 1366, 1335, 1266, 1227.

Nuclear Magnetic Resonance Spectrum (CD$_3$OD, 270 MHz), δ ppm: 1.31 (9H, singlet); 2.05–2.17 (1H, multiplet); 2.68–2.99 (3H, multiplet); 3.70–3.79 (1H, multiplet); 4.04–4.16 (2H, multiplet); 4.22–14 4.46 (6H, multiplet); 5.08 (2H, singlet); 7.11–14 7.42 (10H, multiplet).

EXAMPLE 73

1-[(26S,3S)-3-(N$^2$-Benzyloxycarbonyl-L-asparaginyl)-amino-2-hydroxy-4-phenylbutyryl]-4,4-difluoro-N-t-butyl-L-prolinamide Following a procedure similar to that described in Example 1, but using 222 mg (0.5 mmol) of (2S,3S)-3-(N$^2$-benzyloxycarbonyl-L-asparaginyl)amino-2-hydroxy-4-phenylbutyric acid and 153 mg (0.5 mmol) of N-t-butoxycarbonyl-4,4-difluoro-N-t-butyl-L-prolinamide,
24 mg of the title compound were obtained as a colorless powder, melting at 101°–103° C.

Elemental analysis: Calculated for $C_{31}H_{39}N_5O_7 \cdot \frac{1}{2}H_2O$ (molecular weight: 640.69): C, 58.126%; H, 6.29%; N, 10.93%; F, 5.93%. Found: C, 58.26%; H, 6.30%; N, 10.87%; F, 5.53%.

Mass spectrum (m/z): 632 ($M^+$+1), 614, 594, 540, 515, 497, 424, 398, 368, 351, 290, 264, 210, 165, 120, 91 (base peak).

Infrared Absorption Spectrum (KBr), $v_{max}$ cm$^{-1}$: 3328, 1668, 1531, 1531, 1455, 1395, 1368, 1257, 1227, 1149, 1101, 1047.

Nuclear Magnetic Resonance Spectrum (CD$_3$OD, 270 MHz), δ ppm: 1.32 (9H, singlet); 2.34–2.50 (2H, multiplet); 2.58–2.71 (2H, multiplet); 2.73–2.94 (2H, multiplet); 4.05–4.29 (3H, multiplet); 4.40–4.46 (2H, multiplet); 4.59 (1H, doublet of doublets, J=7.3 & 8.5 Hz); 5.08 (2H, singlet); 7.11–7.35 (10H, multiplet).

EXAMPLE 74

1-[(26S,3S)-3-(N$^2$-Benzyloxycarbonyl-L-asparaginyl)-amino-2-hydroxy-4-phenylbutyryl]-4,4-dimethoxy-N-t-butyl-L-prolinamide 10 ml of benzene were added to a solution of 2.1 g (7.43 mmol) of 1-t-butoxycarbonyl-4-oxo-N-t-butyl-L-prolinamide (prepared as described in Preparation 3) dissolved in a mixture of 20 ml of methanol and 10 ml of a 4N solution of hydrogen chloride in dioxane, and the mixture was concentrated by evaporation under reduced pressure. Addition of benzene and concentration of the mixture by evaporation under reduced pressure were repeated three times. In the course of these operations, elimination of the t-butoxycarbonyl group and ketalization of the oxo group proceeded simultaneously. A solution of the hydrochloride thus obtained and 3.29 g (7.43 mmol) of (2S,3S)-3-(N$^2$-benzyloxycarbonyl-L-asparaginyl)amino-2-hydroxy-4-phenylbutyric acid dissolved in 20 ml of dimethylformamide was cooled with ice. 1.49 g (8.27 mmol) of diethyl cyanophosphate were then added to the cooled solution, after which 2.25 g (22.28 mmol) of triethylamine were added dropwise, and the resulting mixture was stirred for 3 hours. At the end of this time, the reaction mixture was concentrated by distillation under reduced pressure. The concentrate was then mixed with a 10% w/v aqueous solution of citric acid and then extracted with ethyl acetate. The extract was washed with a 10% w/v aqueous solution of sodium hydrogencarbonate and with a saturated aqueous solution of sodium chloride, in that order, after which it was dried over anhydrous sodium sulfate. The solvent was removed by distillation under reduced pressure, and the residue was purified by preparative thin layer chromatography, using a 10:1 by volume mixture of methylene chloride and methanol as the developing solvent, to give 2.7 g of the title compound as a colorless powder, melting at 100°–105° C.

Elemental analysis: Calculated for $C_{33}H_{45}N_5O_9 \cdot \frac{1}{2}H_2O$ (molecular weight: 664.76): C, 59.63%; H, 6.97%; N, 10.54%. Found: C, 59.68%; H, 6.68%; N, 10.52%.

Mass spectrum (m/z): 623 ($M^+$–32), 606, 555, 532, 523, 515, 506, 448, 415, 398, 369, 288, 256, 199, 156, 108 (base peak).

Infrared Absorption Spectrum (KBr), $v_{max}$ cm$^{-1}$: 3328, 1668, 1534, 1455, 1393, 1366, 1322, 1228, 1129, 1089, 1051.

Nuclear Magnetic Resonance Spectrum (CD$_3$OD, 270 MHz), δ ppm: 1.31, 1.33 (together 9H, each singlet); 2.03

(1H, doublet of doublets, J=8.7 & 13.0 Hz); 2.41–2.49 (2H, multiplet); 2.54–2.64 (1H, multiplet); 2.76–2.88 (2H, multiplet); 3.25 (3H, singlet); 3.29 (3H, singlet); 3.66 (1H, doublet, J=11.1 Hz); 4.04 (1H, doublet, J=11.1 Hz); 4.24–4.31 (1H, multiplet); 4.36–4.46 (3H, multiplet); 5.08 (2H, singlet); 7.116–7.36 (10H, multiplet).

EXAMPLE 75

1-{(2S,3S)-3-[$N^2$-{4-[N-(4-Morpholinocarbonyl-1-piperazinylacetyl)-N-methylamino]phenoxy}acetyl-L-asparaginyl]amino-2-hydroxy-4-phenylbutyryl}-N-t-butyl-L-prolinamide Following a procedure similar to that described in Example 38, but using 12.3 mg (0.1 mmol) of 4-morpholinocarbonylpiperazine formate and 37.3 mg (0.05 mmol) of 1-[(2S,3S)-3-{$N^2$-[4-(N-bromoacetyl-N-methylamino)phenoxy]acetyl-L-asparaginyl}amino-2-hydroxy-4-phenylbutyryl]-N-t-butyl-L-prolinamide, 30 mg of the title compound were obtained as a colorless powder, melting at 126°–129° C.

Elemental analysis: Calculated for $C_{43}H_{61}N_9O_{10}$·3/2$H_2O$ (molecular weight: 891.04): C, 57.96%; H, 7.24%; N, 14.15%. Found: C, 57.85%; H, 7.08%; N, 13.95%.

Nuclear Magnetic Resonance Spectrum (hexadeuterated dimethyl sulfoxide, 270 MHz), δ ppm: 1.30–1.32 (9H, multiplet); 1.57–2.02 (6H, multiplet); 2.08–2.21 (2H, multiplet); 2.28–2.34 (2H, multiplet); 2.53–2.82 (6H, multiplet); 2.85–3.2 (2H, multiplet); 3.24–3.34 (6H, multiplet); 3.37–3.59 (3H, multiplet); 3.65–3.78 (6H, multiplet); 4.22–4.35 (2H, multiplet); 4.44–4.53 (5H, multiplet); 4.68–4.74 (2H, multiplet); 5.75–6.1 (1H, multiplet); 6.2–6.4 (1H, multiplet); 6.45–6.53 (2H, multiplet); 6.96 (2H, doublet, J=8.7 Hz); 7.14–7.29 (5H, multiplet); 7.43 (1H, doublet, J=8.2 Hz); 7.91–7.92 (1H, multiplet).

EXAMPLE 76

(4S)-1-[(26S,3S)-3-(2-Benzyloxycarbonylaminopropenoyl)amino-2-hydroxy-4-phenylbutyryl]-4-chloro-N-t-butyl-L-prolinamide Following a procedure similar to that described in Example 66, but using 120 mg (0.31 mmol) of (4S)-[1-(2 S,3S)-3-amino-2-hydroxy-4-phenylbutyryl]-4-chloro-N-t-butyl-L-prolinamide [prepared as described in Preparation 21(b)] and 80 mg (0.31 mmol) of 2-benzyloxycarbonylaminopropenoic acid, 49 mg of the title compound were obtained as a colorless powder, melting at 64°–69° C.

Elemental analysis: Calculated for $C_{30}H_{37}N_4O_6Cl$·2/3$H_2O$ (molecular weight: 597.10): C, 60.34%; H, 6.47%; N, 9.38%; Cl, 5.94%. Found: C, 60.25%; H, 6.49%; N, 9.68%; Cl, 5.98%.

EXAMPLE 77

(4S)-{(26S,3S)-3-[26(S)-Benzyloxycarbonylamino-4-methylsulfonylbutyryl]amino-2-hydroxy-4-phenyl-butyryl}-4-chloro-N-t-butyl-L-prolinamide 200 mg of 3-chloroperoxybenzoic acid were added to a solution of 100 mg (0.15 mmol) of (4S)-1-[(2S,3S)-3-(N-benzyloxycarbonyl-L-methionyl)amino-2-hydroxy-4-phenylbutyryl]-4-chloro-N-t-butyl-L-prolinamide (prepared as described in Example 66) in methylene chloride, and the resulting mixture was stirred for 22 hours. The reaction mixture was then washed with a 1N aqueous solution of sodium hydroxide and worked-up in the same manner as described in Example 66. The resulting crude product was purified by preparative thin layer chromatography, using a 8:1 by volume mixture of methylene chloride and methanol as the developing solvent, and triturated with hexane, to give 60 mg of the title compound as a colorless powder, melting at 99°–112° C.

Elemental analysis: Calculated for $C_{32}H_{43}N_4O_8Cl$ S·½$H_2O$ (molecular weight: 688.23): C, 55.84%; H, 6.53%; N, 8.25%; Cl, 5.22%; S, 4.56%. Found: C, 55.98%; H, 6.61%; N, 8.19%; Cl, 5.32%; S, 4.60%.

Mass spectrum (m/z): 580 ($M^+$–98), 544, 543, 476, 418, 404, 341, 340, 91 (base).

Infrared Absorption Spectrum (KBr), $v_{max}$ cm$^{-1}$: 3351, 1665, 1455, 1424, 1393, 1364, 1302, 1131.

Nuclear Magnetic Resonance Spectrum ($CD_3OD$, 270 MHz), δ ppm: 1.31 (9H, singlet); 1.91–2.14 (3H, multiplet); 2.66–3.10 (8H, multiplet); 3.69–3.79 (1H, multiplet); 4.11–4.44 (6H, multiplet); 5.08 (2H, singlet); 7.10–7.40 (10H, multiplet).

EXAMPLE 78

(4S)-1-{(26S,3S)-3-[$N^2$-(1-Methylindazol-3-yl-carbonyl)-L-asparaginyl]amino-2-hydroxy-4-phenylbutyryl}-4-chloro-N-t-butyl-L-prolinamide Following a procedure similar to that described in Example 16, but using 170 mg (0.28 mmol) of (4S)-1-[(2 S,3S)-3-($N^{26}$-t-butoxycarbonyl-L-asparaginyl)amino-2-hydroxy-4-phenylbutyryl]-4-chloro-N-t-butyl-L-prolinamide (prepared as described in Example 65) and 50 mg (0.28 mmol) of 1-methylindazole-3-carboxylic acid, 125 mg of the title compound were obtained as a colorless powder, melting at 129°–134° C.

Elemental analysis: Calculated for $C_{32}H_{40}N_7O_6Cl$·2/3$H_2O$ (molecular weight: 666.16): C, 57.69%; H, 6.25%; N, 14.72%; Cl, 5.32%. Found: C, 57.79%; H, 6.69%; N, 14.71%; Cl, 5.38%.

Mass spectrum (m/z): 653 ($M^+$), 619, 602, 564, 519, 502, 483, 406, 376, 375, 159, (base).

Infrared Absorption Spectrum (KBr), $v_{max}$ cm$^{-1}$: 3343, 1660, 1527, 1487, 1433, 1395, 1365.

Nuclear Magnetic Resonance Spectrum ($CD_3OD$, 270 MHz), δ ppm: 1.21–1.33 (9H, multiplet); 2.02–2.18 (1H, multiplet); 2.63–2.95 (5H, multiplet); 3.68–3.80 (1H, multiplet); 4.14 (3H, singlet); 4.30–4.46 (5H, multiplet); 4.84–4.95 (1H, multiplet); 6.90–7.07 (3H, multiplet); 7.11–7.35 (3H, multiplet); 7.41–7.65 (2H, multiplet); 8.18–8.28 (1H, multiplet).

EXAMPLE 79

(4S)-1-{(26S,3S)-3-[$N^2$-(5-Methoxy-2-indolylcarbonyl)L-asparaginyl]amino-2-hydroxy-4-phenylbutyryl}-4-chloro-N-t-butyl-L-prolinamide Following a procedure similar to that described in Example 16, but using 150 mg (0.26 mmol) of (4S)-1-[(2S,3S)-3-($N^{26}$-t-butoxycarbonyl-L-asparaginyl)amino-2-hydroxy-4-phenylbutyryl]-4-chloro-[-t-butyl-L-prolinamide (prepared as described in Example 65) and 50 mg (0.26 mmol) of 5-methoxyindole-2-carboxylic acid, 117 mg of the title compound were obtained as a colorless powder, melting at 144°–151° C.

Elemental analysis: Calculated for $C_{33}H_{41}N_6O_7Cl\cdot\frac{1}{2}H_2O$ (molecular weight: 678.17): C, 58.44%; H, 6.24%; N, 12.39%; Cl, 5.23%. Found: C, 58.27%; H, 6.11%; N, 12.15%; Cl, 5.32%.

Mass spectrum (m/z): 653 ($M^+15$), 422, 421, 346, 104 (base).

Infrared Absorption Spectrum (KBr), $v_{max}$ cm$^{-1}$: 3338, 1655, 1531, 1452, 1433.

Nuclear Magnetic Resonance Spectrum (CD$_3$OD, 270 MHz), δ ppm: 1.25–1.38 (9H, multiplet); 2.04–2.17 (1H, multiplet); 2.52–2.94 (5H, multiplet); 3.69–3.84 (4H, multiplet); 4.29–4.46 (5H, multiplet); 4.84–4.95 (1H, multiplet); 6.89–7.27 (8H, multiplet); 7.32–7.39 (1H, multiplet).

EXAMPLE 80

(4S)-1-{(2S,3S)-3-[N$^2$-(Isobenzoxazolyl-3-carbonyl)-L-asparaginyl]amino-2-hydroxy-4-phenylbutyryl}-4-chloro-N-t-butyl-L-prolinamide Following a procedure similar to that described in Example 16, but using 180 mg (0.3 mmol) of (4S)-1-[(2S,3S)-3-(N$^2$-t-butoxycarbonyl-L-asparaginyl)amino-2-hydroxy-4-phenylbutyryl]-4-chloro-N-t-butyl-L-prolinamide (prepared as described in Example 65) and 50 mg (0.3 mmol) of isobenzoxazole-3-carboxylic acid, 30 mg of the title compound were obtained as a colorless powder, melting at 118°–127° C.

Elemental analysis: Calculated for $C_{31}H_{37}N_6O_7Cl\cdot H_2O$ (molecular weight: 659.13): C, 56.49%; H, 5.96%; N, 12.75%; Cl, 5.38%. Found: C, 56.37%; H, 5.80%; N, 12.75%; Cl, 5.82%.

Mass spectrum (m/z): 625 ($M^+-15$), 589, 588, 524, 488, 487, 104 (base).

Infrared Absorption Spectrum (KBr), $v_{max}$ cm$^{-1}$: 3340, 1665, 1530, 1498, 1430, 1393, 1366, 1224.

Nuclear Magnetic Resonance Spectrum (CD$_3$OD, 270 MHz), δ ppm: 1.25–1.34 (9H, multiplet); 2.05–2.15 (1H, multiplet); 2.65–2.99 (5H, multiplet); 3.70–3.80 (1H, multiplet); 4.31–4.46 (5H, multiplet); 4.85–4.96 (1H, multiplet); 6.91–7.33 (5H, multiplet); 7.45–7.52 (1H, multiplet); 7.68 7.78 (2H, multiplet); 8.17–8.23 (1H, multiplet).

EXAMPLE 81

(4S)-1-(2S,3S)-3-[N$^2$-(1-Methyl-3-indolylcarbonyl)-L-asparaginyl)amino-2-hydroxy-4-phenylbutyryl}-4-chloro-N-t-butyl-L-prolinamide Following a procedure similar to that described in Example 16, but using 180 mg (0.29 mmol) of (4S)-1-[(2S,3S)-3-(N$^2$-t-butoxycarbonyl-L-asparaginyl)amino-2-hydroxy-4-phenylbutyryl]-4-chloro-N-t-butyl-L-prolinamide (prepared as described in Example 65) and 50 mg (0.29 mmol) of 1-methylindole-3-carboxylic acid, 44 mg of the title compound were obtained as a colorless powder, melting at 129°–137° C.

Elemental analysis: Calculated for $C_{33}H_{41}N_6O_6Cl\cdot\frac{2}{3}H_2O$ (molecular weight: 665.17): C, 59.58%; H, 6.42%; N, 12.64%; Cl, 5.33%. Found: C, 59.43%; H, 6.26%; N, 12.45%; Cl, 5.36%.

Mass spectrum (m/z): 637 ($M^+-15$), 518, 500, 481, 410, 362, 158 (base).

Infrared Absorption Spectrum (KBr) $v_{max}$ cm$^{-1}$: 3343, 1660, 1536, 1468, 1432, 1393, 1376, 1367.

Nuclear Magnetic Resonance Spectrum (CD$_3$OD, 270 MHz), δ ppm: 1.29 (9H, singlet); 2.04–2.18 (1H, multiplet); 2.57–2.97 (5H, multiplet); 3.68–3.89 (4H, multiplet); 4.18–4.46 (5H, multiplet); 4.83–4.94 (1H, multiplet); 6.89–7.02 (3H, multiplet); 7.10–7.30 (4H, multiplet); 7.35–7.49 (1H, multiplet); 7.72–7.80 (1H, multiplet); 8.05–8.13 (1H, multiplet).

EXAMPLE 82

(4S)-1-{(2S,3S)-3-(N$^2$-(7-Methoxy-2-benzofurancarbonyl)-L-asparaginyl]amino-2-hydroxy-4-phenylbutyryl}-4-chloro-N-t-butyl-L-prolinamide Following a procedure similar to that described in Example 16, but using 155 mg (0.26 mmol) of (4S)-1-[(2S,3S)-3-(N$^2$-t-butoxycarbonyl-L-asparaginyl)amino-2-hydroxy-4-phenylbutyryl]-4-chloro-N-t-butyl-L-prolinamide (prepared as described in Example 65) and 50 mg (0.26 mmol) of 7-methoxy-2-benzofurancarboxylic acid, 114 mg of the title compound were obtained as a colorless powder, melting at 125°–136° C.

Elemental analysis: Calculated for $C_{33}H_{40}N_5O_8Cl\cdot\frac{1}{2}H_2O$ (molecular weight: 679.166): C, 58.37%; H, 6.09%; N, 10.31%; Cl, 5.226%. Found: C, 58.59%; H, 6.116%; N, 10.09%; Cl, 5.14%.

Mass spectrum (m/z): 619 ($M^+-50$), 582, 518, 517, 450, 422, 393, 392, 175 (base).

Infrared Absorption Spectrum (KBr), $v_{max}$ cm$^{-1}$: 339, 1656, 1589, 1492, 1428, 1274, 1207.

Nuclear Magnetic Resonance Spectrum (CD$_3$OD, 270 MHz) δ ppm: 1.29 (7H, singlet); 1.35 (2H, singlet); 2.05–2.18 (1H, multiplet); 2.60–2.96 (5H, multiplet); 3.70–3.80 (1H, multiplet); 4.00 (3H, singlet); 4.31–4.44 (5H, multiplet); 4.85–4.94 (1H, multiplet); 6.91–7.30 (8H, multiplet); 7.46–7.51 (1H, multiplet).

EXAMPLE 83

(4S)-1-{(2S,3S)-3-[N$^2$-(5-Fluoro-2-indolylcarbonyl)-L-asparaginyl]amino-2-hydroxy-4-phenylbutyryl}-4-chloro-N-t-butyl-L-prolinamide Following a procedure similar to that described in Example 16, but using 29 mg (0.16 mmol) of 5-fluoroindole-2-carboxylic acid and 85 mg (0.16 mmol) of (4S)-1-[(2S,3S)-3-(L-asparaginyl)amino-2-hydroxy-4-phenylbutyryl-4-chloro-N-t-butyl-L-prolinamide hydrochloride, 73 mg of the title compound were obtained as a colorless powder, melting at 141°–143° C.

Elemental analysis: Calculated for $C_{32}H_{39}N_6O_6ClF\cdot H_2O$ (molecular weight: 676.17): C, 56.86%; H, 6.11%; N, 12.43%; Cl, 5.24%; F, 2.81%. Found: C, 57.08%; H, 6.04%; N, 12.27%; Cl, 5.28%; F, 2.66%.

Nuclear Magnetic Resonance Spectrum (CD$_3$OD, 270 MHz), δ ppm: 1.08 (9H, singlet); 1.9–1.97 (1H, multiplet); 2.42–2.50 (1H, multiplet); 2.51–2.75 (5H, multiplet); 3.56, 3.58 (1H, doublet of doublets, J=8.4 & 10.5 Hz); 4.07–4.11 (1H, multiplet); 4.26–4.39 (3H, multiplet); 4.46–4.53 (1H, multiplet); 4.79–4.84 (1H, multiplet); 5.05 (1H, doublet, J=9.1 Hz).; 6.88 (1H, broad singlet); 6.96–7.06 (3H, multiplet); 7.03–7.09 (2H, multiplet); 7.13–7.16 (1H, multiplet); 7.28–7.3 (3H, multiplet); 7.41–7.47 (2H, multiplet); 7.56 (1H, singlet); 7.93 (1H, doublet, J=8.7 Hz); 8.56 (1H, doublet, J=8.1 Hz).

EXAMPLE 84

(4S)-1-{(2S,3S)-3-[N²-(6-Nitro-2-quinoxalinecarbonyl)-L-asparaginyl]amino-2-hydroxy-4-phenylbutyryl}-4-chloro-N-t-butyl-L-prolinamide Following a procedure similar to that described in Example 14, but using 490 mg (0.92 mmol) of 1-[3-(L-asparaginyl)amino-2-hydroxy-4-phenylbutyryl]-4-chloro-N-t-butyl-L-prolinamide hydrochloride and 220 mg (1.01 mmol) of 6-nitroquinoxaline-2-carboxylic acid (prepared as described in Preparation 22), 190 mg of the title compound were obtained as a pale yellow powder, melting at 153°–156° C.

Elemental analysis: Calculated for $C_{32}H_{37}N_8O_8Cl.1.25H_2O$ (molecular weight: 719.66):

C, 53.40%; H, 5.53%; N, 15.57%; Cl, 4.93%. Found: C, 53.66%; H, 5.47%; N, 15.24%; Cl, 6.28%.

Mass spectrum (m/z): 679 ($M^+-17$), 660, 643, 613, 580, 544, 449, 418, 315, 288, 253, 203, 175, 104, 58.

Infrared Absorption Spectrum (KBr), $v_{max}$ cm$^{-1}$: 351, 1671, 1537.

Nuclear Magnetic Resonance Spectrum (CDCl$_3$, 270 MHz), δ ppm: 1.29 (9H, singlet); 2.52–2.95 (6H, multiplet); 3.74–3.82 (1H, multiplet); 4.21–4.37 (2H, multiplet); 4.40–4.57 (3H, multiplet); 4.93–5.01 (1H, multiplet); 6.22 (1H, broad singlet); 6.33–6.48 (2H, multiplet); 6.88–7.28 (6H, multiplet); 7.70 (1H, doublet, J=7.9 Hz); 8.28–8.34 (1H, multiplet); 8.57–8.64 (1H, multiplet); 9.05–9.11 (1H, multiplet); 9.68–9.72 (1H, multiplet).

EXAMPLE 85

(4S)-1-{(2S,3S)-3- [N²-(6-Amino-2-quinoxalinecarbonyl)-L-asparaginyl]amino-2-hydroxy-4-phenylbutyryl}-4-chloro-N-t-butyl-L-prolinamide acetate Following a procedure similar to that described in Example 17, 130 mg (0.19 mmol) of (4S)-1-{(2S,3S)-3-[N²-(6-nitro-2-quinoxalinecarbonyl)-L-asparaginyl]amino-2-hydroxy-4-phenylbutyryl}-4-chloro-N-t-butyl-L-prolinamide (prepared as described in Example 84) were reduced, and the product was then purified by preparative thin layer chromatography, using a 16:4:1 by volume mixture of chloroform, methanol and 32% v/v aqueous acetic acid as the developing solvent, to give 36 mg of the title compound as a yellow powder, melting at 171°–174° C.

Elemental analysis: Calculated for $C_{32}H_{39}N_8O_6Cl.C_2H_4O_2.0.75H_2O$ (molecular weight: 740.72): C, 55.13%; H, 6.06%; N, 15.13%; Cl, 4.79%. Found: C, 55.05%; H, 5.81%; N, 15.41%; Cl, 5.38%.

Mass spectrum (m/z): 649 ($M^+-18$), 603, 577, 551, 523, 509,423, 393, 368, 313, 285, 236, 211, 109, 70, 57.

Infrared Absorption Spectrum (KBr), $v_{max}$ cm$^{-1}$: 351, 1669, 1522, 1493.

Nuclear Magnetic Resonance Spectrum (CD$_3$OD, 270 MHz), δ ppm: 1.28 (9H, singlet); 1.96 (3H, singlet); 2.01–2.18 (1H, multiplet); 2.65–2.97 (5H, multiplet); 3.70–3.78 (1H, multiplet); 4.31–4.47 (5H, multiplet); 4.82–4.92 (1H, multiplet); 6.86–7.46 (7H, multiplet); 7.83 (1H, doublet, J=9.2 Hz); 9.14 (1H, singlet).

EXAMPLE 86

1-[(2S,3S)-3-(N²-Benzyl-L-asparaginyl)amino-2-hydroxy-4-phenylbutyryl]-N-t-butyl-L-prolinamide Following a procedure similar to that described in Example 67, but using 500 mg (1.01 mmol) of 1-[3-(L-asparaginyl)amino-2-hydroxy-4-phenylbutyryl]-N-t-butyl-L-prolinamide hydrochloride and 123 μl (1.21 mmol) of benzaldehyde, 510 mg of the title compound were obtained as a colorless powder, melting at 96°–99° C.

Elemental analysis: Calculated for $C_{30}H_{40}N_5O_5.0.5H_2O$ (molecular weight: 559.67): C, 64.38%; H, 7.38%; N, 12.51%. Found: C, 64.52%; H, 7.71%; N, 12.08%.

EXAMPLE 87

1-[(2S,3S)-3-(N²-Benzyl-N²-methyl-L-asparaginyl)amino-2-hydroxy-4-phenylbutyryl]-N-t-butyl-L-prolinamide Following a procedure similar to that described in Example 67, but using 200 mg (0.36 mmol) of 1-[(2S,3S)-3-(N²-Benzyl-L-asparaginyl)amino-2-hydroxy-4-phenylbutyryl]-N-t-butyl-L-prolinamide (prepared as described in Example 86) and 41 μl (0.54 mmol) of 37% formalin, 149 mg of the title compound were obtained as a colorless powder, melting at 97°–100° C.

Elemental analysis: Calculated for $C_{31}H_{42}N_5O_5.0.25H_2O$ (molecular weight: 569.19):

C, 65.41%; H, 7.53%; N, 12.31%. Found: C, 65.27%; H, 7.48%; N, 12.21%.

EXAMPLE 88

1-[(2S,3S)-3-(N²-Benzyloxycarbonyl-N²-methyl-L-asparaginyl)amino-2-hydroxy-4-phenylbutyryl]-N-t-butyl-L-prolinamide Following a procedure similar to that described in Example 17, 120 mg (0.21 mmol) of 1-[(2S,3S)-3-(N²-benzyl-N²-methyl-L-asparaginyl)amino-2-hydroxy-4-phenylbutyryl]-N-t-butyl-L-prolinamide (prepared as described in Example 87) were subjected to debenzylation, to give 104 mg of 1-[(2S,3S)-3-(N²-methyl-L-asparaginyl)amino-2-hydroxy-4-phenylbutyryl-N-t-butyl-L-prolinamide hydrochloride. A procedure similar to that described in Example 30 was then repeated, except that 51 mg (0.10 mmol) of this hydrochloride and 16 μl (0.11 mmol) of benzyloxycarbonyl chloride were used as starting materials, to obtain 50 mg of the title compound as a colorless powder, melting at 100°–103° C.

Elemental analysis: Calculated for $C_{32}H_{42}N_5O_7.0.5H_2O$ (molecular weight: 617.73): C, 62.21%; H, 7.02%; N, 11.34%. Found: C, 62.07%; H, 6.94%; N, 11.44%.

Mass spectrum (m/z): 610 ($M^++1$), 593, 502, 429, 401, 384, 304, 228, 171, 129, 91, 70.

Infrared Absorption Spectrum (KBr), $v_{max}$ cm$^{-1}$: 3340, 1675, 1536.

Nuclear Magnetic Resonance Spectrum (CDCl$_3$, 270 MHz), δ ppm: 1.28 (9H, singlet); 1.85–2.04 (2H, multiplet); 2.10–2.45 (5H, multiplet); 2.50–2.92 (4H, multiplet); 3.61–3.80 (2H, multiplet); 4.32–4.55 (3H, multiplet); 4.94–5.18 (3H, multiplet); 5.45–5.60 (1H, multiplet); 5.95–6.05 (1H, multiplet); 6.36–6.50 (1H, multiplet); 6.75–6.84 (1H, multiplet); 6.95–7.45 (10H, multiplet).

EXAMPLE 89

1-{(2S,3S)-3-[N²-(4-Benzyloxycarbonylaminophenoxy)-acetyl-N²-N²-methyl-L-asparaginyl]amino-2-hydroxy-4-phenylbutyryl}-N-t-butyl-L-prolinamide Following a procedure similar to that described in Example 16, but using 45 mg (0.088 mmol) of 1-[(2S,3S)-3-(N²-methyl-L-asparaginyl)amino-2-hydroxy-4-phenylbutyryl]-N-t-butyl-L-prolinamide hydrochloride (prepared as described in Example 88) and 29 mg (0.097 mmol) of 4-benzyloxycarbonylaminophenoxyacetic acid, 54 mg of the title compound were obtained as a colorless powder, melting at 119°–121° C.

Elemental analysis: Calculated for $C_{40}H_{49}N_6O_9 \cdot 2H_2O$ (molecular weight: 7 93.81): C, 60.51%; H, 6.73%; N, 11.59%. Found: C, 60.54%; H, 6.46%; N, 10.49%.

EXAMPLE 90

1-[(2S,3S)-3-(N²-Benzyloxycarbonyl-L-asparaginyl)amino-2-hydroxy-4-phenylbutyryl]-N-(1,1-dimethyl-2-hydroxypropyl)-L-prolinamide 79 mg (0.24 mmol) of N-benzyloxycarbonyl-N-(1,1-dimethyl-2-hydroxypropyl)-L-prolinamide were subjected to debenzyloxycarbonylation in a similar manner to that described in Example 17, and then the resulting product was condensed with 106 mg (0.24 mmol) of (2S,3S)-3-(N²-benzyloxycarbonyl-L-asparaginyl)amino-2-hydroxy-4-phenylbutyric acid in a similar manner to that described in Example 1, to give 98 mg of the title compound as a colorless powder, melting at 102°–104° C.

Elemental analysis: Calculated for $C_{32}H_{43}N_5O_8 \cdot 0.75H_2O$ (molecular weight: 639.22): C, 60.12%; H, 7.02%; N, 10.96%. Found: C, 60.17%; H, 6.91%; N, 10.90%.

EXAMPLE 91

(4S)-1-[(2S,3S)-3-{N²-[2(S)-Benzyloxycarbonylamino-3-(tetrahydrofuran-2-yloxy)propanoyl]-L-asparaginyl}amino-2-hydroxy-4-phenylbutyryl]-4-chloro-N-t-butyl-L-prolinamide Following a procedure similar to that described in Example 16, but using 100 mg (0.26 mmol) of (4S)-1-[2S,3S)-3-(N²-t-butoxycarbonyl-L-asparaginyl)amino-2-hydroxy-4-phenylbutyryl]-4-chloro-N-t-butyl-L-prolinamide (prepared as described in Example 65) and 2-benzyloxycarbonylamino-3-(tetrahydrofuran-2-yloxy)propionic acid, 83 mg of the title compound were obtained as a colorless powder, melting at 64°–71° C.

Elemental analysis: Calculated for $C_{34}H_{45}N_4O_8Cl \cdot \frac{1}{2}H_2O$ (molecular weight: 682.20): C, 59.86%; H, 6.80%; N, 8.21%; Cl, 5.20%. Found: C, 59.86%; H, 6.75%; N, 7.69%; Cl, 4.89%.

EXAMPLE 92

(4S)-1-{(2S,3S)-3-[2(S)-Benzyloxycarbonylamino-4-methanesulfonylbutanoyl]amino-2-hydroxy-4-phenylbutyryl}-4-chloro-N-t-butyl-L-prolinamide 4 ml of a 1:1 by volume mixture of methanol and a by volume aqueous solution of hydrogen peroxide were added to 80 mg (0.12 mmol) of (4S)-1-[(2S,3S)-3-(N-benzyloxycarbonyl-L-methionyl)amino-2-hydroxy-4-phenylbutyryl]-4-chloro-N-t-butyl-L-prolinamide (prepared as described in Example 66), and the resulting mixture was stirred for 30 minutes. At the end of this time, the reaction mixture was concentrated by distillation under reduced pressure, and the concentrate was extracted with methylene chloride. The extract was dried over anhydrous sodium sulfate, and the solvent was removed by distillation under reduced pressure, to give 70 mg of the title compound as a colorless powder, melting at 99°–103° C.

Elemental analysis: Calculated for $C_{32}H_{43}N_4O_7ClS \cdot \frac{1}{2}H_2O$ (molecular weight: 672.23): C, 57.17%; H, 6.60%; N, 8.34%; Cl, 5.27%; S, 4.77%. Found: C, 57.13%; H, 6.48%; N, 8.30%; Cl, 5.28%; S, 4.75%.

EXAMPLE 93

(4S)-1-[(2S,3S)-3-(2-Benzyloxycarbonylamino-3-dimethylphosphonobutanoyl)amino-2-hydroxy-4-phenylbutyryl]-4-chloro-N-t-butyl-L-prolinamide Following a procedure similar to that described in Example 66, but using 115 mg (0.3 mmol) of (4S)-1-[(2S,3S)-3-amino-2-hydroxy-4-phenylbutyryl]-4-chloro-N-t-butyl-L-prolinamide [prepared as described in Preparation 21(b)] and 100 mg of 2-benzyloxycarbonylamino-3-dimethylphosphonobutyric acid, and then purifying the product by preparative thin layer chromatography, using a 8:1 by volume mixture of methylene chloride and methanol as the developing solvent, 52 mg of the title compound were obtained as a colorless powder from the upper fraction, melting at 93°–100° C.

Elemental analysis: Calculated for $C_{32}H_{44}N_4O_9ClP \cdot \frac{1}{2}H_2O$ (molecular weight: 704.14): C, 54.58%; H, 6.44%; N, 7.96%; Cl, 5.04%; P, 4.40%. Found: C, 54.50%; H, 6.33%; N, 7.97%; Cl, 5.33%; P, 4.37%.

Mass spectrum (m/z): 677 (M⁺–17), 642, 585, 540, 487, 450, 433, 383, 91 (base).

Infrared Absorption Spectrum (KBr), $v_{max}$ cm⁻¹: 319, 1722, 1675, 1534, 1499, 1455, 1393, 1366, 1329, 1251, 1230.

Nuclear Magnetic Resonance Spectrum (CD₃OD, 270 MHz), δ ppm: 1.32 (9H, singlet); 1.91–2.19 (3H, multiplet); 2.65–2.81 (2H, multiplet); 2.90–3.00 (1H, multiplet); 3.56–3.68 (6H, multiplet); 3.69–3.80 (1H, multiplet); 4.26–4.46 (6H, multiplet); 5.02–5.19 (2H, multiplet); 7.12–7.41 (10H, multiplet).

EXAMPLE 94

(4S)-[(2S,3S)-3-(2-Benzyloxycarbonylamino-3-dimethylphosphonobutanoyl)amino-2-hydroxy-4-phenylbutyryl]-4-chloro-N-t-butyl-L-prolinamide 57 mg of the title compound were recovered as a colorless powder, melting at 90°–95° C, from the lower fraction of the preparative thin layer chromatography carried out as described in Example 93.

Elemental analysis: Calculated for $C_{32}H_{44}N_4O_9ClP \cdot \frac{1}{2}H_2O$ (molecular weight: 704.14): C, 54.58%; H, 6.44%; N, 7.96%; Cl, 5.04%; P, 4.40%. Found: C, 54.40%; H, 6.22%; N, 8.00%; Cl, 5.16%; P, 4.24%.

Mass spectrum (m/z): 699 (M⁺+1), 678, 677, 586, 541, 540, 451, 434, 384, 383, 356, 326, 104 (base).

Infrared Absorption Spectrum (KBr), $v_{max}$ cm⁻¹: 3323, 1721, 1668, 1534, 1499, 1455, 1428, 1394, 1366, 1329, 1252, 1229.

Nuclear Magnetic Resonance Spectrum (CD$_3$OD, 270 MHz), δ ppm: 1.31 (9H, singlet); 1.93–2.17 (2H, multiplet); 2.20–2.38 (1H, multiplet); 2.67–3.00 (3H, multiplet); 3.58–3.78 (7H, multiplet); 4.22–4.46 (6H, multiplet); 5.01–5.18 (2H, multiplet); 7.10–7.40 (10H, multiplet).

PREPARATION 1

(2S,3S)-3-(N$^2$-Benzyloxycarbonyl-L-asparaginyl) amino-2-hydroxy-4-phenylbutyric acid 2.26 g of the p-nitrophenyl ester of benzyloxycarbonyl-L-asparagine and 1.89 ml (13.6 mmol) of triethylamine were added, whilst ice-cooling, to a solution of 900 mg (3.9 mmol) of (2S,3S)-3-amino-2-hydroxy-4-phenylbutyric acid hydrochloride in 15 ml of dimethylformamide, and the mixture was stirred at 4° C. for 2 days. At the end of this time, the solvent was removed by distillation under reduced pressure, and the resulting residue was mixed with 1N aqueous hydrochloric acid to cause crystallization. The crystals were collected by filtration and washed first with water and then with ethyl acetate, to give 1.52 g of the title compound as colorless crystals, melting at 225°–227° C.

Elemental analysis: Calculated for C$_{22}$H$_{25}$N$_3$O$_7$.H$_2$O (molecular weight: 461.5):

C, 57.26%; H, 5.90%; N, 9.11%. Found: C, 57.33%; H, 5.61%; N, 9.18%.

PREPARATION 2

(4S)-1-t-Butoxycarbonyl-4-chloro-N-t-butyl-L-prolinamide

A mixture of 1.0 g (3.50 mmol) of (4R)-10t-butoxy-carbonyl-4-hydroxy-N-t-butyl-L-prolinamide (prepared as described in Preparation 5), 30 ml of carbon tetrachloride and 1.56 g (5.95 mmol) of triphenylphosphine was heated under reflux for 2 hours. At the end of this time, insoluble materials were filtered off and then washed with a large quantity of diethyl ether. The combined washings and filtrate was concentrated by evaporation under reduced pressure, and the resulting residue was purified by column chromatography through silica gel, using a 1:4 by volume mixture of ethyl acetate and hexane as the eluent. The resulting crude product was recrystallized from a mixture of methylene chloride and hexane, to give 950 mg of the title compound as colorless crystals, melting at 149°–150° C.

Elemental analysis: Calculated for C$_{14}$H$_{25}$N$_2$O$_3$Cl (molecular weight: 304.82): C, 55.17%; H, 8.27%; N, 9.19%; Cl, 11.63%. Found: C, 55.31%; H, 8.30%; N, 8.97%; Cl, 11.64%.

PREPARATION 3

1-t-Butoxycarbonyl-4-oxo-N-t-butyl-L-prolinamide

A solution of 1.21 g (15.51 mmol) of dimethyl sulfoxide in 5 ml of methylene chloride was added to a solution of 0.98 g (7.72 mmol) of oxalyl chloride in 20 ml of methylene chloride at −50° to −60° C. After 5 minutes, a solution of 2.0 g (7.00 mmol) of (4R)-1-t-butoxycarbonyl-4-hydroxy-N-t-butyl-L-prolinamide (prepared as described in Preparation 5) in 40 ml of methylene chloride was added to the resulting mixture. The mixture was stirred for 15 minutes, after which 3.5 g (35.00 mmol) of triethylamine were added, and the mixture was stirred for a further 5 minutes. The temperature of the reaction mixture was then allowed to rise to room temperature, and the mixture was stirred for a further 1 hour. At the end of this time, the reaction mixture was poured into ice-water and extracted with methylene chloride. The organic extract was washed with a 10% w/v aqueous solution of sodium hydrogencarbonate and with a saturated aqueous solution of sodium chloride, in that order, after which it was dried over anhydrous sodium sulfate. The solvent was then removed by distillation under reduced pressure, and the resulting residue was recrystallized from a mixture of methylene chloride and diethyl ether, to give 1.47 g of the title compound as colorless crystals, melting at 147°–149° C.

Elemental analysis: Calculated for C$_{14}$H$_{24}$N$_2$O$_4$ (molecular weight: 284.34): C, 59.14%; H, 8.51%; N, 9.85%. Found: C, 58.90%; H, 8.35%; N, 9.67%.

PREPARATION 4

(4S)-1-Benzyloxycarbonyl-4-hydroxy-N-t-butyl-L-prolinamide 4.56 g (16.58 mmol) of diphenylphosphoryl azide, 1.50 g (20.55 mmol) of t-butylamine and 2.78 g (27.80 mmol) of triethylamine were successively added, whilst ice-cooling, to a solution of 3.68 g (13.90 mmol) of (4S)-1-benzyloxycarbonyl-4-hydroxy-L-proline in 30 ml of dimethylformamide, and the mixture was stirred for 5 hours. At the end of this time, the reaction mixture was poured into ice-water and extracted with ethyl acetate. The organic extract was washed with a 10% w/v aqueous solution of citric acid, with a 10% w/v aqueous solution of sodium hydrogencarbonate and with a saturated aqueous solution of sodium chloride, in that order, after which the resulting mixture was dried over anhydrous sodium sulfate. The solvent was then removed by distillation under reduced pressure, and the residue was recrystallized from a mixture of methylene chloride and diethyl ether, to give 1.10 g of the title compound as colorless crystals, melting at 129°–130° C.

Elemental analysis: Calculated for C$_{17}$H$_{24}$N$_2$O$_4$ (molecular weight: 320.39): C, 63.73%; H, 7.55%; N, 8.74%. Found: C, 64.00%; H, 7.47%; N, 8.80%.

PREPARATION 5

(4R)-1-t-Butoxycarbonyl-4-hydroxy-N-t-butyl-L-prolinamide 17.16 g (62.40 mmol) of diphenylphosphoryl azide, 5.70 g (78.08 mmol) of t-butylamine and 10.4 g (104.00 mmol) of triethylamine were added, in that order, to a solution of 12.0 g (51.95 mmol) of (4S)-1-t- butoxycarbonyl-4-hydroxy-L-proline in 100 ml of dimethylformamide, whilst ice-cooling, and the mixture was stirred for 5 hours. At the end of this time, the reaction mixture was poured into ice-water and extracted with ethyl acetate. The organic extract was washed with a 10% w/v aqueous solution of citric acid, with a 10% w/v aqueous solution of sodium hydrogencarbonate and with a saturated aqueous solution of sodium chloride, in that order, after which the mixture was dried over anhydrous sodium sulfate. The solvent was then removed by distillation under reduced pressure, and the resulting residue was recrystallized from ethyl acetate, to give 10.0 g of the title compound as colorless crystals, melting at 192°–193° C.

Elemental analysis: Calculated for C$_{14}$H$_{26}$N$_2$O$_4$ (molecular weight: 286.37): C, 58.72%; H, 9.15%; N, 9.78%. Found: C, 58.49%; H, 9.33%; N, 9.59%.

PREPARATION 6

(4S)-1-t-Butoxycarbonyl-4-morpholino-N-t-butyl-L-prolinamide

6(a) (4R)-1-t-Butoxycarbonyl-4-(p-toluenesulfonyloxy)-N-t-butyl-L-prolinamide 12.0 g (63.16 mmol) of p-toluenesulfonyl chloride were added, whilst ice-cooling, to a solution of 10.0 g (34.97 mmol) of (4R)-1-t-butoxycarbonyl-4-hydroxy-1-t-butyl-L-prolinamide (prepared as described in Preparation 5) in 100 ml of pyrrolidine, and the mixture was stirred at room temperature for 10 hours. At the end of this time, the reaction mixture was poured into ice-water and extracted with ethyl acetate. The organic extract was washed with a 10% w/v aqueous solution of citric acid, with a 10% w/v aqueous solution of sodium hydrogencarbonate and with a saturated aqueous solution of sodium chloride, in that order. The mixture was then dried over anhydrous sodium sulfate, after which the solvent was removed by distillation under reduced pressure, and the resulting residue was purified by column chromatography through silica gel, using a 1:2 by volume mixture of ethyl acetate and hexane as the eluent. The resulting crude product was recrystallized from a mixture of ethyl acetate, diethyl ether and hexane to give 8.60 g of the title compound as colorless crystals, melting at 125°–127° C.

Elemental analysis: Calculated for $C_{21}H_{32}N_2O_6S$ (molecular weight: 440.56): C, 57.25%; H, 7.32%; N, 6.36%; S, 7.28%. Found: C, 57.41%; H, 7.09%; N, 6.47%; S, 7.31%.

6(b) (4S)-1-t-Butoxycarbonyl-4-morpholino-N-t-butyl-L-prolinamide

A mixture of 1.0 g (2.27 mmol) of (4R)-1-t-butoxycarbonyl-4-(p-toluenesulfonyloxy)-N-t-butyl-L-prolinamide [prepared as described in step (a) above] and 5 g of morpholine was heated at 80° C. for 3 hours, whilst stirring. At the end of this time, the excess morpholine was removed by distillation under reduced pressure, and the residue was mixed with a saturated aqueous solution of sodium hydrogencarbonate. It was then extracted with ethyl acetate. The extract was dried over anhydrous sodium sulfate, and the solvent was removed by distillation under reduced pressure. The resulting residue was recrystallized from a mixture of methylene chloride and diethyl ether, to give 650 mg of the title compound as colorless crystals, melting at 172°–173° C.

Elemental analysis: Calculated for $C_{18}H_{33}N_3O_4$ (molecular weight: 355.46): C, 60.82%; H, 9.36%; N, 11.82%. Found: C, 60.51%; H, 9.28%; N, 11.80%.

PREPARATION 7 t-Butyl ester of (4R)-1-t-butoxycarbonyl-4-t-butoxy-L-proline 50 g of isobutene and 5 ml of concentrated aqueous sulfuric acid were added, whilst ice-cooling, to a solution of 10.0 g (0.043 mol) of (4R)-1-t-butoxycarbonyl-4-hydroxy-L-proline in 50 ml of methylene chloride, and the mixture was stirred overnight at room temperature in a sealed vessel. At the end of this time, the reaction mixture was poured into ice-water and extracted with methylene chloride. The organic extract was washed with a 10% w/v aqueous solution of citric acid, with a 10% w/v aqueous solution of sodium hydrogencarbonate and with a saturated aqueous solution of sodium chloride, in that order, after which it was dried over anhydrous sodium sulfate. The solvent was then removed by distillation under reduced pressure, and the residue was purified by column chromatography through silica gel, using a 1:10 by volume mixture of ethyl acetate and hexane as the eluent, to give 1.0 g of the t-butyl ester of (4R)-1-t-butoxycarbonyl-4-t-butoxy-L-proline as a colorless oil. The column was then eluted with a 1:1 by volume mixture of ethyl acetate and hexane, to give a further 1.30 g of the title compound as a colorless oil.

Elemental analysis: Calculated for $C_{13}H_{25}NO_3$ (molecular weight: 243.35): C, 64.16%; H, 10.36%; N, 5.76%. Found: C, 63.92%; H, 10.33%; N, 5.63%.

Mass spectrum (m/z): 244 ($M^+$+1).

PREPARATION 8

(4S)-1-t-Butoxycarbonyl-4-bromo-N-t-butyl-L-prolinamide 5.0 g (15.11 mmol) of carbon tetrabromide and 3.9 g (14.89 mmol) of triphenylphosphine were added to a solution of 2.86 g (10.0 mmol) of (4E)-1-t-butoxycarbonyl-4-hydroxy-N-t-butyl-L-prolinamide (prepared as described in Preparation 5) in 60 ml of tetrahydrofuran, and the mixture was heated under reflux for 1 hour. At the end of this time, insoluble materials were filtered off, and the filter cake was washed with a large quantity of diethyl ether. The filtrate and the washings were combined, and the combined solution was concentrated by evaporation under reduced pressure. The concentrate was purified by column chromatography through silica gel, using a 1:4 by volume mixture of ethyl acetate and hexane as the eluent. This crude product was recrystallized from a mixture of diethyl ether and hexane, to give 3.25 g of the title compound as colorless crystals, melting at 159°–160° C.

Elemental analysis: Calculated for $C_{14}H_{25}N_2O_3Br$ (molecular weight: 3492.7): C, 48.14%; H, 7.21%; N, 8.02%; Br, 22.88%. Found: C, 48.00%; H, 7.13%; N, 8.03%; Br, 23.03%.

PREPARATION 9

(1S,4S)-5-t-Butoxycarbonyl-2,5-oxazabicyclo[2.2.1]heptan-3-one 6.96 g (40.01 mmol) of diethyl azodicarboxylate were added dropwise, whilst ice-cooling, to a solution of 4.6 g (19.91 mmol) of (4R)-1-t-butoxyqarbonyl-L-proline and 10.5 g (40.08 mmol) of triphenylphosphine in 50 ml of tetrahydrofuran, and the mixture was stirred at room temperature for 2 hours. At the end of this time, insoluble materials were filtered off, and the filter cake was washed with diethyl ether. The filtrate was concentrated by evaporation under reduced pressure, and the concentrate was purified by column chromatography through silica gel, using a 1:4 by volume mixture of ethyl acetate and hexane as the eluent. The resulting crude product was recrystallized from a mixture of ethyl acetate and hexane, to give 2.7 g of the title compound as colorless crystals, melting at 115°–116° C.

Elemental analysis: Calculated for $C_{10}H_{15}NO_4$ (molecular weight: 213.23): C, 56.33%; H, 7.09%; N, 6.57%. Found: C, 56.02%; H, 6.93%; N, 6.64%.

PREPARATION 10

(1S,4S)-5-t-Butoxycarbonyl-2-t-butyl-2,5-diazabicyclo[2.2.1]heptan-3-one 2.28 ml (4.56 mmol) of a 2M solution of benzylmagnesium bromide in tetrahydrofuran were added dropwise, whilst ice-cooling, to a solution of 1 g (2.27 mmol) of (4 R)-1-t-butoxycarbonyl-4-(p-toluenesulfonyloxy)-N-t-butyl-L-prolinamide [prepared as described in Preparation 6(a)] in 15 ml of tetrahydrofuran, and the mixture was stirred at room temperature for 3 hours. At the end of this time, the reaction mixture was poured into ice-water and extracted with ethyl acetate. The organic extract was washed with a 10% w/v aqueous solution of citric acid, with a 10% w/v aqueous of sodium hydrogencarbonate and with a saturated aqueous solution of sodium chloride, in that order. The mixture was dried over anhydrous sodium sulfate, after which the solvent was removed by distillation under reduced pressure. The residue was purified by column chromatography through silica gel, using a 1:3 by volume mixture of ethyl acetate and hexane as the eluent. The resulting crude product was recrystallized from a mixture of methylene chloride, diethyl ether and hexane, to give 260 mg of the title compound as colorless crystals, melting at 167°–168° C.

Elemental analysis: Calculated for $C_{14}H_{24}N_2O_3$ (molecular weight: 268.36): C, 62.66%; H, 9.01%; N, 10.44%. Found: C, 62.68%; H, 9.16%; N, 10.41%.

PREPARATION 11

(4S)-1-t-Butoxycarbonyl-4-phenylthio-N-t-butyl-L-prolinamide 0.45 g (3.41 mmol) of sodium thiophenolate was added to a solution of 1.23 g (3.08 mmol) of (4 R)-1-t-butoxycarbonyl-4-(p-toluenesulfonyloxy)-N-t-butyl-L-prolinamide [prepared as described in Preparation 6(a)] in 10 ml of a 2:1 by volume mixture of dimethylformamide and ethyl acetate, and the mixture was stirred for 3 hours. At the end of this time, the reaction mixture was poured into a 10% w/v aqueous solution of sodium hydrogen-carbonate and extracted with ethyl acetate. The organic extract was dried over anhydrous sodium sulfate, and then the solvent was removed by distillation under reduced pressure. The resulting residue was purified by preparative thin layer chromatography, using a 1:3 by volume mixture of ethyl acetate and hexane as the developing solvent, to give 1.0 g of the title compound as a colorless powder, melting at 119°–121° C.

Elemental analysis: Calculated for $C_{20}H_{30}N_2O_3S$ (molecular weight: 378.54): C, 63.46%; H, 7.99%; N, 7.40%; S, 8.47%. Found: C, 63.31%; H, 7.74%; N, 7.35%; S, 8.77%.

PREPARATION 12

(3R)-1-t-Butoxycarbonyl-3-t-butyldimethylsilyloxy-N-t-butyl-L-prolinamide

12(a) (3S)-1-t-Butoxycarbonyl-3-t-butyldimethylsilyloxy-L-prolinol 0.4 ml of formic acid were added to a solution of 800 mg (1.90 mmol) of (2R,3S)-1-t-butoxycarbonyl-2-benzyloxymethyl-3-t-butyldimethylsilyloxypyrrolidine [which had been prepared from 1-t-butoxycarbonyl-D-seline benzyl ether in a similar manner to that described by W. R. Ewing et al. in Heterocycles, 27, 2843 (1988)] in 8 ml of methanol, and the mixture was stirred for 3 hours in the presence of 400 mg of palladium black under an atmosphere of hydrogen. At the end of this time, the catalyst was filtered off, and the filtrate was freed from the solvent by distillation under reduced pressure. The residue was purified by column chromatography through silica gel, using a 6:1 by volume mixture of hexane and ethyl acetate as the eluent, to give 620 mg of the title compound as an oil.

Mass spectrum (m/z): 332 ($M^+$+1), 244, 218, 200, 57.

Elemental analysis: Calculated for $C_{16}H_{33}NO_4Si.0.1H_2O$ (molecular weight: 340.01): C, 56.87%; H, 9.84%; N, 4.12%. Found: C, 57.06%; H, 9.63%; N, 4.16%.

12(b) (3R)-1-t-Butoxycarbonyl-3-t-butyldimethylsilyloxy-L-proline 0.7 ml of Jones' reagent (chromium trioxide/4N aqueous sulfuric acid: Bowden, Heibron, Jones & Weedon, J. Chem. Soc., 1946, 39) was added, whilst ice-cooling, to a solution of 245 mg (0.74 mmol) of (3 R)-1-t-butoxycarbonyl-3-t-butyldimethylsilyloxy-L-prolinol [prepared as described in step (a) above] in 10 ml of acetone, and the mixture was stirred at 0° C. for 2 hours. At the end of this time, the reaction mixture was diluted with water and extracted with diethyl ether. The extract was washed with a saturated aqueous solution of sodium chloride and dried over anhydrous sodium sulfate. The solvent was then removed by distillation under reduced pressure, and the residue was triturated with hexane, to give 191 mg of the title compound as colorless crystals, melting at 146°–147° C.

Elemental analysis: Calculated for $C_{16}H_{31}NO_5Si$ (molecular weight: 345.50): C, 55.62%; H, 9.04%; N, 4.05%. Found: C, 55.47%; H, 8.85%; N, 4.05%.

12(c) (3R)-1-t-Butoxycarbonyl-3-t-butyldimethylsilyloxy-N-t-butyl-L-prolinamide 95 µl (0.68 mmol) of triethylamine and 89 µl (0.68 mmol) of isobutyl chloroformate were added at –40° C. to a solution of 214 mg (0.62 mmol) of (3 R)-1-t-butoxycarbonyl-3-t-butyldimethylsilyloxy-L-proline [prepared as described in step (b) above] in 5 ml of tetrahydrofuran, and the temperature of the mixture was allowed to rise slowly to –10° C., after which the mixture was stirred for 20 minutes. The reaction mixture was then cooled to –15° C. and 325 µl (3.10 mmol) of t-butylamine were added. The mixture was then stirred at the same temperature for 14 hours. At the end of this time, the reaction mixture was mixed with a 5% w/v aqueous solution of citric acid and extracted with ethyl acetate. The organic extract was washed with a saturated aqueous solution of sodium chloride and dried over anhydrous sodium sulfate. The solvent was removed by distillation under reduced pressure, and the resulting residue was purified by flash chromatography through silica gel, using a 4:1 by volume mixture of hexane and ethyl acetate as the eluent, to give 118 mg of the title compound as colorless crystals, melting at 67°–69° C.

Elemental analysis: Calculated for $C_{20}H_{40}N_2O_4Si$ (molecular weight: 400.62): C, 59.96%; H, 10.06%; N, 6.99%. Found: C, 59.68%; H, 10.04%; N, 7.07%.

PREPARATION 13

(3S)-1-t-Butoxycarbonyl-N-t-butyl-3-hydroxy-L-prolinamide

13(a) (2R,3R)-1-t-Butoxycarbonyl-2-benzyloxymethyl-3-hydroxypyrrolidine

A solution of 2.01 g (7.68 mmol) of tetrabutylammonium fluoride in 5 ml of tetrahydrofuran was added, whilst ice-cooling, to a solution of 2.16 g (5.12 mmol) of (2S,3S)-1-t-butoxycarbonyl-2-benzyloxymethyl-3-t-butyldimethylsilyloxypyrrolidine in 5 ml of tetrahydrofuran, and the mixture was stirred at room temperature for 4 hours. At the end of this time, the reaction mixture was diluted with ethyl acetate, and the organic extract was washed with 0.5N aqueous hydrochloric acid, with a 5% w/v aqueous solution of sodium hydrogencarbonate and with a saturated aqueous solution of sodium chloride, in that order. The reaction mixture was then dried over anhydrous sodium sulfate, after which the solvent was removed by distillation under reduced pressure. The resulting residue was then purified by column chromatography through silica gel, using a 3:1 by volume mixture of hexane and ethyl acetate as the eluent, to give 1.57 g of the title compound as an oil.

Mass spectrum (m/z): 307 (M$^+$), 251, 145, 130, 86, 57.

Elemental analysis:

Calculated for $C_{17}H_{25}NO_4Si.H_2O$ (molecular weight: 309.18): C, 66.04%; H, 8.22%; N, 4.53%. Found: C, 65.95%; H, 8.20%; N, 4.58%.

13(b) (2R,3S)-1-t-Butoxycarbonyl-3-benzoyloxy-2-benzyloxymethylpyrrolidine

A solution of 0.52 ml (3.31 mmol) of diethyl azodicarboxylate in 5 ml of tetrahydrofuran was slowly added at room temperature to a solution of 1.00 g (3.25 mmol) of (2R,3R)-1-t-butoxycarbonyl-2-benzyloxymethyl-3-hydroxypyrrolidine [prepared as described in step (a) above], 0.87 g (3.31 mmol) of triphenylphosphine and 0.42 g (3.47 mmol) of benzoic acid in 5 ml of tetrahydrofuran, and the mixture was stirred for 14 hours. At the end of this time, the reaction mixture was diluted with ethyl acetate and washed with a 5% w/v aqueous solution of citric acid, with a 5% w/v aqueous solution of sodium hydrogencarbonate and with a saturated aqueous solution of sodium chloride, in that order. The reaction mixture was then dried over anhydrous sodium sulfate, and the solvent was removed by distillation under reduced pressure. The resulting residue was purified by flash chromatography through silica gel, using a 20:1 by volume mixture of hexane and ethyl acetate as the eluent, to give 1.05 g of the title compound as an oil.

Mass spectrum (m/z): 411 (M$^+$), 290, 234, 190, 105, 91, 57.

Elemental analysis: Calculated for $C_{20}H_{29}NO_5$ (molecular weight: 411.48): C, 70.05%; H, 7.10%; N, 3.40%. Found: C, 70.14%; H, 7.10%; N, 3.73%.

13(c) (3S)-1-t-Butoxycarbonyl-3-benzoyloxy-N-t-butyl-L-prolinamide

Following a procedure similar to that described in Preparation 12, but using (2R,3S)-1-t-butoxycarbonyl-3-benzoyloxy-2-benzyloxymethyl-pyrrolidine [prepared as described in step (b) above] as a starting material, the title compound was obtained as colorless crystals, melting at 132°–134° C.

Elemental analysis: Calculated for $C_{21}H_{30}N_2O_5.0.25H_2O$ (molecular weight: 394.97): C, 63.86%; H, 7.78%; N, 7.09%. Found: C, 64.10%; H, 7.63%; N, 7.30%.

13(d) (3S)-1-t-Butoxycarbonyl-3-hydroxy-N-t-butyl-L-prolinamide 0.17 ml (0.17 mmol) of a 1N aqueous solution of sodium hydroxide was added, whilst ice-cooling, to a solution of 63 mg (0.16 mmol) of (3S)-1-t-butoxycarbonyl-3-benzoyloxy-N-t-butyl-L-prolinamide [prepared as described in step (c) above] in 1 ml of methanol and the mixture was stirred at 0° C. for 30 minutes. At the end of this time, the reaction mixture was neutralized with 1N aqueous hydrochloric acid, and the solvent was removed by distillation under reduced pressure. The resulting residue was diluted with ethyl acetate. The ethyl acetate solution was washed with a 5% w/v aqueous solution of citric acid, with a 5% aqueous solution of sodium hydrogencarbonate and with a saturated aqueous solution of sodium chloride, in that order. The reaction mixture was then dried over anhydrous sodium sulfate, and the solvent was removed by distillation under reduced pressure. The residue was purified by column chromatography through silica gel, using a 1:1 by volume mixture of hexane and ethyl acetate as the eluent, to give 36 mg of the title compound as colorless crystals, melting at 122°–124° C.

Elemental analysis: Calculated for $C_{14}H_{26}N_2O_6$ (molecular weight: 286.36): C, 58.72%; H, 9.15%; N, 9.78%. Found: C, 58.70%; H, 9.18%; N, 9.65%.

PREPARATION 14

Ethyl 4-(benzyloxycarbonylamino)phenoxyacetate

14(a) 4-(N-Benzyloxycarbonylamino)phenol 10.1 g (0.12 mol) of sodium hydrogencarbonate and 17.2 ml (0.12 mol) of benzyloxycarbonyl chloride were added at 0° C. to a suspension of 12.5 g (0.11 mol) of p-aminophenol in 100 ml of a 1:1 by volume mixture of dioxane and water, and the mixture was stirred at room temperature for 18 hours. At the end of this time, the reaction mixture was acidified with 2N aqueous hydrochloric acid and extracted with ethyl acetate. The organic extract was washed with water and dried over anhydrous sodium sulfate. The solvent was removed by distillation under reduced pressure, and the residue was triturated with a 1:1 by volume mixture of hexane and diethyl ether, to give 22.8 g of the title compound as colorless crystals, melting at 156°–157° C.

Elemental analysis: Calculated for $C_{14}H_{13}NO_3$ (molecular weight: 243.52): C, 69.12%; H, 5.39%; N, 5.76%. Found: C, 69.23%; H, 5.52%; N, 5.80%.

14(b) Ethyl 4-(benzyloxycarbonylamino)phenoxyacetate 1.89 g (45.2 mmol) of sodium hydride (as a 55% w/w dispersion in mineral oil) were added, whilst ice-cooling, to a solution of 10.0 g (41.1 mmol) of 4-(benzyloxycarbonylamino)phenol [prepared as described in step (a) above] in 100 ml of dimethylformamide, and the mixture was stirred for 5 minutes. 5.01 ml (45.2 mmol) of ethyl bromoacetate were then added to the resulting mixture, after which the mixture was stirred at room temperature for 3 hours. At the end of this time, the reaction mixture was neutralized with 1N aqueous hydrochloric acid, and the solvent was removed by distillation under reduced pressure. The residue was mixed with ethyl acetate, and the resulting organic solution was washed with a 5% w/v aqueous solution of citric acid, with a 5% w/v aqueous solution of sodium hydrogencarbonate and with a saturated aqueous solution of sodium chloride, in that order. The reaction mixture was then dried over anhydrous sodium sulfate, and the organic solvent was removed by distillation under reduced pressure. The residue was purified by column chromatography through silica gel, using a gradient elution method, with mixtures of hexane and ethyl acetate in ratios ranging from 10:1 to 6:1 by volume as the eluent, to give 11.7 g of the title compound as colorless crystals, melting at 85°–86° C.

Elemental analysis: Calculated for $C_{18}H_{19}NO_5$ (molecular weight: 329.34): C, 65.64%; H, 5.82%; N, 4.25%. Found: C, 65.57%; H, 5.89%; N, 4.31%.

PREPARATION 15

4-(Benzyloxycarbonylamino)phenoxyacetic acid 1.67 ml (1.67 mmol) of a 1N aqueous solution of sodium hydroxide were added, whilst ice-cooling, to a solution of 500 mg (1.52 mmol) of ethyl 4-(benzyloxycarbonylamino) phenoxyacetate (prepared as described in Preparation 14) in 10 ml of methanol, and the mixture was stirred at room temperature for 1 hour. At the end of this time, the reaction mixture was neutralized by the addition of 1N aqueous hydrochloric acid, and the solvent was removed by distillation under reduced pressure. The residue was diluted with ethyl acetate, and the resulting organic solution was washed with a 5% w/v aqueous solution of citric acid and with a saturated aqueous solution of sodium chloride, in that order. The reaction mixture was then dried over sodium sulfate, and the organic solvent was removed by distillation under reduced pressure. The concentrate was triturated with diethyl ether, to give 417 mg of the title compound as colorless crystals, melting at 152°–154° C.

Elemental analysis: Calculated for $C_{16}H_{15}NO_5$ (molecular weight: 301.29): C, 63.78%; H, 5.02%; N, 4.65%. Found: C, 63.84%; H, 5.13%; N, 4.64%.

PREPARATION 16

Ethyl 4-(N-benzyloxycarbonyl-N-methylamino) phenoxyacetate 0.29 g (6.83 mmol) of sodium hydride (as a 55% w/w dispersion in mineral oil) was added, whilst ice-cooling, to a solution of 1.50 g (4.55 mmol) of ethyl 4-(benzyloxycarbonylamino)phenoxyacetate (prepared as described in Preparation 14) in 9 ml of dimethylformamide, and the mixture was stirred for 20 minutes, after which 0.57 ml (9.10 mmol) of methyl iodide was added to the reaction mixture. The mixture was then stirred at room temperature for 4 hours. At the end of this time, the reaction mixture was neutralized with 1N aqueous hydrochloric acid, and the solvent was removed by distillation under reduced pressure. The resulting residue was mixed with ethyl acetate, and the resulting organic solution was washed with 1N aqueous hydrochloric acid, with a 5% w/v aqueous solution of sodium hydrogencarbonate, with a 5% w/v aqueous solution of sodium thiosulfate and with a saturated aqueous solution of sodium chloride, in that order. The reaction mixture was then dried over anhydrous sodium sulfate, and the solvent was removed by distillation under reduced pressure. The resulting residue was purified by preparative thin layer chromatography, using a 3:2 by volume mixture of hexane and ethyl acetate as the developing solvent, to give 0.69 g of the title compound as an oil.

Mass spectrum (m/z): 343 (M⁺), 299, 208, 91.

Elemental analysis: Calculated for $C_{19}H_{21}NO_5$ (molecular weight: 343.34): C, 66.46%; H, 6.16%; N, 4.08%. Found: C, 66.37%; H, 6.29%; N, 4.10%.

PREPARATION 17

4-(N-Benzyloxycarbonyl-N-methylamino) phenoxyacetic acid

Following a procedure similar to that described in Preparation 15, but using 240 mg (0.70 mmol) of ethyl 4-(N-benzyloxycarbonyl-N-methylamino)phenoxyacetate (prepared as described in Preparation 16), 220 mg of the title compound were obtained as white powder, melting at 96°–97° C.

Elemental analysis: Calculated for $C_{17}H_{17}NO_5$ (molecular weight: 315.31): C, 64.75%; H, 5.44%; N, 4.44%. Found: C, 65.09%; H, 5.69%; N, 4.41%.

PREPARATION 18

Ethyl 4-(N,N-dimethylamino)phenoxyacetate 1.93 ml (1.93 mmol) of 1N aqueous hydrochloric acid were added to a solution of 600 mg (1.75 mmol) of ethyl 4-(N-benzyloxycarbonyl-N-methylamino)phenoxyacetate (prepared as described in Preparation 16) in 18 ml of methanol, and the mixture was stirred at room temperature for 1.5 hours in the presence of a palladium-on-charcoal catalyst, under an atmosphere of hydrogen. At the end of this time, the catalyst was removed by filtration, and the filtrate was freed from the solvent by distillation under reduced pressure. The resulting residue was mixed with benzene, and the mixture was dehydrated by azeotropic distillation. This operation was repeated again, to give ethyl 4-methylaminophenoxyacetate as a residue. The whole of this residue was dried in vacuo and then dissolved in 2 ml of dimethylformamide. 186 mg (1.75 mmol) of sodium carbonate and 0.12 ml (1.93 mmol) of methyl iodide were added to the solution, and the mixture was stirred at room temperature for 48 hours. At the end of this time, the reaction mixture was concentrated by evaporation under reduced pressure, and the concentrate was mixed with ethyl acetate. The resulting organic mixture was washed with a 5% w/v aqueous solution of sodium hydrogencarbonate, with a 5% w/v aqueous solution of sodium thiosulfate and with a saturated aqueous solution of sodium chloride, in that order. The reaction mixture was then dried over anhydrous sodium sulfate, and the solvent was removed by distillation under reduced pressure. The resulting residue was purified by preparative thin layer chromatography, using a 1:1 by volume mixture of hexane and ethyl acetate as the developing solvent, to give 129 mg of the title compound as an oil.

Mass spectrum (m/z): 223 (M⁺), 194, 136.

Elemental analysis: Calculated for $C_{12}H_{17}NO_3$ (molecular weight: 223.26): C, 64.55%; H, 7.68%; N, 6.27%. Found: C, 64.26%; H, 7.72%; N, 6.24%.

PREPARATION 19

4-[N-(N-t-Butoxycarbonylsarcosyl)-N-methylamino] phenoxyacetic acid 0.12 ml (0.72 mmol) of diethyl cyanophosphate and 0.20 ml (1.43 mmol) of triethylamine were added, whilst ice-cooling, to a solution of 160 mg (0.65 mmol) of ethyl 4-methylaminophenoxyacetate (prepared as an intermediate in Preparation 18) and 135 mg (0.72 mmol) of t-butoxycarbonylsarcosine in 2 ml of dimethylformamide, and the mixture was stirred at room temperature for 14 hours. At the end of this time, the reaction mixture was concentrated by evaporation under reduced pressure, and the residue was diluted with ethyl acetate. The resulting organic mixture was washed with a 5% w/v aqueous solution of citric acid, with a 5% w/v aqueous solution of sodium hydrogencarbonate and with a saturated aqueous solution of sodium chloride, in that order. The reaction mixture was then dried over anhydrous sodium sulfate, and the solvent was removed by distillation under reduced pressure. The residue was purified by preparative thin layer chromatography, using a 30:1 by volume mixture of methylene chloride and methanol as the developing solvent, to give 120 mg of ethyl 4-[N-(N-t-butoxycarbonylsarcosyl)-N-methylamino]phenoxyacetate as an oil. In a similar manner to that described in Preparation 15, 200 mg (0.55 mmol) of this compound were hydrolyzed to give 170 mg of the title compound as an amorphous substance.

Mass spectrum: 352 (M⁺), 237, 181.

Elemental analysis: Calculated for $C_{17}H_{24}N_2O_6 \cdot 0.7H_2O$ (molecular weight: 352.38): C, 55.94%; H, 7.01%; N, 7.68%. Found: C, 55.94%; H, 6.62%; N, 7.80%.

PREPARATION 20

4-[N-(N-t-Butoxycarbonylglycyl)-N-methylamino] phenoxyacetic acid

Following a procedure similar to that described in Preparation 19, but using t-butoxycarbonylglycine as a starting material, the title compound was obtained as a white powder, melting at 146°–155° C.

Elemental analysis: Calculated for $C_{16}H_{22}N_2O_6$ (molecular weight: 338.35): C, 56.80%; H, 6.55%; N, 8.28%. Found: C, 56.62%; H, 6.52%; N, 8.34%.

PREPARATION 21(a)

(4S)-1-[(2S,3S)-3-(N,N-Dibenzylamino)-2-hydroxy-4-phenylbutyryl]-4-chloro-N-t-butyl-L-prolinamide 12.2 g (0.04 mol) of (4S)-N-t-butoxycarbonyl-4-chloro-N-t-butyl-L-prolinamide were treated with 50 ml of a 4N solution of hydrogen chloride in dioxane, in order to remove the t-butoxycarbonyl group. The product thus obtained and 15.0 g (0.04 mol) of (2S,3S)-3-(N,N-dibenzylamino)-2-hydroxy-4-phenylbutyric acid were dissolved in 50 ml of dimethylformamide, and the solution was cooled with ice. 8.48 ml (52.0 mmol) of diethyl cyanophosphate, and then 11.2 ml (0.08 mmol) of triethylamine, were then added dropwise to the resulting mixture, which was then stirred for 1 day. At the end of this time, the reaction mixture was concentrated by evaporation under reduced pressure, and the concentrate was diluted with ethyl acetate. The diluted solution was washed with a 5% w/v aqueous solution of citric acid and with a 5% w/v aqueous solution of sodium hydrogencarbonate, in that order, after which it was dried over anhydrous sodium sulfate. The solvent was then removed by distillation under reduced pressure, and the resulting residue was purified by column chromatography, using a 1:1 by volume mixture of ethyl acetate and hexane as the eluent, to give 20.0 g of the title compound as a colorless powder, melting at 64°–67° C.

Elemental analysis: Calculated for $C_{33}H_{40}N_3O_3Cl \cdot \frac{1}{3}H_2O$ (molecular weight: 568.14): C, 69.76%; H, 7.22%; N, 7.40%; Cl, 6.24%. Found: C, 70.02%; H, 7.28%; N, 7.33%; Cl, 6.09%.

PREPARATION 21(b)

(4S)-1-[(2S,3S)-3-Amino-2-hydroxy-4-phenylbutyryl]-4-chloro-N-t-butyl-L-prolinamide A solution of 20.0 g (35.6 mmol) of (4S)-1-[(2S,3S)-3-(N,N-dibenzylamino)-2-hydroxy-4-phenylbutyryl]-4-chloro-N-t-butyl-L-prolinamide dissolved in 200 ml of a 4.5% by volume solution of formic acid in methanol was stirred in the presence of 3 g of palladium black at room temperature for 3 hours and then at 40° C. for 2 hours. At the end of this time, the catalyst was removed by filtration, and the filtrate was concentrated by evaporation under reduced pressure. The concentrate was then diluted with ethyl acetate. The diluted solution was washed with a saturated aqueous solution of sodium hydrogencarbonate and then dried over anhydrous sodium sulfate. The solvent was removed by distillation under reduced pressure, and the resulting residue was dissolved in benzene. Hexane was added to the resulting solution, to obtain 13.1 g of the title compound as a colorless powder, melting at 126°–130° C.

Elemental analysis: Calculated for $C_{19}H_{28}N_3O_3Cl$ (molecular weight: 381.90): C, 59.76%; H, 7.39%; N, 11.00%; Cl, 9.28%. Found: C, 59.74%; H, 7.19%; N, 10.98%; Cl, 9.41%.

PREPARATION 22

6-Nitroquinoxaline-2-carboxylic acid 15.3 ml (0.1 mol) of a 40% w/v aqueous solution of pyruvic aldehyde were added to a suspension of 15.3 g (0.1 mol) of 4-nitro-1,2-phenylenediamine in 800 ml of a 1:1 by volume mixture of isopropanol and water, and the resulting mixture was heated under reflux for 3 hours. At the end of this time, the mixture was cooled, and the crystals which had precipitated were collected by filtration and recrystallized from ethanol. The filtrate was concentrated by distillation under reduced pressure, and the concentrate was triturated with ethanol to cause crystallization. A total of 15.5 g of 2-methyl-6-nitroquinoxaline were obtained as crude yellow-brown crystals. 12.5 g (0.066 mol) of this crude 2-methyl-6-nitroquinoxaline were suspended in 200 ml of toluene, and 13.2 g of selenium dioxide were added to the suspension. The resulting mixture was then heated under reflux for 4 hours. It was then cooled, after which insoluble materials were filtered off and the filtrate was freed from the solvent by distillation under reduced pressure. The residue was mixed with 400 ml of acetone. 420 ml (0.13 mol) of a 5% aqueous solution of potassium permanganate were then slowly added at room temperature and with stirring to the resulting mixture, which was then stirred at room temperature for 2.5 hours. At the end of this time, insoluble materials were filtered off and the filtrate was freed from acetone by distillation under reduced pressure. The aqueous layer thus obtained was washed with diethyl ether and then acidified with concentrated hydrochloric acid to precipitate crystals. These crystals were dissolved in a 1N aqueous solution of sodium hydroxide, and insoluble materials were filtered off. The filtrate was again acidified with concentrated hydrochloric acid to precipitate crystals, which were recrystallized from a mixture of acetone and diethyl ether, to give 9.9 g of the title compound as pale yellow-brown crystals, melting at 208°–210° C.

Elemental analysis: Calculated for $C_9H_5N_3O_4$ (molecular weight: 219.15): C, 49.32%; H, 2.30%; N, 19.18%. Found: C, 49.30%; H, 2.67%; N, 19.33%.

Mass spectrum (m/z): 219 (M⁺), 175, 129.

Infrared Absorption Spectrum (KBr), $\nu_{max}$ cm$^{-1}$: 1713, 1541, 1344.

Nuclear Magnetic Resonance Spectrum (CD$_3$COCD$_3$), δppm: 8.47 (1H, doublet, J=9.2 Hz); 8.70 (1H, doublet of doublets, J=2.6 & 9.2 Hz); 9.01 (1H, doublet, J=2.0 Hz); 9.66 (1H, singlet).

We claim:

1. A compound of the formula

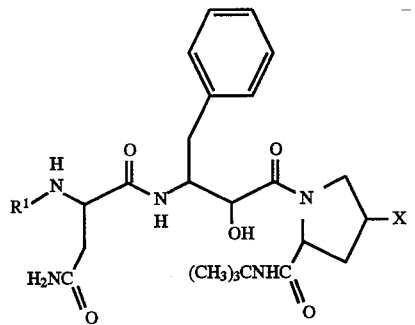

wherein

X is a chlorine atom, and

R¹ is selected from the group consisting of

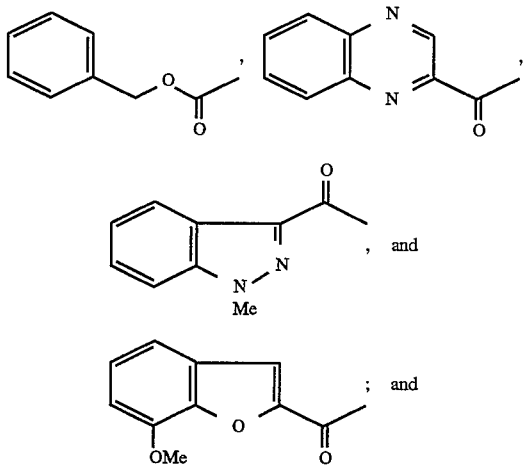

pharmaceutically acceptable salts and esters thereof.

2. The compound of claim 1, selected from the group consisting of 1-[3-(N²-benzyloxycarbonyl-L-asparaginyl)-amino-2-hydroxy-4-phenylbutyryl]-N-t-butyl-4-chloro-L-prolinamide and pharmaceutically acceptable salts and esters thereof.

3. The compound of claim 1, selected from the group consisting of 1-{3-[N²-(2-quinoxalinecarbonyl)-L-asparaginyl]amino-2-hydroxy-4-phenylbutyryl}-N-t-butyl-4-chloro-L-prolinamide and pharmaceutically acceptable salts and esters thereof.

4. The compound of claim 1, selected from the group consisting of 1-{3-(N²-(7-methoxy-2-benzofurancarbonyl)-L-asparaginyl]amino-2-hydroxy-4-phenylbutyryl}-4-chloro-N-t-butyl-L-prolinamide and pharmaceutically acceptable salts and esters thereof.

5. The compound of claim 1, selected from the group consisting of 1-{3-[N²-(1-methylindazol-3-yl-carbonyl)-L-asparaginyl]amino-2-hydroxy-4-phenylbutyryl}-4-chloro-N-t-butyl-L-prolinamide and pharmaceutically acceptable salts and esters thereof.

6. A compound selected from the group consisting of:

1-{3-[N²-(2-quinoxalinecarbonyl)-L-asparaginyl]amino-2-hydroxy-4-phenylbutyryl}-N-t-butyl-4-chloro-L-prolinamide;

1-{3-[N²-(4-aminophenoxyacetyl)-L-asparaginyl]amino-2-hydroxy-4-phenylbutyryl]-4-chloro-N-t-butyl-L-prolinamide;

1-[{3-[N²-(4-benzyloxycarbonylaminophenoxy)acetyl-L-asparaginyl]amino-2-hydroxy-4-phenylbutyryl}-4-chloro-N-t-butyl-L-prolinamide;

1-{3-(N²-(7-methoxy-2-benzofurancarbonyl)-L-asparaginyl]amino-2-hydroxy-4-phenylbutyryl}-4-chloro-N-t-butyl-L-prolinamide;

1-{3-[N²-(1-methylindazol-3-ylcarbonyl)-L-asparaginyl]amino-2-hydroxy-4-phenylbutyryl}-4-chloro-N-t-butyl-L-prolinamide;

and pharmaceutically acceptable salts and esters thereof.

* * * * *